US006399629B1

(12) United States Patent
Chamberland et al.

(10) Patent No.: US 6,399,629 B1
(45) Date of Patent: Jun. 4, 2002

(54) EFFLUX PUMP INHIBITORS

(75) Inventors: Suzanne Chamberland, Los Gatos, CA (US); Yohei Ishida, Tokyo (JP); Ving J Lee, Los Altos; Roger Leger, Mountain View, both of CA (US); Kiyoshi Nakayama, Chiba (JP); Toshiharu Ohta, Tokyo (JP); Masami Ohtsuka, Tokyo (JP); Thomas E. Renau, Santa Clara, CA (US); William J. Watkins, Sunnyvale, CA (US); Zhijia J. Zhang, Foster City, CA (US)

(73) Assignee: Microcide Pharmaceuticals, Inc., Mountain View, CA (US)

(*) Notice: Subject to any disclaimer, the term of this patent is extended or adjusted under 35 U.S.C. 154(b) by 0 days.

(21) Appl. No.: 09/108,906

(22) Filed: Jul. 1, 1998

Related U.S. Application Data
(60) Provisional application No. 60/087,514, filed on Jun. 1, 1998.

(51) Int. Cl.$^7$ .................. A61K 31/47; A61K 31/40; C07D 217/18; C07D 207/00
(52) U.S. Cl. .................. 514/313; 514/408; 514/423; 548/518; 548/537; 546/159
(58) Field of Search .................... 514/313, 408, 514/423; 546/159; 548/518, 537

(56) References Cited

FOREIGN PATENT DOCUMENTS

| EP | 0 696 593 A2 | 2/1996 |
| WO | 93/21215 | 10/1993 |
| WO | 98/17625 | 4/1998 |

OTHER PUBLICATIONS

Bray et al., "Rapid optimization of organic reactions on solid phase using the multipin approach: Synthesis of 4–amino-proline analogues by reductive amination," *Tetrahedron Letters* 36(28):5081–5084 (1995).
Ahmed et al., "A protein that activates expression of a multidrug efflux transporter upon binding the transporter substrates," *Journal of Biological Chemistry* 269(45):28506–28513.
Bergeron, "A review of models for the therapy of experimental infections," *Scand. J. Infect. Dis. Suppl.* 14:189–206 (1978).
Davis, "Activity of gentamicin, tobramycin, polymyxin B, and colistimethate in mouse protection tests with Pseudomonas aeruginosa," *Antimicrobial Agents and Chemotherapy* 8(1):50–53 (1975).
Day et al., "A simple method for the study in vivo of bacterial growth and accompanying host response," *Journal of Infection* 2:39–51 (1980).
Erickson et al., "Inhibition of rat passive cutaneous anaphylaxis by 3–(tetrazol–5–yl) quinolines," *J. Med. Chem.* 22(7):816–823 (1979).

Goodman et al. (Eds.) *Goodman and Gilman's: The Pharmacological Basis of Therapeutics* 8$^{th}$ Ed., Pergamon Press (1975).
Gordon et al., "Design of novel inhibitors of aminopeptidases. Synthesis of peptide–derived diamino thiols and sulfur replacement analogues of bestatin," *J. Med. Chem.* 31:2199–2211 (1988).
Greene et al., *Protective Groups in Organic Synthesis* 2$^{nd}$ Ed., John Wiley & Sons, Inc. (1991) (Table of Contents Only).
Kelly et al., "Surface characteristics of Pseudomonas aeruginosa grown in a chamber implant model in mice and rats," *Infect and Immunity* 57(2):344–350 (1989).
Klein et al., "Identification and initial structure–activity relationships of a novel class of nonpeptide inhibitors of blood coagulation factor Xa," *J. Med. Chem.* 41:437–450 (1998).
Larock, *Comprehensive Organic Transformations: A Guide to Functional Group Preparations* VCH (1992) (Table of Contents Only).
Lorian (Ed.) *Antibiotics in Laboratory Medicine* 4$^{th}$ Ed., Williams & Wilkins, pp. 333–338 (1996).
Malouin et al., "Outer membrane and porin characteristics of Serratia marcescens grown in vitro and in rat intraperitoneal diffusion chambers," *Infection and Immunity* 58(5):1247–1253 (1990).
Marui et al., "Chemical modification of fumagillin. III. Modification of the spiro–epoxide," *Chem. Pharm. Bull.* 43(4):588–593 (1995).
*Methods for Dilution of Antimicrobial Susceptibility Tests for Bacteria that Grow Aerobically–Fourth Edition; Approved Standard.* NCCLS Document M7–A4, vol. 17, No. 2 (1997).
Murray, "Can antibiotic resistance be controlled?" *New Engl. J of Med.* 330(17):1229–1230 (1994).
Nikaido, "Prevention of drug access to bacterial targets: Permeability barriers and active efflux," *Science* 264:382–388 (1994).
Ocain et al., "Synthesis of sulfur–containing analogues of bestatin. Inhibition of aminopeptidases by α–thiolbestatin analogues," *J. Med. Chem.* 31:2193–2199 (1988).
Ram et al., "Synthesis of potential antifilarial agents. 1. 1–(5–Benzoylbenzimidazol–2–yl)–3–alkyl– and –arylureas," *J. Med. Chem.* 27:914–917 (1984).
Reinhoudt et al., "Synthesis of heteroaromatic compounds with 'Enamine' reactivity," *Synthesis* pp. 368–337 (1978).
Reitz et al., "The biochemical mechanisms of resistance by streptococci to the antibiotics D–Cycloserine and O–Carbamyl–D–Serine," *Biochem J.* 6(8):2561–2570 (1967).

(List continued on next page.)

*Primary Examiner*—Deborah C. Lambkin
(74) *Attorney, Agent, or Firm*—Lyon & Lyon LLP

(57) ABSTRACT

Compounds are described which have efflux pump inhibitor activity. Also described are methods of using such efflux pump inhibitor compounds and pharmaceutical compositions which include such compounds.

59 Claims, No Drawings

OTHER PUBLICATIONS

Santoro et al., "Rat model of experimental endocarditis," *Infection and Immunity* 19(3):915–918 (1978).

Sato et al., "Antimicrobial activity of DU–6859, a new potent fluoroquinolone, against clinical isolates," *Antimicrobial Agents and Chemotherapy* 36(7):1491–1498 (1992).

Seoane et al., "Reversal of MarR binding to the regulatory region of the marRAB operon by structurally unrelated inducers," *Abstr. of the Am. soc. for Microbiol. Gen. Meeting, Las Vegas NV, Abstr. H–26* (1994).

Speer et al., "Bacterial resistance to tetracycline: Mechanisms, transfer, and clinical significance," *Clinical Microbiology Reviews* 5(4):387–399 (1992).

Spratt, "Resistance to antibiotics mediated by target alterations," *Science* 264:388–393 (1994).

Tanaka et al., "Antimicrobial activity of DV–7751a, a new fluoroquinolone," *Antimicrobial Agents and Chemotherapy* 37(10)2112–2118 (1993).

Vogelman et al., "In vivo postantibiotic effect in a thigh infection in neutropenic mice," *Journal of Infectious Diseases* 157(2):287–298 (1988).

Yanagisawa et al., "Angiotensin–converting enzyme inhibitors: Perhydro–1,4–thiazepin–5–one derivatives," *J. Med. Chem.* 30:1984–1991 (1987).

EFFLUX PUMP INHIBITORS

RELATED APPLICATION

This application claims the benefit of Chamberland et al., U.S. Provisional Application No. 60/087,514, filed Jun. 1, 1998, entitled EFFLUX PUMP INHIBITORS, which is hereby incorporated by reference in its entirety.

BACKGROUND

This invention relates to the field of antimicrobial agents and to methods for identification and characterization of potential antimicrobial agents. More particularly, this invention relates to antimicrobial agents for which the mode of action involves cellular efflux pumps and the regulation of efflux pumps.

The following background material is not admitted to be prior art to the pending claims, but is provided only to aid the understanding of the reader.

Antibiotics have been effective tools in the treatment of infectious diseases during the last half century. From the development of antibiotic therapy to the late 1980s there was almost complete control over bacterial infections in developed countries. The emergence of resistant bacteria, especially during the late 1980s and early 1990s, is changing this situation. The increase in antibiotic resistant strains has been particularly common in major hospitals and care centers. The consequences of the increase in resistant strains include higher morbidity and mortality, longer patient hospitalization, and an increase in treatment costs. (B. Murray, 1994, *New Engl. J. Med.* 330:1229–1230.)

The constant use of antibiotics in the hospital environment has selected bacterial populations that are resistant to many antibiotics. These populations include opportunistic pathogens that may not be strongly virulent but that are intrinsically resistant to a number of antibiotics. Such bacteria often infect debilitated or immunocompromised patients. The emerging resistant populations also include strains of bacterial species that are well known pathogens, which previously were susceptible to antibiotics. The newly acquired resistance is generally due to DNA mutations, or to resistance plasmids (R plasmids) or resistance-conferring transposons transferred from another organism. Infections by either type of bacterial population, naturally resistant opportunistic pathogens or antibiotic-resistant pathogenic bacteria, are difficult to treat with current antibiotics. New antibiotic molecules which can override the mechanisms of resistance are needed.

Bacteria have developed several different mechanisms to overcome the action of antibiotics. These mechanisms of resistance can be specific for a molecule or a family of antibiotics, or can be non-specific and be involved in resistance to unrelated antibiotics. Several mechanisms of resistance can exist in a single bacterial strain, and those mechanisms may act independently or they may act synergistically to overcome the action of an antibiotic or a combination of antibiotics. Specific mechanisms include degradation of the drug, inactivation of the drug by enzymatic modification, and alteration of the drug target (B. G. Spratt, *Science* 264:388 (1994)). There are, however, more general mechanisms of drug resistance, in which access of the antibiotic to the target is prevented or reduced by decreasing the transport of the antibiotic into the cell or by increasing the efflux of the drug from the cell to the outside medium. Both mechanisms can lower the concentration of drug at the target site and allow bacterial survival in the presence of one or more antibiotics which would otherwise inhibit or kill the bacterial cells. Some bacteria utilize both mechanisms, combining a low permeability of the cell wall (including membranes) with an active efflux of antibiotics. (H. Nikaido, *Science* 264:382–388 (1994)).

In some cases, antibiotic resistance due to low permeability is related to the structure of the bacterial membranes. In general, bacteria can be divided into two major groups based on the structure of the membranes surrounding the cytoplasm. Gram-positive (G+) bacteria have one membrane, a cytoplasmic membrane. In contrast, Gram-negative (G−) bacteria have two membranes, a cytoplasmic membrane and an outer membrane. These bacterial membranes are lipid bilayers which contain proteins and may be associated with other molecules. The permeability of bacterial membranes affects susceptibility/resistance to antibiotics because, while there are a few molecular targets of antibiotics, e.g., penicillin-binding proteins, that are accessible from the outer leaflet of the cytoplasmic membranes, the principal targets for antibiotics are in the cytoplasm or in the inner leaflet of the cytoplasmic membrane. Therefore for an antibiotic which has a target in the cytoplasmic membrane, in Gram-negative bacteria that antibiotic will first need to cross the outer membrane. For a target in the cytoplasm, an antibiotic will need to cross the cytoplasmic membrane in Gram-positive bacteria, and both the outer and cytoplasmic membranes in Gram-negative bacteria. For both membranes, an antibiotic may diffuse through the membrane, or may cross using a membrane transport system.

For Gram-negative bacteria, the lipid composition of the outer membrane constitutes a significant permeability barrier. The outer layer of this outer membrane contains a lipid, lipopolysaccharide (LPS), which is only found in the outer membrane of Gram-negative bacteria The lipid layer of the outer membrane is highly organized in a quasi-crystalline fashion and has a very low fluidity. Because of the low fluidity of the lipid layer of the outer membrane, even lipophilic antibiotics will not diffuse rapidly through the lipid layer. This has been shown experimentally, hydrophobic probe molecules have been shown to partition poorly into the hydrophobic portion of LPS and to permeate across the outer membrane bilayer at about one-fiftieth to one-hundredth the rate through the usual phospholipid bilayers (like the cytoplasmic membrane bilayer).

Some antibiotics may permeate through water-filled porin channels or through specific transport systems. Many of the porin channels, however, provide only narrow diameter channels which do not allow efficient difflusion of the larger antibiotic molecules. In addition, many porin channels are highly hydrophilic environments, and so do not efficiently allow the passage of hydrophobic molecules. Thus, the outer membrane acts as a molecular sieve for small molecules. This explains, in part, why Gram-negative bacteria are generally less susceptible to antibiotics than Gram-positive bacteria, and why Grain-negative bacteria are generally more resistant to large antibiotics, such as glycopeptides, that cannot cross the outer membrane.

The cytoplasmic membrane also provides a diffusion barrier for some antibiotics. However, since the fluidity of the lipid layer of the cytoplasmic membrane is higher than that of the outer membrane of Gram-negative bacteria, drugs that show some lipophilicity will be able to permeate through the lipid layer. Other drugs, such as phosphonomycin or D-cycloserine that have very low solubility in a lipophilic environment will cross the cytoplasmic membrane by using a transport system. In this case, though, if the transport system is not synthesized, the bacteria will become resistant to the drug (Peitz et al., 1967, *Biochem. J.* 6: 2561).

Decreasing the permeability of the outer membrane, by reducing either the number of porins or by reducing the number of a certain porin species, can decrease the susceptibility of a strain to a wide range of antibiotics due to the decreased rate of entry of the antibiotics into the cells. However, for most antibiotics, the half-equilibration times are sufficiently short that the antibiotic could exert its effect unless another mechanism is present. Efflux pumps are an example of such other mechanism. Once in the cytoplasm or periplasm a drug can be transported back to the outer medium. This transport is mediated by efflux pumps, which are constituted of proteins. Different pumps can efflux specifically a drug or group of drugs, such as the NorA system that transports quinolones, or Tet A that transports tetracyclines, or they can efflux a large variety of molecules, such as certain efflux pumps of *Pseudomonas aeruginosa*. In general, efflux pumps have a cytoplasmic component and energy is required to transport molecules out of the cell. Some efflux pumps have a second cytoplasmic membrane protein that extends into the periplasm. At least some efflux pumps of *P. aeruginosa* have a third protein located in the outer membrane.

Efflux pumps are involved in antibiotic resistance since, in some cases, they can remove a significant fraction of the antibiotic molecules which manage to enter the cells, thereby maintaining a very low intracellular antibiotic concentration. To illustrate, *P. aeruginosa* laboratory-derived mutant strain 799/61, which does not produce any measurable amounts of efflux pump is 8 to 10 fold more susceptible to tetracycline and ciprofloxacin than the parent strain *P. aeruginosa* 799, which synthesizes efflux pumps. Also, null mutants of mexA, the cytoplasmic component of a *P. aeruginosa* efflux pump, are more susceptible to antibiotics than the wild type.

The physiological role of efflux pumps has not been clearly defined yet. They are involved in drug resistance but they also are involved in the normal physiology of the bacterial cell. The efflux pump coded in the mexA operon of *P. aeruginosa* has been shown to be regulated by the iron content of the medium, and it is co-regulated with the synthesis of the receptors of siderophores. Siderophores are molecules that are needed for bacterial growth under iron starvation conditions, such as during infection of an animal. They are synthesized in the cytoplasm and exported when the bacterial cell needs iron. Siderophores scavenge iron within the infected animal and return the iron to the microbe to be used for essential microbial processes. Since there is essentially no free iron in the bodies of animals, including the human body, the production of siderophores by infecting bacteria is an important virulence factor for the progress of the infection.

Even organisms normally surrounded by a cell envelope of relatively high permeability can develop resistance by decreasing the permeability of the envelope. When an agent mainly diffuses across the barrier through a specific channel, mutational loss of the channel can be an efficient mechanism for resistance. A "nonclassical" beta-lactam compound, imipenem, shows an exceptional activity against *P. aeruginosa*, mainly because this agent diffuses though a specific channel, OprD, whose physiological function appears to be that of the transport of basic amino acids. However, *P. aeruginosa* could become resistant to imipenem by simply losing the oprD channel, and currently a large fraction of *P. aeruginosa* strains isolated from the hospital environment are resistant as a result of this modification. In a similar manner, beta-lactam compounds designed to mimic iron-chelating compounds (siderophores) during their transport through the outer membranes are known to select mutants that are defective in the specific transport of these siderophores.

In summary, the above discussion indicates that cellular factors affecting transport (both active and passive transport) of antibiotics into bacterial cells are important components of antibiotic resistance for many bacterial species.

SUMMARY

This invention concerns particular compounds which are efflux pump inhibitors, and which are therefore compounds which inhibit cellular efflux pumps of bacteria or other microbes. Such efflux pumps export substrate molecules from the cytoplasm in an energy-dependent manner, and the exported substrate molecules can include antibacterial agents. Such efflux pump inhibitors are useful, for example, for treating microbial infections by reducing the export of a co-administered antimicrobial agent or by preventing the export of a compound synthesized by microbes (e.g, bacteria) to allow or improve their growth. An example of reducing the export of such a compound is inhibiting iron availability for the microbe by reducing the export of siderophores. Thus, this invention also provides compositions which include such efflux pump inhibitors and methods for treating microbial infections using those compositions.

The general identification and use of efflux pump inhibitors is described in co-pending U.S. patent applications, Trias et al., EFFLUX PUMP INHIBITORS, application Ser. No. 08/427,088, filed Apr. 21, 1995; Trias et al., EFFLUX PUMP INHIBITORS, Appl. No. not yet assigned, filed Jul. 22, 1997; and Trias et al., PCT Application PCT/US96/05469, International Publication WO96/33285, which are hereby incorporated by reference in their entireties including drawings. Screening methods described therein were used to identity some of the efflux inhibitor compounds of the present invention, and additional compounds were synthesized and tested which were structurally related to the active compounds identified through screening.

The efflux pump inhibitors of the present invention have structures which are shown by the generic structure in Table 1 below:

TABLE 1

Generic Structure 1

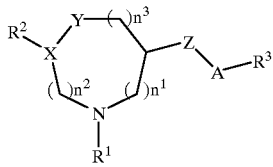

| | |
|---|---|
| $n^1$ | 0, 1 |
| $n^2$ | 0, 1, 2, 3 |
| $n^3$ | 0, 1, 2 |
| $n^1 + n^2 + n^3$ | 1, 2, 3, 4 |
| X | N; |
| | $CR^{2a}$; $R^{2a}$ = H, lower alkyl; |
| | $CR^{2b}$; $R^{2b}$ = OH, F |
| | (where $R^2$ does not begin with N, S or O) |
| Y | Single bond; |
| | $NR^{23}$; $R^{23}$ = H, lower alkyl; |
| | S, O |
| $R^1$ | H |

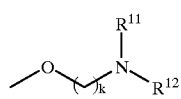

Q = CO, SO, $SO_2$
$R^{11}$ and/or $R^{12}$ = H, lower alkyl
k = 1, 2, 3, 4
—$(CH_2)_k$— may be substituted by lower alkyl, $NH_2$, NHR, OH, or may be replaced by an unsaturated chain

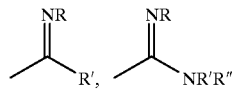

R, R', R" = H, lower alkyl $R^2$  Where X = N, same as $R^1$
Where X = CR,

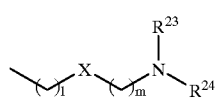

l, m = 0, 1, 2, 3;
X = O, S, SO, $SO_2$, single bond, double bond, triple bond, cyclopropyl;
—$(CH_2)_l$— and —$(CH_2)_m$— may be substituted by lower alkyl;
$R^{23}$ = H, lower alkyl, α- and β- aminoacyl;
$R^{24}$ = H, lower alkyl Z  Single bond

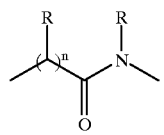

n = 0, 1, 2, 3;
R = independently H, lower alkyl, arylalkyl

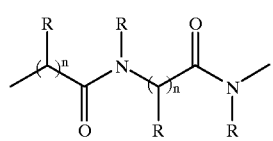

n = 0, 1, 2, 3;
R = independently H, lower alkyl, arylalkyl

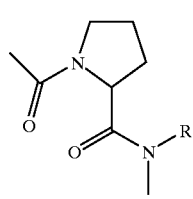

R = independently H, lower alkyl, arylalkyl

TABLE 1-continued

Generic Structure 1

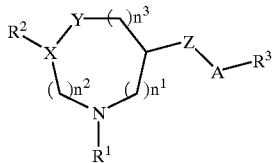

| | | |
|---|---|---|
| | 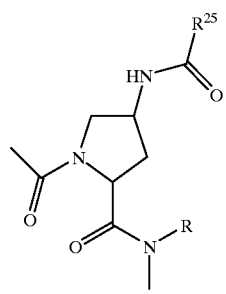 | R = independently H, lower alkyl, arylalkyl;<br>$R^{25}$ = arylalkyl, where the alkyl chain may be substituted by OH, F |
| | 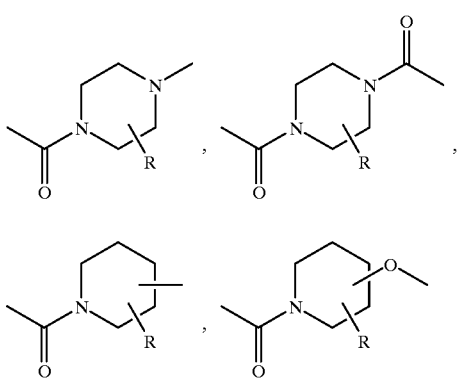 | R = independently H, lower alkyl, arylalkyl |
| Z | 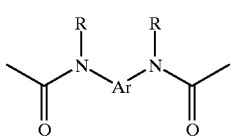 | R = independently H, lower alkyl;<br>Ar = aryl |
| | 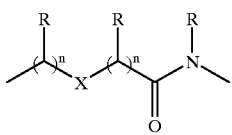 | n = independently 0, 1, 2;<br>X = O, S;<br>R = independently H, lower alkyl |
| | 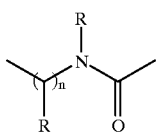 | n = 0, 1, 2, 3;<br>R = independently H, lower alkyl |
| | 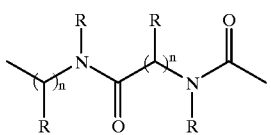 | n = independently 0, 1, 2, 3;<br>R = independently H, lower alkyl |
| A | Single bond | |

TABLE 1-continued

Generic Structure 1

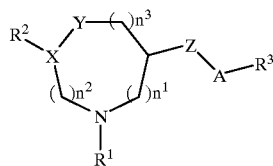

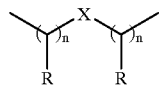

| | |
|---|---|
| | n = independently 0, 1, 2, 3; |
| | X = O, S, single bond, double bond, triple bond, cycloalkane, heterocycloalkane |
| | R = independently H, lower alkyl |
| R³    H | |
| Optionally substituted aryl, tetrahydronaphthyl, indanyl, thienyl, furyl, pyridyl, quinolyl, isoquinolyl, quinazolyl, benzimidazolyl, benzothiazolyl, benzoxazolyl | Substituents = one or more lower alkyl or alkenyl, halogeno, fluoroalkyl, hydroxy, alkyloxy, alkylthio, mercapto, amino, monosubstituted amino, disubstituted amino |
| Optionally substituted cycloalkyl | Ring size 3–6<br>Substituents = one or more lower alkyl or alkenyl, halogeno, fluoroalkyl, hydroxy, alkyloxy, alkylthio, mercapto, amino, monosubstituted amino, disubstituted amino |

Where there are centers of asymmetry, the absolute stereochemistry can be either R or S-configuration and any combination of configuration. Even racemic materials fulfill the structural generics descriptions.

In the generic descriptions of compounds of this invention, the number of atoms of a particular type in a substituent group is generally given as a range. For example, an alkyl group containing from 1 to 4 carbon atoms is indicated as alkyl ($C_1$–$C_4$), or as ($C_{1-4}$) alkyl. Such a range reference is intended to include specific references to groups having each of the number of atoms within the specified range including the endpoints. Other numbers of atoms and other types of atoms are indicated in a similar manner. For example, $C_{1-4}$ includes each of $C_1$, $C_2$, $C_3$, and $C_4$ individually and any subgroup of the range.

Unless otherwise indicated, the term "alkyl" refers to a branched or unbranched aliphatic hydrocarbon group, preferably having from 1 to 6 carbon atoms, and more preferably 1 to 4 carbon atoms. Preferably the hydrocarbon group is saturated. The alkyl group may optionally be substituted, and some preferred substituents include alkoxy, alkylthio, halogen, amino, monosubstituted amino, disubstituted amino, and carboxy groups.

The term "lower alkyl" refers to an aliphatic hydrocarbon having 1 to 6 carbons, and preferably 1 to 4 carbon atoms. The lower alkyl group may optionally be substituted; preferred substituents include alkoxy, alkylthio, halogen, amino, monosubstituted amino, disubstituted amino, and carboxy.

The term "branched alkyl" refers to a branched aliphatic hydrocarbon. The branched alkyl group is preferably 3 to 10 carbons, and most preferably 3 to 6 carbons. The branched alkyl group may optionally be substituted and some preferred substituents include alkoxy, alkylthio, halogen, amino, monosubstituted amino, disubstituted amino, and carboxy.

The term "haloalkyl" refers to a lower alkyl group which is substituted with a halogen. Thus, the term "fluoroalkyl" refers to a lower alkyl group which is substituted with a fluorine. The term "perfluoroalkyl" refers to a lower alkyl group which is substituted with a fluorine atom in every available position except for where the lower alkyl group is attached to the main chain.

The term "carboxyalkyl" refers to a chemical moiety with formula —$(R)_n$—COOH, where R is an alkyl moiety, preferably a saturated alkyl, and where n is 0–5.

The term "hydroxyalkyl" refers to a chemical moiety with the formula —$(R)_n$—OH, where R is an alkyl moiety and where n is 1–4.

The term "alkoxy" or "alkyloxy" refers to a chemical substituent of formula —OR, where R is a saturated or unsaturated lower alkyl moiety.

The term "alkylthio" refers to a chemical substituent of formula —SR, where R is hydrogen or a saturated or unsaturated lower alkyl moiety.

The term "aryl" refers to an aromatic group which has at least one ring having a conjugated π electron system and includes both carbocyclic aryl (e.g., phenyl) and heterocyclic aryl groups (e.g. pyridine). The aryl group is preferably 6 to 14 carbons, more preferably 6 to 10 carbons. Aryl moieties include monocyclic, bicyclic, and tricyclic rings, where each ring has preferably five or six members. The aryl moiety may be optionally monosubstituted or disubstituted independently with lower alkyl or alkenyl, hydroxyl, alkoxy, alkylthio, halogen, haloalkyl, mercapto, amino, monosubstituted amino, and disubstituted amino.

The term "carbocyclic" refers to a compound or group which contains one or more covalently closed ring structures, and that the atoms forming the backbone of the ring are all carbon atoms. The term thus distinguishes carbocyclic from heterocyclic rings in which the ring backbone contains at least one non-carbon atom. A "cycloalkane" or "cyclic alkane" or "cycloalkyl" is a carbocyclic group in which the ring is an optionally substituted cyclic aliphatic hydrocarbon, i.e., a cyclic alkyl group preferably with 3, 4, 5, or 6 ring carbons. Thus, a "cyclopropyl" group has 3 ring carbon atoms.

A "heterocycloalkane" or "heterocycloalkyl" refers to a heterocyclic group in which the carbon atom portion of the ring or rings is optionally substituted alkyl, preferably lower alkyl.

Thus, the term "azaheterocycle" refers to a heterocyclic group which includes at least one nitrogen atom in a ring. Preferably the azaheterocyclic group is a N-morpholinyl, N-piperazinyl, N-pyrrolidinyl, N-imidazolyl, N-pyrrolyl, N-pyrazolyl, N-triazolyl, and N-tetrazolyl group. The azaheterocyclic group may also be substituted as recognized in the art, forming a substituted azaheterocycle, preferably a 2-(or 3-) lower alkylmorpholinyl, 2-(3- or 4-) lower alkylpiperazinyl, 2-(or 3-) lower alkylpyrrolidinyl, 2-(or 3-) lower alkylmorpholinyl, 2-(or 3-) lower alkylpyrrolyl group.

"Halogen" or "halo" refers to F, Br, Cl, or I, but is preferably F or Br, and more preferably is F.

"Hydroxyl" or "hydroxy" refers to the group —OH.

The term "amino" means the group NRR', where R and R' may independently be alkyl or hydrogen or hydroxyl, but preferably are hydrogen. The term "monosubstituted amino" refers to an amino group in which one of R or R' is alkyl. The term "disubstituted amino" refers to an amino group in which R and R' are each independently alkyl or hydroxyl.

The term "thienyl" refers to a group which has the core ring structure of Structure A below. The thienyl group may be attached to the rest of the molecule through position 2 or 3 on the ring and may be optionally independently substituted with one or more lower alkyl or alkenyl, hydroxy, alkoxy, alkylthio, mercapto, halogen, haloalkyl, amino, monosubstituted amino, or disubstituted amino (substituents as indicated for group $R^3$ in Table 1).

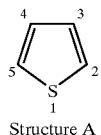

Structure A

The term "furyl" refers to a group which has the core ring structure of Structure B. The furyl group may be attached to the rest of the molecule through position 2 or 3 on the ring and may be optionally independently substituted with one or more lower alkyl or alkenyl, hydroxy, alkoxy, alkylthio, mercapto, halogen, haloalkyl, amino, monosubstituted amino, or disubstituted amino (substituents as indicated for group $R^3$ in Table 1).

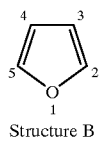

Structure B

The term "pyridyl" refers to a group which has the core ring structure of Structure C. The pyridyl group may be attached to the rest of the molecule through position 2, 3, or 4 on the ring and may be optionally substituted independently with lower alkyl, or alkenyl, hydroxy, alkoxy, alkylthio, mercapto, halogen, haloalkyl, amino, monosubstituted amino, or disubstituted amino (substituents as indicated for group $R^3$ in Table 1).

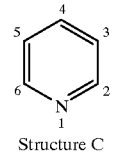

Structure C

The term "quinolyl" refers to a group having the core ring structure below. The quinolyl group may be attached to the rest of the molecule through positions 2,3,4,5,6,7, or 8. The group may optionally be independently substituted by one or more groups as indicated for the thienyl group above and in Table 1 for the group $R^3$.

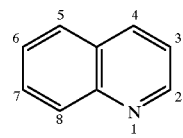

The term "isoquinolyl" refers to a group with core ring structure shown below. The isoquinolyl group may be attached to the rest of the molecule through positions 1,3,4,5,6,7, or 8. The group may optionally be substituted independently by one or more groups as indicated for the thienyl group above and in Table 1 for the group $R^3$.

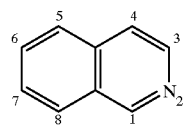

The term "quinazolyl" refers to a group which has the core ring structure below.

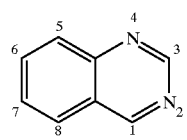

The group may be attached to the rest of the molecule through positions 1,3,5,6,7, or 8. The group may optionally be substituted independently by one or more groups as indicated for the thienyl group above and in Table 1 for the group $R^3$.

"Mercapto" or "thiol" refers to the group —SH.

The term "tetrahydronaphthyl" refers to a group which has a core ring structure of a phenyl ring fused to a cyclohexyl ring, as shown in the structure below, where the attachment to the rest of the molecule can be on either the phenyl ring or on the cyclohexyl ring. The group may optionally be substituted independently as indicated in Table 1 for the group $R^3$.

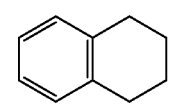

The term "indanyl" refers to a group which has the core bicyclic ring structure below.

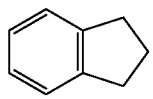

which may optionally be independently substituted as indicated in Table 1 for the group $R^3$. The group may be attached to the rest of the molecule through either the phenyl ring or through the 5-membered ring.

The term "arylalkyl" refers to a lower alkyl group substituted with an aryl group. An example of an arylalkyl group is benzyl where a methyl group is substituted with phenyl. The lower alkyl group may be optionally substituted with a lower alkyl, alkoxy, allylthio, halogen, amino, monosubstituted amino, or disubstituted amino. The arylalkyl group may be aryl-substituted where the aryl group is optionally substituted with a lower alkyl, alkoxy, alkylthio, halogen, amino, monosubstituted amino, or disubstituted amino.

The term "thienylalkyl" refers to a lower alkyl group substituted with a thienyl group. The lower alkyl group may be optionally substituted with a lower alkyl, alkoxy, alkylthio, halogen, amino, monosubstituted amino, or disubstituted amino. The thienylalkyl group may be thienyl-substituted where the thienyl group is optionally substituted with a lower alkyl, alkoxy, alkylthio, halogen, amino, monosubstituted amino, or disubstituted amino.

The term "furylalkyl" refers to a lower alkyl group substituted with a furyl group. The lower alkyl group may be optionally substituted with a lower alkyl, alkoxy, alkylthio, halogen, amino, monosubstituted amino, or disubstituted amino. The furylalkyl group may be furyl-substituted where the furyl group is optionally substituted with a lower alkyl, alkoxy, alkylthio, halogen, amino, monosubstituted amino, or disubstituted amino.

The term "pyridylalkyl" refers to a lower alkyl group substituted with a pyridyl group. The lower alkyl group may be optionally substituted with a lower alkyl, alkoxy, alkylthio, halogen, amino, monosubstituted amino, or disubstituted amino. The pyridylalkyl group may be pyridyl-substituted where the pyridyl group is optionally substituted with a lower alkyl, alkoxy, alkylthio, halogen, amino, monosubstituted amino, or disubstituted amino.

The term "benzothienylalkyl" refers to a lower alkyl group substituted with a benzothienyl group. The lower alkyl group may be optionally substituted with a lower alkyl, alkoxy, alkylthio, halogen, amino, monosubstituted amino, or disubstituted amino. The benzothienylalkyl group may be benzothienyl-substituted where the benzothienyl group is optionally substituted with a lower alkyl, alkoxy, alkylthio, halogen, amino, monosubstituted amino, or disubstituted amino.

The term "indolyalkyl" refers to a lower alkyl group substituted with an indole group. The lower allyl group may be optionally substituted with a lower alkyl, alkoxy, alkylthio, halogen, amino, monosubstituted amino, or disubstituted amino. The indolyalkyl group may be indole-substituted where the indole group is optionally substituted with a lower alkyl, alkoxy, alkylthio, halogen, amino, monosubstituted amino, or disubstituted amino.

The term "quinolinylalkyl" refers to a lower alkyl group substituted with an quinolinyl group. The lower alkyl group may be optionally substituted with a lower alkyl, alkoxy, alkylthio, halogen, amino, monosubstituted amino, or disubstituted amino. The quinolinylalkyl group may be quinolinyl-substituted where the quinolinyl group is optionally substituted with a lower alkyl, alkoxy, alkylthio, halogen, amino, monosubstituted amino, or disubstituted amino.

The term "isoquinolinylalkyl" refers to a lower alkyl group substituted with an isoquinolinyl group. The lower alkyl group may be optionally substituted with a lower alkyl, alkoxy, alkylthio, halogen, amino, monosubstituted amino, or disubstituted amino. The isoquinolinylalkyl group may be isoquinolinyl-substituted where the quinolinyl group is optionally substituted with a lower alkyl, alkoxy, alkylthio, halogen, amino, monosubstituted amino, or disubstituted amino.

The term "quinoxalinylalkyl" refers to a lower alkyl group substituted with an quinoxalinyl group. The lower alkyl group may be optionally substituted with a lower alkyl, alkoxy, alkylthio, halogen, amino, monosubstituted amino, or disubstituted amino. The quinoxalinylalkyl group may be quinoxalinyl-substituted where the quinolinyl group is optionally substituted with a lower allyl, alkoxy, alkylthio, halogen, amino, monosubstituted amino, or disubstituted amino.

The term "quinazolinylalkyl" refers to a lower alkyl group substituted with an quinazolinyl group. The lower alkyl group may be optionally substituted with a lower alkyl, alkoxy, alkylthio, halogen, amino, monosubstituted amino, or disubstituted amino. The quinazolinylalkyl group may be quinazolinyl-substituted where the quinazolinyl group is optionally substituted with a lower alkyl, alkoxy, alkylthio, halogen, amino, monosubstituted amino, or disubstituted amino.

The term "benzimidazolylalkyl" refers to a lower alkyl group substituted with an benzimidazolyl group. The lower alkyl group may be optionally substituted with a lower alkyl, alkoxy, alkylthio, halogen, amino, monosubstituted amino, or disubstituted amino. The benzimidazolylalkyl group may be benzimidazolyl-substituted where the quinazolinyl group is optionally substituted with a lower alkyl, alkoxy, alkylthio, halogen, amino, monosubstituted amino, or disubstituted amino.

The term "benzothiazolylalkyl" refers to a lower alkyl group substituted with an benzothiazolyl group. The lower alkyl group may be optionally substituted with a lower alkyl, alkoxy, allylthio, halogen, amino, monosubstituted amino, or disubstituted amino. The benzothiazolylalkyl group may be benzothiazolyl-substituted where the quinazolinyl group is optionally substituted with a lower alkyl, alkoxy, alkylthio, halogen, amino, monosubstituted amino, or disubstituted amino.

The term "benzoxazolylalkyl" refers to a lower alkyl group substituted with an benzoxazolyl group. The lower alkyl group may be optionally substituted with a lower alkyl, alkoxy, alkylthio, halogen, amino, monosubstituted amino, or disubstituted amino. The benzoxazolylalkyl group may be benzoxazolyl-substituted where the benzoxazolyl group is optionally substituted with a lower alkyl, alkoxy, alkylthio, halogen, amino, monosubstituted amino, or disubstituted amino.

The term "benzofuranyl" refers to a group which has the core ring structure of Structure A. The benzofuranyl group may be optionally substituted with lower alkyl, alkoxy, alkylthio, halogen, amino, monosubstituted amino, or disubstituted amino.

The term "benzothienyl" refers to a group which has the core ring structure of Structure B. The benzothienyl group may be optionally substituted with lower alkyl, alkoxy, alkylthio, halogen, amino, monosubstituted amino, or disubstituted amino.

The term "indolyl" refers to a group which has the core ring structure of Structure C. The indolyl group may be optionally substituted with lower alkyl, alkoxy, alkylthio, halogen, amino, monosubstituted amino, or disubstituted amino.

The term "benzimidazolyl" refers to a group which has the core ring structure of Structure D. The benzimidazolyl group may be optionally substituted with lower alkyl, alkoxy, alkylthio, halogen, amino, monosubstituted amino, or disubstituted amino.

The term "benzothiazolyl" refers to a group which has the core ring structure of Structure F. The benzothiazolyl group may be optionally substituted with lower alkyl, alkoxy, alkylthio, halogen, amino, monosubstituted amino, or disubstituted amino.

The term "benzoxazolyl" refers to a group which has the core ring structure of Structure E. The benzoxazolyl group may be optionally substituted with lower alkyl, alkoxy, alkylthio, halogen, amino, monosubstituted amino, or disubstituted amino.

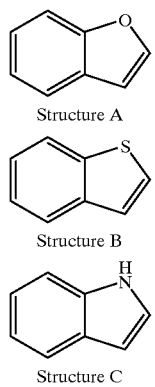

Structure A

Structure B

Structure C

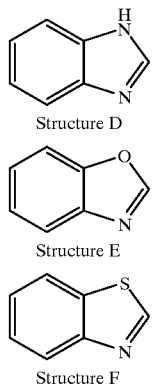

Structure D

Structure E

Structure F

The term "α-amino acyl" refers to a group $RCH(NR^1R^2)C(O)—$ where $NR^1R^2$ is an optionally substituted amino group and R is H or a saturated or unsaturated hydrocarbon, preferably of 1–6, more preferably 1–4 carbon atoms. The term "β-amino acyl" refers to a group $R—CH(NR^1R^2)CH_2C(O)—$, where the components are as just described.

The term "(alpha-aminoacyl)amido" refers to a group having an amide linkage and which is alpha-amino substituted. Preferably the group is an amide-linked alpha-amino acid, which may optionally be substituted, for example, glycylamido, D-alanylamido, D-aspartylamido, D-glutamylamido, D-leucylamido, D-phenylalanylamido, D-phenylglycylamido, D-tyrosylamido.

The term "aminoalkyl" refers to an amino substituted lower alkyl group, preferably $(CH_2)_nR^bR^c$ where n=1–4; $R^b$ and/or $R^c$ is H, lower alkyl, aryl.

In preferred embodiments, certain efflux pump inhibitors of the present invention have structures which are shown by the generic structure in Table 2 below:

TABLE 2

Preferred Embodiment 1

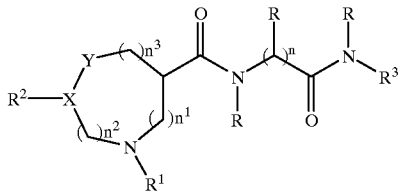

| | |
|---|---|
| n | 1, 2 |
| $n^1$ | 0, 1 |
| $n^2$ | 0, 1, 2, 3 |
| $n^3$ | 0, 1, 2 |
| $n^1 + n^2 + n^3$ | 1, 2, 3, 4 |
| X | N; |
| | $CR^{2a}$; $R^{2a}$ = H, lower alkyl; |
| | $CR^{2b}$; $R^{2b}$ = OH, F |
| | (where $R^2$ does not begin with N, S or O) |
| Y | Single bond; |
| | $NR^{23}$; $R^{23}$ = H, lower alkyl; |
| | S, O |
| $R^1$ | H |

TABLE 2-continued

Preferred Embodiment 1

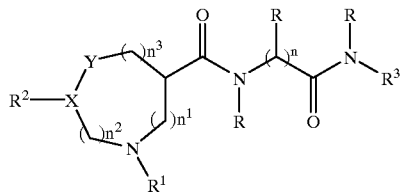

| | | |
|---|---|---|
| | 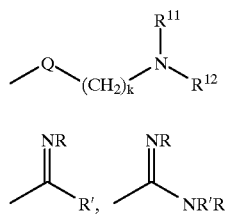 | Q = CO, SO, SO$_2$<br>R$^{11}$ and/or R$^{12}$ = H, lower alkyl<br>k = 1, 2, 3, 4<br>—(CH$_2$)$_k$— may be substituted by lower alkyl, NH$_2$, NHR, OH, or may be replaced by an unsaturated chain |
| | 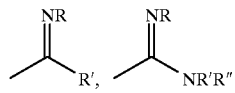 | R, R', R" = H, lower alkyl |
| R$^2$ | Where X = N, same as R$^1$<br>Where X = CR, | |
| | 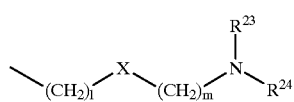 | l, m = 0, 1, 2, 3;<br>X = O, S, SO, SO$_2$, single bond, double bond, triple bond, cyclopropyl;<br>—(CH$_2$)$_l$— and —(CH$_2$)$_m$— may be substituted by lower alkyl;<br>R$^{23}$ = H, lower alkyl, α- and β- aminoacyl;<br>R$^{24}$ = H, lower alkyl |
| R | independently H, lower alkyl, arylalkyl | |
| R$^3$ | Optionally substituted aryl, tetrahydronaphthyl, indanyl, thienyl, furyl, pyridyl, quinolyl, isoquinolyl, quinazolyl, benzimidazolyl, benzothiazolyl, benzoxazolyl | Substituents = one or more lower alkyl or alkenyl, halogeno, fluoroalkyl, hydroxy, alkyloxy, alkylthio, mercapto, amino, monosubstituted amino, disubstituted amino |
| | Optionally substituted cycloalkyl | Ring size 3–6<br>Substituents = one or more lower alkyl or alkenyl, halogeno, fluoroalkyl, hydroxy, alkyloxy, alkylthio, mercapto, amino, monosubstituted amino, disubstituted amino |

Where there are centers of asymmetry, the absolute stereochemistry can be either R or S-configuration and any combination of configuration; even racemic materials fulfill the structural generics description.

In preferred embodiments, certain efflux pump inhibitors of the present invention have structures which are shown by the generic structure in Table 3 below:

TABLE 3

Preferred Embodiment 2

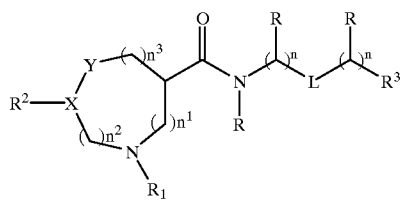

| | |
|---|---|
| n | 1, 2 |
| n$^1$ | 0, 1 |
| n$^2$ | 0, 1, 2, 3 |
| n$^3$ | 0, 1, 2 |
| n$^1$ + n$^2$ + n$^3$ | 1, 2, 3, 4 |
| X | N; |
| | CR$^{2a}$; R$^{2a}$ = H, lower alkyl; |

TABLE 3-continued

Preferred Embodiment 2

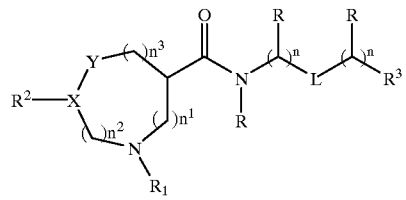

| | | |
|---|---|---|
| Y | $CR^{2b}$; $R^{2b}$ = OH, F (where $R^2$ does not begin with N, S or O) Single bond; $NR^{23}$; $R^{23}$ = H, lower alkyl; S, O | |
| $R^1$ | H | |
| | [structure: O-(CH$_2$)$_k$-N(R$^{11}$)(R$^{12}$)] | Q = CO, SO, SO$_2$ $R^{11}$ and/or $R^{12}$ = H, lower alkyl k = 1, 2, 3, 4 —(CH$_2$)$_k$— may be substituted by lower alkyl, NH$_2$, NHR, OH, or may be replaced by an unsaturated chain |
| | [structures: NR=C(CH$_3$)R', NR=C(CH$_3$)NR'R''] | R, R', R" = H, lower alkyl |
| $R^2$ | Where X = N, same as $R^1$ Where X = CR, | |
| | [structure: (CH$_2$)$_l$-X-(CH$_2$)$_m$-N(R$^{23}$)(R$^{24}$)] | l, m = 0, 1, 2, 3; X = O, S, SO, SO$_2$, single bond, double bond, triple bond, cyclopropyl; —(CH$_2$)$_l$— and —(CH$_2$)$_m$— may be substituted by lower alkyl; $R^{23}$ = H, lower alkyl, α- and β- aminoacyl; $R^{24}$ = H, lower alkyl |
| L | O, S, NR, single bond, double bond | |
| R | | |
| $R^3$ | independently H, lower alkyl, arylalkyl Optionally substituted aryl, tetrahydronaphthyl, indanyl, thienyl, furyl, pyridyl, quinolyl, isoquinolyl, quinazolyl, benzimidazolyl, benzothiazolyl, benzoxazolyl | Substituents = one or more lower alkyl or alkenyl, halogeno, fluoroalkyl, hydroxy, alkyloxy, alkylthio, mercapto, amino, monosubstituted amino, disubstituted amino |
| | Optionally substituted cycloalkyl | Ring size 3–6 Substituents = one or more lower alkyl or alkenyl, halogeno, fluoroalkyl, hydroxy, alkyloxy, alkylthio, mercapto, amino, monosubstituted amino, disubstituted amino |

Where there are centers of asymmetry, the absolute stereochemistry can be either R or S-configuration and any combination of configuration; even racemic materials fulfill the structural generics description.

In preferred embodiments, certain efflux pump inhibitors of the present invention also have structures which are shown by the generic structure in Table 4 below:

TABLE 4

Preferred Embodiment 3

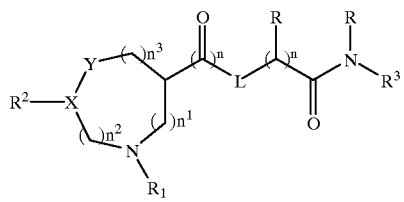

| | |
|---|---|
| n | 1, 2 |
| $n^1$ | 0, 1 |
| $n^2$ | 0, 1, 2, 3 |
| $n^3$ | 0, 1, 2 |
| $n^1 + n^2 + n^3$ | 1, 2, 3, 4 |
| X | N; <br> $CR^{2a}$; $R^{2a}$ = H, lower alkyl; <br> $CR^{2b}$; $R^{2b}$ = OH, F <br> (where $R^2$ does not begin with N, S or O) |
| Y | Single bond; <br> $NR^{23}$; $R^{23}$ = H, lower alkyl; <br> S, O |
| $R^1$ | H |

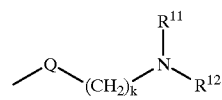

Q = CO, SO, $SO_2$
$R^{11}$ and/or $R^{12}$ = H, lower alkyl
k = 1, 2, 3, 4
—$(CH_2)_k$— may be substituted by lower alkyl, $NH_2$, NHR, OH, or may be replaced by an unsaturated chain

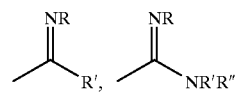

R, R', R" = H, lower alkyl $R^2$     Where X = N, same as $R^1$
Where X = CR,

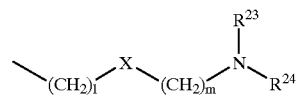

l, m = 0, 1, 2, 3;
X = O, S, SO, $SO_2$, single bond, double bond, triple bond, cyclopropyl;
—$(CH_2)_l$— and —$(CH_2)_m$— may be substituted by lower alkyl;
$R^{23}$ = H, lower alkyl, α- and β- aminoacyl;
$R^{24}$ = H, lower alkyl

L

R       O, S, NR, single bond, double bond $R^3$    independently H, lower alkyl,
Optionally substituted aryl,         Substituents = one or more lower alkyl or alkenyl,
tetrahydronaphthyl, indanyl, thienyl, halogeno, fluoroalkyl, hydroxy, alkyloxy, alkylthio, mercapto,
furyl, pyridyl, quinolyl, isoquinolyl,  amino, monosubstituted amino, disubstituted amino
quinazolyl, benzimidazolyl,
benzothiazolyl, benzoxazolyl
Optionally substituted cycloalkyl     Ring size 3–6
                                      Substituents = one or more lower alkyl or alkenyl,
                                      halogeno, fluoroalkyl, hydroxy, alkyloxy, alkylthio, mercapto,
                                      amino, monosubstituted amino, disubstituted amino Where there are centers of asymmetry, the absolute stereochemistry can be either R or S-configuration and any combination of configuration; even racemic materials fulfill the structural generics description.

In preferred embodiments, certain efflux pump inhibitors of the present invention also have structures which are shown by the generic structure in Table 5 below:

TABLE 5

Preferred Embodiment 4

| | | |
|---|---|---|
| n | 1, 2 | |
| $n^1$ | 0, 1 | |
| $n^2$ | 0, 1, 2, 3 | |
| $n^3$ | 0, 1, 2 | |
| $n^1 + n^2 + n^3$ | 1,2,3,4 | |
| X | N; $CR^{2a}$; $R^{2a}$ = H, lower alkyl; $CR^{2b}$; $R^{2b}$ = OH, F (where $R^2$ does not begin with N, S or O) | |
| Y | Single bond; $NR^{23}$; $R^{23}$ = H, lower alkyl; S, O | |
| $R^1$ | H | |
| | [structure: –O–Q–(CH₂)ₖ–N(R¹¹)(R¹²)] | Q = CO, SO, SO₂; $R^{11}$ and/or $R^{12}$ = H, lower alkyl; k = 1, 2, 3, 4; —(CH₂)ₖ— may be substituted by lower alkyl, NH₂, NHR, OH, or may be replaced by an unsaturated chain |
| | [structures: C(=NR)R′ and C(=NR)NR′R″] | R, R′, R″ = H, lower alkyl |
| $R^2$ | Where X = N, same as $R^1$ | |
| | Where X = CR, | |
| | [structure: —(CH₂)ₗ—X—(CH₂)ₘ—N(R²³)(R²⁴)] | l, m = 0, 1, 2, 3; X = O, S, SO, SO₂, single bond, double bond, triple bond, cyclopropyl; —(CH₂)ₗ— and —(CH₂)ₘ— may be substituted by lower alkyl; $R^{23}$ = H, lower alkyl, α- and β-aminoacyl; $R^{24}$ = H, lower alkyl |
| R | independently H, lower alkyl, arylalkyl | |
| $R^3$ | Optionally substituted aryl, tetrahydronaphthyl, indanyl, thienyl, furyl, pyridyl, quinolyl, isoquinolyl, quinazolyl, benzimidazolyl, benzothiazolyl, benzoxazolyl | Substituents = one or more lower alkyl or alkenyl, halogeno, fluoroalkyl, hydroxy, alkyloxy, alkylthio, mercapto, amino, monosubstituted amino, disubstituted amino |
| | Optionally substituted cycloalkyl | Ring size 3–6 Substituents = one or more lower alkyl or alkenyl, halogeno, fluoroalkyl, hydroxy, alkyloxy, alkylthio, mercapto, amino, monosubstituted amino, disubstituted amino |

Where there are centers of asymmetry, the absolute stereochemistry can be either R or S-configuration and any combination of configuration; even racemic materials fulfill the structural generics description.

In preferred embodiments, certain efflux pump inhibitors of the present invention also have structures which are shown by the generic structure in Table 6 below:

TABLE 6

Preferred Embodiment 5

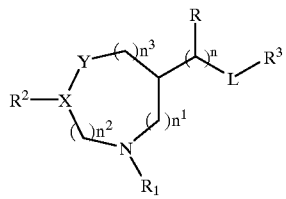

| | | |
|---|---|---|
| n | 1, 2 | |
| $n^1$ | 0, 1 | |
| $n^2$ | 0, 1, 2, 3 | |
| $n^3$ | 0, 1, 2 | |
| $n^1 + n^2 + n^3$ | 1, 2, 3, 4 | |
| X | N; $CR^{2a}$; $R^{2a}$ = H, lower alkyl; $CR^{2b}$; $R^{2b}$ = OH, F (where $R^2$ does not begin with N, S or O) | |
| Y | Single bond; $NR^{23}$; $R^{23}$ = H, lower alkyl; S, O | |
| $R^1$ | H | |
| | —Q—(CH$_2$)$_k$—N(R$^{11}$)R$^{12}$ | Q = CO, SO, SO$_2$<br>$R^{11}$ and/or $R^{12}$ = H, lower alkyl<br>k = 1, 2, 3, 4<br>—(CH$_2$)$_k$— may be substituted by lower alkyl, NH$_2$, NHR, OH, or may be replaced by an unsaturated chain |
| | =N—R with R', and =N— with NR'R'' | R, R', R'' = H, lower alkyl |
| $R^2$ | Where X = N, same as $R^1$<br>Where X = CR, | |
| | —(CH$_2$)$_l$—X—(CH$_2$)$_m$—N(R$^{23}$)R$^{24}$ | 1, m = 0, 1, 2, 3;<br>X = O, S, SO, SO$_2$, single bond, double bond, triple bond, cyclopropyl;<br>—(CH$_2$)$_l$— and —(CH$_2$)$_m$— may be substituted by lower alkyl; $R^{23}$ = H, lower alkyl, α- and β-aminoacyl; $R^{24}$ = H, lower alkyl |
| L | O, S, NR, single bond, double bond | |
| R | independently H, lower alkyl, arylalkyl | |
| $R^3$ | Substituted aryl, tetrahydronaphthyl, indanyl, thienyl, furyl, pyridyl, quinolyl, isoquinolyl, quinazolyl, benzimidazolyl, benzothiazolyl, benzoxazolyl | Substituents = one or more lower alkyl or alkenyl, halogeno, fluoroalkyl, hydroxy, alkyloxy, alkylthio, mercapto, amino, monosubstituted amino, disubstituted amino |
| | Substituted cycloalkyl | Ring size 3–6<br>Substituents = one or more lower alkyl or alkenyl, halogeno, fluoroalkyl, hydroxy, alkyloxy, alkylthio, mercapto, amino, monosubstituted amino, disubstituted amino |

Where there are centers of asymmetry, the absolute stereochemistry can be either R or S-configuration and any combination of configuration; even racemic materials fulfill the structural generics description.

The generic compound descriptions above should be understood to specifically include additional narrower generic descriptions in which the possible substituents for one or more of the specified substituent groups or substitutions is limited to a subset of the listed groups.

In the claims, the substituents and moieties for the compounds described by sub-generic structures 2, 3, 4, 5, and 6 are as described for Structure 1 unless specified differently.

Compounds within the generic description above can be obtained by synthetic chemistry methods known to those skilled in the chemical arts as exemplified in the Examples below. Specific compound examples within the generic description are provided in the Detailed Description below.

A particularly appropriate example of a microbe appropriate for the use of an efflux pump inhibitor is a pathogenic bacterial species, *Pseudomonas aeruginosa*, which is intrinsically resistant to many of the commonly used antibacterial agents. Exposing this bacterium to an efflux pump inhibitor can significantly slow the export of an antibacterial agent from the interior of the cell or the export of siderophores. Therefore, if another antibacterial agent is administered in conjunction with the efflux pump inhibitor, the antibacterial agent, which would otherwise be maintained at a very low intracellular concentration by the export process, can accumulate to a concentration which will inhibit the growth of the bacterial cells. This growth inhibition can be due to either bacteriostatic or bactericidal activity, depending on the specific antibacterial agent used. While *P. aeruginosa* is an example of an appropriate bacterium, other bacterial and microbial species may contain similar broad substrate pumps, which actively export a variety of antimicrobial agents, and thus can also be appropriate targets.

In addition as suggested above, for some microbial, e.g., bacterial, species, efflux pump inhibitors can decrease the virulence of the microbe, for example, by inhibiting the transport of factors important for pathogenicity. Again using *P. aeruginosa* as an example, inhibition of an efflux pump in this bacterium inhibits the uptake of iron, which is important for pathogenicity. The mechanism of bacterial iron transport involves molecules called siderophores, which are synthesized and exported by bacterial cells via efflux pumps. These siderophores bind tightly to iron scavenged from the host, and are then taken up by the bacteria. In this way, the iron needed for bacterial metabolism is obtained, and an infection can be maintained.

Therefore, illustrating the utility of efflux pump inhibitors, inhibiting the efflux pump of *P. aeruginosa* allows obtaining one or more of the following biological effects:

1. *P. aeruginosa* strains will become susceptible to antibiotics that could not be used for treatment of pseudomonad infections, or become more susceptible to antibiotics which do inhibit pseudomonal growth.

2. *P. aeruginosa* strains will become more susceptible to antibiotics currently used for treatment of pseudomonad infections.

3. Virulence of *P. aeruginosa* will be attenuated because the availability of iron will be hampered.

4. The inhibition of the pump or of one of the components of the pump may be lethal or prevent growth.

Obtaining even one of these effects provides a potential therapeutic treatment for infections by this bacterium. Also, as previously mentioned, similar pumps are found in other microorganisms. Some or all of the above effects can also be obtained with those microbes, and they are therefore also appropriate targets for detecting or using efflux pump inhibitors. Thus, the term "microbes" include, for example, bacteria, fuingi, yeasts, and protozoa.

As indicated, the bacterium to be inhibited through the use of an efflux pump inhibitor can be from other bacterial groups or species, such as one of the following: *Pseudomonas aeruginosa, Pseudomonas fluorescens, Pseudomonas acidovorans, Pseudomonas alcaligenes, Pseudomonas putida, Stenotrophomonas maltophilia, Burkholderia cepacia, Aeromonas hydrophilia, Escherichia coli, Citrobacter freundii, Salmonella typhimurium, Salmonella typhi, Salmonella paratyphi, Salmonella enteritidis, Shigella dysenteriae, Shigellaflexneri, Shigella sonnei, Enterobacter cloacae, Enterobacter aerogenes, Klebsiella pneumoniae, Klebsiella oxytoca, Serratia marcescens, Francisella tularensis, Morganella morganii, Proteus mirabilis, Proteus vulgaris, Providencia alcalifaciens, Providencia rettgeri, Providencia stuartii, Acinetobacter calcoaceticus, Acinetobacter haemolyticus, Yersinia enterocolitica, Yersinia pestis, Yersinia pseudotuberculosis, Yersinia intermedia, Bordetella pertussis, Bordetella parapertussis, Bordetella bronchiseptica, Haemophilus influenzae, Haemophilus parainfluenzae, Haemophilus haemolyticus, Haemophilus parahaemolyticus, Haemophilus ducreyi, Pasteurella multocida, Pasteurella haemolytica, Branhamella catarrhalis, Helicobacter pylori, Campylobacter fetus, Campylobacter jejuni, Campylobacter coli, Borrelia burgdorferi, Vibrio cholerae, Vibrio parahaemolyticus, Legionella pneumophila, Listeria monocytogenes, Neisseria gonorrhoeae, Neisseria meningitidis,* Kingella, Moraxella, *Gardnerella vaginalis, Bacteroides fragilis, Bacteroides distasonis,* Bacteroides 3452A homology group, *Bacteroides vulgatus, Bacteroides ovalus, Bacteroides thetaiotaomicron, Bacteroides uniformis, Bacteroides eggerthii, Bacteroides splanchnicus, Clostridium difficile, Mycobacterium tuberculosis, Mycobacterium avium, Mycobacterium intracellulare, Mycobacterium leprae, Corynebacterium diphtheriae, Corynebacterium ulcerans, Streptococcus pneumoniae, Streptococcus agalactiae, Streptococcus pyogenes, Enterococcus faecalis, Enterococcus faecium, Staphylococcus aureus, Staphylococcus epidermidis, Staphylococcus saprophyticus, Staphylococcus intermedius, Staphylococcus hyicus* subsp. *hyicus, Staphylococcus haemolyticus, Staphylococcus hominis, Staphylococcus saccharolyticus*.

The term "efflux pump" refers to a protein assembly which exports substrate molecules from the cytoplasm or periplasm of a cell, in an energy dependent fashion. Thus an efflux pump will typically be located in the cytoplasmic membrane of the cell (spanning the cytoplasmic membrane). In Gram-negative bacteria the pump may span the periplasmic space and there may also be portion of the efflux pump which spans the outer membrane. Certain efflux pumps will include a polypeptide which has at least 50% amino acid sequence similarity with a polypeptide which is part of the *Pseudomonas aeruginosa* mexA/mexB/oprM efflux pump or the efflux pump overexpressed by *P. aeruginosa* Strain K385, or the efflux pump overexpressed by *P. aeruginosa* Strain PAO4098E. Due to the described sequence similarity of a component polypeptide of the efflux pump, such an efflux pump is termed a *Pseudomonas aeruginosa*-type efflux pump.

The term "non-tetracycline-specific efflux pump" refers to an efflux pump which is not highly specific for tetracycline (relative to other antibiotics) and thus is not a tetracycline (tetracycline-specific) efflux pump. The term thus includes broad substrate pumps (efflux a number of compounds with varying structural characteristics) and pumps which are highly specific for compounds (including antibiotics) other than tetracyclines. Tetracycline efflux pumps are involved in specific resistance to tetracycline in bacteria. (Speer et al., 1992, *Clin. Microbiol. Rev.* 5: 387–399.) As noted, these pumps are highly specific for tetracyclines, and their presence confers high tetracycline resistance to the cell. However, they do not confer resistance to other antibiotics. The genes for the tetracycline pump components are found in plasmids in Gram-negative as well as in Gram-positive bacteria and can be divided in two main groups, tetA(A–E), and tetK and tetL. TetA-E tetracycline resistance determinants contain a structural gene, tetA, which is a tetracycline specific pump, and a repressor gene, tetR, that mediates inducible resistance to tetracyclines. Tetracycline efflux pumps belonging to this group are designated tetA(A), teA(B), tetA(D), and tetA(), and are found in Enterobacteriaceae and other Gram-negative bacteria TetK and TetL are pumps involved in tetracycline resistance in Gram-positive bacteria. The genes are regulated via translational attenuation and are not homologous to tetA group.

An "efflux pump inhibitor" is a compound which specifically interferes with the ability of an efflux pump to export its normal substrate, or other compounds such as an antibiotic. The inhibitor may have intrinsic antimicrobial (e.g., antibacterial) activity of its own, but at least a significant portion of the relevant activity is due to the efflux pump inhibiting activity. Of particular interest in this invention, are compounds which inhibit the export or activity of efflux pumps which have a broad substrate range which includes antibacterial agents. The term "non-tetracycline-specific efflux pump inhibitor" refers to an efflux pump inhibitor which inhibits a non-tetracycline-specific efflux pump. The term "*Pseudomonas aeruginosa*-type efflux pump inhibitor" refers to an efflux pump inhibitor which inhibits a *Pseudomonas aeruginosa*-type efflux pump. A "*Pseudomonas aeruginosa* efflux pump inhibitor" is an efflux pump inhibitor which inhibits the export activity of an efflux pump found in *Pseudomonas aeruginosa*.

By "comprising" is meant including, but not limited to, whatever follows the word "comprising". Thus, use of the term "comprising" indicates that the listed elements are required or mandatory, but that other elements are optional and may or may not be present. By "consisting of" is meant including, and limited to, whatever follows the phrase "consisting of". Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

In another aspect, this invention provides a method for treating a microbial infection, e.g., a bacterial infection, in an animal by administering to an animal suffering from such an infection an efflux pump inhibitor as described above in an amount sufficient to reduce efflux pump activity.

In a preferred embodiment, the inhibitor is one which decreases the pathogenicity of the microbe. Such a decrease in pathogenicity can be obtained, for example, by interfering with bacterial iron acquisition by inhibiting the transport of siderophores. The pathogenicity may also be reduced by reducing or eliminating the microbial products which cause tissue-damaging effects to the host. Other methods of reducing pathogenicity are, however, also within this aspect. The animal may be, for exanple, chickens and turkeys, and in certain preferred embodiments is a mammal, e.g., a human.

In certain preferred embodiments, the microbial infection may be due to bacteria, which may, for example, be any of the bacterial species indicated above, but specifically including *Pseudomonas aeruginosa*.

In a related aspect, this invention provides a method of treating an animal suffering from a microbial infection by administering to the animal an efflux pump inhibitor in an amount sufficient to reduce efflux pump activity. In this aspect, the efflux pump inhibitor in one which reduces the in vivo viability of a microbe involved in the infection. By reducing the in vivo viability, the infected animal can more readily clear its body of the infection, or the microbes may even be killed. In particular embodiments the animal is a mammal. Also in particular embodiments, the microbe may be from one of a variety of pathogenic bacterial species, specifically including those listed above.

The term "in vivo viability" refers to the ability of a microbe, e.g., a bacterium, to survive or grow in a host, such as an animal. Therefore, an efflux pump inhibitor which reduces the in vivo viability of a microbe may stop the growth of the microbe and/or kill the microbe. Such efflux pump inhibitors, therefore are antimicrobial agents.

In a further related aspect, this invention includes a method for prophylactic treatment of an animal, e.g., a mammal. In this method, an efflux pump inhibitor which reduces the pathogenicity of a microbe is administered to a mammal at risk of a microbial infection, e.g., a bacterial infection.

In a related aspect, the invention provides a method for treating a microbial infection in an animal, specifically including in a mammal, by treating an animal suffering from such an infection with an antimicrobial agent and an efflux pump inhibitor which increase the susceptibility of the microbe for that antimicrobial agent. In this way a microbe involved in the infection can be treated using the antimicrobial agent in smaller quantities, or can be treated with an antimicrobial agent which is not therapeutically effective when used in the absence of the efflux pump inhibitor. Thus, this method of treatment is especially appropriate for the treatment of infections involving microbial strains which are difficult to treat using an antimicrobial agent alone due to a need for high dosage levels (which can cause undesirable side effects), or due to lack of any clinically effective antimicrobial agents. However, it is also appropriate for treating infections involving microbes which are susceptible to particular antimicrobial agents as a way to reduce the dosage of those particular agents. This can reduce the risk of side effects, but can also reduce the selection effect for highly resistant microbes resulting from the consistent high level use of a particular antimicrobial agent. In particular embodiments the microbe is a bacterium, which may, for example, be from any of the groups or species indicated above Also in particular embodiments various antibacterial agents can be used. These include quinolones, tetracyclines, glycopeptides, aminoglycosides, beta-lactams, rifamycins, coumermycins, macrolides, and chloramphenicol. In particular embodiments an antibiotic of the above classes can be, for example, one of the following:

Beta-Lactam Antibiotics imipenem, meropenem, biapenem, cefaclor, cefadroxil, cefamandole, cefatrizine, cefazedone, cefazolin, cefixime, cefinenoxime, cefodizime, cefonicid, cefoperazone, ceforanide, cefotaxime, cefotiam, cefpimizole, cefpiramide, cefpodoxime, cefsulodin, ceftazidime, cefteram, ceftezole, ceflibuten, ceftizoxime, ceftriaxone, cefuroxime, cefuzonam, cephaacetrile, cephalexin, cephaloglycin, cephaloridine, cephalothin, cephapirin, cephradine, cefmetazole, cefoxitin, cefotetan, azthreonam, carumonam, flomoxef, moxalactam, amidinocillin, amoxicillin, ampicillin, azlocillin, carbenicillin, benzylpenicillin, carfecillin, cloxacillin, dicloxacillin, methicillin, mezlocillin, nafcillin, oxacillin, penicillin G, piperacillin, sulbenicillin, temocillin, ticarcillin, cefditoren, SC004, KY-020, cefdinir, ceftibuten, FK-312, S-1090, CP-0467, BK-218, FK-037, DQ-2556, FK-518, cefozopran, ME1228, KP-736, CP-6232, Ro 09-1227, OPC-20000, LY206763

Macrolides
 azithromycin, clarithromycin, erytiromycin, oleandomycin, rokitamycin, rosaramicin, roxithromycin, troleandomycin Quinolones
 amifloxacin, cinoxacin, ciprofloxacin, enoxacin, fleroxacin, flumequine, lomefloxacin, nalidixic acid, norfloxacin, ofloxacin, levofloxacin, oxolinic acid, pefloxacin, rosoxacin, temafloxacin, tosufloxacin, sparfloxacin, clinafloxacin, PD131628, PD138312, PD140248, Q-35, AM-1 155,NM394, T-3761, rufloxacin, OPC-17116, DU-6859a (identified in Sato, K. et al., 1992, *Antimicrob Agents Chemother.* 37:1491–98), DV-7751a (identified in Tanaka, M. et al., 1992, *Antimicrob. Agents Chemother.* 37:2212–18)

Tetracyclines and Oxazolidinones
 chlortetracycline, demeclocycline, doxycycline, lymecycline, methacycline, minocycline, oxytetracycline, tetracycline, lenazolide, eperozolid Aminoplycosides
 amikacin, arbekacin, butirosin, dibekacin, fortimicins, gentamicin, kanamycin, meomycin, netilmicin, ribostamycin, sisomicin, spectinomycin, streptomycin, tobramycin, clindamycin, lincomycin.

In a further related aspect, this invention includes a method for prophylactic treatment of a mammal. In this method, an antimicrobial agent and an efflux pump inhibitor is administered to a mammal at risk of a microbial infection, e.g., a bacterial infection.

In the context of the response of a microbe, such as a bacterium, to an anti-microbial agent, the term "susceptibility" refers to the sensitivity of the microbe for the presence of the antimicrobial agent. So, to increase the susceptibility means that the microbe will be inhibited by a lower concentration of the antimicrobial agent in the medium surrounding the microbial cells. This is equivalent to saying that the microbe is more sensitive to the antimicrobial agent. In most cases the minimum inhibitory concentration (MIC) of that antimicrobial agent will have been reduced.

As used herein, the term "treating" refers to administering a pharmaceutical composition for prophylactic and/or therapeutic purposes. The term "prophylactic treatment" refers to treating a patient who is not yet infected, but who is susceptible to, or otherwise at risk of, a particular infection. The term "therapeutic treatment" refers to administering treatment to a patient already suffering from an infection. Thus, in preferred embodiments, treating is the administration to a mammal (either for therapeutic or prophylactic purposes) of therapeutically effective amounts of a potentiator and an antibacterial (or antimicrobial) agent in combination (either simultaneously or serially).

By "therapeutically effective amount" or "pharmaceutically effective amount" is meant an amount of an efflux pump inhibitor, or amounts individually of an efflux pump inhibitor and an antimicrobial agent, as disclosed for this invention, which have a therapeutic effect, which generally refers to the inhibition to some extent of the normal metabolism of microbial cells causing or contributing to a microbial infection. The doses of efflux pump inhibitor and antimicrobial agent which are useful in combination as a treatment are therapeutically effective amounts. Thus, as used herein, a therapeutically effective amount means those amounts of efflux pump inhibitor and antimicrobial agent which, when used in combination, produce the desired therapeutic effect as judged by clinical trial results and/or model animal infection studies. In particular embodiments, the efflux pump inhibitor and antimicrobial agent are combined in pre-determined proportions and thus a therapeutically effective amount would be an amount of the combination. This amount and the amount of the efflux pump inhibitor and antimicrobial agent individually can be routinely determined by one of skill in the art, and will vary, depending on several factors, such as the particular microbial strain involved and the particular efflux pump inhibitor and antimicrobial agent used. This amount can further depend upon the patient's height, weight, sex, age and medical history. For prophylactic treatments, a therapeutically effective amount is that amount which would be effective if a microbial infection existed.

A therapeutic effect relieves, to some extent, one or more of the symptoms of the infection, and includes curing an infection. "Curing" means that the symptoms of active infection are eliminated, including the elimination of excessive members of viable microbe of those involved in the infection. However, certain long-term or permanent effects of the infection may exist even after a cure is obtained (such as extensive tissue damage).

The term "microbial infection" refers to the invasion of the host mammal by pathogenic microbes. This includes the excessive growth of microbes which are normally present in or on the body of a mammal. More generally, a microbial infection can be any situation in which the presence of a microbial population(s) is damaging to a host mammal. Thus, a mammal is "suffering" from a microbial infection when excessive numbers of a microbial population are present in or on a mammal's body, or when the effects of the presence of a microbial population(s) is damaging the cells or other tissue of a mammal. Specifically, this description applies to a bacterial infection.

The term "admninistration" or "administering" refers to a method of giving a dosage of an antimicrobial pharmaceutical composition to a mammal, where the method is, e.g., topical, oral, intravenous, intraperitoneal, or intramuscular. The preferred method of administration can vary depending on various factors, e.g., the components of the pharmaceutical composition, the site of the potential or actual bacterial infection, the microbe involved, and the severity of an actual microbial infection.

The term "mammal" is used in its usual biological sense. Thus, it specifically includes humans, cattle, horses, dogs, and cats, but also includes many other species.

In another aspect, this invention also features a method of inhibiting a membrane channel in a cellular membrane, involving contacting the membrane channel with a membrane channel inhibitor, where the inhibitor reduces the effluxing capacity of the membrane channel. In specific embodiments, at least one polypeptide of the membrane channel has at least 50% amino acid sequence similarity with a polypeptide of the mexA/mexB/oprM efflux pump, or of the efflux pump overexpressed by *Pseudomonas aeruginosa* Strain K385.

As used herein, the term "membrane channel" refers to a protein assembly located in the cellular membrane of a cell which allows the transport of one or more types of molecules across the membrane. Such transport may be either passive transport in response to concentration gradients, or may be active transport which depends upon a cellular energy source.

A "membrane channel inhibitor" then is, similar to an efflux pump inhibitor, a compound which slows or prevents the transport of molecules across the cellular membrane using the corresponding membrane channel.

This invention also features a method of enhancing the antimicrobial activity of an antimicrobial agent against a microbe, in which such a microbe is contacted with an efflux pump inhibitor, e.g., a non-tetracycline specific efflux pump inhibitor, to an efflux pump in the cell, and an antibacterial agent. The efflux pump inhibitor is a compound as described above. Thus, this method makes an antimicrobial agent more effective against a cell which expresses an efflux pump when the cell is treated with the combination of an antimicrobial agent and a non-tetracycline-specific efflux pump inhibitor. In particular embodiments the microbe is a bacterium or a fungus, such as any of those indicated in the first aspect above; the antibacterial agent can be selected from a number of structural classes of antibiotics including, e.g., beta-lactams, glycopeptides, aminoglycosides, quinolones, tetracyclines, rifamycins, coumermycins, macrolides, and chloramphenicol. In particular embodiments an antibiotic of the above classes can be as stated above.

In a further aspect this invention provides pharmaceutical compositions effective for treatment of an infection of an animal, e.g., a mammal, by a microbe, such as a bacterium or a fungus. The composition includes a pharmaceutically acceptable carrier and an efflux pump inhibitor as described above. In preferred embodiments, such compositions contain efflux pump inhibitors which are themselves effective antimicrobial agents, even in the absence of another antimicrobial agent (i.e., have intrinsic antimicrobial activity). Thus, pharmaceutical compositions including such efflux pump inhibitors can be used either alone or in conjunction with another antimicrobial agent. Also in preferred embodiments, the efflux pump inhibitors in pharmaceutical compositions of this aspect are efflux pump inhibitors which enhance the effectiveness of an antimicrobial agent other than the efflux pump inhibitor, so such compositions would generally be used in combination with such other antimicrobial agent. The invention also provides pharmaceutical compositions similarly effective for treatment of an infection of a mammal which include an efflux pump inhibitor and an antimicrobial agent. Similarly, the invention provides antimicrobial formulations which include an antimicrobial agent, an efflux pump inhibitor, and a carrier. In preferred embodiments, the antimicrobial agent is an antibacterial agent.

A "carrier" or "excipient" is a compound or material used to facilitate administration of the compound, for example, to increase the solubility of the compound. Solid carriers include, e.g., starch, lactose, dicalcium phosphate, sucrose, and kaolin. Liquid carriers include, e.g., sterile water, saline, buffers, non-ionic surfactants, and edible oils such as oil, peanut and sesame oils. In addition, various adjuvants such as are commonly used in the art may be included. These and other such compounds are described in the literature, e.g., in the Merck Index, Merck & Company, Rahway, N.J. Considerations for the inclusion of various components in pharmaceutical compositions are described, e.g., in Gilman et al. (Eds.) (1990); *Goodman and Gilman's: The Pharmacological Basis of Therapeutics*, 8th Ed., Pergamon Press.

In yet another aspect, the invention provides a method of suppressing growth of a microbe, e.g., a bacterium, expressing an efflux pump, e.g., a non-tetracycline-specific efflux pump. As illustrated by the case where the microbe is a bacterium, the method involves contacting that bacterium with an efflux pump inhibitor, e.g., a non-tetracycline-specific efflux pump inhibitor, in the presence of a concentration of antibacterial agent below the MIC of the bacterium. This method is useful, for example, to prevent or cure contamination of a cell culture by a bacterium possessing an efflux pump. However, it applies to any situation where such growth suppression is desirable.

In a related aspect, the invention provides a method of suppressing growth of a microbe, e.g., a bacterium, which involves contacting the microbe with an efflux pump inhibitor which reduces the expression of a component of an efflux pump. Such an inhibitor can act on the regulation of that expression in number of different ways. It may, for example, enhance the production of a repressor molecule which prevents expression of an efflux pump component. Another possible mechanism is if the inhibitor blocks the release of a repressor molecule. Examples of such a repressor is MarR in *E. coli* (Seoane and Levy, 1994, *Abstr. of the Am. Soc. for Microbiol. Gen. Meeting*, Las Vegas, Nev., Abstr. H-26). An example of a positive regulator is BmrR in *Bacillus subtilis* (Ahmed et al., 1994, *J. Biol. Chem.*).

In another related aspect, the invention provides a method for reducing a population of a microbe, e.g., a bacterial strain, involving contacting the population with an efflux pump inhibitor which inhibits a component of an efflux pump expressed in the microbe in that population, which is essential for the growth of the microbe expressing that efflux pump. In particular embodiments, that component is a cytoplasmic membrane component. As indicated above, such efflux pump inhibitors may act in various ways, including, but not limited to, acting directly on the essential component, or acting to inhibit the expression of that component.

The term "reducing a population" means that the microbes of that population are being killed. This is distinguished from the action of a static agent, e.g., a bacteriostatic agent, which prevents the bacteria from growing and multiplying but does not kill the microbes. Accordingly, in the context of this aspect, an "essential component" of an efflux pump is one which is essential to the in vivo survival of the microbe, i.e., the survival in a host.

In yet another aspect, this invention provides a method for enhancing growth of an animal by administering an efflux pump inhibitor to the animal, which inhibits an efflux pump expressed in a bacterial strain in the animal, and which inhibits the growth of that bacterial strain. Such a growth enhancing effect may result from the reduced energy consumption by the bacteria, which increases the food energy available to the animal. This method is appropriate, for example, for use with cattle, swine, and fowl such as chickens and turkeys.

In an additional aspect, the invention provides novel compounds having efflux pump activity. These compounds have chemical structures as described above.

As indicated above, while the present invention is presently exemplified by activity against bacteria, compounds of the present invention also have activity against other microbes, for example against yeasts and/or other fungi.

Thus, the above aspects also include embodiments in which described compounds are active or effective against such other microbes.

In a further aspect, the invention provides a method of making a pharmaceutical composition comprising the steps of identifying an efflux pump inhibitor having a chemical structure as set forth in Structure 1 or Structure 2, or the sub-generic structures 3, 4, 5, and 6, as described herein; synthesizing said efflux pump inhibitor in an amount sufficient to provide a therapeutic response; and preparing a pharmaceutical composition containing said efflux pump inhibitor. The efflux pump inhibitor may have the chemical structure as described above. The pharmaceutical composition may also contain one or more antimicrobial agents, e.g., as identified above, and one or more carriers, diluents, and excipients. Further, in preferred embodiments, the efflux inhibitor compound is active against a microbe, e.g., a bacteriam, as identified above.

Other features and advantages of the invention will be apparent from the following description of the preferred embodiments, and from the claims.

DESCRIPTION OF THE PREFERRED EMBODIMENTS

Identification of Efflux Pump Inhibitors

Initial identification of efflux pump inhibitors having structures as described was performed using a screening method as generally described in Trias et al., EFFLUX PUMP INHIBITORS, U.S. application Ser. No. 08/427,088; Trias et al., EFFLUX PUMP INHIBITORS, U.S. application No. not yet assigned, filed Jul. 22, 1997; and Trias et al., International Publication WO96/05469. In particular, the screening method based on inhibition of microbial growth in the presence of a subinhibitory concentration of an antibacterial agent which is normally effluxed by the test microbe and a concentration of a test compound was used for identifying some of the active compounds disclosed herein. In this method, inhibition of growth of the microbe is indicative that export of the antibacterial agent is inhibited by the test compound, and that the test compound is therefore an efflux pump inhibitor. The mode of action of the test compound so identified can then be confirmed as inhibiting active efflux. However, other screening methods for detecting efflux pump inhibitors can also be used, specifically including the additional methods described in the above references.

Synthesis of Derivatives of Efflux Pump Inhibitors from Screening

Exemplary compounds of the present invention were synthesized by methods as described in the Examples below. Those skilled in the art will understand how to synthesize additional compounds within the scope of this invention based on the described syntheses and the knowledge of those skilled in the art of chemical synthesis.

Susceptibility Testing

Particular exemplary efflux pump inhibitor compounds within the generic descriptions of the compounds of this invention were evaluated for potentiation effect. The in vitro microbiological data for antibiotic potentiation is presented in Tables 7 and 8 below.

For compounds labeled with the prefix 'M', potentiation effect is observed by the reduction of the minimum inhibitory concentration of levofloxacin in the presence of the experimental efflux pump inhibitor. The activity of efflux pump inhibitors (EPI) in combination with fluoroquinolones, such as levofloxacin, is assessed by the checkerboard assay (Antimicrobial Combinations. In Antibiotics in Laboratory Medicine, Ed. Victor Lorian, M.D., Fourth edition, 1996, pp 333–338) using broth microdilution method performed as recommended by the National Committee for Clinical Laboratory Standards (1997). Methods for Dilution of Antimicrobial Susceptibility Tests for Bacteria That Grow Aerobically—Fourth Edition; Approved Standard. NCCLS Document M7-A4, Vol 17 No.2). The test organism used is *Pseudomonas aeruginosa* PAM1001. The compounds of this invention demonstrate pump inhibitory activity against a broad-range of *P. aeruginosa* overproducing singular efflux pumps (MexAB, MexCD, and MexEF) and clinical strains containing multiple efflux pumps, not limited to the Mex classification. The compounds tabulated below are representative of the described invention.

In these assays, multiple dilutions of two drugs, namely the EPI and levofloxacin, are being tested, alone and in combination, at concentrations equal to, above and below their respective minimal inhibitory concentrations (MICs). In the case of EPI, most of these compounds are devoid of intrinsic antimicrobial activity and are tested up to the maximum concentration of 40 µg/mL. The MIC of levofloxacin against *P. aeruginosa* PAM1001 is 4 µg/mL.

The EPI tested are readily soluble in water and stock solutions are prepared at a final concentration of 2 mg/mL. Stock solutions are further diluted, according to the needs of a particular assay, in Mueller Hinton Broth (MHB). Stock solution can be stored at −80° C. Quinolones are solubilized according to the instructions of the manufacturers, at a concentration of 1 mg/mL. They are then further diluted in MHB. Stock solution can be stored at −80° C.

The checkerboard assay is performed in microtiter plates. Levofloxacin is diluted in the x axis, each column containing a single concentration of levofloxacin. The EPI is diluted in the y axis, each row containing an equal concentration of EPI. The result of these manipulations is that each well of the microtiter plate contains a unique combination of concentrations of the two agents. Each EPI are tested independently.

The assay is performed in MHB with a final bacterial inoculum of $5 \times 10^5$ CFU/mL (from an early-log phase culture). Microtiter plates are incubated during 20 h at 35° C. and are read using a microtiter plate reader (Molecular Devices) at 650 nm as well as visual observation using a microtiterplate reading mirror. The MIC is defined as the lowest concentration of quinolone, within the combination, at which the visible growth of the organism is completely inhibited.

For compounds labeled with the prefix 'D', potentiation is measured by inhibition of growth of *Pseudomonas aeruginosa* PAM1001 at varying concentrations of efflux pump inhibitors (EPIs) in the presence of levofloxacin (0.25 microg/mL). Bacteria are grown in Mueller Hinton Broth (MHB, Difco) with an initial inoculum of $1 \times 10^6$ CFU/mL. Kinetics of bacterial growth is monitored, during 18 h of incubation at 37° C., by measurement of the culture absorbance at 650 nm using a 96-well plate spectrophotometer (SpectraMax, Molecular Devices). The inhibitory effect of EPIs is expressed as a percentage of growth inhibition compared to a control bacterial culture grown in the presence of 0.25 microg/mL levofloxacin but without EPIs.

Efflux Pump Inhibitors for Table 7

| Compound | Structure |
|---|---|
| M1 | (2R,4S)-4-(2-Amionoacetamido)-N-[(1R-)-3-phenyl-1-(3-quinolylcarbamoyl)propyl]-2-pyrrolidinecarboxamide |
| M2 | (2R,4S)-4-(2-Aminoacetamido)-N-[(1R)-3-phenyl-1-(3-phenyl)propylcarbamoyl]propyl]-2-pyrrolidinecarboxamide |
| M3 | (2S,4R)-4-(2-Aminoacetamido)-N-[(1R)-3-phenyl-1-(3-quinolylcarbamoyl)propyl]-2-pyrrolidinecarboxamide |
| M4 | (2S,4R)-4-(2-Aminopropionamido]-N-[(1R)-3-pheyl-1-(3-quinolylcarbamoyl)propyl]-2-pyrrolidinecarboxamide |
| M5 | (2S,4R)-4-(Aminompropionamido)-N-[(1R)-3-phenyl-1-(3-quinolylcarbamolyl)propyl]-2-pyrrolidinecarboxamide |
| M6 | (2S,4R)-4-[3-(Aminopropionamido])-N-[(1R)-3-phenyl-1-(3-quinolylcarbamoyl)propyl]-2-pyrrolidinecarboxamide |
| M7 | (2S,4R)-4-(Amino-N-[(1R)-3-pheynl-1-(3-quinolylcarbamoyl)propyl]-2-pyrrolidinecarboxamide |
| M8 | (2S,4R)-4-(Aminoacetamido)-N-[(1R)-3-methyl-1-[(3-quinolylcarbamoyl)butyl]-2-pyrrolidinecarboxamide |
| M9 | (2S,4S0-4-(2-Amino-N-methylacetamido)-N-](1R)-3-phenyl-1-(3-quinolylcarbamoyl)propyl]-2-pyrrolidinecarboxamide |
| M10 | (2S,4R)-4-(2-Aminoacetamido)-N-[(1R)-3-3-methyl-1-(6-methoxy-8-methyl-3-quinolylcarbamoyl)butyl]-2-pyrrolidinecarboxamide |
| M11 | (2S,4R)-4-(2-Aminoacetamido)-N-[(1R)-3-phenyl-1-(6,7-dimethyl-3-quinolylcarbamoyl)propyl]-2-pyrrolidinecarboxamide |
| M12 | (2S,4R)-4-(2-Aminoacetamido)-N-[(1R)-2-(4-methoxyphenyl)-1-(3-quinolylcarbamoyl)ethyl]-2-pyrrolidinecarboxamide |
| M13 | (2R,4R)-4-(Aminomethyl)-N-[(1R)-3-methyl-1-quinolylcarbanioyl)bulyl]-2-pyrrolidinecarboxamide |
| M14 | (2R,4R)-4-(Aminomethyl)-N-[(1R)-3-phenyl-1-(6-ethyl-3-quiolylcarbamoyl)propyl]-2-pyrrolidinecarboxamide |
| M15 | (2S,4R)-4-(2-Aminoacetamido)-N-methyl-N-[(1R)-3-phenyl-1-(3-quinolylcarbamoyl)propyl]-2-pyrrolidiecarboxamide |
| M16 | (2R,4R)-4-(Aminomethyl)-N-[(1R)-3-phenyl-1-(3-quinolylcarbamoyl)propyl]-2-pyrrolidinecarboxamide |
| M17 | (2R,4R)-4-(2-Aminoacetamido)-N-[(1R)-3-phenyl-1-(3-quinolylcarbamoyl)propyl]-2-pyrrolidinecarboxamide |
| M18 | (2S,4R)-4-(2-Aminoacetamido)-N-[(1R)-3-phenyl-1-(6-ethyl-3-quinolylcarbamoyl)propyl]-2-pyrrolidinecarboxamide |
| M19 | (2S,4R)-4-(2-Aminoacetamido)-N-[(1R)-3-methyl-1-(6-ethyl-3-quinolylcarbamoyl)butyl]-2-pyrrolidinecarboxamide |
| M20 | (2R,4R)-4-(2-Aminoacetamideo)-N-[(1R)-2-(4-fluorophenyl)-1-(3-quinolylcarbamoyl)ethyl]-2-pyrrolidinecarboxamide |
| M21 | (2S,4R)-4-(2-Aminoacetamido)-N-[(1R)-2-(4-fluorophenyl)-1-(3-quinolylcarbamoyl)ethyl]-2-pyrrolidinecarboxamide |
| M22 | (2S,4R)-1-(2-Aminoacetamido)-N-[(1R)-3-phenyl-1-(6-methoxy-8-methyl-3-quinolylcarbamoyl)propyl]2-pyrrolidinecarboxamide |
| M23 | (2S,4R)-4-(2-Aminoacetamido)-N-[(1R)-2-(4-hydroxyphenyl)-1-(3-quinolylcarbamoyl)ethyl]-2-pyrrolidinecarboxamide |
| M24 | (2S,4S)-4-(Aminomethyl)-N-[(1R)-3-phenyl-1-(3-quinolylcarbamoyl)propyl]-2-pyrrolidinecarboxamide |
| M25 | (2R,4R)-4-(Amiomethyl)-N-[(1R)-2-(4-hydroxyphenyl)-1-(6-ethyl-3-quinolylcarbamoyl)ethyl]-2-pyrrolidinecarboxamide |
| M26 | (2S,4R)-4-(2-Aminoacetamido)-N-[(1R)-3-phenyl-1-(5-chloro-2-hydroxyphenylcarbamoyl)propyl]-2-pyrrolidinecarboxamide |
| M27 | (2S,4R)-4-(2-Aminoacetamido)-N-[(1R)-3-phenyl-1-(4,5-dimethyl-2-hydroxyphenylcarbamoyl)propyl]-2-pyrrolidinecarboxamide |
| M28 | (2S,4R)-4-(2-Aminoacetamido)-N-[(1R)-3-phenyl-1-(2-hydroxy-5-methylphenylcarbamoyl)propyl]-2-pyrrolidinecarboxamide |
| M29 | (2R,4R)-4-(Aminomethyl)-N-[(1R)-3-pheyl-1-(6-quinolylcarbamoyl)propyl]-2-pyrrolidinecarboxamide |
| M30 | (2R,4R)-4-(Aminomethyl)-N-[(1R)-3-pheyl-1-(8-quinolylcarbamoyl)propyl]-2-pyrrolidinecarboxamide |
| M31 | (2R,4R)-4-(Aminomethyl)-N-[(1R)-2-(4-fluoropheyl)-1-(3-quinolylcarbamoyl)ethyl]-2-pyrrolidinecarboxamide |
| M32 | (2R,4R)-4-(Aminomethyl)-N-[(1R)-3-phenyl-1-[3-quinolylmethyl)carbamoyl]propyl]-2-yrrolidinecarboxamide |
| M33 | (2R,4R)-4-(Aminomethyl)-N-methyl-N-[(1R)-3-phenyl-1-(3-quinolylcarbamoyl)propyl]-2-pyrrolidinecarboxamide |
| M34 | (2R,4R)-4-(Aminomethyl)-N-[(1R)-3-methyl-1-(3-quinolylcarbamoly)butyl]-2-pyrrolidinecarboxamide |
| M35 | (2R,4R)-4-(Aminomethyl)-N-[(1R)-3-pheyl-1-(6-fluoro-3-quinolylcarbamoyl)propyl]-2-pyrrolidinecarboxamide |
| M36 | (2R,4R)-4-(Aminomethyl)-N-[(1R)-4-methyl-1-(3-quinolylcarbamoyl)pentyl]-2-pyrrolidinecarboxamide |
| M37 | (2R,4R)-4-(Aminomethyl)-N-[(1R)-3-phenyl-1-(5-fluoro-2-hydroxyphenylcarbamoyl)propyl]-2-pyrrolidinecarboxamide |
| M38 | (2R,4R)-4-(Aminomethyl)-N-[(1R)-3-phenyl-1-(2-hydroxy-5-methylphenylcarbamoyl)propyl]-2-pyrrolidinecarboxamide |
| M39 | (2R,4R)-4-(Aminomethyl)-N-[(1R)-3-pheyl-1-(5-chloro-2-hydroxyphenylcarbamoyl)propyl]-2-pyrrolidinecarboxamide |
| M40 | (2R,4R)-4-(Aminomethyl)-N-methyl-N-[(1R)-3-methyl-1-(6-ethyl-3-quinolylcarbamoyl)butyl]-2-pyrrolidinecarboxamide |
| M41 | (2R,4S0-4-(2-Aminoacetamideo)-N-(2-phenylethyl)-N-(3-quinolylcarbamoyl)ethyl]-2-pyrrolidinecarboxamide |
| M42 | (2R,4S)-4-[(2R)-2-Aminopropionamido]-N-(2-phenylethyl)-N-(3-quinolylcarbamoyl)ethyl]-2-pyrrolidinecarboxamide |
| M43 | (2S,4R)-4-(2-Aminoacetamideo)-N-(2-phenylethyl)-N-(3-quinolylcarbamoyl)ethyl]-2-pyrrolidinecarboxamide |
| M44 | (2R,4S)-4-(2-Aminoacetamideo)-N-(2-methylpropyl)-N-(7-ethyl-3-quinolylcarbamoyl)ethyl]-2-pyrrolidinecarboxamide |
| M45 | (2R,4R)-4-(Aminomethyl)-N-(2-phenylethyl)-N-(3-quinolylcarbamoyl)ethyl]-2-pyrrolidinecarboxamide |
| M46 | (2R,4R)-4-(2-Aminoacetamido)-N-(2-phenylethyl)-N-(3-quinolylcarbamoyl)methyl]-2-pyrrolidinecarboxamide |
| M47 | (2R,4S)-4-[(2R)-2-Aminopropionamido]-N-(3,3-dimethylbutyl)-N-(3-quinolylcarbamoyl)methyl]-2-pyrrolidinecarboxamide |
| M48 | (2R,4R)-4-(Aminomethyl)-N-[(1R)-3-phenyl-1-[(2-quinolyloxy)methyl]propyl]-2-pyrrolidinecarboxamide |
| M49 | (2R,4S)-4-(2-Aminoacetamido)-N-[(1R)-3-methyl-1-[(2-naphthyloxy)methyl]butyl]-2-pyrrolidinecarboxamide |
| M50 | (2S,4R)-4-(2-Aminoacetamido)-N-[(1R)-3-phenyl-1-[(4-chlorophenylthio)methyl]propyl]-2-pyrrolidinecarboxamide |
| M51 | (2S,4R)-4-[(2R)-2-Aminopropionamido]-N-[(1R)-3-phenyl-1-[(4-chlorophenylthio)methyl]propyl]-2-pyrrolidinecarboxamide |
| M52 | (2R,4S)-4-[(2R)-2-Aminopropionamido]-N-[(1R)-3-phenyl-1-[(4-chlorophenylthio)methyl]propyl]-2-pyrrolidinecarboxamide |
| M53 | (2S,4R)-4-(2-Aminoacetamido)-N-[(1R)-3-phenyl-1-[(3-quinolythio)methyl]propyl]-2-pyrrolidinecarboxamide |
| M54 | (2S,rR)-4-(2-Aminoacetamido)-N-[(1R)-3-phenyl-1-[(2-quinolyloxy)methyl]propyl]-2-pyrrolidinecarboxamide |
| M55 | (2S,4R)-4-(2-Aminoacetamido)-N-[(1R)-3-phenyl-1-[(2-quinolythio)methyl]propyl]-2-pyrrolidinecarobxamide |
| M56 | (2S,4R)-4-(2-Aminoacetamido)-N-[(1R)-3-phenyl-1-(phenylthiomethyl)propyl]-2-pyrrolidinecarboxamide |
| M57 | (2S,4R)-4-(2-Aminoacetamido)-N-[(1R)-3-phenyl-1-[(4-fluorophenylthio)methyl]propyl]-2-pyrrolidinecarboxamide |
| M58 | (2S,4R)-4-(2-Aminoacetamido)-N-[(1R)-3-methyl-1-[(2-quinolyoxy)methyl]butyl]-2-pyrrolidinecarboxamide |
| M59 | (2R,4R)-4-(Aminomethyl)-N-[(1R)-3-methyl-1-[(3-quiolyloxy)methyl]butyl]-2-pyrrolidinecarboxamide |
| M60 | (2S,4R)-4-(2-Aminoacetamido)-N-[(1R)-3-methyl-1-[(4-chlorophenylthio)methyl]butyl]-2-pyrrolidinecarboxamide |
| M61 | (2R,4R)-4-(Aminomethyl)-N-[(1R)-3-methyl-1-[(4-chlorophenylthio)methyl]butyl]-2-pyrrolidinecarboxamide |
| M62 | (2R,4R)-4-(Aminomethyl)-N-[(2S)-2-(6-methyl-3-quinolylcarboxamido)-4-phenylbutyl]-2-pyrrolidinecaroxamide |
| M63 | (2R,4R)-4-(Aminomethyl)-N-[(1R)-3-phenyl-1-[(6-methyl-3-quinolylcarboxamido)methyl]propyl]-2-pyrrolidinecaroxamide |
| M64 | (2S,4R)-4-(2-Aminoacetamido)-N-[(1R)-1-[(RS)-(5,6-dimethyl-2-benzoxazoly)hydroxymethyl]-3-pheylpropyl]-2-pyrrolidinecarboxamide |
| M65 | (2S,4R)-4-[(2R)-2-Aminopropionamido]-N-[(1R)-1-[(RS)-(5,6-dimethyl-2-benzoxaaolyl)hydroxymethyl]-3-phenylpropyl]-2-pyrrolidinecarboxamide |
| M66 | (2R,4S)-4-[(2R)-2-Aminopropionamido]-N-[(1R)-1-[(RS)-(5,6-dimethyl-2-benzoxaaolyl)hydroxymethyl]-3-phenylpropyl]-2-pyrrolidinecarboxamide |
| M67 | (2S,4R)-4-(2-Aminoacetamido)-N-[(1R)-1-[5,6-dimethyl-2-benzoxaxolyl)hydroxymethyl]-3-phenylpropyl]-2-pyrrolidinecarboxamide |
| M68 | (2R,4R)-4-(Aminomethyl)-N-[(1R)-1-[(RS)-(5-1,1-dimethyl)ethyl-2-benzoxazolyl)hydroxymethyl]-3-phenylpropyl]-2-pyrrolidinecarboxamide |
| M69 | (2R,4R)-4-(Aminomethyl)-2-[((1S)-3-phenyl-1-(3-quiolylcarbamoyl)propyl)oxymethyl]pyrrolidine |
| M70 | (2R,4R)-4-(Amiomethyl)-2-[((1R)-3-phenyl-1-(3-quiolylcarbamoyl)propyl)oxymethyl]pyrrolidie |

-continued

Efflux Pump Inhibitors for Table 7

| Compound | Structure |
|---|---|
| M71 | (2R,4R)-4-(Aminomethyl)-2 (2-quiolyloxymethyl)pyrrolidne |
| M72 | (2R,4R)-4-(Aminomethyl)-2-(6-methyl-3-quinolylcarboxamidomethyl)pyrrolidine |
| M73 | (2S,4R)-4-(2-Aminoacetamido)-2-(5-benzyl-2-benzmidazolyl)pyrrolidine |
| M74 | (2R,4R)-4-(Aminomethyl)-2-(5-benzyl-2-benzimidazolyl)pyrrolidine |
| M75 | (2S,4R)-4-(2-Aminoacetamido)-2-(1-(2-phenyl)ethyl-2-benzimidazolyl)pyrrolidine |
| M76 | (2S,4R)-4-(2-Aminoacetamido)-2-(1-(3-aminopropyl)-2-benzimidazolyl)pyrrolidine |
| M77 | (2S,4R)-4-(2-Aminoacetamido)-N-[(1R)-1-(2-benzoxazolyl)-3-pheylpropyl]-2-pyrrolidinexarboxamide |
| M78 | (2S,4R)-4-(2-Aminoacetamido)-N-[(1S)-1-(2-benzimidazoly)-3-phenylpropyl]-2-pyrrolidinecarboxamide |
| M79 | (2S,4R)-4-(2-Aminoacetamido)-N-[(5-benzyl-2-benzimidazolyl)methyl]-2-pyrrolidinexarboxamide |
| M80 | (2S,4R)-4-(2-Aminoacetamido)-N-[(1-(2-phenyl)ethyl-2-benzimidazoly)methyl]-2-pyrrolidinexarboxamide |
| M81 | (2S,4R)-4-(2-Aminoacetamido)-N-[(5-1,1-dimethyl)ethyl-2-benzimidazolyl)methyl]-2-pyrrolidinecarboxamide |
| M82 | (2S,4R)-4-(2-Aminoacetamido)-N-[(5-(1-hydroxy-1-phenyl)methyl-2-benzimidazolyl)methyl]-2-pyrrolidinecarboxaniide |
| M83 | (2S,4R)-4-(2-Aminoacetamido)-N-[(1S)-1-(5-benzyl-2-benzimidazolyl)ethyl]-2-pyrrolidinecarboxamide |
| M84 | (2S,4R)-4-(2-Aminoacetamido)-N-[(1R)-1-(2-benzthiazolyl)-3-phenylpropyl]-2-pyrrolidinecarboxamide |
| M85 | (2S,4R)-4-(2-Aminoacetamido)-N-[(1S)-1-(2-benzoxazoiyl)-3-phenylpropyl]-2-pyrrolidinecarboxamide |
| M86 | (2R,4R)-4-(Aminomethyl)-N-[(5-benzyl-2-benzimidazolyl)methyl]-2-pyrrolidinecarboxamide |
| M87 | (2R,4S)-4-(Aminomethyl)-N-[(5-benzyl-2-benzimidazoiyl)methyl]-2-pyrrolidinecarboxamide |
| M88 | (2R,4R)-4-(Aminomethyl)-N-[(5-phenyloxy-2-benzimidazolyl)methyl]-2-pyrrolidinecarboxamide |
| M89 | (2R,4R)-4-(Aminomethyl)-N-[(5-phenyl-2-benzimidaxolyl)methyl]-2-pyrrolidinecarboxamide |
| M90 | (2S,4R)-4-(2-Aminoethylthio)-N-[(1R)-3-phenyl-1-(3-quinolylcarbamoyl)propyl]-2-pyrrolidinecarboxamide |
| M91 | (2S,4R)-4-(2-Aminoethyloxy)-N-[(1R)-3-phenyl-1-(3-quinolylcarbamoyl)propyl]-2-pyrrolidinecarboxamide |
| M92 | (2S,4R)-4-(2-Aminoethyloxy)-N-(6-(1,1-dimethyl)ethyl-3-quinolyl)-2-pyrrolidinecarboxamide |
| M93 | (2S,4RS)-4-(3-Aminopropyl)-N-[(1R)-3-phenyl-1-(3-quiolylcarbamoyl)propyl]-2-pyrrolidinecarboxamide |
| M94 | (2S,4R)-4-(2-Aminoacetamido)-N-[5-(p-chlorophenyl)tetrahydro-3-thienyl]-2-pyrrolidinecarboxamide |
| M95 | (2S,4R)-4-(Guanadinyl)-N-[(1R)-3-phenyl-1-(3-quinolylcarbamoyl)propyl]-2-pyrrolidinecarboxamide |
| M96 | (2S,4R)-4-(2-Aminoacetamido)-N-[7-ethyl-3-quinolyl]-2-pyrrolidinecarboxamide |
| M97 | (2R,4R)-4-(Aminomethyl)-N-[6-(1,1-dimethyl)ethyl-3-quiolyl]-2-pyrrolidinecarboxamide |
| M98 | (2S,4R)-4-(2-Aminoacetamido)-N-(5-benzyl-2-hydroxyphenyl)-2-pyrrolidinecarboxamide |
| M99 | (2S,4R)-4-(2-Aminoacetamido)-N-[4-benzyl-2-benzimidazolyl)ethyl]-2-pyrrolidinecarboxamide |
| M100 | (2R,4R)-4-(Aminomethyl)-N-(6-ethyl-3-quinolyl)-2-pyrrolidinecarboxamide |
| M101 | (2R,4R)-4-(Aminomethyl)-N-(5-benzyl-2-benzimidazolyl)-2-pyrrolidinecarboxamide |
| M102 | (2S,4R)-4-(2-Aminoacetamido)-N-(5-benzyl-2-benzimidazolyl)-2-pyrrolidinecarboxamide |
| M103 | (2R,4R)-4-(Aminomethyl)-N-[(1R)-3-phenyl-1-[(3-quinolylcarboxamido)methyl]propyl]-2-pyrrolidinecarboxamide |
| M104 | trans-4-Glycylamino-D-Prolyl-D-Proline-(6-isopropyl)-3-quinolylamide |

TABLE 7

Levofloxacin MIC Against *P. aerugiuosa* PAM1001 in Presence of Efflux Pump Inhibitor (EPI)
Minimum Inhibitory Concentration ($\mu$g/mL)

| Compound | EPI Conc. 0 µg/mL | EPI Conc. 0.625 µg/mL | EPI Conc. 1.25 µg/mL | EPI Conc. 2.5 µg/mL | EPI Conc. 5 µg/mL | EPI Conc. 10 µg/mL | EPI Conc. 20 µg/mL | EPI Conc. 40 µg/mL |
|---|---|---|---|---|---|---|---|---|
| M1 | 4 | 4 | 4 | 4 | 2 | 0.06 | 0.015 | 0.015 |
| M2 | 4 | 4 | 4 | 4 | 2 | 2 | 0.25 | 0.125 |
| M3 | 4 | 4 | 4 | 2 | 2 | 0.06 | 0.008 | 0.008 |
| M4 | 4 | 4 | 4 | 4 | 2 | 2 | 1 | 0.015 |
| M5 | 4 | 4 | 4 | 4 | 2 | 2 | 0.50 | 0.008 |
| M6 | 4 | 4 | 4 | 4 | 4 | 2 | 0.06 | 0.015 |
| M7 | 4 | 4 | 4 | 4 | 4 | 4 | 4 | 0.06 |
| M8 | 2 | 2 | 2 | 2 | 2 | 2 | 1 | 0.25 |
| M9 | 4 | 4 | 4 | 4 | 4 | 4 | 2 | 0.06 |
| M10 | 4 | 4 | 4 | 4 | 4 | 4 | 1 | 0.06 |
| M11 | 4 | 4 | 4 | 4 | 4 | 0.06 | 0.06 | 0.03 |
| M12 | 4 | 4 | 4 | 4 | 4 | 2 | 1 | 0.06 |
| M13 | 4 | 4 | 4 | 2 | 1 | 0.06 | 0.06 | 0.06 |
| M14 | 4 | 4 | 4 | 2 | 0.03 | 0.03 | 0.03 | |
| M15 | 4 | 4 | 4 | 4 | 4 | 1 | 0.06 | 0.015 |
| M16 | 4 | 4 | 4 | 2 | 1 | 0.125 | 0.03 | 0.03 |
| M17 | 4 | 4 | 4 | 4 | 4 | 2 | 0.015 | 0.015 |
| M18 | 2 | 2 | 2 | 2 | 1 | 0.015 | 0.015 | 0.008 |
| M19 | 4 | 4 | 4 | 4 | 2 | 0.25 | 0.03 | 0.03 |
| M20 | 4 | 4 | 4 | 4 | 2 | 0.50 | 0.125 | 0.015 |
| M21 | 4 | 4 | 4 | 2 | 2 | 0.25 | 0.06 | 0.015 |
| M22 | 4 | 4 | 4 | 4 | 4 | 0.50 | 0.03 | 0.015 |
| M23 | 4 | 4 | 4 | 4 | 2 | 2 | 1 | 0.25 |
| M24 | 4 | 4 | 4 | 2 | 1 | 0.5 | 0.06 | 0.03 |
| M25 | 4 | 4 4 | 4 | 4 | 4 | 0.5 | 0.015 | |
| M26 | 4 | 4 | 4 | 4 | 2 | 0.25 | 0.06 | 0.008 |
| M27 | 4 | 4 | 4 | 4 | 2 | 1 | 0.06 | 0.06 |
| M28 | 4 | 4 | 4 | 4 | 2 | 0.5 | 0.125 | 0.06 |
| M29 | 4 | 4 | 4 | 2 | 1 | 0.25 | 0.06 | 0.03 |

TABLE 7-continued

Levofloxacin MIC Against *P. aerugiuosa* PAM1001 in Presence of Efflux Pump Inhibitor (EPI)
Minimum Inhibitory Concentration (μg/mL)

| Compound | EPI Conc. 0 μg/mL | EPI Conc. 0.625 μg/mL | EPI Conc. 1.25 μg/mL | EPI Conc. 2.5 μg/mL | EPI Conc. 5 μg/mL | EPI Conc. 10 μg/mL | EPI Conc. 20 μg/mL | EPI Conc. 40 μg/mL |
|---|---|---|---|---|---|---|---|---|
| M30 | 4 | 4 | 4 | 4 | 4 | 2 | 0.03 | 0.015 |
| M31 | 4 | 4 | 4 | 4 | 1 | 0.25 | 0.03 | 0.03 |
| M32 | 4 | 4 | 4 | 4 | 2 | 1 | 0.25 | 0.25 |
| M33 | 4 | 4 | 4 | 2 | 1 | 0.03 | 0.015 | 0.015 |
| M34 | 4 | 4 | 4 | 4 | 4 | 2 | 1 | 0.5 |
| M35 | 4 | 4 | 4 | 4 | 2 | 0.5 | 0.03 | 0.03 |
| M36 | 4 | 4 | 4 | 2 | 1 | 0.5 | 0.03 | 0.06 |
| M37 | 44 | 4 | 4 | 2 | 1 | 0.03 | 0.03 | 0.03 |
| M38 | 4 | 4 | 4 | 2 | 1 | 0.125 | 0.06 | 0.06 |
| M39 | 4 | 4 | 2 | 0.5 | 0.25 | 0.015 | 0.015 | 0.015 |
| M40 | 4 | 4 | 2 | 1 | 0.125 | 0.125 | 0.125 | 0.06 |
| M41 | 4 | 4 | 2 | 2 | 0.25 | 0.008 | 0.008 | 0.008 |
| M42 | 4 | 4 | 4 | 4 | 4 | 0.50 | 0.06 | 0.06 |
| M43 | 4 | 4 | 4 | 2 | 0.25 | 0.125 | 0.125 | 0.06 |
| M44 | 4 | 4 | 4 | 4 | 1 | 0.06 | 0.015 | 0.03 |
| M45 | 4 | 4 | 4 | 1 | 0.50 | 0.03 | 0.015 | 0.015 |
| M46 | 4 | 4 | 4 | 4 | 4 | 4 | 1 | 0.5 |
| M47 | 4 | 4 | 4 | 4 | 4 | 4 | 2 | 0.03 |
| M48 | 4 | 4 | 4 | 4 | 2 | 0.125 | 0.03 | 0.015 |
| M49 | 4 | 4 | 4 | 4 | 4 | 1 | 0.125 | 0.06 |
| M50 | 4 | 4 | 2 | 0.06 | 0.03 | 0.008 | 0.008 | 0.008 |
| M51 | 4 | 4 | 4 | 2 | 0.25 | 0.06 | | |
| M52 | 4 | 4 | 4 | 4 | 2 | 0.50 | 0.125 | 0.015 |
| M53 | 4 | 4 | 4 | 4 | 4 | 4 | 0.06 | 0.03 |
| M54 | 4 | 4 | 4 | 4 | 4 | 0.125 | 0.06 | 0.03 |
| M55 | 4 | 4 | 4 | 4 | 4 | 2 | 1 | 0.06 |
| M56 | 4 | 4 | 4 | 4 | 2 | 0.125 | 0.06 | 0.03 |
| M57 | 4 | 4 | 4 | 2 | 2 | 0.25 | 0.06 | 0.015 |
| M58 | 4 | 4 | 4 | 4 | 4 | 4 | 0.25 | 0.125 |
| M59 | 4 | 4 | 4 | 4 | 4 | 1 | 0.5 | 0.125 |
| M60 | 4 | 4 | 4 | 4 | 0.06 | 0.06 | 0.03 | 0.015 |
| M61 | 4 | 4 | 4 | 4 | 0.5 | 0.25 | 0.06 | |
| M62 | 4 | 4 | 4 | 4 | 4 | 2 | 0.5 | 0.015 |
| M63 | 4 | 4 | 4 | 4 | 2 | 1 | 0.008 | 0.015 |
| M64 | 4 | 4 | 4 | 4 | 4 | 4 | 4 | 0.015 |
| M65 | 4 | 4 | 4 | 4 | 4 | 4 | 0.06 | 0.015 |
| M66 | 4 | 4 | 4 | 4 | 4 | 0.125 | 0.015 | 0.015 |
| M67 | 4 | 4 | 4 | 4 | 4 | 0.5 | 0.03 | |
| M68 | 4 | 4 | 4 | 4 | 4 | 4 | 0.5 | 0.015 |
| M69 | 4 | 4 | 2 | 2 | 0.125 | 0.125 | 0.125 | 0.06 |
| M70 | 4 | 4 | 2 | 1 | 1 | 0.125 | 0.125 | 0.06 |
| M71 | 4 | 4 | 4 | 4 | 4 | 4 | 2 | 0.5 |
| M72 | 4 | 4 | 4 | 4 | 4 | 4 | 2 | 0.5 |
| M73 | 4 | 4 | 4 | | | | | |
| M74 | 4 | 4 | 1 | 1 | | | 0.015 | 0.06 |
| M75 | 4 | 4 | 4 | 4 | 4 | 4 | 1 | 0.03 |
| M76 | 4 | 4 | 2 | 2 | 1 | 1 | 0.50 | 0.25 |
| M77 | 4 | 4 | 4 | 4 | 4 | 4 | 2 | 0.125 |
| M78 | 4 | 4 | 4 | 4 | 4 | 2 | 1 | 0.125 |
| M79 | 4 | 4 | 4 | 4 | 4 | 2 | 1 | 0.125 |
| M80 | 4 | 4 | 4 | 4 | 2 | 0.25 | 0.06 | 0.06 |
| M81 | 4 | 4 | 4 | 4 | 2 | 1 | 0.25 | 0.03 |
| M82 | 4 | 4 | 4 | 2 | 1 | 0.25 | 0.125 | 0.06 |
| M83 | 4 | 4 | 4 | 4 | 4 | 4 | 2 | 0.008 |
| M84 | 4 | 4 | 4 | 4 | 4 | 4 | 0.50 | 0.06 |
| M85 | 4 | 4 | 4 | 4 | 4 | 2 | 0.50 | 0.03 |
| M86 | 4 | 4 | 2 | 2 | 1 | 0.125 | 0.06 | 0.015 |
| M87 | 4 | 4 | 4 | 1 | 0.125 | 0.06 | 0.03 | |
| M88 | 4 | 4 | 4 | 4 | 2 | 1 | 0.25 | 0.008 |
| M89 | 4 | 4 | 4 | 4 | 2 | 2 | 0.03 | 0.03 |
| M90 | 4 | 4 | 4 | 4 | 4 | 4 | 4 | 0.06 |
| M91 | 4 | 4 | 4 | 4 | 2 | 0.5 | 0.125 | 0.03 |
| M92 | 4 | 4 | 4 | 4 | 4 | 2 | 0.06 | 0.008 |
| M93 | 4 | 4 | 2 | 0.25 | 0.125 | 0.015 | 0.015 | 0.008 |
| M94 | 4 | 4 | 4 | 4 | 2 | 2 | 0.50 | 0.03 |
| M95 | 4 | 4 | 4 | 4 | 4 | 4 | 0.03 | 0.015 |
| M96 | 4 | 4 | 4 | 4 | 4 | 4 | 2 | 0.015 |
| M97 | 4 | 4 | 4 | 2 | 0.5 | 0.125 | 0.015 | 0.008 |
| M98 | 4 | 4 | 4 | 4 | 4 | 1 | 0.03 | 0.008 |
| M99 | 4 | 4 | 4 | 4 | 4 | 4 | 0.06 | 0.03 |
| M100 | 4 | 4 | 4 | 4 | 4 | 2 | 2 | 0.25 |
| M101 | 4 | 4 | 4 | 2 | 1 | 0.5 | 0.03 | 0.03 |
| M102 | 4 | 4 | 4 | 4 | 2 | 0.06 | 0.008 | |

TABLE 7-continued

Levofloxacin MIC Against *P. aerugiuosa* PAM1001 in Presence of Efflux Pump Inhibitor (EPI)
Minimum Inhibitory Concentration (µg/mL)

| Compound | EPI Conc. 0 µg/mL | EPI Conc. 0.625 µg/mL | EPI Conc. 1.25 µg/mL | EPI Conc. 2.5 µg/mL | EPI Conc. 5 µg/mL | EPI Conc. 10 µg/mL | EPI Conc. 20 µg/mL | EPI Conc. 40 µg/mL |
|---|---|---|---|---|---|---|---|---|
| M103 | 4 | 4 | 4 | 4 | 2 | 1 | 0.03 | 0.015 |
| M104 | 4 | 4 | 4 | 2 | 2 | 1 | 0.015 | 0.008 |

Efflux Pump Inhibitors for Table 8

| Compound | Structure |
|---|---|
| D101 | trans-4-Amino-L-Prolyl-trans-4-((R)-2-Hydroxy-4-Phenylbutyrylamino-L-Proline 3 -Quinolylamide |
| D103 | trans-4-Glycylamino-L-Prolyl-trans-4-((R)-2-Hydroxy-4-Phenylbutyramino)-L-Proline 3-Quinolylamide |
| D104 | cis-4-Glycylamino-L-Prolyl-trans-4-((R)-2-Hydroxy-4-Phenylbutyrylamino)-L-Proline 3 -Quinolylamide |
| D105 | trans-4-Glycylamino-D-Prolyl-trans-4-((R)-2-Hydroxy-4-Phenylbutyrylamino)-L-proline 3-Quinolylamide |
| D106 | trans-4-(N-Methylglycylamino)-L-Prolyl-trans-4-((R)-2-Hydroxy-4-Phenylbutyrylamino)-L-Proline 3-Quinolylamide |
| D108 | trans-4-((S)-3-Amino-2-Hydroxypropionylamino)-L-Prolyl-trans-4-((R)-2-Hydroxy-4-Phenylbutyrylamino)-L-Proline 3- |
| D109 | trans-4-Aminomethyl-L-Prolyl-trans-4-((R)-2-Hydroxy-4-Phenylbutyrylamino)-L-Proline 3-Quinolylamide |
| D110 | 4-(2-Aminoethyl)-L_Prolyl-trans-4-((R)-2-Hydroxy-4-Phenylbutyrylamino)-L-Proline 3 -Quinolylamide |
| D111 | 1-(N-Methylglycyl)-trans-4-Amino-L-Prolyl-trans-4-((R)-2-Hydroxy-4-Phenylbutyrylamino)-L-Proline 3-Ouinolylamide |
| D112 | trans-4-Amino-L-Pipecolinoyl-trans-4-((R)-2-Hydroxy-4-Phenylbutyrylamino)-L-Proline 3-Quinolylamide |
| D113 | cis-4-Amino-L-Pipecolinoyl-trans-4-((R)-2-Hydroxy-4-Phenylbutyrylamino)-L-Proline 3 -Quinolylamide |
| D114 | trans-4-Glycylamino-L-Pipecolinoyl-trans-4-((R)-2-Hydroxy-4-Phenylbutyrylamino)-L-Proline 3 -Quinolylamide |
| D115 | cis-4-Glycylamino-L-Pipecolinoyol-trans-4-((R)-2-Hydroxy-4-Phenylbutyrylamino)-L-Proline 3-Quinolylamide |
| D121 | D-Omithyl-trans-4-(4-Phenylbutanoyl)amino-L-Proline-5-Indanylamide |
| D122 | L-Omithyl-cis-4-(4-phenylbutanoyl)amino-L-proline-5-Indanylamide |
| D124 | D-Ornithyl-cis-4-(4-Phenylbutanoyl)amino-L-Proline 5-Indanylamide |
| D125 | 4-Hydroxy-L-Ornithyl-trans-4-(4-Phenylbutanoyl)amino-L-Proline 5-Indanylamide |
| D201 | trans-4-Glycylamino-L-Prolyl-D-Homophenylalanine 3-Quinolylamide |
| D202 | trans-4-Amino-L-Prolyl-D-Homophenylalanine 3-Quinolylamide |
| D203 | trans-4-Glycylamino-L-Prolyl-D-Homophenylalamine 5-Indanylamide |
| D204 | trans-4-Glycylamino-L-Prolyl-D-Homophenylalamine 3,4-Dimethylphenylamide |
| D205 | trans-4-Glycylamino-L-Prolyl-D-Homophenylalanine 3,5-Dimethylphenylamide |
| D206 | trans-4-Glycylamino-L-Prolyl-D-Homophenylalanine 4-Chloro-3-Methylphenylamide |
| D210 | trans-4-Glycylamino-L-Prolylglycine 4-Benzylphenylamide |
| D301 | trans-4-Glyclamino-L-Proline 4-Phenoxyphenylamide |
| D302 | trans-4-Glycylamino-L-Proline 4-(4'-Methylphenoxy)phenylamide |
| D303 | trans-4-Glycylamino-L-Proline 4-(4'-Chlorophenoxy)phenylamide |
| D304 | trans-4-Glycylamino-L-Proline 4-Phenylaminophenylamide |
| D306 | trans-4-Glycylamino-L-Proline 3-Biphenylamide |
| D307 | trans-4-Glycylamino-D-proline 3-Biphenylamide |
| D308 | trans-4-Glycylamino-L-Proline 4-Benzylphenylamide |
| D313 | trans-4-Glycylamino-L-Proline 4-tert-Butylphenylamide |
| D316 | trans-4-Glycylmino-L-Proline 4-Phenylbenzylamide |
| D317 | trans-4-Glycylamino-L-Proline 4-Benzyloxvphenlamide |
| D318 | trans-4-Glycylamino-L-Proline 3-Benzyloxyphenylamide |
| D319 | trans-4-Glycylamino-L-Proline 4-(Phenylthiomethyl)phenylamide |
| D320 | trans-4-Glycylamino-L-Proline 4-Benzylthiophenylamide |
| D321 | trans-4-((S)-3-Amino-2-Hydoxypropionylamino)-L-Proline 4-Phenoxyphenylamide |
| D322 | trans-4-(2-Aminoethylsulfonylamino)-L-Proline 4-Phenoxyphenylamide |
| D326 | trans-4-Glycylamino-L-Proline 4-Phenylthiazol-2-ylamide |
| D327 | trans-4-Glycylamino-L-Proline 3-(6-Benzyl)quinolylamide |
| D329 | trans-4-Amino-L-Pipecolinoyl-(4-Phenoxyphenyl)amide |
| D330 | trans-4-Glycylamino-L-Pipecolinoyl 4-Phenoxyphenylamide |
| D331 | trans-4-Aminomethyl-L-Proline 4-Phenoxyphenylamide |
| D401 | 1-(trans-4-Glycylamino-L-Prolyl)-4-(3-Chlorophenyl)piperazine |
| D402 | 1-[trans-4-((2S)-3-Amino-2-Hydroxypropionylamino)-D-Prolyl]-4-(3-Chloro-2-Methylphenyl)peperazine |
| D403 | 1-(N-trans-4-Glycylamino-L-Prolyl)-4-(4-Chlorophenyl)piperazine |
| D405 | 1-(trans-4-Glycylamino-L-Prolyl)-4-(2-Chlorophenyl)piperazine |
| D407 | 1-(trans-4-Aminomethyl-L-Prolyl)-4-(3-Chloro-2-methylphenyl)piperazine |
| D408 | 1-(trans-4-Glycylamino-L-Prolyl)-4-(4-Phenylbutanoyl)piperazine |
| D409 | (2R)-4-Benzyl-1-(trans-4-Glycylamino-D-Prolyl)-2-Phenethylpiperazine |
| D413 | 1-(trans-4-Glycylamino-L-Prolyl)-4-(4-Benzyloxyphenoxy)piperidine |
| D414 | 1-(trans-4-Glycylamino-L-Prolyl)-4-(3,5-Dichlorophenoxy)piperidine |
| D415 | 1-(trans-4-Glycylamino-D-Prolyl)-4-(3,5-Dichlorophenoxy)piperidine |
| D416 | trans-4-Glycylamino-L-Prolyl-4-(2-Chloro-5-Methylphenoxy)piperidine |
| D501 | (2S,4R)-4-Glycylamino-2-(4-Biphenyloxy)methylpyrrolidine |
| D502 | (2S,4R)-4-Glycylamino-2-(3-Biphenyloxy)methylpyrrolidine |
| D503 | (2R,4S)-4-Glycylamino-2-(4-Biphenyloxy)methylpyrrolidine |
| D504 | (2R,4S)-4-Glycylamino-2-(3-Biphenyloxy)methylpyrrolidine |
| D601 | trans-4-(3-Biphenyloxy)-L-Proline 2-Aminoethylamide |
| D602 | (2S,4R)-2-(2-Amino-1-hydroxyethyl)-4-(3-biphenyloxy)pyrrolidine |

-continued

Efflux Pump Inhibitors for Table 8

| Compound | Structure |
|---|---|
| D701 | 1-(N-trans-4-Glycylamino-L-Prolylamino)-3-(4-Phenylpropanoylamino)benzene |
| D702 | 2-(trans-4-Glycylanino-L-Prolylamino)-6-(4-Phenylpropanoylamino)pyridine |
| D801 | (2S,4R)-4-Glycylamino-2-((E and Z)-4-Phenylstyryl)pyrrolidine |

TABLE 8

Inhibition of growth of *P. aeruginosa* PAM1001 in Presence of Efflux Pump Inhibitor (EPI) and Levofloxacin (0.25 μg/mL) Inhibition (%)

| Example Number | Concentration of Compound | | | | |
|---|---|---|---|---|---|
| | 2.5 μg/mL | 5 μg/mL | 10 μg/mL | 20 μg/mL | 40 μg/mL |
| D101 | NT | NT | NT | 20 | 94 |
| D103 | 17 | 6 | 99 | 100 | 100 |
| D104 | 18 | 19 | 14 | 62 | 100 |
| D105 | 19 | 18 | 50 | 99 | 101 |
| D106 | 19 | 19 | 20 | 19 | 100 |
| D108 | 23 | 22 | 22 | 100 | 101 |
| D109 | 17 | 21 | 98 | 100 | 100 |
| D110 | 20 | 20 | 100 | 100 | 100 |
| D111 | 20 | 20 | 19 | 27 | 100 |
| D112 | 20 | 20 | 17 | 58 | 101 |
| D113 | 20 | 32 | 15 | 15 | 100 |
| D114 | 20 | 22 | 90 | 100 | 100 |
| D115 | 15 | 16 | 8 | 50 | 100 |
| D121 | 15 | 99 | 100 | 100 | 100 |
| D122 | 16 | 99 | 100 | 100 | 99 |
| D123 | 19 | 59 | 100 | 100 | 100 |
| D124 | 19 | 100 | 100 | 100 | 100 |
| D125 | 15 | 100 | 100 | 100 | 100 |
| D201 | 17 | 9 | 99 | 100 | 100 |
| D202 | NT | NT | NT | 21 | 86 |
| D203 | 18 | 17 | 100 | 100 | 100 |
| D204 | 18 | 16 | 3 | 100 | 100 |
| D205 | 16 | 13 | 100 | 100 | 100 |
| D206 | 16 | 10 | 100 | 99 | 100 |
| D207 | 20 | 17 | 94 | 100 | 100 |
| D208 | 18 | 17 | 99 | 100 | 100 |
| D210 | 14 | 16 | 12 | 99 | 100 |
| D301 | 17 | 14 | 81 | 99 | 99 |
| D302 | 22 | 17 | 97 | 100 | 100 |
| D303 | 18 | 91 | 100 | 100 | 99 |
| D304 | 17 | 15 | 10 | -11 | 100 |
| D306 | 19 | 7 | 93 | 100 | 99 |
| D307 | 24 | 5 | 90 | 100 | 100 |
| D308 | 16 | 14 | 98 | 100 | 100 |
| D313 | 17 | 17 | 96 | 99 | 99 |
| D316 | 20 | 20 | 21 | 82 | 100 |
| D317 | 20 | 18 | -1 | 99 | 99 |
| D318 | 17 | 16 | 19 | 99 | 99 |
| D319 | 19 | 18 | 99 | 100 | 100 |
| D320 | 23 | 21 | 97 | 100 | 100 |
| D321 | 15 | 14 | 84 | 100 | 100 |
| D322 | 19 | 19 | 17 | 99 | 100 |
| D326 | 18 | 19 | 17 | 13 | 74 |
| D327 | 20 | 19 | 99 | 100 | 100 |
| D329 | 20 | 20 | 17 | 16 | 97 |
| D330 | 19 | 18 | 12 | 100 | 100 |
| D331 | 17 | 9 | -10 | 100 | 100 |
| D401 | 21 | 19 | 15 | 4 | 96 |
| D402 | 19 | 71 | 99 | 100 | 101 |
| D403 | 25 | 22 | 22 | 4 | 61 |
| D405 | 20 | 19 | 16 | -11 | 58 |
| D407 | 100 | 100 | 99 | 99 | 98 |
| D409 | 22 | 16 | 99 | 100 | 100 |
| D413 | 13 | 8 | 97 | 100 | 100 |
| D414 | 19 | 98 | 100 | 100 | 100 |
| D415 | 13 | 99 | 100 | 100 | 100 |
| D416 | 21 | 11 | 87 | 99 | 99 |
| D501 | 1 | 98 | 100 | 100 | 98 |
| D502 | 13 | 88 | 99 | 100 | 100 |
| D503 | 22 | 15 | 100 | 100 | 100 |
| D504 | 22 | 3 | 74 | 100 | 99 |
| D601 | 20 | 18 | 16 | 86 | 100 |
| D602 | 98 | 99 | 100 | 100 | 100 |
| D603 | 13 | 97 | 100 | 100 | 100 |
| D701 | 17 | 10 | 96 | 100 | 100 |
| D702 | 19 | 15 | 82 | 100 | 100 |
| D801 | 8 | 63 | 99 | 99 | 99 |

In vivo Evaluation of Efflux Pump Inhibitor Compounds

Inhibitors of the bacterial efflux pumps are generally initially characterized in vitro. Those which show effective inhibition of the pump(s) and which show synergistic activity with antibiotics are selected for evaluation in vivo. Efficacy testing will be done using standard procedures. Primary efficacy evaluation may be done using the murine septicemia model (M. G. Bergeron, 1978, *Scand. J. Infect. Dis. Suppl.* 14:189–206; S. D. Davis, 1975, *Antimicrob. Agents Chemother.* 8:50–53). In this model a supra-lethal dose of bacteria is used to challenge the rodents. Treatment is initiated, varying either or both time(s) of treatment and dose of antibiotic. In these experiments both the antibiotic and the efflux pump inhibitor doses are varied. A positive result is indicated by significant increase in protection from the lethal infection by the combination of the potentiator (the efflux pump inhibitor) and the antibiotic versus the antibiotic alone.

A second efficacy model which is used is the mouse soft tissue infection model (Vogelman et al., 1988, *J. Infect. Dis.* 157:287–298). In this model anesthetized mice are infected with an appropriate titer of bacteria in the muscle of the hind thigh. Mice are either neutropenic (cyclophosphamide treated at 125 mg/kg on days −4, −2, and 0) or immunocompetent. The infecting dose is commonly $10^5$–$10^6$ colony forming units per animal. Treatment with the combination of the efflux pump inhibitor and/or antibiotics follows infection, or can occur before infection. The proliferation (or death) of the bacteria within the thigh muscle is monitored over time. Effective combinations show greater activity than the antibiotic alone. Activity is defined as reduction in growth rate of the test bacteria in the murine tissue.

Another model useful for assessing the effectiveness of the efflux pump inhibitors is the diffusion chamber model (Malouin et al., 1990, *Infect. Immun.* 58:1247–1253; Day et al., *J. Infect.* 2:39–51; Kelly et al., 1989, *Infect. Immun.* 57:344–350). In this model rodents have a difflusion chamber surgically placed in their peritoneal cavity. The chamber can consist of a polypropylene cylinder with semipermeable membranes covering the cylinder ends. Difflusion of peritoneal fluid into and out of the chamber provides nutrients for the microbes. The proliferation of the bacteria in the presence and absence of the antibiotic/efflux pump inhibitor is compared to the antibiotic alone. Dose ranging of the combination and the antibiotic alone are done to assess effectiveness of the antimicrobial and combinations.

A tertiary model useful as a stringent test of the efflux pump inhibitor/antibiotic combination is the endocarditis model (J. Santoro and M. E. Levinson, 1978, *Infect. Immun.* 19:915–918). Either rats or rabbits are effectively used in this model. The effectiveness of combinations of efflux inhibitor and antibiotic are compared to antibiotic alone. The end point is usually viable cells remaining in the cardiac vegetations at the end of treatment.

The examples of infection models provided are not limiting. As understood by those skilled in the art, other models can be utilized as appropriate for a specific infecting microbe. In particular, cell-based infection models may be used in some circumstances instead of animal models.

Pharmaceutical Compositions and Modes of Administration

The particular compound that is an efflux pump inhibitor can be administered to a patient either by itself, or in combination with an antimicrobial, e.g., antibacterial, agent, or in pharmaceutical compositions where it is mixed with a suitable carrier(s) or excipient(s) or diluent(s). A combination of an efflux pump inhibitor with an antimicrobial agent can be of at least two different types. In one, a quantity of an efflux pump inhibitor is combined with a quantity of an antimicrobial agent in a mixture, e.g., in a solution or powder mixture. In such mixtures, the relative quantities of the inhibitor and the antimicrobial agent may be varied as appropriate for the specific combination and expected treatment. In a second type of combination an inhibitor and an antimicrobial agent can be covalently linked in such manner that the linked molecule can be cleaved within the cell. However, the term "in combination" can also refer to other possibilities, including serial administration of an inhibitor and another antimicrobial agent. In addition, an efflux pump inhibitor and/or another antimicrobial agent may be administered in pro-drug forms, i.e. the compound is administered in a form which is modified within the cell to produce the functional form. In treating a patient exhibiting a disorder of interest, a therapeutically effective amount of an agent or agents such as these is administered. A therapeutically effective dose refers to that amount of the compound(s) that results in amelioration of symptoms or a prolongation of survival in a patient, and may include elimination of a microbial infection.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred. The data obtained from these cell culture assays and animal studies can be used in formulating a range of dosage for use in human. The dosage of such compounds lies preferably within a range of circulating concentrations that include the $ED_{50}$ with little or no toxicity. The dosage may vary within this range depending upon the dosage form employed and the route of administration utilized. It is preferable that the therapeutic serum concentration of an efflux pump inhibitor should be in the range of 0.1–100 µg/mL.

For any compound used in the method of the invention, the therapeutically effective dose can be estimated initially from cell culture assays. For example, a dose can be formulated in animal models to achieve a circulating plasma concentration range that includes the $IC_{50}$ as determined in cell culture. Such information can be used to more accurately determine useful doses in humans. Levels in plasma may be measured, for example, by HPLC.

In particular preferred embodiments, the efflux inhibitor in a pharmaceutical composition has a structure as shown by the generic structures described above.

The exact formulation, route of administration and dosage can be chosen by the individual physician in view of the patient's condition. (See e.g. Fingl et al., in THE PHARMACOLOGICAL BASIS OF THERAPEUTICS, 1975, Ch. 1 p. 1). It should be noted that the attending physician would know how to and when to terminate, interrupt, or adjust administration due to toxicity, or to organ dysfunctions. Conversely, the attending physician would also know to adjust treatment to higher levels if the clinical response were not adequate (precluding toxicity). The severity of the condition may, for example, be evaluated, in part, by standard prognostic evaluation methods. Further, the dose and perhaps dose frequency, will also vary according to the age, body weight, and response of the individual patient. A program comparable to that discussed above may be used in veterinary medicine.

Depending on the specific infection being treated, such agents may be formulated and administered systemically or locally. Techniques for formulation and administration may be found in *Remington's Pharmaceutical Sciences*, 18th ed., Mack Publishing Co., Easton, Pa. (1990). Suitable routes may include oral, rectal, transdermal, vaginal, transmucosal, or intestinal administration; parenteral delivery, including intramuscular, subcutaneous, intramedullary injections, as well as intra-thecal, direct intraventricular, intravenous, intraperitoneal, intranasal, or intraocular injections, just to name a few.

For injection, the agents of the invention may be formulated in aqueous solutions, preferably in physiologically compatible buffers such as Hank's solution, Ringer's solution, or physiological saline buffer. For such transmucosal administration, penetrants appropriate to the barrier to be permeated are used in the formulation. Such penetrants are generally known in the art.

Use of pharmaceutically acceptable carriers to formulate the compounds herein disclosed for the practice of the invention into dosages suitable for systemic administration is within the scope of the invention. With proper choice of carrier and suitable manufacturing practice, the compositions of the present invention, in particular, those formulated as solutions, may be administered parenterally, such as by intravenous injection. The compounds can be formulated readily using pharmaceutically acceptable carriers well known in the art, into dosages suitable for oral administration. Such carriers enable the compounds of the invention to be formulated as tablets, pills, capsules, liquids, gels, syrups, slurries, suspensions and the like, for oral ingestion by a patient to be treated.

Pharmaceutical compositions suitable for use in the present invention include compositions wherein the active ingredients are contained in an effective amount to achieve its intended purpose. Determination of the effective amounts is well within the capability of those skilled in the art, especially in light of the detailed disclosure provided herein.

In addition to the active ingredients, these pharmaceutical compositions may contain suitable pharmaceutically acceptable carriers including excipients and auxiliaries which facilitate processing of the active compounds into preparations which can be used pharmaceutically. The preparations formulated for oral administration may be in the form of tablets, dragees, capsules, or solutions. The pharmaceutical compositions of the present invention may be manufactured in a manner that is itself known, e.g., by means of conventional mixing, dissolving, granulating, dragee-making, levitating, emulsifying, encapsulating, entrapping or lyophilizing processes.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dye-stuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added.

EXAMPLES

The compounds of the present invention may be readily prepared in accordance with the following synthesis schemes, as illustrated in the specific examples provided. However, those skilled in the art will recognize that other synthetic pathways for forming the compounds of this invention can be utilized, and that the following is provided merely by way of example, and is not limiting to the present invention. It will be further recognized that various protecting and deprotecting strategies will be employed which are standard in the art (see, e.g., "Protective Groups in Organic Synthesis" by Greene and Wuts). Those skilled in the art will recognize that the selection of any particular protecting group (e.g., amine and carboxyl protecting groups) will depend on the stability of the protected moiety with regard to the subsequent reaction conditions and will understand the appropriate selections.

Further illustrating the knowledge of those skilled in the art is the following sampling of the extensive chemical literature:

1) "Chemistry of the Amino Acids" by J. P. Greenstein and M. Winitz, Wiley and Sons, Inc. New York, N.Y. (1961).
2) "Comprehensive Organic Transformations" by R. Larock, VCH Publishers (1989)
3) T. D. Ocain and D. H. Rich, J. Med. Chem., 31, pp. 2193–2199 (1988).
4) E. M. Gordon, J. D. Godfrey, N. G. Delaney, M. M. Assad, Von Langen, and D. W. Cushman, J. Med. Chem., 31, pp. 2199–2210 (1988).
5) "Practice of Peptide Synthesis" by M. Bodanszy and A. Bodansky, Springer-Verlag, New York, N.Y. (1984).
6) "Protective Groups in Organic Synthesis" by T. Greene and P. Wuts (1991).
7) "Asymmetric Synthesis: Construction of Chiral Molecules Using Amino Acids" by G. M. Coppola and H. F. Schuster, John Wiley and Sons, New York, N.Y. (1987).
8) "The Chemical Synthesis of Peptides" J. Jones, Oxford University Press, New York, N.Y. (1991).
9) "Introduction to Peptide Chemistry" by P. D. Bailey, John Wiley an Sons, New York, N.Y. (1992).
10) "Synthesis of Optically Active a-Amino Acids" by R. M. Williams, Pergamon Press, Oxford, U.K. (1989).

TYPE I

Compound D101 (A)–(E)

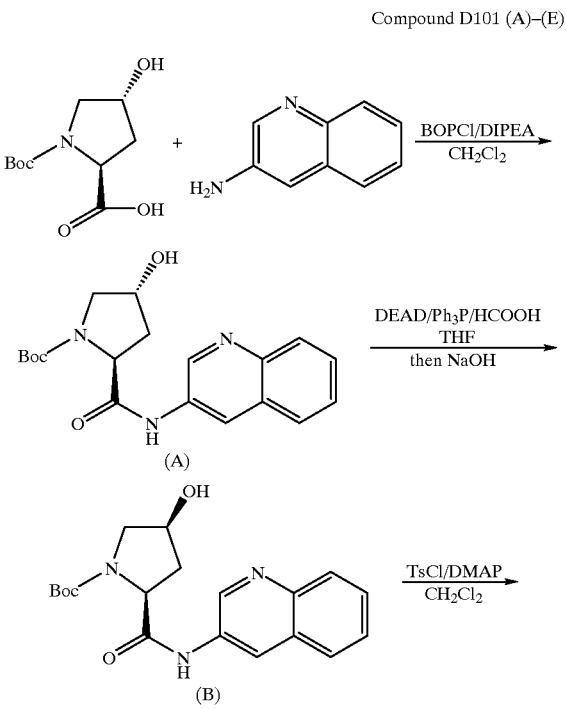

51
-continued
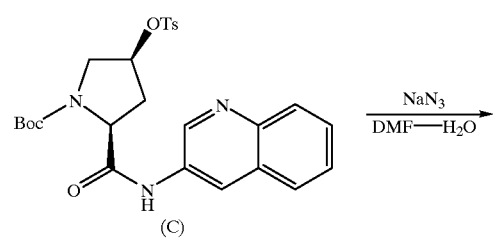
(C)
NaN₃ / DMF—H₂O →
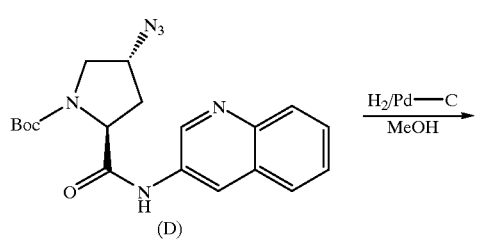
(D)
H₂/Pd—C / MeOH →
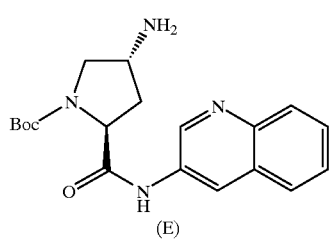
(E)
(F)
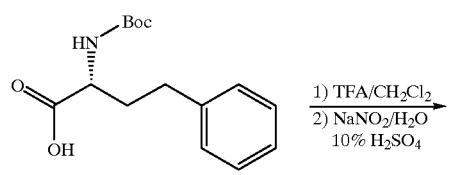
1) TFA/CH₂Cl₂
2) NaNO₂/H₂O
   10% H₂SO₄
→
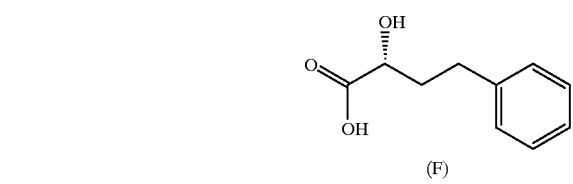
(F) (G)–(H)
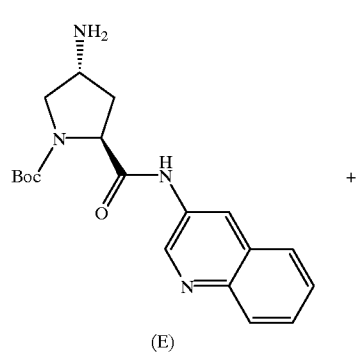
(E)
+
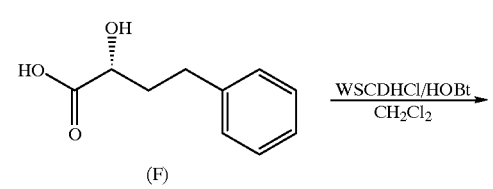
(F)
WSCDHCl/HOBt / CH₂Cl₂ →
52
-continued
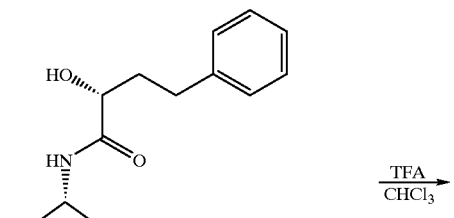
(G)
TFA / CHCl₃ →
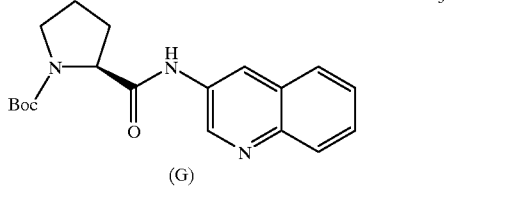
(H)
(I)–(O)
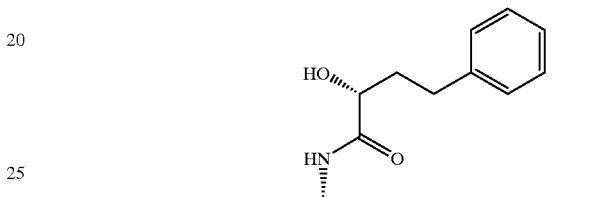
DEAD/PPh₃ / HCOOH/THF →
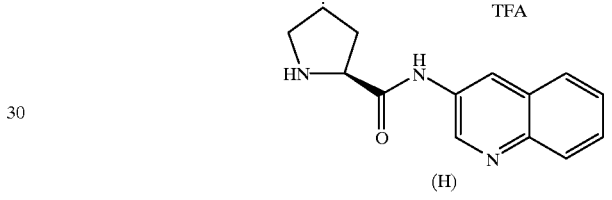
(I)
NaOH—H₂O / THF →
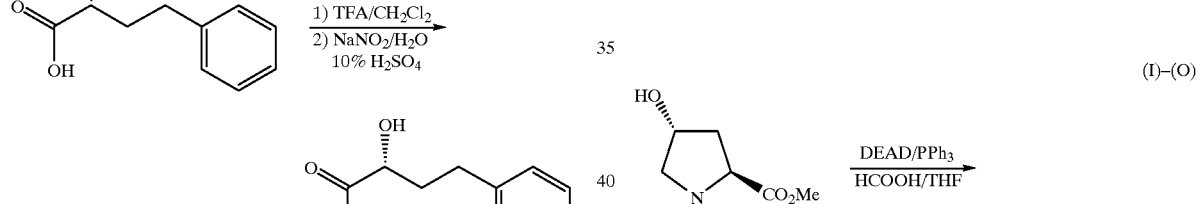
(J)
TsCl/DMAP / CH₂Cl₂ →
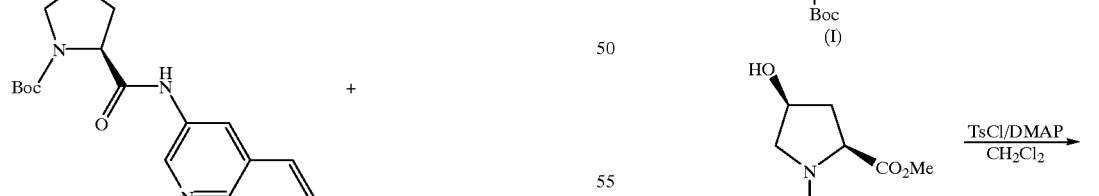
(K)
NaN₃ / DMF—H₂O →

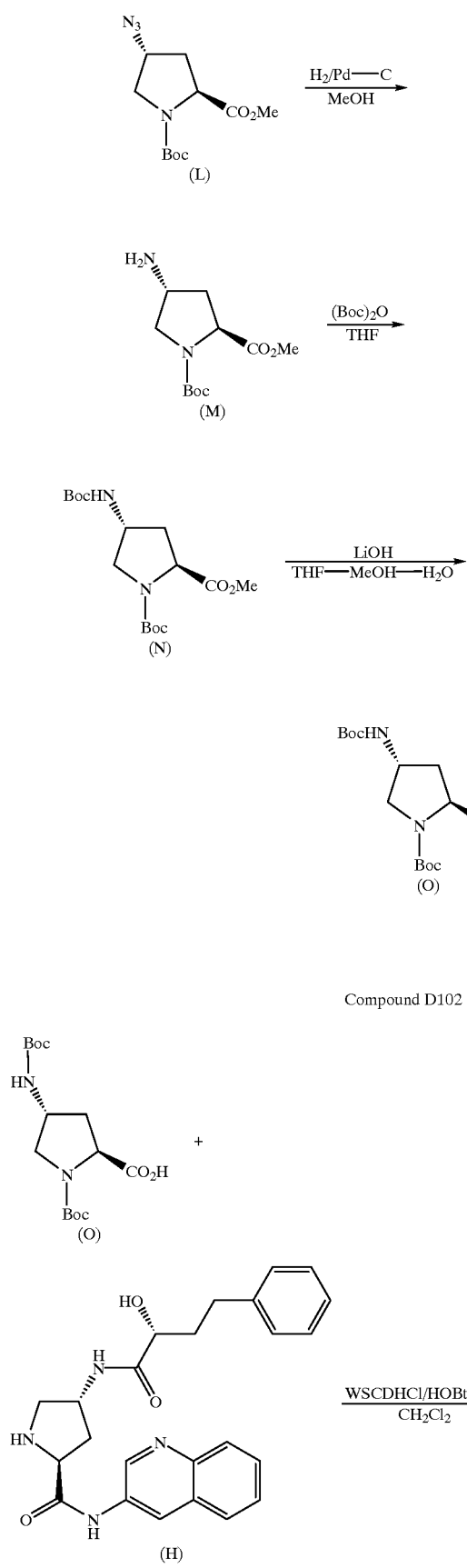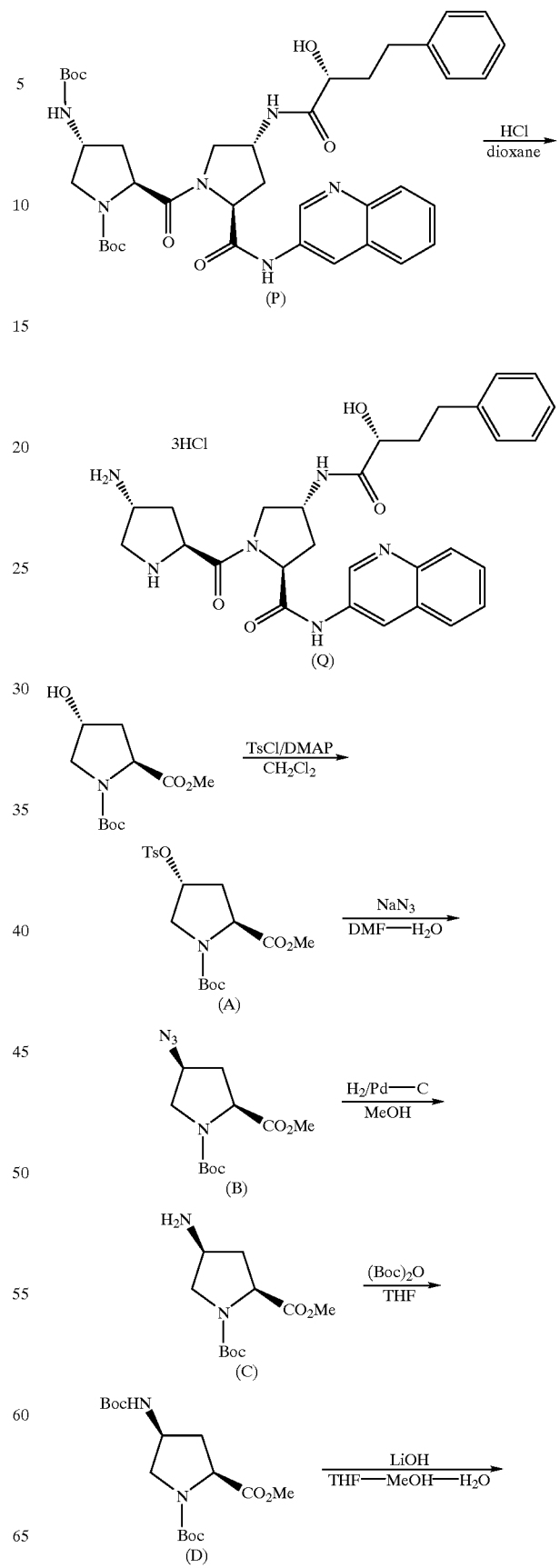

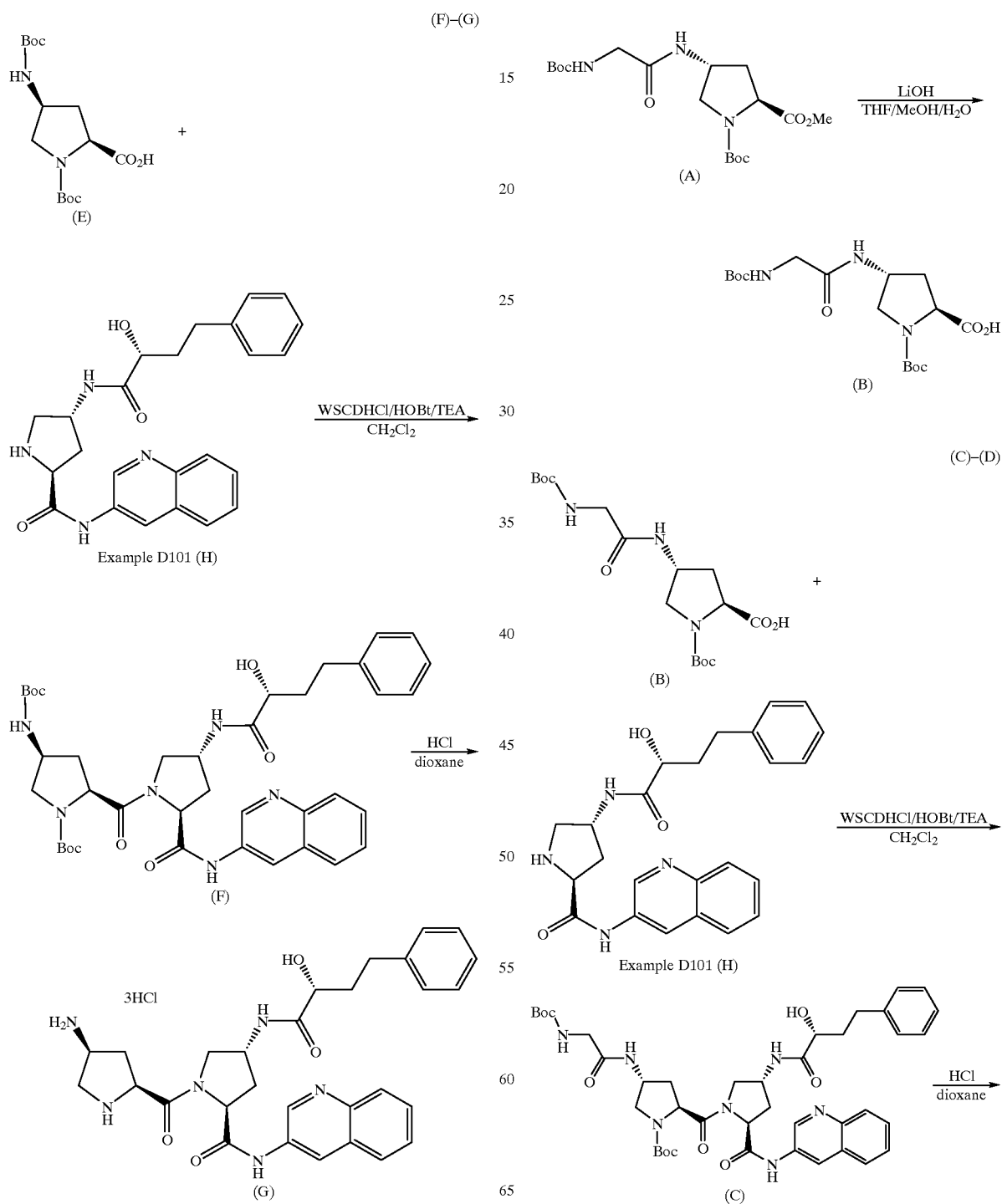

-continued
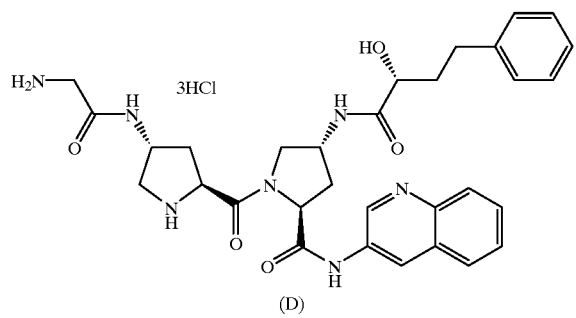
(D)
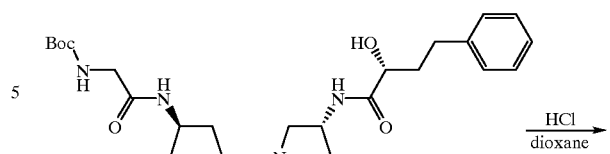
Compound D104 (A)–(B)
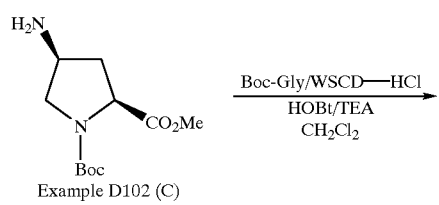
Example D102 (C)
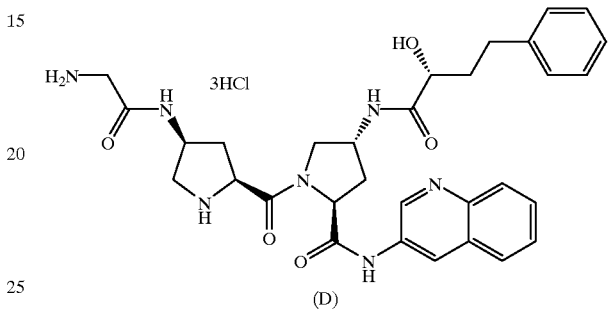
(D)
Compound D105 (A)–(F)
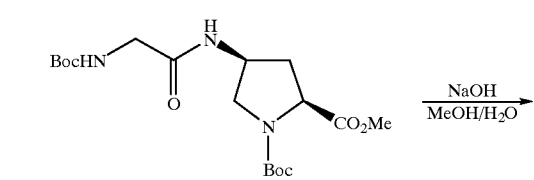
(A)
(A)
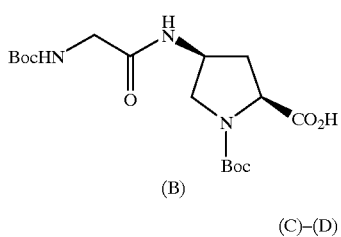
(B)
(C)–(D)
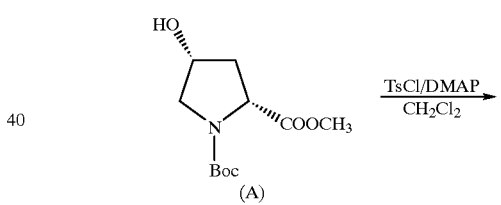
(B)
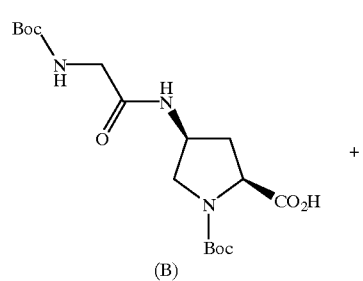
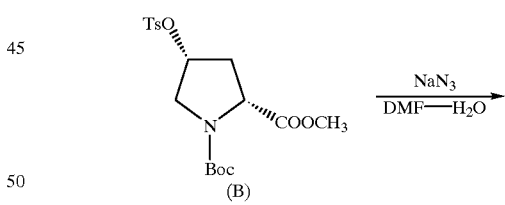
(C)
+
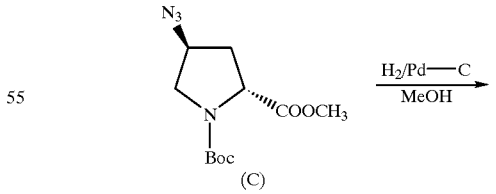
(D)
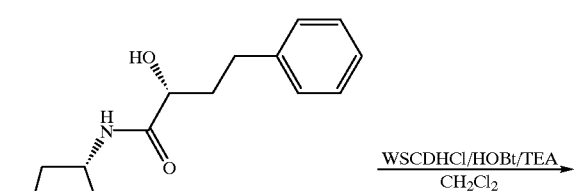
Example D101 (H)
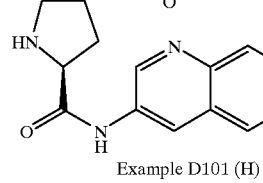
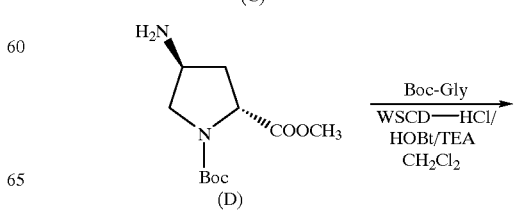

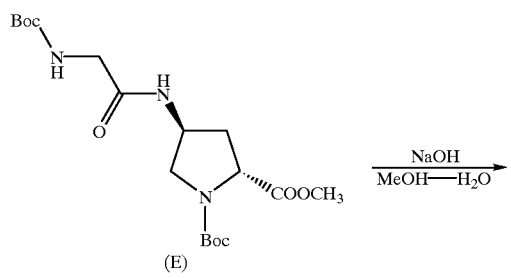
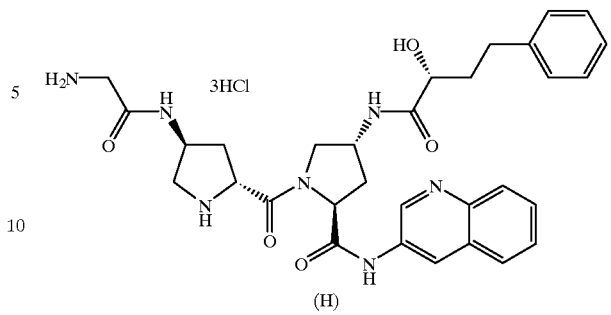
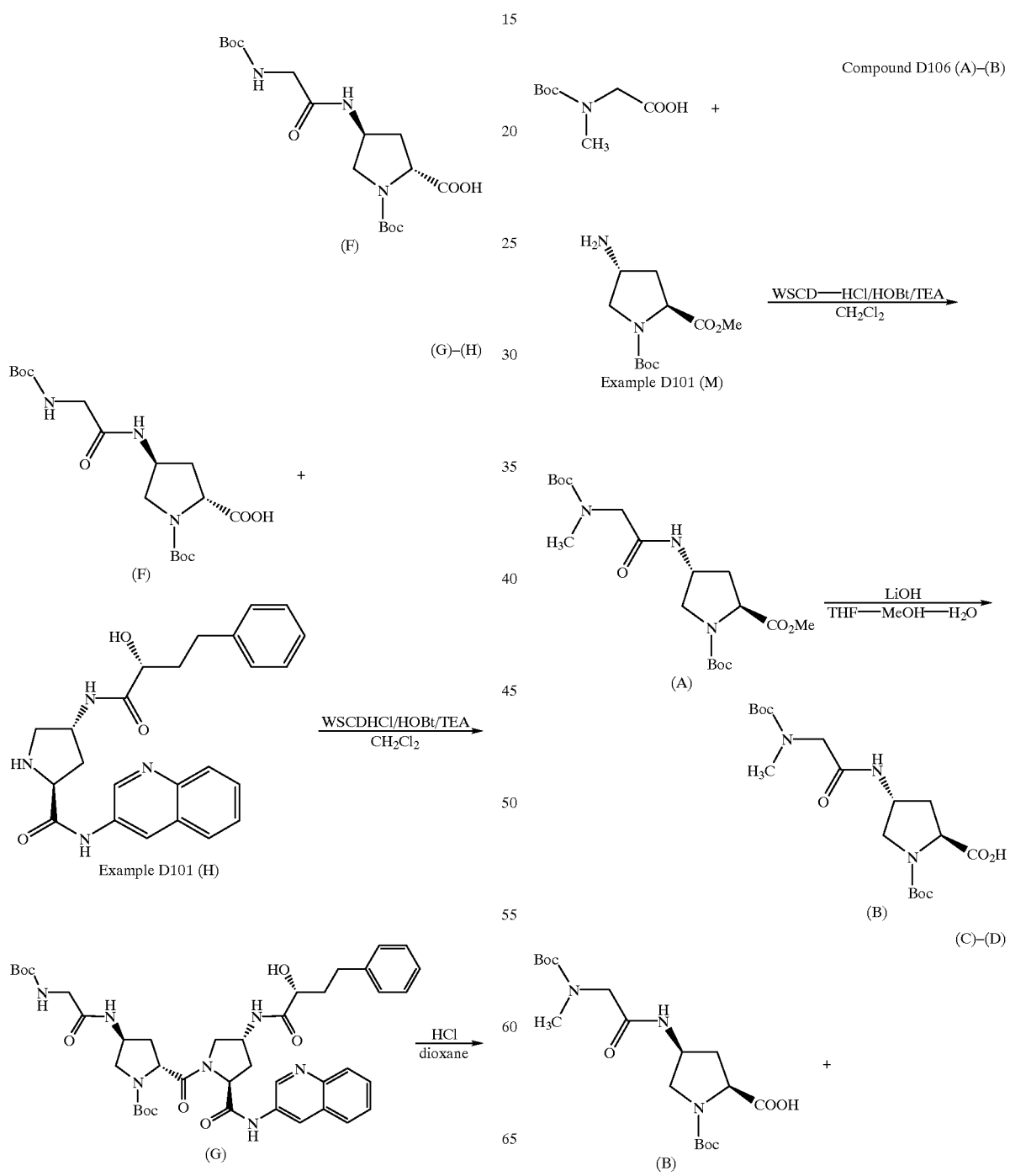
Compound D106 (A)–(B)
Example D101 (M)
(A)
(B)
(C)–(D)

61
-continued
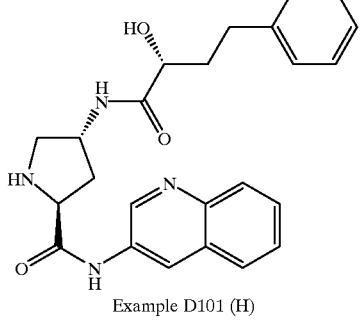
Example D101 (H)
WSCDHCl/HOBt/TEA / CH₂Cl₂ →
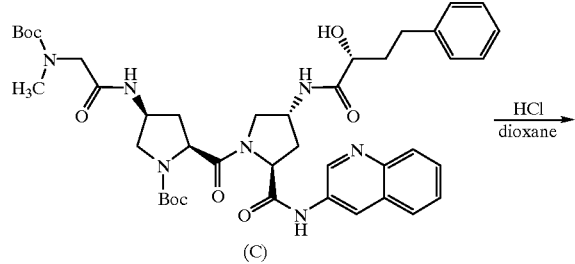
(C)
HCl / dioxane →
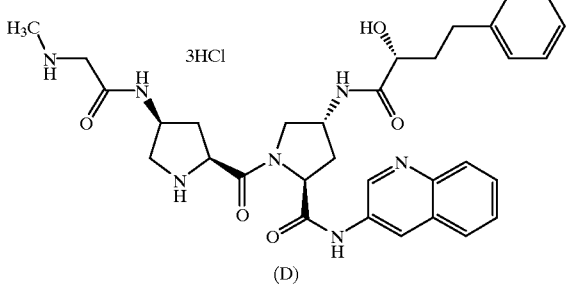
Compound D107 (A)–(B)
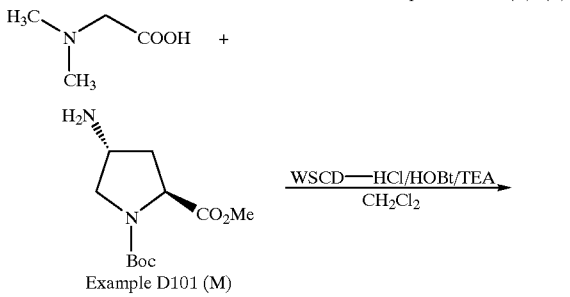
Example D101 (M)
WSCD—HCl/HOBt/TEA / CH₂Cl₂ →
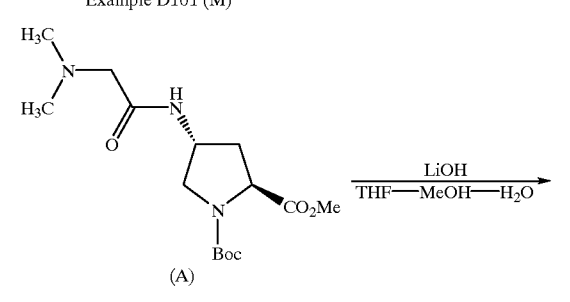
(A)
LiOH / THF—MeOH—H₂O →
62
-continued
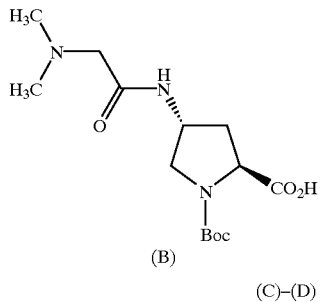
(B)
(C)–(D)
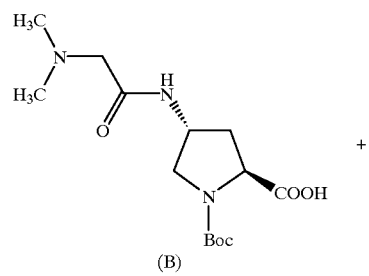
(B)
+
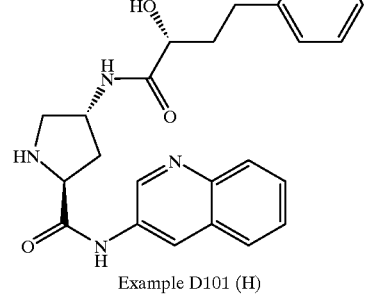
Example D101 (H)
WSCDHCl/HOBt/TEA / CH₂Cl₂ →
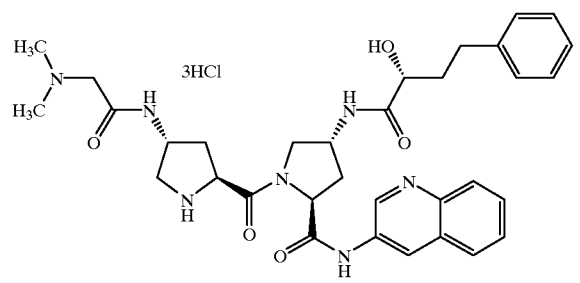
(C)
HCl / dioxane →
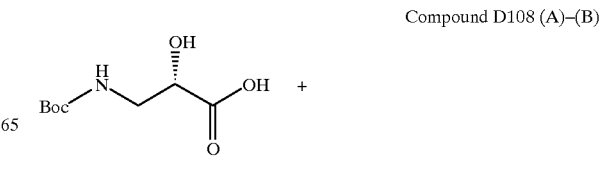
(D)
Compound D108 (A)–(B)
+

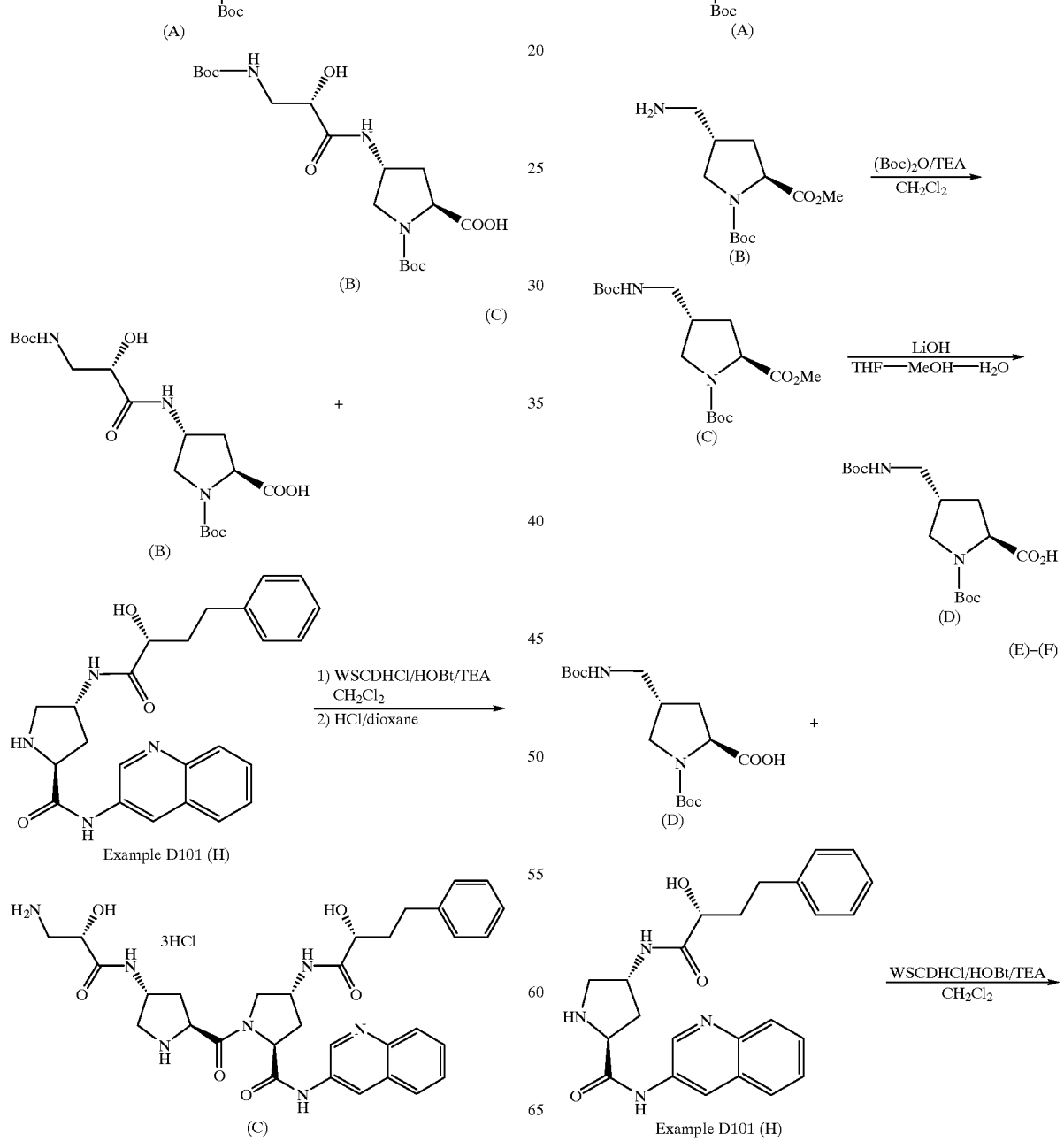

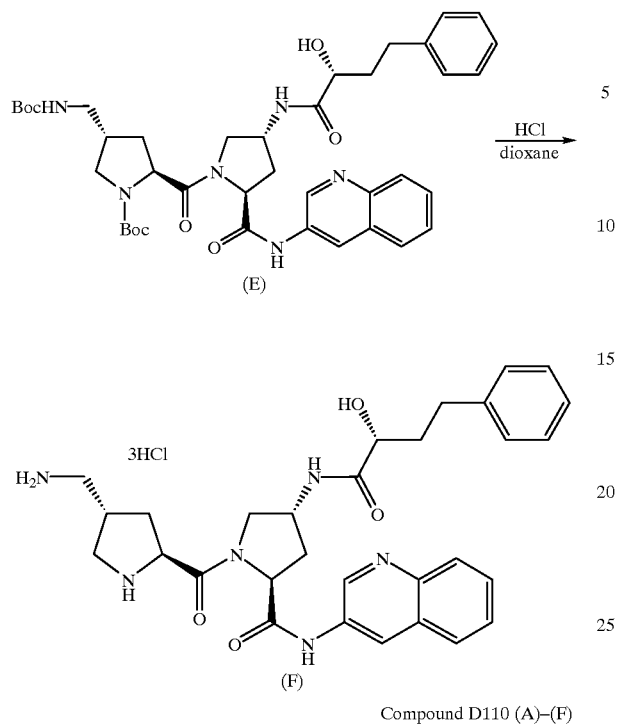
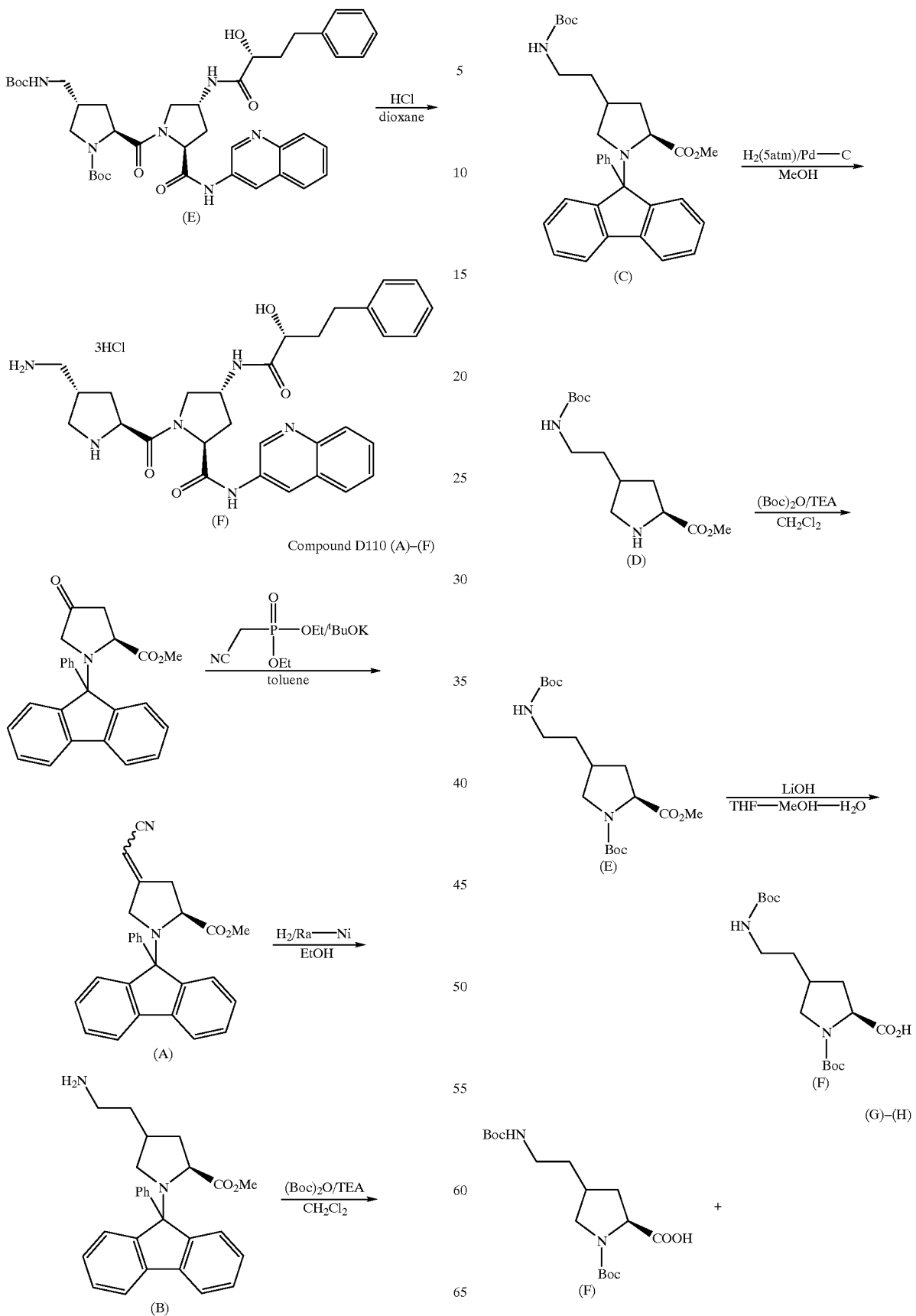
Compound D110 (A)–(F)

-continued
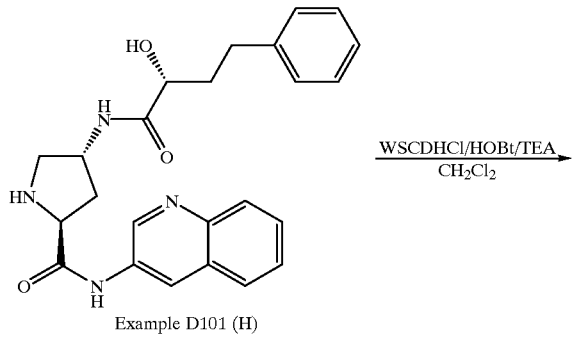
Example D101 (H)
WSCDHCl/HOBt/TEA / CH₂Cl₂ →
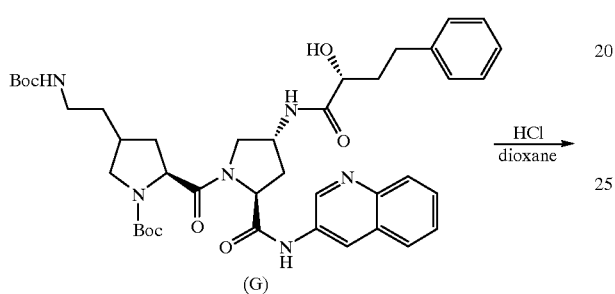
(G)
HCl / dioxane →
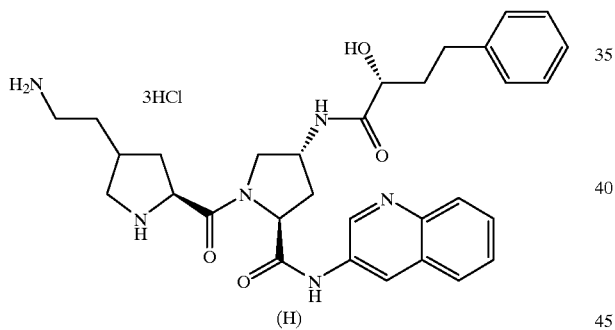
(H)
Compound D111 (A)–(F)
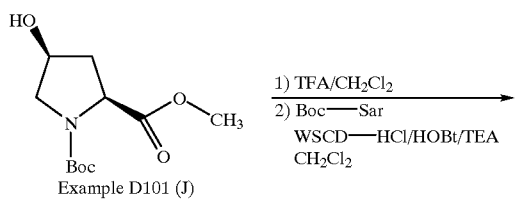
Example D101 (J)
1) TFA/CH₂Cl₂
2) Boc—Sar
WSCD—HCl/HOBt/TEA
CH₂Cl₂
→
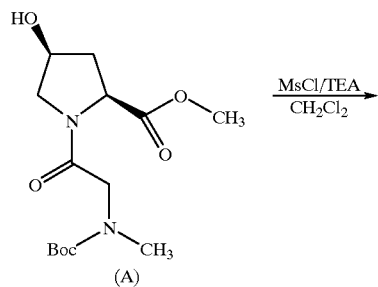
(A)
MsCl/TEA / CH₂Cl₂ →
-continued
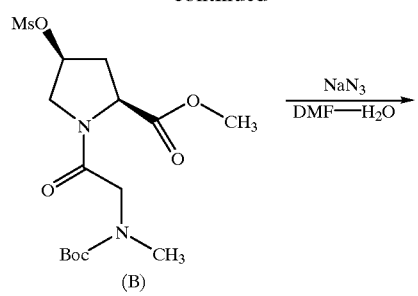
(B)
NaN₃ / DMF—H₂O →
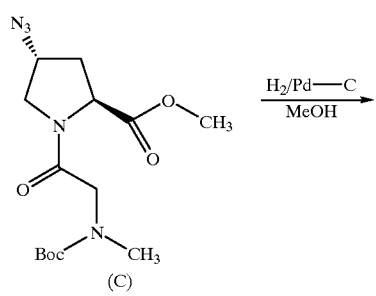
(C)
H₂/Pd—C / MeOH →
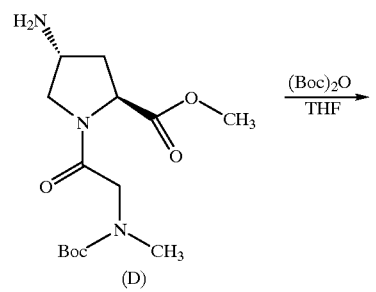
(D)
(Boc)₂O / THF →
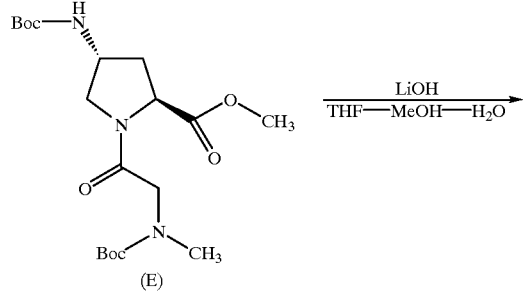
(E)
LiOH / THF—MeOH—H₂O →
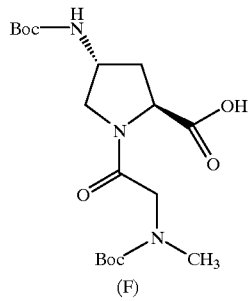
(F)

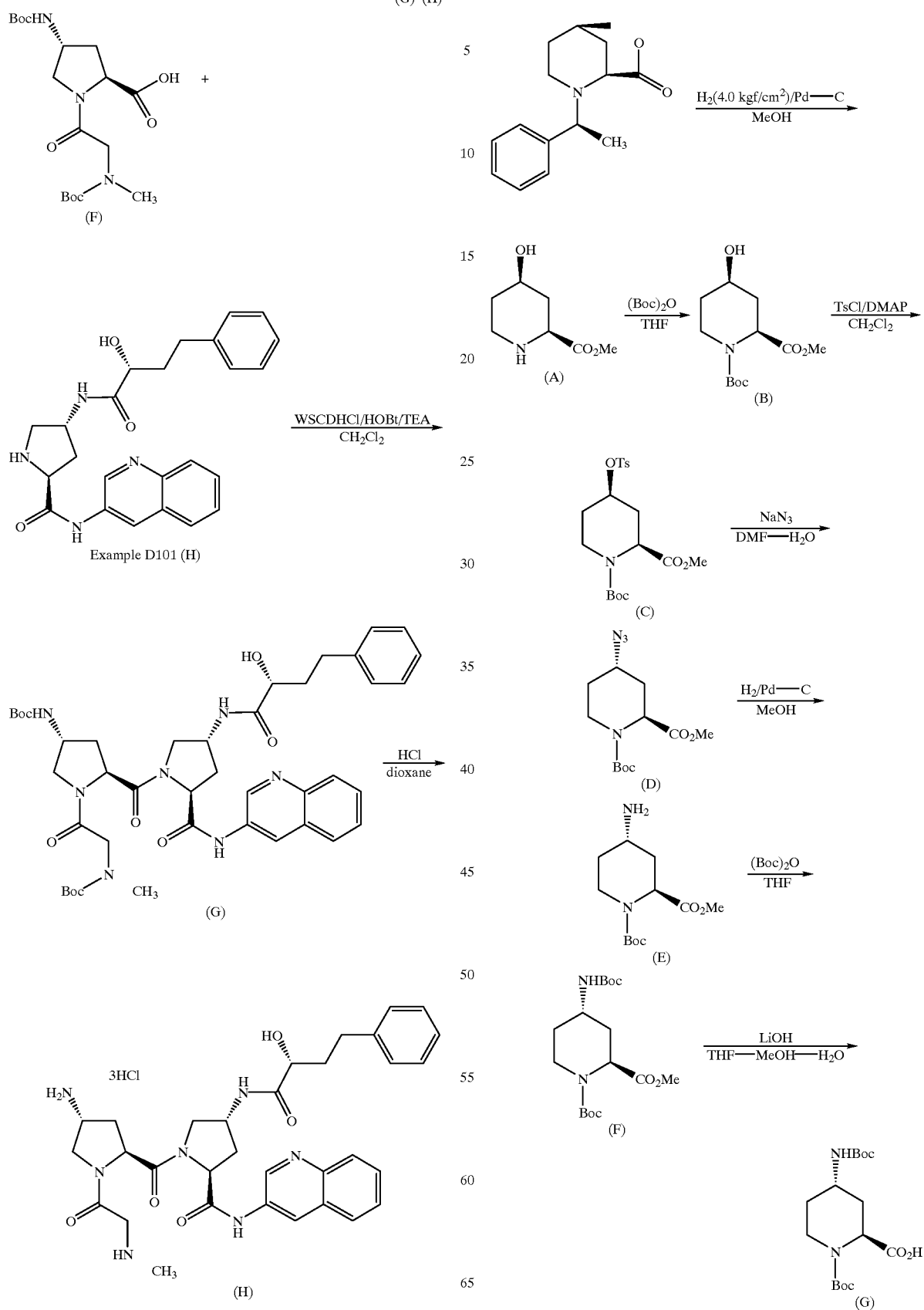

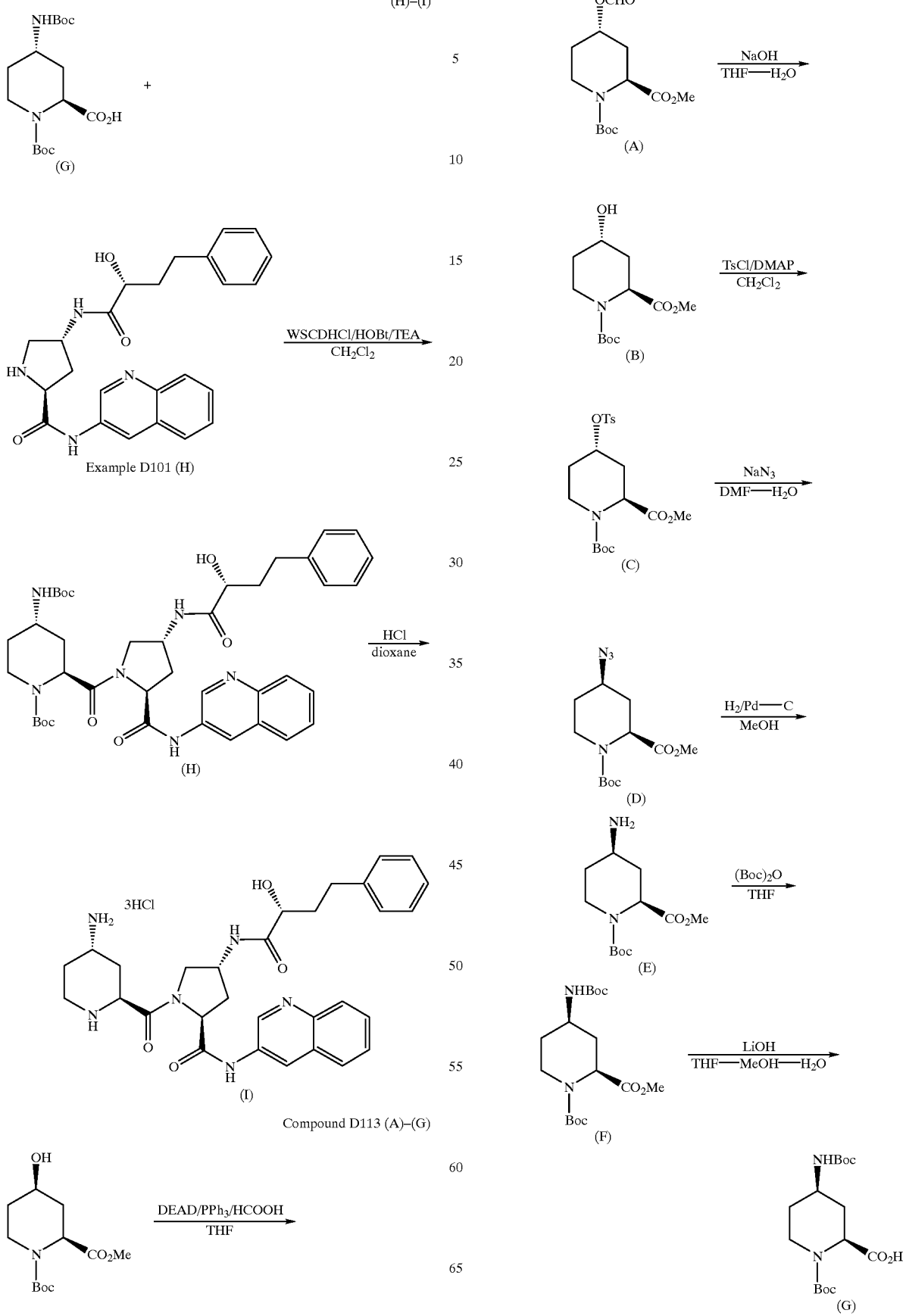
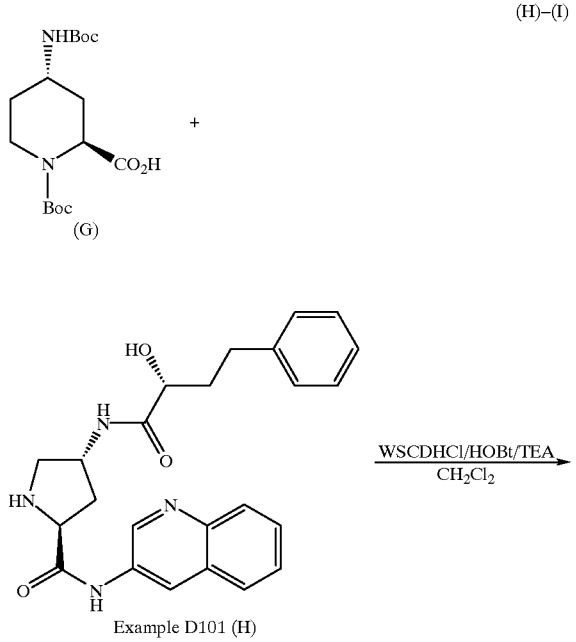

-continued
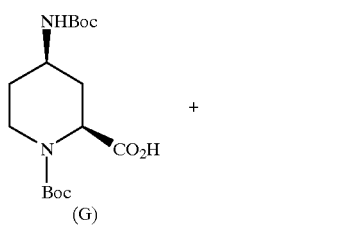
(G)
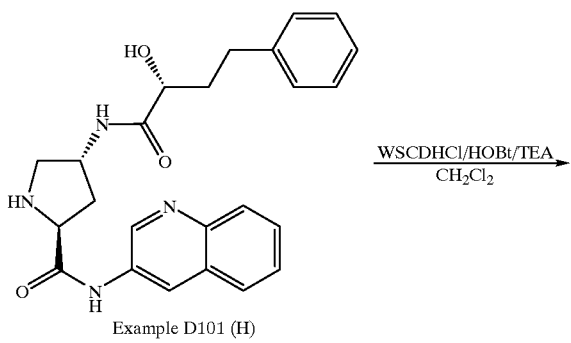
Example D101 (H)
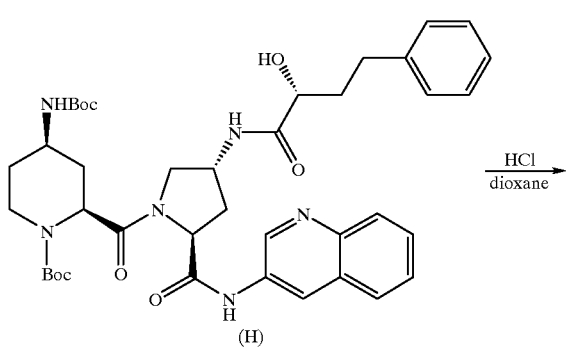
(H)
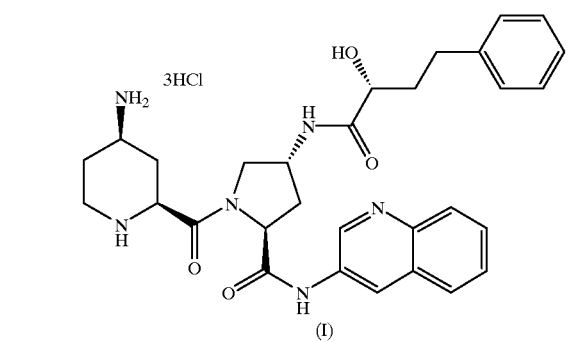
Compound D114 (A)–(B)
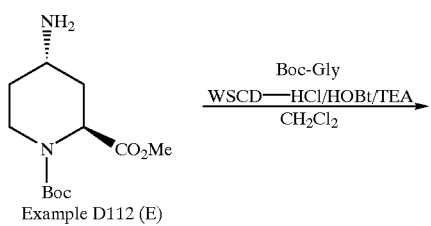
Example D112 (E)
(H)–(I)
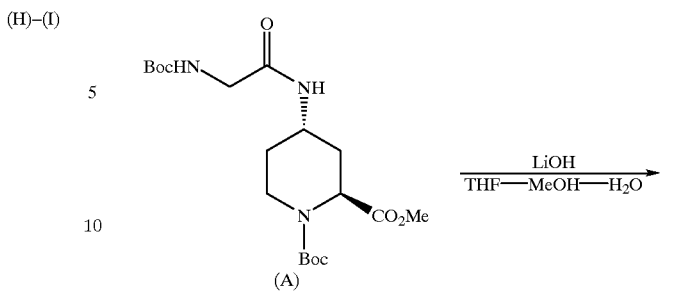
(A)
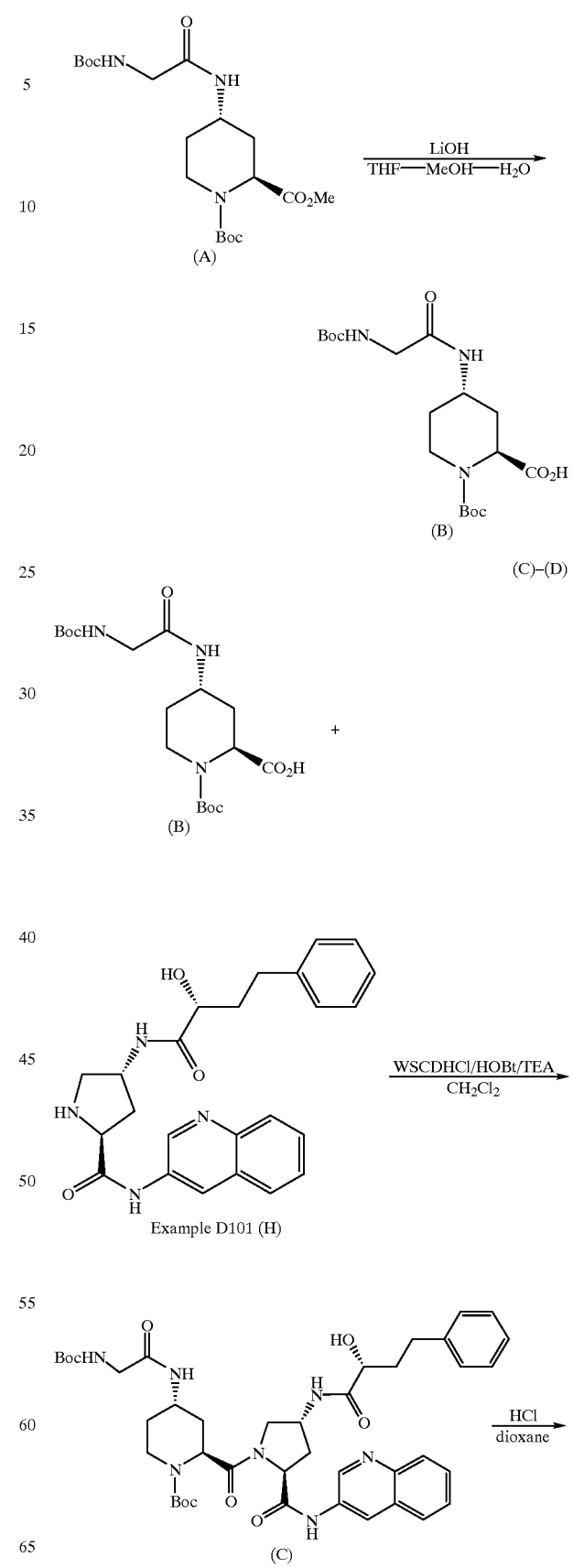

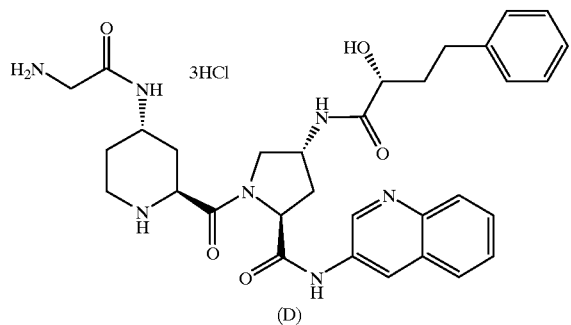
Compound D115 (A)–(B)
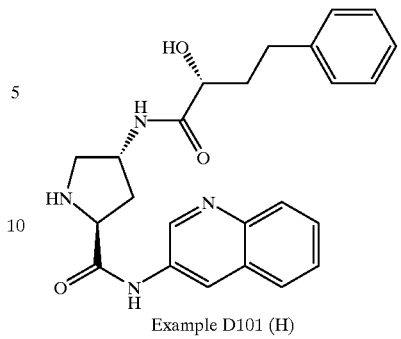
Example D101 (H)
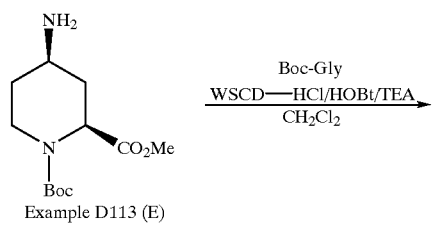
Example D113 (E)
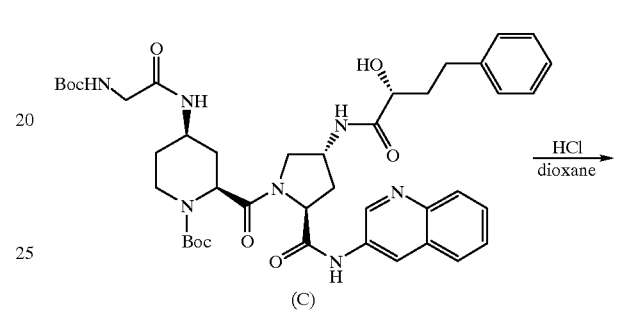
(C)
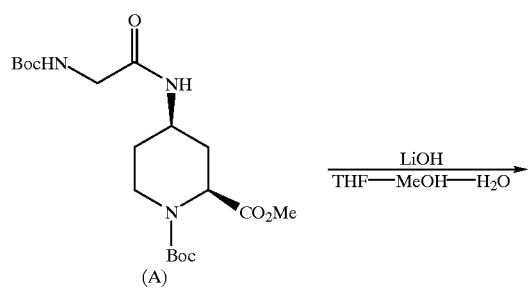
(A)
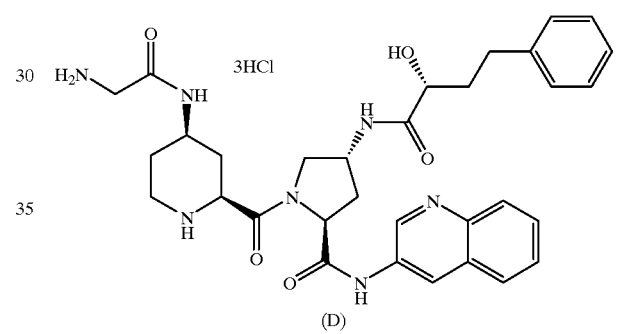
(D)
Compound D116 (A)–(B)
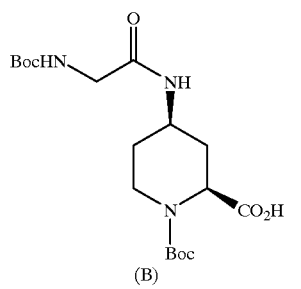
(B)
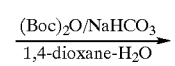
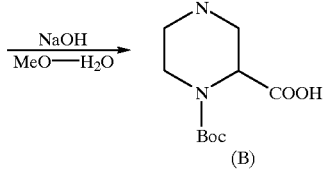
(C)–(D)
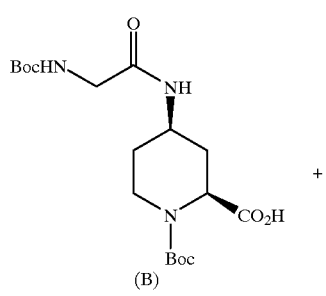
(B)
+
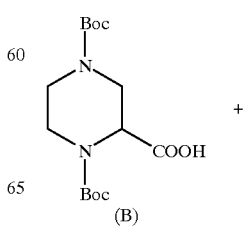
(B)
+

-continued
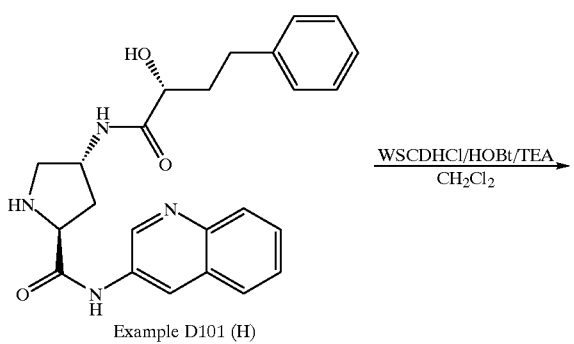
Example D101 (H)
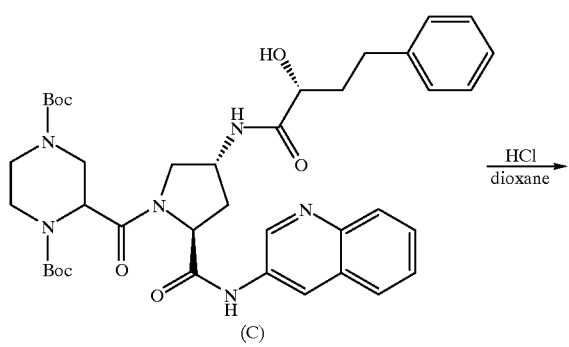
(C)
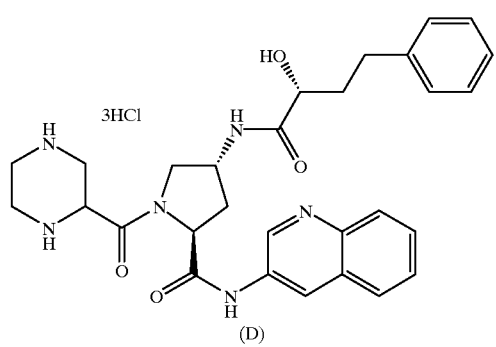
Compound D117 (A)–(B)
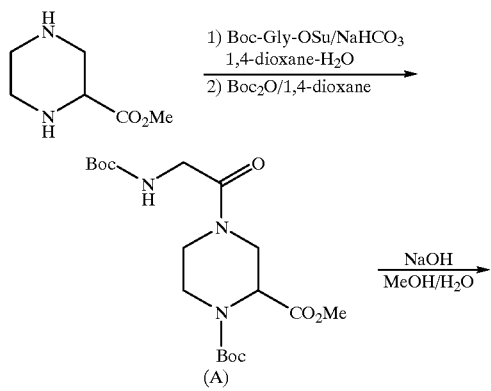
-continued
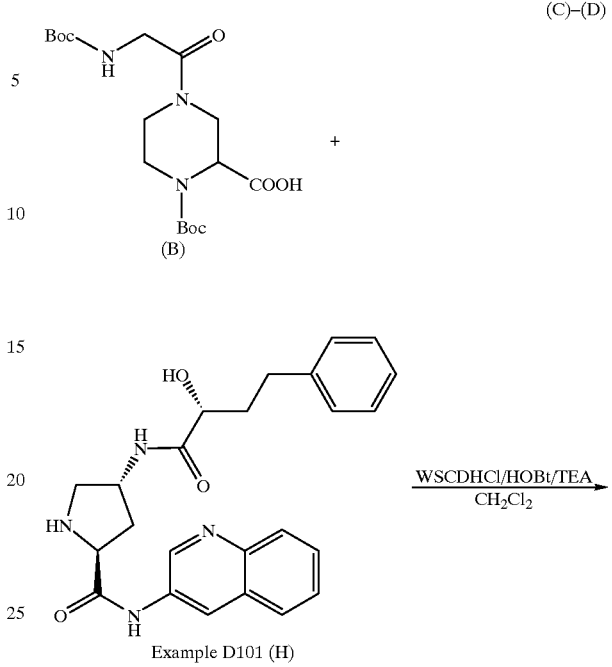
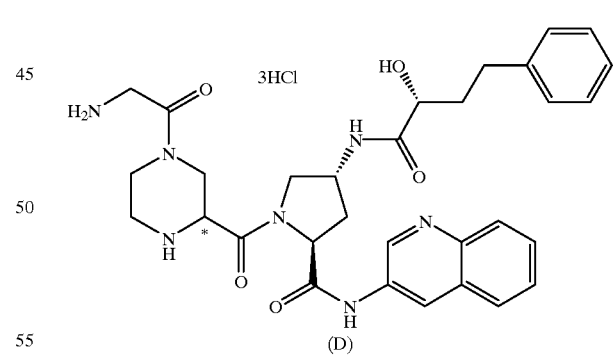
Compound D118 (A)
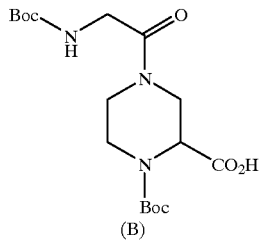
(B)
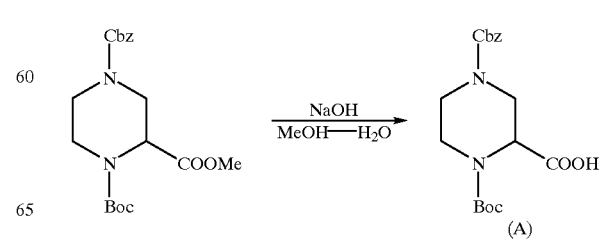

-continued (B)-(E)

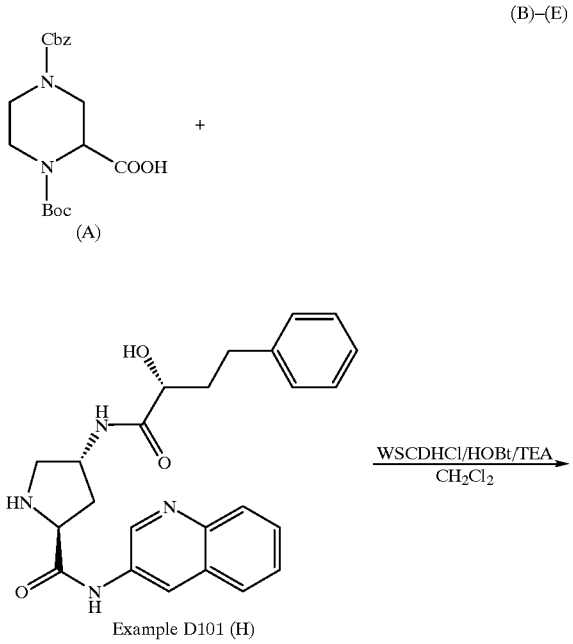

Example D101 (H)

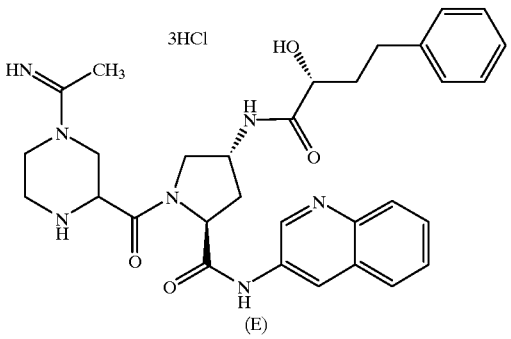

(E)

Compound D101—trans-4-Amino-L-Prolyl-trans-4-((R)-2-Hydroxy-4-Phenylbutyrylamino)-L-Proline 3-Quinolylamide Trihydrochloride (A) trans-4-Hydroxy-N-tert-Butoxycarbonyl-L-Proline 3-Quinolylamide Bis(2-oxo-3-oxazolidinyl)phosphinic chloride (5.72 g) was added to a solution of trans-4-hydroxy-N-tert-butoxycarbonyl-L-proline (3.47 g), 3-aminoquinoline (2.17 g), and diisopropylethylamine (5 mL) in dichloromethane (100 mL) at 0° C. After stirring at room temperature for 45 hr, the solvent was removed in vacuo. Ethyl acetate (500 mL) and 2 N sodium carbonate (500 mL) were added to the residue. The separated organic layer was washed with brine, dried over anhydrous sodium sulfate, and evaporated in vacuo. The residue was purified by silica gel column chromatography (chloroform:methanol=50:1 to 30:1, 20:1, and 10:1, v/v) to afford the title compound (5.85 g) as a colorless sticky oil: $^1$H NMR (400 MHz, CD$_3$OD) δ 1.3–1.5 (m, 9H), 2.1–2.2 (m, 1H), 2.3–2.4 (m, 1H), 3.5–3.7 (m, 2H), 4.4–4.6 (m, 2), 7.61 (m, 1H), 7.69 (m, 1H), 7.88 (m, 1H), 7.97 (m, 1H), 8.71–8.76 (m, 1H), and 8.93–8.94 (m, 1H).

(B) N-tert-Butoxycarbonyl-cis-4-Hydroxy-L-Proline 3-Quinolylamide

Diethyl azodicarboxylate (40% solution in toluene, 1.4 mL) was added to a solution of triphenylphosphine (808 mg) in tetrahydrofuran (5 mL) at ñ15° C. After stirring at −15° C. to 0° C. for 30 min, trans-4-hydroxy-N-tert-butoxycarbonyl-L-proline 3-quinolylamide (A, 729 mg), and formic acid (100 mL) were added. After stirring at room temperature for 3.5 hr, formic acid (100 mL) was added, and stirring was continued for 2 hr. Then additional Mitsunobu reagent which was prepared from triphenylphosphine (803 mg) and diethyl azodicarboxylate (40% solution in toluene, 1.4 mL) was added. After the resulting solution was stirred for 3 hr, 1 N sodium hydroxide (20 mL) was added at 0° C. and stirred at room temperature for 1.5 hr. Then water (100 mL) was added to the reaction mixture and the solvents were evaporated in vacuo. The residue was extracted with ethyl acetate and the extract was washed with brine, dried over anhydrous sodium sulfate, and evaporated in vacuo. The residue was purified by silica gel column chromatography (chloroform then chloroform:methanol=30:1, v/v) to afford the title compound (576 mg) as a pale yellow sticky oil: $^1$H NMR (400 MHz, CD$_3$OD) δ 1.3–1.6 (m, 9H), 1.9–2.2 (m, 1H), 2.3–2.6 (m, 1H), 3.4–3.7 (m, 3H), 4.24.5 (m, 1H), 7.60 (m, 1H), 7.70 (m, 1H), 7.90 (m, 1H), 7.98 (m, 1H), 8.72 (m, 1H), and 8.92 (m, 1H).

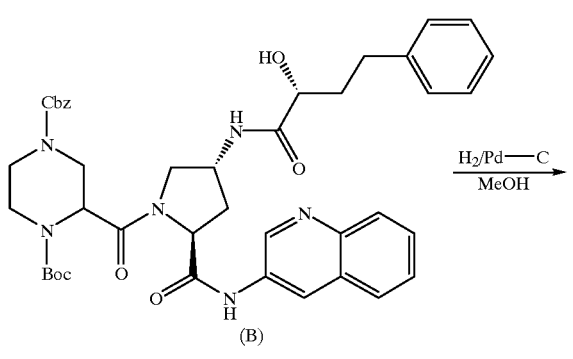

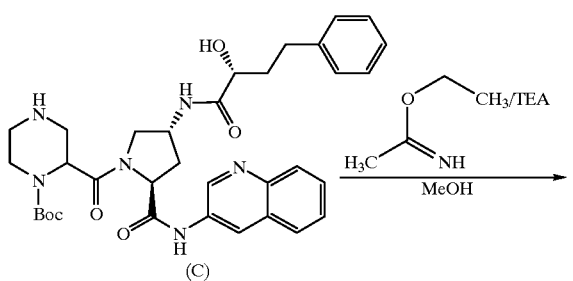

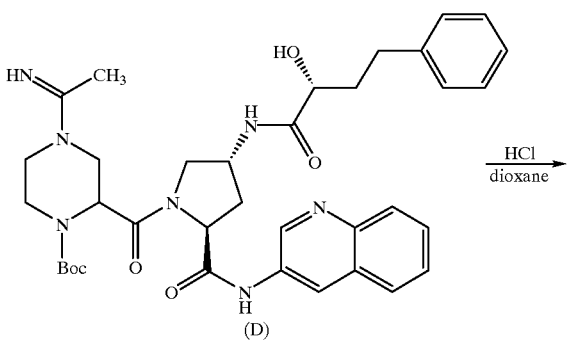

(C) N-tert-Butoxycarbonyl-cis-4-p-Toluenesulfonyloxy-L-Proline 3-Quinolylamide

4-Dimethylaminopyridine (395 mg) and p-toluenesulfonyl chloride (468 mg) were added to a solution of N-tert-butoxycarbonyl-cis-4-hydroxy-L-proline 3-quinolylamide (B, 572 mg) in dichloromethane (10 mL) at 0° C. After stirring at room temperature for 2.5 hr, additional 4-dimethylaminopyridine (399 mg) and p-toluenesulfonyl chloride (465 mg) were added. Additional 4-dimethylaminopyridine (400 mg) and p-toluenesulfonyl chloride (467 mg) were added again after 2 hr. The resulting solution was stirred at room temperature for 14 hr, and the solvent was evaporated in vacuo. The residue was diluted with ethyl acetate, and washed with 0.5 M citric acid, saturated sodium hydrogen carbonate, and brine. The organic layer was dried over anhydrous sodium sulfate and evaporated in vacuo. The residue was purified by silica gel column chromatography (chloroform then chloroform:methanol=50:1, v/v) to afford the title compound (805 mg) as a pale yellow sticky oil: $^1$H NMR (400 MHz, $CD_3OD$) δ 1.3–1.5 (m, 9H), 2.23 (m, 3H), 2.3–2.7 (m, 2H), 3.4–3.8 (m, 2H), 4.5 (m, 1H), 5.25 (m, 1H), 7.20 (m, 2H), 7.7–7.9 (m, 5H), 8.00 (d, 1H), 8.58 (br s, 1H), and 8.85 (br s, 1H).

(D) trans-4-Azido-N-tert-Butoxycarbonyl-L-Proline 3-Quinolyilamide

Sodium azide (206 mg) was added to a stirred solution of N-tert-butoxycarbonyl-cis-4-p-toluenesulfonyloxy-L-proline 3-quinolylamide (C, 805 mg) in N,N-dimethylformamide (8 mL)-water (1.5 mL). After sting at 70° C. for 4 hr, the solvents were removed in vacuo. The residue was diluted with ethyl acetate, and washed with water and brine. The organic layer was dried over anhydrous sodium sulfate and evaporated in vacuo. The residue was purified by silica gel column chromatography (chloroform:ethyl acetate=1:1 to 1:2, v/v) to afford the title compound (532 mg) as a pale yellow sticky oil: $^1$H NMR (400 MHz, $CD_3OD$) δ 1.3–1.5 (m, 9H), 2.32 (m, 1H), 2.47 (m, 1H), 3.63 (m, 1H), 3.72 (m, 1H), 4.38 (m, 1H), 4.48 (m, 1H), 7.60 (m, 1H), 7.69 (m, 1H), 7.90 (m, 1H), 7.98 (m, 1H), 8.72–8.75 (m, 1H), and 8.92–8.93 (m, 1H).

(E) trans-4-Amino-N-tert-Butoxycarbonyl-L-Proline 3-Quinolylamide

A mixture of trans-4-azido-N-tert-butoxycarbonyl-L-proline 3-quinolylamide (D, 526 mg) and 10% palladium on activated carbon (102 mg) in methanol (15 mL) was stirred at room temperature for 4 hr under hydrogen. The catalysts were removed by filtration and washed with methanol. The combined organic layers were evaporated in vacuo. The residue was purified by silica gel column chromatography (chloroform:methanol=20:1 to 5: 1, v/v) to afford the title compound (477 mg) as a colorless sticky oil.

(F) (R)-2-Hydroxy-4-Phenylbutyric Acid

Trifluoroacetic acid (40 mL) was added to a solution of N-tert-butoxycarbonyl-D-homophenylalanine (4.00 g) in dichloromethane (40 mL) at 0° C. After stirring at 0†° C. for 5 min and at room temperature for 40 min, the reaction mixture was evaporated in vacuo. The residue was dissolved in 10% sulfuric acid (80 mL), and the solution was warmed up to 60° C. After removing the bath, a solution of sodium nitrite (5.93 g) in water (5 mL) was added to the solution, and the solution was stirred at 60° C. for 7 hr. Then additional solution of sodium nitrite (1.98 g) in water (1.5 mL) was added, and the resulting solution was stirred at 60° C. for 2.5 hr. After cooling, urea (6.02 g) was added to the reaction mixture, and the whole was extracted with ethyl acetate. The extract was washed with saturated sodium hydrogen carbonate. The aqueous phase was acidified with 1 N hydrochloric acid, and extracted with ethyl acetate. The combined organic layers were washed with brine, dried over anhydrous sodium sulfate, and evaporated in vacuo to afford the title compound (2.51 g) as a white solid: $^1$H NMR (400 MHz, $CDCl_3$) δ 1.92–2.10 (m, 1H), 2.10–2.27 (m, 1H), 2.80 (t, J=7.8 Hz, 2H), 4.20–4.32 (m, 1H), 5.12 (br s, 2H), and 7.12–7.40 (m, 5H).

(G) N-tert-Butoxycarbonyl-trans-4-((R)-2-Hydroxy-4-Phenylbutyrylamino)-L-Proline 3-Quinolylamide 1-Hydroxybenzotriazole (147 mg) and 1-(3-dimethylaminopropyl)-3-ethylcarbodiimide hydrochloride (766 mg) were added to a stirred solution of trans-4-amino-N-tert-butoxycarbonyl-L-proline 3-quinolylamide(E, 1.30 g) and (R)-2-hydroxy-4-phenylbutanoic acid (F, 720 mg) in dichloromethane (40 mL) at 0° C. The mixture was stirred at room temperature overnight. The reaction mixture was diluted with chloroform and washed with saturated sodium hydrogen carbonate and brine. The organic layer was dried over anhydrous sodium sulfate and evaporated in vacuo. The residue was purified by silica gel column chromatography (chloroform:methanol=100:1, v/v) to give the title compound (1.85 g) as a colorless foam: $^1$H NMR (400 MHz, $CDCl_3$) δ 1.45 (m, 9H), 1.70 (m, 2H), 1.94 (m, 1H), 2.15 (m, 1H), 2.75 (m, 2H), 3.29 (m, 1H), 3.80 (m, 1H), 4.11 (m, 1H), 4.53 (m, 1H), 4.60 (m, 1H), 6.76 (m, 1H), 7.15–7.26 (m, 5H), 7.48 (m, 1H), 7.57 (m, 1H), 7.73 (m, 1H), 7.95 (d, J=16.8 Hz, 1H), 8.68 (s, 1H), and 8.69 (s,1H).

(H) trans-4-((R)-2-Hydroxy-4-Phenylbutrylamino)-L-Proline 3-Quinolylamide

N-tert-butoxycarbonyl-trans-4-((R)-2-hydroxy-4-phenylbutyrylamino)-L-proline 3-quinolylamide (1.55 g) was dissolved in trifluoroacetic acid (10 mL)-chloroform (20 mL). After stirring for 1 hr, the reaction mixture was evaporated in vacuo. The residue was diluted with chloroform, and washed with saturated sodium hydrogen carbonate. The organic layer was dried over anhydrous sodium sulfate and evaporated in vacuo to give the title compound (888 mg) as a colorless foam.

(I) N-tert-Butoxycarbonyl-cis-4-Formyloxy-L-Proline Methyl Ester

Diethyl azodicarboxylate (2.2 mL) was added to a cold (−15° C.) stirred solution of triphenyl phosphine (3.67 g) in tetrahydrofuran (40 mL). After stirring at 0° C. for 100 min, a solution of N-tert-butoxycarbonyl-trans-4-hydroxy-L-proline methyl ester (2.29 g) in tetrahydrofuran (20 mL) and formic acid (2.20 mL) were added. The mixture was stirred at room temperature for 14 hr, the solvent was removed and coevaporated several times with toluene in vacuo. The residue was diluted with toluene and precipitated solids were removed by filtration which was washed with toluene. The combined organic layers were evaporated in vacuo and the residue was purified by silica gel column chromatography (chloroform then chloroform:methanol=15:1, v/v) to give the title compound (4.07 g) as a pale yellow oil: $^1$H NMR (400 MHz, $CDCl_3$) δ 1.39–1.50 (m, 9H), 2.25–2.34 (m, 1H), 2.43–2.60 (m, 1H), 3.54–3.67 (m, 1H), 3.72–3.83 (m, 1H), 3.75 (s, 3H), 4.37–4.55 (m, 1H), 5.35–4.41 (m, 1H), and 7.97 (s, 1H).

(J) N-tert-Butoxycarbonyl-cis-4-Hydroxy-L-Proline Methyl Ester

A solution of 1 N aqueous sodium hydroxide (6 mL) was added to a cold (0†° C.) stirred solution of N-tert-butoxycarbonyl-cis-4-formyloxy-L-proline methyl ester (I, 4.07 g) in tetrahydrofuran (6 mL). After stirring at 0° C. for 3 hr, a solution of 1 N aqueous sodium hydroxide (3 mL) was added and additionally stirred at 0° C. for 30 min. The mixture was evaporated in vacuo. The residue was diluted with ethyl acetate and washed with brine. The organic layer was dried over anhydrous sodium sulfate and evaporated in vacuo. The residue was purified by silica gel column chromatography (ethyl acetate:chloroform=1:5 to 1:1, v/v) to give the title compound (2.77 g) as a colorless oil: $^1$H NMR (400 MHz, CDCl$_3$) δ 1.35–1.54 (m, 9H), 1.78 (br s, 1H), 2.00–2.15 (m, 1H), 2.27–2.39 (m, 1H), 3.50–3.59 (m, 1H), 3.61–3.71 (m, 1H), 3.63–3.77 (m, 1H), 3.78–3.80 (m, 3H), 4.29 (dd, J=1.5, 9.8 Hz, 1H), and 4.33–4.39 (m, 1H).

(K) N-tert-Butoxycarbonyl-cis-4-(p-Toluenesulfonyloxy)-L-Proline Methyl Ester

4-Dimethylaminopyridine (2.28 g) and p-toluenesulfonyl chloride (2.66 g) were added to a cold (0° C.) stirred solution of N-tert-butoxycarbonyl-cis-4-hydroxy-L-proline methyl ester (J, 2.76 g) in dichloromethane (50 mL). After stirring at room temperature for 16 hr, the solvent was removed in vacuo. The residue was diluted with ethyl acetate, and washed with 0.5 M saturated citric acid, water, and brine. The organic layer was dried over anhydrous sodium sulfate and evaporated in vacuo to give the title compound (3.10 g) as a pale yellow oil: $^1$H NMR (400 MHz, CDCl$_3$) δ 1.35–1.52 (m, 9H), 2.30–2.53 (m, 2H), 2.46 (s, 3H), 3.51–3.78 (m, 2H), 3.68–3.69 (s, 3H), 4.30–4.56 (m, 1H), 5.00–5.09 (m, 1H), 7.32–7.38 (m, 1H), and 7.74–7.79 (m, 1H).

(L) trans-4-Azido-N-tert-Butoxycarbonyl-L-Proline Methyl Ester

Sodium azide (1.01 g) was added to a stirred solution of N-tert-butoxycarbonyl-cis-4-p-toluenesulfonyloxy-L-proline methyl ester (K, 3.10 g) in N,N-dimethylformamide (30 mL)-water (5 mL). After stirring at 65° C. for 15 hr, the solvents were removed in vacuo. The residue was diluted with ethyl acetate and washed with water and brine. The organic layer was dried over anhydrous sodium sulfate and evaporated in vacuo to give the title compound (2.00.g) as a pale yellow oil: $^1$H NMR (400 MHz, CDCl$_3$) δ 1.38–1.52 (m, 9H), 2.01–2.25(m, 1H), 2.27–2.40 (m, 1H), 3.44–3.62 (m, 1H), 3.71 (dd, J=5.4, 11.7 Hz, 1H), 3.74–3.75 (m, 3H), 4.16–4.25 (m, 1H), and 4.30–4.46 (m, 1H).

(M) trans-4-Amino-N-tert-Butoxycarbonyl-L-Proline Methyl Ester

A mixture of trans-4-azido-N-tert-butoxycarbonyl-L-proline methyl ester (L, 2.00 g) and 10% palladium on activated carbon (601 mg) in methanol (60 mL) was stirred at room temperature for 2.5 hr under hydrogen. The catalysts were removed by filtration and washed with methanol. The combined organic layers were evaporated in vacuo to give the title compound (1.85 g) as a colorless oil: $^1$H NMR (400 MHz, CDCl$_3$) δ 1.41–1.46 (m, 9H), 1.99–2.22 (m, 2H), 2.63 (br s, 2H), 3.13–3.35 (m, 1H), 3.67–3.79 (m, 2H), 3.73 (s, 3H), and 4.36–4.47 (m, 1H).

(N) N-tert-Butoxycarbonyl-trans-4-(N-tert-Butoxycarbonylamino)-L-Proline Methyl Ester Di-tert-butyl dicarbonate (589 mL) was added to a stirred solution of trans-4-amino-N-tert-butoxycarbonyl-L-proline methyl ester (M, 418 mg) in tetrahydrofuran (15 mL). The mixture was stirred at room temperature for 15 hr and evaporated in vacuo. The residue was purified by silica gel column chromatography (ethyl acetate:hexane=1:2, v/v) to give the title compound (678 mg) as a white solid: $^1$H NMR (400 MHz, CDCl$_3$) δ 1.35–1.56 (m, 18H), 2.08–2.28 (m, 2H), 3.17–3.38 (m, 1H), 3.63–3.82 (m, 2H), 3.73 (s, 1H), 4.21–4.42, (m, 1H), and 4.64 (br s, 1H).

(O) N-tert-Butoxycarbonyl-trans-4-(N-tert-Butoxycarbonylamino)-L-Proline

A solution of lithium hydroxide monohydrate (86 mg) in water (7 mL) was added to a cold (0° C.) stirred solution of N-tert-butoxycarbonyl-trans-4-(tert-butoxycarbonylamino)-L-proline methyl ester (N, 589 mg) in tetrahydrofuran (21 mL)-methanol (7 mL). The mixture was stirred at room temperature for 5 hr and evaporated in vacuo. The residue was diluted with water and washed with ether. The aqueous layer was acidified with 1 N hydrochloric acid and extracted with ethyl acetate. The organic layer was washed with brine, dried over anhydrous sodium sulfate, and evaporated in vacuo to give the title compound (222 mg) as a colorless foam: $^1$H NMR (400 MHz, CDCl$_3$) δ 1.35–1.57 (m, 18H), 2.05–2.52 (m, 2H), 3.19–3.37 (m, 1H), 3.66–3.81 (m, 1H, 4.17–4.45 (m, 2H), and 4.63–4.87 (m, 1H).

(P) N-tert-Butoxycarbonyl-trans-4-(N-tert-Butoxycarbonylamino)-L-Prolyl-trans-4-((R)-2-Hydroxy-4-Phenylbutyrylamino)-L-Proline 3-Quinolylamide Triethylamine (30 μL), 1-hydroxybenzotriazole (28 mg), and 1-(3-dimethylaminopropyl)-3-ethylcarbodiimide hydrochloride (42 mg) were added to a cold (0° C.) stirred solution of N-tert-butoxycarbonyl-trans-4-(N-tert-butoxycarbonylamino)-L-proline (O, 76 mg) and trans-4-((R)-2-hydroxy-4-phenylbutyrylamino)-L-proline 3-quinolylamide(H, 76 mg) in dichloromethane (10 mL). The mixture was stirred at room temperature for 16.5 hr and evaporated in vacuo. The residue was diluted with ethyl acetate and washed with 1 N hydrochloric acid, water, saturated sodium hydrogen carbonate, and brine. The organic layer was dried over anhydrous sodium sulfate and evaporated in vacuo. The residue was purified by preparative thin layer chromatography (Whatman, PLK5F Silica Gel 50, 20 cm×20 cm×2 mm, methanol:chloroform=1:20, v/v) to give the title compound (90 mg) as a colorless foam: $^1$H NMR (400 MHz, CDCl$_3$) δ 1.44 (s, 9H), 1.45 (s, 9H), 1.69–1.84 (m, 5H), 1.90–2.03 (m, 1H), 2.09–2.28 (m, 3H), 2.68–2.83 (m, 3H). 3.39–3.46 (m, 1H), 3.50–3.56 (m, 1H), 3.74–3.81 (m, 1H), 3.93–3.99 (m, 1H), 4.01–4.08 (m, 1H), 4.29–4.37 (m, 1H), 4.45–4.53 (m, 2H), 4.57–4.76 (m, 2H), 4.91–4.98 (m, 1H), 7.15–7.30 (m, 5H), 7.38–7.53 (m, 2H), 7.63–7.70 (m, 1H), 7.81–7.87 (m, 1H), 8.57–8.60 (m, 1H), 8.66–8.70 (br s, 1H), and 9.93 (br s, 1H).

(Q) trans-4-Amino-L-Prolyl-trans-4-((R)-2-Hydroxy-4-Phenylbutylamino)-L-Proline 3-Quinolylamide Trihydrochloride A solution of 4 N hydrochloric acid in 1,4-dioxane (4 mL) was added to N-tert-butoxycarbonyl-trans-4-(N-tert-butoxycarbonylglycylamino)-L-prolyl-trans-4-((R)-2-hydroxy-4-phenylbutyrylamino)-L-proline 3-quinolylamide (P, 90 mg) at 0° C., and methanol was added until insoluble materials were disappeared. After stirring for 2 hr, the reaction mixture was evaporated and coevaporated several times with hexane and ethanol in vacuo to give pale yellow solids. The solids were washed with ether to afford the title compound (62 mg) as a colorless solid: $^1$H-NMR (400 MHz, D$_2$O) δ 1.86–2.03(m, 2H), 2.28–2.47(m, 2H), 2.53–2.69(m, 4H), 3.42–3.50(m, 1H), 3.58–3.66(m, 1H), 3.86–3.94(m, 2H), 4.03–4.14(m, 2H), 4.38–4.46(m, 1H), 4.76–4.83(m, 1H), 4.87–4.94(m, 1H), 7.11–7.29(m, 5H), 7.78–7.84(m, 1H), 7.91–7.98(m,1H), 8.04–8.12(m, 2H), 8.91–8.94(m, 1H), and 9.03–9.28(m, 1H):; IR (KBr) 3300, 3023, 2937, 2852, 1701, 1657, 1651, 1610, 1574, 1549, 1495, 1485, and 1454 cm$^{-1}$; mass spectrum (FAB+) m/e 531 (M+1); Anal. Calcd for C$_{29}$H$_{34}$ $_{N6}$O$_4$.3HCl.3H$_2$O, C; 50.18, H; 6.24, N; 12.10. Found: C; 50.45, H; 6.15, N; 11.28.

Compound D102—cis-4-Amino-L-Prolyl-trans-4-((R)-2-Hydroxy-4-Phenylbutyrylamino)-L-Proline 3-Quinolylamide Trihydrochloride (A) N-tert-Butoxycarbonyl-trans-4-(p-Toluenesulfonyloxy)-L-Proline Methyl Ester The title compound (928 mg) was similarly prepared, as described in Compound D101 (K), except the starting material was N-tert-butoxycarbonyl-trans-4-hydroxy-L-proline methyl ester (600 mg): $^1$H NMR (400 MHz, CDCl$_3$) δ 1.36–1.47 (m, 9H), 2.08–2.20 (m, 1H), 2.38–2.58 (m, 1H), 2.46 (s, 3H), 3.53–3.66 (m, 2H), 3.72 (s, 3H), 4.31–4.42 (m, 1H), 4.99–5.10 (m, 1H), 7.36 (d, J=8.3 Hz, 2H), and 7.79 (d, J=8.3 Hz, 2H).

(B) cis-4-Azido-N-tert-Butoxycarbonyl-L-Proline Methyl Ester

The title compound (615 mg) was similarly prepared, as described in Compound D101 (L), except the starting material was N-tert-butoxycarbonyl-trans-4-p-toluenesulfonyloxy-L-proline methyl ester (A, 928 mg): $^1$H NMR (400 MHz, CDCl$_3$) δ 1.36–1.54 (m, 9H), 2.10–2.25 (m, 1H), 2.40–2.54 (m, 1H), 3.42–3.54 (m, 1H), 3.66–3.83 (m, 1H), 3.76 (s, 3H), 4.11–4.21 (m, 1H), and 4.30–4.47 (m, 1H).

(C) cis-4-Amino-N-tert-Butoxycarbonyl-L-Proline Methyl Ester

The title compound (406 mg) was similarly prepared, as described in Compound D101 (M), except the starting material was cis-4-azido-N-tert-butoxycarbonyl-L-proline methyl ester (B, 928 mg): $^1$H NMR (400 MHz, CDCl$_3$) δ 1.35–1.54 (m, 9H),1.60 (s, 2H), 1.77–1.84 (m, 1H), 2.40–2.50 (m, 1H), 3.22–3.28 (m, 1H), 3.50–3.56 (m, 1H), 3.63–3.77 (m, 1H), 3.74–3.75 (m, 3H), and 4.22–4.34 (m, 1H).

(D) N-tert-Butoxycarbonyl-cis-4-(N-tert-Butoxycarbonylamino)-L-Proline Methyl Ester The title compound (598 mg) was similarly prepared, as described in Compound D101 (N), except the starting material was cis-4-amino-N-tert-butoxycarbonyl-L-proline methyl ester (C, 406 mg): $^1$H NMR (400 MHz, CDCl$_3$) δ 1.37–1.50 (m, 18H),1.70–1.77 (m, 1H), 2.39–2.53 (m, 1H), 3.36–3.53 (m, 1H), 3.65 (dd, J=5.9, 11.2 Hz, 1H), 3.77–3.78 (m, 3H), 4.25 (dd, J=2.9,9.8 Hz, 1H), 4.28–4.37 (m, 1H), and 5.36–5.49 (m, 1H).

(E) N-tert-Butoxycarbonyl-cis-4-(N-tert-Butoxycarbonylamino)-L-Proline

The title compound (349 mg) was similarly prepared, as described in Compound D101 (O), except the starting material was tert-butoxycarbonyl-cis-4-(N-tert-butoxycarbonylamino)-L-proline methyl ester (D, 598 mg): $^1$H NMR (400 MHz, CDCl$_3$) δ 1.38–1.54 (m, 18H), 2.29–2.38 (m, 2H), 3.38–3.51 (m, 1H), 3.55–3.73 (m, 1H), 4.21–4.32 (m, 1H), 4.38–4.46 (m, 1H), and 5.34–5.44 (m, 1H).

(F) N-tert-Butoxycarbonyl-cis-4-(N-tert-Butoxycarbonylamino)-L-Prolyl-trans-4-((R)-2-Hydroxy-4-Phenylbutyrylamino)-L-Proline 3-Quinolylamide The title compound (78 mg) was similarly prepared, as described in Compound D101 (P), except the starting material was N-tert-butoxycarbonyl-cis-4-(N-tert-butoxycarbonylamino)-L-proline (E, 61 mg): $^1$H NMR (400 MHz, CDCl$_3$) δ 1.37–1.50 (m, 18H), 1.63–2.00 (m, 5H), 2.10–2.20 (m, 2H), 2.47–2.57 (m, 1H), 2.69–2.82 (m, 2H), 3.37–3.46 (m, 1H), 3.52–3.60 (m, 1H), 3.70–3.78 (m, 1H), 3.94–4.01 (m, 1H), 4.04–4.12 (m, 1H), 4.35–4.53 (m, 3H), 4.95–5.00 (m, 1H), 5.91–6.00 (m, 1H), 7.15–7.31 (m, 4H), 7.38–7.46 (m, 1H), 7.48–7.56 (m, 1H), 7.61–7.68 (m, 1H), 7.83–7.92 (m, 1H), 8.60–8.68 (m, 1H), and 9.84 (s, 1H).

(G) cis-4-Amino-L-Prolyl-trans-4-((R)-2-Hydroxy-4-Phenylbutyrylamino)-L-Proline 3-Quinolylamide Trihydrochloride The title compound (38 mg) was similarly prepared, as described in Compound D101 (Q), except the starting material was N-tert-butoxycarbonyl-cis-4-(N-tert-butoxycarbonylamino)-L-prolyl-trans-4-(R)-2-hydroxy-4-phenylbutyryl)amino-L-proline 3-quinolylamide (F, 78 mg): $^1$H NMR (400 MHz, D$_2$O) δ 1.93–2.13 (m, 2H), 2.13–2.20 (m, 1H), 2.37–2.55 (m, 21), 2.67–2.77 (m, 3H), 3.55–3.62 (m, 1H), 3.66–3.75 (m, 1H), 3.95–4.03 (m, 2H), 4.10–4.30 (m, 2H), 4.44–4.54 (m, 1H), 4.79–4.92 (m, 2H), 7.19–7.48 (m, 5H), 7.83–7.90 (m, 1H), 7.96–8.03 (m, 1H), 8.10–8.19 (m, 2H), 8.95–8.98 (m, 1H), and 9.28–9.31 (m, 1H); IR (KBr) 3325, 3024, 2925, 1701, 1655, 1649, 1610, 1574, 1550, 1485, and 1454 cm$^{-1}$; mass spectrum (FAB+) m/e 531 (M+1); Anal. Calcd for C$_{29}$H$_{34}$N$_6$O$_4$·3HCl·2.5H$_2$O: C, 50.84; H, 6.17; N, 12.20. Found: C, 51.06; H, 6.17; N, 11.75.

Compound D103—trans-4-Glycylamino-L-Prolyl-trans-4-((R)-2-Hydroxy-4-Phenylbutyrylamino)-L-Proline 3-Quinolylamide Trihydrochloride (A) N-tert-Butoxycarbonyl-trans-4-(N-tert-Butoxycarbonylglcyamino)-L-Proline Methyl Ester Triethylamine (292 μL), 1-hydroxybenzotriazole (267 mg), and 1-(3-dimethylaminopropyl)-3-ethylcarbodiimide hydrochloride (401 mg) were added to a cold (0° C.) stirred solution of trans-4-amino-N-tert-butoxycarbonyl-L-proline methyl ester (Compound D101 (M), 426 mg) and N-tert-butoxycarbonylglycine (367 mg) in dichloromethane (20 mL) were added. The mixture was stirred at room temperature for 14 hr and evaporated in vacuo. The residue was diluted with ethyl acetate and washed with 1 N hydrochloric acid, water, saturated sodium hydrogen carbonate, and brine. The organic layer was dried over anhydrous sodium sulfate and evaporated in vacuo. The residue was purified by silica gel column chromatography (methanol:chloroform=1:20, v/v) to give the title compound (749 mg) as a colorless foam: $^1$H NMR (400 MHz, CDCl$_3$) δ 1.33–1.52 (m, 18H), 2.10–2.30 (m, 2H), 3.20–3.43 (m, 1H), 3.65–3.84 (m, 6H), 4.24–4.42 (m, 1H), 4.52 (br s, 1H), 6.49 (br s, 1H), and 7.24 (br s, 1H).

(B) N-tert-Butoxycarbonyl-trans-4-(N-tert-Butoxycarbonylglycylamino)-L-Proline

The title compound (521 mg) was similarly prepared, as described in Compound D101 (O), except the starting material was N-tert-butoxycarbonyl-trans-4-(N-tert-butoxycarbonylglycylamino)-L-proline methyl ester (A, 749 mg): $^1$H NMR (400 MHz, CDCl$_3$) δ 1.34–1.49 (m, 18H), 2.14–2.33 (m, 2H), 3.23–3.38 (m, 5H), 3.55–3.76 (m, 3H), 4.25–4.36 (m, 1H), 4.38–4.49 (m, 1H), and 4.79–4.91 (m, 1H).

(C) N-tert-Butoxycarbonyl-trans-4-(N-tert-Butoxcarbonylglycylamino)-L-Prolyl-trans-4-((R)-2-Hydroxy-4-Phenylbutyrylamino-L-Proline 3-Quinolylamide Triethylamine (31 μL), 1-hydroxybenzotriazole (28 mg), and 1-(3-dimethylaminopropyl)-3-ethylcarbodiimide hydrochloride (42 mg) were added to a cold (0° C.) stirred solution of N-tert-butoxycarbonyl-trans-4-(N-tert-butoxycarbonylglycylamino)-L-proline(B, 71 mg) and trans-4-((R)-2-hydroxy-4-phenylbutyryl-amino)-L-proline 3-quinolylamide (Compound D101 (I), 77 mg) in dichloromethane (10 mL). The mixture was stirred at room temperature for 5.5 hr and evaporated in vacuo. The residue was diluted with ethyl acetate and washed with 1 N hydrochloric acid, water, saturated sodium hydrogen carbonate, and brine. The organic layer was dried over anhydrous sodium sulfate and evaporated in vacuo. The residue was purified by preparative thin layer chromatography (Whatman, PLK5F Silica Gel 50, 20 cm×20 cm×2 mm, methanol:chloroform=1:20, v/v) to give the title compound (48 mg) as a colorless foam: $^1$H NMR (400 MHz, CDCl$_3$) δ 1.34–1.50 (m, 18H), 1.82–2.29 (m, 6H), 2.57–2.87 (m, 3H), 3.39–3.46 (m, 1H), 3.51–3.60 (m, 1H), 3.72–3.84 (m, 3H), 3.93–4.02 (m, 2H), 4.46–4.50 (m, 3H), 4.91–5.00 (m, 2H), 5.23–5.39 (m, 1H), 6.71–6.87 (m,1H), 7.14–7.36 (m, 4H), 7.38–7.54 (m, 2H), 7.63–7.69 (m, 1H), 7.81–7.88 (m, 1H), 8.58–8.62 (m, 1H), 8.67–8.72 (m, 1H), and 9.88–9.94 (m, 1H).

(D) trans-4-Glycolamino-L-Prolyl-trans-4-((R)-2-Hydroxy-4-Phenylbutyrylamino)-L-Proline 3-Quinolylamide Trihydrochloride A solution of 4 N hydrochloric acid in 1,4-dioxane (4 mL) was added to N-tert-butoxycarbonyl-trans-4-(N-tert-butoxycarbonylglycylamino)-L-prolyl-trans-4-((R)-2-hydroxy-4-phenylbutyrylamino)-L-proline 3-quinolylamide (C, 69 mg) at 0° C., and methanol was added until insoluble materials were disappeared. After stirring for 2 hr, the reaction mixture was evaporated and coevaporated several times with hexane and ethanol in vacuo to give pale yellow solids. The solids were washed with ether to afford the title compound (34 mg): $^1$H NMR (400 MHz, D$_2$O) δ 1.92–2.21 (m, 2H), 2.35–2.53 (m, 3H), 2.56–2.74 (m, 3H), 3.39 (dd, J=4.9, 12.2 Hz, 1H), 3.64–3.76(m, 2H), 3.79 (s, 2H), 3.91–3.98 (m, 1H), 4.10–4.16 (m, 1H), 4.42–4.57 (m, 2H), 4.82–4.90 (m, 2H), 7.19–7.36 (m, 5H), 7.81–7.88 (m, 1H), 7.95–8.01 (m, 1H), 8.09–8.16 (m, 2H), 8.91–8.95 (m, 1H), and 9.25–9.29 (m, 1H); IR (KBr) 3213, 3026, 2945, 1687, 1650, 1610, 1574, 1552, and 1454 cm$^{-1}$; mass spectrum (FAB+) m/e 588 (M+1); Anal. Calcd for C$_{31}$H$_{37}$N$_7$O$_5$.3HCl.3.5H$_2$O: C, 48.98; H, 6.23; N, 12.89. Found: C, 49.15; H, 6.22; N, 12.50.

Compound D104—cis-4-Glycylamino-L-Prolyl-trans-4-((R)-2-Hydroxy-4-Phenylbutyrylamino)-L-Proline 3-Quinolylamide Trihydrochloride (A) N-tert-Butoxycarbonyl-cis-4-(N-tert-Butoxycarbonylglycylamino)-L-Proline Methyl Ester Triethylamine (1.13 mL), 1-hydroxybenzotriazole (1.04 g), and 1-(3-dimethylamino-propyl)-3-ethylcarbodiimide hydrochloride (1.56 g) were added to a solution of cis-4-amino-N-tert-butoxycarbonyl-L-proline methyl ester (Compound D102 (C), 1.65 g) and N-tert-butoxycarbonylglycine (1.42 g) in dichloromethane (100 mL) at 0° C. The mixture was stirred at room temperature for 19 hr and evaporated in vacuo. The residue was diluted with ethyl acetate and washed with 10% citric acid, saturated sodium hydrogen carbonate, and brine. The organic layer was dried over anhydrous sodium sulfate and evaporated in vacuo to give the title compound (2.84 g) as a colorless foam.

(B) N-tert-Butoxycarbonyl-cis-4-(N-tert-Butoxycarbonylglycylamino)-L-Proline

A solution of 1 N sodium hydroxide (10 mL) was added to a solution of N-tert-butoxycarbonyl-cis-4-(N-tert-butoxycarbonylglycylamino)-L-proline methyl ester (A, 2.83 g) in methanol (30 mL). The mixture was stirred at room temperature for 2 hr and evaporated in vacuo. The residue was diluted with water and washed with ether. The aqueous layer was acidified with 10% citric acid and extracted with ethyl acetate. The organic layer was washed with brine, dried over anhydrous sodium sulfate, and evaporated in vacuo to give the title compound (2.48 g) as a colorless foam: $^1$H NMR (400 MHz, CDCl$_3$) δ 1.43–1.47 (m, 18H), 2.05 (s, 2H), 2.20–2.50 (m, 1H), 3.44–3.47 (m, 1H), 3.60–3.95 (m, 3H), 4.12–4.15 (m, 1H), and 4.28–4.52 (m, 3H).

(C) N-tert-Butoxycarbonyl-cis-4-(N-tert-Butoxycarbonylglyclamino)-L-Proline-trans-4-((R)-2-Hydroxy-4-Phenylbutyrylamino-L-Proline 3-Quinolylamide Triethylamine (40), 1-hydroxybenzotriazole (36 mg), and 1-(3-dimethylamino-propyl)-3-ethylcarbodiimide hydrochloride (55 mg) were added to a solution of trans-4-((R)-2-hydroxy-4-phenylbutyrylamino)-L-proline 3-quinolylamide (Compound D101 (H), 100 mg) and N-tert-butoxycarbonyl-cis-4-(N-tert-butoxycarbonylglycylamino)-L-proline (B, 112 mg) in dichloromethane (10 mL) at 0° C. The mixture was stirred at room temperature for 19 hr and evaporated in vacuo. The residue was diluted with ethyl acetate and washed with 10% citric acid, saturated sodium hydrogen carbonate, and brine. The organic layer was dried over anhydrous sodium sulfate and evaporated in vacuo. The residue was purified by silica gel column chromatography (methanol:chloroform=1:50 to 1:20, v/v) to give the title compound (99 mg) as a colorless powder: $^1$H NMR (400 MHz, CDCl$_3$) δ 1.38–1.54 (m, 18H), 2.02–2.36 (m, 3H), 2.60–2.70 (m, 1H), 2.73 (t, 2H), 3.50–3.60 (m, 1H), 3.73–3.95 (m, 3H), 4.30–4.42 (m, 2H), 4.50–4.70 (m, 3H), 7.18–7.48 (m, 9H), 8.09 (br s, 1H), 8.66 (br s, 1H), and 10.15 (br s, 1H).

(D) cis-4-Glycylamino-L-Prolyl-trans-4-((R)-2-Hydroxy-4-Phenylbutyrylamino-L-Proline 3-Quinolylamide Trihydrochloride A solution of 4 N hydrochloric acid in 1,4-dioxane (5 mL) was added to N-tert-butoxycarbonyl-cis-4-(N-tert-butoxycarbonylglycylamino)-L-proline-trans-4-((R)-2-hydroxy-4-phenylbutyrylamino)-L-proline 3-quinolylamide (C, 69 mg) at 0° C., and methanol (5 mL) was added to dissolve insoluble materials. After stirring for 1 hr, the reaction mixture was evaporated and coevaporated three times with 1,4-dioxane and ether in vacuo to give pale yellow solids. The solids were washed with ether to afford the title compound (77 mg) as a colorless solid: $^1$H NMR (400 MHz, D$_2$O) δ 1.99–2.17 (m, 3H), 2.41–2.57 (m, 2H), 2.76 (t, J=8.0 Hz, 2H), 2.30–3.09 (m, 1H), 3.41–3.46 (m, 1H), 3.67–3.84 (m, 4H), 3.78 (s, 2H), 3.96–4.00 (m, 1H), 4.17–4.20 (m, 1H), 4.51–4.54 (m, 1H), 4.62–4.68 (m, 1H), 4.884.93 (m, 1H), 7.25–7.40 (m, 5H), 7.90 (t, J=8.0 Hz, 1H), 8.04 (t, J=8.0 Hz, 1H), 8.17 (d, J=8.0 Hz, 1H), 8.19 (d, J=8.0 Hz, 1H), 8.99 (s, 1H), and 9.33 (s, 1H); mass spectrum (FAB+) m/e 588 (M+1); Anal. Calcd. For C$_{31}$H$_{37}$N$_7$O$_5$.3HCl.3/2H$_2$O: C, 51.42; H, 5.99; N, 13.54. Found: C, 51.73; H, 6.10; N, 13.13.

Compound D105—trans-4-Glycylamino-D-Prolyl-trans-4-((R)-2-Hydroxy-4-Phenylbutyrylamino)-L-proline 3-Quinolylamide Trihydrochloride (A) N-tert-Butoxycarbonyl-cis-4-Hydroxy-D-Proline Methyl Ester A solution of 2 M (triimethylsilyl)diazomethane in hexane (4 mL) was added to a solution of cis-4-hydroxy-N-tert-butoxycarbonyl-D-proline (916 mg) at 0° C. After stirring at room temperature for 1 hr, a solution of 2 M (trimethylsilyl) diazomethane in hexane (6 mL) was added additionally and stirred at room temperature for 30 min. The solvents were evaporated in vacuo to afford the title compound (971 mg) as a pale yellow oil.

(B) N-tert-Butoxycarbonyl-cis-4-(p-Toluenesulfonyloxy)-D-Proline Methyl Ester

4-Dimethylaminopyridine (1.21 g) and p-toluenesulfonyl chloride (1.51 g) were added to a solution of N-tert-butoxycarbonyl-cis-4-hydroxy-D-proline methyl ester (A, 971 mg) in dichloromethane (20 mL). After stirrng at room temperature for 4 hr, the solvent was removed in vacuo. The residue was diluted with ethyl acetate, and washed with 10% citric acid, water, and brine. The organic layer was dried over anhydrous sodium sulfate and evaporated in vacuo. The residue was purified by silica gel column chromatography (chloroform then chloroform:ethyl acetate=1:50, v/v) to give the title compound (1.65 g) as a colorless oil.

(C) trans-4-Azido-N-tert-Butoxycarbonyl-D-Proline Methyl Ester

Sodium azide (515 mg) was added to a stirred solution of N-tert-butoxycarbonyl-cis-4-(p-toluenesulfonyloxy)-D-proline methyl ester (B, 1.65 g) in N,N-dimethylformamide (10 mL)-water (2 mL). After stirring at 80–90° C. for 1 hr, the solvents were removed in vacuo. The residue was diluted with ethyl acetate and washed with water and brine. The organic layer was dried over anhydrous sodium sulfate and evaporated in vacuo to give the title compound (1.04 g) as a colorless oil.

(D) trans-4-Amino-N-tert-Butoxycarbonyl-D-Proline Methyl Ester

A mixture of trans-4-azido-N-tert-butoxycarbonyl-D-proline methyl ester (C, 1.04 g) and 10% palladium on activated carbon (500 mg) in methanol (30 mL) was stirred at room temperature for 1.5 hr under hydrogen. The catalysts were removed by filtration and washed with methanol. The combined organic layers were evaporated in vacuo to give the title compound (0.90 g) as a colorless oil.

(E) N-tert-Butoxyearbonl-trans-4-(N-tert-Butoxycarbonylglycylamino)-D-Proline Methyl Ester Triethylamine (183 µL), 1-hydroxybenzotriazole (167 mg), and 1-(3-dimethylaminopropyl)-3-ethylcarbodiimide hydrochloride (251 mg) were added to a solution of N-tert-butoxycarbonylglycine (230 mg) and trans-4-amino-N-tert-butoxycarbonyl-D-proline methyl ester (D, 267 mg) in dichloromethane (20 mL). The mixture was stirred at room temperature for 15 hr and evaporated in vacuo. The residue was diluted with ethyl acetate and washed with 10% citric acid, saturated sodium hydrogen carbonate, and brine. The organic layer was dried over anhydrous sodium sulfate and evaporated in vacuo to give the title compound (499 mg) as a white solid.

(F) N-tert-Butoxycarbonyl-trans-4-(N-tert-Butoxycarbonylglycylamino-D-Proline

A solution of 1 N sodium hydroxide (1.5 mL) was added to a solution N-tert-butoxycarbonyl-trans-4-(N-tert-butoxycarbonylglycylamino)-D-proline methyl ester (E, 499 mg) in methanol (20 mL). The mixture was stirred at room temperature for 6 hr and evaporated in vacuo. The residue was diluted with water and washed with ether. The aqueous layer was acidified with 10% citric acid and extracted with ethyl acetate. The organic layer was washed with brine, dried over anhydrous sodium sulfate, and evaporated in vacuo to give the title compound (2.48 g) as a colorless solid: $^1$H NMR (400 MHz, CDCl$_3$) δ 1.38–1.48 (m, 18H), 2.17–2.32 (m, 2H), 3.30–3.31 (m, 4H), 3.63–3.78 (m, 3H), 4.28–4.39 (m, 1H), and 4.41–4.46 (m, 1H).

(G) N-tert-Butoxycarbonyl-trans-4-(N-tert-Butoxycarbonylglycylamino)-D-Prolyl-trans-4-((R)-2-Hydroxy-4-Phenylbutyrylamino)-L-proline 3-Quinolylamide Triethylamine (40 µL), 1-hydroxybenzotriazole (36 mg), and 1-(3-dimethylaminopropyl)-3-ethylcarbodiimide hydrochloride (55 mg) were added to a solution of N-tert-butoxycarbonyl-trans-4-(N-tert-butoxycarbonylglycylamino)-D-proline (F, 112 mg) and trans-4-((R)-2-hydroxy-4-phenylbutyrylamino)-L-proline 3-quinolylamide (Compound D101 (H), 100 mg) in dichloromethane (10 mL) at 0° C. The mixture was stirred at room temperature for 18 hr and evaporated in vacuo. The residue was diluted with ethyl acetate and washed with 1 N hydrochloric acid, water, saturated sodium hydrogen carbonate, and brine. The organic layer was dried over anhydrous sodium sulfate and evaporated in vacuo. The residue was purified by silica gel column chromatography (methanol:chloroform=1:50 to 1:20, v/v) to give the title compound (124 mg) as a colorless solid: $^1$H NMR (400 MHz, CDCl$_3$) δ 1.34–1.44 (m, 18H), 1.86–1.92 (m, 1H), 2.03–2.14 (m, 1H), 2.21–2.64 (m, 3H), 2.71–2.75 (m, 2H), 3.33–3.75 (m, 4H), 3.94–4.10 (m, 2H), 4.21–4.78 (m, 3H), 7.14–7.27 (m, 5H), 7.51–7.71 (m, 2H), 7.83–7.99 (m, 2H), 8.70–8.72 (m, 1H), and 8.96–9.05 (m, 1H).

(H) trans-4-Glycylamino-D-Prolyl-trans-4-((R)-2-Hydroxy-4-Phenylbutyrylamino)-L-proline 3-Quinolylamide A solution of N-tert-butoxycarbonyl-trans-4-(N-tert-butoxycarbonylglycylamino)-D-prolyl-trans-4-((R)-2-hydroxy-4-phenylbutyrylamino)-L-proline 3-quinolylamide (G, 120 mg) at 0° C., and methanol (3 mL) was added to dissolve until insoluble materials. After stirring for 2 hr, the reaction mixture was evaporated and coevaporated with 1,4-dioxane and ether in vacuo to give solid. The solids were washed with ether to afford the title compound (97 mg) as a colorless solid: $^1$H NMR (400 MHz, D$_2$O) δ 1.86–2.03 (m, 2H), 2.24–2.45 (m, 3H), 2.59–2.63 (m, 2H), 3.32 (m, 1H), 3.40–3.45 (m, 1H), 3.60–3.70 (m, 3H), 3.92–4.07 (m, 2H), 4.35–4.42 (m, 2H), 4.61–4.79 (m, 4H), 7.06–7.24 (m, 5H), 7.76 (t, 1H), 7.90 (t, 1H), 8.03 (d, 1H), 8.05(d, 1H), 8.86(s,1H), and 9.21 (s, 1H); mass spectrum (FAB+) m/e 588 (M+1); Anal. Calcd. For C$_{31}$H$_{37}$N$_7$O$_5$.3HCl.2H$_2$O: C, 50.79; H, 6.05; N, 13.37. Found: C, 51.09; H, 6.07; N, 12.97.

Compound D106—trans(N-Methylglycylamino)-L-Prolyl-trans-4-((R)-2-Hydroxy-4-Phenylbutyrylamino)-L-Proline 3-Quinolylamide Trihydrochloride (A) N-tert-Butoxycarbonyl-trans-4-(N-tert-Butoxycarbonyl-N-Methylglycylamino)-L-Proline Methyl Ester The title compound (293 mg) was similarly prepared, as described in Compound D103 (A), except the starting material was N-tert-butoxycarbonyl-N-methylglycine (188 mg): $^1$H NMR (400 MHz, CDCl$_3$) δ 1.37–1.52 (m, 18H), 2.08–2.10 (m, 2H), 2.93 (s, 3H), 3.22–3.37 (m, 1H), 3.74 (s, 3H), 3.76–3.89 (m, 3H), 4.25–4.41 (m, 1H), 4.54 (br s, 1H), and 6.52 (br s, 1H).

(B) N-tert-Butoxycarbonyl-trans-4-(N-tert-Butoxycarbonyl-N-methylglycylamino)-L-Proline The title compound (265 mg) was similarly prepared, as described in Compound D101 (O), except the starting material was N-tert-butoxycarbonyl-trans-4-(N-tert-butoxycarbonyl-N-methylglycylamino)-L-proline methyl ester (A, 293 mg): $^1$H NMR (400 MHz, CDCl$_3$) δ 2.10–2.50 (m, 2H), 2.94(s, 3H), 3.20–3.45(m, 1H), 3.70–3.92(m, 3H), 4.26–4.59(m, 1H), 5.13(br s, 1H), and 6.75(br s, 1H).

(C) N-tert-Butoxycarbonyl-trans-4-(N-tert-Butoxycarbonyl-N-Methylglycylamino)-L-Prolyl-trans-4-((R)-2-Hydroxy-4-Phenylbutyrylamino)-L-Proline 3-Quinolylamide The title compound (143 mg) was similarly prepared, as described in Compound D101 (P), except the starting material was N-tert-butoxycarbonyl-trans-4-(N-tert-butoxycarbonyl-N-methylglycylamino)-L-proline (B, 102 mg): $^1$H NMR (400 MHz, CDCl$_3$) δ 1.35–1.55 (m, 18H), 1.90–2.02 (m, 1H), 2.09–2.38 (m, 5H), 2.53–2.65 (m, 1H), 2.68–2.84 (m, 2H), 2.95 (s, 3H), 3.43 (dd, J=4.4, 11.2 Hz, 1H), 3.55–3.63 (m, 1H), 3.88–4.01 (m, 2H), 4.47–4.60 (m, 3H), 4.73 (br s, 1H), 4.90 (t, J=8.3 Hz, 1H), 6.69–6.81 (m, 1H), 7.15–7.48 (m, 6H), 7.72–7.80 (m, 1H), 7.58–7.65 (m, 1H), 8.54–8.68 (m, 2H), and 9.97 (br s, 1H).

(D) trans-4-(N-Methylglycylamino)-L-Prolyl-trans-4-((R)-2-Hydroxy-4-Phenyl-butyrylamino)-L-Proline 3-Quinolylamide Trihydrochloride The title compound (106 mg) was similarly prepared, as described in Compound D101 (Q), except the starting material was N-tert-butoxycarbonyl-trans-4-(N-tert-butoxycarbonyl-N-methylglycylamino)-L-prolyl-trans-4-((R)-2-hydroxy-4-phenylbutyryl)amino-L-proline 3-quinolylamide (C, 143 mg): $^1$H NMR (400 MHz, D$_2$O) δ 1.86–2.08 (m, 2H), 2.29–2.48 (m, 2H), 2.52–2.73 (m, 4H), 2.68 (s, 3H), 3.35 (dd, J=4.9, 12.7 Hz, 1H), 3.60–3.71 (m, 2H), 3.82 (s, 2H), 3.87–3.93 (m, 1H), 4.07–4.12 (m, 1H), 4.39–4.52 (m, 2H), 4.77–4.86 (m, 2H), 7.13–7.31 (m, 5H), 7.78–7.84 (m, 1H), 7.92–7.98 (m, 1H), 8.06–8.13 (m, 2H), 8.90–8.94 (m, 1H), and 9.24–9.28 (m, 1H); IR (KBr) 3338, 3313, 3055, 3026, 1682, 1655, 1610, 1574, 1554, 1462, and 1456 cm$^{-1}$; mass spectrum (FAB+) m/e 602 (M+1); Anal. Calcd for C$_{32}$H$_{39}$N$_7$O$_5$·3HCl·2.5H$_2$O: C, 50.83; H, 6.27; N, 12.97. Found: C, 51.20; H, 6.45; N, 12.62.

Compound D107—trans-4-(N,N-Dimethylglycylamino)-L-Prolyl-trans-4-((R)-2-Hydroxy-4-Phenylbutyrylamino)-L-Proline 3-Quinolylamide Trihydrochloride (A) N-tert-Butoxycarbonyl-trans-4-(N,N-Dimethylglycylamino)-L-Proline Methyl Ester Triethylamine (362 μL), 1-hydroxybenzotriazole (160 mg), and 1-(3-dimethylamino-propyl)-3-ethylcarbodiimide hydrochloride (249 mg) were added to a mixture of N-tert-butoxycarbonyl-trans-4-amino-L-proline methyl ester (Compound D101 (M), 264 mg) and N,N-dimethylglycine hydrochloride (181 mg) in dichloromethane (10 mL) at 0° C. After stirring at 0° C. for 30 min and at room temperature for 18 hr, the solvent was removed in vacuo. The residue was diluted with saturated sodium hydrogen carbonate and extracted with ethyl acetate. The organic layer was washed with brine, dried over anhydrous sodium sulfate, and evaporated in vacuo. The residue was purified by silica gel column chromatography (chloroform then chloroform:methanol=50:1 to 30:1, v/v) to afford the title compound (264 mg) as a pale yellow oil. The compound appears as a mixture of rotamers: $^1$H NMR (400 MHz, CDCl$_3$) δ 1.42 and 1.46 (each s, total 9H), 2.28 (s, 6H), 2.13–2.40 (m, 2H), 2.94 (s, 2H), 3.22–3.43 (m, 1H), 3.74 (s, 3H), 3.75–3.88 (m, 1H), 4.28–4.48 (m, 1H), and 4.50–4.62 (m, 1H).

(B) N-tert-Butoxycarbonyl-trans-4-(N,N-Dimethylglycylamino)-L-Proline

A solution of lithium hydroxide monohydrate (40 mg) in water (1 mL) was added to a solution of N-tert-butoxycarbonyl-trans-4-(N,N-dimethylglycylamino)-L-proline methyl ester (A, 264 mg) in tetrahydrofuran (3 mL)-methanol (1 mL) at 0° C. After stirring at room temperature for 4 hr, acetic acid (55 L) was added to the reaction mixture at 0° C. The resulting solution was evaporated in vacuo to afford the crude title compound, which is used in the subsequent step.

(C) N-tert-Butoxycarbonyl-trans-4-(N,N-Dimethylglycyl)amino-L-Prolyl-trans-4-((R)-2-Hydroxy-4-Phenylbutyrylamino)-L-Proline 3-Quinolylamide Triethylamine (33 μL), 1-hydroxybenzotriazole (30 mg), and 1-(3-dimethylaminopropyl)-3-ethylcarbodiimide hydrochloride (46 mg) were added to a suspension of the crude N-tert-butoxycarbonyl-trans-4-(N,N-dimethylglycylamino)-L-proline (B) and trans-4-((R)-2-hydroxy-4-phenylbutyrylamino)-L-proline 3-quinolylamide (Compound D101 (H), 84 mg) in dichloromethane (5 mL) at 0° C. After stirring at 0° C. for 30 min and at room temperature for 14 hr, the solvent was removed in vacuo. The residue was diluted with saturated sodium hydrogen carbonate and extracted with chloroform-methanol (10:1,v/v). The organic layer was washed with brine, dried over anhydrous sodium sulfate, and evaporated in vacuo. The residue was purified by preparative thin layer chromatography (Whatman, PLK5F Silica Gel 150, chloroform:methanol=10:1, v/v) to afford the title compound (76 mg) as a colorless glassy solid: mass spectrum (EI+) m/e 715 (M+); (FAB+) m/e 716 (M+1).

(D) trans-4-(N,N-Dimethylglycylamino)-L-Prolyl-trans-4-((R)-2-Hydroxy-4-Phenylbutyrylamino)-L-Proline 3-Quinolylamide Trihydrochloride N-tert-Butoxycarbonyl-trans-4-(N,N-dimethylglycylamino)-L-prolyl-trans-4-((R)-2-hydroxy-4-phenylbutyrylamino)-L-proline 3-quinolylamide (C, 76 mg) was dissolved in 4 N hydrogen chloride in 1,4-dioxane (10 mL) at 0° C., and stirred at 0†° C. for 5 min and at room temperature for 3 hr. The solution was evaporated in vacuo, and the residue was purified by HPLC (Shiseido, Capeell Pak C$_{18}$ UG120, 3 cm×25 cm, 0.02 N hydrochloric acid:methanol=55:45, v/v) and freeze-dried from water to afford the title compound (28 mg) as a pale yellow powder: $^1$H NMR (400 MHz, D$_2$O) δ 1.83–2.07 (m, 2H), 2.22–2.47 (m, 3H), 2.47–2.68 (m, 3H), 2.81 (s, 6H), 3.26–3.39 (m, 1H), 3.52–3.70 (m, 2H), 3.80–3.98 (m, 3H), 4.00–4.08 (m, 1), 4.31–4.52 (m, 2H), 4.68–4.84 (m, 2H), 7.07–7.29 (m, 5H), 7.73–7.81 (m, 1H),7.86–7.95 (m, 1H), 7.99–8.12 (m, 2H), 8.87 (s, 1H), and 9.21 (s, 1H); IR (KBr) 3367, 3025, 2952, 1654, 1648, 1610, 1571, 1554, and 1454 cm$^{-1}$; mass spectrum (FAB+) m/e 616 (M+1); high-resolution mass (FAB) m/e Calcd for C$_{33}$H$_{41}$ $_{N7}$O$_5$: 616.3247. Found: 616.3237.

Compound D108—trans-4-((S)-3-Amino-2-Hydroxypropionylamino)-L-Prolyl-trans-4-((R)-2-Hydroxy-4-Phenylbutyrylamino)-L-Proline 3-Quinolylamide Trihydrochlonde (A) N-tert-Butoxycarbonyl-trans-4-((S)-3-tert-Butoxycarbonylamino-2-Hydroxypropionylamino)-L-Proline Methyl Ester The title compound (113 mg) was similarly prepared as a colorless oil, as described in Compound D103 (A), except the starting materials were N-tert-butoxycarbonyl-trans-4-amino-L-proline methyl ester (Compound D101 (M), 97 mg) and (s)-3-tert-butoxycarbonylamino-2-hydroxypropionic acid (74 mg). The compound appears as a mixture of rotamers: $^1$H NMR (400 MHz, CDCl$_3$) δ 1.41, 1.44 and 1.46 (each s, total 18H), 2.11–2.32 (m, 3H), 3.16–3.39 (m, 1H), 3.40–3.63 (m, 2H), 3.74 (s, 3H), 3.77–3.90 (m, 1H), 4.13–4.20 (m, 1H), 4.29–4.45 (m, 1H), 4.56–4.63 (m, 1H), 5.40–5.53 (m, 1H), and 7.20–7.33 (m, 1H).

(B) N-tert-Butoxycarbonyl-trans-4-((S)-3-tert-Butoxycarbonylamino-2-Hydroxypropionylamino)-L-Proline The title compound (103 mg) was similarly prepared as a colorless oil, as described in Compound D101 (O), except the starting material was N-tert-butoxycarbonyl-trans-4-((S)-3-tert-butoxycarbonylamino-2-hydroxypropionyl)amino-L-proline methyl ester (A, 113 mg). The compound appears as a mixture of rotamers: $^1$H NMR (400 MHz, CD$_3$OD) δ 1.43, 1.44 and 1.46 (each s, total 18H), 2.19–2.37 (m, 2H), 3.18–3.50 (m, 3H), 3.70–3.83 (m, 1H), 4.00–4.12 (m, 1H), 4.25–4.40 (m, 1H), and 4.42–4.57 (m, 1H).

(C) trans-4-((S)-3-Amino-2-Hydroxypropionylamino)-L-Prolyl-trans-4-((R)-2-Hydroxy-4-Phenylbutrylamino)-L-Proline 3-Quinolylamide Trihydrochloride The title compound (58 mg) was similarly prepared, as described in Compound D101 (P) and (Q), except the starting materials were N-tert-butoxycarbonyl-trans-4-((s)-3-tert-butoxycarbonylamino-2-hydroxypropionylamino)-L-proline (B, 103 mg) and trans-4-((R)-2-hydroxy-4-phenylbutyrylamino)-L-proline 3-quinolylamide (Compound D101 (H), 137 mg): $^1$H NMR (400 MHz, D$_2$O) δ 1.91–2.12 (m, 2H), 2.30–2.52 (m, 3H), 2.58–2.75 (m, 3H), 3.11 (dd, J=13.2, 8.4 Hz, 1H), 3.32 (dd, J=13.2, 4.0 Hz, 1H), 3.40 (dd, J=12.3, 5.4 Hz, 1H), 3.64 (dd, J=10.9, 4.3 Hz, 1H), 3.70 (dd, J=12.3, 6.9 Hz, 1H), 3.91 (dd, J=10.9, 6.2 Hz, 1H), 4.11 (dd, J=7.2, 4.6 Hz, 1H), 4.37–4.97 (m, 2H), 4.98–4.58 (m, 1H), 4.75–4.91 (m, 2H), 7.15–7.43 (m, 5H), 7.73 (t, J=8.0 Hz, 1H), 7.82–7.89 (m, 1H), 8.02 (t, J=8.8 Hz, 2H), 8.70 (d, J=2.0 Hz, 1H), and 9.04 (d, J=2.0 Hz, 1H); IR (KBr) 3297, 3025,2944, 1654, 1648, 1610, 1571, and 1454 cm$^{-1}$; mass spectrum (FAB+) m/e 618 (M+1); Anal Calcd for C$_{32}$H$_{39}$N$_7$O$_6$.3HCl.4H$_2$O: C, 48.09; H, 6.31; N, 12.27. Found: C, 48.45; H, 6.14; N, 11.94.

Compound D109—trans-4-Aminomethyl-L-Prolyl-trans-4-((R)-2-Hydroxy-4-Phenylbutyrylamino)-L-Proline 3-Quinolylamide Trihydrochloride (A) N-tert-Butoxycarbonyl-trans-4-Cyano-L-Proline Methyl Ester Sodium cyanide (245 mg) was added to a stirred solution of N-tert-butoxycarbonyl-cis-4-p-toluenesulfonyloxy-L-proline methyl ester (Compound D101 (K), 1.00 g) in N,N-dimethylformamide (10 mL)-water (22 mL). After stirring at 65° C. for 16 hr, the solvents were removed in vacuo. The residue was diluted with ethyl acetate, and washed with water and brine. The organic layer was dried over anhydrous sodium sulfate and evaporated in vacuo. The residue was purified by silica gel column chromatography (ethyl acetate:toluene=1:20, v/v) to give the title compound (197 mg): $^1$H NMR (400 MHz, CDCl$_3$) δ 1.40 (s, 9H), 2.33–2.52 (m, 2H), 3.25 (m, 1H), 3.69 (m, 1H), 3.75 (s, 3H), 3.90 (m, 1H), and 4.37–4.49 (m, 1H).

(B) trans-4-Aminomethyl-N-tert-Butoxycarbonyl-L-Proline Methyl Ester

A mixture of N-tert-butoxycarbonyl-trans-4-cyano-L-proline methyl ester (A, 197 mg) and Raney-Ni (100 mg) in ethanol (6 mL) was stirred at room temperature for 21 hr under hydrogen. The catalysts were removed by filtration and washed with ethanol. The filtrate was evaporated in vacuo to give the title compound (204 mg).

(C) N-tert-Butoxycarbonyl-trans-4-(N-tert-Butoxycarbonylaminomethyl)-L-Proline Methyl Ester Triethylamine (129 μL) and a solution of di-tert-butyl dicarbonate (203 mg) in dichloromethane (1 mL) was added to a stirred solution of trans-4-aminomethyl-N-tert-butoxycarbonyl-L-proline methyl ester (B, 200 mg) in dichloromethane (3 mL). The mixture was stirred at room temperature for 13 hr and evaporated in vacuo. The residue was purified by silica gel column chromatography (methanol:chloroform=1:100, v/v) to give the title compound (204 mg): $^1$H NMR (400 MHz, CDCl$_3$) δ 1.40 (s, 9H), 1.46 (s, 9H), 1.98–2.05 (m, 2H), 2.50 (m, 1H), 3.09–3.17 (m, 3H), 3.69 (m, 1H), 3.73 (s, 3H), 4.264.38 (m, 1H), and 4.61 (m, 1H).

(D) N-tert-Butoxycarbonyl-trans-4-(N-tert-Butoxycarbonylaminomethyl)-L-Proline

Lithium hydroxide monohydrate (29 mg) was added to a stirred solution of trans-4-(N-tert-butoxycarbonylaminomethyl)-N-tert-butoxycarbonyl-L-proline methyl ester (C, 204 mg) in tetrahydrofuran (1 mL)-methanol (1 mL)-water (1 mL) at 0° C. The mixture was stirred at room temperature for 4 hr. The reaction mixture was acidified with 10% citric acid and extracted with chloroform. The organic layer was washed with brine, dried over anhydrous sodium sulfate and evaporated in vacuo to give the title compound (167 mg).

(E) N-tert-Butoxycarbonyl-trans-4-(N-tert-Butoxycarbonylaminomethyl)-L-Prolyl-trans-4-((R)-2-Hydroxy-4-Phenylbutyrylamino)-L-Proline 3-Quinolylamide Triethylamine (36 μL), 1-hydroxybenzotriazole (9 mg) and 1-(3-dimethylamino-propyl)-3-ethylcarbodiimide hydrochloride (49 mg) were added to a stirred solution of N-tert-butoxycarbonyl-trans-4-(N-tert-butoxycarbonylamino)methyl-L-Proline (D, 80 mg) and trans-4-((R)-2-hydroxy-4-phenylbutrylamino)-L-proline 3-quinolylamide (CompoundDlol (H), 97 mg) in dichloromethane (4 mL) at 0° C. The mixture was stirred at room temperature overnight. The reaction mixture was diluted with chloroform and washed with saturated sodium hydrogen carbonate and brine. The organic layer was dried over anhydrous sodium sulfate and evaporated in vacuo. The residue was purified by silica gel column chromatography (chloroform:methanol=100:1, v/v) to give the title compound (97 mg) as a colorless foam: $^1$H NMR (400 MHz, CDCl$_3$) δ 1.41 (s, 9H), 1.45 (s, 9H), 1.97–2.31 (m, 6H), 2.71 (m, 1H), 2.74 (m, 2H), 3.21 (m, 2H), 3.64 (m, 2H), 3.79 (m, 1H), 3.91 (m, 1H), 4.49–4.55 (m, 2H), 4.79 (m, 1H), 4.93 (m, 2H), 7.17–7.52 (m, 9H), 8.49 (s, 1H), 8.57 (s, 1H), and 10.2 (m, 1H).

(F) trans-4-Aminomethyl-L-Prolyl-trans-4-((R)-2-Hydroxy-4-Phenylbutylamino)-L-Proline 3-Quinolylamide Trihydrochloride trans-4-(N-tert-Butoxycarbonylaminomethyl-N-tert-butoxycarbonyl-L-prolyl-trans-4-((R)-2-hydroxy-4-phenylbutyrylamino)-L-proline 3-quinolylamide (E, 97 mg) was dissolved in 4 N hydrogen chloride in 1,4-dioxane (2 mL) and methanol (1 mL). After stirring for 2 hr, the solution was evaporated in vacuo, and the residue was purified by HPLC (Shiseido, Capcell Pak C$_{18}$ UG120, 3 cm×25 cm, 0.02 N hydrochloric acid:methanol=60:40, v/v) and freeze-dried from water to afford the title compound (44 mg) as a powder: $^1$H NMR (400 MHz, D$_2$O) δ 2.02–2.1 1 (m, 2H), 2.44–2.48 (m, 2H), 2.53 (m, 2H), 2.73–2.78 (m, 3H), 3.19–3.24 (m, 3H), 3.70 (dd, J=11.2, 4.4 Hz, 1H), 3.82 (dd, J=11.2, 7.3 Hz, 1H), 4.02 (dd, J=10.2, 5.9 Hz, 1H), 4.19 (m, 1H), 4.54 (m, 1H), 4.90 (m, 1H), 7.27–7.40 (m, 5H), 7.94 (t, J=7.8 Hz, 1H), 8.08 (t, J=7.8 Hz, 1H), 8.22 (m, 2H), 9.07 (s, 1H), and 9.40 (s, 1H).

Compound D110—4-(2-Aminoethyl)-Prolyl-trans-4-((R)-2-Hydroxy-4-Phenylbutylamino)-L-Proline 3-Quinolylamide Trihydrochloride (A) 4-Cyanomethylene-N-(9'-Phenylfluoren-9'-yl)-L-Proline Methly Ester Potassium tert-butoxide (146 mg) was added to a stirred solution of 4-oxo-N-(9'-phenylfluoren-9'-yl)-L-proline methyl ester (1.00 g) and diethyl cyanomethylphosphonate (422 L) in toluene (4 mL) at 0° C. under argon. After stirring at room temperature for 1.5 hr, the reaction mixture was diluted with ethyl acetate and washed with brine. The organic layer was dried over anhydrous sodium sulfate and evaporated in vacuo. The residue was purified by silica gel column chromatography (ethyl acetate:hexane=1:7, v/v) to give the title compound as two diastereomers, A (42 mg), B (56 mg), and a mixture of A and B (139 mg).

Diastereomer A: $^1$H NMR (400 MHz, CDCl$_3$) δ 2.76 (d, J=3.9 Hz, 2H), 3.27 (s, 3H), 3.61 (t, J=5.9 Hz, 1H), 3.77 (d, J=16.6 Hz, 1H), 4.09 (d, J=16.6 Hz, 1H), 5.19 (t, J=2.0 Hz, 1H), 7.24–7.28 (m, 5H), 7.36–7.48 (m, 6H), and 7.68–7.71 (m, 2H).

Diastereomer B: $^1$H NMR (400 MHz, CDCl$_3$) δ 2.58 (m, 2H), 3.25 (s, 3H), 3.53 (dd, J=7.8 and 3.4 Hz,1H), 3.99 (d, J=17.5 Hz, 1H), 4.24 (d, J=17.5 Hz, 1H), 5.19 (t, J=2.0 Hz, 1H), 7.24–7.28 (m, 5H), 7.36–7.48 (m, 6H), and 7.69 (t, J=7.3 Hz, 2H).

(B) 4-(2-Aminoethyl)-N-(9'-Phenylfluoren-9'-yl)-L-Proline Methyl Ester

A mixture of 4-cyanomethylene-N-(9'-phenylfluoren-9'-yl)-L-proline methyl ester (A, 139 mg) and Raney-Ni (100 mg) in ethanol (4 mL) was stirred at room temperature for 16 hr under hydrogen and for 3 hr under hydrogen at 5 atm. The catalysts were removed by filtration and washed with ethanol. The filtrate was evaporated in vacuo to give the title compound (152 mg).

(C) 4-[2-(tert-Butoxycarbonylamino)ethyl]-N-(9'-Phenylfluoren-9'-yl)-L-Proline Methyl Ester Triethylamine (62 μL) and solution of di-tert-butyl dicarbonate (97 mg) in dichloromethane (1 mL) was added to a stirred solution of 4-(2-aminoethyl)-N-(9'-phenylfluoren-9'-yl)-L-proline methyl ester (B, 152 mg) in dichloromethane (3 mL). The mixture was stirred at room temperature for 4 hr. The reaction mixture was diluted with dichloromethane and washed with brine. The organic layer was dried over anhydrous sodium sulfate and evaporated in vacuo. The residue was purified by silica gel column chromatography (ethyl acetate:hexane=1:7, v/v) to give the title compound (131 mg).

(D) 4-[2-(tert-Butoxycarbonylamino)ethyl]-L-Proline Methyl Ester

A mixture of 4-[2-(tert-butoxycarbonylamino)ethyl]-N-(9'-Phenylfluoren-9'-yl)-L-proline methyl ester (C, 131 mg) and 5% palladium on activated carbon (20 mg) in methanol (4 mL) was stirred under hydrogen at 5 atm for 5 hr. The catalysts were removed by filtration and washed with methanol. The filtrate was evaporated in vacuo to give the title compound (69 mg):

(E) N-tert-Butoxycarbonyl-4-[2-(tert-Butoxycarbonylamino)ethyl]-L-Proline Methyl Ester Triethylamine (47 μL) and solution of di-tert-butyl dicarbonate (67 mg) in dichloromethane (1 mL) was added to a stirred solution of 4-[2-(tert-butoxycarbonyl-amino)ethyl]-L-proline methyl ester (D, 69 mg) in dichloromethane (2 mL). After stirring at room temperature for 4 hr, the reaction mixture was diluted with dichloromethane and washed with brine. The organic layer was dried over anhydrous sodium sulfate and evaporated in vacuo. The residue was purified by silica gel column chromatography (methanol:chloroform=1:100, v/v) to give the title compound (50 mg).

(F) N-tert-Butoxycarbonyl-4-(N-tert-Butoxycarbonyl-2-Aminoethyl)-L-Proline

Lithium hydroxide monohydrate (7 mg) was added to a solution of N-tert-butoxycarbonyl-4-[2-(tert-butoxycarbonylamino)ethyl]-L-proline methyl ester (E, 50 mg) in tetrahydrofuran (0.5 mL)-methanol (0.5 mL)-water (0.5 mL). After stirring at room temperature for 4 hr, the reaction mixture was acidified with 10% citric acid and extracted with chloroform. The organic layer was washed with brine, dried over anhydrous sodium sulfate, and evaporated in vacuo to give the title compound (52 mg).

(G) N-tert-Butoxycarbonyl-4-[2-(tert-Butoxycarbonylamino)ethyl]-L-Prolyl-trans-4-((R)-2-Hydroxy-4-Phenylbutyrylamino)-L-Proline 3-Quinolylamide Triethylamine (21 μL), 1-hydroxybenzotriazole (9 mg) and 1-(3-dimethylaminopropyl)-3-ethylcarbodiimide hydrochloride (28 mg) were added to a solution of N-tert-butoxycarbonyl-4-[2-(tert-butoxycarbonylamino)ethyl]-L-Proline (48 mg) and trans-4-((R)-2-hydroxy-4-phenylbutyrylamino)-L-proline 3-quinolylamide (Compound D101 (H), 56 mg) in dichloromethane (3 mL) at 0° C. The mixture was stirred at room temperature overnight. The reaction mixture was diluted with chloroform and washed with saturated sodium hydrogen carbonate and brine. The organic layer was dried over anhydrous sodium sulfate and evaporated in vacuo. The residue was purified by preparative silica gel thin layer chromatography (chloroform:methanol=12:1, v/v) to give the title compound (47 mg) as a colorless foam: $^1$H NMR (400 MHz, CDCl$_3$) δ 1.40 (s, 9H), 1.48 (s, 9H), 1.71 (m, 2H), 1.99 (m, 1H), 2.13–2.51 (m, 6H), 2.75 (m, 2H), 3.16 (m, 2H), 3.63 (m, 1H), 3.73 (m, 1H), 3.87 (m, 1H), 3.90 (m, 1H), 4.38 (m, 1H), 4.53 (m, 1H), 4.80 (m, 1H), 4.82 (m, 1H), 5.50 (m, 1H), 7.15–7.64 (m, 9H), 7.68 (m, 1H), and 8.54 (m, 2H).

(H) 4-(2-Aminoethyl)-L-Prolyl-trans-4-((R)-2-Hydroxy-4-Phenylbutyrylamino)-L-Proline 3-Quinolylamide Trihydrochloride 4-N-tert-Butoxycarbonylaminoethyl-N-tert-butoxycarbonyl-L-prolyl-trans-4-((R)-2-hydroxy-4-phenylbutyrylamino)-L-proline 3-quinolylamide (G, 44 mg) was dissolved in 4 N hydrogen chloride in 1,4-dioxane (2 mL) and methanol (0.5 mL). After stirring for 2 hr, the reaction mixture was evaporated in vacuo to give white solids. The solids were washed with ether to afford the title compound (39 mg) as a powder: $^1$H NMR (400 MHz, D$_2$O) δ 1.77 (m, 1H), 1.86–1.93 (m, 2H), 2.05 (m, 1H), 2.12 (m, 1H), 2.47 (m, 1H), 2.54 (m, 2H), 2.78 (t,J=7.3 Hz, 2H), 2.92 (m, 1H), 3.08–3.13 (m, 3H), 3.86 (m, 2H), 4.00 (m, 1H), 4.20 (m,1H), 4.55 (m, 1H), 4.73 (m, 1H), 4.92 (m, 1H), 7.28–7.41 (m, 5H), 7.94 (t, J=7.8 Hz, 1H), 8.08 (t, J=7.8 Hz, 1H), 8.22 (t, J=9.3 Hz, 1H), 9.06 (s, 1H), and 9.39 (s, 1H).

Compound D111—1-(N-Methylglycyl)-trans-4-Amino-L-Prolyl-trans-4-((R)-2-Hydroxy-4-Phenylbutyrylamino)-L-Proline 3-Quinolylamide Trihydrochloride (A) 1-(N-tert-Butoxycarbonyl-N-Methylglycyl)-cis-4-Hydroxy-L-Proline Methyl Ester Trifluoroacetic acid (10 mL) was added to a solution of N-tert-butoxycarbonyl-cis-4-hydroxy-L-proline methyl ester (Compound D101 (J), 1.10 g) in dichloromethane (10 mL) at 0° C. After stirring at 0° C. for 10 min and at room temperature for 3 hr, the mixture was evaporated in vacuo to give a crude N-tert-butoxycarbonyl-cis-4-hydroxy-L-proline trifluoroacetate. The crude N-tert-butoxycarbonyl-cis-4-hydroxy-L-proline trifluoroacetate was dissolved in dichloromethane (20 mL), and N-tert-butoxycarbonyl-sarcosine (844 mg), triethylamine (1.25 mL), 1-hydroxybenzotriazole (663 mg), and 1-(3-dimethylaminopropyl)-3-ethylcarbodiimide hydrochloride (856 mg) were added at 0° C. After stirring at 0° C. for 30 min and at room temperature for 17 hr, the solvent was removed in vacuo. The residue was diluted with 1 N hydrochloric acid and extracted with ethyl acetate. The organic layer was washed with saturated sodium hydrogen carbonate, water, and brine, dried over anhydrous sodium sulfate, and evaporated in vacuo. The residue as purified by silica gel column chromatography (chloroform then chloroform-methanol=50:1 to 30:1, v/v) to afford the title compound (452 mg) as a colorless oil. The compound appears as a mixture of rotamers: $^1$H NMR (400 MHz, CDCl$_3$) δ 1.42 and 1.46 (each s, total 9H), 2.04–2.14 (m, 1H), 2.26–2.39 (m, 1H), 2.94 (s, 3H), 3.52–4.17 (m, 4H), 3.75 and 3.77 (each s, total 3H), 4.17–4.28 (m, 1H), and 4.38–4.62 (m, 2H).

(B) 1-(N-tert-Butoxycarbonyl-N-Methylglycyl)-cis-4-Methanesulfonyloxy-L-Proline Methyl Ester Triethylamine (678 μL) and methanesulfonyl chloride (342 L) were added to a solution of 1-(N-tertbutoxycarbonyl-N-methylglycyl)-cis-4-hydroxy-L-proline methyl ester (A, 699 mg) in dichloromethane (15 mL) at 0° C. After stirring at 0° C. for 45 min and at room temperature for 45 min, the reaction mixture was diluted with chloroform. The organic layer was washed with 10% citric acid, saturated sodium hydrogen carbonate, and brine, dried over anhydrous sodium sulfate, and evaporated in vacuo to afford the title compound (0.82 g) as a pale yellow oil.

(C) trans-4-Azido-1-(N-tert-Butoxycarbonyl-N-Methylglycyl)-L-Proline Methyl Ester Sodium azide (675 mg) was added to a solution of 1-(N-tert-butoxycarbonyl-N-methylglycyl)-cis-4-methanesulfonyloxy-L-proline methyl ester (B, 0.82 g) in N,N-dimethylformamide (10 mL)-water (1 mL). After stirring at 70° C. for 3 hr, the solvents were removed in vacuo, and the residue was diluted with chloroform. The organic layer was washed with water and brine, dried over anhydrous sodium sulfate, and evaporated in vacuo to afford the title compound (0.75 g) as a pale yellow oil.

(D) trans-4-Amino-1-(N-tert-Butoxycarbonyl-N-Methylglycyl)-L-Proline Methyl Ester 10% Palladium on activated carbon (75 mg) was added to a solution of trans-4-azido-1-(N-tert-butoxycarbonyl-N-methylglycyl)-L-proline methyl ester (C, 0.75 g) in methanol (50 mL), and the mixture was stirred under a hydrogen atmosphere at room temperature for 16 hr. After the catalyst were removed by filtration, the filtrate was evaporated in vacuo to afford the title compound (0.54 g).

(E) trans-4-(N-tert-Butoxycarbonylamino)-1-(N-tert-Butoxycarbonyl-N-Methylglycyl)-L-Proline Methyl Ester A solution of di-tert-butyl dicarbonate (907 mg) in tetrahydrofuran (5 mL) was added to a solution of trans-4-amino-1-(N-tert-butoxycarbonyl-N-methylglycyl)-L-proline methyl ester (D, 0.54 g) in tetrahydrofuran (20 mL). After stirring at room temperature for 6 hr, a solution of di-tert-butyl dicarbonate (907 mg) in tetrahydrofuran (5 mL) was added again and stirred for 16 hr. The solvent was removed in vacuo, and the residue was purified by silica gel column chromatography (chloroform then chloroform-methanol=50:1,v/v) to afford the title compound (292 mg) as a colorless foam. The compound appears as a mixture of rotamers: $^1$H NMR (400 MHz, CDCl$_3$) δ 1.43 (s, 9H), 1.46 (s, 9H), 2.05–2.18 (m, 1H), 2.18–2.35 (m, 1H), 2.94 and 2.98 (each s, total 3H), 3.30–3.94 (m, 4H), 3.73 (s, 3H), 4.21–4.41 (m, 1H), 4.52–4.62 (m, 1H), 4.62–4.72 (m, 0.51), and 5.13–5.23 (m, 0.5H); mass spectrum (EI+) m/e 415 (M+); (FAB+) m/e 416 (M+1).

(F) trans-4-(N-tert-Butoxycarbonylamino)-1-(N-tert-Butoxycarbonyl-N-Methylglycyl)-L-Proline A solution of lithium hydroxide monohydrate (35 mg) in water (2 mL) was added to a solution of trans-4-(N-tert-butoxycarbonylamino)-1-(N-tert-butoxycarbonyl-N-methylglycyl)-L-proline methyl ester (E, 289 mg) in tetrahydrofuran (6 mL)-methanol (2 mL) at 0° C. After stirring at 0° C. for 10 min and at room temperature for 15 hr, the solvents were removed in vacuo. The residue was diluted with water and washed with diethyl ether. The aqueous layer was acidified with 1 N hydrochloric acid, and extracted with ethyl acetate. The organic layer was washed with brine, dried over anhydrous sodium sulfate, and evaporated in vacuo to afford the title compound (258 mg) as a colorless oil. The compound appears as a mixture of rotamers: $^1$H NMR (400 MHz, CDCl$_3$) δ 1.36 (s, 9H), 1.38 (s, 9H), 2.03–2.30 (m, 1.5H), 2.62–2.94 (m, 3.5H), 3.20–4.02 (m, 4H), 4.07–4.42 (m, 1H), 4.46–4.62 (m 1H), 5.24–5.62 (m, 0.5H), 5.70–5.82 (m, 0.5H), and 8.60 (br s, 1H).

(G) trans-4-(N-tert-Butoxycarbonylamino-1-N-tert-Butoxycarbonyl-N-Methylglycyl)-L-Prolyl-trans-4-((R)-2-Hydroxy-4-Phenylbutyrylamino)-L-Proline 3-Quinolylamide Triethylamine (33 μL), 1-hydroxybenzotriazole (29 mg), and 1-(3-dimethylamino-propyl)-3-ethylcarbodiimide hydrochloride (45 mg) were added to a solution of trans-4-(N-tert-butoxycarbonylainino)-1-(N-tert-butoxycarbonyl-N-methylglycyl)-L-proline (F, 118 mg) and trans-4-((R)-2-hydroxy-4-phenylbutyrrylamino)-L-proline 3-quinolylamide (Compound D101 (H), 82 mg) in dichloromethane (5 mL) at 0° C. After stirring at 0° C. for 1 hr and at room temperature for 18.5 hr, the solvent was removed in vacuo. The residue was diluted with 10% citric acid and extracted with ethyl acetate. The organic layer was washed with water, saturated sodium hydrogen carbonate and brine, dried over anhydrous sodium sulfate, and evaporated in vacuo. The residue was purified by preparative thin layer chromatography (Whatman PLK5F Silica Gel 150, chloroform:methanol= 30;1, v/v, ×2) to afford the title compound (149 mg) as a colorless glassy solid.

(H) trans-4-Amino-1-(N-Methylglycyl)-L-Prolyl-trans-4-((R)-2-Hydroxy-4-Phenyl-butyrylamino-L-Proline 3-Quinolylamide Trihydrochloride 4 N Hydrogen chloride in 1,4-dioxane (10 mL) was added to a solution of trans-4-N-tert-butoxycarbonylamino-1-(N-tert-butoxycarbonyl-N-methylglycyl)-L-prolyl-trans-4-((R)-2-hydroxy-4-phenylbutyrylamino)-L-proline 3-quinolylamide (G, 149 mg) at 0° C. After stirring at 0° C. for 10 min and at room temperature for 2 hr, the solvent was evaporated in vacuo. Ethanol and diethyl ether were added to the residue, and the solid was collected by filtration, washed with diethyl ether, and freeze-dried from water to afford the title compound (127 mg) as a pale yellow powder: $^1$H NMR (400 MHz, D$_2$O) δ 1.90–2.15 (m, 2H), 2.30–3.00 (m, 4H), 2.75 (s, 3H), 3.55–4.30 (m, 9H), 4.42–4.60 (m, 1H), 4.66–4.90 (m, 2H), 4.90–5.15 (m, 1H), 7.12–7.46 (m, 5H), 7.80–7.94 (m, 1H), 7.94–8.06 (m, 1H), 8.06–8.27 (m, 2H), (s, 1H), and 9.31 (s, 1H); IR (KBr) 3396, 3023, 2944, 1654, 1612, 1573, and 1550 cm$^{-1}$; mass spectrum (FAB+) m/e 602 (M+1); Anal. Calcd for C$_{32}$H$_{39}$N$_7$O$_5$.3HCl.2H$_2$O: C, 51.44; H, 6.21; N, 13.12. Found: C, 51.10; H, 6.31; N, 12.70.

Compound D112—trans-4-Amino-L-Pipecolinoyl-trans-4-((R)-2-Hydroxy-4-Phenylbutyrylamino)-L-Proline 3-Quinolylamide Trihydrochloride (A) cis-4-Hydroxy-L-Pipecolinic Acid Methyl Ester A mixture of (1S,5R)-2-((S)-1-phenylethyl)-6-oxa-2-azabicyclo[3.2.1]octan-7-one (2.95 g) and 10% palladium on activated carbon (570 mg) in methanol (75 mL) was stirred at room temperature for 6 hr under hydrogen (3.5 kgf/cm$^2$). The catalysts were removed by filtration and washed with methanol. The combined organic layers were evaporated in vacuo. A mixture of the residue and 10% palladium on activated carbon (500 mg) in methanol (75 mL) was stirred at room temperature for 8 hr under hydrogen (3.5 kgf/cm$^2$). The catalysts were removed by filtration and washed with methanol. The combined organic layers were evaporated in vacuo. The mixture of the residue and 10% palladium on activated carbon (504 mg) in methanol (75 mL) was stirred at room temperature for 8 hr under hydrogen (4.0 kgf/cm$^2$). The catalysts were removed by filtration and washed with methanol. The combined organic layers were evaporated in vacuo to give the title compound (2.11 g): $^1$H NMR (400 MHz, CDCl$_3$) δ 1.32–1.49 (m, 2H), 1.83 (br s, 2H), 1.93–1.95 (m, 1H), 2.27–2.32 (m, 1H), 2.61–2.69 (m, 1H), 3.22 (dt, J=12.7, 3.9 Hz, 1H), 3.39 (dd, J=2.9, 10.7 Hz, 1H), 3.71–3.78 (m, 1H), and 3.75 (m, 3H).

(B) N-tert-Butoxycarbonyl-cis-4-Hydroxy-L-Pipecolinic Acid Methyl Ester

Di-tert-butyl dicarbonate (4.39 mL) was added to a stirred solution of cis-4-hydroxy-L-pipecolinic acid methyl ester (A, 2.11 g) in methanol (40 mL). After the mixture was stirred at room temperature for 15 hr, additional di-tert-butyl dicarbonate (2.91 mL) was added to the mixture. The mixture was stirred at room temperature for 4 hr and evaporated in vacuo. The residue was purified by silica gel column chromatography (ethyl acetate:hexane=1:3 to 1:2, v/v) to give the title compound (2.80 g) as a colorless oil: $^1$H-NMR (400 MHz, CDCl$_3$) δ 1.47 (s, 9H), 1.60–1.84 (m, 3H), 1.91 (ddd, J=2.4, 6.8, 14,2 Hz, 1H), 2.42 (d, J=14.2 Hz, 1H), 3.23–3.48 (m, 1H), 3.67–3.91 (m, 1H), 3.74 (s, 3H), 4.15 (m, 1H), and 4.66–4.83 (m, 1H).

(C) N-tert-Butoxycarbonyl-cis-4-p-Toluenesulfonyloxy-L-Pipecolinic Acid Methyl Ester The title compound (1.41 g) was similarly prepared, as described in Compound D101 (K), except the starting material was N-tert-butoxycarbonyl-cis-4-hydroxy-L-pipecolinic acid methyl ester (s, 920 mg): $^1$H NMR (400 MHz, CDCl$_3$) δ 1.33–1.53 (m, 9H), 1.55–1.68 (m, 2H), 1.77–1.95 (m, 2H), 2.45 (s, 3H), 2.54 (d, J=14.7 Hz, 1H), 3.14–3.43 (m, 1H), 3.67 (s, 3H), 3.77–3.97(m, 1H), 4.83 (br s, 1H), 7.34 (d, J=7.8 Hz, 1H), and 7.76 (d, J=8.3 Hz, 1H).

(D) trans-4-Azido-N-tert-Butoxycarbonyl-L-Pipecolinic Acid Methyl Ester

The title compound (870 mg) was similarly prepared, as described in Compound D101 (L), except the starting material was N-tert-butoxycarbonyl-cis-4-p-toluenesulfonyloxy-L-pipecolinic acid methyl ester (C, 1.41 g): $^1$H NMR (400 MHz, CDCl$_3$) δ 1.35–1.57 (m, 10H), 1.61–1.73 (m, 1H), 1.86–2.03 (m, 1H), 2.40–2.55 (m, 1H), 2.85–3.13 (m, 1H), 3.28–3.41 (m, 1H), 3.76 (m, 3H), 4.00–4.24 (m, 1H), and 4.90–5.12 (m, 1H).

(E) trans-4-Amino-N-tert-Butoxycarbonyl-L-Pipecolinic Acid Methyl Ester

The title compound (692 mg) was similarly prepared, as described in Compound D101 (M), except the starting material was trans- 4-azido-N-tert-butoxycarbonyl-L-pipecolinic acid methyl ester (D, 870 mg): $^1$H NMR (400 MHz, CDCl$_3$) δ 1.15–1.32 (m, 1H), 1.35–1.58 (m, 12H), 1.72–1.85 (m, 1H), 2.28–2.39 (m, 1H), 2.64–2.76 (m, 1H), 2.86–3.09 (m, 1H), 3.69–3.37 (m, 3H), 3.92–4.15 (m, 1H), and 4.75–5.05 (m, 1H).

(F) N-tert-Butoxycarbonyl-trans-4-(N-tert-Butoxycarbonylamino)-L-Pipecolinic Acid Methyl Ester The title compound (236 mg) was similarly prepared, as described in Compound D101 (N), except the starting material was trans-4-amino-N-tert-butoxycarbonyl-L-pipecolinic acid methyl ester (E, 201 mg): $^1$H NMR (400 MHz, CDCl$_3$) δ 1.16–1.33 (m, 1H), 1.33–1.65 (m, 10H), 1.97 (br s, 1H), 2.47 (br s, 1H), 2.92–3.15 (m, 1H), 3.45 (br s, 1H), 3.75 (s, 3H), 3.92–4.14 (m, 1H), 4.36 (br s, 1H), and 4.74–5.03 (m, 1H).

(G) N-tert-Butoxycarbonyl-trans-4-(N-tert-Butoxycarbonylamino)-L-Pipecolinic Acid The title compound (234 mg) was similarly prepared, as described in Compound D101 (O), except the starting material was N-tert-butoxycarbonyl-trans-4-(N-tert-butoxycarbonylamino)-L-pipecolinic acid methyl ester (F, 236 mg): $^1$H NMR (400 MHz, CDCl$_3$) δ 1.18–1.33 (m, 1H), 1.35–1.56 (m, 19H), 1.97 (br s, 1H), 2.53 (br s, 1H), 3.00–3.20 (m, 1H), 3.57 (br s, 1H), 3.94–4.16 (m, 1H), 4.48 (br s, 1H), and 4.78–5.07 (m, 1H).

(H) N-tert-Butoxycarbonyl-trans-4-(N-tert-Butoxycarbonylamino)-L-Pipecolinoyl-trans-4-((R)-2-Hydroxy-4-Phenylbutyrylamino)-L-Proline 3-Quinolylamide The title compound (189 mg) was similarly prepared, as described in Compound D101 (P), except the starting material was N-tert-butoxycarbonyl-trans-4-(N-tert-butoxycarbonylamino)-L-pipecolinic acid (G, 234 mg): $^1$H NMR (400 MHz, CD$_3$OD) δ 1.22–1.52 (m, 19H), 1.52–1.68 (m, 1H), 1.82–1.95 (m, 2H), 1.97–2.09 (m, 1H), 2.18–2.45 (m, 3H), 3.33–4.15 (m, 6H), 4.62–4.79 (m, 2H), 4.97–5.05 (m, 1H), 7.09–7.28 (m, 5H), 7.57 (t, J=7.6 Hz, 1H), 7.67 (t, J=7.8 Hz, 1H), 7.88 (d, J=8.3 Hz, 1H), 7.96 (d, J=8.8 Hz, 1H), 8.71 (br s, 1H), and 8.89 (d, J=2.4 Hz, 1H).

(I) trans-4-Amino-L-Pipecolinoyl-trans-4-((R)-2-Hydroxy-4-Phenylbutyrylamino)-L-Proline 3-Quinolylamide Trihydrochloride The title compound (76 mg) was similarly prepared, as described in Compound D101 (Q), except the starting material was N-tert-butoxycarbonyl-trans-4-(N-tert-butoxycarbonylamino)-L-pipecolinoyl-trans-4-((R)-2-hydroxy-4-phenylbutyryl)amino-L-proline 3-quinolylamide (H, 189 mg): $^1$H NMR (400 MHz, D$_2$O) δ 1.83–2.02 (m, 3H), 2.12–2.4 5(m, 5H), 2.55–2.68b (m, 2H), 3.26–3.35 (m, 1H), 3.53–3.69 (m, 3H), 3.89 (dd, J=5.9, 10.7 Hz, 1H), 4.04 (dd, J=4.4, 7.3 Hz, 1H), 4.33–4.41 (m, 1H), 4.59–4.73 (m, 1H), 4,78 (t, J=7.6 Hz, 1H), 7.09–7.27 (m, 5H), 7.75 (t, J=7.6 Hz, 1H), 7.89 (t, J=7.3 Hz, 1H), 8.02–8.05 (m, 2H), 8.85 (br s, 1H), and 9.17 (d, J=2.0 Hz, 1H); IR (KBr) 3359, 2924, 1655, 1610, 1574, 1543, 1495, and 1452 cm$^{-1}$; mass spectrum (FAB+) m/e 545 (M+1); Anal. Calcd for C$_{30}$H$_{36}$N$_6$O$_4$.3HCl.2H$_2$O: C, 52.22; H, 16.28; N, 12.18. Found: C, 52.09; H, 6.24; N, 12.07.

Compound D113—cis-4-Amino-L-Pipecolinoyl-trans-4-((R)-2-Hydroxy-4-Phenylbutyrylamino)-L-Proline 3-Quinolylamide Trihydrochloride (A) N-tert-Butoxycarbonyl-trans-4-Formyloxy-L-Pipecolinic Acid Methyl Ester The title compound (1.22 g) was similarly prepared, as described in Compound D101 (I), except the starting material was N-tert-butoxycarbonyl-cis-4-hydroxy-L-pipecolinic acid methyl ester (Compound D112 (B), 1.81 g): $^1$H NMR (400 MHz, CDCl$_3$) δ 1.34–1.61 (m, 10H), 1.80 (dt, J=6.4, 12.2 Hz, 1H), 1.92–2.11 (m, 1H), 2.38–2.59 (m, 1H), 2.93–3.19 (m, 1H), 3.77 (s, 3H), 3.96–4.20 (m, 1H), 4.77–5.13 (m, 2H), and 8.02 (s, 1H).

(B) N-tert-Butoxycarbonyl-trans-4-Hydroxy-L-Pipecolinic Acid Methyl Ester

The title compound (991 mg) was similarly prepared, as described in Compound D101 (J), except the starting material was N-tert-butoxycarbonyl-trans-4-formyloxy-L-pipecolinic acid methyl ester (A, 1.22 g): $^1$H NMR (400 MHz, CDCl$_3$) δ 1.33–1.55 (m, 10H), 1.55–1.69 (m, 1H), 1.80–1.99 (m, 2H), 2.45 (br s, 1H), 2.83–3.12 (m, 1H), 3.59–3.69 (m, 1H), 3.73 (s, 3H), 3.93–4.17 (m, 1H), and 4.74–5.09 (m, 1H).

(C) N-tert-Butoxycarbonyl-trans-4-(p-Toluenesulfonyloxy)-L-Pipecolinic Acid Methyl Ester The title compound (1.53 g) was similarly prepared, as described in Compound D101 (K), except the starting material was N-tert-butoxycarbonyl-trans- 4-hydroxy-L-pipecolinic acid methyl ester (B, 991 mg): $^1$H NMR (400 MHz, CDCl$_3$) δ 1.44 (s, 9H), 1.55–1.68 (m, 1H), 1.70–1.85 (m, 1H), 1.89–1.98 (m, 1H), 2.25–2.40 m, 1H), 2.46 (s, 3H), 2.79–3.07 (m, 1H), 3.70 (s, 3H), 3.91–4.15 (m, 1H), 4.40–4.52 m, 1H), and 4.72–5.03 (m, 1H).

(D) cis-4-Azido-N-tert-Butoxycarbonyl-L-Pipecolinic Acid Methyl Ester

The title compound (978 mg) was similarly prepared, as described in Compound D101 (L), except the starting material was N-tert-butoxycarbonyl-trans-4-p-toluenesulfonyloxy-L-pipecolc acid methyl ester (C, 1.53 g): $^1$H NMR (400 MHz, CDCl$_3$) δ 1.46 (s, 9H), 1.56–1.84 (m, 2H), 1.95 (ddd, J=2.9, 6.8, 14.7 Hz, 1H), 2.42–2.59 (m, 1H), 3.07–3.35 (m, 1H), 3.71–4.00 (m, 2H), 3.78 (s, 3H), and 4.58–4.93 (m, 1H).

(E) cis-4-Amino-N-tert-Butoxycarbonyl-L-Pipecolinic Acid Methyl Ester

The title compound (747 mg) was similarly prepared, as described in Compound D101 (M), except the starting material was cis-4-azido-N-tert-butoxycarbonyl-L-pipecolinic acid methyl ester (D, 978 mg): $^1$H NMR (400 MHz, CDCl$_3$) δ 1.24–1.64 (m, 11H), 1.65–1.75 (m, 1H), 1.79 (d, J=11.7 Hz, 1H), 1.83–1.96 (m, 1H), 2.13–2.24 (m, 1H), 3.11–3.60 (m, 2H), 3.72 (m, 3H), 3.85–4.18 (m, 1H), and 4.40–4.75 (m, 1H).

(F) N-tert-Butoxycarbonyl-cis-4-(N-tert-Butoxycarbonylamino)-L-Pipecolinic Acid Methyl Ester The title compound (195 mg) was similarly prepared, as described in Compound D101 (N), except the starting material was cis-4-amino-N-tert-butoxycarbonyl-L-pipecolinic acid methyl ester (E, 215 mg): $^1$H NMR (400 MHz, CDCl$_3$) δ 1.32–1.56 (m, 19H), 1.67–1.95 (m, 2H), 2.44 (d, J=13.7 Hz, 1H), 3.21 (br s, 1H), 3.74 (s, 3H), 3.84 (m, 2H), and 4.72 (m, 2H).

(G) N-tert-Butoxycarbonyl-cis-4-(N-tert-Butoxycarbonylamino)-L-Pipecolinic Acid

The title compound (178 mg) was similarly prepared, as described in Compound D101 (O), except the starting material was N-tert-butoxycarbonyl-cis-4-(N-tert-butoxycarbonylamino)-L-pipecolinic acid methyl ester (F, 195 mg): $^1$H NMR (400 MHz, CDCl$_3$) δ 1.37–1.54 (m, 18H), 1.57–1.80 (m, 3H), 2.68–2.80 (m, 1H), 3.33–3.55 (m, 1H), 3.69 (br s, 1H), 3.74–3.98 (m, 1H), 4.60–4.79 (m, 1H), and 7.49 (br s, 1H).

(H) N-tert-Butoxycarbonyl-cis-4-(N-tert-Butoxycarbonylamino)-L-Pipecolinoyl-trans-4-((R)-2-Hydroxy-4-Phenylbutyrylamino)-L-Proline 3-Quinolylamide The title compound (182 mg) was similarly prepared, as described in Compound D101 (P), except the starting material was N-tert-butoxycarbonyl-cis-4-(N-tert-butoxycarbonylamino)-L-pipecolinic acid (G, 178 mg): $^1$H NMR (400 MHz, CD$_3$OD) δ 1.15–1.54 (m, 19H), 1.56–1.68 (m, 1H), 1.76–1.95 (m, 2H), 1.98–2.09 (m, 1H), 2.11–2.20 (m, 1H), 2.28–2.46 (m, 2H), 2.73 (t, J=8.1 Hz, 2H), 3.47–3.85 (m, 4H), 4.03 (dd, J=3.7, 8.1 Hz, 1H), 4.55–4.72 (m, 2H), 4.76 (t, J=6.8 Hz, 1H), 7.10–7.29 (m, 5H), 7.59 (t, J=7.6 Hz, 1H), 7.65–7.69 (m, 1H), 7.87 (d, J=7.8 Hz, 1H), 7.96 (d, J=8.3 Hz, 1H), 8.71 (br s, 1H), and 8.91 (br s, 1H).

(I) cis-4-Amino-L-Pipecolinoyl-trans-4-((R)-2-Hydroxy-4-Phenylbutyrylamino)-L-Proline 3-Quinolylamide Trihydrochloride The title compound (93 mg) was similarly prepared, as described in Compound D101 (Q), except the starting material was N-tert-butoxycarbonyl-cis-4-(N-tert-butoxycarbonylamino)-L-pipecolinoyl-trans-4-((R)-2-hydroxy-4-phenylbutyryl)amino-L-proline 3-quinolylamide (H, 182 mg): $^1$H NMR (400 MHz, D$_2$O) δ 1.68–2.03 (m, 4H), 2.19–2.34 (m, 2H), 2.35–2.44 (m, 1H), 2.53–2.69 (m, 3H), 3.12 (dt, J=2.9, 13.2 Hz, 1H), 3.50–3.69 (m, 3H), 3.91 (dd, J=6.1, 11.0 Hz, 1H), 4.04 (dd, J=4.2, 7.1 Hz, 1H), 4.34 (dd, J=2.9, 12.7 Hz, 1H), 4.38 (t, J=5.4 Hz, 1H), 4.77 (t, J=7.3 Hz, 1H), 7.09–7.29 (m, 5H), 7.75 (t, J=7.8 Hz, 1H), 7.89 (t, J=7.6 Hz, 1H), 8.00–8.09 (m, 2H), 8.85 (br s, 1H), and 9.18 (br s, 1H); IR (KBr) 3410, 2918, 1655, 1612, 1574, 1556, 1493, and 1456 cm$^{-1}$; mass spectrum (FAB+) m/e 545 (M+1); Anal. Calcd for C$_{30}$H$_{36}$N$_6$O$_4$.3HCl.4H$_2$O: C, 49.62; H, 6.53; N, 11.57. Found: C, 49.58; H, 6.13; N, 11.36.

Compound D114—trans-4-Glycylamino-L-Pipecolinoyl-trans-4-((R)-2-Hydroxy-4-Phenylbutyrylamino)-L-Proline 3-Quinolylamide Trihydrochloride (A) N-tert-Butoxycarbonyl-trans-4-(N-tert-Butoxycarbonylglycylamino)-L-Pipecolinic Acid Methel Ester The title compound (333 mg) was similarly prepared, as described in Compound D103 (A), except the starting material was N-tert-butoxycarbonyl-trans-4-amino-L-pipecolinic acid methyl ester (Compound D112 (E), 209 mg): $^1$H NMR (400 MHz, CDCl$_3$) δ 1.20–1.69 (m, 20H), 1.99–2.02 (m, 1H), 2.41–2.49(m, 1H), 2.95–3.16 (m, 1H), 3.69–3.86 (m, 6H), 3.95–4.16 (m, 1H), 4.79–5.15 (m, 2H), and 5.90–6.05 (m, 1H).

(B) N-tert-Butoxycarbonyl-trans-4-(N-tert-Butoxycarbonylglcylamino)-L-Pipecolinic Acid The title compound (313 mg) was similarly prepared, as described in Compound D101 (O), except the starting material was N-tert-butoxycarbonyl-trans-4-(N-tert-butoxycarbonylglycylamino)-L-pipecolinic acid methyl ester (A, 333 mg): $^1$H NMR (400 MHz, CDCl$_3$) δ 1.19–1.64 (m, 20H), 1.95 (br d, J=12.2 Hz, 1H), 2.47 (br d, J=11.7 Hz, 1H), 3.00–3.21 (m, 1H), 3.68–4.04 (m, 4H), 4.81–5.06 (m, 1H), 5.40 (br s, 1H), and 6.37–6.57 (m, 1H).

(C) N-tert-Butoxycarbonyl-trans-4-(N-tert-Butoxycarbonylglycylamino)-L-Pipecoinoyl-trans-4-((R)-2-Hydroxy-4-Phenylbutyrylamino)-L-Proline 3-Quinolylamide The title compound (381 mg) was similarly prepared, as described in Compound D101 (P), except the starting material was N-tert-butoxycarbonyl-trans-4-(N-tert-butoxycarbonylglycylamino)-L-pipecolinic acid (B, 313 mg): $^1$H NMR (400 MHz, CDCl$_3$) δ 1.35–1.52 (m, 18H), 1.52–1.81 (m, 5H), 1.86–1.99 (m, 1H), 2.06–2.33 (m, 2H), 2.71–2.88 (m, 2H), 3.49 (s, 2H), 3.60–3.78 (m, 2H), 3.78–3.89 (m, 1H), 3.89–4.03 (m, 2H), 4.03–4.14 (m, 1H), 4.374.46 (m, 1H), 4.60–4.70 (m, 1H), 4.81–4.88 (m, 1H), 5.06–5.20 (m, 2H), 6.14–6.21 (m, 1H), 6.87 (d, J=6.4 Hz, 1H), 7.17–7.30 (m, 5H), 7.50 (t, J=7.1 Hz, 1H), 7.61 (t, J=7.1 Hz, 1H), 7.81 (d, J=7.3 Hz, 1H), 8.01 (d, J=8.3 Hz, 1H), 8.67 (s, 1H), 8.89 (d, J=1.2 Hz, 1H), and 9.30 (s, 1H).

(D) trans-4-Glycylamino-L-Pipecolinoyl-trans-4-((R)-2-Hydroxy-4-Phenylbutylamino-L-Proline 3-Quinolylamide Trihydrochloride The title compound (218 mg) was similarly prepared, as described in Compound D101 (Q), except the starting material was N-tert-butoxycarbonyl-trans-4-(N-tert-butoxycarbonylglycly)amino-L-pipecolinoyl-trans-4-((R)-2-hydroxy-4-phenylbutyryl)amino-L-proline 3-quinolylamide (C, 370 mg): $^1$H NMR (400 MHz, D$_2$O) δ 1.79–2.04 (m, 5H), 2.21–2.30 (m, 1H), 2.33–2.42 (m, 2H), 2.57–2.64 (m, 2H), 3.11–3.20 (m, 1H), 3.37–3.45 (m, 1H), 3.53–3.60 (m, 1H), 3.73 (d, J=1.5 Hz, 1H), 3.79 (dd, J=6.4, 10.3 Hz, 1H), 4.03 (dd, J=4.4, 7.3 Hz, 1H), 4.13–4.19 (m, 1H), 4.27–4.36 (m, 2H), 4.57–4.77 (m, 1H), 7.09–7.27 (m, 5H), 7.73 (t, J=7.6 Hz, 1H), 7.86 (t, J=7.8 Hz, 1H), 8.01 (dd, J=4.2, 8.1 Hz, 1H), 8.80 (d, J=2.0 Hz, 1H), and 9.14 (d, J=2.4 Hz, 1H); IR (KBr) 3381, 3219, 3057, 3026, 2952, 1651, 1612, 1574, 1554, 1495, 1487, and 1454 cm$^{-1}$; mass spectrum (FAB+) nme 602 (M+1); Anal. Calcd for C$_{32}$H$_{39}$N$_7$O$_5$.3HCl.2H$_2$O: C, 51.44; H, 6.21; N, 13.12. Found: C, 51.51; H, 6.36; N, 12.92.

Compound D115—cis-4-Glycylamino-L-Pipecolinoyl-trans-4-((R)-2-Hydroxy-4-Phenylbutyrylamino)-L-Profine 3-Quinolylamide Trihydrochloride (A) N-tert-Butoxycarbonyl-cis-4-(N-tert-Butoxycarbonylglycylamino)-L-Pipecolinic Acid Methyl Ester The title compound (256 mg) was similarly prepared, as described in Compound D103 (A), except the starting material was N-tert-butoxycarbonyl-cis-4-amino-L-pipecolinic acid methyl ester (Compound D113 (E), 211 mg): $^1$H NMR (400 MHz, CDCl$_3$) δ 1.35–1.64 (m, 18H), 1.73–1.83 (m, 2H), 1.94–2.04 (m, 1H), 2.15–2.33 (m, 1H), 3.15 (br s, 1H), 3.69–3.82 (m, 4H), 3.85–3.95 (m, 1H), 4.15–4.22 (m, 1H), 4.75 (br s, 1H), 5.01 (br s, 1H), 5.74 (br s, 1H), and 6.68 (br s, 1H).

(B) N-tert-Butoxycarbonyl-cis-4-(N-tert-Butoxycarbonylglycylamino)-L-Pipecolinic Acid The title compound (207 mg) was similarly prepared, as described in Compound D101 (O), except the starting material was N-tert-butoxycarbonyl-trans-4-(N-tert-butoxycarbonylglycylamino)-L-pipecolinic acid methyl ester (A, 256 mg).

(C) N-tert-Butoxycarbonyl-cis-4-(N-tert-Butoxycarbonylglycylamino)-L-Pipecolinoyl-trans-4-(R)-2-Hydroxy-4-Phenylbutyrylamino)-L-Proline 3-Quinolylamide The title compound (202 mg) was similarly prepared, as described in Compound D101 (P), except the starting material was N-tert-butoxycarbonyl-cis-4-(N-tert-butoxycarbonylglycylamino)-L-pipecolinic acid (207 mg).

(D) trans-4-Glycylamino-L-Pipecolinoyl-cis-4-((R)-2-Hydroxy-4-Phenylbutyrylamino)-L-Proline 3-Quinolylamide Trihydrochloride The title compound (63 mg) was similarly prepared, as described in Compound D101 (Q), except the starting material was N-tert-butoxycarbonyl-cis-4-(N-tert-butoxycarbonylglycyly)amino-L-pipecolinoyl-trans-4-((R)-2-hydroxy-4-phenylbutyryl)amino-L-proline 3-quinolylamide (C, 202 mg): $^1$H NMR (400 MHz, D$_2$O) δ 1.56–1.78 (m, 2H), 1.92–2.11 (m, 2H), 2.11–2.22 (m, 1H), 2.33–2.42 (m, 1H), 2.42–2.51 (m, 1H), 2.51–2.60 (m, 1H), 2.67–2.76 (m, 2H), 3.14–3.25 (m, 1H), 3.15–3.61 (m, 1H), 3.65–3.71 (m, 1H), 3.76 (s, 2H), 3.95–4.03 (m, 1H), 4.09–4.21 (m, 2H), 4.34–4.41 (m, 1H), 4.43–4.50 (m, 1H), 4.70–4.88 (m, 1H), 7.21–7.34 (m, 5H), 7.79–7.86 (m, 1H), 7.93–7.99 (m, 1H), 8.11 (d, J=8.8 Hz, 2H), 8.89 (br s, 1H and 9.22 (br s, 1H); IR (KBr) 3381, 3219, 3059, 2945, 1651, 1612, 1572, 1554, 1493, and 1454 cm$^{-1}$; mass spectrum (FAB+) m/e 602 (M+1); Anal. Calcd for C$_{32}$H$_{39}$N$_7$O$_5$·3HCl·2H$_2$O: C, 51.44; H, 6.21; N, 13.12. Found: C, 51.16; H, 6.13; N, 12.85.

Compound D116—1-(Piperazin-2-ylcarbonyo-trans-4-((R)-2-Hydroxy-4-Phenylbutyrylamino)-L-Proline 3-Quinolylamide Trihydrochloride (A) Methyl 1,4-Di-(N-tert-Butoxycarbonyl)-2-Piperazinecarboxylate A solution of di-tert-butyl dicarbonate (1.20 g) in 1,4-dioxane (5 mL) was added to a solution of methyl 2-piperazinecarboxylate (520 mg) in 1,4-dioxane (15 mL)-saturated aqueous sodium hydrogen carbonate (20 mL). The mixture was stirred at room temperature for 1 hr, additional di-tert-butyl dicarbonate (0.80 g) was added. After stirring overnight, the solvents were evaporated in vacuo. A solution of 10% citric acid was added to the residue and extracted with ethyl acetate. The organic layer was washed with saturated sodium hydrogen carbonate and brine, dried over anhydrous sodium sulfate, and evaporated in vacuo. The residue was purified by silica gel column chromatography (chloroform then methanol:chloroform=1:100, v/v) to give the title compound (290 mg) as a colorless powder: $^1$H NMR (400 MHz, CDCl$_3$) δ 1.44 (s, 18H), 3.74 (s, 3H), and 4.55 (m, 1H).

(B) 1,4-Di-(N-tert-Butoxycarbonyl)-2-Piperazinecarboxylic Acid

A solution of 1 N sodium hydroxide (1.2 mL) was added to a solution methyl 1,4-di-(N-tert-butoxycarbonyl)-2-piperazinecarboxylate (A, 290 mg) in methanol (10 mL). The mixture was stirred at room temperature for 12 hr and evaporated in vacuo. The residue was diluted with water and washed with ether. The aqueous layer was acidified with 10% citric acid and extracted with ethyl acetate. The organic layer was washed with brine, dried over anhydrous sodium sulfate, and evaporated in vacuo to give the title compound (230 mg) as a colorless foam: $^1$H NMR (400 MHz, CDCl$_3$) δ 1.44 (s,18H) and 4.56–4.75 (m, 1H).

(C) 1,4-Di-(N-tert-Butoxycarbonyl)piperazin-2-ylcarbonyl)-trans-4-((R)-2-Hydroxy-4-Phenylbutyrylamino)-L-Proline 3-Quinolylamide Triethylamine (26 μL), 1-hydroxybenzotriazole (24 mg), and 1-(3-dimethylaminopropyl)-3-ethylcarbodiimide hydrochloride (36 mg) were added to a solution of trans-4-((R)-2-hydroxy-4-phenylbutrrylamino)-L-proline 3-quinolylamide (Compound D101 (H), 74 mg) and methyl 1,4-di-(N-tert-butoxycarbonyl)-2-piperazinecarboxylic acid (B, 62 mg) in dichloromethane (10 mL) at 0° C. The mixture was stirred at room temperature for 19 hr and evaporated in vacuo. The residue was diluted with ethyl acetate and washed with 10% citric acid, saturated sodium hydrogen carbonate, and brine. The organic layer was dried over anhydrous sodium sulfate and evaporated in vacuo. The residue was purified by silica gel column chromatography (chloroform then methanol:chloroform=1:50, v/v) to give the title compound (76 mg) as a colorless powder: $^1$H NMR (400 MHz, CDCl$_3$) δ 1.20–4.83 (m, 18H), 7.14–7.25 (m, 5H), 7.58–7.97 (m, 4H), and 8.69–8.94 (m, 2H).

(D) 1-(Piperazin-2-ylcarbonyl)-trans-4-((R)-2-Hydroxy-4-Phenylbutyrylamino)-L-Proline 3-Quinolylamide Trihydrochloride A solution of 4 N hydrochloric acid in 1,4-dioxane (5 mL) was added to 1,4-di-(N-tert-butoxycarbonyl)piperazin-2-ylcarbonyl)-trans-4-((R)-2-hydroxy-4-phenylbutyrylamino)-L-proline 3-quinolylamide (C, 76 mg) at 0° C., and methanol (2 mL) was added to dissolve insoluble materials. After stirring for 1.5 hr, the reaction mixture was evaporated and coevaporated three times with 1,4-dioxane and ether in vacuo to give pale yellow solids. The solids were washed with ether to afford the title compound (64 mg) as a colorless solid: $^1$H NMR (400 MHz, D$_2$O) δ 1.92–2.05 (m, 2H), 2.34–2.48 (m, 1H), 2.67(t, 2H), 3.24–4.89 (m, 13H), 7.15–7.32 (m, 5H), 7.83 (t, 1H), 7.96 (t, 1H), 8.09–8.16 (m, 2H), 8.94 (d, 1H), and 9.27 (d, 1H); mass spectrum (FAB+) m/e 531 (M+1); Anal. Calcd. for C$_{29}$H$_{34}$N$_6$O$_4$·3HCl·3H$_2$O: C, 50.06; H, 6.26; N, 12.08. Found: C, 50.56; H, 6.34; N, 1.48.

Compound D117—1-(4-Glycylpiperazin-2-ylcarbonyl)-trans-4-((R)-2-Hydroxy-4-Phenylbutyrylamino)-L-Proline 3-Quinolylamide Trihydrochloride (A) Methyl 1-tert-Butoxycarbonyl-4-(N-tert-butoxycarbonylglycyl)piperazine-2-carboxylate A solution of O-(N-tert-butoxycarbonylglycyl)succinimide (409 mg) in 1,4-dioxane (5 mL) was added dropwise to a mixture of Methyl Piperazine-2-carboxylate (326 mg) in 1,4-dioxane (5 mL) and saturated sodium hydrogen carbonate (5 mL) and the reaction mixture was stirred vigorously for 4 hr. After removal of solvent, the residue was extracted with chloroform. The organic layer was dried over anhydrous sodium sulfate and evaporated in vacuo to give a residue, which was diluted with 1,4-dioxane (10 mL) and Di-tert-butyl dicarbonate (323 mg) was added. After the reaction mixture had been stirred for 16 hr, the solvent was removed in vacuo. The residue was purified by silica gel column chromatography (chloroform:methanol= 99:1, v/v) to give the title compound (195 mg) as a colorless oil: $^1$H-NMR (400 MHz, CD$_3$OD) δ 1.44 and 1.49 (each s, total 18H), 2.70–3.45 (m, 2H), 3.65–4.00 (m, 6H), and 4.25–4.40 (m, 1H).

(B) 1-tert-Butoxycarbonyl-4-(N-tert-butoxycarbonylglycyl) piperazine-2-carboxylic acid A solution of 1 N sodium hydroxide (728 mL) was added to a stirred solution of Methyl 1-tert-butoxycarbonyl-4-(N-tert-butoxycarbonylglycyl)piperazine-2-carboxylate (A, 195 mg) in methanol (3 mL). The mixture was stirred at room temperature for 23 hr and evaporated in vacuo. The residue was diluted with water and washed with ether. The aqueous layer was acidified with 1 N hydrochloric acid and extracted with ethyl acetate. The organic layer was dried over anhydrous sodium sulfate and evaporated in vacuo to give the title compound (186 mg) as a colorless solid: $^1$H NMR (400 MHz, CD$_3$OD) δ 1.44 (br s, 18H) and 2.70–4.80 (m, 9H).

(C) 1-[4-(N-tert-Butoxycarbonylglycyl)-1-tert-butox carbonUlpioerazin-2-ylcarbonyl]-trans-4-((R)-2-hydroxy-4-phenylbutyrylamino)-L-proline 3-Quinolylamide The title compound (206 mg) was similarly prepared, as described in Compound D101 (P), except the starting materials were 1-tert-butoxycarbonyl-4-(N-tert-butoxycarbonylglycyl)piperazine-2-carboxylic acid (B, 168 mg), triethylamine (67 L), 1-hydroxybenzotriazole (54 mg), 1-(3-dimethylaminopropyl)-3-ethylcarbodiimide hydrochloride (92 mg), and trans-4-((R)-2-hydroxy-4-phenylbutyryl)amino-L-proline 3-quinolylamide (Compound D101 (1H), 186 mg) as a colorless foam: $^1$H NMR (400 MHz, CD$_3$OD) δ 1.25–1.50 (m, 18H), 1.80–1.95 (m, 1H), 2.00–2.10 (m, 1H), 2.30–2.45 (m, 2H), 2.65–2.80 (m, 2H), 3.00–4.80 (m, 14H), 7.10–7.30 (m, 5H), 7.50–7.60 (m, 1H), 7.60–7.70 (m, 1H), 7.80–7.90 (m, 1H), 7.90–8.00 (m, 1H), 8.65–8.80 (m, 1H), and 8.80–9.00 (, 1H).

(D) 1-(4-Glycylpiperanin-2-ylcarbonyl)-trans-4-((R)-2-hydroxy-4-phenylbutyryl-amino)-L-proline 3-Quinolylamide Trihydrochloride A solution of 4 N hydrochloric acid in 1,4-dioxane (5 mL) was added to 1-[4-(N-tert-Butoxycarbonylglycyl)-1-tert-butoxycarbonylpiperazin-2-ylcarbonyl]-trans-4-((R)-2-hydroxy-4-phenylbutyryl)amino-L-proline 3-Quinolylamide (C, 206 mg) at room temperature and methanol was added until insoluble materials were disappeared. After stirring for 2 hr, the reaction mixture was evaporated and coevaporated several times with ethanol in vacuo to give colorless solids as diastereomeric mixture, which was separated by HPLC (SHISEIDO Capcell Pak C$_{18}$ UG120, 3 cm×25 cm, 0.02 N hydrochloric acid:methanol= 65:35, v/v) to afford the title compound as a isomer A (68 mg) and isomer B (52 mg). isomer A: $^1$H NMR (400 MHz, D$_2$O) δ 1.85–2.00 (m, 2H), 2.25–2.45 (m, 2H), 2.64 (t, J=7.3 Hz, 2H), 3.05–3.30 (m, 2H), 3.40–3.55 (m, 2H), 3.65–3.70 (m, 1H), 3.85–4.20 (m, 4H), 4.30–4.55 (m, 2H), 4.65–4.85 (m, 3H), 7.10–7.30 (m, 5H), 7.75–7.80 (m, 1H), 7.85–7.90 (m, 1H), 8.00–8.10 (m, 2H), 8.85 (br s, 1H), and 9.19 (br s, 1H); mass spectrum (FAB+) m/e 588 (M+1); Anal. Calcd for C$_{31}$H$_{37}$N$_7$O$_5$.3HCl.4H$_2$O: C, 48.41; H, 6.29; N, 12.75. Found: C, 48.33; H, 6.13; N, 12.42.

isomer B: $^1$H NMR (400 MHz, D$_2$O) δ 1.80–2.00 (m, 2H), 2.34 (t J=7.8 Hz, 2H), 2.60 (t, J=7.8 Hz, 2H), 3.00–3.10 (m, 1H), 3.10–3.25 (m, 1H), 3.35–3.55 (m, 3H), 3.80–4.10 (m, 4H), 4.30–4.50 (m, 2H), 4.55–4.75 (m, 3H), 7.05–7.20 (m, 5H), 7.70–7.80 (m, 1H), 7.80–7.90 (m, 1H), 7.95–8.05 (m, 2H), 8.85 (br s, 1H), and 9.20 (br s, 1H); mass spectrum (FAB+) m/e 588 (M+1); Anal. Calcd for C$_{31}$H$_{37}$N$_7$O$_5$.3HCl.4.5H$_2$O: C, 47.85; H, 6.35; N, 12.60. Found: C, 48.09; H, 6.17; N, 12.43.

Compound D118—(4-Acetimidoylpiperazin-2-ylcarbonyl)-trans-4-((R)-2-Hydroxy-4-Phenylbutyrylamino)-L-Proline 3-Quinolylamide Trihydrochloride (A) 1-tert-Butoxycarbonyl-4-Benzyloxycarbonylpiperazine-2-Carboxylic Acid 1 N Sodium hydroxide solution (0.92 mL) was added to a solution of methyl 1-tert-butoxycarbonyl-4-benzyloxycarbonylpiperazinyl-2-carboxylate (346 mg) in methanol (5 mL). After stirring at room temperature for 3 hr, the solvents were removed in vacuo. The residue was diluted with water and washed with diethyl ether. The aqueous layer was acidified with 1 N hydrochloric acid and extracted with ethyl acetate. The organic layer was washed with brine, dried over anhydrous sodium sulfate, and evaporated in vacuo to afford the title compound (237 mg) as a pale yellow oil. The compound appears as a mixture of rotamers: $^1$H NMR (400 MHz, CDCl$_3$) δ 1.44 and 1.47 (each s, total 9H), 2.82–3.05 (m, 1H), 3.05–3.42 (m, 2H), 3.72–3.97 (m, 1H), 3.97–4.19 (m, 1H), 4.554.90 (m, 2H), 5.00–5.28 (m, 2H), and 7.20–7.42 (m, 5H).

(B) (1-tert-Butoxycarbonyl-4-Benzyloxycarbonylpiperazin-2-ylcarbonyl)-trans-4-((R)-2-Hydroxy-4-Phenylbutyrylamino)-L-Proline 3-Quinolylamide trans-4-((R)-2-hydroxy-4-phenybutyrylamino)-L-proline 3-quinolylamide (Compound D101 (H), 272 mg) and 1-tert-butoxycarbonyl-4-benzyloxycarbonylpiperazine-2-ylcarboxylic acid (A, 237 mg) were coupled using the same procedure of Compound D101 (P) to afford the title compound (171 mg) as a colorless glassy solid: mass spectrum (FAB+) m/e 765 (M+1).

(C) (1-tert-Butoxycarbonylpiperazin-2-ylcarbonyl)-trans-4-((R)-2-Hydroxy-4-Phenylbutyrylamino-L-Proline 3-Quinolylamide A mixture of (1-tert-butoxycarbonyl-4-benzyloxycarbonylpiperazin-2-ylcarbonyl)-trans-4-((R)-2-hydroxy-4-phenylbutyrylamino)-L-proline 3-quinolylamide (B, 171 mg) and 10% palladium on activated carbon (wet, 17 mg) in methanol (10 mL) was stirred at room temperature for 18 hr under a hydrogen atmosphere. The catalyst was removed by filtration and washed with methanol. The combined organic layers were evaporated in vacuo to afford the title compound (129 mg) as a colorless oil.

(D) (1-tert-Butoxycarbonyl-4-Acetimidoylpiperazin-2-ylcarbonyl)-trans-4-((R)-2-Hydroxy-4-Phenylbutyrylamino)-L-Proline 3-Quinolylamide Triethylamine (143 μL) was added to a solution of ethyl acetimidate hydrochloride (127 mg) and [(1-tert-butoxycarbonylpiperazinyl)-2-carbonyl]-trans-4-((R)-2-hydroxy-4-phenylbutyrylamino)-L-proline 3-quinolylamide (C, 129 mg) in methanol (5 mL) at 0° C. After stirring at 0° C. for 5 min and at room temperature for 7 hr, ethyl acetimidate hydrochloride (127 mg) and triethylamine (143 L) were added again to the solution at 0° C. After stirring at 0° C. for 5 min and at room temperature for 16 hr, the solvent was removed in vacuo to afford crude the title compound, which was used in the subsequent step.

(E) (4-Acetimidoylpiperazin-2-ylcarbonyl)-trans-4-((R)-2-Hydroxy-4-Phenylbutyryl-amino)-L-Proline 3-Quinolylamide Trihydrochloride 4 N Hydrochloric acid in 1,4-dioxane (10 mL) was added to crude (1-tert-butoxycarbonyl-4-acetimidoylpiperazin-2-ylcarbonyl)-trans-4-((R)-2-hydroxy-4-phenylbutyrylamino)-L-proline 3-quinolylamide (D) at 0° C. After stirring at 0° C. for 10 min and at room temperature for 10 min, methanol (2 mL) was added until insoluble materials were disappeared. After stirring for 1 hr, the solvents were removed in vacuo. The residue was purified by HPLC (Shiseido, Capcell Pak $C_{18}$ UG120, 3 cm×25 cm, 0.02 N hydrochloric acid:methanol=70:30 to 60:40, v/v) and freeze-dried from water to afford the title compound (37 mg) as a pale yellow powder. The compound appears as a mixture of rotamers: $^1$H NMR (400 MHz, $D_2O$) δ 1.78–2.00 (2H, m), 2.26 and 2.32 (each s, total 3H), 2.20–2.43 (m, 1H), 2.52–2.66 (m, 2H), 3.18–3.72 (m, 6H), 3.87–4.13 (m, 3H), 4.30–4.44 (m, 2H), 4.52–4.66 (m, 1H), 4.73–4.82 (m, 1H), 7.04–7.27 (m, 5H), 7.77 (t, J=7.8 Hz, 1H), 7.92 (t, J=7.8 Hz, 1H), 8.00–8.12 (m, 2H), 8.91 (s, 1H), and 9.25 (s, 1H); IR (KBr) 3064, 1658, 1612, 1571, 1550, 1494, and 1454 $cm^{-1}$; mass spectrum (FAB+) m/e 572 (M+1); Anal.Calcd for $C_{31}H_{37}N_7O_4\cdot 3HCl\cdot 6.1H_2O$: C, 47.07; H, 6.65; N, 12.40. Found: C, 46.68; H, 6.11; N, 12.02.

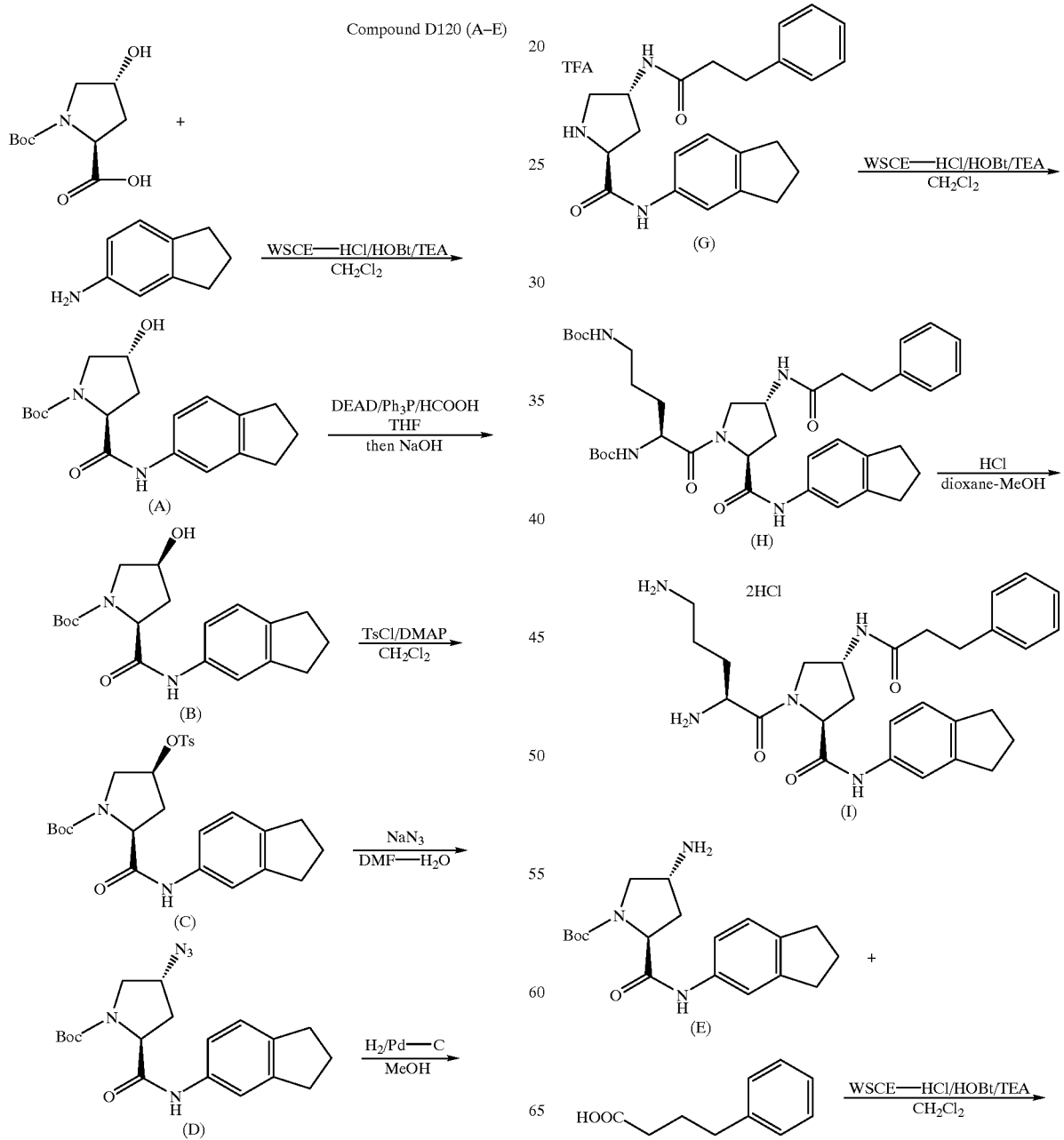

Compound D120 (A–E)

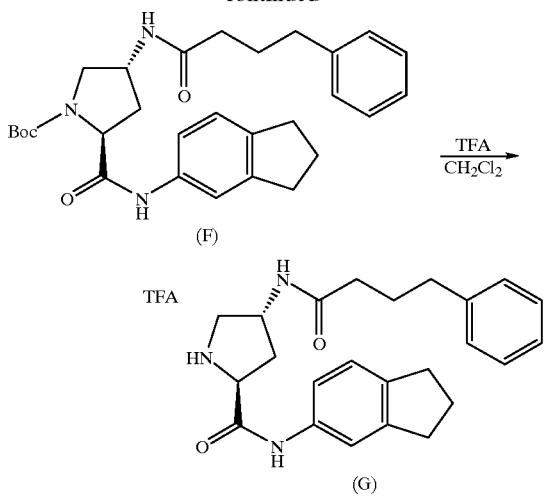

Compound D120-L-Ornithyl-trans-4-(4-Phenylbutanoyl)amino-L-Proline 5-Indanylamide Dihydrochloride (A) trans-4-Hdroxy-N-tert-Butoxycarbonyl-L-Proline 5-Indanylamide 1-Hydroxybenzotriazole (15.4 g) and 1-(3-dimethylaminopropyl)-3-ethylcarbodiimide hydrochloride (21.8 g) were added to a stirred solution of trans-4-hydroxy-N-tert-butoxycarbonyl-L-proline (21.9 g), 5-aminoindane (13.0 g), and triethylarnine (15.9 mL) in dichloromethane (500 mL) at 0° C. The mixture was stirred at room temperature overnight. The reaction mixture was diluted with ethyl acetate and washed with 0.5 M citric acid, saturated sodium hydrogen carbonate and brine. The organic layer was dried over anhydrous sodium sulfate and evaporated in vacuo to give the title compound (37.3 g) as a pale sticky oil: $^1$H NMR (400 MHz, CDCl$_3$) δ 1.3–1.6 (m, 9H), 1.9–2.1 (m, 4H), 2.6–2.9 (m, 4H), 3.4–3.8 (m, 2H), 4.56 (m, 2H), 7.12–7.18 (m, 2H), and 7.46 (s, 1H).

(B) cis-4-Hydroxy-N-tert-Butoxycarbonyl-L-Proline 5-Indanylamide

Diethyl azodicarboxylate (40% solution in toluene, 60 mL) was added to a solution of triphenylphosphine (34.3 g) in tetrahydrofuran (400 mL) at −15° C. After stirring at −15° C. to 0° C. for 30 min, trans-4-hydroxy-N-tert-butoxycarbonyl-L-proline 5-indanylamide (A, 34.3 g), and formic acid (4.3 mL) were added. After stirring at room temperature for 3 hr, the solvents were evaporated in vacuo. Toluene was added to the residue, and insoluble solid was removed. The filtrate was then purified by silica gel column chromatography (chloroform then chloroform: ethyl acetate=1:1, v/v) to afford a pale yellow sticky oil (69.2 g). The oil was dissolved in tetrahydrofuran (500 mL) and 1 N sodium hydroxide (100 mL) was added at 0° C. After stirring for 1.5 hr, the solvents were evaporated in vacuo. The residue was extracted with ethyl acetate and the extract was washed with brine, dried over anhydrous sodium sulfate, and evaporated in vacuo. The residue was purified by silica gel column chromatography (chloroform then chloroform:methanol=20:1, v/v) to afford the title compound (34.1 g) as a pale brown sticky oil: $^1$H NMR (400 MHz, CD$_3$OD) δ 1.3–1.6 (m, 9H), 2.07 (m, 3H), 2.49 (m, 1H), 2.87 (m, 4H), 3.55 (m, 2H), 4.2–4.4 (m, 2H), 7.14 (d, 1H), 7.24 (d, J=7.3 Hz, 1H), and 7.44 (s, 1H).

(C) cis-4-p-Toluenesulphonyloxy-N-tert-Butoxycarbonyl-L-Proline 5-Indanylamide

4-Dimethylaminopyridine (4.1 g) and p-toluenesulphonyl chloride (4.8 g) were added to a solution of cis-4-hydroxy-N-tert-butoxycarbonyl-L-proline 5-indanylamide (B, 5.8 g) in dichloromethane (85 mL) at 0° C. After stirring at room temperature for 6 hr, additional 4-dimethylaminopyridine (1.0 g) and p-toluenesulphonyl chloride (1.6 g) were added. The resulting solution was stirred at room temperature for 19 hr, and the solvent was evaporated in vacuo. The residue was diluted with ethyl acetate, and washed with 0.5 M citric acid, saturated sodium hydrogen carbonate, and brine. The organic layer was dried over anhydrous sodium sulfate and evaporated in vacuo to afford the title compound (7.4 g) as a pale brown sticky oil: $^1$H NMR (400 MHz, CD$_3$OD) δ 1.3–1.6 (m, 9H), 2.10 (m, 2H), 2.2 (m, 1H), 2.39 (s, 3H), 2.5 (m, 1H), 2.88 (m, 4H), 3.68 (m, 2H), 4.3–4.4 (m, 1H), 5.17 (m, 1H), 7.15 (m, 2H), 7.31–7.35 (m, 3H), and 7.73 (d, J=7.8 Hz, 2H).

(D) trans-4-Azido-N-tert-Butoxycarbonyl-L-Proline 5-Indanylamide

Sodium azide (663 mg) was added to a stirred solution of cis-4-(p-toluenesulphonyoxy-N-tert-butoxycarbonyl-L-proline 5-indanylamide (C, 2.5 g) in N,N-dimethylformamide (30 mL)-water (5 mL). After stirring at 70° C. for 19 hr, the solvents were removed in vacuo. The residue was diluted with ethyl acetate, and washed with water and brine. The organic layer was dried over anhydrous sodium sulfate and evaporated in vacuo to afford the title compound (2.1 g) as a pale brown solid: $^1$H NMR (400 MHz, CD$_3$OD) δ 1.3–1.5 (m, 9H), 2.07 (m, 2H), 2.23 (m, 1H), 2.4 (m, 1H), 2.87 (m, 4H), 3.58 (d, J=11.7 Hz, 1H), 3.67 (dd, J=11.7, 4.9 Hz, 1H), 4.34–4.41 (m, 2H), 7.13 (m, 1H), 7.27 (m, 1H), and 7.46 (m, 1H).

(E) trans-4-Amino-N-tert-Butoxcarbonyl-L-Proline 5-Indanylamide

A mixture of trans-4-azido-N-tert-butoxycarbonyl-L-proline 5-indanylamide (D, 2.0 g) and 10% palladium on activated carbon (613 mg) in methanol (60 mL) was stirred at room temperature for 2.5 hr under hydrogen. The catalysts were removed by filtration and washed with methanol. The combined organic layers were evaporated in vacuo. The residue was purified by silica gel column chromatography (chloroform:methanol=20:1 to 5:1, v/v) to afford the title compound (1.7 g) as a colorless sticky oil: $^1$H NMR (400 MHz, CD$_3$OD) δ 1.3–1.5 (m, 9H), 2.07 (m, 2H), 2.29 (m, 2H), 2.87 (m, 4H,), 3.3–3.4 (m, 1H), 3.9 (m, 2H), 4.45 (m, 1H), 7.14 (m, 1H), 7.26 (m, 1H), and 7.45 (m, 1H).

(F) trans-4-(4-Phenylbutanoyl)amino-N-tert-Butoxcarbonyl-L-Proline 5-Indanylamide 1-Hydroxybenzotriazole (987 mg) and 1-(3-dimethylaminopropyl)-3-ethylcarbodiimide hydrochloride (1.4 g) were added to a stirred suspension of trans-4-amino-tert-butoxycarbonyl-L-proline 5-indanylamide (E, 1.70 g), 4-phenylbutanoic acid (880 mg) and triethylamine (1.0 mL) in tetrahydrofuran (50 mL) at 0° C. for 2.5 hr. N,N-Dimethylformamide (50 mL) was added, then the mixture was stirred at room temperature overnight. The reaction mixture was diluted with ethyl acetate and washed with 1 N HCl, saturated sodium hydrogen carbonate and brine. The organic layer was dried over anhydrous sodium sulfate and evaporated in vacuo. The residue was purified by silica gel column chromatography (chloroform:ethyl acetate=4:1 to 1:2, v/v) to give the title compound (2.10 g) as a colorless sticky oil: $^1$H NMR (400 MHz, CD$_3$OD) δ 1.3–1.5 (m, 9H), 1.91 (m, 2H), 2.06 (m, 2H), 2.2 (m, 4H), 2.62 (t, J=7.8 Hz, 2H), 2.86 (m, 4H), 3.3–3.4 (m, 1H), 3.79 (m, 1H), 4.35 (m, 1H), 4.45 (m, 1H), 7.13–7.27 (m, 7H), and 7.44 (s, 1H,).

(G) trans-4-Phenylbutanoyl)amino-L-Proline 5-Indanylamide Trifluoroacetate trans-4-(4-Phenylbutanoyl)amino-N-tert-butoxycarbonyl-L-proline 5-indanylamide (F, 2.10 g) was dissolved in trifluoroacetic acid (10 mL)-dichloromethane (30 mL). After stirring for 2 hr, the reaction mixture was evaporated in vacuo. Toluene and methanol were added to the residue, then evaporated in vacuo to give the title compound (2.39 g) as a colorless sticky oil.

(H) $N^1,N^4$-Di-tert-Butoxycarbonyl-L-Ornithyl-trans-4-(4-Phenylbutanoyl)amino-L-Proline 5-Indanylamide Triethylamine (0.14 mL), 1-hydroxybenzotriazole (60 mg), and 1-(3-dimethylamino-propyl)-3-ethylcarbodiimide hydrochloride (78 mg) were added to a cold (0° C.) stirred solution of trans-4-(4-phenylbutanoyl)amino-L-proline 5-indanylamide trifluoroacetate (G, 137 mg) and $N^1,N^4$-di-tert-butoxycarbonyl-L-ornithine (85 mg) in dichloromethane (5 mL). The mixture was stirred at room temperature for 14 hr and evaporated in vacuo. The residue was diluted with ethyl acetate and washed with 1 N hydrochloric acid, water, saturated sodium hydrogen carbonate, and brine. The organic layer was dried over anhydrous sodium sulfate and evaporated in vacuo. The residue was purified by silica gel column chromatography (chloroform:ethyl acetate=1:1 to 1:2, v/v) to give the title compound (136 mg) as a colorless sticky oil: $^1$HNMR (400 MHz, $CD_3OD$) δ 1.4–1.5 (m, 18H), 1.58 (m, 3H), 1.76 (m, 1H), 1.94 (m, 2H), 2.05 (m, 2H), 2.2–2.4 (m, 4H), 2.64 (t, J=7.6 Hz, 2H), 2.85 (m, 4H), 3.07 (m, 2H), 3.8–3.9 (m, 2H), 4.28 (m, 1H), 4.54 (m, 1H), 4.62 (m, 1H), 7.10–7.27 (m, 7H), and 7.42 (s, 1H).

(I) L-Ornithyl-trans-4-(4-Phenylbutanoyl)amino-L-Proline 5-Indanylamide

A solution of 4N hydrochloric acid in 1,4-dioxane (5 mL) was added to $N^1,N^4$-di-tert-butoxycarbonyl-L-ornithyl-trans-4-(4-phenylbutanoyl)amino-L-proline 5-indanylamide (H, 136 mg) at 0° C., and methanol was added until insoluble materials were disappeared. After stirring for 2 hr, the reaction mixture was evaporated and coevaporated several times with ethanol in vacuo to give pale yellow solids. The solids were washed with ether-ethanol to afford the title compound (101 mg) as a colorless solid: $^1$H NMR (400 MHz, $D_2O$) δ 1.73 (m, 2H), 1.8–2.1 (m, 6H), 2.2–2.4 (m, 4H), 2.60 (t, J=7.3 Hz, 2H), 2.82 (m, 4H), 2.98 (t, J=7.8 Hz, 2H), 3.60 (dd, J=11.0, 3.7 Hz, 1H), 3.87 (dd, J=11.0, 5.6 Hz, 1H), 4.35 (m, 2H), 4.65 (t, J=7.6 Hz, 1H), and 7.11–7.32 (m, 8H); mass spectrum (FAB+) m/e 506 (M+1); Anal. Calcd for $C_{29}H_{39}N_5O_3$·2HCl·2.5$H_2O$: C, 55.86; H, 7.43; N, 11.23. Found: C, 55.90; H, 7.31; N, 11.07.

Compound D121-D-Ornithyl-trans-4-(4-Phenylbutanoyl)amino-L-Proline 5-Indanylamide (A) $N^1,N^4$-Di-tert-Butoxycarbonyl-D-Ornithyl-trans-4-(4-Phenylbutanoyl)amino-L-Proline 5-Indanylamide The the title compound (147 mg) was similarly prepared, as described in Compound D120 (H), except the starting material was trans-4-(4-phenylbutanoyl)amino-L-proline 5-indanylamide trifluoroacetate (Compound D120 (G), 140 mg): $^1$H NMR (400 MHz, $CD_3OD$) δ 1.35–1.45 (m, 18H), 1.4–1.8 (m, 4H), 1.92 (m, 2H), 2.05 (m, 2H), 2.22 (m, 2H), 2.2–2.4 (m, 2H), 2.63 (m, 2H), 2.85 (m, 4H), 3.03 (m, 2H), 3.55 (m, 1H), 4.07–4.12 (m, 1H), 4.25 (m, 1H), 4.50 (m, 1H), 4.63 (dd, J=8.3, 5.4 Hz, 1H), 7.10–7.31 (m, 7H), and 7.41 (s, 1H).

(B) D-Ornithyl-trans-4-(4-Phenylbutanoyl)amino-L-Proline 5-Indanylamide

The title compound (110 mg) was similarly prepared, as described in Compound D120 (I), except the starting material was $N^1,N^4$-di-tert-butoxycarbonyl-D-ornithyl-trans-4-(4-phenylbutanoyl)amino-L-proline 5-indanylamide (A, 147 mg): $^1$H NMR (400 MHz, $D_2O$) δ 1.74 (m, 2H), 1.90 (m, 4H), 2.02 (m, 2H), 2.2–2.4 (m, 4H), 2.62 (m, 2H), 2.84 (m, 4H), 2.92 (m, 2H), 3.46 (dd, J=10.3, 5.9 Hz, 1H), 4.02 (dd, J=10.5, 6.1 Hz, 1H), 4.3–4.4 (m, 2H), 4.65 (t, J=6.8 Hz, 1H), and 7.14–7.44 (m, 8H); mass spectrum (FAB+) m/e 506 (M+1); Anal. Calcd for $C_{29}H_{39}N_5O_3$·2HCl·2.5$H_2O$: C, 55.86; H, 7.43; N, 11.23. Found: C, 55.58; H, 7.34; N, 11.02.

Compound D122-L-Ornithyl-cis-4-(4-phenylbutanoyl)amino-L-proline 5-Indanylamide (A) cis-4-Azido-N-tert-Butoxycarbonyl-L-Proline 5-Indanylamide The title compound (621 mg) was similarly prepared, as described in Compound D120 (D), except the starting material was trans-4-p-toluenesulphonyoxy-N-tert-butoxycarbonyl-L-proline 5-indanylamide(798 mg): $^1$H NMR (400 MHz, $CD_3OD$) δ 1.3–1.5 (m, 9H), 2.07 (m, 3H), 2.61 (m, 1H), 2.87 (m, 4H), 3.42 (dd, J=11.0, 5.1 Hz, 1H), 3.76 (dd, J=11.2, 6.4 Hz, 1H), 4.25–4.45 (m, 2H), 7.14 (m, 1H), 7.22 (m, 1H), and 7.42 (s, 1H).

(B) cis-4-Amino-N-tert-Butoxycarbonyl-L-Proline 5-Indanylamide

The title compound (600 mg) was similarly prepared, as described in Compound D120 (E), except the starting material was cis-4-azido-N-tert-butoxycarbonyl-L-proline 5-indanylamide (A, 618 mg).

(C) cis-4-(4-Phenylbutanoyl)amino-N-tert-Butoxycarbonyl-L-Proline 5-Indanylamide The title compound (776 mg) was similarly prepared, as described in Compound D120 (F), except the starting material was cis-4-amino-N-tert-butoxycarbonyl-L-proline 5-indanylamide (B. 600 mg): $^1$H NMR (400 MHz, $CD_3OD$) δ 1.3–1.5 (m, 9H), 1.90 (m, 3H), 2.06 (m, 2H), 2.20 (m, 2H), 2.59 (m, 3H), 2.85 (m, 4H), 3.3–3.4 (m, 1H), 3.7–3.8 (m, 1H), 4.34.5 (m, 2H), 7.13–7.31 (m, 7H), and 7.47 (m, 1H).

(D) cis-4-(4-Phenylbutanoyl)amino-L-Proline 5-Indanylamide Trifluoroacetate

The title compound (896 mg) was similarly prepared, as described in Compound D120 (G), except the starting material was cis-4-(4-phenylbutanoyl)amino-N-tert-butoxycarbonyl-L-proline 5-indanylamide (C, 765 mg).

(E) $N^1,N^4$-Di-tert-Butoxycarbonyl-L-Ornithyl-cis-4-(4-Phenylbutanoyl)amino-L-Proline 5-Indanylamide The title compound (142 mg) was similarly prepared, as described in Compound D120 (H), except the starting material was cis-4-(4-phenylbutanoyl)amino-L-proline 5-indanylamide trifluoroacetate (D, 160 mg): $^1$H NMR (400 MHz, $CD_3OD$) δ 1.3–1.5 (m, 18H), 1.58 (m, 3H), 1.74 (m, 1H), 1.91 (m, 3H), 2.05 (m, 2H), 2.21 (t, J=7.6 Hz, 2H), 2.60 (m, 3H), 2.84 (t, J=7.1 Hz, 4H), 3.03 (m, 2H), 3.49 (m, 1H), 4.6 (m, 1H), 4.30 (m, 1H), 4.56 (m, 2H), 7.10–7.25 (m, 7H), and 7.44 (s, 1H).

(F) L-Ornithyl-cis-4-(4-Phenylbutanoyl)amino-L-Proline 5-Indanylamide

The title compound (100 mg) was similarly prepared, as described in Compound D120 (I), except the starting material was $N^1,N^4$ di-tert-butoxycarbonyl-L-omithyl-cis-4-(4-phenylbutanoyl)amino-L-proline 5-indanylamide (E, 142 mg): $^1$H NMR (400 MHz, $D_2O$) δ 1.7–2.1 (m, 9H), 2.22 (m, 2H), 2.55 (t, J=7.3 Hz, 2H), 2.63 (m, 1H), 2.7–2.9 (m, 4H), 2.98 (t, J=7.6 Hz, 2H), 3.45 (dd, J=10.5, 6.6 Hz, 1H), 4.06 (dd, J=10.7, 6.8 Hz, 1H), 4.41 (m, 2H), 4.65 (t, J=7.6 Hz, 1H), 7.12–7.29 (m, 8); mass spectrum (FAB+) m/e 506 (M+1); Anal. Calcd for $C_{29}H_{39}N_5O_3$·2HCl·2.5$H_2O$: C, 55.86; H, 7.43; N, 11.23. Found: C, 56.23; H, 7.32; N, 11.18.

Compound D124-D-Ornithylcis-4-(4-Phenylbutanoyl)amino-L-Proline 5-Indanylamide Dihydrochloride (A) $N^1,N^4$-Di-tert-Butoxycarbonyl-D-Ornithyl-cis-4-(4-Phenylbutanoyl)amino-L-Proline 5-Indanylamide The title compound (127 mg) was similarly prepared, as described in Compound D120 (H), except the starting material was cis-4-(4-phenylbutanoyl)amino-L-proline 5-indanylamide trifluoroacetate (127 mg): $^1$H NMR (400 MHz, CD$_3$OD) δ 1.3–1.5 (m, 18H), 1.5–1.6 (m, 3H), 1.7 (m, 1H), 1.86 (m, 2H), 2.0–2.2 (m, 5H), 2.54 (m, 3H), 2.83 (m, 4H), 3.06 (m, 2H), 3.72 (m, 1H), 3.95 (m, 1H), 4.30 (m, 1H), 4.45 (m, 1H), 4.56 (m, 1H), 7.07–7.30 (m, 7l), and 7.46 (m, 1H).

(B) D-Ornithyl-cis-4-(4-Phenylbutanoyl)amino-L-Proline 5-Indanylamide

The title compound (86 mg) was similarly prepared, as described in Compound D120 (I), except the starting material was N$^1$,N$^4$-di-tert-butoxycarbonyl-D-ornithyl-cis-4-(4-phenylbutanoyl)amino-L-proline 5-indanylamide (A, 127 mg): $^1$H NMR (400 MHz, D$_2$O) δ 1.82 (m, 4H), 1.8–2.1 (m, 5H), 2.20 (m, 2H), 2.50 (t, J=7.6 Hz, 2H), 2.65 (m, 1H), 2.81 (m, 4H), 3.04 (t, J=7.6 Hz, 2H), 3.67 (dd, J=11.0, 4.6 Hz, 1H), 3.97 (dd, J=11.0, 6.6 Hz, 1H), 4.40 (t, J=6.1 Hz, 1H), 4.46 (m, 1H), 4.64 (dd, J=9.0, 4.6 Hz, 1H), 7.1–7.4 (m, 8H); mass spectrum (FAB+) m/e 506 (M+1); Anal. Calcd for C$_{29}$H$_{39}$N$_5$O$_3$.2HCl.1.5H$_2$O: C, 57.52; H, 7.32; N, 11.56. Found: C, 67.40; H, 7.51; N, 11.41.

Compound D125-4-Hydroxy-L-Ornithyl-trans-4-(4-Phenylbutanoyl)amino-L-Proline 5-Indanylamide Dihydrochloride (A) N-tert-Butoxycarbonyl-O-Benzyl-L-Homoserine Methyl Ester Potassium carbonate (2.07 g), methyl iodide (1.25 mL) were added to a solution of N-tert-butoxycarbonyl-O-benzyl-L-homoserine (3.10 g) in DMF (15 mL). After stirring at room temperature for 5 hr, the solvent was removed in vacuo. Ethyl acetate and water were added to the residue. The separated organic layer was washed with brine, dried over sodium sulfate, and evaporated in vacuo to give the title compound (3.13 g) as a pale yellow oil: $^1$H NMR (400 MHz, CDCl$_3$) δ 1.44 (m, 9H), 1.95–2.15 (m, 2H), 3.55 (m, 2H), 3.68 (s, 3H), 4.44 (m, 1H), 4.45 (d, J=11.6 Hz, 1H), 4.49 (d, J=11.7 Hz, 1H), 5.47 (m, 1H), and 7.27–7.37 (m, 5H).

(B) (S)-2-tert-Butoxycarbonylamino-4-Butanolide

A mixture of N-tert-butoxycarbonyl-O-benzyl-L-homoserine methyl ester (A, 3.13 g) and 10% palladium on activated carbon (0.93 g) in methanol (160 mL) was stirred at room temperature for 14.5 hr under hydrogen. The catalysts were removed by filtration and washed with methanol. The combined organic layers were evaporated in vacuo. The residue was purified by silica gel column chromatography (chloroform:methanol=40:1 to 20:1, v/v) to afford the title compound (1.65 g) as a white powder: $^1$H NMR (400 MHz, CDCl$_3$) δ 1.4–1.5 (m, 9H), 2.20 (m, 1H), 2.77 (m, 1H), 4.25 (m, 1H), 4.35 (m, 1H), 4.45 (t, J=8.8 Hz, 1H), 5.07 (m, 1H).

(C) N-tert-Butoxycarbonyl-O-Benzyl-L-Homoseryl-trans-4-(4-Phenylbutanoyl)amino-L-Proline 5-Indanylamide The title compound (600 mg) was similarly prepared, as described in Compound D120 (H), except the staring material was trans-4-(4-phenylbutanoyl)amino-L-proline 5-indanylamide trifluoroacetate (B, 541 mg) and N-tert-butoxycarbonyl-O-benzyl-L-homoserine (332 mg).

(D) N-tert-Butoxycarbonyl-L-Homoseryl-trans-4-(4-Phenylbutanoyl)amino-L-proline 5-Indanylamide The title compound (474 mg) was similarly prepared, as described in Compound D120 (E), except the starting material was N-tert-butoxycarbonyl-O-benzyl-L-homoseryl-trans-4-(4-phenylbutanoyl)amino-L-proline 5-indanylamide (C, 541 mg): $^1$H NMR (400 MHz, CD$_3$OD) δ 1.43 (m, 9H), 1.78 (m, 1H), 1.94 (m, 3H), 2.05 (m, 2H), 2.24 (m, 3H), 2.30 (m, 1H), 2.64 (d, J=7.6 Hz, 2H), 2.85 (m, 4H), 3.67 (m, 2H), 3.83 (m, 1H), 3.94 (m, 1H), 4.4–4.6 (m, 2H), 4.63 (t, J=7.6 Hz, 1H), 7.10–7.28 (m, 7H), 7.41 (s, 1H).

(E) (S)-2-tert-Butoxgcarbonylamino-3-Formylpropanoyl-trans-4-(4-Phenylbutanoyl)amino-L-Proline 5-Indanylamide A solution of dimethylsulphoxide (0.3 mL) in dichloromethane (0.8 mL) was added to a solution of oxalyl chloride (0.2 mL) in dichloromethane (0.5 mL) at −60° C. The mixture was stirred for 10 minutes at the same temperature. A solution of N-tert-butoxycarbonyl-L-homoseryl-trans-4-(4-phenylbutanoyl)amino-L-proline 5-indanylamide (470 mg) in dichloromethane (2.0 mL) was then added to the mixture. After stirring at −40° C. for 2.5 hr, triethylamine (0.6 mL) was added to the mixture. The reaction mixture was allowed to warm up to room temperature, and stirred for 1 hr at room temperature, then diluted with ethyl acetate and water. The separated organic layer was dried over sodium sulfate, and evaporated in vacuo. The residue was purified by silica gel column chromatography (chloroform:methanol=50:1 to 20:1, v/v) to afford title compound (427 mg) as a colorless sticky oil: $^1$H NMR (400 MHz, CDCl$_3$) δ 1.4–1.5 (m, 9H), 1.9–2.1 (m, 6H), 2.1–2.4 (m, 3H), 2.55–2.70 (m, 3H), 2.8–2.9 (m, 4H), 3.74.2 (m, 2H), 4.25–4.80 (m, 2H), 7.28–7.30 (m, 8H), 9.70 (s, 1H).

(F) (S)-2-tert-Butoxycarbonylamino-4-Hydroxy-5-Nitropentanol-trans-4-(4-Phenylbutanoyl)amino-L-Proline 5-Indanlamide Nitromethane (0.047 mL) and tetramethylguanidine (0.011 mL) were added to a solution of (S)-2-tert-butoxycarbonylamino-3-formylpropanoyl-trans-4-(4-phenylbutanoyl)amino-L-proline 5-indanylamide (E, 262 mg) in tetrahydrofuran (2.5 mL). The mixture was stirred for 4 hr at room temperature, then evaporated in vacuo. Ethyl acetate and water were added to the residue. The separated organic layer was dried over sodium sulfate, and evaporated in vacuo to afford the title compound (257 mg) as a pale brown sticky oil: $^1$H NMR (400 MHz, CDCl$_3$) δ 1.3–1.6 (m, 9H), 1.8–2.2 (m, 9H), 2.2–2.5 (m, 1H), 2.62 (t, J=7.1 Hz, 2H), 2.82 (m, 4H), 3.6–4.2 (m, 2H), 4.3–4.8 (m, 6H), 7.07–7.39 (m, 8H).

(G) N-tert-Butoxycarbonyl-4-Hydroxy-L-Ornithyl-trans-4-(4-Phenylbutanoyl)amino-L-Proline 5-Indanylamide A mixture of (S)-2-tert-butoxycarbonylamino-4-hydroxy-5-nitropentanoyl-trans-4-(4-phenylbutanoyl)amino-L-proline 5-indanylamide (F, 257 mg) and Raney-nickel (0.6 mL, suspension in ethanol) in ethanol (3 mL) was stirred at room temperature for 18 hr under hydrogen. The catalysts were removed by filtration and washed with ethanol. The combined organic layers were evaporated in vacuo to afford the title compound (1.7 g) as a colorless sticky oil: $^1$H NMR (400 MHz, CD$_3$OD) δ 1.25–1.50 (m, 9H), 1.6–1.9 (m, 2H), 1.94 (m, 2H), 2.06 (m, 2H), 2.24 (m, 2H), 2.2–2.4 (m, 2H), 2.64 (t, J=7.3 Hz, −2H), 2.7–3.0 (m, 6H), 3.654.15 (m, 3H), 4.5–4.7 (m, 3H), 7.11–7.28 (m, 7H), 7.40 (m, 1H).

(H) 4-Hydroxy-L-Ornithyl-trans-4-(4-Phenylbutanoyl) amino-L-Proline 5-Indanylamide The title compound (102 mg) was similarly prepared, as described in Compound D120 (I), except the starting material was N-tert-Butoxycarbonyl-4-hydroxy-L-ornithyl-trans-4-(4-phenylbutanoyl)amino-L-proline 5-indanylamide (G, 109 mg): $^1$H NMR (400 MHz, D$_2$O) δ 1.7–2.1 (m, 6H), 2.1–2.3 (m, 4H), 2.53 (t, J=7.1 Hz, 2H), 2.75 (m, 4H), 2.90 (m, 1H), 3.05 (m, 1H), 3.52 (m, 1H), 3.75–4.15 (m, 2H), 4.27 (m, 1H), 4.40 (m, 1H), 4.6–4.8 (m, 1H), and 7.04–7.25 (m, 8H); mass spectrum (FAB+) m/z 522 (M+1); Anal. Calcd for C$_{29}$H$_{39}$N$_5$O$_4$·2HCl·4.5H$_2$O: C, 51.55; H, 7.46; N, 10.37. Found: C, 51.46; H, 6.97; N, 10.09.
TYPE II
Compound D201 (A)–(B)
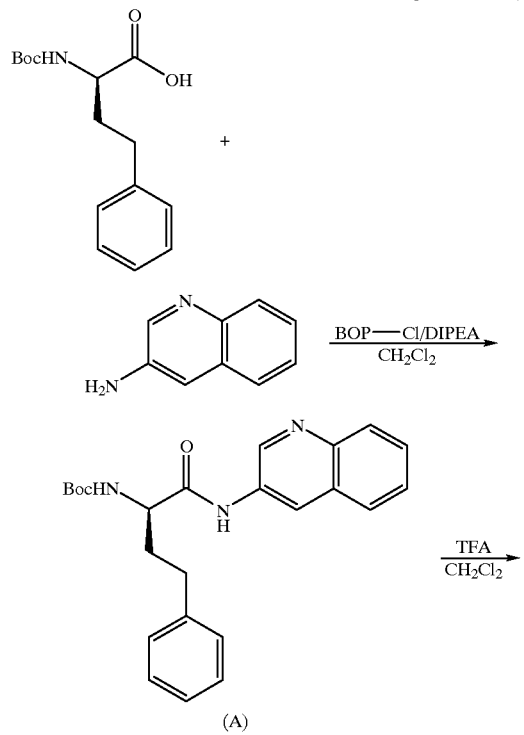
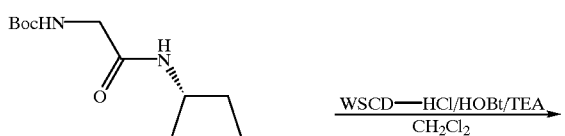
Example D103 (B)
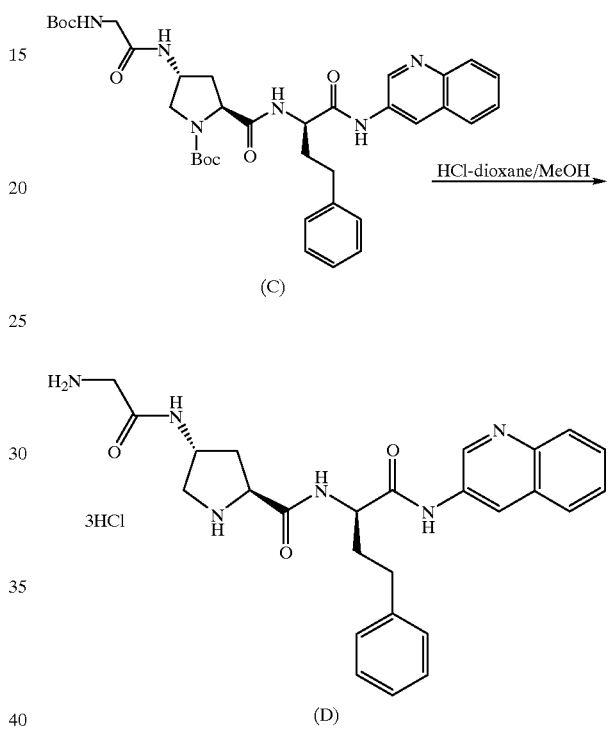
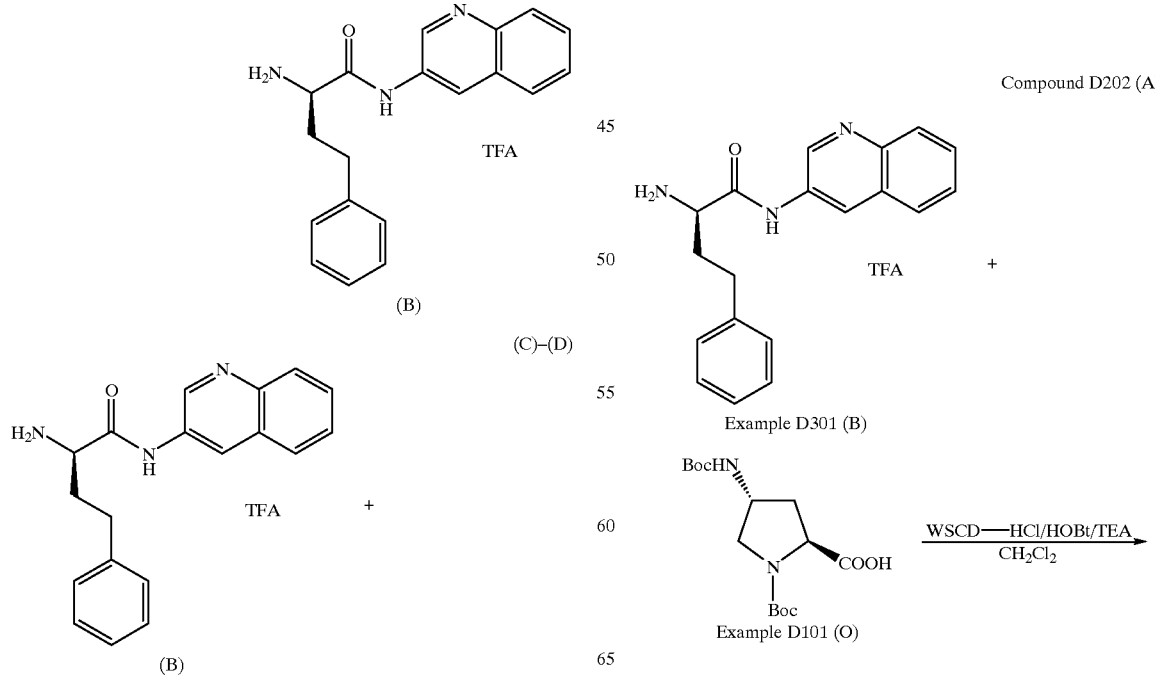
Compound D202 (A)–(B)
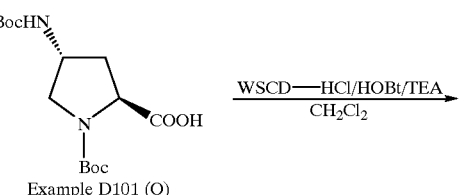
Example D301 (B)
Example D101 (O)

117
-continued
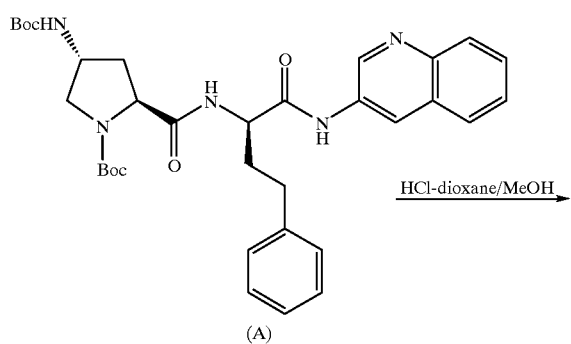
(A)
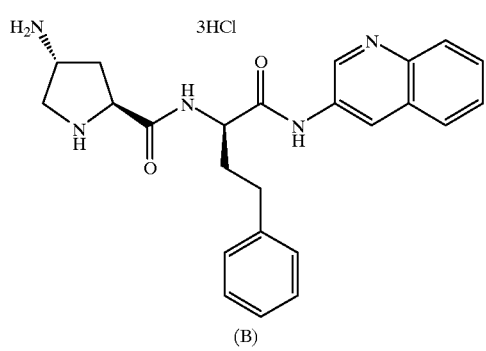
Compound D203 (A)–(B)
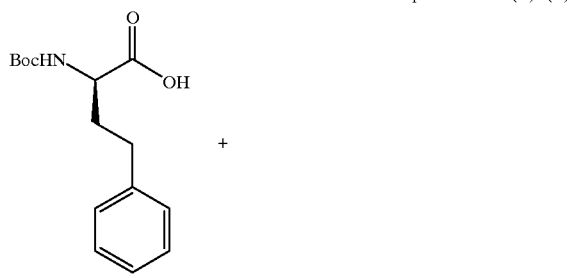
+
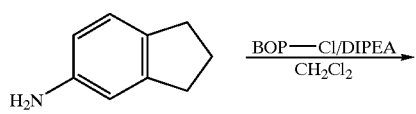
(A)
118
-continued
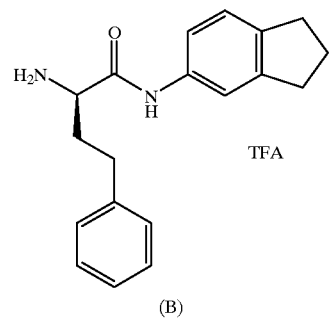
(B)
(C)–(D)
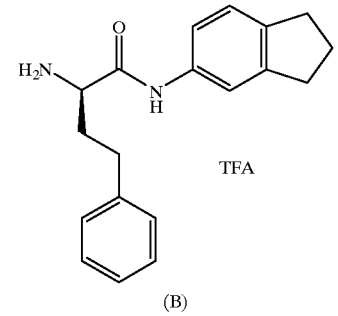
(B)
+
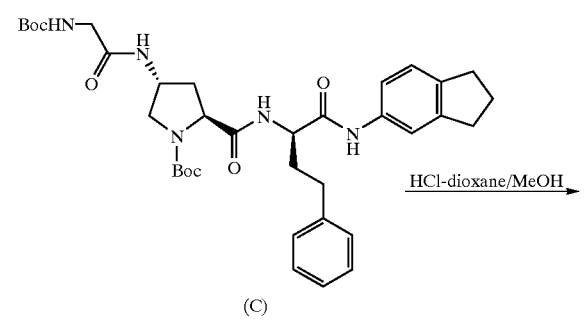
Example D103 (B)
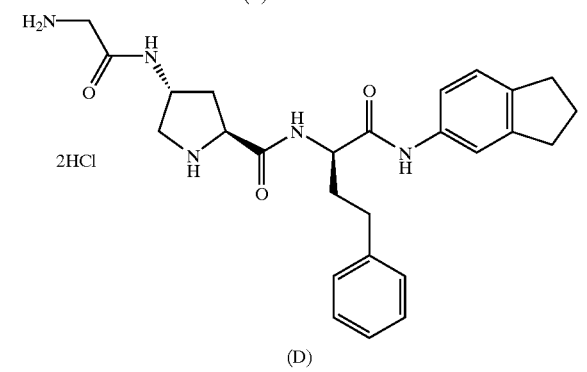
(D)

Compound D204 (A)–(B)
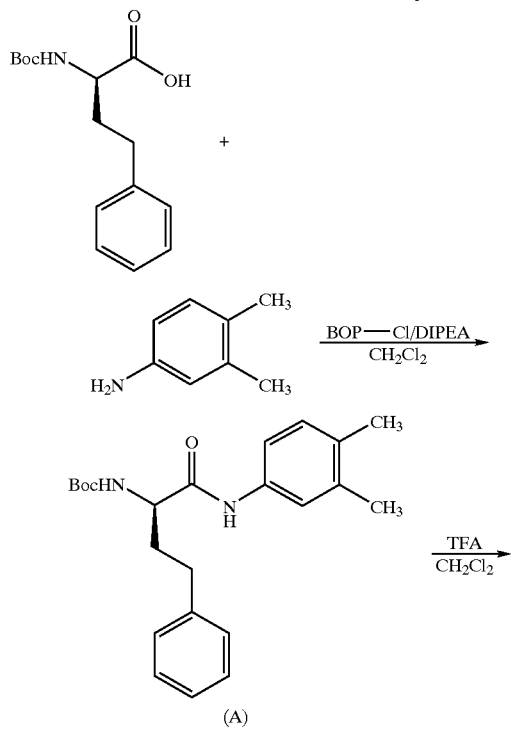
(C)–(D)
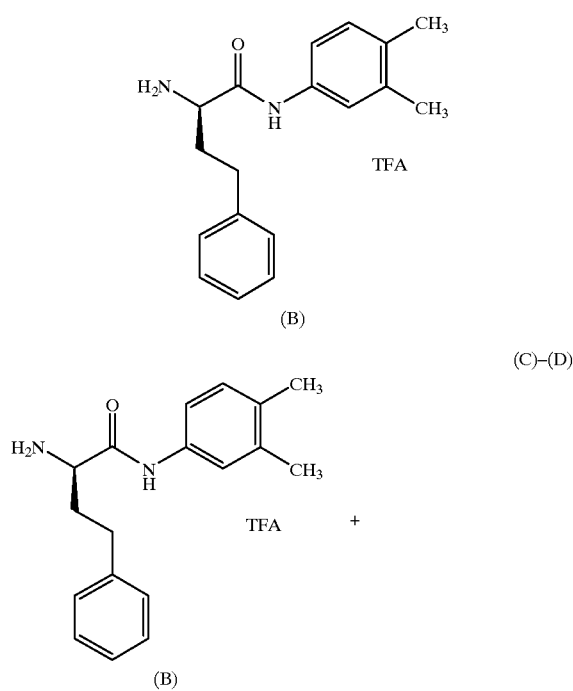
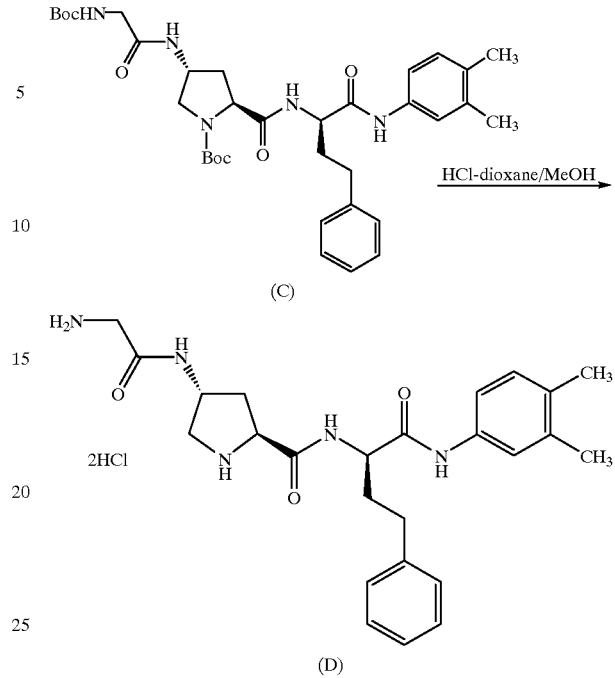
Compound D205 (A)–(B)
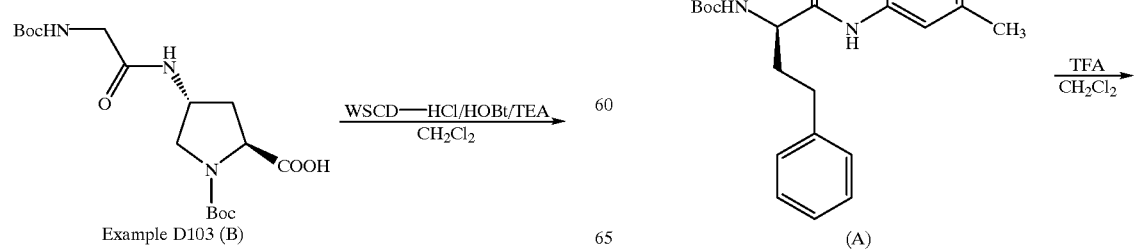

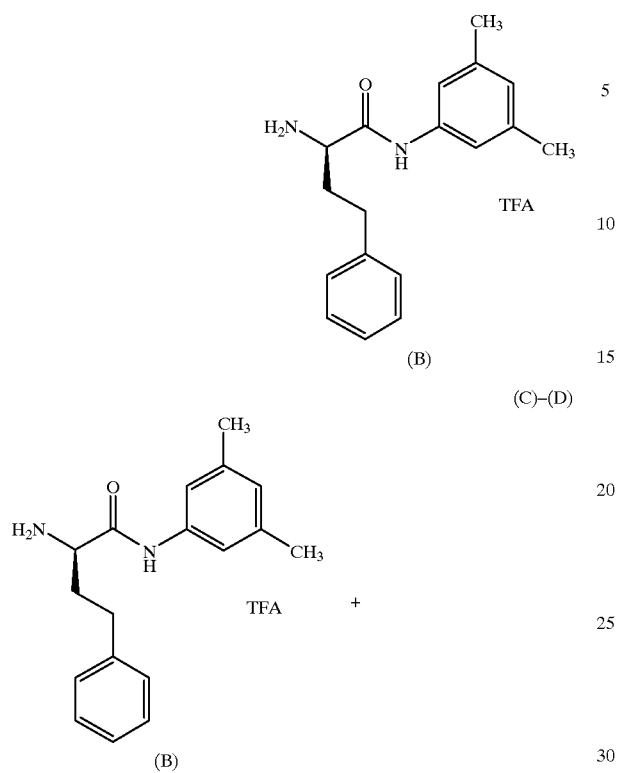
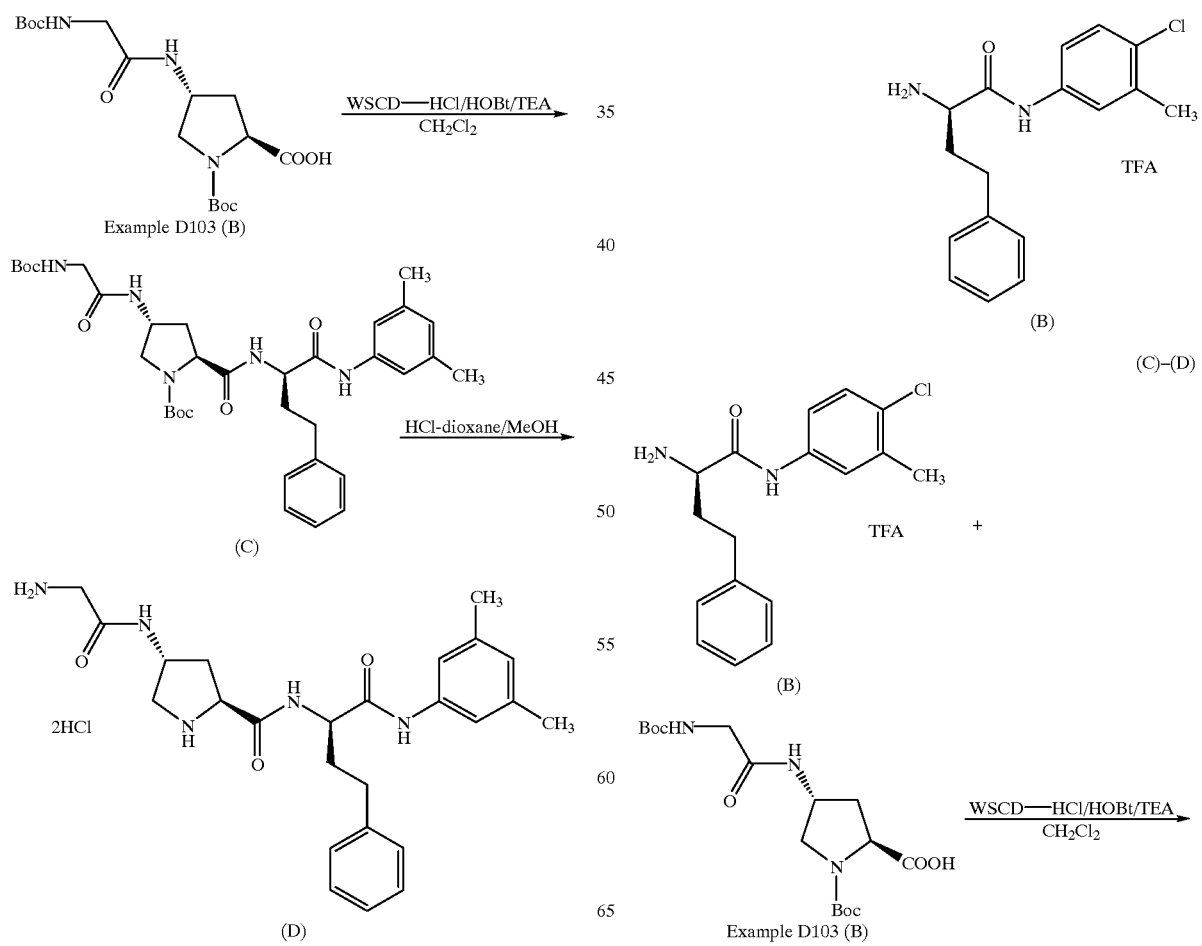
Compound D206 (A)–(B)

123

-continued

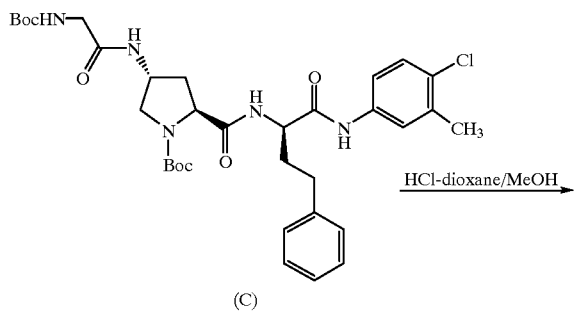

(C)

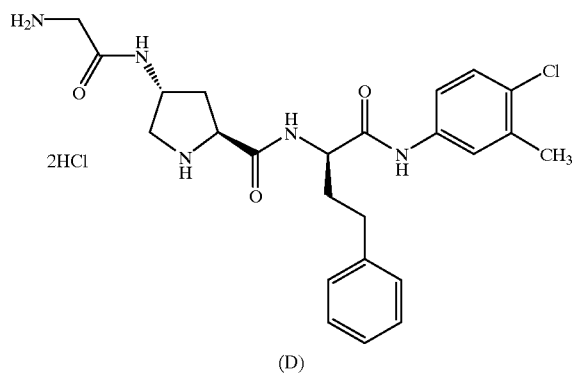

(D)

Compound D210 (A)–(B)

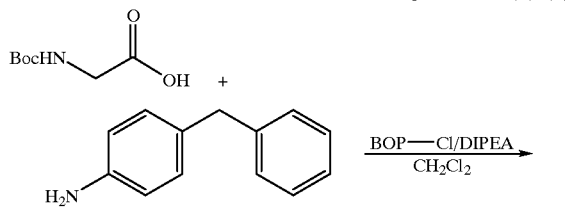

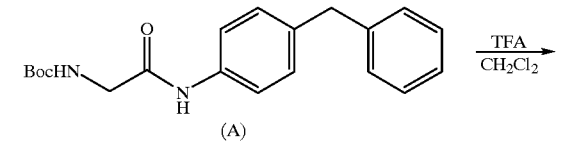

(C)–(D)

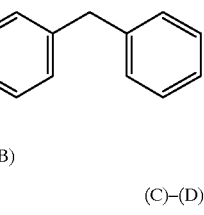

+

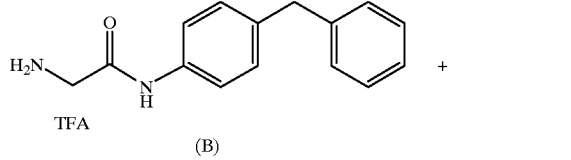

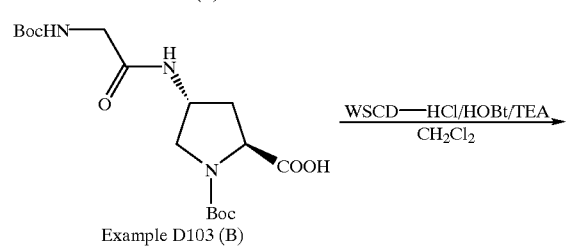

Example D103 (B)

124

-continued

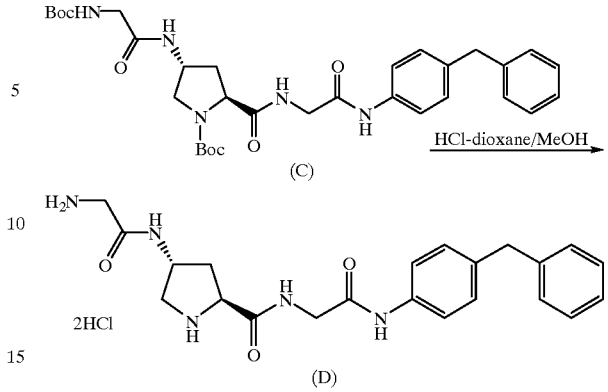

Compound D201—trans-4-Glycylamino-L-Prolyl-D-Homophenylalanine 3-Quinolylamide Trihydrochloride (A) N-tert-Butoxycarbonyl-D-Homophenylalanine 3-Quinolylamide Bis(2-oxo-3-oxazolidinyl)phosphinic chloride (829 mg) and N,N-diisopropylethylamine (1.13 mL) were added to a solution of 3-aminoquinoline (391 mg) and N-tert-butoxycarbonyl-D-homophenylalanine (1.13 g) in dichloromethane (15 mL) at 0° C. After stirring at 0° C. for 10 min and at room temperature for 19 hr, the solvent was removed in vacuo. The residue was diluted with 10% citric acid and extracted with ethyl acetate. The organic layer was washed with water, saturated sodium hydrogen carbonate, and brine, dried over anhydrous sodium sulfate, and evaporated in vacuo. The residue was purified by silica gel column chromatography (chloroform then chloroform: methanol=50:1, v/v) to afford the title compound (813 mg) as a pale yellow oil: $^1$H NMR (400 MHz, CDCl$_3$) δ 1.49 (s, 9H), 2.00–2.10 (m, 1H), 2.27–2.39 (m, 1H), 2.80 (t, J=7.8 Hz, 2H), 4.20–4.29 (m, 1H), 4.98–5.07 (m, 1H), 7.19–7.33 (m, 5H), 7.51–7.55 (m, 1H), 7.62 (t, J=7.8 Hz, 1H), 7.78 (d, J=8.4 Hz, 1H), 8.02 (d, J=8.8 Hz, 1H), and 8.68–8.80 (m, 3H).

(B) D-Homophenylalanine 3-Quinolylamide Trifluoroacetate

Trifluoroacetic acid (2 mL) was added to a solution of N-tert-butoxycarbonyl-D-homophenylalanine 3-quinolylamide (A, 114 mg) in dichloromethane (2 mL) at 0° C. After stirring at 0° C. for 5 min and at room temperature for 40 min, the reaction mixture was evaporated and coevaporated three times with toluene and diethyl ether in vacuo to afford the title compound (151 mg) as a pale yellow solid.

(C) trans-4-(N-tert-Butoxycarbonylglyclamino)-N-tert-Butoxycarbonyl-L-Prolyl-D-Homophenylalanine 3-Quinolylamide Triethylamine (118 μl), 1-hydroxybenzotriazole (35 mg), and 1-(3-dimethylamino-propyl)-3-ethylcarbodiimide hydrochloride (54 mg) were added to a mixture of trans-4-(N-tert-butoxycarbonylglycylamino)-N-tert-butoxycarbonylproline (Compound D103 (B), 9 mg) and D-homophenylalanine 3-quinolylamide trifluoroacetate (B, 151 mg) in dichloromethane (5 mL) at 0° C. After stirring at 0° C. for 10 min and at room temperature for 20 hr, the solvent was removed in vacuo. The residue was diluted with 10% citric acid and extracted with ethyl acetate. The organic layer was washed with water, saturated sodium hydrogen carbonate, and brine, dried over anhydrous sodium sulfate, and evaporated in vacuo. The residue was purified by preparative thin layer chromatography (Whatman, PLK5F Silica Gel 150 Å, chloroform: methanol=30:1, v/v, ×2) to afford the title compound (162 mg) as a colorless oil. The compound appears as a mixture of rotamers: $^1$H NMR (400 MHz, CD$_3$OD) δ 1.40 and 1.45 (each s, total 18H), 1.93–2.50 (m, 4H), 2.66–2.90 (m, 2H), 3.31–3.47 (m, 1H), 3.60–3.90 (m, 3H), 4.39–4.72 (m, 3H), 7.10–7.33 (m, 5H), 7.51–7.61 (m, 1H), 7.61–7.72 (m, 1H), 7.82 (t, J=7.3 Hz, 1H), 7.96 (d, J=7.8 Hz, 1H), 8.67–8.79 (m, 1H), 8.91–9.00 (m, 0.5H), and 9.05–9.13 (m, 0.5H).

(D) trans-4-Glycylamino-L-Prolyl-D-Homophenylalanine 3-Quinolylamide Trihydrochloride A solution of 4 N hydrogen chloride in 1,4-dioxane (10 mL) was added to a solution of trans-4-(N-tert-butoxycarbonylglycylamino)-N-tert-butoxycarbonyl-L-prolyl-D-homophenylalanine 3-quinolylamide (C, 162 mg) in methanol (10 mL) at 0° C. After stirring at 0° C. for 5 min and at room temperature for 3 hr, the solution was concentrated in vacuo. The residue was purified by HPLC(Shiseido, Capcell Pak C$_{18}$ UG120, 3 cm×25 cm, 0.02 N hydrochloric acid: methanol=65:35, v/v) and freeze-dried from water to afford the title compound (90 mg) as a pale yellow powder: $^1$H NMR (400 MHz, D$_2$O) δ 2.18–2.43 (m, 3H), 2.43–2.57 (m, 1H), 2.74–2.96 (m, 2H), 3.40 (dd, J=12.2,4.4 Hz, 1H), 3.76–3.87 (m, 3H), 4.45–4.60 (m, 2H), 4.61–4.73 (m, 1H), 7.01–7.17 (m, 1H), 7.17–7.31 (m, 4H), 7.86 (t, J=7.8 Hz, 1H), 8.00 (t, J=7.8 Hz, 1H), 8.04–8.19 (m, 2H), 8.81 (s, 1H), and 9.15 (s, 1H); IR (KBr) 3388, 3205, 3037, 1685, 1681, 1610, 1571, 1552, 1496, 1486, and 1454 cm$^{-1}$; mass spectrum (EI+) m/e 474 (M+); (FAB+) m/e 475 (M+1); Anal. Calcd for $_{26}$H$_{30}$N$_6$O$_3$.3HCl.3H$_2$O: C, 48.95; H, 6.16; N, 13.17. Found: C, 49.16; H, 5.90; N, 13.15.

Compound D202—trans-4-Amino-L-Prolyl-D-Homophenylalanine 3-Quinolylamide Trihydrochloride (A) N-tert-Butoxcarbonyl-trans-4-(N-tert-Butoxycabonylamino)-L-Prolyl-D-Homophenalalanine 3-Quinolylamide Trifluoroacetic acid (2 mL) was added to a cold (0° C.) stirred solution of N-tert-butoxycarbonyl-D-homophenylalanine 3-quinolylamide (68 mg) in dichloromethane (2 mL). The mixture was stirred at room temperature for 30 min and concentrated in vacuo to give trifuluoroacetate (84 mg). Triethylamine (51 µL), 1-hydroxybenzotriazole (23 mg) and 1-(3-dimethylaminopropyl)-3-ethylcarbodiimide hydrochloride (35 mg) were added to a cold (0° C.) stirred solution of the trifluoroacetate (84 mg) and N-tert-butoxycarbonyl-trans-4-(N-tert-butoxycarbonyl-amino)-L-broline (Compound D101 (O), 50 mg) in dichloromethane (30 mL). The mixture was stirred at room temperature for 19.5 hr and concentrated in vacuo. The residue was diluted with ethyl acetate and washed with 1 N hydrochloric acid, water, saturated sodium hydrogen carbonate and brine. The organic layer was dried over anhydrous sodium sulfate and concentrated in vacuo. The residue was purified by silica gel column chromatography (dichloromethane then ethyl acetate:dichloromethane=1:5 to 1:1, v/v) to give the title compound (75 mg) as white solids: $^1$H NMR (400 MHz, CDCl$_3$) δ 1.39 (s, 9H), 1.46 (s, 9H), 2.08–2.18 (m, 2H), 2.30–2.40 (m, 2H), 2.44–2.55 (m, 2H), 2.79 (t, J=7.3 Hz, 2H), 3.32–3.40 (m, 1H), 3.69–3.73 (m, 1H), 4.06–4.15 (m, 1H), 4.25–4.33 (m, 1H), 4.58–4.72 (m, 2H), 6.38–6.46 (m, 1H), 7.17–7.35 (m, 5H), 7.52 (t, J=7.6 Hz, 1H), 7.58–7.66 (m, 1H), 7.78 (d, J=7.8 Hz, 1H), 8.04 (d, J=8.3 Hz, 1H), 8.73 (br, 1H), 8.99 (br, 1H), and 9.21 (br, 1H).

(B) trans-4-Amino-L-Prolyl-D-Homophenylalanine Quinoline-3-Amide Trihydrochloride The title compound (55 mg) was similarly prepared, as described in Compound D101(Q), except the starting material was N-tert-butoxycarbonyl-trans-4-(N-tert-butoxycabonylamino)-L-prolyl-D-homophenylalanine 3-quinolylamide (A, 75 mg): $^1$HNMR (400 MHz, D$_2$O) δ 2.12–2.31 (m, 2H), 2.43–2.63 (m, 2H), 2.65–2.83 (m, 2H), 3.42 (dd, J=6.1, 12.9 Hz, 1H), 3.87 (dd, J=7.6, 12.9 Hz, 1H), 4.07–4.16 (m, 1H), 4.41 (t, J=6.4 Hz, 1H), 4.61–4.81 (m, 1H), 6.98 (t, J=6.1 Hz, 1H), 7.10–7.20 (m, 4H), 7.73 (t, J=7.8 Hz, 1H), 7.87 (t, J=7.8 Hz, 1H), 8.00 (d, J=8.3 Hz, 2H), 8.64 (br, 1H), and 8.97 (br, 1H); IR (KBr) 3381, 3205, 3025, 2929, 1682, 1610, 1572, 1550, 1495, 1489, and 1454 cm$^{-1}$; mass spectrum (FAB+) m/e 418 (M+1); Anal. Calcd for C$_{24}$H$_{27}$N$_5$O$_2$.3HCl.2H$_2$O: C, 51.21; H, 6.09; N, 12.44. Found: C, 52.58; H, 6.06; N, 12.26.

Compound D203—trans-4-Glycylamino-L-Prolyl-D-Homophenylalanine 5-Indanylamide Dihydrochloride (A) N-tert-Butoxycarbonyl-D-Homophenylalanine 5-Indanylamide The title compound (524 mg) was similarly prepared, as described in Compound D201 (A), except the starting material was 5-aminoindane (206 mg): $^1$H NMR (400 MHz, CDCl$_3$) δ 1.46 (s, 9H), 1.95–2.10 (m, 3H), 2.21–2.30 (m, 1H), 2.75 (t, 2H), 2.84–2.91 (m, 4H), 4.13 (br s, 1H), 5.02 (br s, 1H), 7.15–7.32 (m, 7H), 7.46 (s, 1H).

(B) D-Homophenylalanine 5-Indanylamide Trifluoroacetate

The title compound (388 mg) was similarly prepared, as described in Compound D201 (B), except the starting material was N-tert-butoxycarbonyl-D-homophenylalanine 5-indanylamide (A, 524 mg): $^1$H NMR (400 MHz, CDCl$_3$) δ 1.85–1.95 (m, 1H), 2.03–2.10 (m, 2H), 2.23–2.35 (m, 1H), 2.72–2.82 (m, 2H), 2.82–2.97 (m, 4H), 3.47–3.50 (m, 1H), 7.14–7.30 (m, 7H), 7.56 (s, 1H).

(C) trans-4-(N-tert-Butoxycarbonylglyclamino)-N-tert-Butoxycarbonyl-L-Prolyl-D-Homophenylalanine 5-Indanylamide The title compound (820 mg) was similarly prepared, as described in Compound D201 (C), except the starting material was D-homophenylalanine 5-indanylamide trifluoroacetate (B, 379 mg): $^1$H NMR (400 MHz, CD$_3$OD) δ 1.41–1.45(m, 18H), 1.77 (s, 2H), 2.01–2.07 (m, 2H), 2.20–2.40 (m, 1H), 2.71–2.77 (m, 2H), 2.81–2.84 (m, 4H), 3.71–3.76 (m, 2H), 4.62–4.64 (m, 1H), 5.35 (br s, 1H), 7.10–7.29 (m, 7H), 7.46 (br s, 1H).

(D) trans-4-Glycylamino-L-Prolyl-D-Homoyhenylalanine 5-Indanylamide Dihydrochloride The title compound (603 mg) was similarly prepared, as described in Compound D201 (I), except the starting material trans-4-(N-tert-butoxycarbonylglycylamino)-N-tert-butoxycarbonyl-L-prolyl-D-homophenylalanine 5-indanylamide (C, 810 mg): $^1$H NMR (400 MHz, D$_2$O) δ 1.88–1.98 (m, 2H), 2.04–2.18 (m, 2H), 2.20–2.26 (m, 1H), 2.34–2.37 (m, 1H), 2.64–2.70 (m, 2H), 2.70–2.78 (m, 4H), 3.22–3.26 (m, 1H), 3.54–3.67 (m, 1H), 3.71 (s, 2H), 4.26–4.29 (m, 1H), 4.40–4.47 (m, 2H), 6.98–7.00 (m, 1H), 7.13–7.19 (m, 5H), 7.24–7.27 (m, 2H); mass specrum (FAB+) m/e 464 (M+1); Anal. Calcd for C$_{26}$H$_{33}$N$_5$O$_3$2HClH$_2$O: C, 56.32; H, 6.73; N, 12.63. Found: C, 56.75; H, 6.72; N, 12.45.

Compound D204—trans-4-Glycylamino-L-Prolyl-D-Homophenylalanine 3,4-Dimethylphenylamide Dihydrochloride (A) N-tert-Butoxycarbonyl-D-Homophenylalanine 3,4-Dimethylphenylamide The title compound (1.40 g) was similarly prepared, as described in Compound D201 (A), except the starting materials were 3,4-dimethylaniline (435 mg) and N-tert-butoxycarbonyl-D-homophenylalanine (1.10 g): $^1$H NMR (400 MHz, CDCl$_3$) δ 1.46 (s, 9H), 1.92–2.08 (m, 1H), 2.21 (s, 3H), 2.22 (s, 3H), 2.15–2.32 (m, 1H), 2.74 (t, J=7.8 Hz, 2H), 4.11–4.23 (m, 1H), 5.02–5.18 (m, 1H), 7.05 (d, J=8.3 Hz, 1H), 7.13–7.44 (m, 7H), and 8.03 (br s, 1H).

(B) D-Homophenylalanine 3,4-Dimethylphenylamide Trifluoroacetate

The title compound (313 mg) was similarly prepared, as described in Compound D201 (B), except the starting material was N-tert-butoxycarbonyl-D-homophenylalanine 3,4-dimethylphenylamide (A, 302 mg).

(C) trans-4-(N-tert-Butoxycarbonylglycylamino)-N-tert-Butoxycarbonyl-L-Prolyl-D-Homophenylalanine 3,4-Dimethylphenylamide The title compound (321 mg) was similarly prepared, as described in Compound D201 (C), except the starting material was D-homophenylalanine 3,4-dimethylphenylamide trifluoroacetate (B, 313 mg). The compound appears as a mixture of rotamers: $^1$H NMR (400 MHz, CD$_3$OD) δ 1.41 and 1.45 (each s, total 18H), 1.90–2.40 (m, 4H), 2.21 (s, 3H), 2.22 (s, 3H), 2.58–2.81 (m, 2H), 3.30–3.43 (m, 1H), 3.60–3.83 (m, 3H), 4.30–4.58 (m, 3H), 7.17 (d, J=8.3 Hz, 1H), and 7.14–7.47 (m, 7H).

(D) trans-4-Glycylamino-L-Prolyl-D-Homophenylalanine 3,4-Dimethylphenylamide Dihydrochloride The title compound (258 mg) was similarly prepared, as described in Compound D201 (D), except the starting material was trans-4-(N-tert-butoxycarbonylglycylamino)-N-tert-butoxycarbonyl-L-prolyl-D-homophenylalanine 3,4-dimethylphenylamide (C, 321 mg): $^1$H NMR (400 MHz, D$_2$O) δ 2.00–2.47 (m, 4H), 2.14 (s, 6H), 2.58–2.80 (m, 2H), 3.31 (dd, J=12.7, 4.4 Hz, 1H), 3.66 (dd, J=12.7, 6.4 Hz, 1H), 3.62–3.80 (m, 2H), 4.29 (t, J=6.8 Hz, 1H), 4.39–4.50 (m, 1H), 4.53 (t, J=7.8 Hz, 1H), and 6.93–7.33 (m, 8H); IR (KBr) 3401, 3218, 3060, 2944, 1671, 1616, 1598, 1548, 1504, 1454, and 1405 cm$^{-1}$; mass spectrum (EI+) m/e 451 (M+); (FAB+) m/e 452 (M+1); high-resolution mass (FAB) m/e Calcd for C$_{25}$H$_{33}$N$_5$O$_3$: 451.2583. Found: 451.2599.

Compound D205—trans-4-Glycylamino-L-Prolyl-D-Homophenylalanine 3,5-Dimethylphenylamide Dihydrochloride (A) N-tert-Butoxycarbonyl-D-Homophenylalanine 3,5-Dimethylphenylamide The title compound (523 mg) was similarly prepared, as described in Compound D201 (A), except the starting materials were 3,5-dimethylaniline (166 mg) and N-tert-butoxycarbonyl-D-homophenylalanine (420 mg): $^1$H NMR (400 MHz, CDCl$_3$) δ 1.46 (s, 9H), 1.92–2.06 (m, 1H), 2.28 (s, 6H), 2.16–2.30 (m, 1H), 2.74 (t, J=7.8 Hz, 2H), 4.10–4.21 (m, 1H), 4.98–5.11 (m, 1H), 6.75 (s, 1H), 7.09–7.32 (m, 7H), and 8.02 (br s, 1H).

(B) D-Homophenylalanine 3,5-Dimethylphenylamide Trifluoroacetate

The title compound (180 mg) was similarly prepared, as described in Compound D201 (B), except the starting material was N-tert-butoxycarbonyl-D-homophenylalanine 3,5-dimethylphenylamnide (A, 173 mg).

(C) trans-4-(N-tert-Butoxycarbonylglycyamino)-N-tert-Butoxycarbonyl-L-Prolyl-D-Homophenylalanine 3,5-Dimethylphenylamide The title compound (217 mg) was similarly prepared, as described in Compound D201 (C), except the starting material was D-homophenylalanine 3,5-dimethylphenylamide trifluoroacetate (B, 180 mg). The compound appears as a mixture of rotamers: $^1$H NMR (400 MHz, CD$_3$OD) δ 1.42 and 1.45 (each s, total 18H), 1.90–2.43 (m, 4H), 2.25 (s, 6H), 2.55–2.86 (m, 2H), 3.22–3.43 (m, 1H), 3.52–3.88 (m, 3H), 4.30–4.62 (m, 3H), 6.74 (s, 1H), and 7.07–7.40 (m, 7H).

(D) trans-4-Glycylamino-L-Prolyl-D-Homophenylalanine 3,5-Dimethylphenylamide Dihydrochloride The title compound (160 mg) was similarly prepared, as described in Compound D201 (D), except the starting material was trans-4-(N-tert-butoxycarbonylglycylamino)-N-tert-butoxycarbonyl-L-prolyl-D-homophenylalanine 3,5-dimethylphenylamide (C, 217 mg): $^1$H NMR (400 MHz, D$_2$O) δ 2.08–2.55 (m, 4H), 2.24 (s, 6H), 2.68–2.88 (m, 2H), 3.30–3.45 (m, 1H), 3.68–3.90 (m, 3H), 4.32–4.40 (m, 1H), 4.47–4.64 (m, 2H), 6.89–7.01 (m, 3H), and 7.20–7.38 (m, 5H); IR (KBr) 3388, 3218, 3058, 2944, 1681, 1616, 1600, 1556, 1496, and 1454 cm$^{-1}$; mass spectrum (EI+) m/e 451 (M+); (FAB+) m/e 452 (M+1); Anal. Calcd for C$_{25}$H$_{33}$N$_5$O$_3$.2HCl3/2H$_2$O: C, 54.45; H, 6.94; N, 12.70. Found: C, 54.74; H, 6.94; N, 12.30.

Compound D206—trans-4-Glycylamino-L-Prolyl-D-Homophenylalanine 4-Chloro-3-Methylphenylamide Dihydrochloride (A) N-tert-Butoxycarbonyl-D-Homophenylalanine 4-Chloro-3-Methylphenylaide The title compound (389 mg) was similarly prepared, as described in Compound D201 (A), except the starting materials were 4-chloro-3-methylaniline (139 mg) and N-tert-butoxycarbonyl-D-homophenylalanine (302 mg): $^1$H NMR (400 MHz, CDCl$_3$) δ 1.46 (s, 9H), 1.92–2.06 (m, 1H), 2.20–2.32 (m, 1H), 2.34 (s, 3H), 2.75 (t, J=7.8 Hz, 2H), 4.08–4.19 (m, 1H), 4.91–5.03 (m, 1H), 7.25–7.33 (m, 7H), 7.42 (s, 1H), and 8.16 (br s, 1H).

(B) D-Homophenylalanine 4-Chloro-3-Methylphenylamide Trifluoroacetate

The title compound (140 mg) was similarly prepared, as described in Compounds D201 (B), except the starting material was N-tert-butoxycarbonyl-D-homophenyl-alanine 4-chloro-3-methylphenylamide (A, 124 mg).

(C) trans-4-(N-tert-Butoxycarbonylglycyamino-N-tert-Butoxycarbonyl-L-Prolyl-D-Homophenylalanine 4-Chloro-3-Methylpenylamide The title compound (138 mg) was similarly prepared, as described in Compounds D201 (C), except the starting material was D-homophenylalanine 4-chloro-3-methylphenylamide trifluoroacetate (B, 140 mg). The compound appears as a mixture of rotamers: $^1$H NMR (400 MHz, CDCl$_3$—CD$_3$OD (1:10, v/v)) δ 1.42 and 1.46 (each s, total 18H), 1.90–2.43 (m, 4H), 2.32 (s, 3H), 2.55–2.82 (m, 2H), 3.25–3.46 (m, 1H), 3.55–3.88 (m, 3H), 4.27–4.60 (m, 3H), 7.10–7.32 (m, 6H), 7.32–7.64 (m, 1H), and 7.76 (s, 1H).

(D) trans-4-Glycylamino-L-Prolyl-D-Homophenylalanine 4-Chloro-3-Methylphenyl-amide Dihydrochloride The title compound (97 mg) was similarly prepared, as described in Compound D201 (D), except the starting material was trans-4-(N-tert-butoxycarbonylglycylamino)-N-tert-butoxycarbonyl-L-prolyl-D-homophenylalanine 4-chloro-3-methylphenylamide (C, 138 mg): $^1$H NMR (400 MHz, D$_2$O) δ 2.00–2.42 (m, 4H), 2.22 (s, 3H), 2.58–2.78 (m, 2H), 3.18–3.30 (m, 1H), 3.50–3.74 (m, 3H), 4.20–4.32 (m, 1H), 4.32–4.52 (m, 2H), and 7.00–7.32 (m, 8H); IR (KBr) 3199, 3058, 3029, 2956, 2929, 1677, 1610, 1587, 1548, 1496, 1482, 1454, and 1405 cm$^{-1}$; mass spectrum (E+) m/e 471 (M+); (FAB+) m/e 472 (M+1); high-resolution mass (FAB) m/e Calcd for C$_{24}$H$_{30}$ClN$_5$O$_3$: 471.2037. Found: 471.2034.

Compound D210—trans-4-Glycylamino-L-Prolylglycine 4-Benzylphenyl-amide Dihydrochloride (A) N-tert-Butoxycarbonylglycine 4-Benzylphenylamide Bis(2-oxo-3-oxazolidinyl)phosphinic chloride (1.90 g) and N,N-diisopropylethyl-amine (1.5 mL) were added to a solution of 4-aminodiphenylmethane (0.52 g) and N-tert-butoxycarbonylglycine (0.50 g) in dichloromethane (30 mL) at 0° C. After stiriing at 0° C. for 10 min and at room temperature for 17.5 hr, the solvent was removed in vacuo. The residue was diluted with 1 N hydrochloric acid and extracted with ethyl acetate. The organic layer was washed with water, saturated sodium hydrogen carbonate, and brine, dried over anhydrous sodium sulfate, and evaporated in vacuo. The residue was purified by silica gel column chromatography (hexane:ethyl acetate=3:1, v/v) to afford the title compound (0.81 g) as a colorless powder: $^1$H NMR (400 MHz, CDCl$_3$) δ 1.47 (s, 9H), 3.90 (d, 2H), 3.94 (s, 2H), 7.12–7.21 (m, 5H), 7.28 (d, 2H), 7.41 (d, 2H).

(B) Glycine 4-Benzylphenylamide Trifluoroacetate

The title compound (530 mg) was similarly prepared, as described in Compound 201 (B), except the starting material was N-tert-butoxycarbonylglycine 4-benzylphenylamide (A, 810 mg). The compound appears as a mixture of rotamers: $^1$H NMR (400 MHz, CD$_3$OD) δ 3.45 (s, 2H), 3.95 (s, 2H), 7.14–7.21 (m, 5H), 7.28 (d, 2H), 7.51(d, 2H).

(C) trans-4-(N-tert-Butoxycarbonylglycylamino)-N-tert-Butoxycarbonyl-L-Prolylglycine 4-Benzylphenylamide The title compound (164 mg) was similarly prepared, as described in Compound 201 (C), except the starting material was glycine 4-benzylphenylamide trifluoroacetate (B, 74 mg): $^1$H NMR (400 MHz, CDCl$_3$) δ 1.38 (s, 9H), 1.44 (s, 9H), 1.88 (s, 1H), 2.30–2.34 (m, 1H), 3.36–3.38 (m, 1H), 3.75–3.79 (m, 1H), 3.91–3.95 (m, 2H), 4.32–4.35 (m, 1H), 4.47–4.48 (m, 1H), 5.45 (m, 1H), 7.08–7.19 (m, 5H), 7.28 (d, 2H), 7.54 (br s, 2H).

(D) trans-4-Glycylamino-L-Prolylglycine 4-Benzyiphenylamide Dihydrochloride

The title compound (106 mg) was similarly prepared, as described in Compound 202 (D), except the starting material was trans-4-(N-tert-butoxycarbonylglycylamino)-N-tert-butoxycarbonyl-L-prolylglycine 4-benzylphenylamide (C, 160 mg): $^1$H NMR (400 MHz, D$_2$O) δ 2.47 (dd, 2H), 3.38 (dd, 1H), 3.73 (dd, 1H), 3.79 (s, 2H), 3.95 (s, 2H), 4.11 (s, 2H), 4.54 (t, 1H), 4.65 (t, 1H), 4.70–4.76 (m, 1H), 7.21–7.34 (m, 9H); mass spectrum (FAB+) m/e 410 (M+1); Anal. Calcd. For C$_{22}$H$_{27}$N$_5$O$_3$·2HCl·3/2H$_2$O: C, 51.87; H, 6.33; N, 13.75. Found: C, 52.10; H, 6.20; N, 13.79.

TYPE III

Compound D301 (A)–(B)

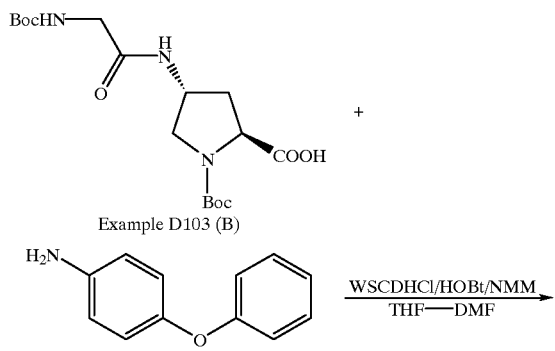

Compound D302 (A)–(B)

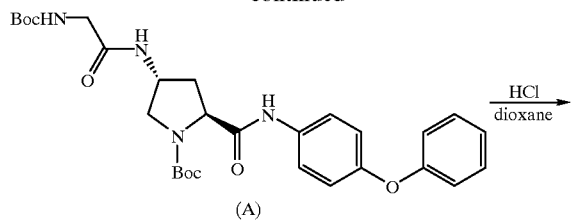
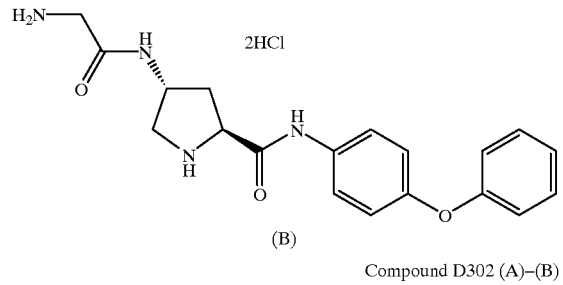

Compound D303 (A)–(B)

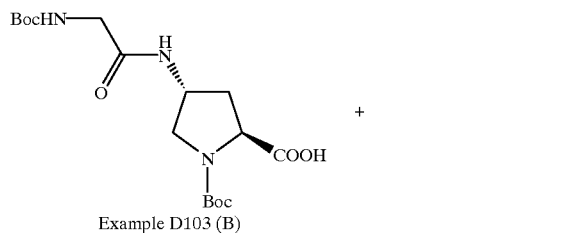
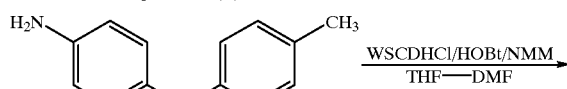
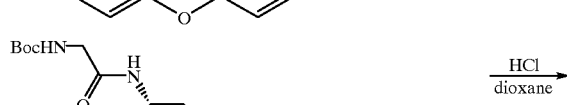
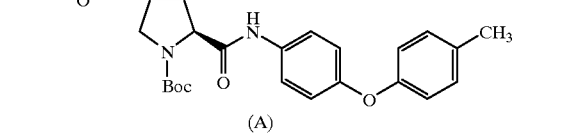
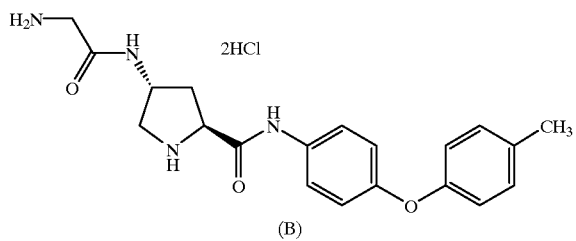
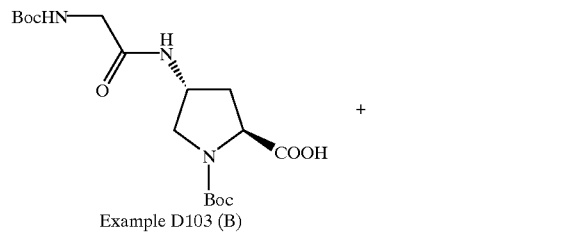
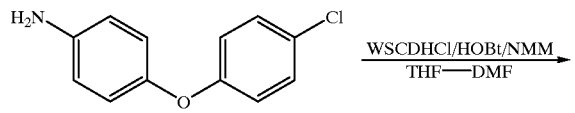

131
-continued
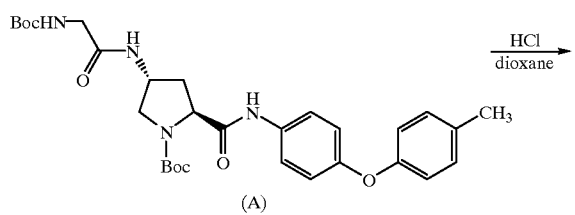
(A)
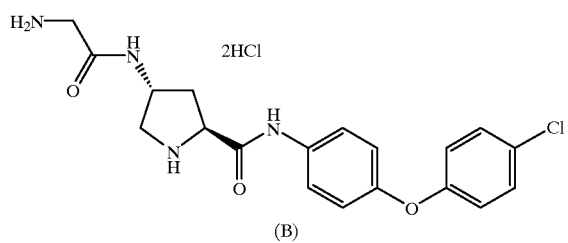
(B)
Compound D304 (A)–(B)
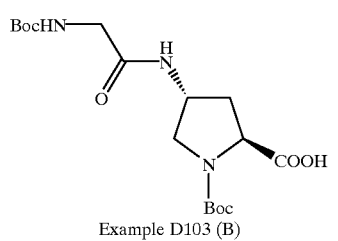
Example D103 (B)
+
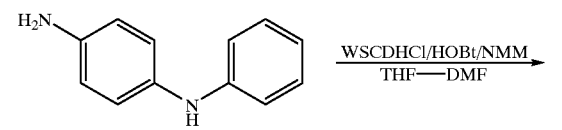
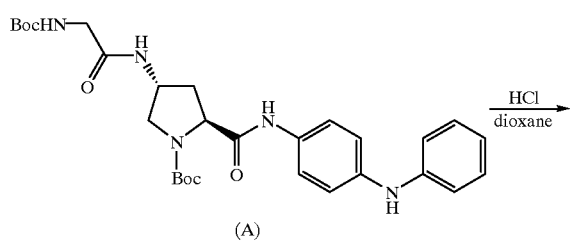
(A)
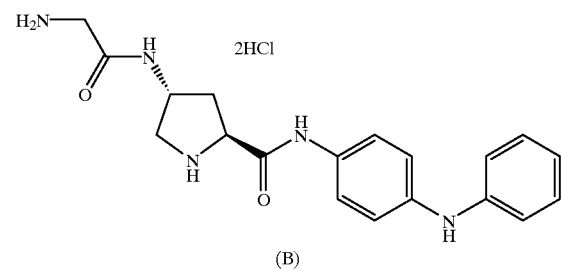
(B)
Compound D306 (A)–(B)
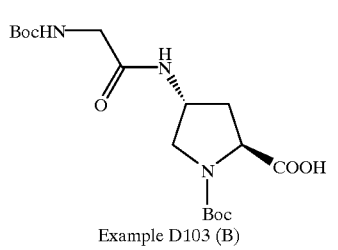
Example D103 (B)
+
132
-continued
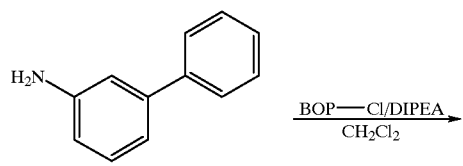
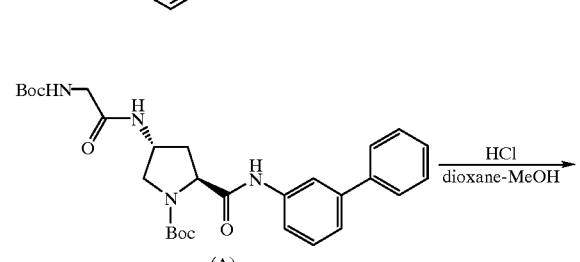
(A)
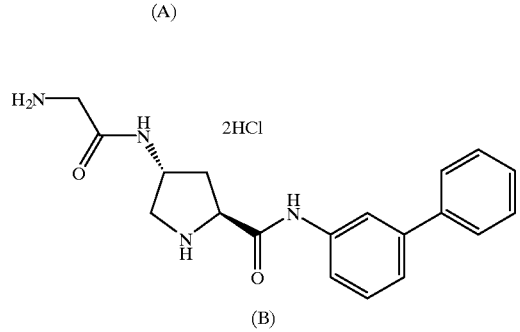
(B)
Compound D307 (A)–(B)
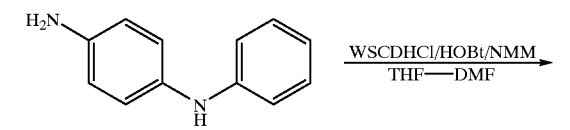
Example D105 (F)
+
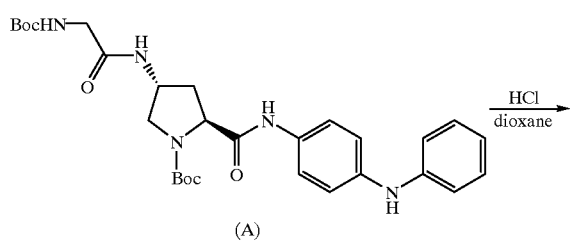
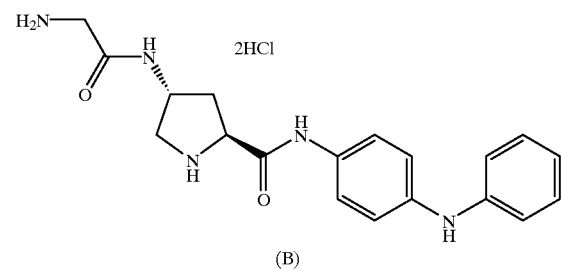
(A)
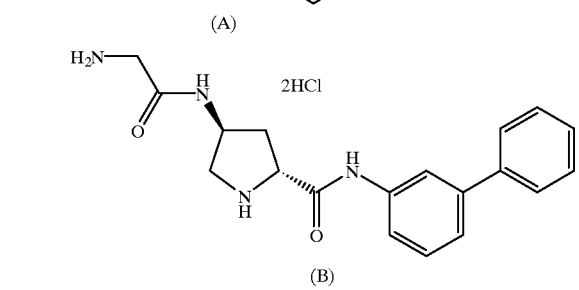
(B)

-continued

Compound D308 (A)–(B)

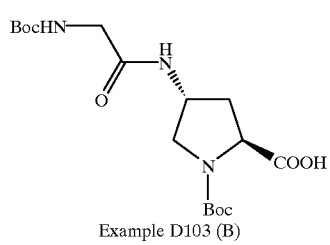

Example D103 (B)

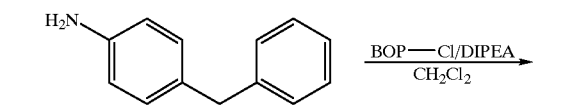

$\xrightarrow{\text{BOP—Cl/DIPEA}}_{\text{CH}_2\text{Cl}_2}$

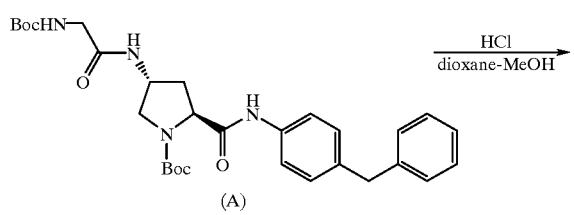

$\xrightarrow{\text{HCl}}_{\text{dioxane-MeOH}}$ (A)

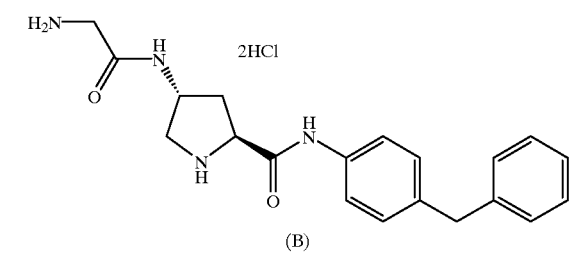

(B)

Compound D313 (A)–(B)

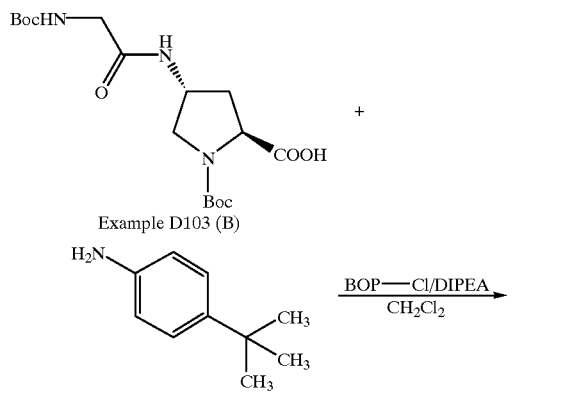

$\xrightarrow{\text{BOP—Cl/DIPEA}}_{\text{CH}_2\text{Cl}_2}$

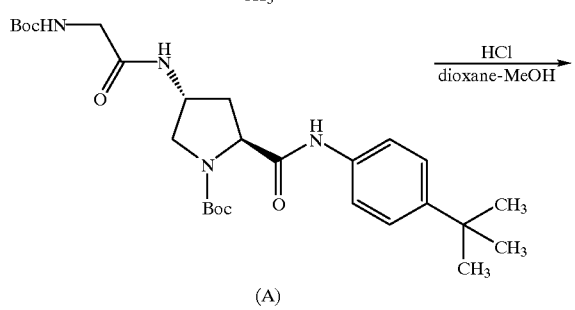

$\xrightarrow{\text{HCl}}_{\text{dioxane-MeOH}}$ (A)

-continued

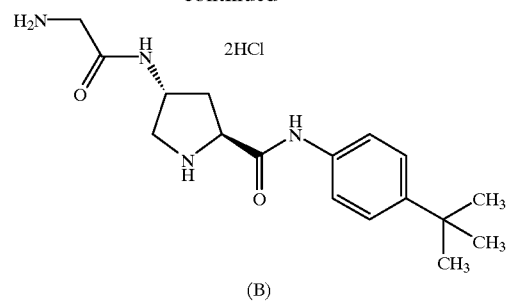

(B)

Compound D314 (A)–(B)

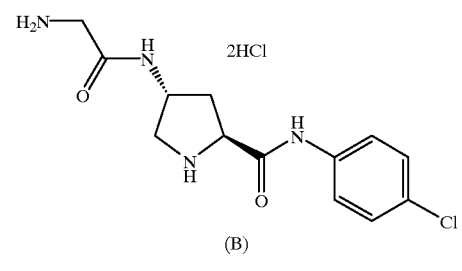

Example D103 (B)

$\xrightarrow{\text{BOP—Cl/DIPEA}}_{\text{CH}_2\text{Cl}_2}$ $\xrightarrow{\text{HCl}}_{\text{dioxane-MeOH}}$ (A)

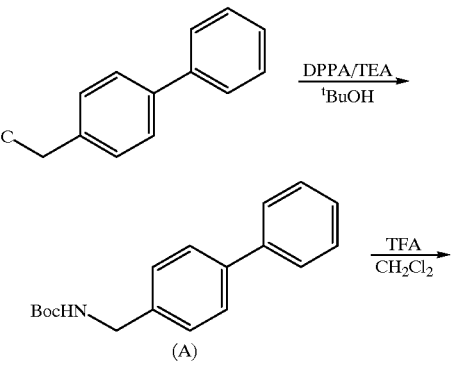

(B)

Compound D316 (A)–(B)

$\xrightarrow{\text{DPPA/TEA}}_{\text{}^t\text{BuOH}}$ $\xrightarrow{\text{TFA}}_{\text{CH}_2\text{Cl}_2}$ (A)

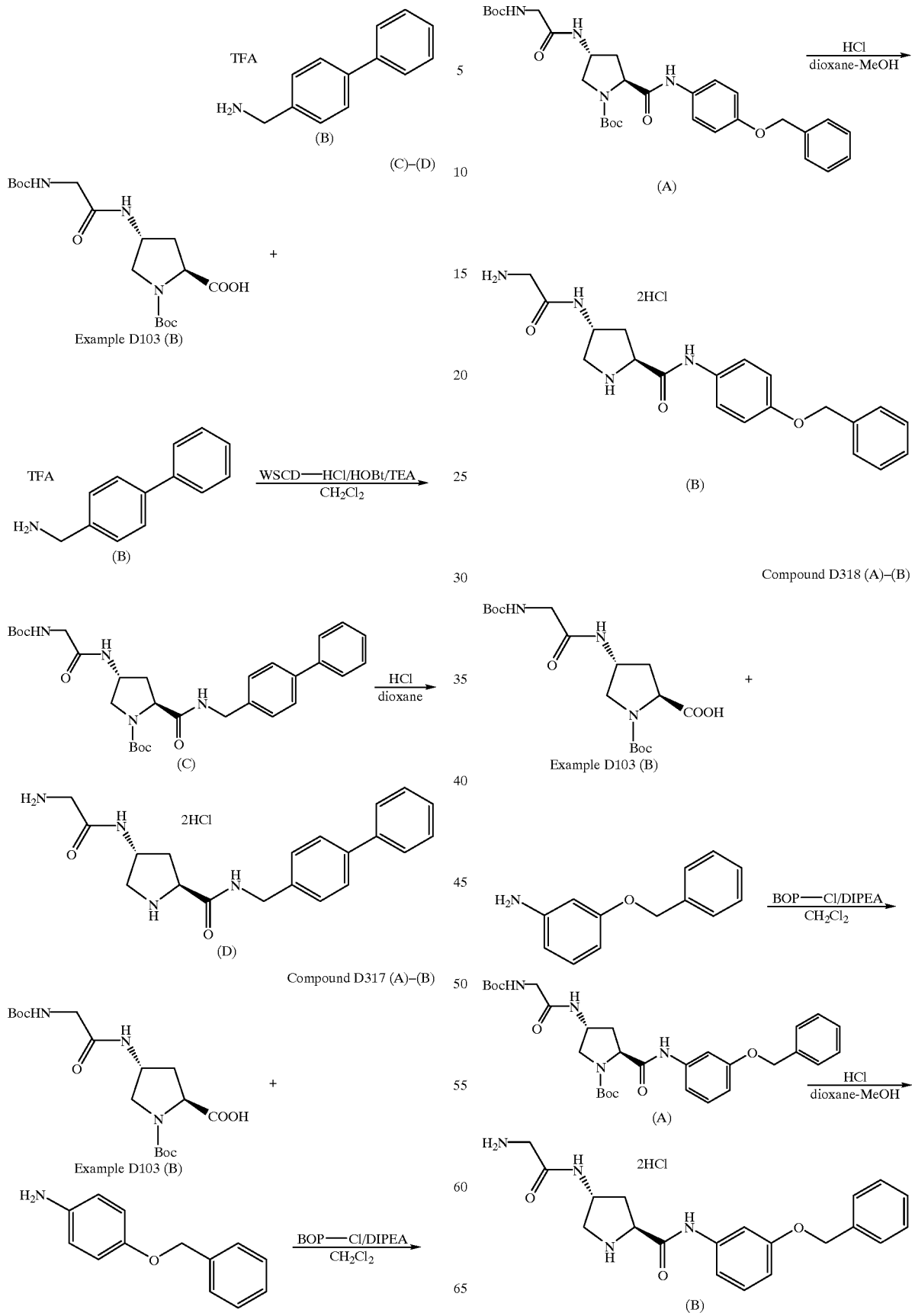

Compound 319 (A)–(B)
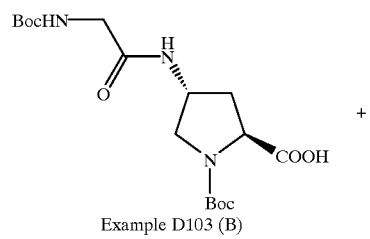
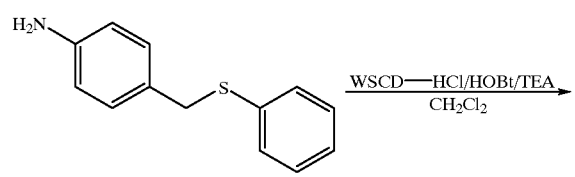
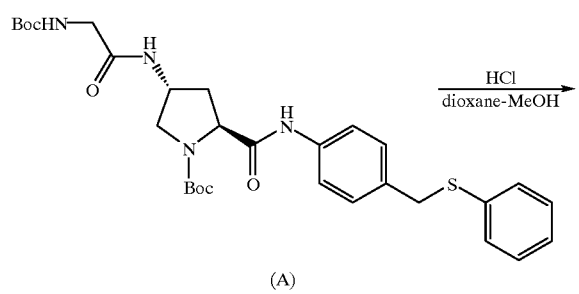
Compound 320 (A)–(B)
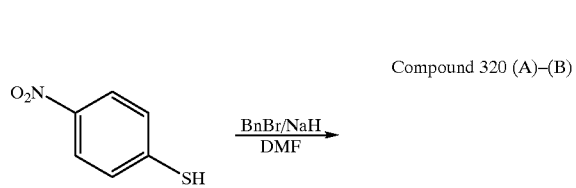
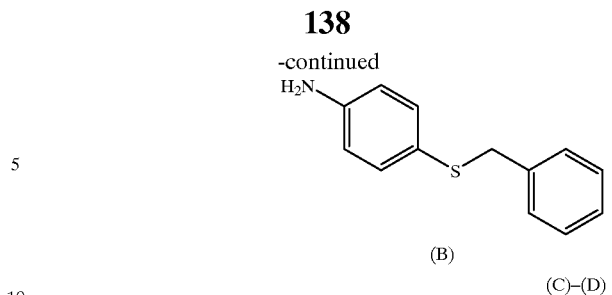
Compound D321 (A)–(F)
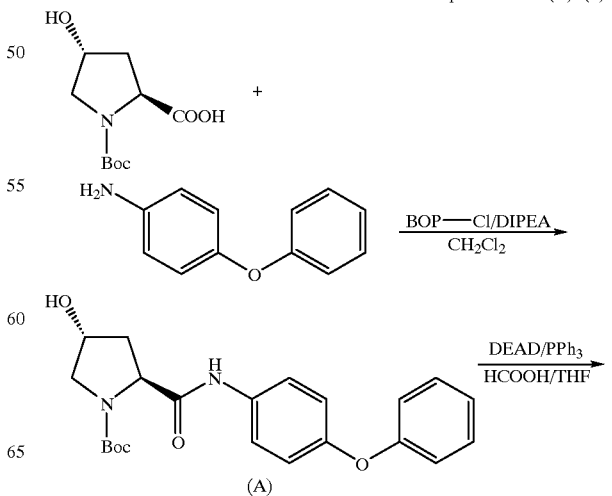

-continued
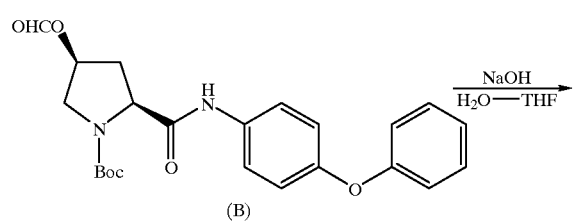
(B)
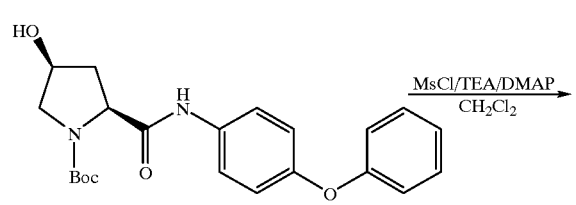
(C)
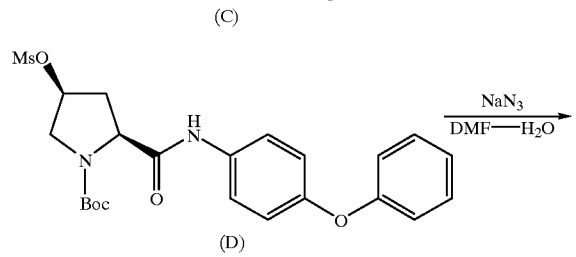
(D)
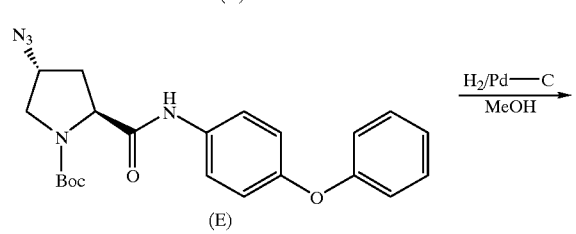
(E)
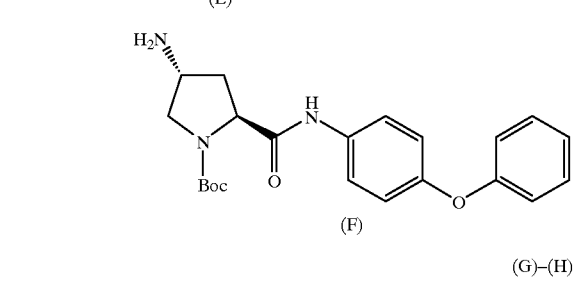
(F)
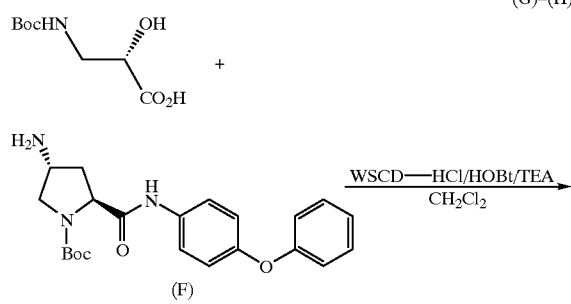
(F)
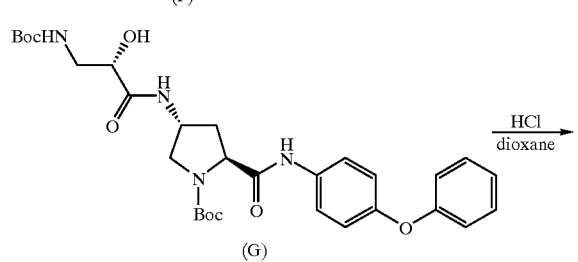
(G)
-continued
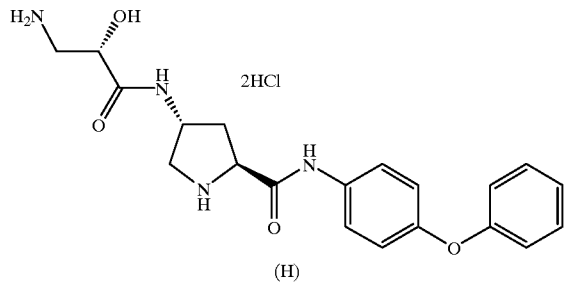
(H)
Compound D322 (A)–(B)
(A)
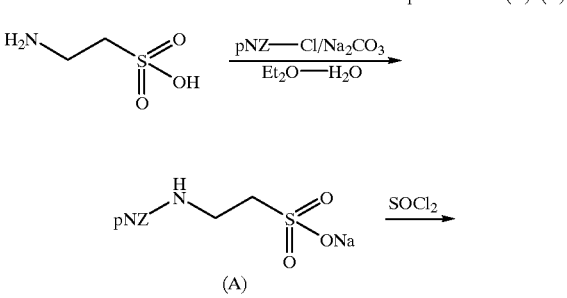
(B)
(C)–(D)
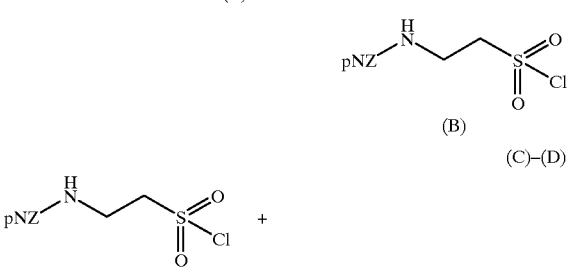
Example D321 (F)
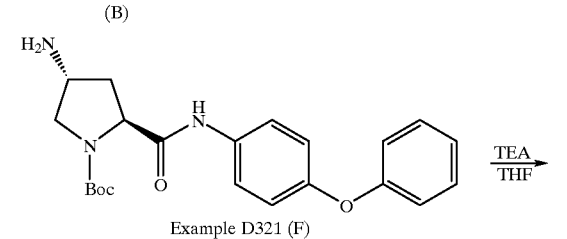
(C)
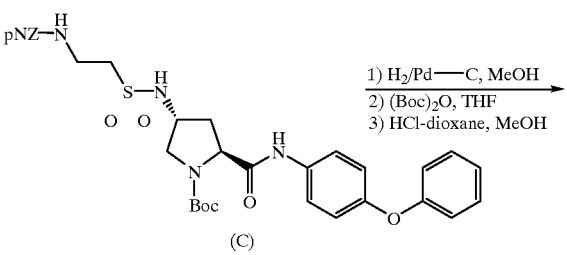
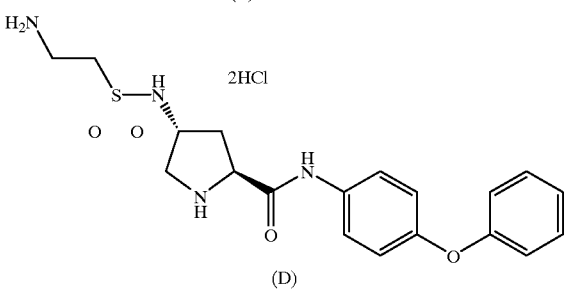
(D)

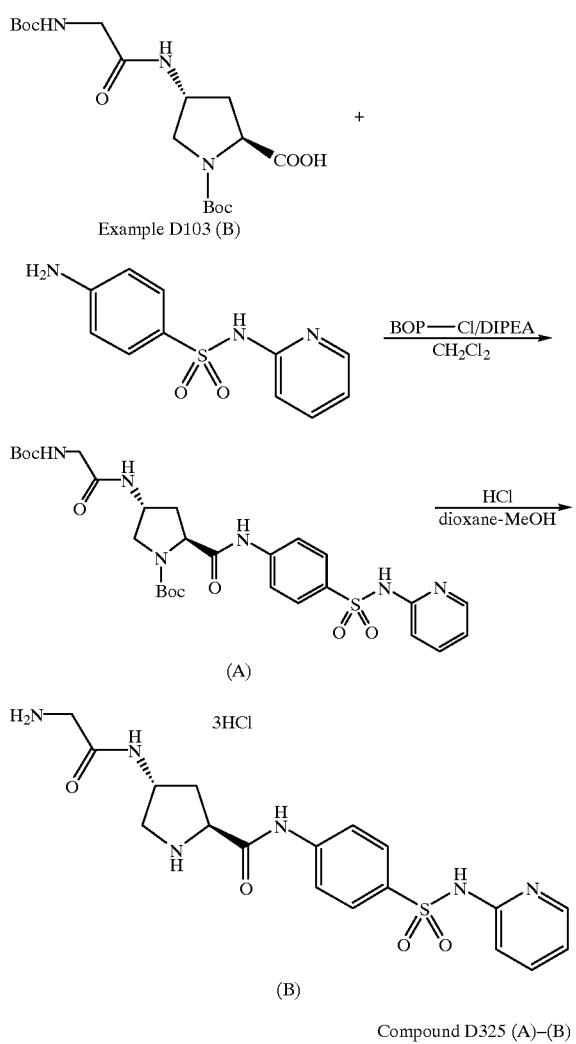
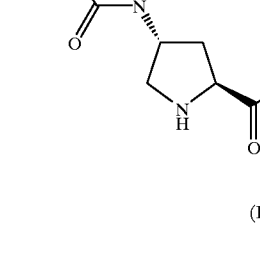
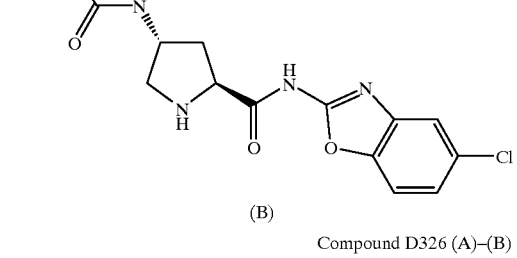

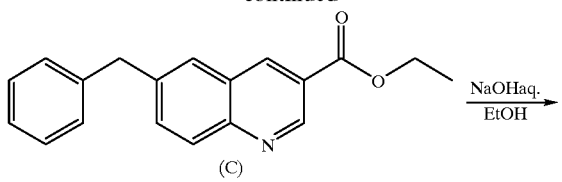
(C)
NaOHaq. / EtOH
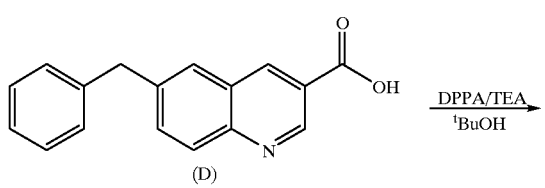
(D)
DPPA/TEA / tBuOH
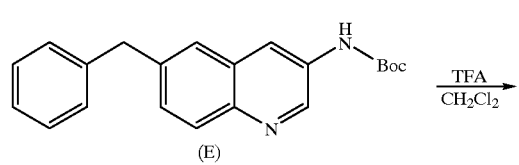
(E)
TFA / CH2Cl2
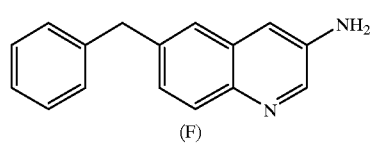
(F)
Compound D327 (G)–(H)
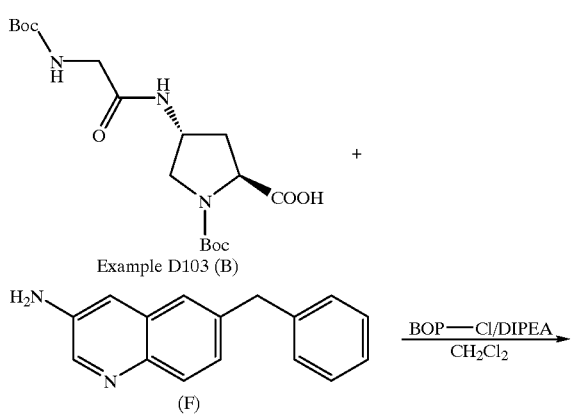
Example D103 (B)
+
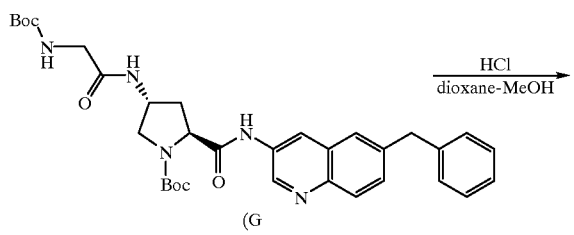
(F)
BOP—Cl/DIPEA / CH2Cl2
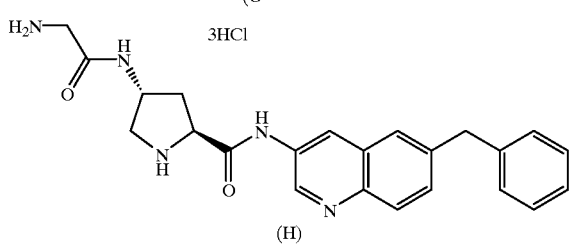
(G)
HCl / dioxane-MeOH
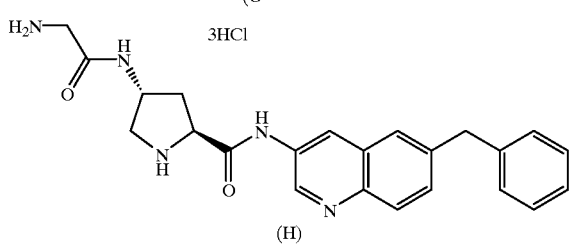
3HCl
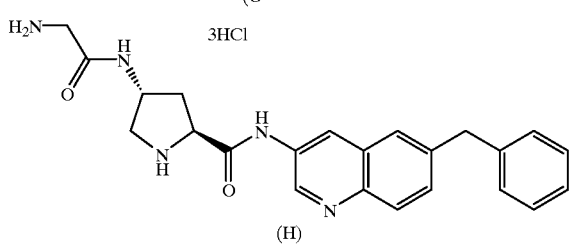
(H)
Compound D328 (A)–(B)
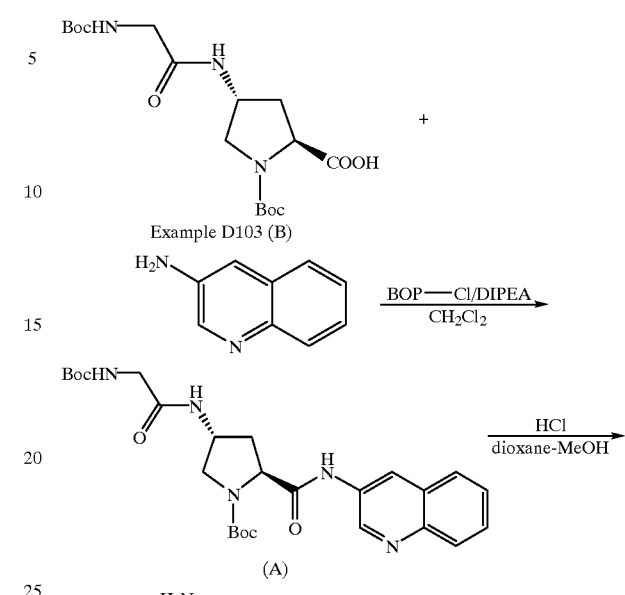
Example D103 (B)
BOP—Cl/DIPEA / CH2Cl2
(A) 2HCl
HCl / dioxane-MeOH
(B)
Compound D329 (A)–(B)
Example D112 (G)
+
WSCD—HCl/HOBt/TEA / CH2Cl2
(A)
HCl / dioxane
2HCl
(B)

Compound D330 (A)–(B)

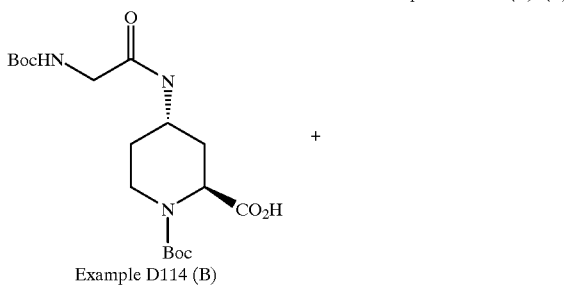
Example D114 (B)

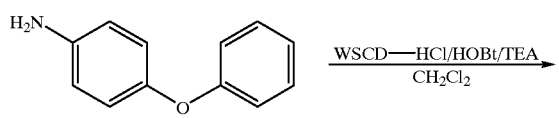

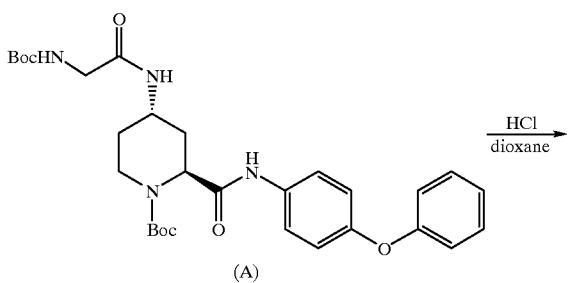
(A)

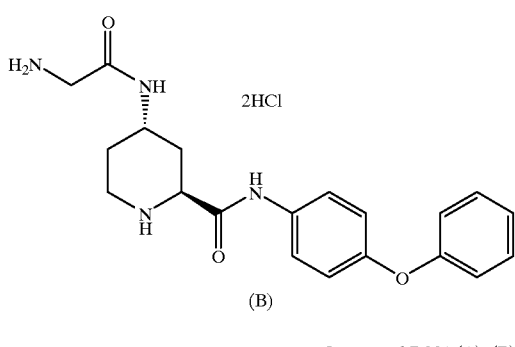
(B)

Compound D331 (A)–(B)

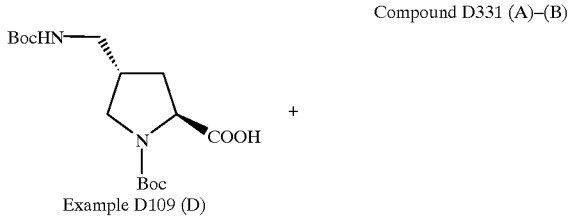
Example D109 (D)

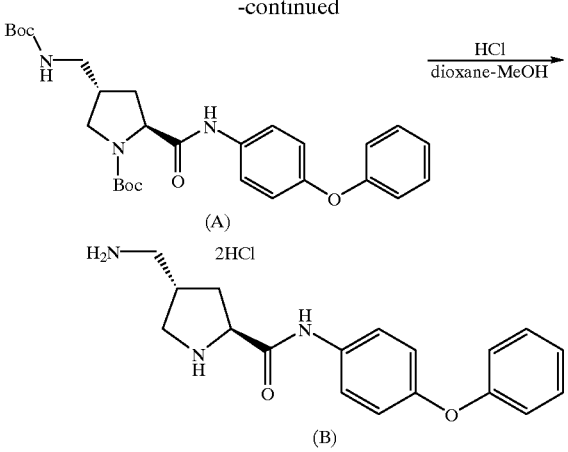
(A)

(B)

Compound D301—trans-4Glycylamino-L-Proline 4-Phenoxyphenylamide Dihydrochloride
(A) trans-4-(N-tert-Butoxycarbonylglcylamlino)-N-tert-butoxycarbonyl-L-Proline 4-Phenoxyphenylamide N-Methylmorpholine (60 μL) and 1-(3-dimethylaminopropyl)-3-ethylcarbodiimide hydrochloride (94 mg) were added to a solution of trans-4-(N-tert-butoxycarbonylglycylamino)-N-tert-butoxycarbonyl-L-proline (Compound D103 (B), 200 mg), 4-phenoxyaniline (96 mg), and 1-hydroxybenzotriazole (70 mg) in tetrahydrofuran (6 mL) and N,N-dimethylformamide (2 mL) at room temperature. After stirring at room temperature for 13 hr, the reaction mixture was partitioned between ethyl acetate and 1 N hydrochloric acid. The organic layer was washed with saturated sodium carbonate and then brine. After drying over anhydrous sodium sulfate, the organic layer was concentrated in vacuo. The residue was washed with hexane to give the title compound (249 mg) as a white powder, which was used in the next reaction without further purification.

(B) trans-4-Glycylamino-L-Proline 4-Phenoxyphenylamide Dihydrochloride

A solution of 4 N hydrochloric acid in 1,4-dioxane (8 mL) was added to a solution of trans-4-(N-tert-butoxycarbonylglycylamino)-N-tert-butoxycarbonyl-L-proline 4-phenoxyphenylamide (A, 249 mg) in 1,4-dioxane (8 mL) at room temperature. After stirring at room temperature for 1 hr, the reaction mixture was concentrated in vacuo. The residue was washed with ether to give the title compound (140 mg) as a white powder: $^1$H NMR (400 MHz, D$_2$O) δ 2.61 (t, J=6.35 Hz, 2 H), 3.49 (dd, J=4.88, 12.21 Hz, 1 H), 3.84 (t, J=6.35 Hz, 1H), 3.87 (s, 2 H), 4.64 (m, 1 H), 4.78 (m, 1H), 7.09 (m, 4 H), 7.23 (t, J=7.3 Hz, 1H), and 7.46 (m, 4 H).

Compound D302—trans-4-Glycylamino-L-Proline 4-(4'-Methylphenoxy)-phenylamide Dihydrochloride
(A) trans-4-(N-tert-Butoxylcarbonylglycylamino)-L-Proline 4-(4'-Methylphenoxy)-phenylamide N-Methylmorpholine (60 μL) and 1-(3-dimethylaminopropyl)-3-ethylcarbodiimide hydrochloride (94 mg) were added to a solution of trans-4-(N-tert-butoxycarbonyl-glycylamino)N-tert-butoxycarbonyl-L-proline (Compound D103 (B), 200 mg), 4-(4'-methylphenoxy)aniline (103 mg), and 1-hydroxybenzotriazole (70 mg) in tetrahydrofuran (6 mL) and N,N-dimethylformamide (2 mL) at room temperature. After stirring at room temperature for 23 hr, the reaction mixture was partitioned between ethyl acetate and 1 N hydrochloric acid. The organic layer was washed with saturated sodium carbonate and then brine. After drying over anhydrous sodium sulfate, the organic layer was concentrated in vacuo. The residue was washed with hexane to give the title compound (238 mg) as a white powder: $^1$H NMR (400 MHz, CDCl$_3$) δ 1.46–1.47 (m, 18 H), 1.99 (br s, 1H), 2.32 (s, 3 H), 2.75 (br s, 1 H), 3.28 (br s, 1 H), 3.76 (m, 3 H), 4.51 (m, 2 H), 5.20 (br s, 1 H), 6.47 (br s, 1H), 6.87 (d,J=8.30 Hz, 2 H), 6.92(d, J=8.79 Hz, 2H), 7.11 (d, J=8.30 Hz, 2 H), 7.44 (d, J=8.79 Hz, 2 H), and 9.30 (br s, 1 H); mass spectrum (EI+) m/e 568 (M$^+$), 468; IR (KBr) 3311, 2978, 1672, 1500, 1408, 1367, 1230, 1163, 872, 854, and 823 cm$^{-1}$; Anal. Calcd for C$_{30}$H$_{40}$N$_4$O$_7$: C, 63.36; H, 7.09; N, 9.85. Found: C, 62.87; H, 6.94; N, 9.72.

(B) trans-4Glycylamino-L-Proline 4-[4'-Methylphenoxy)phenylamide Dihydrochloride A solution of 4 N hydrochloric acid in 1,4-dioxane (6 mL) was added to a solution of trans-4-(N-tert-butoxylcarbonylglycylamino)-L-Proline 4-(4'-methylphenoxy)phenylamide (A, 210 mg) in 1,4-dioxane (6 mL) at room temperature. After stirring at room temperature for 1 hr, the reaction mixture was concentrated in vacuo. The residue was washed with ether to give the title compound (106 mg) as colorless crystals: $^1$H NMR (400 MHz, D$_2$O) δ 1.28 (s, 3 H), 2.59 (m, 2 H), 3.50 (br d, J=8.8 Hz, 1H), 3.82 (t, J=6.0 Hz, 1H), 3.87 (s, 2 H), 4.61 (br s, 1 H), 4.96 (m, 1 H), 6.92 (d, J=7.5 Hz, 2 H), 7.00 (d, J=7.8 Hz, 2 H), 7.19 (d, J=7.5 Hz, 2 H), and 7.43 (d, J=7.8 Hz, 2 H).

Compound D303—trans-4-Glycylamino-L-Proline 4-(4'-Chlorophenoxy)-phenylamide Dihydrochloride (A) trans-4-(N-tert-Butoxycarbonylglycylamino)-N-tert-butoxycarbonyl-L-Proline 4-(4'-Chlorophenoxy)phenylamide N-Methylnorpholine (60 μL) and 1-(3-dimethylaminopropyl)-3-ethylcarbodiimide hydrochloride (94 mg) were added to a solution of trans-4-(N-tert-butoxycarbonylglycylanmino)-N-tert-butoxycarbonyl-L-proline (Compound D103 (B), 200 mg), 4-(4'-chlorophenoxy)aniline (113 mg), and 1-hydroxybenzotriazole (70 mg) in tetrahydrofuran (6 mL) and N,N-dimethylformamide (2 mL) at room temperature. After stirring at room temperature for 23 hr, the reaction mixture was partitioned between ethyl acetate and 1 N hydrochloric acid. The organic layer was washed with saturated sodium carbonate and then brine. After drying over anhydrous sodium sulfate, the organic layer was concentrated in vacuo. The residue was washed with hexane to give the title compound (257 mg) as a colorless powder: $^1$H NMR (400 MHz CDCl$_3$) δ 1.46–1.48 (18 H), 1.99 (br s, 1 H), 2.75 (br s, 1 H), 3.28 (br s, 1 H), 3.76 (m, 3 H), 4.52 (m, 2 H), 5.16 (br s, 1 H), 6.44 (br s, 1 H), 6.89 (d, J=8.79 Hz, 2 H), 6.94 (d, J=8.79 Hz, 2 H), 7.26 (d, J=8.79 Hz, 2 H), 7.48 (d, J=8.79 Hz, 2 H), and 9.40 (br s, 1 H); mass spectrum (EI+) m/e 588 (M$^+$), 488; IR (KBr) 3319, 2978, 1672, 1485, 1412, 1232, 1163, 854, 829, and 771 cm$^{-1}$; Anal. Calcd for C$_{29}$H$_{37}$Cl$_1$N$_4$O$_7$: C, 59.13; H, 6.33; N, 9.51; Cl, 6.02. Found: C, 58.84; H, 6.10; N, 9.75; Cl, 5.84.

(B) trans-4-Glycylamino-L-Proline 4-(4'-Chlorophenoxy)phenylamide Dihydrochloride A solution of 4 N hydrochloric acid in 1,4-dioxane (5 mL) was added to a solution of trans-4-(N-tert-butoxycarbonylglycylamino)-N-tert-butoxycarbonyl-L-proline 4-(4'-chlorophenoxy)phenylamide (A, 230 mg) in 1,4-dioxane (5 mL) at room temperature. After stirring at room temperature for 1 hr, the reaction mixture was concentrated in vacuo. The residue was washed with ether to give the title compound (112 mg) as colorless crystals: $^1$H NMR (400 MHz, D$_2$O) δ 2.31 (quintet, J=7.0 Hz, 1 H), 2.59 (m, 1 H), 3.53 (m, 1 H), 3.74 (m, 1 H), 3.88 (s, 2 H), 4.50 br s, 1 H), 4.80 (m, 1 H), 6.65 (d, J=7.8 Hz, 2 H), 6.72 (d, J=7.8 Hz, 2 H), 7.03 (d, J=7.8 Hz, 2 H), and 7.39 (d, J=7.8 Hz, 2 H).

Compound D304—trans-4-Glycylamino-L-Proline 4-Phenylamino-phenylamide Dihydrochloride (A) trans-4-(N-tert-Butoxycarbonylglycylamino)-N-tert-Butoxycarbonyl-L-Proine 4-Phenylaminophenylamide N-Methylmorpholine (60 μL) and 1-(3-dimethylaminopropyl)-3-ethylcarbodiimide hydrochloride (94 mg) were added to a solution of trans-4-(N-tert-butoxycarbonylglycylamino)-N-tert-butoxycarbonyl-L-proline (Compound D103 (B), 200 mg), 4-phenylaminoaniline (95 mg) and 1-hydroxybenzotriazole (70 mg) in tetrrhydrofuran (6 mL) and N,N-dimethylformamide (2 mL) at room temperature. After stirring at room temperature for 48 hr, the reaction mixture was partitioned between ethyl acetate and 1 N hydrochloric acid. The organic layer was washed with saturated sodium carbonate and then brine. After drying over anhydrous sodium sulfate, the organic layer was concentrated in vacuo. The residue was washed with hexane to give the title compound (257 mg) as a navy blue powder: $^1$H NMR (400 MHz, CDCl$_3$) δ 1.46–1.47 (18 H), 1.99 (br s, 1 H), 2.73 (br s, 1 H), 3.30 (br s, 1H), 3.76 (m, 3 H), 4.52 (m, 2 H), 5.31 (br s, 1 H), 5.69 (br s, 1 H), 6.63 (br s, 1H), 6.89 (t, J=7.0 Hz, 1 H), 7.01 (m, 4 H), 7.24 (m, 2 H), 7.39 (d, J=8.8 Hz, 2 H), and 9.23 (br s, 1 H); mass spectrum (EI+) m/e 553 (M$^+$); IR (KBr) 3329, 2978, 1676, 1516, 1496, 1402, 1252, and 161 cm$^{-1}$.

(B) trans-4-Glycylamino-L-Proline 4-Phenylaminophenylamide Dihydrochloride

A solution of 4 N hydrochloric acid in 1,4-dioxane (7 mL) was added to a solution of trans-4-(N-tert-butoxycarbonylglycylamino)-N-tert-butoxycarbonyl-L-proine 4-phenylaminophenylamide (A, 230 mg) in 1,4-dioxane (7 mL) at room temperature. After stirring at room temperature for 1 hr, the reaction mixture was concentrated in vacuo. The residue was washed with ether to give the title compound (100 mg) as a blue green powder: $^1$H NMR (400 MHz, D$_2$O) δ 2.61 (t, J=7.0 Hz, 2 H), 3.50 (dd, J=4.9, 12.2 Hz, 1 H), 3.85 (t, J=6.3 Hz, 1 H), 3.88 (s, 2 H), 4.64 (m, 1 H), 4.80 (m, 1 H), 7.20 (br s, 5 H), and 7.40 (m, 4 H); mass spectru (EI+) m/e 353 (M$^+$).

Compound D306—trans-4-Glycylamino-L-Proline 3-Biphenylamide Dihydrochloride (A) trans-4-(N-tert-Butoxycarbonylglycylamino)-N-tert-Butoxycarbonyl-L-Proline 3-Biphenylamide The title compound (108 mg) was similarly prepared, as described in Compound D308 (A), except the starting material was 3-aminobiphenyl: $^1$H NMR (400 MHz, CDCl$_3$) δ 1.46 (s, 18H), 2.01 (m, 1H), 2.74 (m, 1H), 3.31 (m, 1H), 3.76–3.83 (m, 3H), 4.55 (m, 2H), 5.41 (m, 1H), 6.78 (m, 1H), 7.27 (s, 1H), 7.34 (t, J=7.3 Hz, 2H), 7.42 (t, J=7.3 Hz, 2H), 7.46 (m, 1H), 7.56 (d, J=7.3 Hz, 2H), 7.81 (s, 1H), and 9.28 (m, 1H).

(B) trans-4-Glycylamino-L-Proline 3-Biphenylamnide Dihydrchloride

The title compound (76 mg) was similarly prepared, as described in Compound D308 (B), except the starting material was trans-4-(N-tert-butoxycarbonylglycylamino)-N-tert-butoxycarbonyl-L-proline 3-biphenylamide (A, 108 mg): $^1$H NMR (400 MHz, D$_2$O) δ 2.59 (dd, J=7.3, 6.4 Hz, 2H), 3.45 (dd, J=12.7, 4.9 Hz, 1H), 3.71 (m, 1H), 3.79 (m, 1H), 3.82 (s, 2H), 4.60 (m, 1H), 4.74 (m, 1H), 7.43–7.53 (m, 6H), 7.68 (d, J=7.8 Hz, 2H), and 7.74 (s, 1H).

Compound D307—trans-4-Glycylamino-D-proline 3-Biphenylamide Dihydrochloride (A) trans-4-(N-tert-Butoxycarbonylglycylamino)-N-tert-Butoxycarbonyl-D-Proline 3-Biphenylamide The title compound (105 mg) was similarly prepared, as described in Compound D308 (A), except the starting materials were 3-aminobiphenyl (35 mg) and trans-4-(N-tert-butoxycarbonylglycylamino)-N-tert-butoxycarbonyl-D-proline (Compound D105 (F), 80.0 mg).

(B) trans-4-Glcylamino-D-proline 3-Biphenylamide Dihydrochloride

The title compound (71 mg) was similarly prepared, as described in Compound D308 (B), except the starting material was trans-4-(N-tert-butoxycarbonylglycylamino)-N-tert-butoxycarbonyl-D-proline 3-biphenylamide (A, 105 mg): $^1$H NMR (D$_2$O) δ 2.64 (t, 2H), 3.49 (dd, 1H), 3.83–3.88 (m, 4H), 4.62–4.68 (m, 1H), 4.77–4.82 (m, 2H), 7.49 (d, 2H), 7.54–7.61 (m, 4H), 7.73 (d, 2H), and 7.80 (s, 1H); mass spectrum (FAB+) m/e 339 (M+1); Anal. Calcd for C$_{19}$H$_{22}$N$_4$O$_2$.2HCl.¾H$_2$O: C, 52.60; H, 6.16; N, 12.91. Found: C, 52.96; H, 6.11; N, 12.49.

Compound D308 trans-4-Glycylamino-L-Proline 4-Benzylphenylamide Dihydrochloride (A) trans-4-(N-tert-Butoxycarbonylglycylamino)-N-tert-Butoxycarbonyl-L-Proline 4-Benzylphenylamide 1-Hydroxybenzotriazole (21 mg) and 1-(3-dimethylaminopropyl)-3-ethylcarbodiimide hydrochloride (65 mg) were added to a solution of 4-benzylaniline (57 mg) and trans-4-(N-tert-butoxycarbonylglycylamino)-N-tert-butoxycarbonyl-L-proline (Compound D103 (B), 120 mg) in dichloromethane (3 mL) at 0° C. The mixture was stirred at room temperature for 4 hr. The reaction mixture was diluted with chloroform and washed with saturated sodium hydrogen carbonate and brine. The organic layer was dried over anhydrous sodium sulfate and concentrated in vacuo. The residue was purified by silica gel column chromatography (chloroform:methanol=100:1, v/v) to give the title compound (158 mg) as a colorless foam: $^1$H NMR (400 MHz, CDCl$_3$) δ 1.44 (s, 18H), 2.01 (m, 1H), 2.70 (m, 1H), 3.26 (m, 1H), 3.75 (m, 3H), 3.91 (s, 2H), 4.50 (m, 2H), 5.53 (m, 1H), 6.79 (m, 1H), 7.08–7.28 (m,7H), 7.40 (d, J=7.8 Hz, 2H), and 9.28 (m, 1H).

(B) trans-4-Glycylamino-L-Proline 4-Benzylphenylamide Dihydrochloride trans-4-(N-tert-Butoxycarbonylglycylamino)-N-tert-butoxycarbonyl-L-proline 4-benzylphenylamide (A, 158 mg) was dissolved in 4 N hydrogen chloride in 1,4-dioxane (6 mL). After stirring for 2 hr, the reaction mixture was evaporated in vacuo to give white solids. The solids were washed with ether to afford the title compound (A, 103 mg): $^1$H NMR (400 MHz, D$_2$O) δ 2.59 (dd, J=7.8, 6.4 Hz, 2H), 3.48 (dd, J=12.7, 4.8 Hz, 1H), 3.83 (dd, J=12.7, 6.4 Hz, 1H), 3.85 (s, 2H), 4.00 (s, 2H), 4.62 (m, 1H), 4.73 (m, 1H), and 7.28–7.42 (m, 9H).

Compound D313—trans-4-Glycylamino-L-Proline 4-tert-Butylphenyl-amide Dihydrochloride (A) trans-4-(N-tert-Butoxycarbonylglycylamino)-N-tert-Butoxycarbonyl-L-Proline 4-tert-Butylphenylamide The title compound (83 mg) was similarly prepared, as described in Compound D308 (A), except the starting material was tert-butylaniline: $^1$H NMR (400 MHz,) δ 1.29 (s, 9H), 1.45 (s, 18H), 1.99 (m, 1H), 2.70 (m, 1H), 3.28 (m, 1H), 3.75–3.78 (m, 3H), 4.52 (m, 2H), 5.44 (m, 1H), 6.79 (m, 1H), 7.31 (d, J=8.8 Hz, 2H), 7.42 (d, J=8.8 Hz, 2H), and 9.28 (m, 1H).

(B) trans-4-Glycylamino-L-Proline 4-tert-Butylphenylamide Dihydrochloride

The title compound (43 mg) was similarly prepared, as described in Compound D308 (B), except the starting material was trans-4-(N-tert-butoxycarbonylglycylamino)-N-tert-butoxycarbonyl-L-proline 4-tert-butylphenylamide (A, 83 mg): $^1$H NMR (400 MHz, D$_2$O) δ 1.28 (s, 9H), 2.57 (dd, J=7.3, 6.4 Hz, 2H), 3.44 (dd, J=12.7, 4.9 Hz, 1H, 3.71 (m, 1H), 3.79 (m, 1H), 3.82 (s, 2H), 4.60 (m, 1H), 4.72 (m, 1H), 7.41 (d, J=8.3 Hz, 2H), and 7.51 (d, J=8.3 Hz, 2H).

Compound D314—trans-4-Glycylamino-L-Proline 4-Chlorophenylamide Dihydrochloride (A) trans-4-(N-tert-Butoxycarbonylglycylamino)-N-tert-Butoxycarbonyl-L-Proline 4-Chlorophenylamide The title compound (134 mg) was similarly prepared, as described in Compound D308 (A), except the starting material was 4-chloroaniline: $^1$H NMR (400 MHz, CDCl$_3$) δ 1.45 (s, 18H), 2.07 (m, 1H), 2.66 (m, 1H), 3.31 (m, 1H), 3.70 (m, 1H), 3.74–3.81 (m, 2H), 4.50 (m, 2H), 5.47 (m, 1H), 6.86 (m, 1H), 7.21 (m, 2H), 7.44 (m, 2H), and 9.52 (m, 1H).

(B) trans-4-Glycylamino-L-Proline 4-Chlorophenylamide Dihydrochloride

The title compound (72 mg) was similarly prepared, as described in Compound D308 (B), except the starting material was trans-4-(N-tert- butoxycarbonylglycylamino)N-tert-Butoxycarbonyl-L-Proline 4-chlorophenylamide (A, 128 mg): $^1$H NMR (400 MHz, D$_2$O) δ 2.57 (dd, J=7.3, 6.8 Hz, 2H), 3.45 (dd, J=12.2, 4.8 Hz, 1H), 3.79 (m, 1H), 3.82 (s, 2H), 4.59 (m, 1H), 4.73 (dd, J=8.3, 7.8 Hz, 1H), and 7.43 (s, 4H).

Compound D316—trans-4-Glycylmino-L-Proline 4-Phenylbenzylamide Dihydrochloride (A) N-tert-Butoxycarbonyl-4-Phenylbenzylamine Diphenylphosphoryl azide (1.12 mL) and triethylamine (789 μl) were added to a solution of 4-biphenylylacetic acid (1.00 g) in 2-methyl-2-propanol (20 mL). The mixture was refluxed for 13 hr and concentrated in vacuo. The residue was diluted with ethyl acetate and washed with 1 N hydrochloric acid, water, saturated sodium hydrogen carbonate, and brine. The organic layer was dried over anhydrous sodium sulfate and concentrated in vacuo to give the title compound (489 mg) as yellow crystals: $^1$H NMR (400 MHz, CDCl$_3$) δ 1.48 (s, 9H), 4.36 (d, J=5.4 Hz, 2H), 4.87(br s, 1H), 7.26–7.27, 7.32–7.45 and 7.55–7.58 (each m, total 9H).

(B) 4-Phenylbenzylamine Trifluoroacetate

Trifluoroacetic acid (2 mL) was added to a solution of N-tert-butoxycarbonyl-(4-phenylylbenzylaine (A, 121 mg) in dichloromethane (2 mL) at 0° C. The mixture was stirred at room temperature for 30 min and concentrated in vacuo to give the title compound (126 mg).

(C) N-tert-Butoxycarbonyl-trans-4-(N-tert-Butoxycabonylglycylamino)-L-Proline 4-Phenylbenzylamide Triethylamine (130 μL), 1-hydroxybenzotriazole (59 mg), and 1-(3-dimethylaminopropyl)-3-ethylcarbodiimide hydrochloride (89 mg) were added to a solution of the 4-phenylbenzylamine trifluoroacetate (B, 126 mg) and trans-4-(N-tert-butoxycarbonylglycylamino)-N-tert-butoxycarbonyl-L-proline (Compound D103 (B), 150 mg) in dichloromethane (10 mL) at 0° C. The mixture was stirred at room temperature for 16 hr and concentrated in vacuo. The residue was diluted with ethyl acetate and washed with 1 N hydrochloric acid, water, saturated sodium hydrogen carbonate, and brine. The organic layer was dried over anhydrous sodium sulfate and concentrated in vacuo. The residue was purified by silica gel column chromatography (chloroform then chloroform:methanol=99:1 to 98:2, v/v) to give the title compound (178 mg) as a colorless foam:$^1$H NMR (400 MHz, CDCl$_3$) δ 1.45 (s, 18H), 1,67 (s, 2H), 2.01 (brs, 1H), 2.64 (br s, 1H), 3.27 (br s, 1H), 3.68–3.81 (m, 3H), 4.23–4.70 (m, 3H), 5.17 (br s, 1H), 6.43 (br s, 1H), 7.32–7.36 (m, 3H), 7.44 (t, J=7.6 Hz, 2H), and 7.53–7.57 (m, 4H).

(D) trans-4-Glycylamino-L-Proline 4-Phenylbenzylamide Dihydrochloride

The title compound (125 mg) was similarly prepared, as described in Compound D301 (B), except the starting material was N-tert-butoxycarbonyl-trans-4-(N-tert-butoxycabonylglycylamino)-L-proline 4-phenylbenzylamide (C, 178 mg): $^1$H NMR (400 MHz, D$_2$O) δ 2.43–2.56 (m, 2H), 3.42–3.46 (1H, m), 3.78 (dd, J=6.6, 12.5 Hz, 1H), 3.83 (s, 2H), 4.44–4.58 (m, 3H) 4.65 (t, J=8.3 Hz, 1H), 7.41–7.48 (m, 3H), 7.51–7.57 (m, 2H), and 7.67–7.75 (m, 4H); IR (KBr) 3641, 3419, 3371, 3205, 3030, 2623, 1685, 1678, 1562, 1498, 1489, 1441, and 1408 cm$^{-1}$; mass spectrum (EI+) m/e 352 (M); Anal. Calcd for C$_{20}$H$_{24}$N$_4$O$_2$.2HCl.0.5H$_2$O: C, 55.30; H, 6.27; N, 12.90. Found: C, 54.95; H1 6.48; N, 12.69.

Compound D317—trans-4-Glycylamino-L-Proline 4-Benzyloxyphenyl-amide Dihydrochloride (A) trans-4-(N-tert-Butoxycarbonylglyclamino)-N-tert-Butoxycarbonyl-L-Proline 4-Benzyloxyphenylamide The title compound (179 mg) was similarly prepared, as described in Compound D308 (A), except the staring material was 4-benzyloxyaniline: $^1$H NMR (400 MHz, CDCl$_3$) δ 1.44 (s, 18H), 2.07 (m, 1H), 2.66 (m, 1H), 3.31 (m, 1H), 3.71–3.80 (m, 3H), 4.51 (m, 2H), 5.01 (s, 2H), 5.48 (m, 1H), 6.88 (m, 3H), 7.28–7.41 (m, 6H), and 9.20 (m, 1H).

(B) trans-4-Glycylamino-L-Proline 4-Benzyloxyphenylamide Dihydrochloride

The title compound (95 mg) was similarly prepared, as described in Compound D308 (B), except the starting material was trans-4-(N-tert-Butoxycarbonylglycylamino)N-tert-butoxycarbonyl-L-proline 4-benzyloxyphenylamide (A, 147 mg): $^1$H NMR (400 MHz, D$_2$O) δ 2.56 (t, J=6.8 Hz, 2H), 3.43 (dd, J=12.2, 4.8 Hz, 1H), 3.78 (dd, J=12.2, 6.8 Hz, 1H), 3.82 (s, 2H), 4.60 (m, 1H), 4.69 (dd, J=8.3, 7.8 Hz, 1H), 5.18 (s, 2H), 7.08 (s, 2H), and 7.36–7.51 (m,7H).

Compound D318—trans-4-Glycylamino-L-Proline 3-Benzyloxyphenyl-amide Dihydrochloride (A) trans-4-(N-tert-Butoxycarbonylglycylamino)-N-tert-Butoxycarbonyl-L-Proline 3-Benzyloxyphenylamide The title compound (135 mg) was similarly prepared, as described in Compound D308 (A), except the starting material was 3-benzyloxyaniline: $^1$H NMR (400 MHz, CDCl$_3$) δ 1.45 (s, 18H), 2.01 (m, 1H), 2.68 (m, 1H), 3.29 (m, 1H), 3.70–3.81 (m, 3H), 4.52 (m, 2H), 5.01 (s, 2H), 5.50 (m, 1H), 6.69 (m, 1H), 6.89 (m, 1H), 7.00 (m, 1H), 7.15 (m, 1H), 7.28–7.42 (m, 6H), and 9.43 (m, 1H).

(B) trans-4-Glycylamino-L-Proline 3-Benzyloxyphenylamide Dihydrochloride

The title compound (96 mg) was similarly prepared, as described in Compound D308 (B), except the starting material was trans-4-(N-tert-butoxycarbonylglycylamino)-N-tert-butoxycarbonyl-L-proline 3-benzyloxyphenylamide (A, 135 mg): $^1$H NMR (400 MHz, D$_2$O) δ 2.57 (dd, J=7.3, 6.8 Hz, 2H), 3.45 (dd, J=12.2, 4.8 Hz, 1H), 3.73 (m, 1H), 3.83 (s, 2H), 4.60 (m, 1H), 4.73 (dd, J=8.3, 7.8 Hz, 1H), 5.17 (s, 2H), 6.94 (d, J=7.8 Hz, 1H), 7.05 (d, J=7.8 Hz, 1H), 7.22 (s, 1H), 7.36 (t, J=8.3 Hz, 1H), and 7.40–7.51 (m, 5H).

Compound D319—trans-4-Glycylamino-L-Proline 4-(Phenylthiomethyl)-phenylamide Dihydrochloride (A) N-tert-Butoxycarbonyl-trans-4-(N-tert-Butoxycarbonylglycyl)amino-L-Proline 4-(Phenylthiomethyl)phenylamide The title compound (223 mg) was similarly prepared, as described in Compound D316 (C), except the starting material was 4-(phenylthiomethyl)aniline (95 mg):$^1$HNMR(400 MHz, CDCl$_3$) δ 1.46 (s, 18H), 1.97 (br, 1H), 2.76 (br, 1H), 3.27 (br, 1H), 3.69–3.84 (m, 3H), 4.07 (s, 2H), 4.44–4.56 (m, 2H), 5.21 (1H, br), 6.48 (1H, br), 7.14–7.32 (m, 7H), and 7.42 (d, J=8.3 Hz, 1H).

(B) trans-4-Glycylamino-L-Proline 4-(Phenylthiomethyl)phenylamide Dihydrochloride The title compound (156 mg) was similarly prepared, as described in Compound D316 (D), except the starting material was N-tert-butoxycarbonyl-trans-4-(N-tert-butoxycarbonylglycyl)amino-L-proline [4-phenylthiomethyl)phenyl]amide (A, 223 mg): $^1$H NMR (400 MHz, D$_2$O) δ 2.44 (t, J=6.8 Hz, 2H), 3.31 (dd, J=4.9, 12.7 Hz, 1H), 3.62–3.68 (m, 1H), 3.70 (s, 2H), 4.06 (s, 2H), 4.42–4.50 (m, 1H), 4.57 (t, J=8.1 Hz, 1H), and 7.13–7.26 (m, 9H); IR (KBr) 3190, 3059, 2629, 1682, 1610, 1550, 1512, 1479, 1437, 1417, and 1398 cm$^{-1}$; mass spectrum (FAB+) m/e 385 (M+1); Anal. Calcd for C$_{20}$H$_{24}$ N$_{24}$N4O$_2$S.2HClH$_2$O: C, 50.53; H, 5.94; N, 11.78; S, 6.74; Cl, 14.91. Found: C, 50.91; H, 5.67; N, 11.84; S. 6.96; Cl, 15.27.

Compound D320—trans-4-Glycylamino-L-Proline 4-Benzylthiophenyl-amide Dihydrochloride (A) Benzyl 4-Nitrophenyl Sulfide Sodium hydride (60% oil suspension, 155 mg) was added to a cold (0° C.) stirred solution of 4-nitrophenol (500 mg) in N,N-dimethylformamide (10 mL). The mixture was stirred at 0° C. for 30 min, benzyl bromide (460 μL) was added to the mixture. The mixture was stirred at room temperature for 2 hr and concentrated in vacuo. The residue was diluted with ethyl acetate and washed with saturated sodium hydrogen carbonate and brine. The organic layer was dried over anhydrous sodium sulfate and concentrated in vacuo. The residue was purified by silica gel column chromatography (ethyl acetate:hexane=1:20 to 1:10, v/v) to give the title compound (704 mg) as yellow plates: $^1$H NMR (400 MHz, CDCl$_3$) δ 4.25 (s, 2H), 7.26–7.40 (m, 7H), and 8.07–8.12 (m, 2H.

(B) 4-Benzylthioaniline

Tin (II) chloride dihydrate (444 mg) was added to a stirred solution of benzyl 4-nitrophenyl sulfide (A, 704 mg) in ethanol (20 mL). The mixture was stirred at 70° C. for 2 hr under nitrogen, allowed to cool down and then poured into ice. The pH was made slightly basic (pH 7–8). The mixture was diluted with ethyl acetate and washed with saturated sodium hydrogen carbonate and brine. The organic layer was dried over anhydrous sodium sulfate and concentrated in vacuo to give the title compound (565 mg) as a brown oil: $^1$H NMR (400 MHz, CDCl$_3$) δ 3.59 (br s, 2H), 3.93 (s, 2H), 6.54–6.57 (m, 2H), and 7.11–7.26 (m, 7H).

(C) N-tert-Butoxycarbonyl-trans-4-(N-tert-Butoxycarbonylylycylamino)-L-Proline 4-Benzylthiophenylamide The title compound (230 mg) was similarly prepared, as described in Compound316 (C), except the starting material was 4-benzylthioaniline (102 mg): $^1$H NMR (400 MHz, CDCl$_3$) δ 1.34–1.60 (m, 18H), 1.98 (br s, 1H), 2.77 (br s, 1H), 3.28 (br s, 1H), 3.69–3.85 (m, 3H), 4.04 (s, 2H), 4.44–4.57 (m, 2H), 5.18 (br s, 1H), 6.44 (br s, 1H), 7.18–7.34 (m, 7H), 7.38–7.47 (m, 2H), and 9.39 (br s, 1H).

(D) trans-4-Glycylamino-L-Proline 4-Benzylthiophenylamide Dihydrochloride

The title compound (169 mg) was similarly prepared, as described in Compound316 (D), except the starting material was N-tert-butoxycarbonyl-trans-4-(N-tert-butoxycarbonylglycylamino)-L-proline 4-(benylthio)phenylamide (C, 230 mg): $^1$H NMR (400 MHz, D$_2$O) δ 2.50 (t, J=7.1 Hz, 2H), 3.38 (dd, J=4.9, 12.2 Hz, 1H), 3.72–3.77 (m, 1H), 3.77 (s, 2H), 4.12 (s, 2H), 4.53 (quintet, J=5.9 Hz, 1H), 4.65–4.83 (m, 1H), 7.19–7.25 (m, 5H), and 7.29–7.39 (m, 4H); IR (KBr) 3367, 3178, 3030, 2623, 1680, 1597, 1543, 1493, 1452, 1439, and 1394 cm$^{-1}$; mass spectrum (FAB+) m/e 385 (M+1); Anal. Calcd for $C_{20}H_{24}N_4O_2S \cdot 2HCl \cdot H_2O$: C, 50.53; H, 5.94; N, 11.78; S, 6.74; Cl, 14.91. Found: C, 50.54; H, 5.73; N, 11.60; S, 6.59; Cl, 15.28.

Compound D321—trans-4-((S)-3-Amino-2-Hydroxypropionylamino)-L-Proline 4-Phenoxyphenylamide Dihydrochloride (A) trans-4-Hydroxy-N-tert-Butoxycarbonyl-L-Proline 4-Phenoxyphenylamide The title compound (24.3 g) was similarly prepared, as described in Compound D301 (A), except the starting materials were 4-aminodiphenylether (10.0 g) and trans-4-hydroxy-N-tert-butoxycarbonyl-L-proline (12.5 g): $^1$H NMR (400 MHz, CDCl$_3$) δ 1.48 (s, 9H), 3.54 (br s, 2H), 4.55 (br s, 2H), 6.95–6.98 (m, 5H), 7.28–7.32 (m, 2H), and 7.46 (d, 2H).

(B) cis-4-Formyloxy-N-tert-Butoxycarbonyl-L-Proline 4-Phenoxyphenylamide

The title compound (34.3 g) was similarly prepared, as described in Compound D101 (I), except the starting material was trans-4-hydroxy-N-tert-butoxycarbonyl-L-proline 4-phenoxyphenylamide (A, 21.5 g): $^1$H NMR (400 MHz, CDCl$_3$) δ 1.48 (s, 9H), 3.54 (br s, 2H), and 4.55 (br s, 2H).

(C) cis-4-Hydroxy-N-tert-Butoxycarbonyl-L-Proline 4-Phenoxyphenylamide

The title compound (19.4 g) was similarly prepared, as described in Compound D101 (J), except the starting material was cis-4-formyloxy-N-tert-butoxycarbonyl-L-proline 4-Phenoxyphenylamide (B, 34.3 g): $^1$H NMR (400 MHz, CDCl$_3$) δ 1.49 (s, 9H), 2.20 (m, 1H), 2.44–2.48 (m, 1H), 3.51 (br s, 2H), 4.42 (br s, 1H), 4.59–4.74 (m, 1H), 6.93–6.98 (m, 5H), 7.26–7.33 (m, 2H), and 7.46 (d, 2H).

(D) N-tert-Butoxycarbonyl-cis-4-Methanesulfonyloxy-L-Proline 4-Phenoxyphenylamide Triethylamine (4.40 mL) and methanesulfonyl chloride (1.95 mL) was added to a cold (0° C.) stirred solution of cis-4-hydroxy-N-tert-butoxycarbonyl-L-proline 4-phenoxyphenylamide (C, 5.02 g) in dichloromethane (100 mL). The mixture was stirred at 0° C. for 2 hr and at room temperature for 45 min. Triethylamine (4.40 mL) and mehanesulfonyl chloride (1.95 mL) was added to the cold (0° C.) stirred mixture. The mixture was stirred at 0° C. to room temperature for 2 hr, and 4-dimethylaminopyridine (1.54 g) was added at 0° C. The mixture was stirred at room temperature for 1 hr and concentrated in vacuo. The residue was diluted with ethyl acetate and washed with 1 N hydrochloric acid, water, saturated sodium hydrogen carbonate, and brine. The organic layer was dried over anhydrous sodium sulfate and concentrated in vacuo to give the title compound (6.49 g).

(E) N-tert-Butoxycarbonyl-trans-4-Azido-L-Proline 4-Phenoxyphenylamide

The title compound (3.99 g) was similarly prepared, as described in Compound D101 (L), except the starting material was N-tert-butoxycarbonyl-cis-4-methanesulfonyloxy-L-proline 4-phenoxyphenylamide (D, 6.49 g): $^1$H NMR (400 MHz, CDCl$_3$) δ 1.51 (s, 9H), 2.07 (br s, 1H), 2.83 (br s, 1H), 3.48 (br s, 1H), 3.57 (br s, 1H), 4.20–4.30 (br s, 1H), 4.59 (br s, 1H), 6.97 (d, J=7.3 Hz, 4H), 7.08 (t, J=7.3 Hz, 1H), 7.31 (t, J=7.8 Hz, 2H), 7.41–7.52 (m, 2H), and 9.41 (br s, 1H).

(F) N-tert-Butoxycarbonyl-trans-4-Amino-L-Proline 4-Phenoxyphenylamide The title compound (3.68 g) was similarly prepared, as described in Compound D101 (M), except the starting material was N-tert-butoxycarbonyl-trans-4-azido-L-proline 4-phenoxyphenylamide (E, 3.99 g): $^1$H NMR (400 MHz, CDCl$_3$) δ 1.50 (s, 9H), 1.72 (br s, 1H), 1.85 (br s, 2H), 2.69 (br s, 1H), 3.06 (br s, 1H), 3.61 (br s, 1H), 3.73 (br s, 1H), 4.56 (br s, 1H), 6.97(d, J=7.3 Hz, 4H), 7.07 (t, J=7.3 Hz, 1H), 7.31 (t, J=7.8 Hz, 2H), 7.47 (d, J=8.8 Hz, 2H), and 9.49 (br s, 1H).

(G) N-tert-Butoxycarbonyl-trans-4-[(S)-3-(N-tert-Butoxycarbonylamino)-2-Hydroxypropionylamino]-L-Proline 4-Phenoxyphenylamide The title compound (168 mg) was similarly prepared, as described in Compound DIO (P), except the starting materials were (2S)-3-(N-tert-butoxycarbonylamino)-2-hydroxypropionic acid (78 mg) and N-tert-butoxycarbonyl-trans-amino-L-proline 4-phenoxyphenylamide (F, 151 mg): $^1$H NMR (400 MHz, CDCl$_3$) δ 2.01 (br s, 1H), 2.80 (br s, 1H), 3.23 (br s, 1H), 3.42–3.52 (m, 1H), 3.54–3.62 (m, 1H), 3.75–3.84 (m, 1H), 4.18 (br s, 1H), 4.50–4.62 (m, 2H), 5.25 (br s, 1H), 5.38 (br s, 1H), 6.92–7.72 (m, 4H), 7.07 (t, J=7.3 Hz, 1H), 7.31 (t, J=7.6 Hz, 2H), 7.47 (d, J=8.8 Hz, 2H), and 9.34 (br s, 1H).

(H) trans-4-((S)-3-Amino-2-Hydroxypropionylamino)-L-Proline 4-Phenoxyphenyl-amide Dihydrochloride The title compound (121 mg) was similarly prepared, as described in Compound D101 (Q), except the starting material was N-tert-butoxycarbonyl-trans-4-[(2S)-3-(N-tert-butoxycarbonylamino)-2-hydroxypropionylamino]-L-proline 4-phenoxyphenylamide (G, 168 mg): $^1$H NMR (400 MHz, D$_2$O) δ 2.43–2.56 (m, 2H), 3.05 (dd, J=8.3, 13.2 Hz, 1H), 3.26 (dd, J=3.9, 13.2 Hz, 1H), 3.37 (dd, J=5.4, 12.2 Hz, 1H), 3.69 (dd, J=6.6, 12.2 Hz, 1H), 4.34 (dd, J=3.9, 8.1 Hz, 1H), 4,47–4,55 (m, 1H), 4.61–4.81 (m, 1H), 6.92–7.01 (m, 4H), 7.05–7.12 (m, 1H), and 7.27–7.36 (m, 4H); IR (KBr) 3199, 3059, 1684, 1616, 1589, 1556, 1506, 1489, 1456, and 1415 cm$^{-1}$; mass spectrum (FAB+) m/e 385 (M+1); Anal. Calcd for $C_{20}H_{24}N_4O_4 \cdot 2HCl \cdot H_2O$: C, 50.53; H, 5.94; N, 11.79. Found: C, 50.39; H, 5.90; N, 11.60.

Compound D322—trans-4-(2-Aminoethylsulfonylamino)-L-Proline 4-Phenoxyphenylamide Dihydrochloride (A) Sodium 2-(4-Nitrobenzyloxycarbonylamino) ethanesulfonate A mixture of 2-aminoethanesulfonic acid (5.0 g) and sodium carbonate (9.4 g) in ethyl ether-water (100 mL, 1:1, v/v), at 0° C., was treated with 4-nitrobenzyl chloroformate (8.6 g). After stirring vigorously at 0° C. for 10 min and at room temperature for 15 hr, ethyl ether was added to the reaction mixture. The precipitates were collected by filtration and washed with ethyl ether to afford the title compound (9.2 g) as a white powder: $^1$H NMR (400 MHz, D$_2$O) δ 2.94 (t, J=6.4 Hz, 2H), 3.39 (t, J=6.4 Hz, 2H), 5.09 (s, 2H), 7.44 (d, J=8.3 Hz, 2H), and 8.11 (d, J=8.3 Hz, 2H).

(B) 2-(4-Nitrobenzyloxycarbonylamino)ethanesulfonyl Chloride

Thionyl chloride (20 mL) was added to sodium 2-(4-nitrobenzyloxycarbonylamino)-ethanesulfonate (A, 1.25 g). After stirring at room temperature for 10 min, the mixture was refluxed for 3 hr and concentrated in vacuo. The residue was suspended in benzene and the mixture was filtered over diatomaceous earth. The filtrate was concentrated in vacuo to afford the title compound (0.1 g) as a white powder: $^1$H NMR (400 MHz, CDCl$_3$) δ 3.82–3.97 (m, 4H), 5.23 (s, 2H), 5.43 (br s, 1H), 7.51 (d, J=8.8 Hz, 2H), and 8.23 (d, J=8.8 Hz, 2H).

(C) trans-4-[2-(4-Nitrobenzyloxycarbonylamino) ethhlsulfonylaminol-N-tert-Butoxycarbonyl-L-Proline 4-Phenoxyphenylamide A solution of 2-(4-nitrobenzyloxycarbonylamino) ethanesulfonyl chloride (B, 0.1 g) in tetrahydrofuran (1 mL) was added to a solution of N-tert-butoxycarbonyl-L-proline 4-phenoxyphenylamide (Compound D321 (F), 123 mg) and triethylamine (47 µl) in tetrahydrofuran (1 mL) at 0° C. After stirring at 0° C. for 5 min and at room temperature for 18 hr, the solvent was evaporated in vacuo. The residue was diluted with 1 N hydrochloric acid and extracted with ethyl acetate. The organic layer was washed with water, saturated sodium hydrogen carbonate, and brine, dried over anhydrous sodium sulfate, and evaporated in vacuo. The residue was purified by silica gel column chromatography (chloroform then chloroform:methanol=50:1, v/v) to afford the title compound (220 mg) as a pale yellow foam: $^1$H NMR (400 MHz, CDCl$_3$) δ 1.47 (s, 9H), 1.82–2.12 (m, 2H), 2.55–2.80 (m, 1H), 3.15–3.40 (m, 2H), 3.55–3.87 (m, 3H), 4.02–4.20 (m, 1H), 4.40–4.65 (m, 1H), 5.18 (s, 2H), 5.45–5.94 (m, 2H), 6.82–7.00 (m, 4H), 7.07 (t, J=7.3 Hz, 1H), 7.30 (t, J=7.8 Hz, 2H), 7.37–7.55 (m, 4H), 8.17 (d, J=8.3 Hz, 2H), and 9.44 (br s, 1H); mass spectrum (FAB+) m/e 683 (M+1).

(D) trans-4-(2-Aminoethylsulfonylamino)-L-Proline 4-Phenoxyphenylamide Dihydrochloride A mixture of trans-4-[2-(4-nitrobenzyloxycarbonylamino)ethylsulfonylamino]-N-tert-butoxycarbonyl-L-proline 4-phenoxyphenylamide (C, 210 mg) and 10% palladium on carbon (21 mg) in methanol (10 mL) was stirred at room temperature for 16 hr under a hydrogen atmosphere. The catalyst was removed by filtration and washed with methanol. The combined organic layer was concentrated in vacuo. A solution of di-tert-butyl carbonate (740 mg) in tetrahydrofuran (10 mL) was added to a solution of the above residue in tetrahydrofuran (10 mL) at room temperature. After stirring at room temperature for 16 hr, the solvent was evaporated in vacuo. The residue was diluted with 10% citric acid and washed with ethyl ether. The aqueous layer was basified with 1 N sodium hydroxide solution and extracted with chloroform. The organic layer was washed with brine, dried over anhydrous sodium sulfate, and evaporated in vacuo. Then, 4 N hydrogen chloride in 1,4-dioxane (10 mL) was added to a solution of the residue in methanol (10 mL) at 0° C. After stirring at 0° C. for 5 min and at room temperature for 1 hr, the reaction mixture was concentrated in vacuo. The residue was washed with ethyl ether and freeze-dried from water to afford the title compound (110 mg) as a pale yellow powder: $^1$H NMR (400 MHz, D$_2$O) δ 2.42–2.62 (m, 2H), 3.33–3.82 (m, 6H), 4.23–4.40 (m, 1H), 4.60–4.75 (m, 1H), and 6.90–7.50 (m, 9H); IR (KBr) 3430, 3064, 2917, 1685, 1617, 1589, 1554, 1506, 1488, 1457, and 1415 cm$^{-1}$; mass spectrum (EI+) m/e 404 (M+); (FAB+) m/e 405 (M+1); high-resolution mass (EI) m/e Calcd for C$_{19}$H$_{24}$ $_{N4}$O$_4$S: 404.1518. Found: 404.1523.

Compound D323—trans-4-Glycylamino-L-Proline 4-(2-Pyridylamino-sulfonyl)phenylamide Trihydrochloride (A) N-tert-Butoxycarbonyl-trans-4-(N-tert-Butoxycarbonylglyaclamino)-L-Proline 4-(2-Pyridylaminosulfonyl)phenylamide N,N-Diisopropylethylamine (211 µL) and bis(2-oxo-3-oxazolidinyl)phosphinic chloride (123 mg) were added to a cold (0° C.) stirred solution of trans-4-(N-tert-butoxycarbonylglycylamino)-N-tert-butoxycarbonyl-L-proline (Compound D103 (B), 157 mg) and sulfapyridine (101 mg) in dichloromethane (30 mL)-N,N-dimethylformamide (10 mL). The mixture was stirred at room temperature for 17 hr and concentrated in vacuo. The residue was diluted with ethyl acetate and washed with 0.5 M citric acid, water, saturated sodium hydrogen carbonate, and brine. The organic layer was dried over anhydrous sodium sulfate and concentrated in vacuo. The residue was purified by silica gel column chromatography (chloroform then chloroform:methanol=99:1 to 95:5, v/v) to give the title compound (101 mg) as a colorless foam: $^1$H NMR (400 MHz, CDCl$_3$) δ 1.30–1.56 (m, 18H), 2.06–2.16 (m, 1H), 2.37–2.48 (m, 1H), 3.47–3.56 (m, 1H), 3.59–3.80 (m, 2H), 3.82–3.90 (m, 1H), 4.40 (br s, 1H), 4.54–4.64 (m, 1H), 5.68–5.80 (m, 1H), 7.00–7.10 (m, 1H), 7.24–7.56 (m, 5H), 7.74–7.86 (m, 2H), 8.49 (br s, 1H), 10.00 (br s, 1H), and 12.55 (br s, 1H).

(B) trans-4-Glycylamino-L-Proline 4-(2-Pyridylaminosulfonyl)phenylamide Trihydrochloride The title compound (75 mg) was similarly prepared, as described in Compound D301 (B), except the starting material was N-tert-butoxycarbonyl-trans-4-(tert-butoxycarbonylglycylamino)-L-proline 4-(2-pyridylaminosulfonyl) phenylamide (A, 101 mg): $^1$H NMR (400 MHz, D$_2$O) δ 2.42–2.49 (m, 2H), 3.33 (dd, J=4.9, 12.7 Hz, 1H), 3.47–3.74 (m, 3H), 4.41–4.51 (m, 1H), 4.56–4.70 (m, 1H), 6.84–6.88 (m, 1H), 7.07 (d, J=8.8 Hz, 1H), 7.53–7.55 (m, 2H), and 7.71–7.83 (m, 4H); IR (KBr) 3311, 3064, 2978, 2933, 1672, 1610, 1506, 1485, 1456, 1412, 1394, and 1367 cm$^{-1}$; mass spectrum (FAB+) m/e 419 (M+1); Anal. Calcd for C$_{18}$H$_{22}$N$_6$O$_4$S.3HCl.1.5H$_2$O: C, 38.96; H, 5.09; N, 15.15; S, 5.78; Cl, 19.17. Found: C, 39.00; H, 5.14; N, 14.36; S, 5.46; Cl, 19.27.

Compound D325—trans-4-Glycylamino-L-Proline 5-Chlorobenzoxazol-2-ylamide Dihydrochloride (A) trans-4-N-tert-Butoxycarbonylglycylamino)-tert-Butoxycarbonyl-L-Proline 5-Chlorobenzoxazol-2-ylamide The title compound (86 mg) was similarly prepared, as described in Compound D316 (C), except the starting material was 2-amino-5-chlorobenzoxazole (52 mg): $^1$H NMR (400 MHz, CDCl$_3$) δ 1.45(s, 18H), 3.77–3.80 (m, 3H), 4.53 (m, 1H), 5.44 (m, 1H), 7.20 (d, 1H), 7.34 (d, 1H), 7.57 (s, 1H).

(B) trans-4-Glycylamino-L-Proline 5-Chlorobenzoxazol-2-ylamide Dihydrochloride

The title compound (106 mg) was similarly prepared, as described in Compound D301 (B), except the starting material was trans-4-(N-tert-butoxycarbonylglycylamino)-N-tert-butoxycarbonyl-L-proline 5-chlorobenzoxazol-2-ylamide (A, 86.0 mg): $^1$H NMR (D$_2$O) δ 2.15–2.21 (m, 2H), 3.33–3.70 (m, 4H), 4.65–4.66 (m, 3H), 6.90 (d, 1H), 7.21 (d, 1H), 7.23 (s, 1H); mass spectrum (FAB+) m/e 388 (M+1): Anal. Calcd for C$_{14}$H$_{16}$N$_5$O$_3$.2HCl.2H$_2$O: C, 37.64; H, 4.96; N, 15.68. Found: C, 38.54; H, 4.96; N, 14.91.

Compound D326 trans 4GlycylaminoL-Proline 4-Phenylthiazol-2-ylamide Trihydrochloride (A) trans-4-(N-tert-Butoxycarbonylglycyamino)-N-tert-Butoxycarbonyl-L-Proline 4-Phenylthiazol-2-ylamide The title compound (88 mg) was similarly prepared, as described in Compound D308 (A), except the starting material was 2-amino-4-phenylthiazole: $^1$H NMR (400 MHz, CDCl$_3$) δ 1.43 (m, 18H), 2.09–2.38 (m, 2H), 3.30 (m, 1H), 3.73 (m, 3H), 4.53–4.66 (m, 2H), 5.71 (m, 1H), 6.91 (m, 1H), 7.12 (s, 1H), 7.30–7.41 (m, 3H), 7.80 (d, J=7.3 Hz, 2H), and 10.89 (m, 1H).

(B) trans-4-Glcylamino-L-Proline 4-Phenylthiazol-2-ylamide Trihydrochloride

The title compound (55 mg) was similarly prepared, as described in Compound D308 (B), except the starting material was trans-4-(N-tert-butoxycarbonylglycylamino)-N-tert-butoxycarbonyl-L-proline 4-phenylthiazol-2-ylamide (A, 88 mg): $^1$H NMR (400 MHz, D$_2$O) δ 2.60 (dd, J=7.8, 6.3 Hz, 2H), 3.47 (dd, J=12.2, 4.8 Hz, 1H), 3.82 (s, 2H), 3.85 (m, 1H), 4.60 (m, 1H), 4.86 (m, 1H), 7.41–7.50 (m, 4H), and 7.82 (d, J=7.8 Hz, 1H).

Compound D327—trans-4-Glycylamino-L-Proline 3-(6-Benzyl)quinolyl-amide Trihydrochloride (A) Ethyl 6-Benzyl-1,4-Dihydro-4-Oxoquinoline-3-Carboxylate A mixture of 4-aminodiphenylmethane (20.3 g) and diethyl ethoxymethylenemalonate (24.3 mL) was heated at 110° C. for 3.5 hr under nitrogen. The resulting mixture was diluted with phenyl ether (50 mL) and heated at 220° C. for 7.5 hr. After cooling, ethyl ether was added to the reaction mixture. The precipitate was collected by filtration, and washed with ethyl ether to afford the title compound (12.6 g) as a pale brown powder: mp 265–270° C.; $^1$H NMR (400 MHz, CDCl$_3$—CD$_3$OD (1:1, v/v)) δ 1.39 (t, J=6.8 Hz, 3H), 4.12 (s, 2H), 4.35 (q, J=6.8 Hz, 2H), 7.14–7.33 (m, 4H), 7.47 (d, J=8.3 Hz, 1H), 7.55 (d, J=8.3 Hz, 1H), 7.65–7.75 (m, 2H), 8.23 (s, 1H), and 8.59 (s, 1H).

(B) Ethyl 6-Benzyl-4-Chloroquinoline-3-Carboxylate

A mixture of ethyl 6-benzyl-1,4-dihydro-4-oxoquinoline-3-carboxylate (A, 1.96 g) and phosphorus oxychloride (10 mL) was refluxed for 15 min. The solution was poured into ice water containing concentrated ammonia solution (15 mL), and the resulting mixture was extracted with dichloromethane. The organic layer was washed with brine, dried over anhydrous sodium sulfate, and evaporated in vacuo to afford crude the title compound (2.77 g) as a brown oil: $^1$H NMR (400 MHz, CDCl$_3$) δ 1.48 (t, J=6.8 Hz, 3H), 4.31 (s, 2H), 4.55 (q, J=6.8 Hz, 2H), 7.18–7.41 (m, 5H), 7.99 (d, J=8.8 Hz, 1H), 8.39 (s, 1H), 8.61 (d, J=8.8 Hz, 1H), and 9.38 (s, 1H).

(C) Ethyl 6-Benzylquinoline-3-Carboxylate

A mixture of crude ethyl 6-benzyl-4-chloroquinoline-3-carboxylate (B, 2.77 g), 10% palladium on activated carbon (0.28 g) and triethylamine (2.8 mL) in ethanol (30 mL) was stirred under a hydrogen atmosphere at room temperature for 19 hr. The catalyst was removed by filtration and the filtrate was concentrated in vacuo. The residue was diluted with water and extracted with dichloromethane. The organic layer was washed with 10% citric acid, saturated sodium hydrogen carbonate, and brine, dried over anhydrous sodium sulfate, and evaporated in vacuo. The residue was purified by silica gel column chromatography (dichloromethane then dichloromethane:ethyl acetate=50:1 to 20:1, v/v) to afford overreduced compound. The hydroquinoline was dissolved in dichloromethane (30 mL) and activated manganese oxide (0.9 g) was added to the solution. After stirring at room temperature for 20 hr, the mixture was filtered through celite and concentrated in vacuo to afford the title compound (1.85 g) as a pale yellow oil: $^1$H NMR (400 MHz, CDCl$_3$) δ 1.45 (t, J=6.8 Hz, 3H), 4.19 (s, 2H), 4.47 (q, J=6.8 Hz, 2H), 7.20–7.38 (m, 5H), 7.63–7.72 (m, 2H), 8.97 (d, J=8.8 Hz, 1H), 8.76 (d, J=1.5 Hz, 1H), and 9.39 (d, J=1.5 Hz, 1H); mass spectrum (EI+) m/e 291 (M+); (FAB+) m/e 292 (M+1).

(D) 6-Benzylquinoline-3-Carboxylic Acid

A solution of ethyl 6-benzylquinoline-3-carboxylate (C, 1.85 g) and 1 N sodium hydroxide solution (7 mL) in ethanol (10 mL) was refluxed for 1.5 hr. After the solvents were removed in vacuo, the residue was diluted with water and washed with ethyl ether. The aqueous layer was acidified with 1 N hydrochloric acid, and the precipitate was collected by filtration to afford the title compound (1.10 g) as a pale yellow powder: mp 203–205° C.; $^1$H NMR (400 MHz, CD$_3$OD) δ 4.22 (s, 2H), 7.10–7.38 (m, 5H), 7.62–7.85 (m, 2H), 8.03 (d, J=8.6 Hz, 1H), 8.89 (s, 1H), and 9.33 (d, J=1.9 Hz, 1H).

(E) 3-N-tert-Butoxycarbonylamino-6-Benzylquinoline

A mixture of 6-benzylquinoline-3-carboxylic acid (D, 0.60 g), diphenylphosphoryl azide (490 μl) and triethylamine (350 μl) in tert-butanol (10 mL) was refluxed for 20 hr. After the solvent was removed in vacuo, the residue was diluted with ethyl acetate. The organic layer was washed with 10% citric acid, saturated sodium hydrogen carbonate, and brine, dried over anhydrous sodium sulfate, and evaporated in vacuo. The residue was purified by silica gel column chromatography (chloroform:methanol=10:1, v/v) to afford the title compound (401 mg) as a pale brown solid: mp 134–136° C.;$^1$H NMR (400 MHz, CDCl$_3$) δ 1.52 (s, 9H), 4.09 (s, 2H), 7.12–7.32 (m, 5H), 7.35–7.50 (m, 3H), 7.93 (d, J=8.8 Hz, 1H), 8.42 (br s, 1H), and 8.61 (d, J=2.4 Hz, 1H).

(F) 3-Amino-6-Benzylquinoline

Trifluoroacetic acid (2 mL) was added to a solution of 3-N-tert-butoxycarbonylamino-6-benzylquinoline (E, 219 mg) in dichloromethane (2 mL) at 0° C. After stirring at 0° C. for 5min and at room temperature for 30 min, the reaction mixture was concentrated in vacuo. The residue was diluted with saturated sodium hydrogen carbonate and extracted with chloroform-methanol (10:1, v/v). The organic layer was washed with brine, dried over anhydrous sodium sulfate, and evaporated in vacuo to afford the title compound (169 mg) as a pale yellow oil.

(G) trans-4-(N-tert-Butoxycarbonylglycylamino)-N-tert-Butoxycarbonyl-L-Proline 3-(6-Benzyl)quinolylamide The title compound (333 mg) was similarly prepared, as described in Compound D301 (A), except the starting materials were trans-4-(N-tert-butoxycarbonylglycylamino)-N-tert-butoxycarbonyl-L-proline (Compound D103 (B), 305 mg) and 3-amino-6-benzylquinoline (F, 169 mg).

(H) trans-4-Glycylamino-L-Proline 3-(6-Benzyl)quinolylamide Trihydrochloride

The title compound (253 mg) was similarly prepared, as described in Compound D301 (B), except the starting material was trans-4-(N-tert-butoxycarbonylglycylamino)-N-tert-butoxycarbonyl-L-proline 3-(6-benzyl)quinolylamide (G, 333 mg): $^1$H NMR (400 MHz, D$_2$O) δ 2.60–2.72 (m, 2H), 3.51 (dd, J=12.2, 4.9 Hz, 1H), 3.77–3.90 (m, 3H), 4.24 (s, 2H), 4.60–4.70 (m, 1H), 4.82–4.92 (m, 1H), 7.22–7.44 (m, 5H), 7.82–7.98 (m, 2H), 8.03 (d, J=8.8 Hz, 1H), 8.82 (d, J=2.0 Hz, 1H), and 9.25 (d, J=1.9 Hz, 1H); IR (KBr) 3380, 3212, 3058, 2952, 2881, 2593, 1689, 1560, 1556, 1490, 1452 and 1442 cm$^{-1}$; mass spectrum (EI+) m/e 403 (M+); (FAB+) m/e 404 (M+1); Anal. Calcd for C$_{23}$H$_{25}$N$_5$O$_2$.3HCl.2H$_2$O: C, 50.33; H, 5.88; N, 12.76. Found: C, 50.61; H, 5.84; N, 12.74.

Compound D328—trans-4-Glycylamino-L-Proline 3-Quinolylamide Trihydrochloride (A) trans-4-(N-tert-Butoxycarbonylglycylamino)-N-tert-Butoxycarbonyl-L-Proline 3-Quinolylamide The title compound (299 mg) was similarly prepared, as described in Compound D301 (A), except the starting materials were trans-4-(N-tert-butoxycarbonylglycylamino)-N-tert-butoxycarbonyl-L-proline (Compound D103 (B), 254 mg) and 3-aminoquinoline (78 mg).

(B) trans-4-Glycylamino-L-Proline 3-Quinolylamide Trihdrochloride

The title compound (215 mg) was similarly prepared, as described in Compound D301 (B), except the starting material was trans-4-(N-tert-butoxycarbonylglycylamino)-N-tert-butoxycarbonyl-L-proline 3-quinolylamide (A, 299 mg): $^1$H NMR (400 MHz, D$_2$O) δ 2.60–2.73 (m, 2H), 3.51 (dd, J=12.7,4.9 Hz, 1H), 3.77–3.92 (m, 3H), 4.60–4.70 (m, 1H), 4.85–4.95 (m, 1H), 7.86–7.98 (m, 1H), 8.02–8.12 (m, 1H), 8.12–8.27 (m, 2H), 9.06 (s, 1H), and 9.42 (d, J=2.0 Hz, 1H); IR (KBr) 3380, 3199, 2944, 1685, 1610, 1571, 1560, 1554, 1484 and 1459 cm$^{-1}$; mass spectrumn (EI+) m/e 313 (M+); (FAB+) m/e 314 (M+1); Anal. Calcd for $C_{16}H_{19}N_5O_2 \cdot 3HCl \cdot 5/4H_2O$: C, 43.16; H, 5.55; N, 15.73. Found C, 43.27; H, 5.71; N, 15.38.

Compound D329-trans-4-Amino-L-Pipecolinoyl-(4-Phenoxyphenyl)-amide Dihydrochloride (A) N-tert-Butoxycarbonyl-trans-4-(N-tert-Butoxcarbonylamino)-L-Pipecolinoyl 4-Phenoxyphenylamide The title compound (208 mg) was similarly prepared, as described in Compound D316 (C), except the starting materials were Ntert-butoxycarbonyl-trans-4-(N-tert-butoxycarbonylamino)-L-pipecolinic acid (Compound 112 (G), 102 mg) and 4-phenoxyaniline (55 mg): $^1$H NMR (400 MHz, $CDCl_3$) δ 1.22–1.61 (m, 18H), 1.64–1.74 (m, 2H), 2.02 (br s, 1H), 2.57 (br s, 1H), 2.95 (br s, 1H), 3.95 (br s, 1H), 4.07 (br s, 1H), 4.40 (br s, 1H), 4.99 (br s, 1H), 6.98 (d, J=8.3 Hz, 4H), 7.08 (t, J=7.3 Hz, 1H), 7.32 (t, J=7.8 Hz, 2H), 7.47 (d, J=8.8 Hz, 2H), and 8.23 (br s, 1H).

(B) trans-4-Amino-L-Pipecolinoyl 4-Phenoxyphenylamide Dihydrochloride

The title compound (73 mg) was similarly prepared, as described in Compound D316 (D), except the starting material was N-tert-butoxycarbonyl-trans-4-(N-tert-butoxycarbonyl)amino-L-pipecolinoyl 4-phenoxyphenylamide (A, 128 mg): $^1$H NMR (400 MHz, $D_2O$) δ 1.91–2.04 (m, 1H), 2.21–2.40 (m, 2H), 2.51–2.62 (m, 1H), 3.39–3.50 (m, 1H), 3.58–3.79 (m, 2H), 4.47–4.58 (m, 1H), 6.98–7.08 (m, 4H), 7.12–7.19 (m, 1H), and 7.34–7.43 (m, 4H); IR (KBr) 3367, 3194, 2924, 2474, 1685, 1610, 1589, 1556, 1506, 1489, 1456, 1442, and 1408 cm$^{-1}$; mass spectrum (EI+) m/e 311 (M); high-resolution mass (EI+) m/e Calcd for $C_{18}H_{21}$ $_{N3}O_2$:311.1634. Found 311.1621.

Compound D330—trans-4-Glycylamino-L-Pipecolinoyl 4-Phenoxy-phenylamide Dihydrochloride (A) N-tert-Butoxycarbonyl-trans-4-N-tert-Butoxycarbonylglycylamino)-L-Pipecolinoyl-4-Phenoxyphenylamide The title compound (208 mg) was similarly prepared, as described in Compound D316 (C), except the starting materials were N-tert-butoxycarbonyl-trans-4-(N-tert-butoxycarbonylglycylamino)-L-pipecolinic acid (Compound D114 (B), 183 mg) and 4-phenoxyaniline (84 mg): $^1$H NMR (400 MHz, $CDCl_3$) δ 1.38–1.62 (m, 18H), 1.66–1.76 (m, 2H), 1.98–2.08 (m, 1H), 2.53 (br s, 1H), 2.98 (br s, 1H), 3.65–3.82 (m, 2H), 4.08 (br s, 1H), 4.23 (br s, 1H), 5.01 (br s, 1H), 5.20 (br s, 1H), 6.08 (br s, 1H), 6.97 (d, J=8.8 Hz, 4H), 7.08 (t, J=7.3 Hz, 1H), 7.32 (t,J=8.1 Hz, 2H), 7.47 (d, J=9.3 Hz, 2H), and 8.24 (br s, 1H).

(B) trans-4-Glycylamino-L-Pipecolinoyl-4-Phenoxphenylamide Dihydrochloride

The title compound (140 mg) was similarly prepared, as described in Compound D316 (D), except the starting material was N-tert-butoxycarbonyl-trans-4-(N-tert-butoxycarbonylglycylamino)-L-pipecolinoyl-(4-phenoxyphenyl)amide (A, 208 mg): $^1$H NMR (400 MHz, $D_2O$) δ 1.88–1.98 (m, 1H), 2.01–2.13 (m, 1H), 2.15–2.24 (m, 1H), 2.34–2.42 (m, 1H), 3.24–3.34 (m, 1H), 3.46–3.54 (m, 1H), 3.82 (s, 2H), 4.24 (d, J=3.4 Hz, 2H), 7.01–7.04 (m, 4H), 7.13–7.17 (m, 1H), and 7.35–7.39 (m, 4H); IR (KBr) 3396, 3199, 3059, 2931, 2467, 1689, 1612, 1589, 1556, 1506, 1489, and 1408 cm$^{-1}$; mass spectum (FAB+) m/e 369 (M+1); Anal. Calcd for $C_{20}H_{24}N_4O_3 \cdot 2HCl \cdot 1.5H_2O$: C, 51.29; H, 6.24; N, 11.96. Found: C, 51.03; H, 6.18; N, 11.40.

Compound D331—trans-4-Aminomethyl-L-Proline 4-Phenoxyphenyl-amide Dihydrochloride (A) trans-4-(N-tert-Butoxycarbonylaminomethyl)-N-tert-Butoxycarbonyl-L-Proline 4-Phenoxyphenylamide N-Methylmorpholine (60 mL) and 1-(3-dimethylaminopropyl)-3-ethylcarbodiimide hydrochloride (94 mg) were added to a solution of trans-4-(N-tert-butoxycarbonylaminomethyl)-N-tert-butoxycarbonyl-L-proline (Compound D109 (D), 206 mg), 4-aminodiphenylether (104 mg), and 1-hydroxybenzotriazole (70 mg) in tetrahydrofuran (6 mL) and N,N-dimethylformamide (2 mL) at room temperature. After stirring at room temperature for 13 hr, the reaction mixture was partitioned between ethyl acetate and 1 N hydrochloric acid. The organic layer was washed with saturated sodium carbonate and then brine. After drying over anhydrous sodium sulfate, the organic layer was concentrated in vacuo. The residue was washed with hexane to give the title compound (182 mg) as colorless plates: $^1$H NMR (400 MHz, $CDCl_3$) δ 1.44–1.49 (18 H), 1.70 (br s, 1H), 2.54 (br s, 2 H), 3.08 (br s, 1H), 3.20 (br s, 2 H), 3.52 (br s, 1 H), 4.52 (br s, 1 H), 4.64 (br s, 1 H), 6.96 (d, J=7.8 Hz, 4 H), 7.07 (t, J=7.3 Hz, 1H), 7.31 (t, J=7.8 Hz, 2 H), 7.47 (d, J=9.3 Hz, 2 H), and 9.49 (br s, 1 H); mass spectrum (EI+) m/e 511 (M+).

(B) trans-4-Aminomethyl-L-Proline 4-Phenoxyphenylamide Dihydrochloride

A solution of 4 N hydrochloric acid in 1,4-dioxane (6 mL) was added to a solution of trans-4-(N-tert-butoxycarbonylaminomethyl)-N-tert-butoxycarbonyl-L-proline 4-phenoxyphenylamide (A, 182 mg) in 1,4-dioxane (6 mL) at room temperature. After stirring at room temperature for 20 min, the reaction mixture was concentrated in vacuo. The residue was washed with ether to give the title compound (95 mg) as a colorless solid: $^1$H NMR (400 MHz, $D_2O$) δ 2.36 (m, 1 H), 2.60 (m, 1H), 2.82 (m, 1 H), 3.23 (m, 3 H), 3.85 (dd, J=7.5, 11.5 Hz, 1 H), 4.73 (dd, J=3.9, 9.3 Hz, 1 H), 7.08 (d, J=6.84 Hz, 2 H), 7.10 (d, J=6.84 Hz, 2 H), 7.22 (t, J=7.0 Hz, 1H), and 7.45 (m, 4 H).

TYPE IV

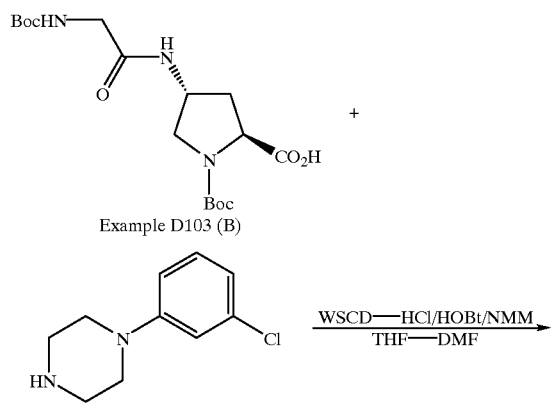

Compound D401 (A)–(B)

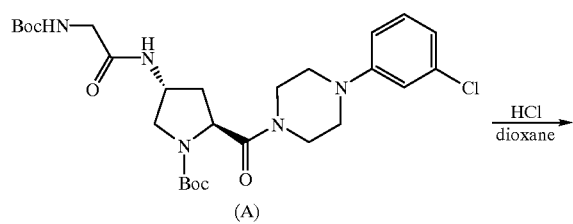
(A)
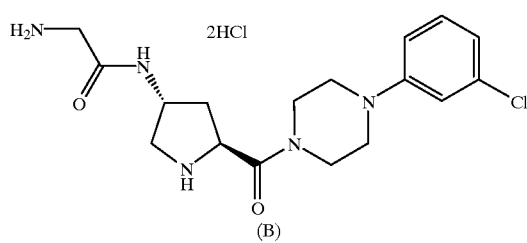
(B)
Compound D402 (A)–(B)
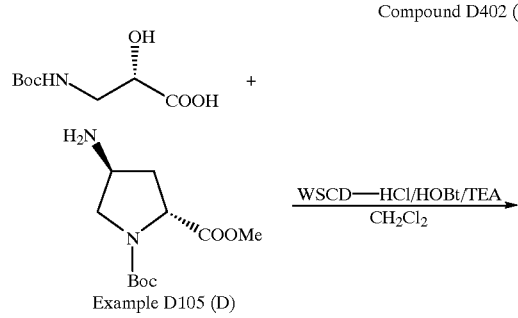
Example D105 (D)
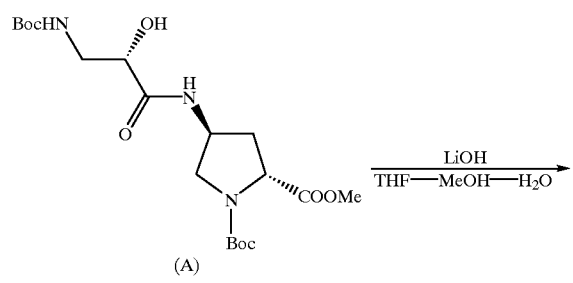
(A)
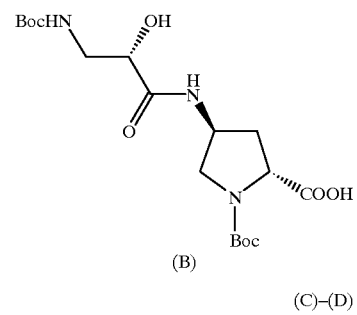
(B)
(C)–(D)
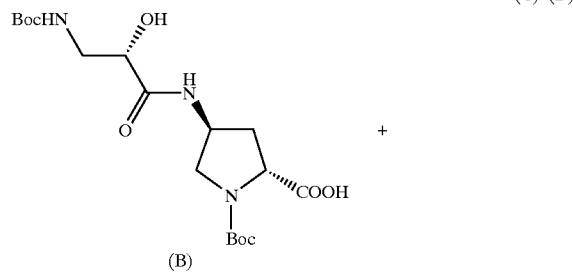
(B)
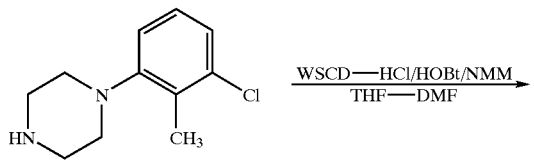
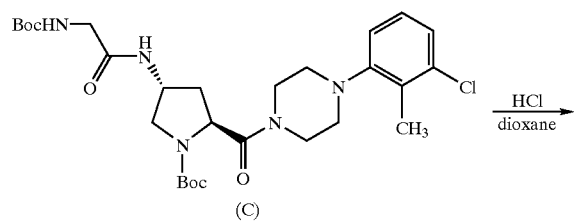
(C)
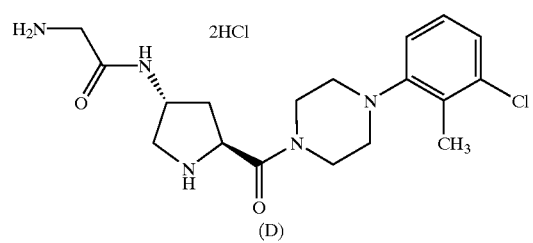
(D)
Compound D403 (A)–(B)
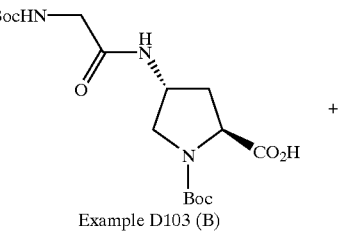
Example D103 (B)
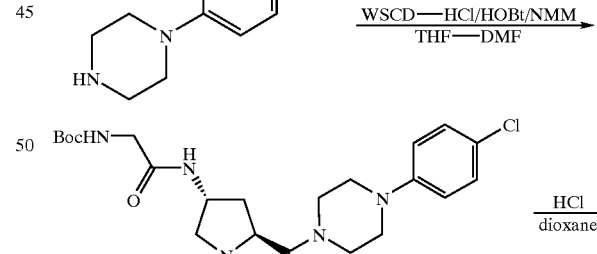
(A)
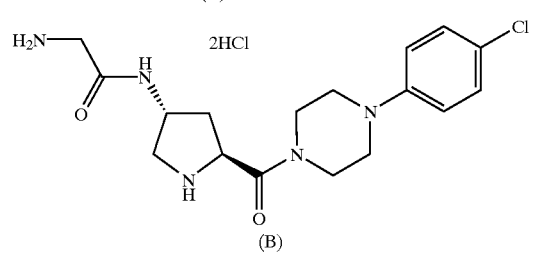
(B)

Compound D404 (A)-(B)
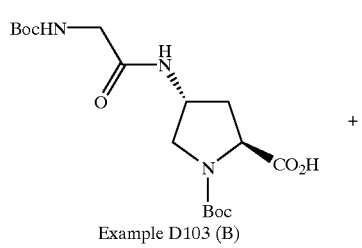
Example D103 (B)
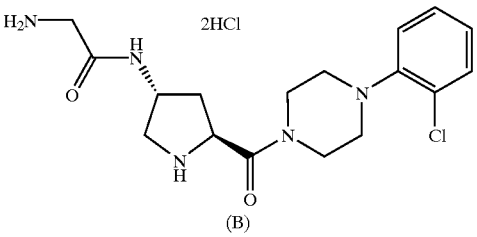
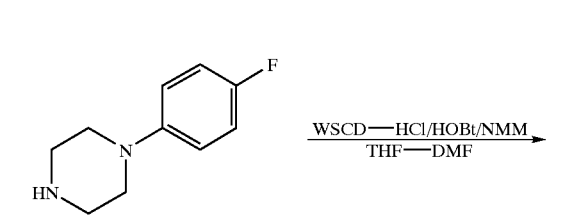
Compound D407 (A)-(B)
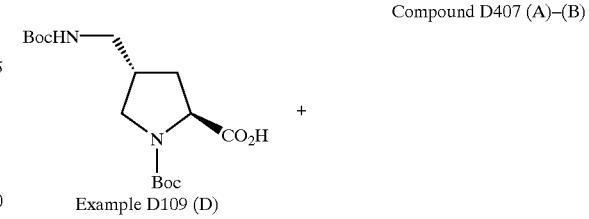
Example D109 (D)
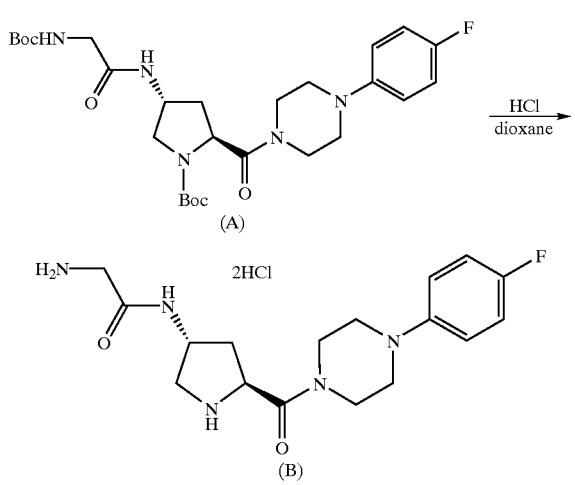
Compound D405 (A)-(B)
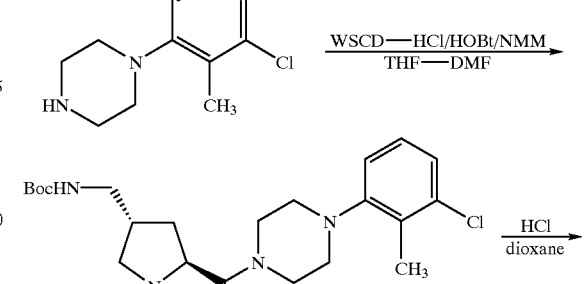
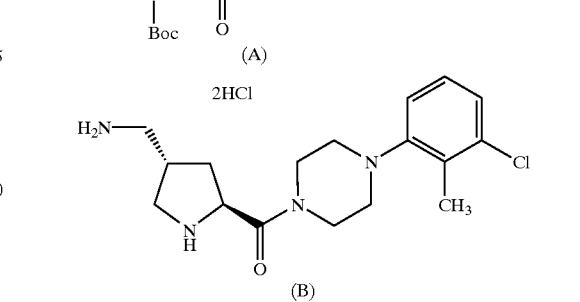
Compound D408 (A)-(B)
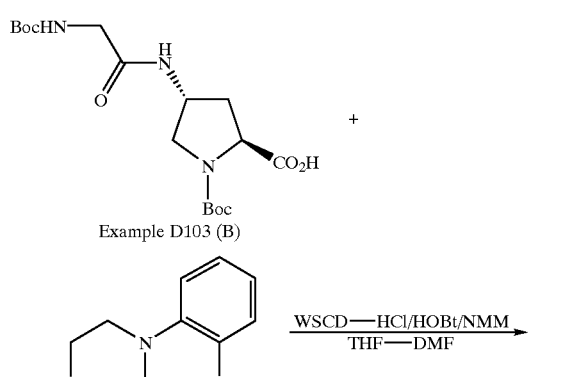
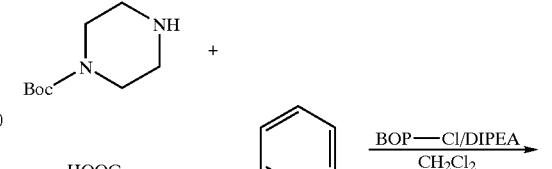
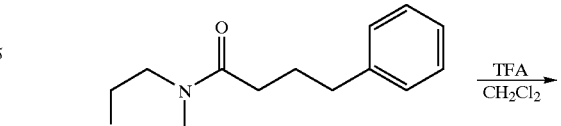
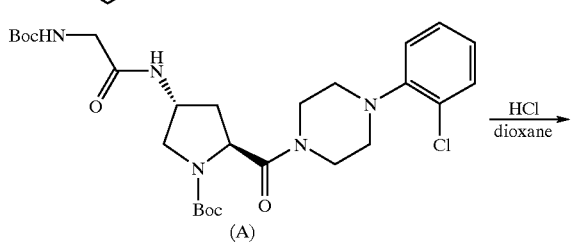
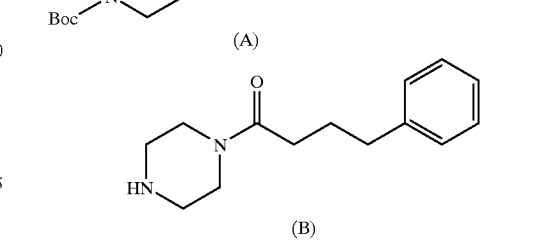

-continued
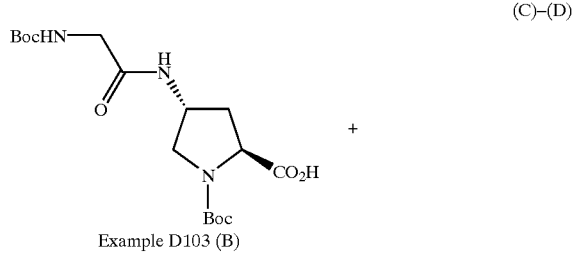
Example D103 (B)
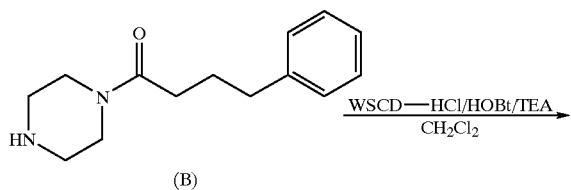
(B)
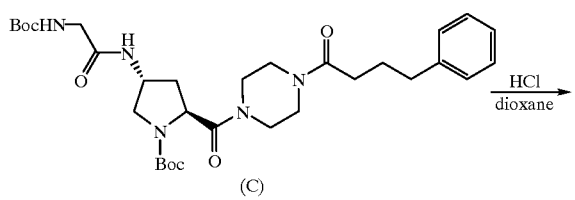
(C)
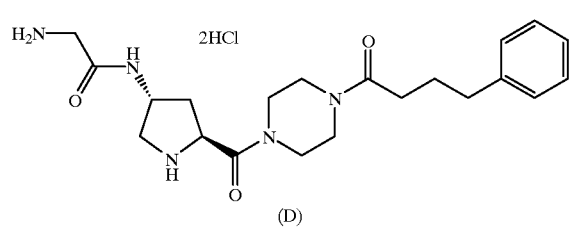
(D)
Compound D409 (A)–(C)
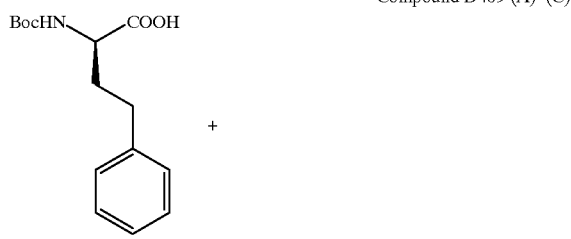
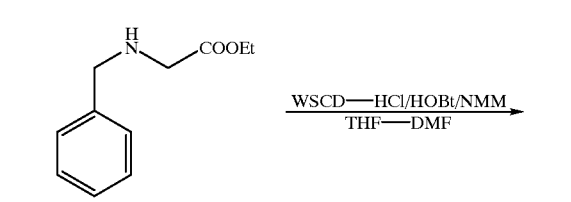
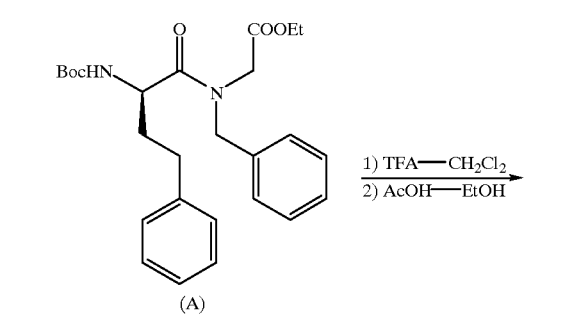
(A)
-continued
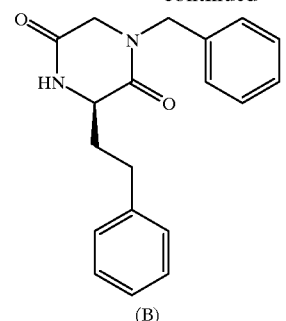
(B)
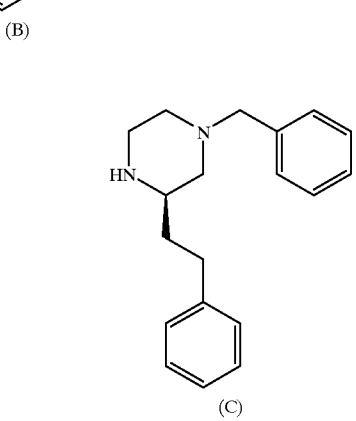
(C)
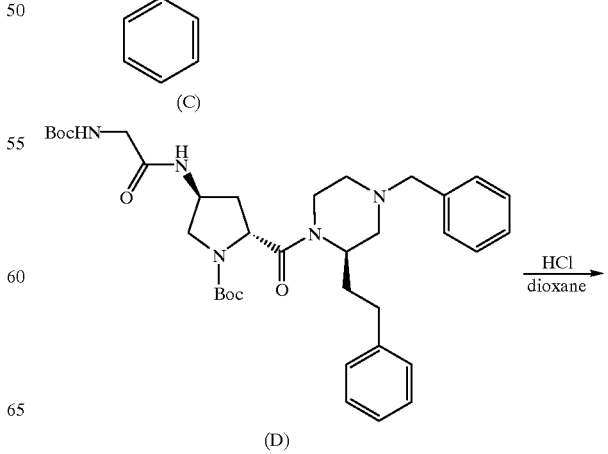
Example D105 (F)

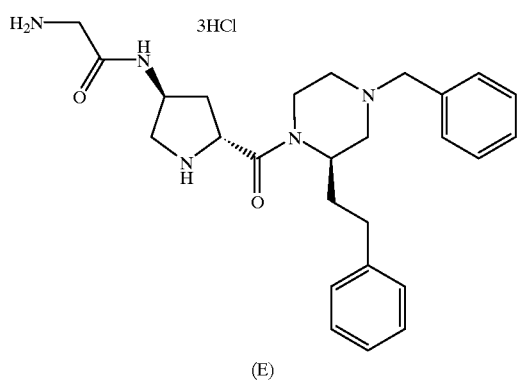
(E)
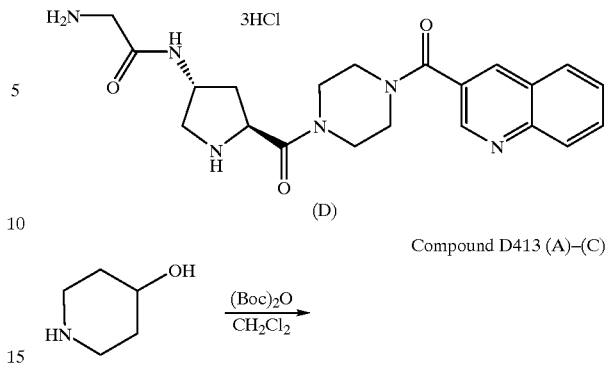
Compound D413 (A)–(C)
Compound D410 (A)–(B)
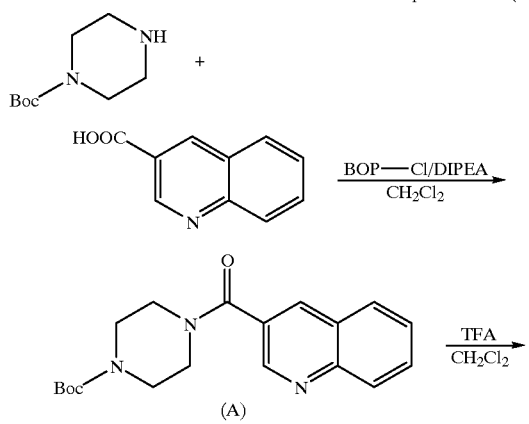
(C)–(D)
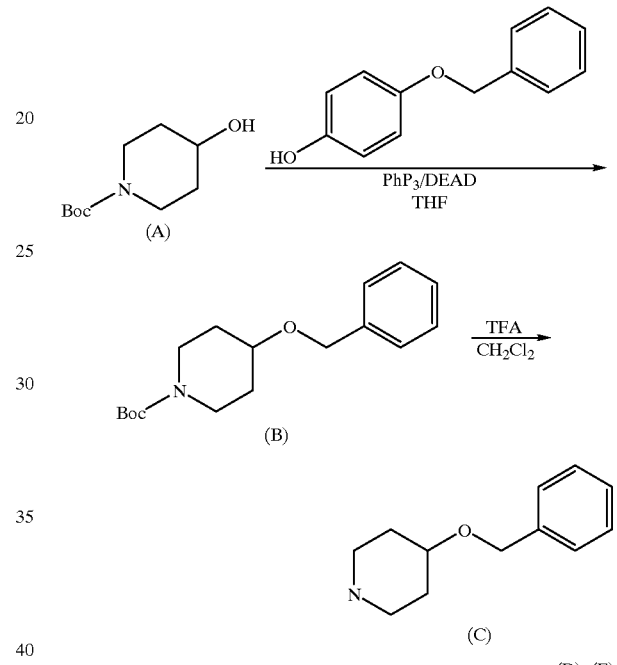
(D)–(E)
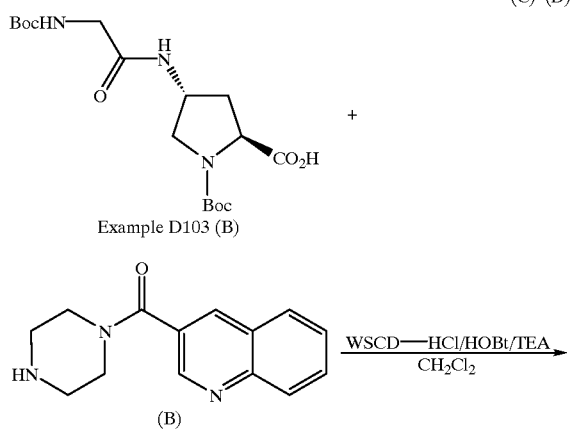
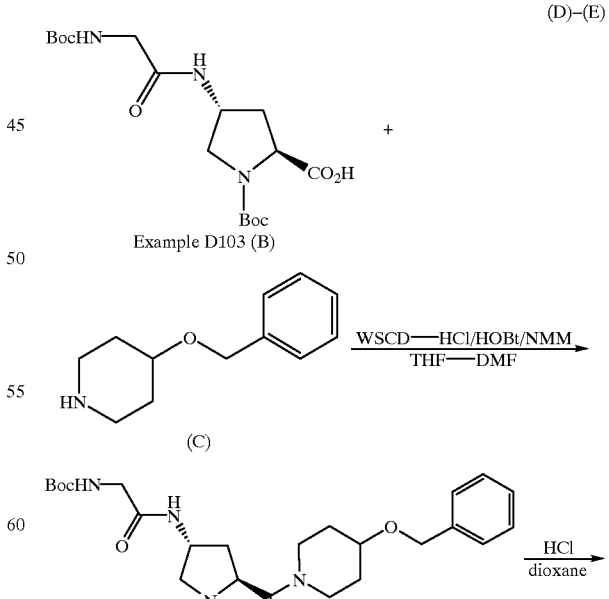

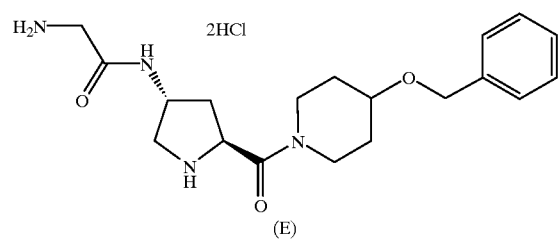
Compound D414 (A)–(B)
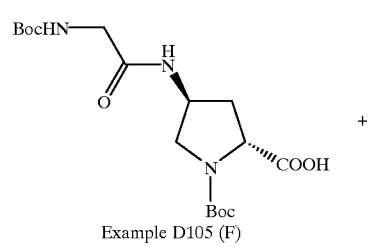
Compound D415 (C)–(D)
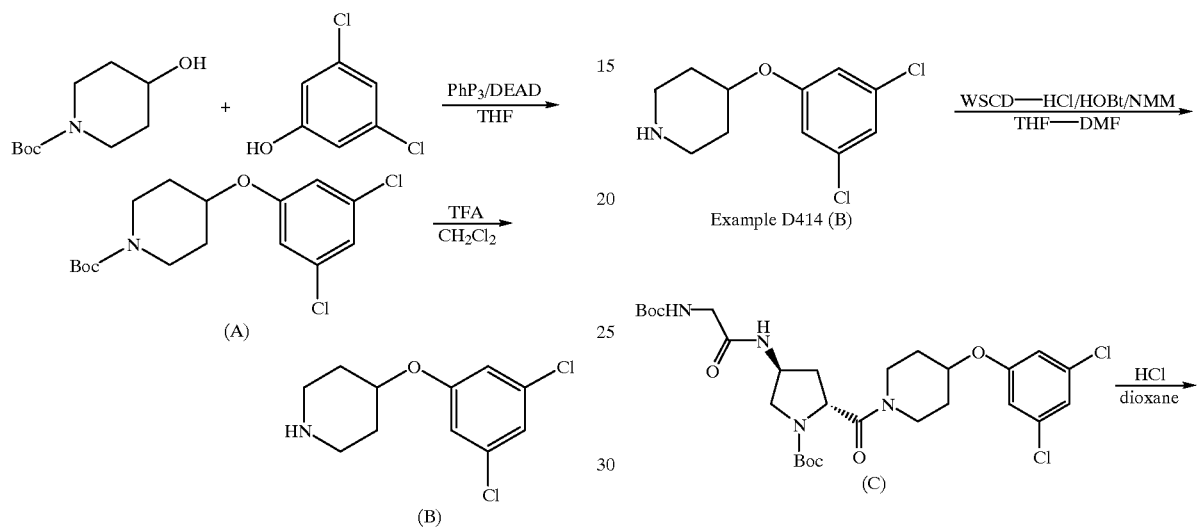
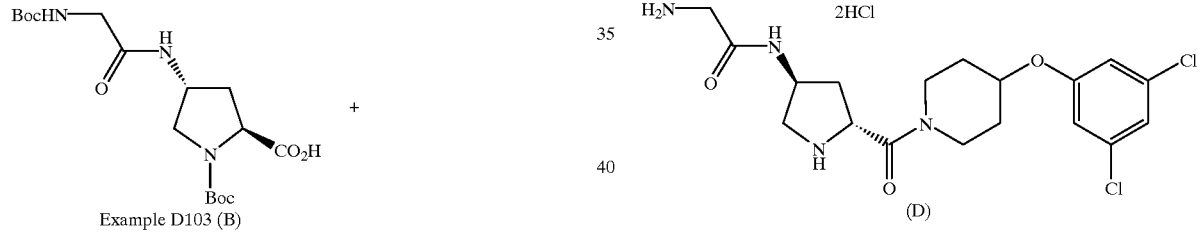
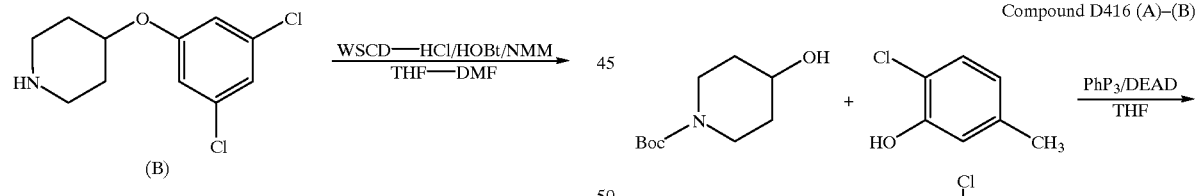
Compound D416 (A)–(B)
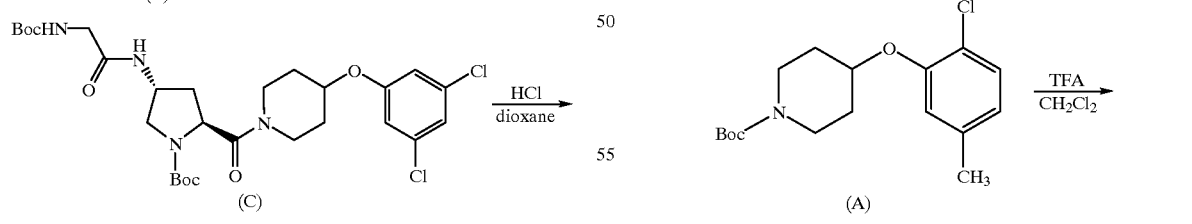
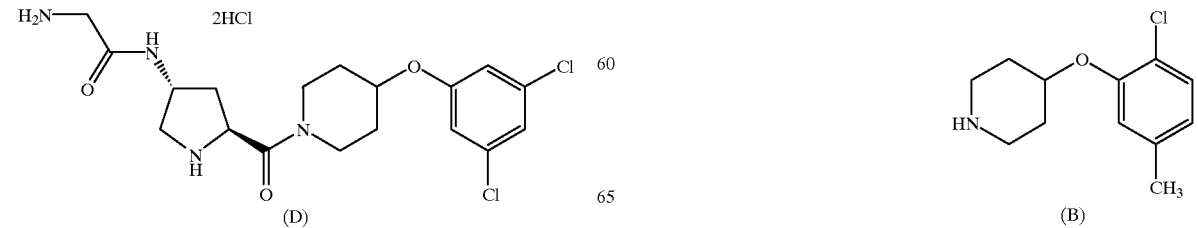

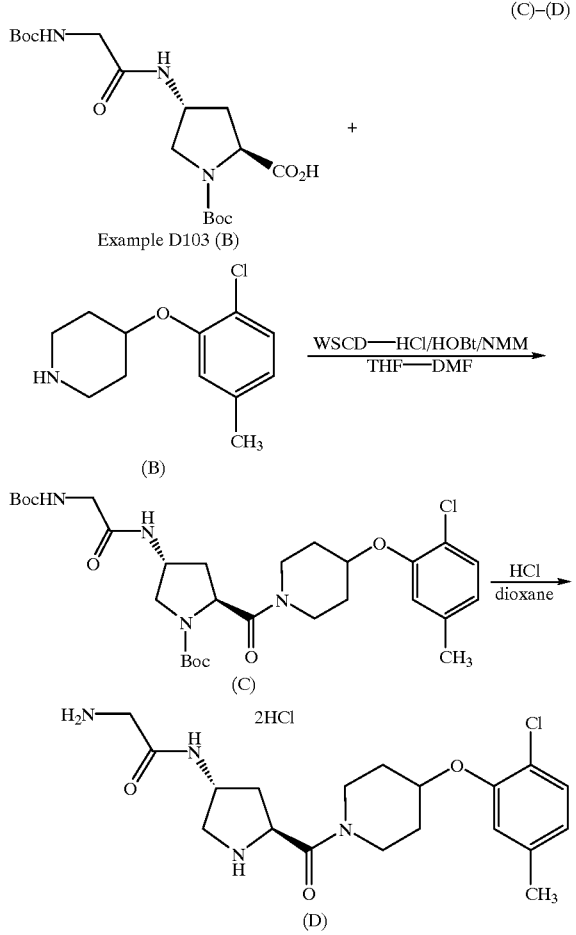

Example D103 (B)

(B)

(C)

(D)

Compound D401—1-(trans-4-Glycylamino-L-Prolyl)-4-(3-Chlorophenyl)-piperazine Dihydrochloride (A) 1-[trans-4-(N-tert-Butoxycarbonylglycylamino)-N-tert-butoxycarbonyl-L-Prolyl]-4-(3-Chlorophenylpiperazine N-Methylmorpholine (60 µL) and 1-(3-dimethylaminopropyl)-3-ethylcarbodiimide hydrochloride (94 mg) were added to a solution of trans-4-(N-tert-butoxycarbonyl-glycylamino)-N-tert-butoxycarbonyl-L-proline (Compound D103 (B), 200 mg), 1-(3-chlorophenyl) piperazine hydrochloride (120 mg) and 1-hydroxybenzotriazole (70 mg) in tetrahydrofuran (6 mL) and N,N-dimethylformamide (2 mL) at room temperature. After stirring at room temperature for 36 hr, the reaction mixture was partitioned between ethyl acetate and 1 N hydrochloric acid. The organic layer was washed with saturated sodium hydrogen carbonate and brine. After drying over anhydrous sodimn sulfate, the organic layer was evaporated in vacuo. The residue was washed with hexane to give the titled compound (297 mg) as a white powder: $^1$H NMR (400 MHz, CDCl$_3$) δ 1.40–1.46 (m, 18H), 2.17 (m, 1.5H), 2.32 (m, 0.5H), 3.18 (br s, 3H), 3.30 (br s, 1H), 3.35 (dd, J=4.5, 11.0 Hz, 0.5H), 3.49 (d, J=11 Hz, 0.5H), 3.63 (br s, 2H), 3.76 (m, 5H), 4.49 (br s, 0.5H), 4.65 (m, 1H), 4.78 (m, 0.5H), 5.20 (br s, 1H), 6.43 (br s, 0.5H), 6.53 (m, 0.5H), 6.78 (m, 1H), 6.84–6.87 (2H), and 7.19 (dd, J=7.5, 15 Hz, 1H); mass spectrum (FAB+) m/e 565 (M); IR (KBr) 3319, 2978, 2931, 1701, 1664, 1595, 1392, 1230, 1161, 1032, 949, and 780 cm$^{-1}$; Anal. Calcd for C$_{27}$H$_{40}$ClN$_5$O$_6$: C, 57.29; H, 7.12; N, 12.37; Cl, 6.26. Found: C, 57.22; H, 7.29; N, 12.22; Cl, 6.17.

(B) 1-(trans-4-Glycylamino-L-Prolyl)-4-(3-Chlorophenyl)piperazine Dihydrochloride A solution of 4 N hydrochloric acid in 1,4-dioxane (8 mL) was added to a solution of 1-[trans-4-(N-tert-butoxycarbonylglycylamino)-N-tert-butoxycarbonyl-L-prolyl]-4-(3-chlorophenyl)piperazine (A, 260 mg) in 1,4-dioxane (8 mL) at room temperature. After stirring at room temperature for 20 min, the reaction mixture was evaporated in vacuo. The residue was washed with ether to give the titled compound (130 mg) as a white powder: $^1$H NMR (400 MHz, D$_2$O) δ 2.32 (m, 1H), 2.49 (m, 1H), 3.24–3.36 (m, 5H), 3.62–3.74 (m, 5H), 3.71 (s, 2H), 4.45 (t, J=5.86 Hz, 1H), 4.92 (t, J=8.0 Hz, 1H), 7.03 (dd, J=2.0, 8.0 Hz, 1H), 7.05 (dd, J=2.0, 8.0 Hz, 7.15 (t, J=2.0 Hz, 1H), and 7.27 (t, J=8.0 Hz, 1H); mass spectrum (EI+) m/e 365 (M); IR (KBr) 3381, 3184, 3059, 2952, 1685, 1655, 1593, 1564, 1485, 1452, 1387, 1234, 935, 777, and 685 cm$^{-1}$; Anal. Calcd for C$_{17}$H$_{24}$ClN$_5$O$_2$.2 HCl.1.5 H$_2$O: C, 43.84; H, 6.28; N, 15.03; Cl, 22.83. Found: C, 43.65; H, 6.25; N, 14.59; Cl, 22.86.

Compound D402—1-[trans-4-((2S)-3-Amino-2-Hydroxypropionylamino)-D-Prolyl]-4-(3-Chloro-2-Methylphenyl)piperazine Dihydrochloride (A) N-tert-Butoxycarbonyl-trans-4-((2S)-N-tert-Butoxncarbonyl-3-Amino-2-Hydroxypropionylamino D-Proline Methyl Ester The title compound (0.82 g) was similarly prepared, as described in Compound101 (E), except the starting materials were trans-4-amino-N-tert-butoxycarbonyl-D-proline methyl ester (Compound D105 (D), 0.65 g) and (2S)-N-tert-butoxycarbonyl-3-amino-2-hydroxypropionic acid (0.60 g). The compound appears as a mixture of rotamers: $^1$H NMR (400 MHz, CDCl$_3$) δ 1.41, 1.44, and 1.45 (each s, total 18H), 2.05–2.35 (m, 3H), 3.20–3.31 (m, 0.5H), 3.34–3.64 (m, 2.5H), 3.74 (s, 3H), 3.70–3.88 (m, 1H), 4.10–4.18 (m, 1H), 4.22–4.31 (m, 0.5H), 4.31–4.43 (m, 0.5H), 4.46–4.73 (m, 1H), 5.03–5.13 (m, 1H), and 7.06–7.20 (m, 1H).

(B) N-tert-Butoxycarbonyl-trans-4-((2S)-N-tert-Butoxycarbonyl-3-Amino-2-Hydroxypropionylamino)-D-Proline The title compound (0.71 g) was similarly prepared, as described in Compound101 (O), except the starting material was N-tert-butoxycarbonyl-trans-4-((2S)-N-tert-butoxycarbonyl-3-amino-2-hydroxypropionylamino)-D-proline methyl ester (A, 0.82 g). The compound appears a mixture of rotamers: $^1$H NMR (400 MHz, CD$_3$OD) δ 1.42, 1.43 and 1.46 (each s, total 18H), 2.18–2.39 (m, 21, 3.25–3.40 (m, 2H), 3.70–3.80 (m, 1H), 4.01–4.09 (m, 1H), 4.27–4.38 (m, 1H), 4.40–4.51 (m, 1H), and 4.89–4.94 (m, 1H).

(C) 1-[N-tert-Butoxycarbonyl-trans-4-((2S)-N-tert-Butoxycarbonyl-3-Amino-2-Hydroxypropionylamino)-D-Prolyl]-4-(3-Chloro-2-Methylphenyl)piperazine The title compound (285 mg) was similarly prepared, as described in Compound D401 (A), except the starting materials were N-tert-butoxycarbonyl-trans-4-((2S)-N-tert-butoxycarbonyl-3-amino-2-hydroxypropionylamino)-D-proline (B, 0.20 g) and 1-(3-chloro-2-methylphenyl) piperazine hydrochloride (130 mg). The compound appears as a mixture of rotamers: $^1$H NMR (400 MHz, CD$_3$OD) δ 1.44 and 1.47 (each s, total 18H), 2.10–2.20 (m, 1H), 2.25–2.42 (m, 1H), 2.38 (s, 3H), 2.82–2.97 (m, 4H), 3.25–3.45 (m, 3H), 3.67–3.83 (m, 5H), 4.02–4.08 (m, 1H), 4.42–4.53 (m, 1H), 4.82–4.97 (m, 1H), 6.95–7.07 (m, 1H), and 7.09–7.17 (m, 2H).

(D) 1-[trans-4-((2S)-3-Amino-2-Hydroxypropionylamino)-D-Prolyl]-4-(3-Chloro-2-Methylphenyl)piperazine Dihydrochloride The title compound (226 mg) was similarly prepared, as described in Compound401 (B), except the starting material was 1-[N-tert-butoxycarbonyl-trans-4-((2S)-N-tert-butoxycarbonyl-3-amino-2-hydroxypropionylamino)D-prolyl]-4-(3-chloro-2-methylphenyl)piperazine (285 mg): $^1$H NMR (400 MHz, $D_2O$) δ 2.20–2.39 (m, 1H), 2.29 (s, 3H), 2.48–2.60 (m, 1H), 2.98–3.18 (m, 414), 3.28 (dd, J=12.7, 3.9 Hz, 1H), 3.38 (dd, J=12.7, 5.4 Hz, 1H), 3.47–3.97 (m, 6H), 4.36 (dd, J=7.8, 3.9 Hz, 1H), 4.44–4.57 (m, 1H), 4.97 (t, J=8.3 Hz, 1H), 7.08 (d, J=8.3 Hz, 1H), 7.16 (dd, J=8.3, 7.8 Hz, 1H), and 7.23 (d, J=7.8 Hz, 1H); IR (KBr) 3299, 2960, 1658, 1604, 1573, 1482, and 1454 cm$^{-1}$; mass spectrum (EI+) nme 409 (M); (FAB+) m/e 410 (M+1); high-resolution mass (EI) m/e Calcd for $C_{19}H_{28}ClN_5O_3$: 409.1881. Found: 409.1882.

Compound D403—1-(N-trans-4-Glycylamino-L-Prolyl)-4-(4-Chlorophenyl)piperazine Dihydrochloride (A) 1-[trans-4-4-(N-tert-Butoxycarbonylglycylamino)-N-tert-Butoxycarbonyl-L-Prolyl]-4-(4-Chlorophenyl)piperazine N-Methylmorpholine (60 µL) and 1-(3-dimethylaminopropyl)-3-ethylcarbodiimide hydrochloride (94 mg) were added to a solution of trans-4-(N-tert-butoxycarbonylglycylamino)-N-tert-butoxycarbonyl-L-proline (Compound D103 (B), 200 mg), 1-(4-chlorophenyl)piperazine (102 mg) and 1-hydroxybenzotriazole (70 mg) in tetrahydrofuran (6 mL) and N,N-dimethylformamide (2 mL) at room temperature. After stirring at room temperature for 14 hr, the reaction mixture was partitioned between ethyl acetate and 1 N hydrochloric acid. The organic layer was washed with saturated sodium hydrogen carbonate and brine. After drying over anhydrous sodium sulfate, the organic layer was evaporated in vacuo. The residue was washed with hexane to give the titled compound (236 mg) as a white foam: $^1$H NMR (400 MHz, $CDCl_3$) δ 1.40–1.46 (18H), 2.18 (br m, 1.51), 2.31 (br m, 0.511), 3.13 (br m, 3.5H), 3.25 (br s, 0.5H), 3.35 (m, 0.5H), 3.49 (br d, J=11 Hz, 0.5H), 3.63 (br s, 2H), 3.78 (br m, 5H), 4.48 (br s, 0.5H), 4.63 (m, 1H), 4.78 (m, 0.5H), 5.13 (br s, 1H), 6.35 (br s, 0.5H), 6.42 (m, 0.5H), 6.78 (m, 1H), 6.84 (m, 2H), and 7.23 (m, 2H); IR (KBr) 3319, 2978, 1701, 1664, 1496, 1392, 1230, 1161, 1032 cm$^{-1}$; Anal. Calcd for $C_{27}H_{40}ClN_5O_6$: C, 57.29; H, 7.12; N, 12.37; Cl, 6.26. Found: C, 57.512; H, 7.28; N, 11.92; Cl, 6.33.

(B) 1-(trans-4-Glycylamino-L-Prolyl)-4-(4-Chlorophenyl)piperazine Dihydrochloride A solution of 4 N hydrochloric acid in 1,4-dioxane (6 mL) was added to a solution of 1-[trans-4-(N-tert-butoxycarbonylglycylamino)-N-tert-butoxycarbonyl-L-prolyl]-4-(4-chlorophenyl)piperazine (A, 210 mg) in 1,4-dioxane (6 mL) at room temperature. After stirring at room temperature for 50 min, the reaction mixture was evaporated in vacuo. The residue was washed with ether to give the titled compound (106 mg) as a white powder: $^1$H NMR (400 MHz, $D_2O$) δ 2.48 (quintet, J=7.3 Hz, 1H), 2.64 (m, 1H), 3.48 (m, 5H), 3.81–3.98 (m, 5H), 3.87 (s, 2H), 4.61 (m, 1H), 5.08 (t, J=8.3 Hz, 1H), 7.32 (d, J=9.0 Hz, 2H), and 7.50 (d, J=9.0 Hz, 2H); mass spectrum (El+) m/e 365 (M).

Compound D404—1-(trans-4-Glycylamino-L-Prolyl)-4-(4-Fluorophenyl)-piperazine Dihydrochloride (A) 1-[trans-4-(N-tert-Butoxycarbonylglcylamino)-N-tert-Butoxycarbonyl-L-Prolyl]-4-[4-Fluophenyl)piperazine N-Methylmorpholine (60 µL) and 1-(3-dimethylaminopropyl)-3-ethylcarbodiimide hydrochloride (94 mg) were added to a solution of trans-4-(N-tert-butoxycarbonyl-glycylamino)-N-tert-butoxycarbonyl-L-proline (Compound D103 (B), 200 mg), 1-(4-fluorophenyl)piperazine (93 mg), and 1-hydroxybenzotriazole (70 mg) in tetrahydrofuran (6 mL) and N,N-dimethylformamide (2 mL) at room temperature. After stirring at room temperature for 13 hr, the reaction mixture was partitioned between ethyl acetate and 1 N hydrochloric acid. The organic layer was washed with saturated sodium hydrogen carbonate and brine. After drying over anhydrous sodium sulfate, the organic layer was evaporated in vacuo. The residue was washed with hexane to give the titled compound (83 mg) as a white powder: $^1$H NMR (400 MHz, $CDCl_3$) δ 1.41–1.46 (18H), 2.17 (m, 1.5H), 2.31 (m, 0.5H), 3.07 (br s, 4H), 3.35 (dd, J=4.39, 11.23 Hz, 0.5H), 3.49 (br d, J=11.23 Hz, 0.5H), 3.62–3.84 (7 H), 4.48 (br s, 0.5H), 4.60 (m, 0.5H), 4.65 (t, J=7.0 Hz, 0.5 Hz), 4.79 (m, 0.5H), 5.16 (br s, 1H), 6.40 (br s, 0.5H), 6.48 (br s, 0.5H), 6.89 (dd, J=4.40, 8.79 Hz, 2H), and 6.99 (m, 2H); mass spectrum (EI+) m/e 549 (M).

(B) 1-(trans-4-Glycylamino-L-Prolyl)-4-[4-Fluorophenyl)piperazine Dihydrochloride A solution of 4 N hydrochloric acid in 1,4-dioxane (2.5 mL) was added to a solution of 1-[trans-4-(N-tert-butoxycarbonylglycylamino)-N-tert-butoxycarbonyl-L-prolyl]-4-(4-fluorophenyl)piperazine (A, 83 mg) in 1,4-dioxane (2.5 mL) at room temperature. After stirring at room temperature for 30 min, the reaction mixture was evaporated in vacuo. The residue was washed with ether to give the titled compound (43 mg) as a white powder: $^1$H NMR (400 MHz, $D_2O$) δ 2.51 (m, 1H), 2.63 (m, 1H), 3.48 (dd, J=4.4, 12 Hz, 1H), 3.57 (m, 4H), 3.82 (m, 1H), 3.85 (s, 2H), 3.93 (br s, 3H), 4.02 (m, 1H), 4.60 (br t, 1H), 5.08 (t, J=8.30 Hz, 1H), 7.28 (t, J=8.5 Hz, 2H), and 7.46 (m, 2H); mass spectrum (EI+) ine 349 (M).

Compound D405–1-(trans-4-Glycylamino-L-Prolyl)-4-(2-Chlorophenyl)-piperazine Dihydrochloride (A) 1-[trans-4-(N-tert-Butoxycarbonylglycylamino)-N-tert-Butoxycarbonyl-L-Prolyl]-4-(2-Chlorophenyal)piperazine N-Methylmorpholine (120 µL) and 1-(3-Dimethylaminopropyl)-3-ethylcarbodiimide hydrochloride (188 mg) were added to a solution of trans-4-(N-tert-butoxycarbonylglycylamino)-N-tert-butoxycarbonyl-L-proline (Compound D103 (B), 400 mg), 1-(2-chlorophenyl)piperazine (202 mg), and 1-hydroxybenzotriazole (140 mg) in tetrahydrofuran (12 mL) and N,N-dimethylformamide (4 mL) at room temperature. After stirring at room temperature for 17 hr, the reaction mixture was partitioned between ethyl acetate and 1 N hydrochloric acid. The organic layer was washed with saturated sodium hydrogen carbonate and brine. After drying over anhydrous sodium sulfate, the organic layer was evaporated in vacuo. The residue was washed with hexane to give the titled compound (571 mg) as a white foam: $^1$H NMR (400 MHz, $CDCl_3$) δ 1.43–1.47 (m, 18H), 2.19 (m, 1.5H), 2.31 (m, 0.5H), 2.95–3.20 (m, 4H), 3.35 (m, 0.5H), 3.49 (d, J=10 Hz, 0.5H), 3.60–3.90 (m, 7 H), 4.50 (br s, 0.5H), 4.60 (m, 0.5H), 4.66 (t, J=7.3 Hz, 0.5H), 4.79 (m, 0.5H), 5.11 (br s, 1H), 6.32 (br s, 0.5H), 6.38 (m, 0.5H), 7.01 (t, J=7.0 Hz, 2H), 7.24 (m, 1H), and 7.38 (t, J=6.8 Hz, 1H); mass spectrum (FAB+) m/e 567 (M+1): IR (KBr) 3311, 2976, 1701, 1649, 1481, 1400, 1365, 1227, 1161, 1030, and 762 cm$^{-1}$; Anal. Calcd for $C_{27}H_{40}ClN_5O_6$: C, 57.29; H, 7.12; N, 12.37; Cl, 6.26. Found: C, 57.45; H, 7.31; N, 11.97; Cl, 6.27.

(B) 1-(trans-4-Glycylamino-L-Prolyl-4-(2-Chlorophenyl)piperazine Dihydrochloride A solution of 4 N hydrochloric acid in 1,4-dioxane (15 mL) was added to a solution of 1-[trans-4-(N-tertbutoxycarbonylglycylamino)-N-tert-butoxycarbonyl-L-prolyl]-4-(2-chlorophenyl)piperazine (A, 530 mg) in 1,4-dioxane (15 mL) at room temperature. After stirring at room temperature for 30 min, the reaction mixture was evaporated in vacuo. The residue was washed with ether to give the titled compound (214 mg) as a white powder: $^1$H NMR (400 MHz, $D_2O$) δ 2.32 (quintet, J=7.33 Hz, 1H), 2.48 (ddd, J=5.0, 8.30, 13.67 Hz, 1H), 3.02 (m, 4H), 3.32 (dd, J=4.9, 12.2 Hz, 1H), 3.60–3.69 (m, 5H), 3.70 (s, 2H), 4.45 (t, J=5.86 Hz, 1H), 4.91 (t, J=4.9, 12.2 Hz, 1H), 7.04 (dt, J=8.0, 8.0, 1.5 Hz, 1H), 7.11 (dd, J=8.0, 1.5 Hz, 1H), 7.24 (dt, J=8.0, 8.0, 1.5 Hz, 1H), and 7.38 (dd, J. 8.0, 1.5 Hz, 1H); mass spectrum (EI+) m/e 365(M).

Compound D407—1-(trans-4-Aminomethyl-L-Prolyl)-4-(3-Chloro-2-methylphenyl)piperazine Dihydrochloride (A) 1-(3-Chloro-2-Methylphenyl)piperazine Hydrochloride A mixture of 6-amino-2-chlorotoluene (158.66 g) and bis-(2-chloroethyl)amine hydrochloride (200.0 g) in chlorobenzene (800 mL) was allowed to reflux for 3 days. After cooling, the reaction mixture was filtered and then washed with ether to give the titled compound (244.3 g) as a white powder: $^1$H NMR (400 MHz, DMSO-$d_6$) δ 2.29 (s, 3H), 3.06 (m, 4H), 3.22 (m, 4H), 7.05 (dd, J=2.0, 6.8 Hz, 1H), 7.17–7.23 (m, 2H), and 9.40 (br s, 2H).

(B) 1-[trans-4-(N-tert-Butoxycarbonylaminomethyl)-N-tert-butoxycarbonyl-L-Prolyl]-4-(3-Chloro-2-Methylphenyl)piperazine N-Methylmorpholine (60 μL) and 1-(3-dimethylaminopropyl)-3-ethylcarbodiimide hydrochloride (94 mg) were added to a solution of trans-4-(N-tert-butoxycarbonylaminomethyl)-N-tert-butoxycarbonyl-L-proline (Compound 109 (D), 120 mg), 1-(3-chloro-2-methylphenyl)piperazine hydrochloride (A, 128 mg) and 1-hydroxybenzotriazole (70 mg) in tetrahydrofuran (6 mL) and N,N-dimethylformamide (2 mL) at room temperature. After stirring at room temperature for 16 hr, the reaction mixture was partitioned between ethyl acetate and 1 N hydrochloric acid. The organic layer was washed with saturated sodium hydrogen carbonate and brine. After drying over anhydrous sodium sulfate, the organic layer was concentrated in vacuo. The residue was washed with hexane to give the titled compound (98 mg) as a white powder: $^1$H NMR (400 MHz, ) δ 1.42–1.59 (18H), 1.80–2.00 (br s, 2H), 2.36 (s, 3H), 2.86 (br s, 4H), 2.98 (br s, 0.5H), 3.23 (br s, 2.5H), 3.60–3.80 (6 H), 4.68 (m, 1H), 6.89 (br m, 1H), and 7.11 (m, 2H); mass spectrum (EI+) m/e 511 (M).

(C) 1-(trans-4-Aminomethyl-L-Prolyl)-4-(3-Chloro-2-Methylphenyl)piperazine Dihydrochloride A solution of 4 N hydrochloric acid in 1,4-dioxane (3 mL) was added to a solution of 1-[trans-4-(N-tert-butoxycarbonylaminomethyl)-N-tert-butoxycarbonyl-L-prolyl]-4-(3-chloro-2-methylphenyl)piperazine (B, 98 mg) in 1,4-dioxane (3 mL) at room temperature. After stirring at room temperature for 20 min, the reaction mixture was concentrated in vacuo. The residue was washed with ether to give the titled compound (61 mg) as a white powder: $^1$H NMR (400 MHz, ) δ 2.37 (s, 3H), 2.40–2.47 (br s, 2H), 2.83 (br s, 1H), 3.07 (br s, 4H), 3.32 (br s, 3H), 3.77 (m, 5H), 5.02 (br s, 1H), 7.09 (m, 1H), and 7.25 (m, 2H).

Compound D408—1-(trans-4-Glycylamino-L-Prolyl)-4-(4-Phenylbutanoyl)piperazine Dihydrochloride (A) 1-N-tert-Butoxycarbonyl-4-(4-phenylbutanoyl)piperazine Bis(2-oxo-3-oxazolidinyl)phosphinic chloride (2.33 g) and diisopropylethylamine (3.2 mL) were added to a solution of N-tert-butoxycarbonylpiperazine (1.13g) and 4-phenylbutyric acid (1.0 g) in dichloromethane (50 mL) at 0° C. After stirring at room temperature for 20 hr, the solvent was evaporated in vacuo. Ethyl acetate and 10% citric acid aqueous solution were added to the residue. The separated organic layer was washed with saturated sodium hydrogen carbonate, dried over sodium sulfate, and evaporated in vacuo to afford the titled compound (2.68 g) as a colorless solid: $^1$H NMR(400 MHz, $CDCl_3$) δ 1.47(s, 9H), 1.98(t, 2H), 2.32 (t, 2H), 2.68 (t, 2H)3.34–3.59 (m, 8H), and 7.17–7.30 (m, 5H).

(B) 4-(4-Phenylbutanoyl)piperazine 1-tert-Butyl-4-(4-phenylbutanoyl)piperazine (A, 2.64 g) was dissolved in trifluoroacetic acid (10 mL)—dichloromethane (10 mL). After siring for 1 hr, the reaction mixture was evaporated in vacuo. Toluene and methanol were added to the residue, then evaporated in vacuo to give the titled compound (1.63 g) as a colorless solid.

(C) 1-[trans-4-(N-tert-Butoxycarbonylglycylamino)-N-tert-Butoxycarbonyl-L-Prolyl]4-(4-Phenylbutanoyl)piperazine Triethylamine (72 μL) and 1-(3-dimethylaminopropyl)-3-ethylcarbodiimide hydrochloride (98.9 mg) were added to a solution of trans-4-(N-tert-butoxycarbonylglycylamino)-N-tert-butoxycarbonyl-L-proline (Compound D103 (B), 144.9 mg), 4-(4-phenylbutanoyl)l-piperazinecarboxylate (B, 100 mg), and 1-hydroxybenzotriazole (65 mg) in dichloromethane at room temperature. After stirring at room temperature for 20 hr, the reaction mixture was partitioned between ethyl acetate and 1 N hydrochloric acid. The organic layer was washed with saturated sodium hydrogen carbonate and brine. After drying over anhydrous sodium sulfate, the organic layer was evaporated in vacuo. The residue was purified by silica gel column chromatography (chloroform:methanol=50:1 to 20:1) to give the titled compound (220 mg) as a white powder: $^1$H-NMR(400 MHz, $CDCl_3$) δ 1.46 (s, 18H), 1.99 (t, 2H), 2.33 (m, 2H), 2.69 (t, 2H), 3.39–3.85 (m, 13H), 7.18–7.31(m, 5H).

(D) 1-(trans-4-Glycylamino-L-prolyl)-4-(4-Phenylbutanoyl)piperazine Dihydrochloride The title compound (156 mg) was similarly prepared, as described in Compound D401 (B), except the starting material was trans-4-Glycylamino-tert-butyl-L-proline-4-(4-phenylbutanoyl)-1-piperazinecarboxylate (C, 220 mg): $^1$H-NMR (400 MHz, $D_2O$) δ 1.76–1.84 (m, 2H), 2.24–2.35 (m, 3H), 2.41–2.48 (m, 1H), 2.57 (t, 2H), 3.31 (dd, 2H), 3.36–3.70 (m, 10H), 4.424.46 (m, 1H), 4.61–4.69 (m, 2H), 4.83–4.88 (m, 1H), and 7.13–7.27 (m, 5H); Anal: Calcd for $C_{21}H_{31}N_5O_3 \cdot 2HCl \cdot 3/4H_2O$: 51.69; H, 7.13; N, 14.35. Found: C, 51.89; H, 7.23; N,14.15; mass spectrum (FAB+) m/e 402 (M+1).

Compound D409—(2R)-4-Benzyl-1-(trans-4-Glycylamino-D-Prolyl)-2-Phenethylpiperazine Trihydrochloride (A) N-tert-Butoxycarbonyl-D-Homophenylanyl-N-Benzylglycine Ethyl Ester N-Methylmorpholine (1.7 mL) and 1-(3-dimethylaminopropyl)-3-ethylcarbodiimide hydrochloride (2.82 g) were added to a solution of N-tert-butoxycarbonyl-D-homophenylalanine (4.32 g), N-benzylglycine ethyl ester (3.00 g), and 1-hydroxybenzotriazole (2.09 g) in tetrahydrofuran (150 mL) and N,N-dimethylformamide (50 mL) at room temperature. After stirring at room temperature for 16 hr, the reaction mixture was partitioned between ethyl acetate and 1 N hydrochloric acid. The organic layer was washed with saturated sodium hydrogen carbonate and brine. After drying over anhydrous sodium sulfate, the organic layer was concentrated in vacuo to give the titled compound (7.04 g) as a pale yellow oil: mass spectrum (EI+) m/e 454 (M).

(B) (3RL)-1-Benzyl-3-Phenethylpiperazine-2,5-Dione

Trifluoroacetic acid (30 mL) was added to a solution N-tert-butoxycarbonyl-D-homophenylalanyl-N-benzylglycine ethyl ester (A, 6.92 g) in dichloromethane (100 mL) at room temperature. After stirring at room temperature for 1 hr, the reaction mixture was concentrated in vacuo. The residue was dissolved in ethanol (800 mL) and acetic acid (3 mL) was added. The mixture was allowed to reflux and stirred for 60 hr. After cooling, the reaction mixture was concentrated in vacuo. The residue was washed with ether to give the titled compound (4.54 g) as white plates: $^1$H NMR (400 MHz, CDCl$_3$) δ 1.20 (m, 2H), 2.74 (m, 2H), 3.80 (AB q, J=17.58 Hz, 1H), 3.86 (AB q, J=17.58 Hz, 1H), 4.09 (br s, 1H), 4.52 (AB q, J=14.65 Hz, 1H), 4.64 (AB q, J=14.65 Hz, 1H), 6.82 (br s, 1H), and 7.19–7.37 (m, 10H); mass spectrum (FAB+) m/e 309 (M+1); IR (KBr) 3240, 3020, 2947, 2902, 1684, 1657, 1469, 1346, 1315, 1126, 968, 795, 752, 729, 694, and 424 cm$^{-1}$; Anal. Calcd for C$_{19}$H$_{20}$N$_2$O$_2$.0.5H$_2$O: C, 71.90; H, 6.67; N, 8.83. Found: C, 72.05; H, 6.42; N, 9.10.

(C) (3R)-1-Benzyl-3-Phenethylpiperazine

Lithium aluminum hydride (1.04 g) was added to a solution of (3R)-1-benzyl-3-phenethylpiperazine-2,5-dione (B, 1.68 g) in tetrahydrofuran (60 mL) at 0° C. After stirring at room temperature for 18 hr, anhydrous sodium sulfate and then water were added at 0° C. The insoluble materials were removed by filtration. The resulting mixture was concentrated in vacuo and then partitioned between chloroform and saturated sodium hydrogen carbonate. The organic layer was dried over anhydrous sodium sulfate and concentrated in vacuo to give the titled compound (1.58 g) as an orange oil, which was used in the next reaction without further purification.

(D) 2R -4-Benzyl-1-[trans-4-(N-tert-butoxycarbonylglycylamino)-N-tert-butoxycarbonyl-D-Prolyl]-2-Phenethylpiperazine N-Methylmorpholine (50 uL) and 1-(3-dimethylaminopropyl)-3-ethylcarbodiimide hydrochloride (71 mg) were added to a solution of trans-4-(N-tert-butoxycarbonylglycylamino)-N-tert-butoxycarbonyl-D-proline (Compound 105 (F), 146 mg), (3R)-1-benzyl-3-phenethylpiperazine (C, 420 mg), and 1-hydroxybenzotriazole (53 mg) in tetrahydrofuran (6 mL) and N,N-dimethylformamide (2 mL) at room temperature. After stirring at room temperature for 21 hr, the reaction mixture was partitioned between ethyl acetate and saturated sodium hydrogen carbonate. The organic layer was washed with brine, dried over anhydrous sodium sulfate, and concentrated in vacuo. The residue was purified by silica gel column chromtography (ethyl acetate) to give the titled compound (161 mg) as a pale yellow powder: $^1$H NMR (400 MHz, CDCl$_3$) δ 1.37–1.46 (m, 18H), 1.83 (dd, J=7.8, 14.6 Hz, 2H), 2.60 (m, 4H), 3.06 (A3 q, J=16.6 Hz, 1H), 3.23 (AB q, J=16.6 Hz, 1H), 3.35–3.60 (m, 7 H), 3.74 (m, 3H), 4.43–4.60 (m, 3H), 5.10 (br s, 1H), 5.90 (br s, 1H), and 7.10–7.35 (m, 10 U); mass spectrum (EI+) m/e 649 (M).

(E) (2R)-4-Benzyl-1-(trans-4-Glycylamino-D-Prolyl)-2-Phenethylpiperazine Trihydrochloride A solution of 4 N hydrochloric acid in 1,4-dioxane (5 mL) was added to a solution of (2R)-4-Benzyl-1-[trans-4-(N-tert-butoxycarbonylglycylamino)-N-tert-butoxycarbonyl-D-Prolyl]-2-Phenethylpiperazine (D, 161 mg) in 1,4-dioxane (5 mL) at room temperature. After stirring at room temperature for 20 min, the reaction mixture was concentrated in vacua. The residue was washed with ether to give the titled compound (103 mg) as a beige powder: $^1$H NMR (400 MHz, D$_2$O) δ 2.00 (m, 2H), 2.19 (m, 1H), 2.41 (quintet, J=7.3 Hz, 1H), 2.58 (m, 1H), 2.71 (m, 2H), 3.18 (t, J=11.7 Hz, 1H), 3.27 (m, 1H), 3.37 (m, 1H), 3.46 (m, 1H), 3.63 (m, 2H), 3.77–3.93 (m, 2H), 3.85 (s, 2H), 4.33–4.49 (m, 3H), 4.58 (m, 1H), 7.24 (t, J=6.8 Hz, 2H), 7.30 (t, J=6.8 Hz, 1H), 7.36 (m, 2H), and 7.48–7.58 (m, 5H).

Compound D410—1-(trans-4-Glycylamino-L-proline)-4-(3-quinolylcarbonyl)piperazine Trihydrochloride (A) 1-tert-Butyl-4-(3-Quinolylcarbonyl)piperazine The title compound (1.55 g) was similarly prepared, as described in Compound D408 (A), except the starting material was N-tert-butoxycarbonylpiperazine (1.0 g) and 3-quinolinecarboxylic acid (0.93 g): $^1$H-NMR(400 MHz, CDCl$_3$) δ 1.48(s, 9H), 3.49–3.82(m, 8H), 7.63, 7.81(t, each 1H), 7.88 (d, 1H), 8.15 (d, 1H), 8.26 (s, 1H), 8.95 (s, 1H).

(B) 1-(3-Quinolylcarbonyl)piperazine

The title compound (495 mg) was similarly prepared, as described in Compound D408 (B), except the starting material was 1-tert-butyl-4-(3-quinolylcarbonyl)piperazine (A, 1.55 g).

(C) 1-[trans-4-(N-tert-Butoxycarbonylglycylamino)-N-tert-Butoxycarbonyl-L-Prolyl]-4-(3-Quinolylcarbonyl) piperazine The title compound (260 mg) was similarly prepared, as described in Compound D408 (C), except the starting material was 1-(3-quinolylcarbonyl)piperazine (B, 144.0 mg): $^1$H NMR (400 M CDCl$_3$) δ 1.45 (s, 18H), 2.15–2.25 (m, 3H), 3.46–3.85 (m, 12H), 7.63 (dd, 1H), 7.81 (dd, 1H), 7.86 (d, 1H), 8.14 (d, 1H), 8.28 (s, 1H), 8.96 (s, 1H).

(D) 1-[trans-4-Glycylamino-L-Prolyl]-4-(3-Quinolylcarbonyl)piperazine Trihydrochloride The title compound (190 mg) was similarly prepared, as described in Compound D408 (D), except the starting material was 1-[trans-4-(N-tert-butoxycarbonylglycylamino)-N-tert-butoxycarbonyl-L-prolyl]-4-(3-quinolylcarbonyl) piperazine (C, 260.0 mg): $^1$H NMR (400 MHz, D$_2$O) δ 2.33–2.28 (m, 1H), 2.51 (m, 1H), 3.33–3.34 (m, 1H), 3.53–3.82 (m, 12H), 4.32–4.43 (m, 1H), 4.61–4.65 (m, 2H), 4.86–4.97 (m, 1H), 7.83–7.87 (m, 1H), 8.05–8.07 (m, 1H), 8.12 (d, 1H), 8.16 (d, 1H), 8.93 (br s, 1H), 9.07 (s, 1H); mass spectrum (FAB+) m/e 411 (M+1); Anal. Calcd for C$_{21}$H$_{26}$N$_6$O$_3$.3HCl.H$_2$O: C, 46.89; H, 5.81; N, 15.62. Found: C, 47.43; H, 6.04; N,14.77.

Compound D413—1-(trans-4-Glycylamino-L-Prolyl)4-(4-Benzyloxyphenoxy)piperidine Dihydrochloride (A) N-tert-Butoxycarbonyl-4-Hydroxpiperidine Di-tert-butyl dicarbonate (25.0 g) was added to a solution of 4-hydroxypiperidine (10.3 g) in dichloromethane (400 mL) at room temperature. After stirring at room temperature for 18 hr, the reaction mixture was concentrated in vacuo and the residue was washed with hexane to give the tided compound (16.2 g) as a white solid: $^1$H NMR (400 MHz, CDCl$_3$) δ 1.46 (s, 9H), 1.42–1.50 (m, 2H), 1.72 (br s, 1H), 1.84 (m, 2H), 3.03 (m, 2H), 3.83 (m, 3H).

(B) N-tert-Butoxycarbonyl-4-(4-Benzyloxyphenoxy) piperidine

Triphenylphosphine (917 mg) was added to a solution of N-tert-butoxycarbonyl-4-hydroxypiperidine (A, 704 mg), 4-benzyloxyphenol (700 mg) and diethyl azodicarboxylate (609 mg) in tetrahydrofuran (20 mL) at room temperature. After stirring at room temperature for 14 hr, the reaction mixture was concentrated in vacuo. The residue was purified by silica gel column chromatography (ethyl acetate:hexane= 1:9, v/v) to give the titled compound (703 mg) as a colorless oil: $^1$H NMR (400 MHz, CDCl$_3$) δ 1.47 (s, 9H), 1.72 (m, 2H), 1.88 (m, 2H), 3.29 (ddd, J=3.9, 7.8, 12.5 Hz, 2H), 3.70 (m, 2H), 4.32 (quintet, J=3.9 Hz, 1H), 5.01 (s, 2H), 6.84–6.91 (m, 4H), and 7.32–7.43 (m, 5H).

(C) 4-(4-Benzyloxyphenoxy)piperidine

Trifluoroacetic acid (6 mL) was added to a solution of N-tert-butoxycarbonyl-4-(4-benzyloxyphenoxy)piperidine (B, 473 mg) in dichloromethane (12 mL) at room temperature. After stirring at room temperature for 20 hr, the reaction was quenched with saturated sodium hydrogen carbonate. The resulting mixture was extracted with chloroform. The organic layer was dried over anhydrous sodium sulfate and concentrated in vacuo to give the titled compound (345 mg) as a yellow brown solid, which was used in the next reaction without further purification.

(D) 1-[trans-4-(N-tert-Butoxycarbonylglyclamino)-N-tert-butoxycarbonyl-L-Prolyl]-4-(4-Benzyloxyphenoxy)piperidine N-Methylmorpholine (60 µL) and 1-(3-dimethylaminopropyl)-3-ethylcarbodiimide hydrochloride (94 mg) were added to a solution of trans-4-(N-tert-butoxycarbonylglycylamino)-N-tert-butoxycarbonyl-L-proline (Compound D103 (B), 200 mg), 4-(4-benzyloxyphenoxy)piperidine (C, 146 mg) and 1-hydroxybenzotriazole (70 mg) in tetrahydrofuran (6 mL) and N,N-dimethylformamide (2 mL) at room temperature. After stirring at room temperature for 17 hr, the reaction mixture was partitioned between ethyl acetate and 1 N hydrochloric acid. The organic layer was washed with saturated sodium hydrogen carbonate and brine. After drying over anhydrous sodium sulfate, the organic layer was concentrated in vacuo. The residue was washed with hexane to give the titled compound (362 mg) as a white solid: $^1$H NMR (400 MHz, CDCl$_3$) δ 1.42–1.46 (18H), 1.60–2.00 (m, 4H), 2.15 (br s, 1.51), 2.28 (br s, 0.5H), 3.30–3.60 (m, 2H), 3.60–3.90 (m, 6 H), 4.42 (br s, 1.5H), 4.64 (m, 1H), 4.78 (m, 0.5H), 5.02 (s, 2H), 5.12 (br s, 1H), 6.39 (br m, 1H), 6.85 (d, J=7.5 Hz, 2), 6.91 (d, J=7.5 Hz, 2H), and 7.33–7.44 (m, 5H); mass spectrum (EI+) m/e 652 (M); IR (KBr) 3302, 2976, 2931, 1697, 1660, 1506, 1402, 1209, 1161, 1026, and 741 cm$^{-1}$.

(E) 1-(trans-4-Glycylamino-L-Prolyl)-4-(4-Benzyloxyphenoxy)piperidine Dihydrochloride A solution of 4 N hydrochloric acid in 1,4-dioxane (9 mL) was added to a solution of 1-[trans-4-(N-tert-butoxycarbonylglycylamino)-N-tert-butoxycarbonyl-L-Prolyl]-4-(4-benzyloxyphenoxy)piperidine (D, 330 mg) in 1,4-dioxane (9 mL) at room temperature. After stirring at room temperature for 30 min, the reaction mixture was concentrated in vacuo. The residue was washed with ether to give the titled compound (186 mg) as a white powder: $^1$H NMR (400 MHz, D$_2$O) δ 1.58 (br s, 2H), 1.83 (br s, 2H), 2.25 (m, 1H), 2.43 (m, 1H), 3.20–3.40 (m, 3H), 3.50–3.70 (m, 3H), 3.70 (s, 2H), 4.41 (m, 1H), 4.85 (t, J=8.30 Hz, 1H), 4.93 (s, 2H), 6.85 (s, 4H), and 7.24–7.31 (m, 5H); mass spectrum (E+) m/e 452; IR (KBr) 3438, 3059, 1689, 1651, 1549, 1508, 1228, 1024, 825, 741, and 698 cm$^{-1}$; Anal. Calcd for C$_{25}$H$_{32}$N$_4$O$_4$·2HCl·0.5H$_2$O: C, 56.18; H, 6.60; N, 10.48; Cl, 13.27. Found: C, 56.56; H, 6.61; N, 10.05; Cl, 12.72.

Compound D414—1-(trans-4-Glycylamino-L-Prolyl)-4-(3,5-dichlorophenoxy)piperidine Dihydrochloride (A) N-tert-Butoxycarbonyl-4-(3,5-Dichlorophenoxy)piperidine Triphenylphosphine (786 mg) was added to a solution of N-tert-butoxycarbonyl-4-hydroxypiperidine (603 mg), 3,5-dichlorophenol (489 mg) and diethyl azodicarboxylate (522 mg) in tetrahydrofuran (15 mL) at room temperature. After stirring at room temperature for 14 hr, the reaction mixture was evaporated in vacuo. The residue was purified by silica gel column chromatography (ethyl acetate:hexane=1:6) to give the titled compound (815 mg) as a colorless oil: $^1$H NMR (400 MHz, CDCl$_3$) δ 1.48 (s, 9H), 1.75 (m, 2H), 1.90 (m, 2H), 3.37 (m, 2H), 3.66 (m, 2H), 4.44 (m, 1H), 6.80 (d, J=1.5 Hz, 2H), and 6.95 (s, 1H); mass spectrum (EI+) m/e 345 (M).

(B) 4-(3,5-Dichlorophenoxy)piperidine

Trifluoroacetic acid (10 mL) was added to a solution of N-tert-butoxycarbonyl-4-(3,5-dichlorophenoxy)piperidine (A, 815 mg) in dichloromethane (20 mL) at room temperature. After stirring at room temperature for 30 min, the reaction mixture was evaporated in vacuo. The residue was partitioned between chloroform and saturated sodium hydrogen carbonate. The organic layer was dried over anhydrous sodium sulfate and then concentrated in vacuo to give the title compound, which was washed with hexane and used in the next reaction without further purification.

(C) 1-[trans-4-(N-tert-Butoxycarbonylglycylamino)-N-tert-Butoxycarbonyl-L-prolyl]-4-(3,5-Dichlorophenoxy)piperidine N-Methylmorpholine (120 µL) and ]-(3-dimethylaminopropyl)-3-ethylcarbodiimide hydrochloride (188 mg) were added to a solution of trans-4-(N-tert-butoxycarbonylglycylamino)-N-tert-butoxycarbonyl-L-proline (Compound D103 (B), 400 mg), 4-(3,5-dichlorophenoxy)piperidine (518 mg), and 1-hydroxybenzotriazole (140 mg) in tetrahydrofuran (12 mL) and N,N-dimethylformamide (4 mL) at room temperature. After stirring at room temperature for 12 hr, the reaction mixture was partitioned between ethyl acetate and 1 N hydrochloric acid. The organic layer was washed with saturated sodium hydrogen carbonate and brine. After drying over anhydrous sodium sulfate, the organic layer was evaporated in vacuo. The residue was washed with hexane to give the titled compound (671 mg) as a white solid: $^1$H NMR (400 MHz, CDCl$_3$) δ 1.43 (s, 9H), 1.46 (s, 9H), 1.70–2.00 (m, 4H), 2.14–2.29 (m, 2H), 3.35–3.82 (m, 8H), 4.51–4.60 (m, 2H), 4.64 (br t, 0.5H), 4.78 (m, 0.5H), 5.11 (br s, 1H), 6.40 (m, 1H), 6.77–6.80 (m, 2H), and 6.96–6.98 (m, 1H); IR (KBr) 3311, 2978, 1701, 1655, 1570, 1441, 1255, 1163, 1049 cm$^{-1}$; mass spectrum (FAB+) m/e 615 (M).

(D) 1-(trans-4-Glycylamino-L-prolyl)-4-(3,5-dichlorophenoxy)piperidine Dihydrochloride A solution of 4 N hydrochloric acid in 1,4-dioxane (13 mL) was added to a solution of 1-[trans-4-(N-tert-butoxycarbonylglycylamino)-N-tert-butoxycarbonyl-L-prolyl]-4-(3,5-dichlorophenoxy)piperidine (C, 640 mg) in 1,4-dioxane (13 mL) at room temperature. After stirring at room temperature for 30 min, the reaction mixture was evaporated in vacuo. The residue was washed with ether to give the titled compound (361 mg) as white crystals: $^1$H NMR (400 MHz, D$_2$O) δ 1.80 (br s, 2H), 2.03 (br s, 2H), 2.40 (m, 1H), 2.61 (m, 1H), 3.46–3.50 (m, 2H), 3.60 (br s, 1H), 3.77 (m, 3H), 3.86 (s, 2H), 4.58 (br s, 1H), 4.72 (br s, 1H), 5.03 (t, J=8.3 Hz, 1H), 7.03 (br s, 2H), and 7.10 (br s, 1H); mass spectrum (EI+) m/e 415.

Compound D415—1trans-4-Glycylamino-D-prolyl)-4-(3,5dichlorophenoxy)piperidine Dihydrochloride (A) 1-[trans-4-(N-tert-Butoxycarbonyglycylamino-N-tert-Butoxycarbonyl-D-Prolyl]-4-(3,5-Dichlorophenoxy)piperidine N-Methylmorpholine (70 µL) and 1-(3-dimethylaminopropyl)-3-ethylcarbodiimide hydrochloride (114 mg) were added to a solution of trans-4-(N-tertbutoxycarbonylglycylamino)-N-tert-butoxycarbonyl-D-proline (Compound D105 (F), 220 mg), 4-(3,5-dichlorophenoxy)piperidine (154 mg) and 1-hydroxybenzotriazole (85 mg) in tetrahydrofuran (8 mL) and N,N-dimethylformamide (2 mL) at room temperature. After stirring at room temperature for 12 hr, the reaction mixture was partitioned between ethyl acetate and 1 N hydrochloric acid. The organic layer was washed with saturated sodium hydrogen carbonate and brine. After drying over anhydrous sodium sulfate, the organic layer was evaporated in vacuo. The residue was washed with hexane to give the titled compound (347 mg) as a white powder.

(B) 1-(trans-4-Glcylamino-D-prolyl)-4-(3,5-Dichlorophenoxy)piperidine Dihydrochloride A solution of 4 N hydrochloric acid in 1,4-dioxane (10 mL) was added to a solution of 1-[trans-4-(N-tert-butoxycarbonylglycylamino)-N-tert-butoxycarbonyl-D-prolyl]-4-(3,5-dichlorophenoxy)piperidine (320 mg) in 1,4-dioxane (10 mL) at room temperature. After stirring at room temperature for 20 min, the reaction mixture was evaporated in vacuo. The residue was washed with ether to give the titled compound (178 mg) as a white crystalline solid: $^1$H NMR (400 MHz, D$_2$O) δ 1.86 (br s, 2H), 2.05 (br s, 2H), 2.44 (quintet, J=7.5 Hz, 1H), 2.63 (ddd, J=5.0, 8.5, 13.5 Hz, 1H), 3.48 (dd, J=4.9, 12.2 Hz, 1H), 3.50 (m, 1H), 3.79–3.87 (m, 3H), 3.82 (dd, J=60, 12.2 Hz, 1H), 3.87 (s, 2H), 4.59 (br quintet, J=6.0 Hz, 1H), 5.04 (dt, J=2.0, 8.0 Hz, 1H), 7.09 (br s, 2H), and 7.17 (br s, 1H).

Compound D416—trans-4-Glycylamino-L-Prolyl-4-(2-Chloro-5-Methylphenoxy)-piperidine Dihydrochloride (A) N-tert-butoxycarbonyl-4-(2-Chloro-5-Methylphenoxy)piperidine Triphenylphosphine (786 mg) was added to a solution of N-tert-butoxycarbonyl-4-hydroxypiperidine (603 mg), 2-chloro-5-methylphenol (428 mg) and diethyl azodicarboxylate (522 mg) in tetrahydrofuran (10 mL) at room temperature. After stirring at room temperature for 18 hr, the reaction mixture was evaporated in vacuo. The residue was purified by silica gel column chromatography (ethyl acetate:hexane=1:6, v/v) to give the titled compound (489 mg) as a colorless oil: $^1$H NMR (400 MHz, CDCl$_3$) δ 1.46 (s, 9H), 1.84 (m, 4H), 2.28 (s, 3H), 3.44 (m, 2H), 3.65 (ddd, J=4.0, 8.0, 12.7 Hz, 2H), 4.49 (m, 1H), 6.69 (d, J=8.0 Hz, 1H), 6.75 (s, 1H), and 7.19 (d, J=8.0 Hz, 1H).

(B) 4-(2-Chloro-5-Methylphenoxy)piperidine

Trifluoroacetic acid (6 mL) was added to a solution of N-tert-butoxycarbonyl-4-(2-chloro-5-methylphenoxy)piperidine (A, 489 mg) in dichloromethane (20 mL) at room temperature. After stirring at room temperature for 30 min, the reaction mixture was evaporated in vacuo. The residue was partitioned between chloroform and saturated sodium hydrogen carbonate. The organic layer was dried over anhydrous sodium sulfate and then concentrated in vacuo to give the titled compound as yellow crystals, which was used in the next reaction without her purification.

(C) 1-[trans-4-(N-tert-Butoxycarbonylglycylamino)-N-tert-Butoxycarbonyl-L-Prolyl]-4-(2-Chloro-5-Methylphenoxy)piperidine N-Methylmorpholine (60 μL) and 1-(3-dimethylaminopropyl)-3-ethylcarbodiimide hydrochloride (94 mg) were added to a solution of trans-4-(N-tert-butoxycarbonylglycylamino)-N-tert-butoxycarbonyl-L-proline (Compound D103 (B), 200 mg), 4-(2-chloro-5-methylphenoxy)piperidine (117 mg) and, 1-hydroxybenzotriazole (70 mg) in tetrahydrofuran (6 mL) and N,N-dimethylformamide (2 mL) at room temperature. After stirring at room temperature for 14 hr, the reaction mixture was partitioned between ethyl acetate and 1 N hydrochloric acid. The organic layer was washed with saturated sodium hydrogen carbonate and brine. After drying over anhydrous sodium sulfate, the organic layer was evaporated in vacuo. The residue was washed with hexane to give the titled compound (309 mg) as a white foam: $^1$H NMR (400 MHz, CDCl$_3$) δ 1.43–1.46 (18H), 1.89 (br s, 4H), 2.16 (br s, 2H), 2.32 (s, 3H), 3.34–3.60 (m, 3H), 3.70–4.00 (m, 5H), 4.49 (br s, 0.5H), 4.62 (m, 2H), 4.79 (br s, 0.5H), 5.11 (br s, 1H), 6.34 (br s, 1H), 6.77 (m, 2H), and 7.24 (m, 1H). Anal. Calcd for C$_{29}$H$_{43}$Cl$_1$N$_4$O$_7$: C, 58.53; H, 7.28; N, 9.41; Cl, 5.96. Found: C, 58.21; H, 7.35; N, 9.25; Cl, 6.03; IR (KBr) 3319, 2978, 2933, 1699, 1666, 1404, 1252, 1165, 1061 cm$^{-1}$; mass spectrum (EI+) m/e 594 (M).

(D) 1-(trans-4-Glycylamino-L-Prolyl)-4-(2-Chloro-5-Methylphenoxy)piperidine Dihydrochloride A solution of 4 N hydrochloric acid in 1,4-dioxane (8 mL) was added to a solution of 1-[trans-4-(N-tert-butoxycarbonylglycylamino)-N-tert-butoxycarbonyl-L-prolyl]-4-(2-chloro-5-methylphenoxy)piperidine (C, 280 mg) in 1,4-dioxane (8 mL) at room temperature. After stirring at room temperature for 20 min, the reaction mixture was evaporated in vacuo. The residue was washed with ether to give the titled compound (142 mg) as a white powder: $^1$H NMR (400 MHz, D$_2$O) δ 1.90–2.01 (4H), 2.32 (s, 3H), 2.43 (m, 1H), 2.61 (br s, 1H), 3.49 (br t, 2H), 3.67 (br s, 1H), 3.79 (m, 4H), 3.85 (s, 2H), 4.58 (br s, 1H), 5.02 (m, 1H), 6.91 (d, J=8.0 Hz, 1H), 7.09 (s, 1H), and 7.35 (d, J=8.0 Hz, 1H); mass spectrum (EI+) m/e 394 (M).

TYPE V

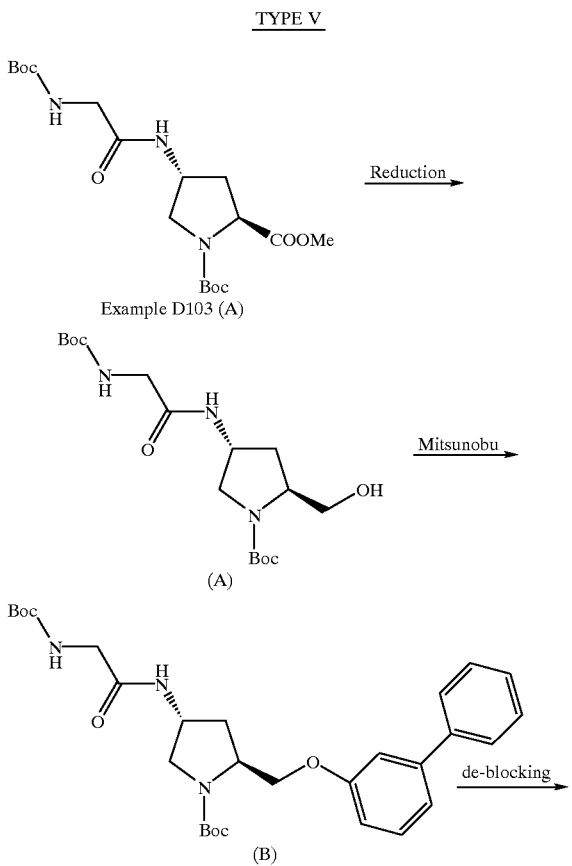

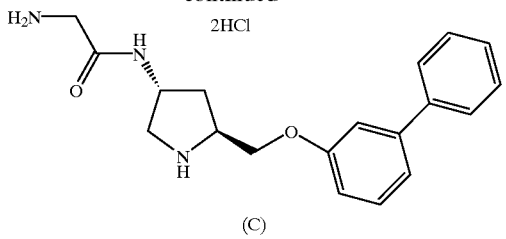

(C)

Compound D501—(2S,4R)-4-Glycylamino-2-(4-Biphenyloxy)-methylpyrrolidine Dihydrochloride (A) (2S,4R)-4-(N-tert-Butoxycarbonylglycylamino)-2-Hydroxymethyl-N-tert-Butoxycarbonylpyrrolidine Methanol (8 mL) was added over a period of 1 hr to a refluxed mixture of trans-4-N-tert-butoxycarbonylglycylamino)-N-tert-butoxycarbonyl-L-proline methyl ester (Compound D103 (B), 1.39 g) and lithium borohydride (328 mg) in tetrahydrofuran (30 mL). After being cooled, water was added to the mixture and the product was extracted twice with chloroform. The combined organic layers were dried over anhydrous sodium sulfate, then evaporated in vacuo and the residue was purified by silica gel column chromatography (chloroform:methanol=95:5, v/v) to give title compound (1.31 g): $^1$H NMR (400 MHz, CDCl$_3$) δ 1.46 (s, 9H), 1.47 (s, 9H), 1.89 (m, 1H), 1.98 (m, 1H), 3.34 (dd, J=11.7, 3.9 Hz, 1H), 3.60 (d, J=5.9 Hz, 1H), 3.64 (d, J=5.9 Hz, 1H), 3.69 (m, 1H), 3.75 (d, J=5.9 Hz, 1H), 4.04 (m, 1H), 4.42 (m, 1H), 4.55 (m, 1H), 5.15 (m, 1H), and 6.44 (m, 1H).

(B) (2S,4R)-4-(N-tert-Butoxycarbonylglycylamino)-2-(4-Biphenyloxy)methyl-N-tert-Butoxycarbonylpyrrolidine Diethyl azodicarboxylate (158 mL) was added to a mixture of (2S,4R)-4-(N-tert-butoxycarbonylglycylamino)-2-hydroxymethyl-N-tert-butoxycarbonylpyrrolidine (A, 310 mg), 4-phenylphenol (148 mg), and triphenyl phosphine (229 mg) in tetrahydrofuran (10 mL) under argon at room temperature. After stirring at room Ad temperature for 17 hr, the mixture was concentrated in vacuo to give a residue, which was purified by silica gel column chromatography (chloroform:methanol=200:1, v/v) to afford title compound (431 mg): $^1$H NMR (400 MHz, CDCl$_3$) δ 1.44 (s, 18H), 2.01 (m, 1H), 2.38 (m, 1H), 3.21 (m, 1H), 3.72 (m, 1H), 3.77 (d, J=4.4 Hz, 2H), 3.99–4.25 (m, 3H), 4.68 (m, 1H), 5.49 (m, 1H), 6.85 (m, 1H), 6.97 (d, J=7.3 Hz, 2H), 7.29 (d, J=7.3 Hz, 1H), 7.40 (t, J=7.3 Hz, 2H), 7.48–7.63 (m, 4H).

(C) (2S,4R)-4-Glycylamino-2-(4-Biphenyloxy)methylpyrrolidine (2S,4R)-4-(N-tert-Butoxycarbonylglycylamino)-2-(4-biphenyloxy)methyl-N-tert-butoxycarbonylpyrrolidine (B, 431 mg) was dissolved in 4 N hydrogen chloride in 1,4-dioxane (4 mL). After stirring for 2 hr, the reaction mixture was evaporated in vacuo to give a white solid. The solid was washed with ether to afford the titled compound (254 mg): $^1$H NMR (400 MHz, D$_2$O) δ 2.33 (m, 1H), 2.44 (m, 1H), 3.45 (dd, J=12.7, 4.4 Hz, 1H), 3.79 (dd, J=12.7, 6.8 Hz, 1H), 3.84 (s, 2H), 4.27 (dd, J=10.7, 6.8 Hz, 1H), 4.36 (m, 1H), 4.47 (d, J=10.7 Hz, 1H), 4.67 (m, 1H), 7.16 (d, J=8.3 Hz, 2H), 7.43 (d, J=7.3 Hz, 1H), 7.53 (t, J=7.3 Hz, 2H), 7.68–7.72 (m, 4H).

Compound D502—(2S,4R)-4-Glycylamino-2-(3-Biphenyloxy)methyl-pyrrolidine Dihydrochloride (A) (2S,4R)-4-(N-tert-Butoxycarbonylglycylamino)-2-(3-Biphenyloxy)methyl-N-tert-Butoxycarbonylpyrrolidine The title compound (142 mg) was similarly prepared, as described in Compound D501 (B), except the starting material was (2S,4R)-4-(N-tert-butoxycarbonyl-glycylamino)-2-hydroxymethyl-N-tert-butoxycarbonylpyrrolidine (200 mg) $^1$H NMR (400 MHz, CDCl$_3$) δ 1.45 (s, 9H), 1.46 (s, 9H), 2.00 (m, 1H), 2.42 (m, 1H), 3.22 (m, 1H), 3.75 (m, 1H), 3.76 (d, J=5.4 Hz, 2H), 4.03–4.27 (m, 3H), 4.67 (m, 1H), 5.12 (m, 1H), 6.29 (m, 1H), 6.89 (m, 1H), 7.14 (m, 1H), 7.18 (d, J=7.3 Hz, 1H), 7.33 (t, J=7.3 Hz, 2H), 7.43 (t, J=7.3 Hz, 2H), 7.58 (d, J=7.3 Hz, 2H).

(B) (2S,4R)-4-Glycylamino-2-(3-Biphenyloxy)methylpyrrolidine

The title compound (79 mg) was similarly prepared, as described in Compound D501 (C), except the starting material was (2S,4R)-4-(N-tert-Butoxycarbonylglycylamino)-2-(2S,4R)4-N-tert-Butoxycarbonylglycylamino)-2-(3-biphenyloxy)methyl-N-tert-butoxycarbonyl-pyrrolidine (142 mg) CDCl$_3$): $^1$H NMR (400 MHz, D$_2$O) δ 2.32 (m, 1H), 2.42 (m, 1H), 3.45 (dd, J=12.7, 4.4 Hz, 1H), 3.79 (dd, J=12.7, 6.8 Hz, 1H), 3.84 (s, 2H), 4.27 (dd, J=10.3, 6.3 Hz, 1H), 4.37 (m, 1H), 4.48 (d, J=12.3 Hz, 1H), 4.67 (m, 1H), 7.06 (d, J=7.8. Hz, 1H), 7.31 (s, 1H), 7.39 (d, J=7.8 Hz, 1H), 7.48 (t, J=7.3 Hz, 2H), 7.55 (t, J=7.3 Hz, 2H), 7.71 (d, J=7.3 Hz, 2H).

Compound D503—(2R,4S)-4-Glycylamino-2-(4-Biphenyloxy)methyl-pyrrolidine Dihydrochloride (A) (2R,4S)-4-(N-tert-Butoxycarbonylglycylamino)-2-Hydroxymethyl-N-tert-Butoxycarbonylpyrrolidine The title compound (1.00 g) was similarly prepared, as described in Compound D501 (A), except the starting material was (trans-4-(N-tert-butoxycarbonylglycylamino)-N-tert-butoxycarbonyl-D-proline methyl ester (1.10 g).

(B) (2R,4S)-4-(Nert-Butoxycarbonylglycylamino)-2-(4-Biphenyloxy)methyl-N-tert-Butoxycarbonylpyrrolidine The title compound (253 mg) was similarly prepared, as described in Compound D501 (B), except the starting material was (2R,4S)-4-(N-tert-butoxycarbonyl-glycylamino)-2-hydroxymethyl-N-tert-butoxycarbonylpyrrolidine (200 mg).

(C) (2R,4S)-4-Glcylamino-2-(4-Biphenyloxy)methylpyrrolidine Dihydrochloride

The title compound (135 mg) was similarly prepared, as described in Compound D501 (C), except the starting material was (2R,4S)-4-(N-tert-butoxycarbonyl-glycylamino)-2-(4-biphenyloxy)methyl-N-tert-butoxycarbonylpyrrolidine (253 mg): $^1$H NMR (400 MHz, D$_2$O) δ 2.33 (m, 1H), 2.44 (m, 1H), 3.45 (dd, J=12.7, 4.4 Hz, 1H), 3.79 (dd, J=12.7, 6.8 Hz, 1H), 3.84 (s, 2H), 4.27 (dd, J=10.7,6.8 Hz, 1H), 4.36 (m, 1H), 4.47 (d, J=10.7 Hz, 1H), 4.67 (m, 1H), 7.16 (d, J 8.3 Hz, 2H), 7.43 (d, J=7.3 Hz, 1H), 7.53 (t, J=7.3 Hz, 2H), 7.68–7.72 (m, 4H).

Compound D504—(2R,4S)-4-Glycylamino-2-(3-Biphenyloxy)methyl-pyrrolidine Dihydrochloride (A) (2R,4S)-4-(N-tert-Butoxycarbonylglycylamino)-2-(3-Biphenyloxy)methyl-N-tert-Butoxycarbonylpyrrolidine The title compound (284 mg) was similarly prepared, as described in Compound D501 (B), except the starting material was (2R,4S)-4-(N-tert-butoxycarbonyl-glycylamino)-2-hydroxymethyl-N-tert-butoxycarbonylpyrrolidine (460 mg): $^1$H NMR (400 MHz, CDCl$_3$) δ 1.45 (s, 9H), 1.46 (s, 9H), 2.00 (m, 1H), 2.42 (m, 1H), 3.22 (m, 1H), 3.75 (m, 1H), 3.76 (d, J=5.4 Hz, 2H), 4.034.27 (m, 3H), 4.67 (m, 1H), 5.12 (m, 1H), 6.29 (m, 1H),6.89 (m, 1H),7.14 (m, 1H),7.18 (d, J=7.3 Hz, 1H), 7.33 (t, J=7.3 Hz, 2H), 7.43 (t, J=7.3 Hz, 2H), 7.58 (d, J=7.3 Hz, 2H).

(B) (2R,4S)-4-Glycylamino-2-(3-Biphenyloxymethylpyrrolidine Dihydrochloride

The title compound (162 mg) was similarly prepared, as described in Compound D501 (B), except the starting material was (2R,4S)4-(N-tert-butoxycarbonyl-glycylamino)-2-(3-biphenyloxy)methyl-N-tert-butoxycarbonylpyrrolidine (284 mg): $^1$H NMR (400 MHz, D$_2$O) δ 2.32 (m, 1H), 2.42 (m, 1H), 3.45 (dd, J=12.7, 4.4 Hz, 1H), 3.79 (dd, J=12.7, 6.8 Hz, 1H), 3.84 (s, 2H), 4.27 (dd, J=10.3, 6.3 Hz, 1H), 4.37 (m, 1H), 4.48 (d, J=12.3 Hz, 1H), 4.67 (m, 1H), 7.06 (d, J=7.8 Hz, 1H), 7.31 (s, 1H), 7.39 (d, J=7.8 Hz, 1H), 7.48 (t, J=7.3 Hz, 2H), 7.55 (t, J=7.3 Hz, 2H), 7.71 (d, J=7.3 Hz, 2H).

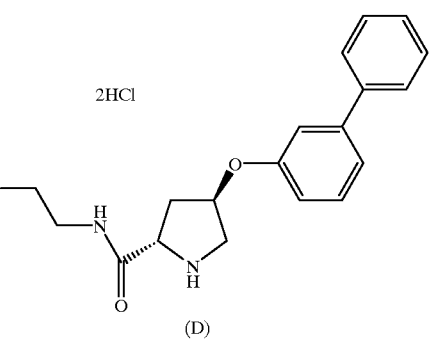

(D)

Compound D602 (A)–(F)

TYPE VI

Compound D601 (A)–(D)

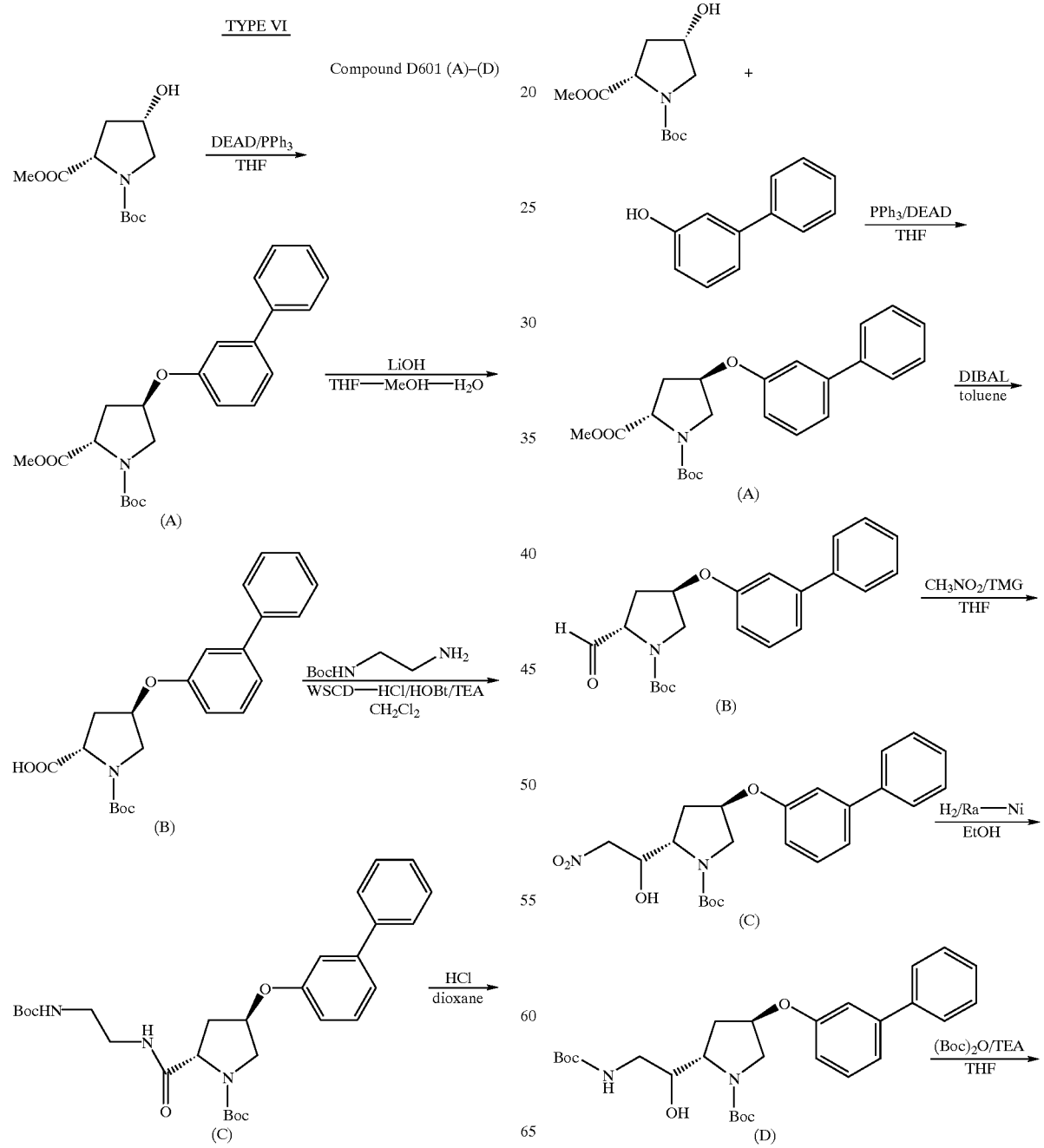

-continued

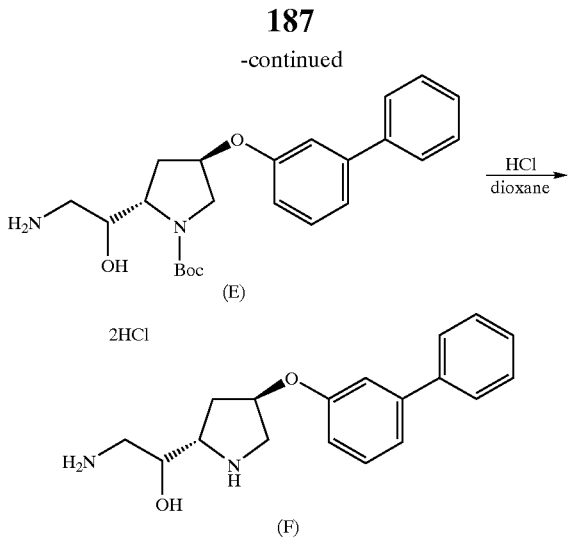

Compound D601—trans-4-(3-Biphenyloxy)-L-Proline 2-Aminoethylamide Dihydrochloride (A) trans-4-(3-Biphenyloxy)-N-tert-Butoxycarbonyl-L-Proline Methel Ester Diethyl azodicarboxylate (DEAD), (2.32 mL) was added to a mixture of cis-4-hydroxy-N-tert-butoxycarbonyl-L-proline methyl ester (3.00 g), 3-phenylphenol (2.19 g), and triphenyl phosphine (3.37 g) in tetrahydrofuran (90 mL) under argon at room temperature. After stirring at room temperature for 19 hr, the mixture was evaporated in vacuo. The residue was purified by silica gel column chromatography (hexane:ethyl acetate=10:1, v/v) to afford title compound (912 mg): $^1$H NMR (400 MHz, CDCl$_3$) δ 1.43 (s, 9H), 2.25 (m, 1H), 2.59 (m, 1H), 3.75 (s, 3H), 3.79–3.84 (m, 2H), 4.48 (m, 1H), 4.97 (m, 1H), 6.85 (m, 1H), 7.07 (s, 1H), 7.21 (m, 1H), 7.35 (m, 2H), 7.42 (m, 2H), and 7.55 (m, 2H).

(B) trans-4-(3-Biphenyloxy-N-tert-Butoxycarbonyl-L-Proline

Lithium hydroxide monohydrate (19 mg) was added to a solution of trans-4-(3-biphenyloxy)-N-tert-butoxycarbonyl-L-proline methyl ester A, (148 mg) in tetrahydrofuran (2 mL)-methanol 1 mL-water (1 mL) at 0° C. The mixture was lo stirred at room temperature for 3 hr. The reaction mixture was acidified with 10% citric acid and extracted with chloroform. The organic layer was washed with brine, dried over anhydrous sodium sulfate and evaporated in vacuo to give the titled compound (141 mg).

(C) trans-4-(3-Biphenyloxy)-N-tert-Butoxycarbonyl-L-Proline 2-(N-tert-Butoxycarbonylamino)ethylamide Triethylamine (56 μL), 1-hydroxybenzotriazole (25 mg), and 1-(3-dimethylaminopropyl)-3-ethylcarbodiimide hydrochloride (78 mg) were added to a solution of trans-4-(3-biphenyloxy)-N-tert-butoxycarbonyl-L-proline (B), (141 mg) and tert-butyl N-(2-aminoethyl)carbamate (65 mg) in dichloromethane (3 mL). After stirring at room temperature overnight, the reaction mixture was diluted with chloroform and washed with saturated sodium hydrogen carbonate and brine. The organic layer was dried over anhydrous sodium sulfate and evaporated in vacuo. The residue was purified by silica gel column chromatography chloroform:methanol=100:1, v/v to give the titled compound (175 mg) as a colorless foam: $^1$H NMR (400 MHz, CDCl$_3$) δ 1.45 (s, 9H), 2.37 (m, 1H), 2.59 (m, 1H), 3.28 (m, 1H), 3.29 (s, 2H), 3.40 (m, 1H), 3.73 (m, 2H), 4.41 (m, 1H), 5.01 (m, 1H), 5.18 (m, 1H), 6.86 (m, 2H), 7.08 (s, 1H), 7.20 (d, J=7.3 Hz, 1H), 7.35 (t, J=7.3 E4z, 2H), 7.43 (t, J=7.3 Hz, 2H), and 7.56 (d, J=7.3 Hz,2H).

(D) trans-4-(3-Biphenyloxy)-L-Proline 2-Aminoethylamide trans-4-(3-Biphenyloxy) N-tert-butoxycarbonyl-L-proline 2-(N-tert-butoxycarbonylamino)ethylamide (C, 175 mg) was dissolved in 4 N hydrogen chloride in 1,4-dioxane (3 mL). After stirring for 2 hr, the reaction mixture was evaporated in vacuo to give a white solid. The solid was washed with ether to afford the titled compound (118 mg): $^1$H NMR (400 MHz, D$_2$O) δ 2.43 (m, 1H), 2.83 (m, 1H), 3.22 (m, 2H), 3.57 (m, 1H), 3.66 (m, 1H), 4.69–4.84 (m, 3H), 5.44 (m, 1H), 7.08 (d, J=8.3 Hz, 1H), 7.32 (s, 1H), 7.43 (d, J=7.8 Hz, 1H), 7.46–7.58 (m, 4H), and 7.73 (m, 2H).

Compound D602—(2S,4R)-2-(2-Amino-1-hydroxyethyl)-4-(3-biphenyloxy)pyrrolidine Dihydrochloride (A) N-tert-Butoxycarbonyl-trans-4-(3-Biphenyloxy)-L-Proline Methyl Ester A solution of diethylazodicarboxylate (829 μL) in tetrahydrofuran (10 mL) was added to a cold (−15° C.) stirred solution of N-tert-butoxycarbonyl-trans-4-hydroxy-L-proline (1.23 g), 3-phenylphenol (896 mg), and triphenyl phosphine (1.38 g) in tetrahydrofuran (30 mL) under argon, After stirring at room temperature for 15.5 hr, the solvent was evaporated and coevaporated several times with toluene in vacuo. The residue was diluted with toluene and precipitated solids were removed by filtration, which was washed with toluene. The combined organic layers were evaporated in vacuo and the residue was purified by silica gel column chromatography (ethyl acetate:hexane=1:10, v/v) to give title compound (837 mg): $^1$H-NMR (400 MHz, CDCl$_3$) δ 1.36–1.50 (m, 9H), 2.18–2.29 (m, 1H), 2.51–2.64 (m, 1H), 3.68–3.89 (m, 5H), 4.40–4.56 (m, 1H), 4.91–5.01 (m, 1H), 6.79–6.87 (m, 1H), 7.04–7.10 (m, 1H), 7.17–7.24 (m, 1H), 7.29–7.39 (m, 2H), 7.39–7.49 (m, 2H), and 7.49–7.60 (m, 2H).

(B) (2S,4R)-4-(3-Biphenyloxy)-N-tert-Butoxycarbonyl-2-Pyrrrolidinecarboxaldehade A 1.0 M solution of diisobutylaluminum hydride in hexane (2.32 mL) was added to a stirred solution of N-tert-butoxycarbonyl-trans-4-(3-biphenyloxy)-L-proline methyl ester (A, 820 mg) at −78° C. under argon. After stirring the same temperature for 2 h, a 1.0 M solution of diisobutylaluminum hydride in hexane (843 μL) was added. And after stirring at the same temperature for 1 h, a 1.0 M solution of diisobutylaluminum hydride in hexane (421 μL) was added. Finally after stirring at the same temperature for 1 hr, the reaction mixture was quenched with saturated ammonium chloride. The precipitated solids were removed by filtration. The organic layer was evaporated in vacuo. The residue was diluted with saturated ammonium chloride and extracted with chloroform. The organic layer was dried over anhydrous sodium sulfate and evaporated in vacuo to give crude the titled compound (754 mg), which was used in the subsequent step.

(C) (2S,4R)-2-(2-Nitro-1-Hydroxyethyl)-4-(3-Biphenyloxy)-N-tert-Butoxycarbonylpyrrolidine 1,1,3,3-Tetramethylguanidine (52 μL) and nitromethane (222 μl) were added to a solution of crude (2S,4R)-4-(3-biphenyloxy)-N-tert-butoxycarbonyl-2-pyrrolidinecarboxaldehyde (B, 754 mg) in tetrahydrofuran (15 mL). The mixture was stirred at room temperature for 3 hr and evaporated in vacuo. The residue was diluted with ethyl acetate and washed with brine. The organic layer was dried over anhydrous sodium sulfate and evaporated in vacuo to give crude the titled compound (877 mg), which was used in the subsequent step.

(D) (2S,4R)-2-(2-Amino-1-Hydroxyethyl)-4-(3-Biphenyloxy)-N-tert-Butoxycarbonylpyrrolidine A mixture of crude (2S,4R)-2-(2-nitro-1-hydroxyethyl)-4-(3-biphenyloxy)-N-tert-butoxycarbonylpynrolidine (C, 877 mg) and Raney-Ni (100 mg) in ethanol (20 mL) was stirred at room temperature for 17 hr under hydrogen. The catalysts were removed by filtration and washed with ethanol. The combined organic layers were evaporated in vacuo to give crude the titled compound (730 mg), which was used in the subsequent step.

(E) (2S,4R)-2-(2-N-tert-Butoxycarbonylamino-1-Hydroxyethyl)-4-(3-Biphenyloxy)-N-tert-Butoxycarbonylpyrrolidine The title compound (389 mg) was similarly prepared, as described in Compound101 (N), except the starting material was crude (2S,4R)-2-(2-amino-1-hydroxyethyl)-4-(3-biphenyloxy)-N-tert-butoxycarbonylpyrrolidine (D, 730 mg):$^1$H NMR (400 MHz, CDCl$_3$) δ 1.44 (s, 18H), 2.13–2.23 (m, 1H), 2.33–2.44 (m, 1H), 2.90–3.00 (m, 1H), 3.40–3.55 (m, 1H), 3.50 (dd, J=4.2, 12.7 Hz, 1H), 3.70 (br, 1H), 3.84 (d, J=12.7 Hz, 1H), 4.19–4.28 (m, 1H), 4.78–4.86 (m, 1H), 4.89 (br, 1H), 5.28–5.36 (m, 1H), 6.84 (dd, J=2.4, 8.3 Hz, 1H), 7.07 (br, 1H), 7.21 (d J=7.3 Hz, 1H), 7.35 (t J=7.8 Hz, 1H), 7.44 (t J=7.8 Hz, 1H), and 7.57 (d, J=7.8 Hz, 2H).

(F) (2S,4R)-2-(2-Amino-1-hydroxyethyl)-4-(3-Biphenyloxy)pyrrolidine Dihydrochloride The title compound (120 mg) was similarly prepared, as described in Compound101 (Q), except the starting material was (2S,4R)-2-(2-N-tert-butoxycarbonylamino-1-hydroxyethyl)-4-(3-biphenyloxy)-N-tert-butoxycarbonylpyrrolidine (E, 199 mg): $^1$H NMR (400 MHz, D$_2$O) δ 2.17–2.27 (m, 1H), 2.33 (dd, J=6.3, 14.2 Hz, 1H), 2.86 (dd, J=10.3, 13.2 Hz, 1H), 2.87 (dd, J=10.3, 13.2 Hz, 1H), 3.13 (dd, J=2.4, 13.2 Hz), 3.59 (d, J=2.4 Hz, 2H), 4.00–4.07 (m, 1H), 4.28–4.36 (m, 1H), 5.24–5.32 (m, 1H), 6.91–6.97 (m, 1H), 7.18 (br, 1H), 7.29 (d, J=7.8 Hz, 1H), 7.32–7.47 (m, 4H), and 7.59 (d, J=7.6 Hz, 2H); IR (KBr) 3305, 2875, 2430, 1597, 1570, 1508, 1475, 1454, and 1417 cm$^{-1}$; mass spectrum (EI+) m/e 299 (M+1); Anal. Calcd for C$_{18}$H$_{22}$N$_2$O$_2$.2HCl: C, 58.23; H, 6.52; N, 7.54. Found: C, 58.00; H, 6.62; N, 6.81.

TYPE VII

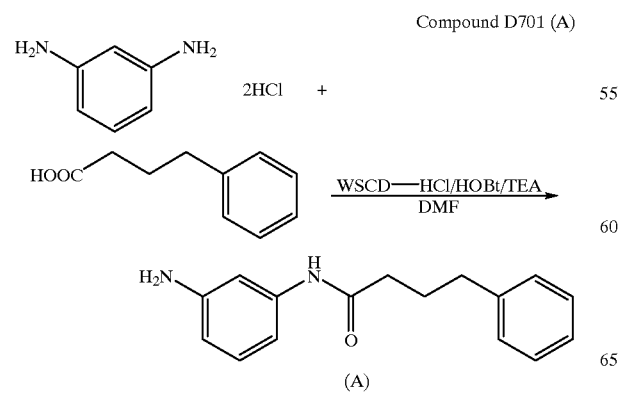

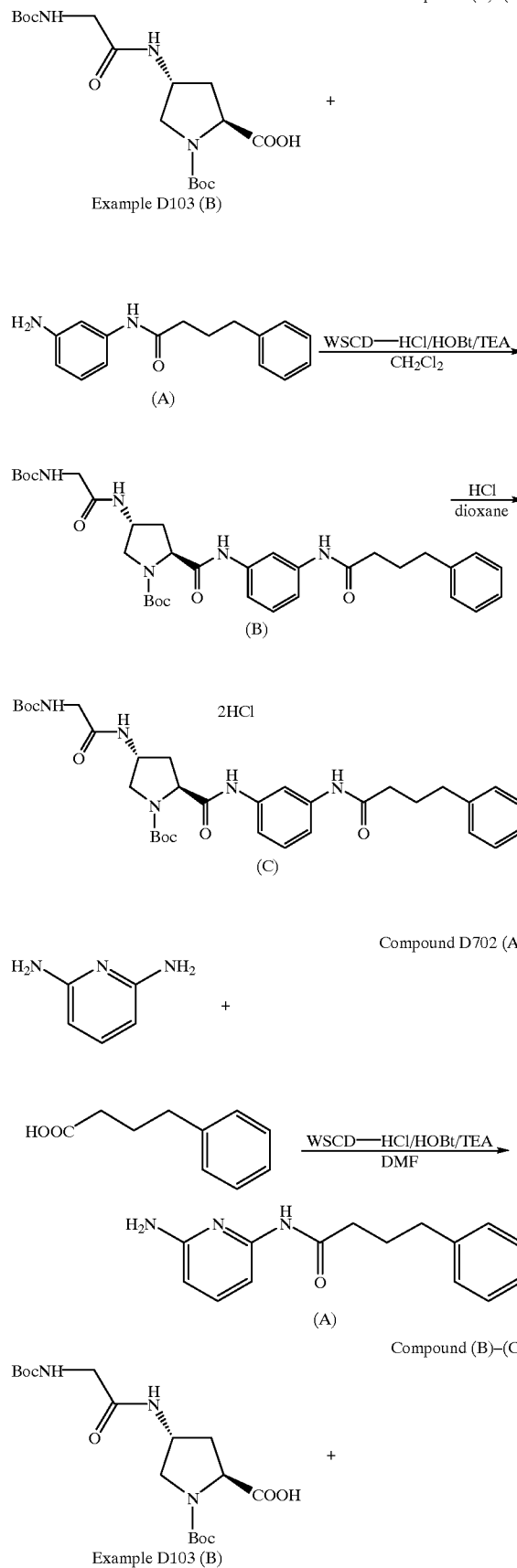

-continued

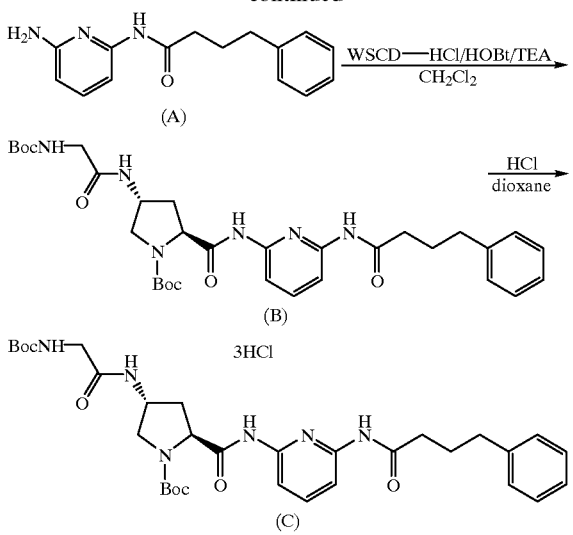

Compound D701—1-(N-trans-4-Glycylamino-L-Prolylamino)-3-(4-Phenylpropanoylamino)benzene Dihydrochloride (A) 3-[4-Phenylpropanoylamino)aniline 1-(3-Dimethylaminopropyl)-3-ethylcarbodiimide hydrochloride (1.17 g), 1-hydroxy-benzotriazole (0.16 g), and triethylamine (1.23g) were added to a mixture of 3,5-diaminobenzene dihydrochloride (1.09 g) and 4phenylbutyric acid (1.00 g) in N,N-dimethylformamide (10 mL). After stirring at room temperature for 21 hr, the reaction mixture was diluted with ethyl acetate and washed with water. The organic layer was extracted with 1 N hydrochloric acid and the aqueous layer was neutralized with sodium hydrogen carbonate. The aqueous layer was extracted with chloroform. The organic layer was dried over anhydrous sodium sulfate, then evaporated in vacuo to give the titled compound (0.22g): $^1$H NMR (400 MHz, CDCl$_3$) δ 1.99 (quint, J=7.3 Hz, 2H), 2.27 (t, J=7.3 Hz, 2H), 2.64 (t, J=7.3 Hz, 2H), 6.36 (d, J=6.3 Hz, 1H), 6.70 (d, J=7.8 Hz, 1H), 7.02 (t, J=7.8 Hz, 1H), 7.09 (s, 1H), 7.1–7.2 (m, 3H), 7.26 (t, J=7.3 Hz, 2H).

(B) 1-[trans-(4-N-tert-Butoxycarbonylglycylamino)-1-N-tert-Butoxycarbonyl-L-Prolylamino]-3-[4-Phenylpropanoylamino)benzene 1-(3-Dimethylaminopropyl)-3-ethylcarbodiimide hydrochloride (82 mg) and 1-hydroxybenzotriazole (9 mg) was added to a mixture of 3-(4-phenylpropanoylamino)aniline (A, 84 mg) and trans-4-(N-tert-butoxycarbonylglycylamino)-N-tert-butoxycarbonyl-L-proline (Compound D103 (B), 139 mg) in dichloromethane (10 mL). After the mixture was sired at room temperature for 17 hr, diluted with chloroform, then washed with sodium hydrogen carbonate and water. The organic layer was dried over anhydrous sodium sulfate, and evaporated in vacuo. The residue was purified by silica gel column chromatography (chloroform:methanol=49:1 v/v) to give the titled compound (177 mg): $^1$H NMR (400 MHz, CDCl$_3$) δ 1.45 (s, 18H), 2.04 (quintet, J=7.3 Hz, 2H), 2.34 (t, J=7.3 Hz, 2H), 2.69 (t, J=7.3 Hz, 2H), 2.7–3.5 (m, 2H), 3.6–3.9 (m, 4H), 4.44.6 (m, 2H), 7.17.7 (m, 9H).

(C) 1-(trans-4-Glycylamino-L-Prolylamino -3-(4-Phenylpropanoylamino)benzene Dihydrochloride A solution of 4 N hydrochloric acid in 1,4-dioxane (5 mL) was added to 1-[trans-(4-N-tert-butoxycarbonylglycylamino)-1-N-tert-butoxycarbonyl-L-prolylamino]-3-(4-phenylpropanoylamino)benzene (B, 163 mg) and stirred at room temperature for 2 hr. The mixture was diluted with ether to give a precipitate, which was washed with ether to give the titled compound (121 mg) as a powder: $^1$H NMR (400 MHz, D$_2$O) δ 1.9–2.1(m, 2H), 2.3–2.4(m, 2H), 2.5–2.6(m, 2H), 2.6–2.7(m, 2H), 3.46(dd, J=4.9,12.7 Hz, 1H), 3.7–3.9(m, 3H), 4.5–4.7(m, 1H), 4.7–4.8(m, 1H), 7.14(d, J=7.8 Hz, 1H), 7.2–7.5(m, 7H), 7.64(d, J=2.0 Hz, 1H).

Compound D702—2-(trans-4-Glycylamino-L-Prolylamino)-6-(4-Phenylpropanoylamino)Pyridine Trihydrochloride (A) 2-Amino-6-(4-Phenylpropanoylamino)pyridine 1-(3-Dimethylaminopropyl)-3-ethylcarbodiimide hydrochloride (1.17 g), 1-hydroxybenzotriazole(0.16 g), and triethylamine (1.23 g) were added to a mixture of 2,6-diaminopyridine (0.66 g) and 4-phenylbutyric acid (1.00 g) in N,N-dimethylformamide (10 mL). After stirring at room temperature for 21 hr, the reaction mixture was diluted with ethyl acetate and washed with water. The organic layer was dried over anhydrous sodium sulfate, then evaporated in vacuo. The residue was purified by silica gel column chromatography (chloroform:methanol=99:1, v/v) to give the titled compound (1.12 g): $^1$H NMR (400 MHz, CDCl$_3$) δ 2.02 (quintet, J=7.8 Hz, 2H), 2.31(t, J=7.3 Hz, 2H), 2.66 (t, J=7.3 Hz, 2H), 6.22 (d, J=7.8 Hz, 1H), 7.1–7.3 (m, 6H), 7.43 (t, J=7.8 Hz, 1H), 7.5–7.6 (m, 1H).

(B) 2-[trans-(4-N-tert-Butoxycarbonylglyclamino)-1-tert-Butoxycarbonyl-L-Prolylamino]-6-(4-Phenylpropanoylamino)pyridine 1-(3-Dimethylaminopropyl)-3-ethylcarbodiimide hydrochloride (230 mg) and 1-hydroxybenzotriazole (26 mg) was added to a mixture of 2-amino-6-(4-phenylpropanoylamino) pyridine (A, 118 mg) and trans-4-N-tert-butoxycarbonylglycylamino-1-tert-butoxycarbonyl-L-proline(Compound D103 (B), 196 mg) in dichloromethane (10 mL). After the mixture was stirred at room temperature for 41 hr, diluted with chloroform, then washed with sodium hydrogen carbonate and water. The organic layer was dried over anhydrous sodium sulfate, and evaporated in vacuo. The residue was purified by silica gel column chromatography (chloroform:methanol=49:1, v/v) to give the titled compound (151 mg): $^1$H NMR (400 MHz, CDCl$_3$) δ 1.46 (s, 18H), 2.06 (quintet, J=7.3 Hz, 2H), 2.39 (t, J=7.3 Hz, 2H), 2.71 (t, J=7.3 Hz, 2H), 2.8–3.5 (m, 2H), 3.7–3.9 (m, 4H), 4.4–4.6 (m, 2H), 7.1–7.9 (m, 8H).

(C) 2-(trans-4-Glycylanino-L-Prolylamino)-6-(4-Phenylpropanoylamino)pyridine Trihydrochloride A solution of 4 N hydrochloric acid in 1,4-dioxane (5 mL) was added to 2-[(trans-4-(N-tert-butoxycarbonylglycylamino)-1-N-tert-butoxycarbonyl-L-prolylamino]-6-( 4-phenylpropanoylamino)pyridine (B, 133 mg) and stirred at room temperature for 2 hr. The mixture was diluted with ether to give a precipitate, which was washed with ether to yield the title compound (111 mg) as a powder: $^1$H NMR (400 MHz, D$_2$O) δ 2.07 (quintet, J=6.8 Hz, 2H), 2.54 (t, J=6.8 Hz, 2H), 2.64 (t, J=6.8 Hz, 2H), 2.73 (t, J=6.8 Hz, 2H), 3.4–3.6 (m, 1H), 3.84.0 (m, 3H), 4.5–4.7 (m, 1H), 4.7–4.9 (m, 1H), 7.1–7.2 (m, 1H), 7.2–7.4 (m, 6H), 8.10 (t, J=8.3 Hz, 1H).

TYPE VIII

Compound D801 (A)–(B)

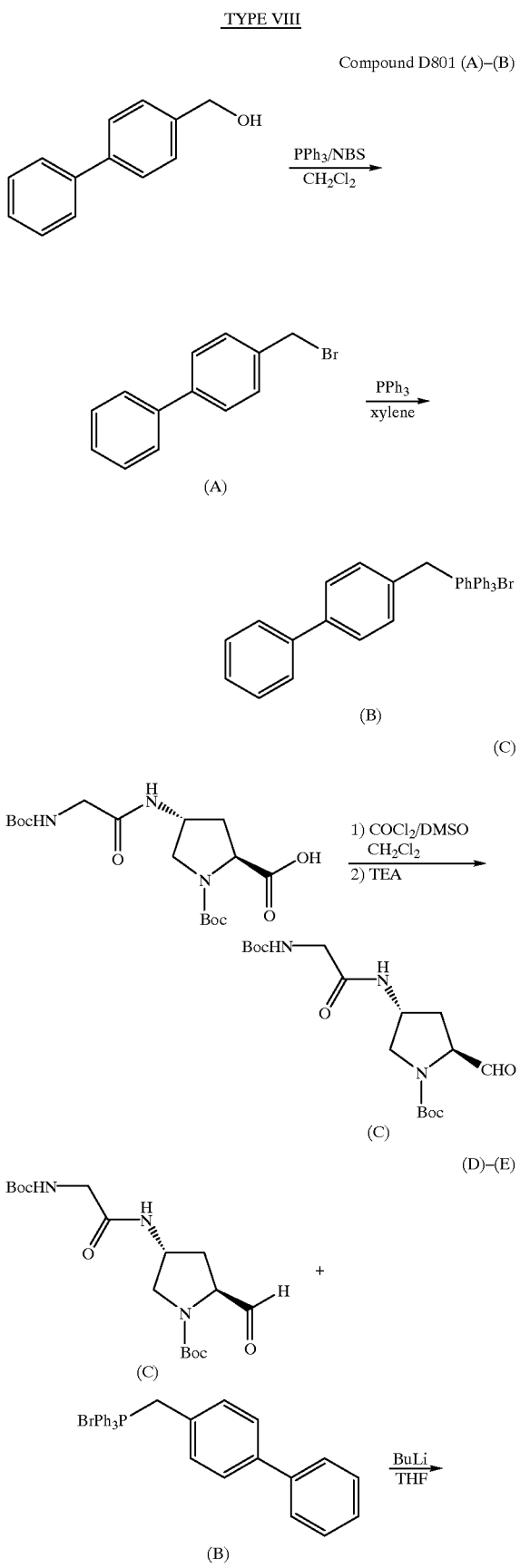

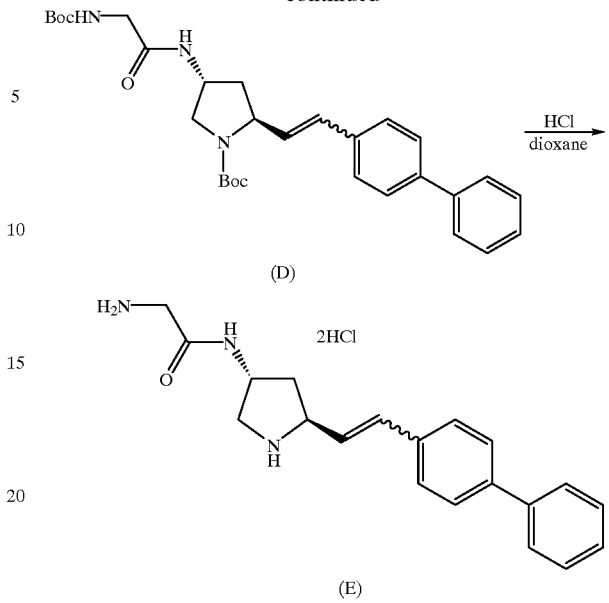

Compound D801—(2S,4R)-4-Glycylamino-2-((E and Z)-4-Phenyistyryl)-pyrrolidine Dihydrochloride (A) 4-Phenylbenzyl Bromide Triphenylphosphine (1.58 g) and N-bromosuccinimide (1.07 g) were added to a stirred solution of 4-hydroxymethylbiphenyl (1.01 g) in dichloromethane (10 mL) under nitrogen. The mixture was stirred at room temperature for 15 hr and evaporated in vacuo. The residue was diluted with chloroform, and washed with saturated sodium hydrogencarobonate, and brine. The organic layer was dried over anhydrous sodium sulfate and evaporated in vacuo. The residue was purified by silica gel column chromatography (ethyl acetate:hexane=1:100 to 1:50, v/v) to give the titled compound (1.26 g) as colorless crystals: $^1$H-NMR (400 MHz, CDCl$_3$) δ 4.55 (s, 2H), 7.33–7.38 (m, 1H), 7.41–7.49 (m, 4H), and 7.54–7.60 (m, 4H).

(B) 4-Phenylbenzyltriphenylphosphonium Bromide

Triphenylphosphine (1.34 g) was added to a stirred solution of 4-phenylbenzyl bromide (1.26 g) in xylene (20 mL). The mixture was refluxed for 19 hr to a give white solid. The solid was washed with toluene and hexane to afford the titled compound (2.35 g).

(C) (2S,4R)-N-tert-Butoxycarbonyl-4-(N-tert-Butoxycarbonylglycylamino)-2-Pyrrolidinecarboxaldehyde The following reaction was carried under argon. Dimethyl sulfoxide (288 µL) was added to a stirred solution of oxalyl chloride (177 mL) in dichloromethane (3 mL) at −78° C. After stirring at the same temperature for 15 min, a solution of (2S,4R)-N-tert-butoxycarbonyl-4-(N-tert-butoxycarbonylglycylamino)-2-hydroxymethylpyrrolidine (151 mg) in dichloromethane (3 mL) was added. The mixture was stirred at −78° C. for 2 hr, and triethylamine (848 µL) was added to the reaction mixture. The mixture was stirred at 0° C. for 1 hr, quenched with saturated ammonium chloride, and extracted with dichloromethane. The organic layer was dried over anhydrous sodium sulfate and evaporated in vacuo. The residue was purified by silica gel column chromatography (chloroform then chloroform:methanol=

195

99:1 to 97:3, v/v) to give the titled compound (147 mg) as a colorless foam.

(D) (2S,4R)-N-tert-Butoxycarbonyl-4-(N-tert-Butoxycarbonylglycylamino)-2-((E and Z)-4-Phenylstyryl)pyrrolidine A solution of 1.63 M butyllithium in hexane (605 µL) was added to a stirred suspension of 4-phenylbenzyltriphenylphosphonium bromide (B, 502 mg) in tetrahydrofuran (10 mL) at −78° C. under argon. The mixture was stirred at the same temperature for 30 min, and a solution of (2S, 4R)-N-tert-butoxycarbonyl-4-(N-tert-butoxycarbonylglycylamino)-2-pyrrolidinecarboxaldehyde (C, 147 mg) in tetrahydrofuran (3 mL) was added. The mixture was stirred at the same temperature for 2 hr, then at 0° C. for 1.5 hr and at room temperature for 18 hr. After the mixture was evaporated in vacuo, the residue was diluted with ethyl acetate and washed with water. The aqueous layer was extracted with chloroform. The organic layer was dried over anhydrous sodium sulfate and evaporated in vacuo. The residue was purified by silica gel column chromatography (chloroform then chloroform:methanol=99:1, v/v) to give the titled compound (143 mg) as a colorless foam. The compound appears as a mixture of stereoisomers (E:Z=2:1) by $^1$HNMR.

(E) 2S,4R)-4-Glycylamino-2-((E and Z)-4-Phenylstyryl)pyrrolidine Dihydrochloride The title compound (93.5 mg) as a mixture of stereoisomers (E:Z=ca. 2:1 by $^1$H NMR) was similarly prepared, as described in Compound D101 (Q), except the starting material was (2S, 4R)-N-tert-butoxycarbonyl-4-(N-tert-butoxycarbonylglycylamino)-2-((E and Z)-4-phenylstyryl)pyrrolidine (D, 143 mg):$^1$H NMR (400 MHz, D$_2$O) δ 2.32–2.44 (m, 2H), 3.29–3.42 (m, 1H), 3.72–3.86 (m, 3H), 4.54–4.70 (m, 2H), 5.79–5.87 and 6.33–6.43 (each m, total 1H), 6.94 (d, J=15.6 Hz, 2/3H), 7.01 (d, J=11.2 Hz, 1/3H), 7.40–7.50 (m, 2H), 7.50–7.60 (m, 2H), 7.60–7.68 (m, 1H), and 7.68–7.83 (m, 4H); IR (KBr) 3396, 3205, 2945, 1701, 1685, 1554, 1487, 1473, 1448, 1439, and 1398 cm$^{-1}$; mass spectrum (EI+) m/e 321 (M); Anal. Calcd for C$_{20}$H$_{23}$N$_3$O.2HCl.1.5H$_2$O: C, 57.01; H, 6.70; N, 9.97. Found: C, 56.97; H, 6.29; N, 9.88.

TYPE IX
Examples for Table 7
Scheme 1

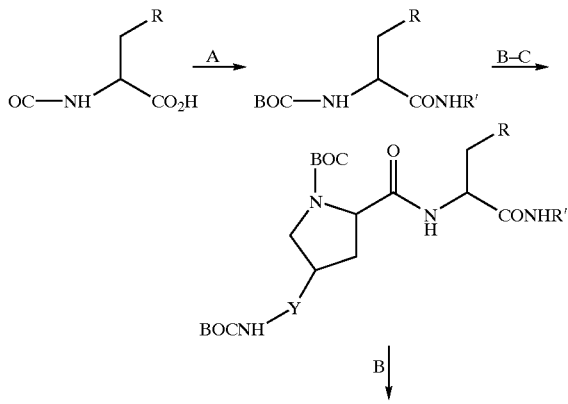

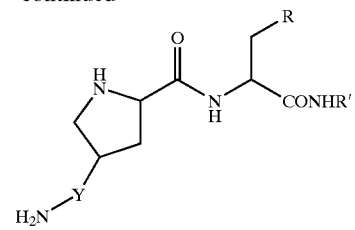

a) amide coupling conditions;
b) CF$_3$COOH;
c) BOC-protected amino acid, coupling agent Compound M1: (2R,4S)-4-(2-Aminoacetamido)-N-[(1R)-3-phenyl-1-(3-quinolylcarbamoyl)propyl]-2-pyrrolidinecarboxamide This compomd was prepaed according to Scheme 1, using the methods described for Compound D201 and coupling the amine from D201(B) with trans-4-(N-tert-butoxycarbonylglycyl)amino-N-tert-butoxycarbonyl-D-proline, to give the title compound: $^1$H NMR (400 MHz, D$_2$O): δ 2.38–2.45 (2H, m), 2.83–3.10 (2H, m), 3.48–3.59 (1H, m), 3.80–3.9 (1H, m), 4.58–4.70 (2H, m), 4.72–4.79 (1H, m), 7.15–7.20 (1H, m), 7.25–7.40 (5H, m), 7.94–8.05 (1H, d), 8.15–8.18 (1H, d) 8.20–8.28 (2H, m), 8.90 (1H, s), 9.25 (1H, s); MS m/e 475 (80, M+1).

Compound M2: (2R,4S)-4-(2-Aminoacetamido)-N-[(1R)-3-phenyl-1-[(3-phenyl)propylcarbamoyl]propyl]-2pyrrolidinecarboxamide This compound was pred as for Compound M1, but repacig 3-aminoquinoline with 3-phenylpropylamine.

Compound M3: (2S,4R)-4-(2-Aminoacetamido)-N-[(1R)-3-pheny-1-(3-quinolylcambamoyl)propyl]-2-pyrrolidinecarboxamide This compound was prepared as for Compound M1, replacig trans-4-(N-tert-butoxycarbonylglycyl)amino-N-tert-butoxycarbonyl-D-proline with trans-4-(N-tert-butoxycarbonylglycyl)amino-N-tert-butoxycarbonyl-L-proline.

Compound M4: (2S,4R)-4-[(2R)-2-Aminoacetamido]-N-[(1R)-3-pheny-1-(3-quinolylcambamoyl)propyl]-2-pyrrolidinecarboxamide This compound was prepared as for Compound M1, replacing trans-4-(N-tert-butoxycarbonylglycyl)amino-N-tert-butoxycarbonyl-D-proline with trans-4-(N-tert-butoxycarbonyl-D-alanyl)amino-N-tert-butoxycarbonyl-L-proline.

Compound M5: (2S,4R)-4-[(2R)-2-Aminoacetamido]-N-[(1R)-3-pheny-1-(3-quinolylcambamoyl)propyl]-2-pyrrolidinecarboxamide This compound was prepared as for Compound M1, replacing trans-4-(N-tert-butoxycarbonylglycyl)amino-N-tert-butoxycarbonyl-D-proline with trans-4-(N-tert-butoxycarbonyl-D-alanyl)amino-N-tert-butoxycarbonyl-D-proline.

Compound M6: (2S,4R)-4-[3-Aminoacetamido]-N-[(1R)-3-pheny-1-(3-quinolylcambamoyl)propyl]-2-pyrrolidinecarboxamide This compound was prepared as for Compound M1, replacng trans-4-(N-tert-butoxycarbonylglycyl)amino-N- tert-butoxycarbonyl-D-proline with trans-4-(N-tert-butoxycarbonyi-β-alanyl)amino-N-tert-butoxycarbonyl-D-proline.

Compound M7: (2S,4R)-4-Amino-N-[(1R)-3-pheny-1-(3-quinolylcambamoyl)propyl]-2-pyrrolidinecarboxamide This compound was prepared as for Compound M1, coupling the amine from D201(B) with trans-4-(N-tert-butoxycarbonyl)amino-N-tert-butoxycarbonyl-L-proline.

Compound M8: (2S,4R)-4-(2-Aminoacetamido)-N-[(1R)-3-methyl-1-(3-quinolylcambamoyl)butyl]-2-pyrrolidinecarboxamide This compound was prepared as for Compound M3, starting from N-tert-butoxycarbonyl-D-leucine insad of N-tert-butoxycarbonyl-D-homopbenylalanine.

Compound M9: (2S,4R)-4-(2-Amino-N-methylacetamido)-N-[(1R)-3-pheny-1-(3-quinolylcambamoyl)propyl]-2-pyrrolidinecarboxamide Trans-4-(N-tert-butoxycarbonylglycyl)amino-N-tert-butoxycarbonyl-L-proline methyl ester was N-methylated (NaH, MeI, THF) and then coupled with the amine from D201(B), as in Compoumd M1.

Compound M10: (2S,4R)-4-(2-Aminoacetamido)-N-[(1R)-3-methyl-1-(6-methoxy-8-methyl-3-quinolylcarbamoyl)butyl]-2-pyrrolidinecarboxamide This compound was prepared as for Compound M8, replacing 3-aminoquinoline with 3-amino-6-methoxy-8-methylquinoline (Erickson, E. H.; Hainline, C. F.; Lenon, L. S.; J. Med. Chem., 1979, 22, 816–823).

Compound M11: (2S,4R)-4-(2-Aminoacetamido)-N-[(1R)-3-pheny-1-(6,7-dimethyl-3-quinolylcambamoyl)propyl]-2-pyrrolidinecarboxamide This compound was prepared as for Compound M3, repacing 3-aminoqunoline with 3-amino-6,7-dimethylquinoline (Ericson, E. H.; Hainline, C. F.; Lenon, L. S.; J. Med. Chem., 1979, 22, 816–823).

Compound M12: (2S,4R)-4-(2-Aminoacetamido)-N-[(1R)-2-(4-methoxyphenyl)-1-(3-quinolylcambamoyl)ethyl]-2-pyrrolidinecarboxamide This compound was prepared as for Compound M3, starting from N-tert-butoxycarbonyl-O-methyl-D-tyrosine instead of N-tert-butoxycarbonyl-D-homophenylalanine.

Compound M13: (2S,4R)-4-(Aminomethyl)-N-[(1R)-3-methyl-1-(6-ethyl-3-quinolylcambamoyl)butyl]-2-pyrrolidinecarboxamide This compound was prepared as for Compound M8, replacing trans-4-(N-tert-butoxycarbonylglycyl)amino-N-tert-butoxycarbonyl-L-proline with trans-4-(N-tert-butoxycarbonylaminomethyl)-N-tert-butoxycarbonyl-D-proline, and 3-aminoquinoline with 3-amino-6-ethylquinoline (Erickson, E. H.; Hainline, C. F.; Lenon, L. S.; J. Med. Chem., 1979, 22, 816–823).

Compound M14: (2S,4R)-4-(Aminomethyl)-N-[(1R)-3-pheny-1-(6-ethyl-3-quinolylcambamoyl)propyl]-2-pyrrolidinecarboxamide This compound was prepared as for Compound M1, replacing trans-4-(N-tert-butoxycarbonylglycyl)amino-N-tert-butoxycarbonyl-D-proline with trans-4-(N-tert-butoxycarbonylaminomethyl)-N-tert-butoxycarbonyl-D-proline, and 3-aminoquinoline with 3-amino-6-ethylquinoline (Erickson, E. H.; Hainline, C. F.; Lenon, L. S.; J. Med. Chem., 1979, 22, 816–823).

Compound M15: (2S,4R)-4-(2-Aminoacetamido)-N-methyl-N-[(1R)-3-phenyl-1-(3-quinolylcarbamoyl)propyl]-2-pyrrolidinecarboxamide This compound was prepared as for Compound M1, replacing N-tert-butoxycarbonyl-D-homophenylalanine with N-tert-butoxycarbonyl-N-methyl-D-homophenylalanine (made by ement of N-tert-butoxycarbonyl-D-homophenylalanine with excess sodiun hydride and methyl iodide in THF).

Compound M16: (2S,4R)-4-(Aminomethyl)-N-[(1R)-3-phenyl-1-(3-quinolylcarbamoyl)propyl]-2-pyrrolidinecarboxamide This compound was prepared as for Compound M1, replacing trans-4-(N-tert-butoxycarbonylglycyl)amino-N-tert-butoxycarbonyl-D-proline with trans-4-(N-tert-butoxycarbonylaminomethyl)-N-tert-butoxycarbonyl-D-proline.

Compound M17: (2S,4R)-4-(2-Aminoacetamido)-N-[(1R)-3-phenyl-1-(3-quinolylcarbamoyl)propyl]-2-pyrrolidinecarboxamide This compound was prepared as for Compound M1, replacing trans-4-(N-tert-butoxycarbonylglycyl)amino-N-tert-butoxycarbonyl-D-proline with cis-4-(N-tert-butoxycarbonylglycyl)amino-N-tert-butoxycarbonyl-D-proline (made by analogy with compound D102(E), starting from the D-proline derivative).

Compound M18: (2S,4R)-4-(2-Aminoacetamido)-N-[(1R)-3-phenyl-1-(6-ethyl-3-quinolylcarbamoyl)propyl]-2-pyrrolidinecarboxamide This compound was prepared as for Compound M3, replacing 3-aminoquinoline with 3-amino-6-ethylquinoline.

Compound M19: (2S,4R)-4-(2-Aminoacetamido)-N-[(1R)-3-methyl-1-(6-ethyl-3-quinolylcarbamoyl)butyl]-2-pyrrolidinecarboxamide This compound was prepared as for Compound M8, replacing 3-aminoquinoline with 3-amino-6-ethylquinoline.

Compound M20: (2S,4R)-4-(2-Aminoacetamido)-N-[(1R)-2-(4-flourophenyl-1-(3-quinolylcarbamoyl)ethyl]-2-pyrrolidinecarboxamide This compound was prepared as for Compound M17, replacing N-tert-butoxycarbonyl-D-homophenylalanine with N-tert-butoxycarbonyl-D-4-fluorophenylalanine.

Compound M21: (2S,4R)-4-(2-Aminoacetamido)-N-[(1R)-2-(4-flourophenyl)-1-(3-quinolylcarbamoyl)ethyl]-2-pyrrolidinecarboxamide This compound was prepared as for Compound M3, replacing N-tert-butoxycarbonyl-D-homophenylalanine with N-tert-butoxycarbonyl-D-4-fluorophenylalanine.

Compound M22: (2S,4R)-4-(2-Aminoacetamido)-N-[(1R)-3-phenyl-1-(6-methoxy-8-methyl-3-quinolylcarbamoyl)propyl]-2-pyrrolidinecarboxamide The compound was prepared as for Compound M3, replacing 3-aminoquinolne with 3-amino-6-methoxy-8-methylquinoline.

Compound M23: (2S,4R)-4-(2-Aminoacetamido)-N-[(1R)-2-(4-hydroxyphenyl-1-(3-quinolylcarbamoyl)propyl]-2-pyrrolidinecarboxamide This compound was prepared as for Compound M3, starting from N-tert-butoxycarbonyl-D-tyrosine instead of N-tert-butoxycarbonyl-D-homophenylalanine.

Compound M24: (2S,4R)-4-(Aminomethyl)-N-[(1R)-3-phenyl-1-(3-quinolylcarbamoyl)propyl]-2-pyrrolidinecarboxamide This compound was prepared as for Compound M16, replacing trans-4-(N-tert-butoxycarbonylaminomethyl)-N-tert-butoxycarbonyl-D-proline trans-4-(N-tert-butoxycarbonylaminomethyl)-N-tert-butoxycarbonyl-L-proline.

Compound M25: (2S,4R)-4-(Aminomethyl)-N-[(1R)-2-(4-hydroxyphenyl-1-(6-ethyl-3-quinolylcarbamoyl)ethyl]-2-pyrrolidinecarboxamide This compound was prepared as for Compound M16, starting from N-tert-butoxycarbonyl-D-tyrosine instead of N-tert-butoxycarbonyl-D-homophenylaanine and coupling with 3-aminoylquinoline instead of 3-aminoquinoline.

Compound M26: (2S,4R)-4-(2-Aminoacetamido)-N-[(1R)-3-phenyl-1-(5-chloro-2-hydrozyphenylcarbamoyl)propyl]-2-pyrrolidinecarboxamide This compound was prepared as for Compound M3, coupling with 5-chloro-2-hydroxyaniline instead of 3-aminoquinoline.

Compound M27: (2S,4R)-4-(2-Aminoacetamido)-N-[(1R)-3-phenyl-1-(4,5-dimethyl-2-hydroxyphenylcarbamoyl)propyl]-2-pyrrolidinecarboxamide This compound was prepared as for Compound M3, coupling with 4,5diethyl-2-hydroxyaniie instead of 3-aminoquinoline.

Compound M28: (2S,4R)-4-(2-Aminoacetamido)-N-[(1R)-3-phenyl-1-(2-hydroxy-5-methylphenylcarbamoyl)propyl]-2-pyrrolidinecarboxamide This compound was prepared as for Compound M3, coupling with 2-hydroxy-5-methylaniline instead of 3-aminoquinoline.

Compound M29: (2S,4R)-4-(Aminomethyl)-N-[(1R)-3-phenyl-1-(6-quinolylcarbamoyl)propyl]-2-pyrrolidinecarboxamide This compound was prepared as for Compound M16, coupling with 6-aminoquinoline instead of 3-aminoquinoline.

Compound M30: (2S,4R)-4-(Aminomethyl)-N-[(1R)-3-phenyl-1-(8-quinolylcarbamoyl)propyl]-2-pyrrolidinecarboxamide This compound was prepared as for Compound M16, coupling with 8-aminoquinoline insteadof 3-aminoquinoline.

Compound M31: (2S,4R)-4-(Aminomethyl)-N-[(1R)-2-(4-fluorophenyl)-1-(3-quinolylcarbamoyl)ethyl]-2-pyrrolidinecarboxamide This compound was prepared as for Conpound M16, starting from N-tert-butoxycarbonyl-D-4-fluoropbenylalanine instead of N-tert-butoxycarbonyl-D-homophenylalanine.

Compound M32: (2S,4R)-4-(Aminomethyl)-N-[(1R)-3-phenyl-1-[(3-quinolylmethyl)carbamoyl]propyl]-2-pyrrolidinecarboxamide This compound was prepared as for Compound M16, coupling with 3-aminomethylqunoiine instead 3-aminoquinoline.

Compound M33: (2S,4R)-4-(Aminomethyl)-N-[(1R)-3-phenyl-1-[(3-quinolylmethyl)carbamoyl]propyl]-2-pyrrolidinecarboxamide This compound was prepared as for Compound M15, trans-4-(N-tert-butoxycarbonylaminomethyl)-N-tert-butoxycarbonyl-D-proline ead of trans-4-(N-tert-butoxycarbonylglycyl)amino-N-tert-butoxycarbonyl-L-proline.

Compound M34: (2S,4R)-4-(Aminomethyl)-N-methyl-N-[(1R)-3-phenyl-1-(3-quinolylcarbamoyl)propyl]-2-pyrrolidinecarboxamide This compound was prepared as for Compound M8, trans-4-(N-tert-butoxycarbonylaminomethyl)-N-tert-butoxycarbonyl-D-proline instead of trans-4-(N-tert-butoxycarbonylglycyl)amino-N-tert-butoxycarbonyl-L-proline.

Compound M35: (2S,4R)-4-(Aminomethyl)-N-[(1R)-3-phenyl-1-(6-flouro-3-quinolylcarbamoyl)propyl]-2-pyrrolidinecarboxamide This compound was prepared as for Compound M16, using 3-amino-6-fluoroquinoline instead of 3-aminoquinoline.

Compound M36: (2S,4R)-4-(Aminomethyl)-N-[(1R)-3-phenyl-1-(6-flouro-3-quinolylcarbamoyl)propyl]-2-pyrrolidinecarboxamide This compound was prepared as for Compoumd M34, starting from N-tert-butoxycarbonyl-D-homoleucine instead of from N-tert-butoxycarbonyl-D-leucine.

Compound M37: (2S,4R)-4-(Aminomethyl)-N-[(1R)-3-phenyl-1-(5-fluro-2-hydroxyphenylcarbamoyl)propyl]-2-pyrrolidinecarboxamide This compound was prepared as for Compound M16, coupling with 5-fluoro-2-hydroxyaniline instead of 3-aminoquinoline.

Compound M15: (2S,4R)-4-(Aminomethyl)-N-[(1R)-3-phenyl-1-(2-hydroxy-5-methylphenylcarbamoyl)propyl]-2-pyrrolidinecarboxamide This compound was prepared as for Compound M16, coupling with 2-hydroxy-5-methylaniline instead of 3-aminoquinoline.

Compound M39: (2S,4R)-4-(Aminomethyl)-N-[(1R)-3-phenyl-1-(5-chloro-2-hydroxyphenylcarbamoyl)propyl]-2-pyrrolidinecarboxamide This compound was prepared as for compound M16, coupling with 5-chloro-2-hydroxyaniline instes of 3-aminoquinoline.

Compound M40: (2S,4R)-4-(Aminomethyl)-N-methyl-N-[(1R)-3-methyl-1-(6-ethyl-3-quinolylcarbamoyl)butyl]-2-pyrrolidinecarboxamide This compound was prepared as for Compound M15, replacing N-tert-butoxycarbonyl-D-homophenylalanine with N-tert-butoxycarbonyl-N-methyl-D-leucine (made by treantment of N-tert-butoxycarbonyl-D-leucine with excess sodium hydride and methyl iodide in 1TF), trans-4-(N-tert-butoxycarbonylglycyl)amino-N-tert-butoxycarbonyl-L-proline with trans-4-(N-tert-butoxycarbonylaminomethyl)-N-tert-butoxycarbonyl-D-proline and coupling with 3-amino-6-ethylquinoline inst of 3-aminoquinoline.

Scheme 2

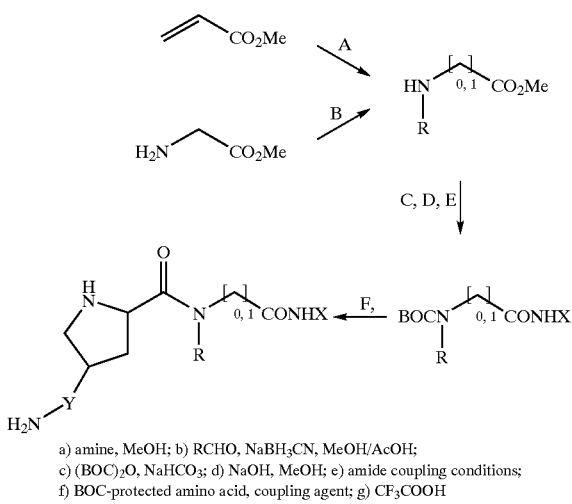

a) amine, MeOH; b) RCHO, NaBH$_3$CN, MeOH/AcOH;
c) (BOC)$_2$O, NaHCO$_3$; d) NaOH, MeOH; e) amide coupling conditions;
f) BOC-protected amino acid, coupling agent; g) CF$_3$COOH

Compound M41: (2S,4R)-4-(2-Aminoacetamido)-N-(2-phenylethyl)-N-(3-quinolylcarbamoyl)ethyl]-2-pyrrolidinecarboxamide This compound was prepared according to Scheme 2, using the following methods:
(A) ∃-N-(phenethyl)alanine methyl ester Methyl acrylate (23 mmol) was added to a solution of methanol (MeOH) (100 mL), phenethylamine (26 mmol) and acetic acid (AcOH) (2.3 mmol) at 0° C. The solution was stirred at room temperature for 14 hr, concentrated to dryness and the resultant oil adsorbed onto 5 g of silica gel and applied to a column prepacked with silica. Elution with CH$_2$Cl$_2$:MeOH:NH$_4$OH (89:9:2, v:v) gave the title compound (2.2 g, 46%): $^1$H NMR (CDCl$_3$) δ 2.50–2.53 (2H, t), 2.79–2.94 (6H, m), 3.66 (3H, s), 7.20–7.32 (5H, m).

(B) ∃-N-(phenethyl)-N-(tert-butoxycarbonyl)alanine methyl ester

The methyl ester from (A) (4.8 mmol) was dissolved in a mixture of water (H$_2$O) (40 mL) and 1,4-dioxane (40 mL). Sodium bicarbonate (NaHCO$_3$) (2 eq., 9.6 mmol) and di-tert-butyl dicarbonate (BOC$_2$O) (7.0 mmol) were added and the solution was stirred at room temperature for 14 hours. The mixture was concentrated in vacuo, neutralized to pH 4 with 5% citric acid (18 mL) and washed with ethyl acetate (EtOAc). The organic layer was collected, dried over sodium sulfate (Na$_2$SO$_4$), filtered and concentrated to dryness to afford the title compound (76%): $^1$H NMR (CDCl$_3$) δ 1.45 (9H, s), 2.45–2.6 (2H), 2.75–2.9 (2H, t), 3.4–3.5 (4H, m), 3.68 (3H, s), 7.20–7.30 (5H, m).

(C) ∃-N-(phenethyl)-N-(tert-butoxycarbonyl)alanyl-quinoline-3-amide

∃-N-phenethyl-N-tert-butoxycarbonyl-alanine methyl ester (2 mmol) was dissolved in methanol (30 mL) and 1M aqueous sodium hydroxide solution (NaOH) (4.0 mL, 4.0 mmol) was added. The reaction was stirred for 14 hr. After concentration in vacuo, the residue was dissolved in H$_2$O (25 mL). The pH of the solution was adjusted to 4 with 5% citric acid and the mixture was extracted with EtOAc (30 mL). The organic layer was dried over Na$_2$SO$_4$, filtered and concentrated to dryness to afford the acid (96%). This was coupled with 3-aminoquinoline using the method described in Compound D201(A), giving the amide in 60% yield: NMR (CDCl$_3$) δ 1.47 (9H, s), 2.71 (2H, s), 2.85–2.88 (2H, t), 3.46–3.50 (2H, t), 3.59–3.62 (2H, t), 7.18–7.33 (5H, m), 7.54–7.56 (1H, t), 7.56–7.64 (1H, t), 7.80–7.82 (1H, d), 8.04–8.06 (1H, d), 8.85–8.87 (2H, m).

(2S,4R)-4-(2-Aminoacetamido)-N-(3-quinolylcarbamoyl)ethyl]-2-pyrrolidinecarboxamide ∃-N-phenethyl-N-tert-butoxycarbonylalanyl-quinoline-3-amide (0.35 mmol) was dissolved in trifluoroacetic acid (TFA) (3 mL) and stirred at room temperature for 1 hr. The solution was concentrated to dryness, coevaporated twice with dichloromethane (CH$_2$Cl$_2$), suspended in CH$_2$Cl$_2$ (10 mL) and treated with diisopropylethylamine (DIEA; 1.2 mmol). Trans-4(2-aminoacetamido)-D-proline (0.35 mmol) was dissolved in CH$_2$Cl$_2$ (10 mL) and DIEA (1.6 mmol) was added. This solution was cooled to 0° C. and bromo-tris (pyrrolidino)phosphonium hexafluorophosphate (PyBroP, 0.35 mmol) was added. After addition of the solution of amine the reaction stirred at room temperature for 1 hr before washing with 1M aqueous hydrochloric acid (HCl) (2×25 mL), saturated NaHCO$_3$ (1×25 mL), and brine (1×25 mL). The organic layer was collected, dried over Na$_2$SO$_4$, filtered and the filtrate adsorbed onto 500 mg of silica gel and applied to a column prepacked with silica Elution with EtOAc:Hexanes (50:50, v:v) gave the coupled product, which was dissolved in TFA (2.5 mL) and stirred at room temperature for 1 hr. The solution was concentrated to dryness, suspended in H$_2$O and applied to a MPLC reverse phase column (1 cm×22 cm amberchrom). Elution at 2 mL/min over 1 hr (gradient of 0 to 60% CH$_3$CN with 0.1% TFA) and lyophylization for 18 hr gave the title compound: $^1$H NMR (D$_2$O) δ 2.05–2.15 (1H, m), 2.18–2.22 (1H, m), 2.29–2.4 (1H, m), 2.5–2.6 (1H, m), 2.83–3.18 (4H, m), 3.25–3.4 (1H, m), 3.5–3.62 (1H, m), 3.64–3.85 (2H, m), 4.1–4.2 (1H, m), 4.37–4.42 (2H, t), 5.17–5.2 (1H, m), 7.24–7.48 (5H, m), 7.9–8.0 (1H, d), 8.05–8.1 (1H, d), 8.18–8.23 (2H, m), 8.9 (1H, s), 9.38 (1H, s).

Compound M42: (2S,4R)-4-[(2R)-2-Aminopropionamido]-N-(2-phenylethyl)-N-(3-quinolylcarbamoyl)ethyl]-2-pyrrolidinecarboxamide This compound was prepared as for Compound M41, replacing trans-4-(N-tert-butoxycarbonylglycyl)amino-N-tert-butoxycarbonyl-D-proline with trans-4-(N-tert-butoxycarbonyl-D-alanyl)amino-N-tert-butoxycarbonyl-D-proline.

Compound M43: (2S,4R)-4-(2-Aminoacetamido)-N-(2-phenylethyl)-N-(3-quinolylcarbamoyl)ethyl]-2-pyrrolidinecarboxamide This compound was prepared as for Compound M41, replacing trans-4-(N-tert-butoxycarbonylglycyl)amino-N-tert-butoxycarbonyl-D-proline with trans-4-(N-tert-butoxycarbonylglycyl)amino-N-tert-butoxycarbonyl-L-proline.

Compound M44: (2S,4R)-4-(2-Aminoacetamido)-N-(2-methylpropyl)-N-(7-ethyl-3-quinolylcarbamoyl)ethyl]-2-pyrrolidinecarboxamide This compound was prepared as for Conpound M41, replacing phenethylamine with 2-methylpropylamine, 3-aminoquinoline with 3-amino-7-ethylquinoline and trans-4-(N-tert-butoxycarbonylglycyl)amino-N-tert-butoxycarbonyl-D-proline with trans-4-(N-tert-butoxycarbonylglycyl)amino-N-tert-butoxycarbonyl-L-proline.

Compound M45: (2S,4R)-4-(Aminoethyl)-N-(2-phenylethyl)-N-(3-quinolylcarbamoyl)ethyl]-2-pyrrolidinecarboxamide This compound was prepared as for Compound M41, replacing trans-4-(N-tert-butoxycarbonylglycyl)amino-N-tert-butoxycarbonyl-D-proline with trans-4-(N-tert-butoxycarbonyl)amino-N-tert-butoxycarbonyl-D-proline.

Compound M46: (2S,4R)-4-(2-Aminoacetamido)-N-(2-phenylethyl)-N-(3-quinolylcarbamoyl)methyl]-2-pyrrolidinecarboxamide This compound was prepared according to Scheme 2, using the following methods:
(A) N-phenethylglycine methyl ester.

Glycine methyl ester hydrochloride (8 mmol) was dissolved in methanol (25 mL) and acetic acid (0.8 mmol) and phenylacetaldehyde (4 mmol) were added at 0° C. Sodium triacetoxyborohydride (8 mmol) was added in 2 portions at 0° C. and the reaction was stirred at this temperature for 1.5 hr before quenching with saturated sodium bicarbonate (15 mL). The solution was washed with $H_2O$ and extracted with EtOAc. The organic layer was collected, dried over $Na_2SO_4$, filtered and the filtrate adsorbed onto 100 mg of silica gel and applied to a column prepacked with silica. Elution with $CH_2Cl_2$:MeOH (97:3, v:v) afforded the title compound (258 mg, 33%): $^1$H NMR (CDCl$_3$) δ 2.94–3.21 (6H, m), 3.83 (3H, s), 7.21–7.32 (5H, m); MS m/e 194 (75, M+1).
(B) N-phenethyl-N-tert-butoxycarbonyl-glycine methyl ester The methyl ester (1.3 mmol) from (A) was dissolved in a mixture of $H_2O$ (10 mL) and 1,4-dioxane (10 mL). Sodium bicarbonate (2.6 mmol) and BOC$_2$O (1.9 mmol)were added and the solution was stirred at room temperature for 14 hr. The mixture was concentrated in vacuo, neutralized to pH 4 with 5% citric acid (5 mL) and washed with EtOAc. The organic layer was collected, dried over $Na_2SO_4$, filtered and concentrated to dryness to afford the title compound (358 mg, 94%): $^1$H NMR (CDCl$_3$) δ 1.44–1.46 (9H, s), 2.80–2.89 (2H, m), 3.46–3.54 (2H, m), 3.73 (3H, s), 3.77 and 3.89 (1H each, s), 7.16–7.31 (5H, m).
(2S,4R)-4-(2-Aminoacetamido)-N-(2-phenylethyl)-N-(3-quinolylcarbamoyl)methyl]-2-pyrrolidinecarboxamide The product from (B) was dissolved in methanol (20 mL) and 1M NaOH (2.4 mL, 2.4 mmol) was added. The reaction was stirred for 14 hr. After concentration in vacuo, the residue was dissolved in $H_2O$ (25 mL). The pH of the solution was adjusted to 4 with 5% citric acid (10 mL) and the title compound extracted with EtOAc (30 mL). The organic layer was dried over $Na_2SO_4$, filtered and concentrated to dryness to afford 311 mg (93%) of the acid, which was coupled with 3-aminoquinoline according to the method described in Compound D201. The product (0.59 mmol) was dissolved in 3 mL of TFA and stirred at room temperature for 1 hr. The solution was concentrated to dryness, co-evaporated twice with $CH_2Cl_2$ and the resultant solid suspended in $CH_2Cl_2$ (10 mL) and dissolved with diisopropylethylamine (DIEA, 1.2 mmol). Trans-4-(2-aminoacetamido)-D-proline (0.39 mmol) was dissolved in $CH_2Cl_2$ (10 mL) and DIEA (1.6 mmol) was added. This solution was cooled to 0° C. and bromo-tris(pyrrolidino) phosphonium hexafluorophosphate (PyBroP, 0.59 mmol) was added. After adding the solution of amine, the mixture was stirred at room temperature for 1 hr and then washed with 1M HCl (2×25 mL), saturated NaHCO$_3$ (1×25 mL) and brine (1×25 mL). The organic layer was collected, dried over $Na_2SO_4$, filtered, and the filtrate adsorbed onto 500 mg of silica gel and applied to a column prepacked with silica The coupled material was eluted from the column with EtOAc:Hexanes (50:50, v:v). After concentration in vacuo, the residuewas dissolved in TFA (2.5 mL) and stirred at room temperature for 1 hr. The solution was concentrated to dryness, suspended in $H_2O$ and applied to a MPLC reverse phase column (1 cm×22 cm amberchrom). The product was eluted from the column at 2 mL/min over 1 hr (gradient of 0 to 60% $CH_3CN$ with 0.1% TFA) and lyophilized for 18 hr to afford the title compound (110 mg): $^1$H NMR (D$_2$O) δ 2.20–2.51 (2H, m), 2.85–3.14 (3H, m), 3.31–3.41 (1H, m), 3.64–3.92 (5H, m), 4.29–4.65 (3H, m), 7.2–7.42 (5H, m), 7.81–8.05 (2H, m), 8.09–8.19 (2H, m), 8.81 (1H, s), 9.20 (1H, s); MS m/e 475 (48, M+1).

Compound M47: (2S,4R)-4-[(2R)-2-Aminopropionamido]-N-(3,3-dimethylbutyl)-N-(3-quinolylcarbamoyl)methyl]-2-pyrrolidinecarboxamide This compound was prepared as for Compound M46, replacing phenethylamine with 3,3-dimnethylbutylamine and trans-4-(N-tert-butoxycarbonylglycyl)amino-N-tert-butoxycarbonyl-D-proline with trans-4-(N-tert-butoxycarbonyl-D-alanyl)amino-N-tert-butoxycarbonyl-D-proline.

Scheme 3

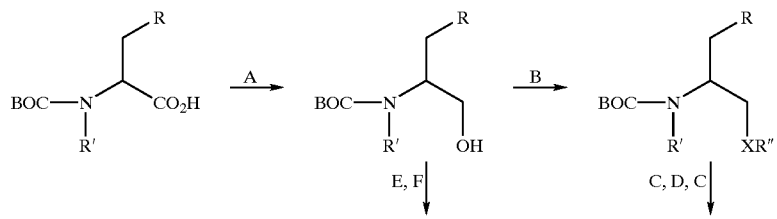

-continued

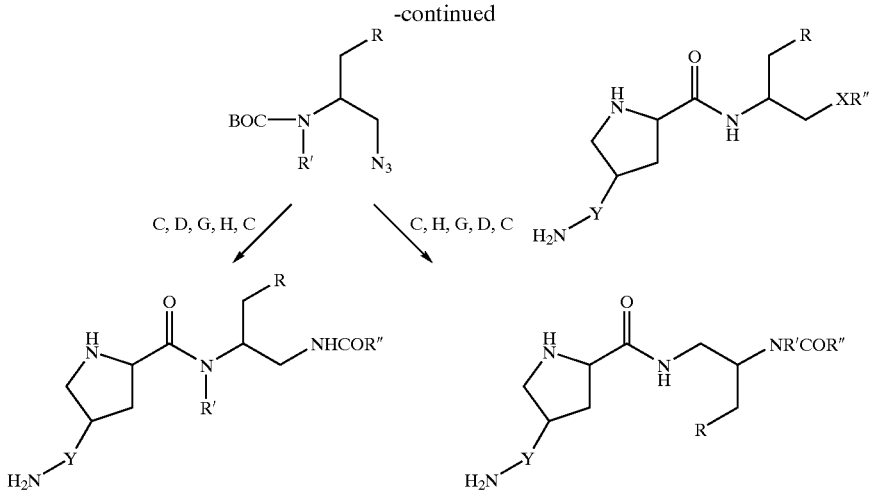

a) BH₃, THF; b) Ph₃P, DEAD, R"OH (X = O) or i) MsCl, Et₃N, ii) R"SH, Et₃N, DMF (X = S);
c) CF₃COOH; d) BOC-protected amino acid, coupling agent; e) MsCl, Et₃N, DMF;
f) NaN₃, NaI, DMF; g) H₂, Pd/C, EtOH; h) amide coupling conditions Compound M48: (2R,4R)-4-(Aminomethyl)-N-[(1R)-3-phenyl-1-[(2-quinolyloxy)methyl]propyl]-2-pyrrolidinecarboxamide (A) N-tert-Butoxycarbonyl-D-homophenylalaninol N-tert-butoxycarbonyl-D-homophenylalanine (36 mmol) was dissolved in tetrahydrofuran (THF) (300 mL) and cooled to 0° C. Borane-THF complex (0.32 M in THF, 320 mL, 9 equivalents) was added dropwise over 2 hr and the solution stirred for an additional 2 hr at 0° C. The reaction mixture was quenched over several hours by the slow addition of MeOH (300 mL) and the resulting solution was concentrated to dryness. The residue was dissolved in EtOAc (200 mL), washed with 1 N NaOH (2×100 mL) and brine (1×75 mL). The organic layer was dried over Na₂SO₄, filtered and the filtrate concentrated to dryness. Recrystallization from hexanes gave the title compound (6.5 g, 84%) as a white solid: ¹H NMR (CDCl₃) δ 1.57 (9H, s), 1.91–1.93 (2H, m), 2.77–2.85 (2H, m), 3.68–3.82 (3H, m), 7.29–7.42 (5H, m); MS m/e 288 (100, M+1).

(B) N-tert-Butoxycarbonyl-(1R)-3-phenyl-1-(2-quinolyloxymethyl)propylamine

N-tert-Butoxycarbonyl-D-homophenylalaninol (1.9 mmol), 2-hydroxyquinoline (2 mmol) and triphenylphosphine (2 mmol) were dissolved in dry THF (20 mL). The solution was cooled to 0° C. and diethyl azodicarboxylate (DEAD) (3.8 mmol) was added dropwise. The reaction mixture was stirred at 0° C. for 3 hr, then at room temperature for 16 hr at which time the solvent was evaporated under reduced pressure and the residue purified by chromatography on silica gel (100% CH₂Cl₂) to give the title compound (240 mg, 33%): ¹H NMR (CDCl₃) δ 1.46 (9H, s), 1.91–1.99 (2H, m), 2.76–2.81 (2H, m), 4.05–4.12 (1H, m), 4.51–4.53 (1H, m), 6.91–6.93 (1H, d), 7.19–7.30 (5H, m), 7.37–7.41 (1H, t), 7.61–7.65 (1H, t), 7.72–7.74 (1H, d), 7.82–7.84 (1H, d), 7.99–8.01 (1H, d); MS m/e 393 (100, M+1).

(C) (2R,4R)-4-(Aminomethyl)-N-[(1R)-3-phenyl-1-[(2-quinolyloxy)methyl]propyl]-2-pyrrolidinecarboxamide N-tert-Butoxycarbonyl-(1R)-3-pheny-1-(2-quinolyloxymethyl)propylamine (0.45 mmol) was deprotected using TFA, coupled with trans-4-(N-tert-butoxycarbonyl)amino-N-tert-butoxycarbonyl-D-proline and deprotected in a manner analogous to Compound M16 to give the title compound: ¹H NMR (D₂O) δ 2.02–2.09 (4H, m), 2.46–2.58 (1H, m), 2.74–2.89 (3H, m), 2.97–3.14 (2H, m), 3.69–3.76 (1H, m), 4.29–4.35 (2H, m), 4.53–4.59 (1H, m), 7.14–7.20 (2H, m), 7.26–7.33 (4H, m), 7.58–7.62 (1H, m), 7.83–7.85 (2H, d), 7.96–7.98 (1H, d), 8.43–8.46 (1H, d); MS m/e 274 (100), 419 (15, M+1).

Compound M49: (2R,4R)-4-(2-Aminoacetamido)-N-[(1R)-3-methyl-1-[(2-naphthyloxy)methyl]butyl]-2-N-(2-pyrrolidinecarboxamide This compound was prepared as for Compound M48, replacing N-tert-butoxycarbonyl-D-homophenylalanine with N-tert-butoxycarbonyl-D-leucine, 2-hydroxyquinoline wih 2-naphthol and trans-4-(N-tert-butoxycarbonylaminomethyl)-N-tert-butoxycarbonyl-D-proline with trans-4-(N-tert-butoxycarbonylglycyl)amino-N-tert-butoxycarbonyl-D-proline.

Compound M50: (2R,4R)-4-(2-Aminoacetamido)-N-[(1R)-3-phenyl-1-[(4-chlorophenylthio)methyl]propyl]-2-N-(2-pyrrolidinecarboxamide This compound was prepared as for Compound M48, replacing 2-hydroxyquinoline with 4-chlorothiophenol and trans-4-(N-tert-butoxycarbonylaminomethyl)-N-tert-butoxycarbonyl-D-proline with trans-4-(N-tert-butoxycarbonylglycyl)amino-N-tert-butoxycarbonyl-L-proline.

Compound M51: (2S,4R)-4-[(2R)-2-Aminopropionamido]-N-[(1R)-3-phenyl-1-[(4-chlorophenylthio)methyl]propyl]-2-pyrrolidinecarboxamide This compound was reed as for Compound M48, replacing 2-hydroxyquinoline with 4-chlorothiophenol and trans-4N-tert-butoxycarbonylaminomethyl)-N-tert-butoxycarbonyl-D-proline with trans-4-(N-tert-butoxycarbonyl-D-alanyl)amino-N-tert-butoxycarbonyl-L-proline.

Compound M52: (2R,4S)-4-[(2-Aminopropionamido]-N-[(1R)-3-phenyl-1-[(4-chlorophenylthio)methyl]propyl]-2-pyrrolidinecarboxamide This compound was prepared as for Compound M48, replacing 2-hydroxyquinoline with 4-chlorothiophenol and trans-4-(N-tert-butoxycarbonylaminomethyl)-N-tert-butoxycarbonyl-D-proline with trans-4-(N-tert-butoxycarbonyl-D-alanyl)amino-N-tert-butoxycarbonyl-D-proline.

Compound M53: (2S,4R)-4-(2-Aminoacetamido)-N-[(1R)-3-phenyl-1-[(3-quinolythio))methyl]propyl]-2-pyrrolidinecarboxamide This compound was prepared as for Compound M48, replacing 2-hydroxyquinoline with 3-thioquinoline and trans-4-(N-tert-butoxycarbonylaminomethyl)-N-tert-butoxycarbonyl-D-proline with trans-4-(N-tert-butoxycarbonyl)amino-N-tert-butoxycarbonyl-L-proline.

Compound M54: (2R,4R)-4-(2-Aminoacetamido)-N-[(1R)-3-phenyl-1-[(2-quinolyloxy)methyl]propyl]-2-N-(2-pyrrolidinecarboxamide This compound was prepared as for Compound M48, replacing trans-4-(N-tert-butoxycarbonylaminomethyl)-N-tert-butoxycarbonyl-D-proline with trans-4-(N-tert-butoxycarbonyl)amino-N-tert-butoxycarbonyl-L-proline.

Compound M55: (2S,4R)-4-(2-Aminoacetamido)-N-[(1R)-3-phenyl-1-[(2-quinolythio)methyl]propyl]-2-pyrrolidinecarboxamide This compound was prepared as for Compound M48, replacing 2-hydroxyquinoline with 2-thioquinoline and trans-4-(N-tert-butoxycarbonylaminomethyl)-N-tert-butoxycarbonyl-D-proline with trans-4-(N-tert-butoxycarbonyl)amino-N-tert-butoxycarbonyl-L-proline.

Compound M56: (2S,4R)-4-(2-Aminoacetamido)-N-[(1R)-3-phenyl-1-(phenylthiomethyl)propyl]-2-pyrrolidinecarboxamide This compound was prepared as for Compound M48, replacing 2-hydroxyquinoline with thiophenol and trans-4-(N-tert-butoxycarbonylaminomethyl)-N-tert-butoxycarbonyl-D-proline with trans-4-(N-tert-butoxycarbonyl)amino-N-tert-butoxycarbonyl-L-proline.

Compound M57: (2S,4R)-4-(2-Aminoacetamido)-N-[(1R)-3-phenyl-1-[(4-florophenylthio)methyl]propyl]-2-pyrrolidinecarboxamide This compound was prepared as for Compound M48, replacing 2-hydroxyquinoline with 4-fluorothioplenol and trans-4-(N-tert-butoxycarbonylaminomethyl)-N-tert-butoxycarbonyl-D-proline with trans-4-(N-tert-butoxycarbonyl)amino-N-tert-butoxycarbonyl-L-proline.

Compound M58: (2S,4R)-4-(2-Aminoacetamido)-N-[(1R)-3-methyl-1-[(2-quinolyloxy)methyl]propyl]-2-pyrrolidinecarboxamide This compound was prepared as for Compound M48, replacing N-tert-butoxycarbonyl-D-homophenylalanine with N-tert-butoxycarbonyl-D-leucine and trans-4-(N-tert-butoxycabonylainomethyl)-Ntert-butoxycarbonyl-D-proline with trans-4-(N-tert-butoxycarbonylglycyl)amino-N-tert-butoxycarbonyl-L-proline.

Compound M59: (2R,4R)-4-(Aminomethyl)-N-[(1R)-3-methyl-1-[(3-quinolyloxy)methyl]butyl]-2-pyrrolidinecarboxamide This compound was prepared as for Compound M48, replacing N-tert-butoxycarbonyl-D-homophenylalanine with N-tert-butoxycarbonyl-D-leucine.

Compound M60: (2S,4R)-4-(2-Aminoacetamido)-N-[(1R)-3-methyl-1-[(4-chlorphenylthio)methyl]butyl]-2-pyrrolidinecarboxamide This corpound was prepared as for Compound M48, replacing N-tert-butoxycarbonyl-D-homophenylalaine with N-tert-butoxycarbonyl-D-leucine, 2-hydroxyquinoline with 4-chlorothiophenol and trans-4-(N-tert-butoxycarbonylaminomethyl)-N-tert-butoxycarbonyl-D-proline with trans-4-(N-tert-butoxycarbonylglycyl)amino-N-tert-butoxycarbonyl-L-proline.

Compound M61: (2R,4R)-4-(Aminomethyl)-N-[(1R)-3-methyl-1-[(4-chlorophenylthio)methyl]butyl]-2-pyrrolidinecarboxamide This compound was prepared as for Compound M48, replacing 2-hydroxyquinoline with 4-chlorothiophenol and trans-4-(N-tert-butoxycarbonylaminomethyl)-N-tert-butoxycarbonyl-D-proline with trans-4-(N-tert-butoxycarbonylglycyl)amino-N-tert-butoxycarbonyl-L-proline.

Compound M62: (2R,4R)-4-(Aminomethyl)-N-[(2S)-2-(6-methyl-3-quinolycarboxamido)-4phenylbutyl]-2-pyrrolidinecarboxamide This compound was prepared according to Scheme 3, using the following methods:
(A) N-tert-Butoxycarbonyl-D-homophenylalaninol
N-tert-butoxycarbonyl-D-homophenylalanine (36 mmol) was dissolved in THF (300 mL) and cooled to 0° C. Borane-THF complex (0.32M in THF, 320 mL, 9 equivalents) was added dropwise over 2 hours and the solution was stirred for an additional 2 hours at 0° C. The reaction mixture was quenched over several hours by the slow addition of MeOH (300 mL) and the solution was concentrated to dryness. The residue was dissolved in EtOAc (200 mL), washed with 1 N NaOH (2×100 mL) and brine (1×75 mL). The organic layer was dried over $NASO_4$, filtered and the filtrate concentrated to dryness. Recrystallization from hexanes gave the title compound (6.5g, 84%) as a white solid: $^1$H NMR (400 MHz, $CDCl_3$) δ 1.57 (9H, s), 1.91–1.93 (2H, m), 2.77–2.85 (2H, m), 3.68–3.82 (3H, m), 7.29–7.42 (5)H, m); MS (relative intensity) nme 288 (100, M+1).

(B) N-tert-butoxycarbonyl-D-homophenylalaninol mesylate
The product from (A) (3.8 mmol) was dissolved in dimethylformamide (DMF) (20 mL) and the solution was cooled to 0° C. Methanesulfonyl chloride (14.4 mmol) and triethylamine $At_3N$) (14.4 mmol) were added. The reaction was stirred at 0° C. for 2 hr, quenched with $H_2O$ (2×25 mL), saturated $NaHCO_3$ (1×25 mL) and brine (1×25 mL). The organic layer was dried over $Na_2SO_4$, filtered and dried to give the title compound (1.2g, 92%) as a white solid: $^1$H NMR (400 MHz, $CDCl_3$) δ 1.60 (9H, s), 1.91–2.05 (2H, m), 2.77–2.90 (2H, m), 3.68–3.82, 3.12 (3H, s), 3.9–4.05 (1H, m), 4.27–4.4 (2H, m), 4.72–4.82 (1H, m), 7.25–7.48 (5H, m).

(C) N-tert-butoxycarbonyl-D-homophenylalanyl azide
The product from (B) (12.6 mmol) was dissolved in DMF (25 mL) and sodium azide ($NaN_3$) (50 mmol) and sodium iodide (NaI) (50 mmol) were added. This solution was warmed at 50° C. for 24 hr then cooled to room temperature, washed with $H_2O$ (3×50 mL), extracted with EtOAc (2×50 mL) and washed with brine (1×25 mL). The organic layer was dried over $Na_2SO_4$, filtered dried to give the title compound (2.8 g, 77%) as an oil.

(D) (2S)-2-(6-methyl-3-quinolycarboxamido)-4-phenylbutylamine

The product from (C) (2.4 mmol) was dissolved in CH$_2$Cl$_2$ (10 mL) and TFA (5 mL) was added in one portion. The reaction was stirred at room temperature for 1 hr, the solvents evaporated to dryness and the residue dissolved in H$_2$O (25 mL). The pH of this solution was adjusted to 8 with saturated NaHCO$_3$ and the title compound extracted with EtOAc (50 mL). The organic layer was washed with brine, dried over Na$_2$SO$_4$, filtered and concentrated to dryness to give the free amine (430 mg, 95%). This was coupled in 42% yield with 6-methylquinoline-3-carboxylic acid using the method described in Compound D201(A). The resulting azide (0.4 mmol) was dissolved in ethanol (EtOH) (20 mL) and 10% Pd/C (50 mg) was added. The reaction was hydrogenated at 1 atmosphere at room temperature for 3 hrs at which time the mixture was filtered over a pad of diatomaceous earth, washed with EtOH (2×15 mL) and the filtrate evaporated to dryness to give the in 41% yield: MS m/e 334 (100, M+1).

(2R,4R)-4-(Aminomethyl)-N-[(2S)-2(6-methyl-3-quimolylcarboxamido)-4-butyl]-2-pyrrolidinecarboxamide The product from (D) (0.17 mmol) was coupled with trans-4-(N-tert-butoxycarbonylaminomethyl-3-N-tert-butoxycarbonyl-D-proline and deprotected using the methods described in Compound D201 to give the title compound: $^1$H NMR (400 MHz, D$_2$O) δ 2.02–2.35 (4H, m), 2.6 (3H, s), 2.65–2.97 (4H, m), 3.15–3.2 (2H, m), 3.31–3.40 (1H, m), 3.51–3.59 (1H, m), 3.67–3.39 (1H, m), 4.23–4.61 (3H, m), 6.91–7.40 (5H, m), 8.05–8.18 (4H, m), 8.8 (1H, s), 9.02 (1H, s); MS m/e 460 (30, M+1).

Compound M63: (2R,4R)-4-(Aminomethyl)-N-[(1R)-3-phenyl-1-[(6-methyl-2-quinolycarboxamido)methyl]propyl]-2-pyrrolidinecarboxamide This compound was prepared according to Scheme 3, using the following methods:
N-tert-butoxycarbonyl-D-homophenylalanyl azide (compound 62(C), 3.4 mmol) was reduced using the method described in the latter part of Compound 62(D) to give the amine (0.926 g, 95%). This was coupled in 55% yield with 6-methylquinoline-3-carboxylic acid using the method described in Compound D201(A). The product was deprotected with TFA, coupled with trans-4-(N-tert-butoxycarbonylaminomethyl)N-tert-butoxycarbonyl-D-proline and deprotected using the methods described in Compound D201 to give the title compound: $^1$H NMR (400 MHz, D$_2$O) δ 1.86–2.35 (5H, m), 2.63 (3H, s), 2.64–2.84 (3H, m), 3.05–3.39 (3H, m), 3.54–3.73 (3H, m), 4.08–4.20 (1H, m), 4.34–4.41 (1H), 7.20–7.35 (5H, m), 8.07–8.16 (3H, m), 9.21–9.27 (2H, d); MS m/e 460 (65, M+1).

Scheme 4

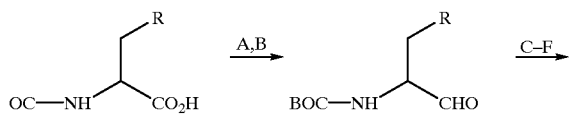

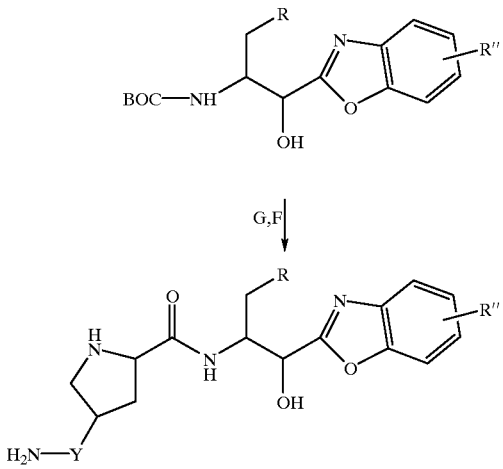

a) MeO(Me)NHHCl, Pybrop, DIEA, DMF; b) LAH, THF, -40° C.; c) Me$_2$C(CN)OH;
d) HCl, EtOH, CHCl$_3$; e) 2-aminophenol, EtOH; f) CF$_3$COOH;
g) BOC-protected amino acid, coupling agent Compound M64: (2S,4R)-4-(2-Aminoacetamido)-N-[(1R)-1[(RS)-(5,6-dimethyl-2-benzoxazolyl)hydroxymethyl]phenylpropyl]-2-pyrrolidinecarboxamide This compound was prepared according to Scheme 4, using the following methods:
(A) N-tert-Butoxycarbonyl-D-homophenylalanine methoxymethylamide A mixture of N-tert-butoxycarbonyl-D-homophenylalanine (3.0 g, 10.7 mmol), methoxymethylamine hydrochloride (1.15 g, 1.1 eq.), PyBrop (5 g, 1 eq.), diisopropylethylamine (5.6 mL, 3 eq.) and dichloromethane (10 mL) was stirred at 25° C. for 10 hours, and the reaction mixture was poured into ethyl acetate and washed successively with water, 1 N HCl, sat. sodium bicarbonate and brine. The combined extracts was dried (Na$_2$SO$_4$) and concentrated in vacuo. Further purification by chromatography over silica gel (45% ethyl acetate/hexane) afforded the title compound (6.76 g) as a white solid: $^1$H NMR (400 MHz, CDCl$_3$) δ 1.46 (s, 9H), 1.85 (m, 1H), 2.04 (m, 1H), 2.72 (m, 2H), 3.17 (s, 3H), 3.63 (s, 3H), 4.69 (m, 1H), 5.25 (bd, 1H, NH), 7.20 (m, 3H) and 7.28 (m, 2H).
(B) N-tert-Butoxycarbonyl-D-homophenylalaninal A cold (−40° C.) solution of lithium aluminum hydride (25.2 mL of a 1M solution, 1.2 eq.) in tetrahydrofuran (165 mL), under nitrogen, was treated with a solution of N-tert-Butoxycarbonyl-D-homophenylalanine methoxymethylamide (6.76 g, 20.9 mmol) in tetrahydrofuran (20 mL) at such a rate as to keep the temperature between −36 to −38° C. After the addition, the temperature was allowed to rise to 7° C. after which the reaction mixture was cooled to −35° C. The mixture was quenched with 2.75M KHSO$_4$ solution and stirred for 1 h whilst warming to 25° C. The aqueous layer was separated and extracted thrice with ether. The combined organics were washed successively thrice with 10% citric acid, water, saturated bicarbonate and brine, dried (MgSO$_4$) and concentrated. The viscous clear residue solidified under vacuum, giving the title compound (5.32 g): $^1$H NMR (400 MHz, CDCl$_3$) δ 1.47 (s, 9H), 1.88 (m, 1H), 2.22 (m, 1H), 2.71 (t, J=7.6 Hz, 2H), 4.24 (m, 1H), 5.18 (bd, 1H, NH), 7.20 (m, 3H), 7.27 (m, 2H) and 9.54 (s, 1H).
(C) (3R)-N-tert-Butoxycarbonyl-5-phenyl-3-amino-2-hydroxypentanonitrile A solution of N-tert-Butoxycarbonyl-D-homophenylalaninal (2.62 g, 11.3 mmol), acetone cyanohydrin (2.5 g, 2.6 eq.), triethylarnine (1.7 mL, 1.1 eq.) and methylene chloride (25 mL) was stirred for 4 h at 24° C. under nitrogen atmosphere. The reaction mixture was concentrated in vacuo and the residue disssolved in ether, washed five times with brine, dried (MgSO$_4$), concentrated and purified by chromatography over silica gel (25% ethyl acetate/hexane), giving the title compound (2.0 g) as a clear oil: $^1$H NMR (400 MHz, CDCl$_3$, 1:1 mixture of diastereomers) δ 1.48 (s, 9H), 1.93 (m, 2.5H), 2.70 (m, 1H), 2.19 m, 0.5H), 2.79 (m, 1H), 3.68 (m, 0.5H), 3.89 (m, 0.5H), 4.50 (m, 0.5H), 4.58 (m, 0.5H), 4.68 (m, 0.5H), 4.92 (bd, 0.5H, NH), 5.11 (bd, 0.5H, NH), 7.21 (m, 3H) and 7.32 (m, 2H).

(D) 2-[(2R)-4-Phenyl-2-amino-1-hydroxybutyl]-5,6-dimethylbenzoxazole

A cold (0° C.) solution of acetyl chloride (5.53 mL) and chloroform (5.53 mL) was treated dropwise with anhydrous ethanol (5.5 mL) over 15 min., under nitrogen atmosphere. A solution of the product from (C) (832 mg, 2.9 mmol), in chloroform (5.5 mL) was added at 0° C. and the mixture was stirred for 1 h. The solvent was removed in vacuo while maintaining the temperature below 20° C., giving a white solid. A solution of the crude imidate, amino-4,5-dimethylphenol (390 mg, 1.2 eq.) and anhydrous ethanol (5.5 mL) was heated to reflux for 6 h and then concentrated in vacuo. The residue was partitioned between ethyl acetate and 1 N NaOH, and the organic layer washed with brine, dried (NaSO$_4$), concentrated and purified firer by chromatography over silica gel (5% methanol/dichloromethane) to give desired product (452 mg) as a white solid: $^1$H NMR (400 MHz, CDCl$_3$, 3:2 mixture of diastereomers) δ 1.83 (m, 1.4H), 1.98 (m, 0.6H), 2.36 and 2.34 (2s, 6H), 2.70 (m, 1H), 2.82 (m, 1H), 3.24 (m, 0.4H), 3.38 (m, 0.6H), 4.74 (d, J=3.0 Hz, 0.6H), 4.86 (d, J=3.6 Hz, 0.4H), 7.13–7.28 (m, 6H), 7.43 (s, 0.6H) and 7.44 (s, 0.4H).

(E) (4S)-N,N'-Bis-tert-butoxycarbonyl-4-(glycinamido)-L-proline-2-[(2R)-4-phenyl-2-amino-1-hydroxybutyl]benzoxazole 2-[(2R)-4-Phenyl-2-amino-1-hydroxybutyl]-5,6-dimethylbenzoxazole (110 mg, 0.35 mmol) was coupled with trans-4-(N-tert-butoxycarbonylglycyl)amino-N-tert-butoxycarbonyl-L-proline (110 mg, 0.75 eq.) using PyBrop (248 mg, 1.5 eq.) and diisopropylethylaine (0.25 mL, 4 eq.), affording the title compound (140 mg, 74%) as a glassy solid. MS (ES+) 537.2. $^1$H NMR (400 MHz, CDCl$_3$, 3:1 mixture of diastereomers) δ 1.43 (bs, 18H), 1.94 (m, 1H), 2.04 (m, 1H), 2.22 (m, 1H), 2.33 (m, 7H), 2.71 (m, 2H), 3.69 (dd, J=16.4; 5.2 Hz, 0.75H), 3.75 (m, 1.25H), 4.28 (m, 1H), 4.3 (m, 1H), 4.97 (m, 1H), 5.41 (m, 1H), 7.09–7.28 (m, 6H), 7.38 (d, J=1.2 Hz, 0.75H) and 7.44 (s, 0.25H).

(F) (2S,4R)-4-(2-Aminoacetamido)-N-[(1R)-1-[(5,6-dimethyl-2-benzoxazolyl)hydroxymethyl]-3-phenylpropyl]-2-pyrrolidinecarboxamide The title compound (81 mg, 62%) was obtained as a white powder by removal of the Boc groups using trifluoroacetic acid followed by reverse phase preparative HPLC. MS (ES+) 480.3 (N+H). $^1$H NMR (300 MHz, D$_2$O) δ 2.03 (m, 1H), 2.14 (m, 1H), 2.33 (s, 3H), 2.36 (s, 3H), 2.38 (m, 2H), 2.72 (m, 2H), 3.30 (dd, J=16.4; 6.8 Hz, 1H), 3.63 (dd, J=16.0; 8.8 Hz, 1H), 3.81 (bs, 2H), 4.27 (m, 1H), 4.46 (m, 2H), 5.05 (d, J=5.2 Hz, 1H), 7.17–7.35 (m, 5H), 7.43 (s, 1H) and 7.47 (s, 1H).

This compound was prepared as in Compound M64, replacing trans-4-4-(N-tert-butoxycarbonylglycyl)amino-N-tert-butoxycarbonyl-L-proline with trans-4-(N-tert-butoxycarbonyl-D-alanyl)amino-N-tert-butoxycarbonyl-L-proline.

Compound M66: (2R,4S)-4-[(2R)-2-Aminopropionanamido]-N-[(1R)-1-[(RS)-(5,6-dimethyl-2-benzoxazolyl)hydroxymethyl]-3-phenylpropyl]-2-pyrrolidinecarboxamide This compound was prepared as in Compound M64, replacing trans-4-(N-tert-butoxycarbonylglycyl)amino-N-tert-butoxycarbonyl-L-proline with trans-4-(N-tert-butoxycarbonyl-D-alanyl)amino-N-tert-butoxycarbonyl-D-proline.

Compound M67: (2S,4R)-4-(2-Aminoacetamido)-N-[(1R)-1-[(RS)-(5,6-dimethyl-2-benzoxazolyl)hydroxymethyl]-3-phenylpropyl]-2-pyrrolidinecarboxamide This compound was prepared as in Compound M64, replacing N-tert-butoxycarbonyl-D-homophenylalarnine withN-tert-butoxycarbonyl-D-leucine.

Compound M68: (2R,4R)-4-(Aminomethyl)-N-[(1R)-1-[(RS)-(5-(1,1-dimethyl)ethyl-2-benzoxazolyl)hydroxymethyl]-3-phenylpropyl]-2-pyrrolidinecarboxamide This compound was prepared as in Compound M64, replacing N-tert-butoxycarbonyl-D-homophenylalanine withN-tert-butoxycarbonyl-D-leucine, amino4,5-dimethylphenol with amino-4-tert-butylphenol and trans-4-(N-tert-butoxycarbonylglycyl)amino-N-tert-butoxycarbonyl-L-proline with trans-4-(N-tert-butoxycarbonylaminomethyl)-N-tert-butoxycarbonyl-D-proline.

Scheme 5

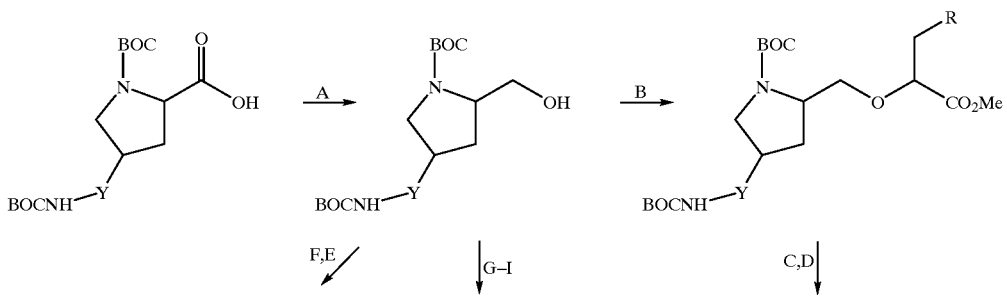

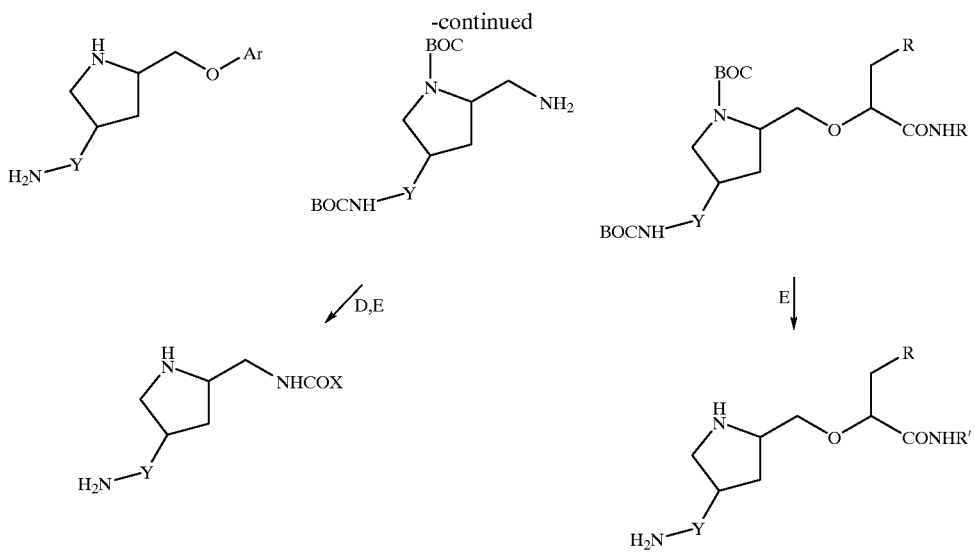

a) BH₃, THF; b) RCH(OTf)CO₂Me, nBuLi, THF; c) LiOH, aq. iPrOH;
d) amide coupling conditions; e) CF₃COOH; f) Ph₃P, DEAD, phenol, THF;
g) MsCl, Et₃N, DMF; h) NaN₃, NaI, DMF; i) H₂, Pd/C, EtOH Compound M69: (2R,4R)-4-(Aminomethyl)-N-[((1S)-3-quinolylcarbamoyl)propyl)oxymethyl] pyrrolidine This compound was prepared according to Scheme 5, using the following methods:

(A) (2R,4R)-4-(N-tert-butoxycarbonylaminomethyl)-2-hydroxymethyl-N-tert-butoxycarbonylpyrrolidine A solution of trans-4-(N-tert-butoxycarbonylaminomethyl)-N-tert-butoxycarbonyl-D-proline (1.0 g, 2.9 mmol) in anhydrous THF (24 mL) was cooled to -10° C. and borane in THF (1M, 26 mL) was added at that temperature. The reaction was left to stir for 5 hours at 0° C. The reaction was quenched with methanol (100 mL) at 0° C. and left for 1.5 hours to stir at 20° C. The solvents were removed in vacuo, and EtOAc (100 mL) was then added to the reaction mixture and the organic phase washed with 1M NaOH (2×50 mL), brine (2×50 mL), dried over Na₂SO₄ and concentrated in vacuo. The residue was purified by silica gel chromatography (50% EtOAc:Hexanes) to give the title compound (433mg, 45%). R_f(60% EtOAc-Hexanes; ninhydrin)=0.29. ¹H NMR (CDCl₃, 300 MHz) δ 1.45 (s, 9 H), 1.47 (s, 9 H), 1.69 (m, 1 H), 2.01 (m, 1 H), 2.47 (m, 1 H), 3.16 (m, 3 H), 3.55–3.77 (m, 2 H), 3.60 (m, 1 H), 3.85 (br m, 1 H). MS: 353.2 (M+Na).

(B) (2R,4R)-4-(N-tert-butoxycarbonylaminomethyl)-2-[((1S)-3-phenyl-1-(carboxymethyl)propyl)oxymethyl]-N-tert-butoxcarbonylpyrrolidine A solution of the product from (A) (0.258 g, 0.78 mmol) in anhydrous THF (7.8 mL) was cooled to −78° C. and n-BuLi in hexanes (2.5M, 0.34 mL, 0.86 mmol) was added. The reaction was warmed to 0° C. and stirred for 30 minutes. (2S)-4-phenyl-2-trifluoromethanesulfonyloxybutanoate methyl ester (Yanagisawa, H.; et al. *J. Med. Chem.*, 1987, 30, 1984–1991) (601 mg, 1.95 mmol) was then added and the reaction was stirred for 1 hour at 0° C. The reaction was warmed to 20° C. for 1.75 hours, cooled to −20° C. and potassium tert-butoxide in iso-propanol (0.78 mL of 1M solution, 0.78 mmol) was added. The reaction was brought to 0° C. and allowed to warm to 20° C. overnight. Solvents were removed in vacuo and EtOAc (50 mL) was added. The organic layer was washed with NaHCO₃ (2×25 mL), brine (2×25 mL), dried over Na₂SO₄, and concentrated in vacuo. The residue was purified by silica gel chromatography (40% EtOAc: Hexanes) to give the title compound (0.242g, 60%). R_f(60% EtOAc-Hexanes; ninhydrin)=0.25. ¹H NMR (CDCl₃; 300 MHz) δ 1.29 (dt, J=7,7, 3 H), 1.62 (s, 18 H), 1.86 (m, 2 H), 2.04 (m, 1 H), 2.33 (m, 1 H), 2.77 (m, 3 H), 3.67–3.20 (m, 3 H), 3.74 (m, 2 H), 4.18 (m, 2 H), 4.28 (q, J=7 Hz, 2 H), 5.15 (t, J=7 Hz, 1H ), 7.33–7.13 (m, 5 H). MS: 521.3 (M+1).

(C) (2R,4R)-4-N-tert-butoxycarbonylaminomethyl)-2-[((1S)-3-phenyl-1-(3-quinolylcarbamoyl)propyl)oxymethyl]-N-tert-butoxycarbonylpyrrolidine The product from (B) (225 mg, 0.43 mmol) was dissolved in 1:1 THF: H₂O (4 mL), lithium hydroxide monohydrate (0.0361 g, 0.86 mmol) was added, and the reaction left overnight at room temperature. The THF was concentrated in vacuo and H₂O (30 mL) was added to the reaction mixture. The reaction was then acidified to pH 3 using 5% citric acid. EtOAc (50 mL) was added and the aqueous phase extracted with EtOAc (3×30 mL). The combined organics were washed with brine (2×50 mL), dried over Na₂SO₄ and concentrated to give the acid. [¹H NMR (CDCl₃; 300 MHz): δ 1.40 (3s, 18 H), 1.44, 1.45, 1.66 (m, 1 H), 2.06 (m, 1 H), 2.44 (m, 1 H), 2.69 (m, 1 H), 3.11 (m, 3 H), 3.41 (m, 3 H), 3.60 (m, 1 H), 3.77 (m, 1 H), 4.08 (m, 2 H), 4.68 (m, 1H), 7.27–7.10 (m, 5 H)] This was coupled with 3-aminoquinoline using the method described in Compound D201(A), giving the title compound (21% yield): R_f(1% CH₃CO₂H: 4% CH₃OH: 95% CH₂Cl₂; ninhydrin)=0.52. ¹H NMR (CDCl₃; 300 MHz) δ 1.40 (s, 9 H), 1.46 (s, 9H), 1.85 (m, 1 H), 2.00 (m, 1 H), 2.24 (m, 2 H), 2.51 (m, 1 H), 2.74 (m, 2 H), 3.15 (m, 2 H), 3.51 (m, 2 H), 3.61 (m, 2 H), 4.00 (m, 1 H), 4.16 (br s, 1 H), 4.91 (br s, 1 H), 7.21 (m, 5 H), 7.54 (t, J=8 Hz, 1 H), 8.89 (s, 1 H), 7.64 (t, J=8 Hz, 1 H), 7.79 (d, J=8 Hz, 1 H), 8.19 (d, J=8 Hz, 1 H), 8.89 (s, 1 H), 9.00 (s, 1 H). MS: 619.4 (M+1).

(D) (2R,4R)-4-Aminomethyl)-2-[((1S)-3-phenyl-1-1-(3-quinolylcarbamoyl)propyl)oxymethyl]pyrrolidine The product from (C) was treated with TFA to give the title compound: MS: 419.3 (M+1).

Compound M70: (2R,4R)-4-(Aminomethyl)-2-[((1R)-3-phenyl-1-(3-quinolylcarbamoyl)propyl)oxymethyl]pyrrolidine This compound was prepared as in Compound M64, replacing (2S)-4-phenyl-2-trifluoromethanesulfonyloxybutanoate methyl ester with (2R)-4-phenyl-2-trifluoromethanesulfonyloxybutanoate methyl ester.

Compound M71: (2R,4R)-4-(Aminomethyl)-2-quinolyloxymethyl)pyrrolidine

This compound was prepared according to Scheme 5 by coupling the product from Compound M64(A) with 2-hydroxyquinoline, using the method described in Compound M48(B), followed by deprotection with TFA as in Compound M16.

Compound M72: (2R,4R)-4-(Aminomethyl)-2-(6-methyl-3-quinolylcarboxamidomethyl)pyrrolidine This compound was prepared according to Scheme 5 by converting the product from Compound M64(A) via the mesylate and azide (cf. Compound M62(B, C)) to the amine. This was coupled with 6-methylquinoline-3-carboxylic acid using the method described in Compound D201(A). Deprotection with TFA as in Compound M16 gave the title compound.

Scheme 6

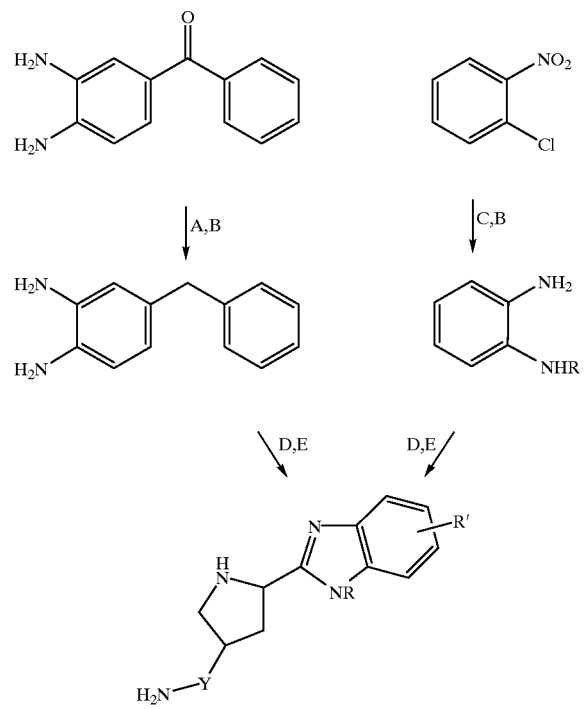

a) NaBH$_4$, MeOH; b) H$_2$, Pd/C; c) RNH$_2$; d) BOC-protected amino acid, coupling agent; e) CF$_3$CO$_2$H

Compound M73: (2R,4R)-4-(2Aminoacetamido)-2-(5-benzyl-2-benzimidazoyl)pyrrolidine This compound was prepared according to Scheme 6, using the following methods:
(A) 4-(1-Hydroxy-1-phenylmethyl)-1,2-diaminobenzene
  3,4-Diaminobenzophenone (5.79 g, 27 mmol) was dissolved in MeOH (80 mL) and cooled to 0° C. A solution of NaBH$_4$ (4.12 g, 109 mmol) in MeOH (30 mL) was added dropwise over 10 min. The mixture was stirred for 2 hours and concentrated to dryness. The residue was dissolved in EtOAc and washed with NaHCO$_3$ (3×50 mL). The organic layer was dried over Na$_2$SO$_4$, filtered and concentrated to afford the title compound (5.3 g, 90%): $^1$HNMR (400 MHz, CDCl$_3$) δ 5.6–5.65 (1H, s), 6.6–6.7 (3H, m), 7.2–7.45 (5H, m).

(B) 1,2-Diamino-4-benzylbenzene
  The product from (A) (5.3 g,25 mmol) was dissolved in MeOH (100 imL). 10% Pd/C (0.57 g) and 6N HCl (12.3 mL, 74 mmol) were added. The mixture was hydrogenated at 50 psi for 18 hrs at room temperature, filtered over a pad of diatomaceous earth and concentrated to dryness. The residue was dissolved in 200 mL EtOAc and washed with saturated NaHCO$_3$ (3×100 mL), brine (1×50 mL), dried over Na$_2$SO$_4$, filtered and concentrated to dryness to give the diamine (4.8 g, 98%): H$^1$ NMR (400 MHz, CDCl$_3$) δ 3.85–3.88 (2H, s), 6.75–6.85 (2H, m), 6.95–7.05 (1H, s), 7.1–7.16 (3H, m), 7.2–7.26 (2H, d).

(C) trans-4-(N-tert-Butoxycarbonylglycyl)amino-N-tert-butoxycarbonyl-L-proline pentafluorophenyl ester
  trans-4-(N-tert-Butoxycarbonylglycyl)amino-N-tert-butoxycarbonyl-L-proline (1.96 g, 5.06 mmol) was dissolved in EtOAc (40 mL) and pentafluorophenol (PFP) (1.03 g, 5.6 mmol) was added in one portion. (1,3-)dicyclohexylcarbodiimide (DCC 1.15 g, 5.6 mmol) was pre-dissolved in EtOAc (10 mL) and added dropwise over 1 minute. A white precipitate immediately formed which, upon stirring for 1 hour, 1:5 was filtered and the filtrate was concentrated to dryness to reveal the title compound in 95% yield.

(D) (2S,4R)4-(2-Aminoacetamido)-2-(5-benlzyl-2-benzimidazolyl)pyrrolidine
  4-Benzyl-1,2-diaminobenzene (0.093 g, 0.47 mmol) was dissolved in EtOAc (10 mL) and the product from (C) (0.25 g, 0.47 mmol) was added in one portion. The mixture was heated at 70° C. for 2 days, then concentrated to dryness. The residue was dissolved in 1,2-dichloroethane (10 mL) and pyridinium (p-)toluenesulfonate (PPTS) (0.058 g, 0.23 mmol) was added in one portion. The reaction was heated at 80° C. for 18 hours and concentrated to dryness. The residue was dissolved in EtOAc (70 mL) and washed with saturated NaHCO$_3$ (3×100 mL), brine, dried over Na$_2$SO$_4$, filtered, concentrated to an oil, and was applied to a column pre-packed with silica The coupled product was eluted from the column with EtOAC/Hexanes (1:1, v:v): $^1$HNMR (400 MHz, CDCl$_3$) δ 1.4–1.5 (18H, s), 3.2–3.3 (2H, m), 3.4–3.45 (2H, s), 3.7–3.85 (3H, b), 4.1–4.15 (1H, s), 5.3–5.4 (2H, b), 7.1–7.3 (5H, m), 7.35–7.4 (1H, s), 7.45–7.5 (1H, s); MS (relative intensity) m/e 350 (100, M+1).

This compound was deprotected by exposure to TFA for 30 minutes. The solution was concentrated to an oil and purified using reverse phase liquid chromatography (Amberchrome : CH$_3$CN/0.1% TFA-H$_2$O) to give the title compound: $^1$H NMR (D$_2$O): δ 2.7–2.85 (1H, m), 2.9–3.0 (1H, m), 3.6–3.65 (1H, d), 3.8–3.9 (2H, s), 3.9–3.95 (1H, q), 4.1–4.15 (2H, s), 5.4–5.55 (1H, t), 7.2–7.35 (5H, m), 7.4–7.5 (1H, d), 7.6–7.75 (2H, m); MS m/e 350 (100, M+1).

Compound M74: (2R,4R)-4-(Aminomethyl)-2-(5-benzyl-2-benzimidazoly)pyrrolidine This compound was prepared as in Compound M73, replacing trans-4-(N-tert-butoxycarbonylglycyl)amino-N-tert-butoxycarbonyl-L-proline with trans-4-(N-tert-butoxycarbonylaminomethyl)-N-tert-butoxycarbonyl-D-proline.

Compound M75: (2S,4R)-4-(Aminoacetamido)-2-(1-(2-phenyl)ethyl-2-benzimidazolyl)pyrrolidine This compound was prepared as in Compound M73, replacing 4-benzyl-1,2-diaminobenzene with N-(2-phenylethyl)-2-aminoaniline, made as follows:

(A) N-(2-Phenylethyl)-2-nitroaniline

1-Chloro-2-nitrobenzene (2 g, 12.7 mmol), phenethylamine (5.1 mL, 40.6 mmol), and N,N-diisopropylethylamine (2.8 mL, 15.3 mmol) were dissolved in 1,2-dichloroethane (20 mL) and heated at reflux for 16 hrs. The mixture was concentrated to an oil which was dissolved in EtOAc (200 mL), washed with dilute HCl (3×50 mL), dried over Na$_2$SO$_4$, filtered and concentrated to dryness to give the title compound (3.0g, 97%): $^1$H NMR (400 MHz, CDCl$_3$) δ 3.0–3.1 (2H, t), 3.5–3.65 (2H, q), 6.65–6.7 (1H, t), 6.85–6.9 (1H, d), 7.25–7.4 (5H, m), 7.45–7.5 (1H, t), 8.15–8.2 (1H, d).

(B) N-(2-Phenylethyl)-2-aminoaniline

N-(2-Phenylethyl)-2-nitroaniline (3.0 g, 12.4 mmol) was dissolved in MeOH (60 mL), and 10% Pd/C (300mg) was added. The mixture was hydrogenated at 1 atm for 18 hrs at room temperature, filtered over a celite pad and concentrated to an oil. The resulting oil was applied to a column prepacked with silica. The title compound was eluted from the column with EtOAc/Hexanes (1:3, v:v).

Compound M76: (2S,4R)-4-(2-Aminoacetamido)-2-(1-(3-aminopropyl)-2-benzimidazolyl)pyrrolidine This compound was prepared as in Compound M73, replacing trans-4-(N-tert-butoxycarbonylglycyl)amino-N-tert-butoxycarbonyl-L-proline with N-tert-butoxycarbonyl-L-proline, and 4-benzyl-1,2-diaminobenzene with N-(3-N-tert-butoxycarbonylaminopropyl)-2-amino-4-benzylaniline, made by the treatment of 2-nitro-4-benzoylchlorobenzene with N-(tert-butoxycarbonyl)diaminopropane in DMSO, and reduction and hydrogenation by analogy with Compound M73 (A–B).

Scheme 7

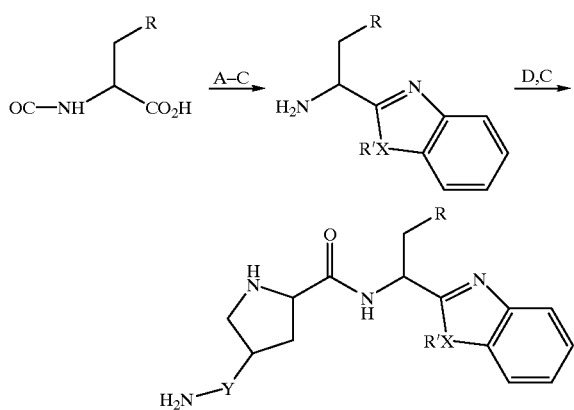

a) pentafluorophenol, DCC, EtOAc; b) i) aryl-1,2-diamine or ii) 2-aminophenol or 2-aminothiophenol, then PPTS; c) CF$_3$COOH; d) BOC-protected amino acid, coupling agent

Compound M77: (2S,4R)-4-(Aminoacetamido)-N-[(1R)-1-(2-benzoxazolyl)-3-phenylpropyl]-2-pyrrolidinecarboxamide This was made according to Scheme 7, using the following methods:

(A) N-(Benzyloxycarbonyl)-D-homophenalalanine pentafluorophenyl ester

N-(Benzyloxycarbonyl)D-homophenylalanine (1.01 g, 3.29 mmol) was dissolved in EtOAc (20 mL) and pentafluorophenol (680 mg, 3.29 mmol) was added in one portion. DCC (0.7 g, 3.29 mmol) was predissolved in EtOAc (10 mL) and added dropwise over 1 minute. A white precipitate immediately formed which, upon stirring for 1 hour, was filtered and the filtrate was concentrated to dryness.

(B) (1R)-1-benzoxazolyl)-3-phenylpropylamine

N-(Benzyloxycarbonyl)-D-homophenylalanine pentafluorophenyl ester (1.5 g, 3.2 mmol) was dissolved in 1,2-dichloroethane (40 mL) and 2-aminophenol (0.36 g, 3.3 mmol) was added. This solution was heated at 80° C. and stirred for 6 hrs at which time PPTS (0.415 g, 1.6 mmol) was added. The resulting mixture was stirred at 80° C. for an additional 96 hrs, then concentrated to dryness. The residue was dissolved in EtOAc (150 mL), washed with NaHCO$_3$ (3×100 mL) and brine (1×60 mL), dried over Na$_2$SO$_4$, filtered, concentrated to an oil, and was applied to a column prepacked with silica. Elution with EtOAC/Hexanes (3:1, v:v) gave the benzoxazole (1.0 g, 78%). This was dissolved in MeOH (50 mL), and 10% Pd/C (100 mg) and triethylamine (2.5 mmol) were added. The mixture was hydrogenated at 50 psi for 16 hrs at room temperature, filtered over a pad of diatomacous earth and concentrated to dryness to give the title compound (530mg): $^1$HNMR (400 MHz, CDCl$_3$) δ 2.5–2.55 (2H, m), 2.7–2.9 (2H, m), 4.6–4.65 (1H, t), 7.1–7.3 (3H, m) 7.35–7.45 (2H, m), 7.55–7.6 (1H, d), 7.75–7.8 (1H, d).

(C) (2S,2R)-4-(2-Aminoacetamido)-N-[(1R)-1-(2-benzoxazolyl)-3-phenylpropyl]-2-pyrrolidinecarboxamide trans-4-(N-tert-Butoxycarbonylglycyl)amino-N-tert-butoxycarbonyl-L-proline pentafluorophenyl ester (Compound M73(C)) (0.15 g, 2.8 mmol) was dissolved in DMF (10 mL). The product from (B) (0.072 g, 2.8 mmol) was added in one portion and the mixture was stirred for 2 hrs at 50° C. The solution was concentrated and the residue was dissolved in EtOAc (50 mL) and washed with saturated NaHCO$_3$ (3×50 mL), brine, dried over Na$_2$SO$_4$, filtered, concentrated to an oil, and applied to a column prepacked with silica. Elution with EtOAc gave the coupled product (90mg): $^1$H NMR (400 MHz, CDCl$_3$) δ 1.4–1.6 (18H, s), 2.35–2.5 (2H, b), 2.8–2.9 (2H, d), 3.8–3.85 (2H, s), 4.45–4.55 (2H, b), 5.1 (1H, s), 5.5–5.6 (1H, s), 7.3–7.5 (7H, m), 7.6 (1H, s), 7.8 (1H, s). This compound was deprotected by exposure to TFA (5 mL) for 30 min, concentration to an oil and purification using reverse phase liquid chromatography (Amberchrome: CH$_3$CN/0.1% TFA-H$_2$O): H$^1$ NMR (D$_2$O) δ 2.3–2.45 (1H, m), 2.46–2.55 (2H, m), 2.7–2.85 (2H, m), 3.4–3.45 (1H, b), 3.7–3.8 (1H, m), 3.8–3.82 (1H, s), 3.83–3.85 (2H, s), 4.5–4.65 (2H, m), 5.1–5.2 (1H, t), 7.1–7.35 (5H, m), 7.4–7.45 (2H, m), 7.6–7.64 (1H, d), 7.65–7.7 (1H, d).

Compound M78: (2S,4R)-4-(2-Aminoacetamido)-N-[(1S)-1-(2-benzimidazolyl)-3-phenyl)methyl]pyrrolidinecarboxamide This compound was prepared as in Compound M77, replacing N-(benzyloxycarbonyl)-D-homophenylalanine with N-(benzyloxycarbonyl)-L-homophenylalanine, and 2-aminophenol with 1,2-diaminobenzene.

Compound M79: (2S,4R)-4-(2-Aminoacetamido)-N-[(5-benzyl)-2-benzimidazoly)methyl]-2-pyrrolidinecarboxamide This compound was prepared as in Compound M77, replacing N-(benzyloxycarbonyl)D-homophenylalanine with N-(benzyloxycarbonyl)glycine, and 2-aminophenol with 1,2-diamino4-benzylbenzene (Compound M73(B)).

Compound M80: (2S,4R)-4-(2-Aminoacetamido)-
N-[(1S)-1-(2-benzimidazolyl)-3-phenyl)methyl]
pyrrolidinecarboxamide This compound was prepared as in Compound M77, replacing N-(benzyloxycarbonyl)-D-homophenylalanine with N-(benzyloxycarbonyl)glycine, and 2-aminophenol with N-(2-phenylethyl)-2-aminoaniline (Compound M75 (A,B)).

Compound M81: (2S,4R)-4-(2-Aminoacetamido)-
N-[(5-(1,1-dimethyl)ethyl-2-benzimidazolyl)
methyl]-2-pyrrolidinecarboxamide This compound was prepared as in Compound M77, replacing N-(benzyloxycarbonyl)-D-homophenylalanine with N-(benzyloxycarbonyl)glycine, and 2-aminophenol with 1,2-diamino-4-tert-butylbenzene.

Compound M82: (2S,4R)-4-(2-Aminoacetamido)-
N-[(5-(1-hydroxy-1-phenyl)methyl-2-
benzimidazolyl)methyl]-2-pyrrolidinecarboxamide This compound was prepared as in Compound M77, replacing N-(Benzyloxycarbonyl)-D-homophenylalanine with N-(Benzyloxycarbonyl)glycine, and 2-aminophenol with 4-(1-hydroxy-1-phenylmethyl)-1,2-diaminobenzene (Compound M73(A)).

Compound M83: (2S,4R)-4-(2-Aminoacetamido)-
N-[(1S)-1-(5-benzyl-2-benzimidazolyl)ethyl]-2-
pyrrolidinecarboxamide This compound was prepared as in Compound M77, replacing N-(Benzyloxycarbonyl)-D-homophenylalanine with N-(Benzyloxycarbonyl)-L-alanine, and 2-aminophenol with 1,2-diamino-4-benzylbenzene.

Compound M84: (2S,4R)-4-(2-Aminoacetamido)-
N-[(1R)-1-(2-benzithiazolyl)-3-phenylpropyl)
methyl]-2-pyrrolidinecarboxamide This compound was prepared as in Compound M77, replacing 2-aminophenol with 2-aminothiophenol.

Compound M85: (2S,4R)-4-(2-Aminoacetamido)-
N-[(1S)-1-(2-benzoxadazolyl)oxo-3-phenylpropyl]-
2-pyrrolidinecarboxamide This compound was prepared as in Compound M77, replacing N-(Benzyloxycarbonyl)-D-homophenylalanine with replacing N-(Benzyloxycarbonyl)-L-homophenylalanine.

Compound M86: (2R,4R)-4-(Aminomethyl)-N-[(5-
benzyl-2-benzimidazolyl)methyl]-2-
pyrrolidinecarboxamide This compound was prepared as in Compound M77, replacing N-(Benzyloxycarbonyl)-D-homophenylalanine with N-(Benzyloxycarbonyl)glycine, 2-aminophenol with 1,2-diamino-4-benzylbenzene and trans-4-(N-tert-butoxycarbonylglycyl)amino-N-tert-butoxycarbonyl-L-proline with trans-4-(N-tert-butoxycarbonylaminomethyl)-N-tert-butoxycarbonyl-D-proline.

Compound M87: (2R,4S)-4-(Aminomethyl)-N-[(5-
benzyl-2-benzimidazolyl)methyl]-2-
pyrrolidinecarboxamide This compound was prepared as in Compound M77, replacing N-(Benzyloxycarbonyl)-D-homophenylalanine with N-(Benzyloxycarbonyl)glycine, 2-aminophenol with 1,2diamino-4-benzylbenzene and trans-4-(N-tert-butoxycarbonylglycyl)amino-N-tert-butoxycarbonyl-L-proline with cis-4-(N-tert-butoxycarbonylaminomethyl)-N-tert-butoxycarbonyl-D-proline.

Compound M88: (2R,4S)-4-(Aminomethyl)-N-[(5-
phenyloxy-2-benzimidazolyl)methyl]-2-
pyrrolidinecarboxamide This compound was prepared as in Compound M77, replacing N-(Benzyloxycarbonyl)-D-homophenylalanine with N-(Benzyloxycarbonyl)glycine, 2-aminophenol with 1,2-diamino-4-phenyloxybenzene and trans-4-(N-tert-butoxycarbonylglycyl)amino-N-tert-butoxycarbonyl-L-proline with trans-4-(N-tert-butoxycarbonylaminomethyl)-N-tert-butoxycarbonyl-D-proline.

Compound M89: (2R,4R)-4-(Aminomethyl)-N-[(5-
phenyl-2-benzimidazolyl)methyl]-2-
pyrrolidinecarboxamide This compound was prepared as in Compound M77, replacing N-(Benzyloxycarbonyl)-D-homophenylalanine with N-(Benzyloxycarbonyl)glycine, 2-aminophenol with 1,2-diamino-4-phenylbenzene and trans-4-(N-tert-butoxycarbonylglycyl)amino-N-tert-butoxycarbonyl-L-proline with trans-4-(N-tert-butoxycarbonylaminomethyl)-N-tert-butoxycarbonyl-D-proline.

Scheme 8

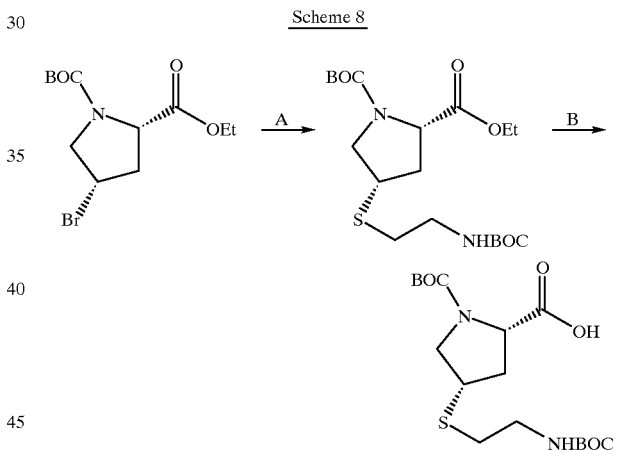

a) BOCNHCH$_2$CH$_2$SH, NaH, THF; b) LiOH, H$_2$O/MeOH/THF

Compound M90: (2S,4R)-4-(2-Aminoethylthio)-N-
[(1R)-3-phenyl-1-(3-quinolylcarbamoyl)propyl]-2-
pyrrolidinecarboxamide This compound was prepared according to Schemes 8 & 1, using the following methods:
(A) N,N'-Bis-(tert-butoxycarbonyl)-trans-4-(2-aminoethanethio)-L-proline ethyl ester Sodium hydride (1.5 eq.) was added to a solution of N-(tert-butoxycarbonyl)-2-aminoethanethiol in dimethylformamide at 0° C. under nitrogen atmosphere. A solution of N-(tert-butoxycarbonyl)-cis-4-bromo-L-proline ethyl ester in dimethylformamide was transferred via cannula and the reaction mixture was warmed to 70° C. and stirred for 4 hours. The mixture was poured into ethyl acetate, washed twice with water, twice with brine, dried (Na$_2$SO$_4$), concentrated and purified by flash chromatography to afford the title compound as a glassy solid: $^1$H NMR (300 MHz, CDCl$_3$) δ

1.28 (m, 3H), 1.42–1.50 (m, 18H), 2.19 (m, 1H), 2.29 (m, 1H), 2.69 (t, J=5.4 Hz, 2H), 3.31 (m, 3H), 3.59 (m, 2H), 3.44 (m, 1H), 3.90 (m, 1H), 4.19 (m, 2H), 4.85 (m, 1H, NH); MS (ES+) 441.3 (M+Na).

(B) N,N'-Bis-(tert-butoxycarbonyl)-trans-4-(2-aminoethanethio)-L-proline

N,N'-Bis-(tert-butoxycarbonyl)-trans-4-(2-aminoethanethio)-L-proline ethyl ester was hydrolyzed by the addition of an aqueous solution of lithium hydroxide (2 eq.) in tetrahydrofuran and methanol and stirring at 25° C. for 1.5 h. Work-up as in (A) gave the title compound: $^1$H NMR (300 MHz, CDCl$_3$) 3 1.52–1.60 (m, 18H), 2.41 (m, 1H), 2.79 (m, 3H), 3.41 (m, 3H), 3.54 (m, 1H), 3.44 (m, 1H), 3.90 (m, 1H), 4.19 (m, 2H), 4.31–4.42 (m, 1H), 4.85 (m, 1H, NH).

(C) (2S,4R)-4-(2-Aminoethylthio)-N-[(1R)-3-phenyl-1-(3-quinolylcarbamoyl)propyl]-2-pyrrolidinecarboxamide The product from (B) was coupled with the amine from D201(B) and deprotected as for Compound M1 to give the title compound: $^1$H NMR (300 MHz, D$_2$O) δ 2.40 (m, 2H), 2.58 (m, 2H), 2.90 (m, 1H), 2.96 (m, 1H), 3.05 (t, J=4.8 Hz, 2H), 3.35 (t, J=5.4 Hz, 2H), 3.51 (m, 1H), 3.88 (m, 2H), 4.61 (m, 1H), 4.79 (m, 1H), 7.21 (m, 1H), 7.36 (m, 4H), 7.93 (t, J=7.2 Hz, 1H), 8.07 (t, J=7.2 Hz, 1H), 8.20 (m, 2H), 8.85 (s, 1H), 9.92 (s, 1H); MS 478.2 (M+H).

Scheme 9

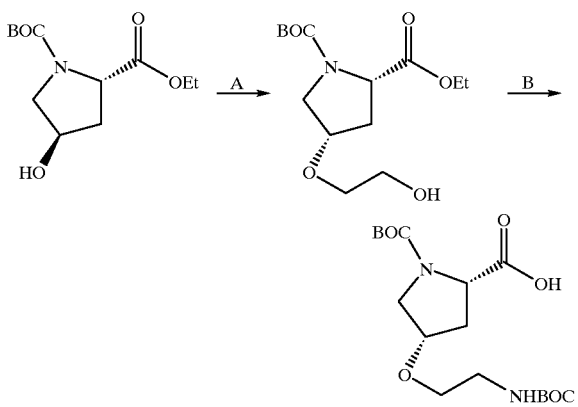

a) NaH, allyl bromide; b) OsO$_4$, NaIO$_4$; c) NaBH$_4$, MeOH; d) MsCl, Et$_3$N; e) NaN$_3$, DMF, f) (PhS)$_2$Sn, DIEA; g) BOC$_2$O, Na$_2$CO$_3$; h) LiOH, H$_2$O/MeOH/THF Compound M91: (2S,4R)-4-(2-Aminoethyloxy)-N-[(1R)-3-phenyl-1-(3-quinolylcarbamoyl)propyl]-2-pyrrolidinecarboxamide This compound was prepared according to Schemes 8 & 1, using the following methods:

(A) N-(tert-butoxycarbonyl)-trans-4-allyloxy-L-proline ethyl ester

Freshly prepared silver oxide (5.32 g, 3 eq.) and allyl iodide (15 mL, 4 eq.) were added to a solution of N-(tert-butoxycarbonyl)-trans-4-hydroxy-L-proline ethyl ester (2.2 g, 7.71 mmol) in dimethylformamide (15 mL) under a nitrogen atmosphere. The reaction mixture was stirred at 25° C. for 12 hours, then at 55° C. for 5 hours. The reaction mixture was filtered, poured into ethyl acetate, washed twice with water, once with brine, dried (Na$_2$SO$_4$), concentrated and purifed by flash chromatography (20% ethyl acetate/hexane) to give the title compound (2.18 g, 94%) as a clear oil. $^1$H NMR (300 MHz, CDCl$_3$) δ 1.38 (m, 3H), 1.48, 1.54 (2s, 9H), 2.17 (m, 1H), 2.23 (m, 1H), 3.58 (bd, J=12.4 Hz, 0.5H), 3.70 (m, 1.5H), 4.05 (m, 2H), 4.22 (m, 3H), 4.43 (m, 1H), 5.29 (dd, J=10.1; 0.7 Hz, 1H), 5.39 (dd, J=17.6; 0.6 Hz, 1H) and 5.99 (m, 1H).

(B) N-(tert-butoxycarbonyl)-trans-4-(2-formylmethylenoxy)-L-proline ethyl ester

A solution of N-(tert-butoxycarbonyl)-trans-4-allyloxy-L-proline ethyl ester (2.14 g, 7.16 mmol) in dioxane (70 mL) was treated with osmium tetroxide (200 pI of a 2.5% sol. in toluene) followed, over 30 minutes, by a solution of sodium periodate (3.06 g, 2 eq.) in water (70 mL). The mixture was stirred vigorously for 1 hour. The mixture was diluted with water and extracted with ether. The organic layer was washed twice with water, once with brine, dried (Na$_2$SO$_4$), concentrated and purified by flash chromatography (30 to 50% ethyl acetate/hexane) to give the title compound (1.42 g, 66%) as a clear oil. $^1$H NMR (300 MHz, CDCl$_3$) δ 1.39 (m, 3H), 1.52, 1.58 (2s, 9H), 2.20 (m, 1H), 2.51 (m, 1H), 3.59–3.62 (m, 3H), 4.29 (m, 1H), 4.59 (m, 3H), 4.49 (m, 1H), 9.80 (s, 1H).

(C) N-(tert-butoxycarbonyl)-trans-4-(2-hydroxyethoxy)-L-proline ethyl ester

Sodium borohydride (118 mg, 1 eq.) was added portionwise to a solution of N-(tert-butoxycarbonyl)-trans-4-(2-formylmethylenoxy)-L-proline ethyl ester (942 mg, 3.1 mmol) in methanol (35 mL) at 0° C. The mixture was stirred for 1 hour, then poured into ethyl acetate, washed twice with 1 N aqueous sodium hydroxide solution, twice with brine, dried (Na$_2$SO$_4$) and concentrated. The product (721 mg, 78%) was used crude: $^1$H NMR (300 MHz, CDCl$_3$) δ 1.39 (m, 3H), 1.51, 1.56 (2s, 9H), 1.60 (bs, 1H, OH), 2.18 (m, 1H), 2.46 (m, 1H), 3.62 (m, 2H), 3.71 (m, 2H), 3.82 (m, 2H), 4.21–4.33 (m, 3H), 4.47 (m, 1H).

(D) N-(tert-butoxycarbonyl)-trans-4-(2-aminoethoxy)-L-proline ethyl ester

This transformation was done in three steps without characterizing the individual intermediates. Mesyl chloride (921 μl, 5 eq.) and triethylamine (1.66 mL, 5 eq.) were quickly added to a solution of N-(tert-butoxycarbonyl)-trans-4-(2-hydroxyethoxy)-L-proline ethyl ester (721 mg, 2.4 mmol) in dichloromethane (25 mL) at 0° C. under nitrogen atmosphere. The reaction mixture was stirred at that temperature for 1 hour, diluted in dichloromethane, washed twice with 1 N HCl, twice with sat NaHCO$_3$, twice with brine, dried (Na$_2$SO$_4$) and concentrated. The crude residue (0.9 g) was dissolved in dimethylformamide (25 mL) and sodium azide (2.48 g, 16 eq.) and anunonium chloride (1.27 g, 10 eq.) were added. The reaction mixture was stirred at 90° C. for 16 h. after which it was cooled and concentrated under reduced pressure and the residue partitioned between dichloromethane and water. The aqueous layer was extracted twice with dichloromethane and the combined organic layers were washed twice with water, twice with brine, dried (Na$_2$SO$_4$) and concentrated. The crude residue (0.76 g) was dissolved in anhydrous tetrrhydrofuran (10 mL) and dry tin chloride (661 mg, 1.5 eq.), thiophenol (1.43 mL, 6 eq.) and triethylamine (4.5 eq.) were added. The reaction mixture was stirred at 25° C. for 1hour, then poured into ethyl acetate and washed with 1 N HCl, 1 N NaOH, brine, dried (Na$_2$SO$_4$) and concentrated. The product (668 mg, 92%) was used crude: $^1$H NMR (300 MHz, CDCl$_3$) δ 1.39 (m, 3H), 1.53, 1.58 (2s, 9H), 2.16 (m, 1H), 2.43 (m, 1H), 2.95 (m, 2H), 3.57 (m, 2H), 3.69 (m, 2H), 4.18 (m, 1H), 4.24 (m, 2H), 4.40 (m, 1H).

(E) N,N'-Bis-(tert-butoxycarbonyl)-trans-4-(2-aminoethoxy)-L-12roline ethyl ester N-(tert-butoxycarbonyl)-trans-4-(2-aminoethoxy)-L-proline ethyl ester (660 mg, 2.19 mmol) was treated as in Compound M41(B) to give the title compound (636 mg, 72%) after flash chromatography (25% ethyl acetate/hexane) as a colorless oil: $^1$HNMR (300 MHz, CDCl$_3$) δ 1.39 (m, 3H), 1.53–1.58 (m, 18H), 2.16 (m, 1H), 2.41 (m, 1H), 3.39 (m, 2H), 3.59 (m, 2H), 3.61 (m, 2H), 4.18 (m, 1H), 4.24 (bq, J=8.0 Hz, 2H), 4.42 (m, 1H).

(F) N,N'-Bis-(tert-butoxycarbonyl)-trans-4-(2-aminoethoxy)-L-proline

A solution of lithium hydroxide (132 mg, 2eq.) in water (5 mL) was added to a solution of N,N'-Bis-(tert-butoxycarbonyl)-trans-4-(2-aminoethoxy)-L-proline ethyl ester (630 mg, 1.57 mmol) in tetrahydrofuran (15 mL). The mixture was stirred at room temperature for 2 hours, acidified with 10% citric acid solution and extracted thrice with ethyl acetate. The combined organic layers were washed brine, dried (Na$_2$SO$_4$), concentrated. The residue (0.59 g) was used crude in the next step. $^1$H NMR (300 MHz, CDCl$_3$) δ 1.53–1.58 (m, 18H), 2.20 (m, 1H), 2.59 (m, 1H), 3.39 (m, 2H), 3.60 (m, 4H), 3.69 (bs, 1H, NH), 4.19 (m, 1H), 4.42 (t, J=9.5 Hz 1H), 4.96 (bs 1H, NH).

(G) (2S,4R)-4-(2-Aminoethyloxy)-N-[(1R)-3-phenyl-1-(3-quinolylcarbamoyl)propyl]-2-pyrrolidinecarboxamide The product from (F) was coupled with the amine from D201(B) and deprotected as for Compound M1 to give thetideompound as abitepowder $^1$H NMR (300 MHz, D$_2$O) δ 2.18 (m, 1H), 2.36 (m, 2H), 2.77 (m, 1H), 2.83 (m, 2H), 3.22 (t, J=6.5 Hz, 2H), 3.54 (dd, J=12.0; 3.2 Hz, 1H), 3.62 (d, J=11.9 Hz, 1H), 3.79 (m, 2H), 4.54 (m, 1H), 4.61 (m, 1H), 7.15 (m, 1H), 7.28, 7.30 (2bs, 4H), 7.79 (t, J=7.4 Hz, 1H), 7.92 (t, J=6.9 Hz, 1H), 8.05 (d, J=8.6 Hz, 1H), 8.09 (d, J=8.9Hz, 1H), 8.64 (d, J=2.4 Hz, 1H), 8.99 (d, J=2.4 Hz, 1H); MS (ES+) 462.3 (M+H).

Compound M92: (2S,4R)-4-(2-Aminoethylthio)-N-(6(1,1-dimethyl)ethyl-3-quinolyl)-2-pyrrolidinecarboxamide This compound was made by coupling the acid from Compound 91(F) with 3-amino-6-tert-butylquinoline and deprotection as for Compound M1.

Scheme 10

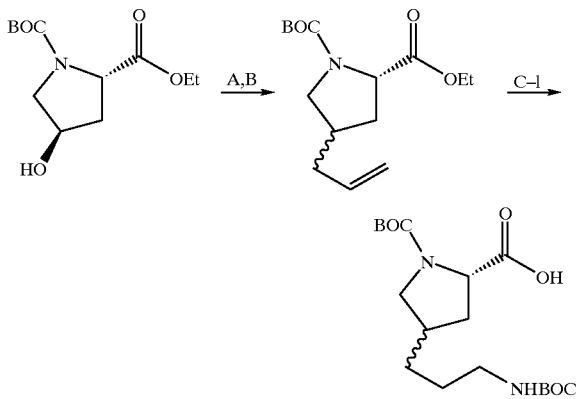

a) Ph$_3$P, CBr$_4$; b) Bu$_3$SnAllyl, AIBN; c) BH$_3$, THF; d) H$_2$O$_2$, NaOH; e) MsCl, Et$_3$N; f) NaN$_3$, DMF; g) H$_2$, Pd/C, MeOH; h) BOC$_2$O, NaHCO$_3$; i) LiOH, H$_2$O/MeOH/THF.

Compound M93: (2S,4RS)-4-(3-Aminopropyl)-N-[(1R)-3-phenyl-1-(3-quinolylcarbamoyl)propyl]-2-pyrrolidinecarboxamide This compound was prepared according to Schemes 10 & 1, using the following methods:
(A) N-(tert-butoxycarbonyl)-4-(2-allyl)-L-proline ethly ester Allyltributyltin (1.72 mL, 2 eq.) and azobisisobutyronitrile (76 mg, 0.15 eq.) were added to a solution of N-Boc-4-R-Bromoproline ethyl ester (1 g, 3.1 mmol) in anhydrous benzene (16 mL) and the reaction mixture was refluxed for 16 hours. The mixture was concentrated and purified by flash chromatography to give the title compound (515 mg, 59%) as a clear oil: $^1$H NMR (400 MHz, CDCl$_3$, 7:3 mixture of diastereomers) δ 1.26 (m, 3H), 1.37–1.44 (m, 9H), 1.60 (m, 1H), 1.92 (m, 1H), 2.18 (m, 2H), 2.39 (m, 1H), 3.00 (t, J=10.1, 0.3H), 3.06 (dd, J=11.5; 9.3 Hz, 0.7H), 3.63–3.80 (m, 1H), 4.18–4.37 (m, 3H), 5.02 (m, 2H), 5.78 (m, 1H); MS (ES+) 306.2 (M+Na).

(B) N-(tert-butoxycarbonyl)-4-(3-hydroxypropyl)-L-proline ethyl ester

Borane.THF complex (1.8 mL of a 1M solution, 0.33 eq.) was added dropwise over 0.5 hours to a solution N-(tert-butoxycarbonyl)-4-(2-allyl)-L-proline ethyl ester (0.5 g, 1.76 mmol) in tetrahydrofuran (18 mL) at 0° C. under nitrogen atmosphere. After 2 h, another portion of borane (1.8 mL, 0.33 eq.) was added and the reaction mixture was stirred 2 h at 0° C. A solution of hydrogen peroxide (30%, 180 μl, 2 eq.) was added followed by 3N sodium hydroxide, until the pH of the solution was 8. The mixture was diluted with water and extracted 5 times with ethyl acetate. The combined organic layers were dried (Na$_2$SO$_4$) and concetrated to give the title compound (579 mg, quantitative) as a clear oil: $^1$H NMR (400 MHz, CDCl$_3$, 7:3 mixture of diastereomers) δ 1.24 (m, 3H), 1.41–1.50 (m, 9H), 1.60 (m, 1H), 1.95 (m, 1H), 2.10 (m, 2H), 2.32 (m, 1H), 2.42 (m, 1H), 3.00 (m, 1H), 3.63 (m, 2H), 3.78 (m, 1H), 4.18–4.37 (m, 4H); MS (ES+) 324.2 (M+Na).

(C) N-(tert-butoxycarbonyl-4-(3-azidopropyl)-L-proline ethyl ester

N-(tert-butoxycarbonyl)-4-(3-hydroxypropyl)-L-proline ethyl ester (550 mg, 1.83 mmol) was converted to the title compound (550 mg, 92%) as a clear oil by mesylation of the alcohol followed by displacement with sodium azide as described in Compound M91(D): $^1$H NMR (400 MHz, CDCl$_3$, 7:3 mixture of diastereomers) δ 1.27 (m, 3H), 1.41–1.48 (m, 9H), 1.59 (m, 1H), 1.86 (m, 1H), 2.11 (m, 2H), 2.3 (m, 1H), 2.42 (m, 1H), 2.97 (m, 1H), 3.29 (m, 2H), 3.78 (m, 1H), 4.18–4.38 (m, 4H).

(D) N-(tert-butoxycarbonyl)-4-(3-aminopropyl)-L-proline ethyl ester

N-(tert-butoxycarbonyl)-4-(3-azidopropyl)-L-proline ethyl ester (1.17 g, 3.58 mmol) was dissolved in anhydrous tetrahydrofuran (40 mL) and dry tin chloride (1.01 g, 1.5 eq.), thiophenol (2.21 mL, 6 eq.) and triethylamine (2.24 mL, 4.5 eq.) were added. The reaction mixture was stirred at 25° C. for Ihour, poured into ethyl acetate, washed with 1 N HCl, 1 N NaOH, brine, dried (Na$_2$SO$_4$) and concentrated. The residue (0.96 g, 90%) was used crude in the next step: $^1$H NMR (400 MHz, CDCl$_3$, 7:3 mixture of diastereomers) δ 1.29 (m, 3H), 1.40–1.56 (m, 9H), 1.84 (m, 1H), 2.10 (m, 1H), 2.39 (m, 1H), 2.42 (m, 1H), 2.72 (m, 2H), 2.99 (m, 2H), 3.76 (m, 2H) 4.18–4.38 (m, 4H).

(E) N,N'-Bis-(tert-butoxycarbonyl)-4-(3-aminopropyl)-L-proline ethyl ester

N-(tert-butoxycarbonyl)-4-(3-aminopropyl)-L-proline ethyl ester (0.96 g, 3.2 mmol) was treated as in Compound M41(B) to give the title compound (1.24 g, 97%) after flash chromatography (50% ethyl acetate/hexane) as a colorless oil: $^1$H NMR (400 MHz, CDCl$_3$, 7:3 mixture of diastereomers) δ 1.29 (m, 3H), 1.39–1.52 (m, 18H), 1.72 (m, 1H), 1.96 (m, 1H), 2.29 (m, 1H), 2.49 (m, 1H), 2.94 (m, 1H), 3.00 (m, 1H), 3.14 (m, 2H), 3.58 (m, 1H), 3.78 (m, 1H), 4.36 (m, 2H), 4.58 (bs, 1H, NH); MS (ES+) 423.2 (M+Na).

(F) N,N'-Bis-(tert-butoxycarbonyl)-4-(3-aminopropyl)-L-proline

N,N'-Bis-(tert-butoxycarbonyl)4-(3-aminopropyl)-L-proline ethyl ester (1.2 g, 3.6 mmol) was hydrolysed by the addition of an aqueous solution of lithium hydroxide (2 eq.) in tetrahydrofuran and methanol and siring at 25° C. for 1.5 hours. The mixture was stirred at room temperature for 2 hours, acidified with 10% citric acid solution and extracted thrice with ethyl acetate. The combined organic layers were washed brine, dried ($Na_2SO_4$), and concentrated to give the title compound (1.1 g, 98%): $^1$H NMR (400 MHz, $CDCl_3$, 7:3 mixture of diastereomers) δ 1.39–1.52 (m, 18H), 1.82 (m, 1H), 2.09 (m, 1H), 2.28 (m, H3), 2.41 (m, H3), 2.99 (m, 2H), 3.10 (m, 2H), 3.76 (m, 2H), 4.18–4.38 (m, 4H); MS (ES+) 395.2 (M+Na).

(G) (2S,4RS)-4-(3-Aminopropyl)-N-[(1R)-3-phenyl-(3-quinolylcarbamoyl)propyl]-2-pyrrolidinecarboxamide The product from (F) was coupled with the arine from D201(B) and deprotected as for Compound M1 to give ihe title compound (47.5 mg, 16%) as a white powder: $^1$H NMR (400 MHz, $CDCl_3$) δ 1.65 (m, 2H), 1.81 (m, 2H), 2.21–2.39 (m, 3H), 2.45 (m, 2H), 2.91 (m, 1H), 2.97 (m, 1H), 3.10 (m, 3H), 3.75 (dd, J=11.6; 7.2 Hz, 1H), 4.61 (t, J=5.6 Hz, 1H), 4.67 (m, 1H), 7.23 (m, 1H), 7.37 (m, 4H), 7.89 (t, J=8.4 Hz, 1H), 8.02 (t, J=7.2 Hz, 1), 8.14 (d, J=9.6 Hz, 1H), 8.17 (d, J=9.2 Hz, 1H), 8.75 (s, 1H), 9.09 (d, J=1.6 Hz, 1H); MS (ES+) 460.3 (M+H).

Scheme 11

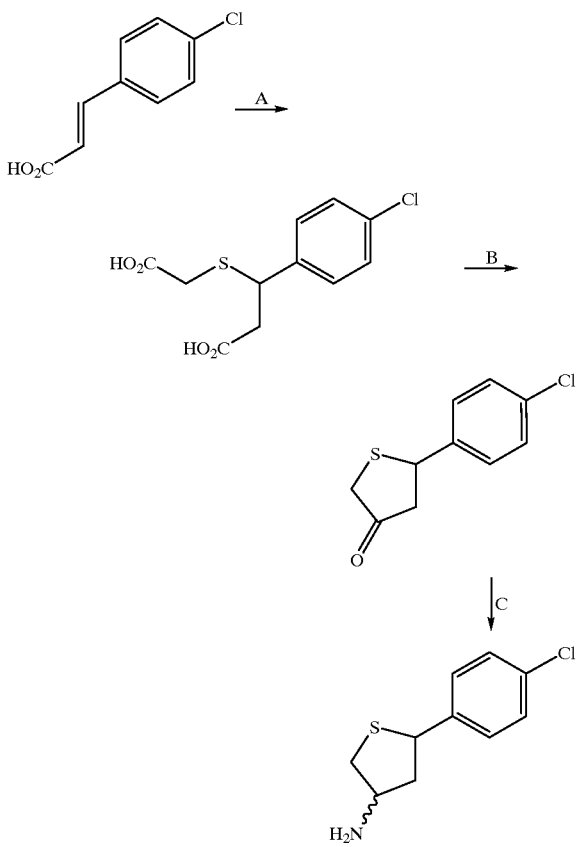

a) $HSCH_2CO_2H$; b) LiOAc, $Ac_2O$; c) $AcONH_4$, $NaBH_4$

Compound M94: (2S,4R)-4-(2-Aminoacetamido)-N-[5(p-chlorophenyl)tetrahydro-3-thienyl]-2-pyrrolidinecarboxamide This compound was prepared according to Schemes 11 & 1. The required amine was made from p-chlorocinnamic acid by cyclisation to the 4-oxotetrahydrothiophene (Reinhardt et al ., Synthesis, 1978, 368–370) followed by reductive amination (Marui et al., Chem. Pharm. Bull., 1995, 43, 588–593). The amine was coupled with trans-4-(N-tert-butoxycarbonylglycyl)amino-N-tert-butoxycarbonyl-L-proline and deprotected as for Compound M1.

Compound M95: (2S,4R)-4-(Guanadinyl)-N-[(1R)-3-phenyl-1-(3-quinolylcarbamoyl)propyl]-2-pyrrolidinecarboxamide N-(tert-Butoxycarbonyl)-cis-4-bromo-L-proline ethyl ester was treated with sodium azide as in Compound M91 (D), coupled with tihe amine from D201(B) as in Compound M1 and reducedas in Compound M91(D). The product (100 mg, 0.19 mmol) was treated with 1-(N,N'-bis-(tert-butoxycarbonyl)-formamidinyl)-1,2-diazole (1.5 eq.) and diisopropylethylamine (5 eq.) in acetonitrile (0.3M) at room temperature overnight. The mixture was concentrated and the residue dissolved in EtOAc, washed with water and brine, dried and concentrated. Purification by flash chromatography to gave the protected guanidine (120 mg). Deprotection in TFA gave the title compound (95%) as a white solid: $^1$H NMR (300 MHz, $D_2O$) δ 2.35 (m, 3H), 2.55 (m, 1H), 2.85 (m, 2H), 3.45 (dd, 1H), 3.80 (dd, 1H), 4.43 (m, 1H), 4.55 (t, 1H), 4.68 (m, 1H), 7.10 (m, 1H), 7.25 (m, 4H), 7.85 (t, 1H), 7.98 (t, 1H), 8.14 (d, 1H), 8.78 (s, 1H), 9.14 (s, 1H); MS (ES+) 460.3 (M+H).

Compound M96: (2S,4R)-4-(2-Aminoacetamido)-N-[7-ethyl-3-quinolyl]-2-pyrrolidinecarboxamide 3-Amino-7-ethylquinoline was coupled with trans-4-(N-tert-butoxycarbonylglycyl)amino-N-tert-butoxycarbonyl-L-proline and deprotected according to Compound M1.

Compound M97: (2R,4R)-4-(Aminomethyl)-N-[6-(1,1-dimethyl)ethyl-3-quinolyl]-2-pyrrolidinecarboxamide 3-Amino-6-butylquinoline was coupled with trans-4-(N-tert-butoxycarbonylaminomethyl)-N-tert-butoxycarbonyl-D-proline and deprotected according to Compound M1.

Compound M98: (2S,4R)-4-(2-Aminoacetamido)-N-(5-benzyl-2-hydroxyphenyl)-2-pyrrolidinecarboxamide 2-Amino5-benzylphenol was coupled with trans-4-(N-tert-butoxycarbonylglycyl)amino-N-tert-butoxycarbonyl-L-proline and deprotected according to Compound M1.

Compound M99: (2S,4R)-4-(2-Aminoacetamido)-N-[2-(4-benzyl-2-benzimidazolyl)ethyl]-2-pyrrolidinecarboxamide This compound was prepared as in Compound M77, replacing N-(benzyloxycarbonyl)-D-homophenylalanine with N-(benzyloxycarbonyl)-β-alanine, and 2-aminophenol with 1,2-diamino-4-benzylbenzene (Compound M73(B)).

Compound M100: (2R,4R)-4-(Aminomethyl)-N-(6-ethyl-3-quinolyl)-2-pyrrolidinecarboxamide 3-Amino-7-ethylquinoline was coupled with trans-4-(N-tert-butoxycarbonylaminomethyl)-tert-butoxycarbonyl-D-proline and deprotected according to Compound M1.

227

Compound M101: (2R,4R)-4-(Aminomethyl)-N-(5-benzyl-2-benzimidazolyl)-2-pyrrolidinecarboxamide 2-Amino-5-benzimidazole(*J. Med Chem.*, 1984, 27, 914–917) was reduced aoofin to Comnpou M73(A,B), coupled with trans-4-(N-tert-butoxycarbonylaminomethyl)-N-tert-butoxycarbonyl-D-proline and deprotected according to Compound M1.

Compound M102: (2S,4R)-4-(2-Aminoacetamido)-N-(5-benzyl-2-benzimidazolyl)-2-pyrrolidinecarboxamide 2-Amino-5-benzoylbenzimidazole(*J. Med. Chem.*, 1984, 27, 914–917) was reduced according to Compounds M73 (A,B), coupled with trans-4-(N-tert-butoxycarbonylglycyl) amino-N-tert-butoxycarbonyl-L-proline and deprotected according to Compound M1.

Compound M103: (2R,4R)-4-(Aminomethyl)-N-[(1R)-3-phenyl-1-[(3-quinolylcarboxamido)methyl]propyl]-2-pyrrolidinecarboxamide (A) N-tert-butoxycarbonyl-3(R)-amino-5-phenylpentanoic acid This compound was prepared in 98% yield from the methyl ester (0.46 mmol) (see Klein et al., *J. Med. Chem.* 1998, 41, 437–450) using the method described in the first part of Compound 41(C): $^1$H NMR (300 MHz, CDCl$_3$): δ 1.57 (9H, s), 2.86–2.10 (2H, m), 2.61–2.84 (4H, m), 7.28–7.41 (5H, m); MS m/e 316 (80, M+Na).

(B) N-tert-butoxycarbonyl-3(R)-amino-5-phenylpentanoyl-quinoline-3-amide

This compound was prepared in 65% yield from N-tert-butoxycarbonyl-3(R)-amino-5-phenylpentanoic acid (0.44 mmol) using the method described in Compound D201(A): $^1$H NMR (300 MHz, CDCl$_3$): δ 1.54 (9H, s), 2.0–2.12 (2H, m), 2.85–2.93 (4H, m), 7.29–7.39 (5H, m), 7.71–7.89 (4H), 8.01–8.05 (2H), 8.37–8.41 (1H); MS m/e 420 (75, M+1).

(C) (2R,4R)-4-(Aminomethyl)-N-[(1R)-3-phenyl-1-[(3-quinolylcarboxamido)methyl]propyl]-2-pyrrolidinecarboxamide This compound was prepared from the product of (B) using the method described in Compound 41(D), but replacing trans-4-(N-tert-butoxycarbonylglycyl)amino-N-tert-butoxycarbonyl-D-proline with trans-4-(N-tert-butoxycarbonylaminomethyl)-N-tert-butoxycarbonyl-D-proline: $^1$H NMR (300 MHz, D$_2$O) δ 1.85–2.11 (3H, m), 2.21–2.38 (3H, m), 2.61–2.81 (6H, m), 3.01–3.21 (3H, m), 3.64–3.81 (2H, m), 4.23–4.40 (3H, m), 7.24–7.37 (5H, m), 7.88–7.93 (1H, d), 8.02–8.11 (1H, d), 8.15–8.20(2H, m), 8.94 (1H, s), 9.30(1H, s); MS m/e 446 (50, M+1).

Compound M104: trans-4-Glycylamino-D-Prolyl-D-Proline-(6-isopropyl)-3-quinolylamide This compound was prepared as for Compound M1, replacing 3-aminoquinoline with 3-amino-6-isopropylquinoline and N-tert-butoxycarbonyl-D-homophenylalanine with and N-tert-butoxycarbonyl-D-proline.

Compound M105: (2R,4R)-4-(Aminomethyl)-N-[(1R)-3-phenyl-1-(7-quinolylcambamoyl)propyl]-2-pyrrolidinecarboxamide This compound was prepared as for Compound M16, coupling with 7-aminoquinoline instead of 3aminoquinoline.

Compound M106: (2R,4R)-4-(Aminomethyl)-N-[(6R)-3-phenyl-1-(7-quinolylcarbamoyl)propyl]-2-pyrrolidinecarboxamide This compound was prepared as for Compound M16, coupling with 5-aminoquinoline instead of 3-aminoinonoline.

228

Compound M107: (2R,4R)-4-(Aminomethyl)-N-[(1R)-3-phenyl-1-(7-quinolylcarbamoyl)ethyl]-2-pyrrolidinecarboxamide This compound was prepared as for Compound M3 1, coupling with 7-aminoquinoline instead of 3-aminoquinoline.

Compound M108: (2R,4R)-4-(Aminomethyl)-N-[(1R)-2-(4fluorophenyl)-1-(7-quinolylcarbamoyl)ethyl]-2-pyrrolidinecarboxamide This compound was prepared as for Compound M31, coupling with 5-aminoquinoline instsad of 3-aminoquinoline.

Compound M109: (2S,4S)-4-(Aminomethyl)-N-[(1R)-3-phenyl-1-(6-quinolylcarbamoyl)propyl]-2-pyrrolidinecarboxamide This compound was prepared as for Compound M29, using trans-4-(N-tert-butoxycarbonylaminomethyl)-N-tert-butoxycarbonyl-L-proline instead of trans-4-(N-tert-butoxycarbonylaminomethyl)-N-tert-butoxycarbonyl-D-proline.

Compound M110: (2S,4S)-4-(Aminomethyl)-N-[(1R)-2-(fluorophenyl)-1-(6-quinolylcarbamoyl)ethyl]-2-pyrrolidinecarboxamide This compound was prepared as for Compound M31, using trans-4-(N-tert-butoxycarbonylaminomethyl)-N-tert-butoxycarbonyl-L-proline instead of trans-4-(N-tert-butoxycarbonylaminomethyl)-N-tert-butoxycarbonyl-D-proline.

All patents and publications mentioned in the specification are indicative of the levels of skill of those skilled in the art to which the invention pertains. All references cited in this disclosure are incorporated by reference to the same extent as if each reference had been incorporated by reference in its entirety individually. One skilled in the art would readily appreciate that the present invention is well adapted to carry out the objects and obtain the ends and advantages mentioned, as well as those inherent therein. The specific compounds and methods described herein as presently representative of preferred embodiments are exemplary and are not intended as limitations on the scope of the invention. Changes therein and other uses will occur to those skilled in the art which are encompassed within the spirit of the invention are defined by the scope of the claims.

It will be readily apparent to one skilled in the art that varying substitutions and modifications may be made to the invention disclosed herein withiout departing from the scope and spirit of the invention. For example, those skilled in the art will recognize that the invention may be practiced using a variety of different compounds within the described generic descriptions.

The invention illustratively described herein suitably may be practiced in the absence of any element or elements, limitation or limitations which is not specifically disclosed herein. Thbus, for example, in each instance herein any of the terms "comprising," "consisting essentially of" and "consisting of" may be replaced with either of the other twco terms. The terms and expressions which have been employed are used as terms of description and not of limitation, and there is not intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

In addition, where features or aspects of the invention are described in terms of Markush groups or other grouping of alternatives, those skilled in the art will recognize that the invention is also thereby described in terms of any individual member or subgroup of members of the Markush group or other group.

Thus, additional embodiments are within the scope of the invention and within the following claims.

What we claim is:

1. A method for treating a microbial infection in an animal, comprising administering to an animal suffering from said infection an efflux pump inhibitor in an amount sufficient to reduce efflux pump activity, wherein said efflux pump inhibitor has the chemical structure of Structure 1 below:

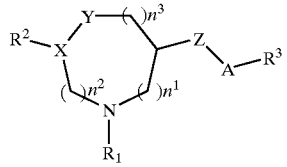

Structure 1 wherein:
$n^1$ is 0;
$n^2$ is 1;
$n^3$ is 1 or 2;
X is $CR^{2a}$; wherein $R^{2a}$ is H or lower alkyl;
Y is a single bond;
$R^1$ is H;
$R^2$ is

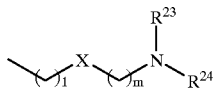

wherein is l is 0, X is a single bond, m is 0, 1, 2 or 3, $R^{23}$ is H, lower alkyl, α- aminoacyl or β-aminoacyl and $R^{24}$ is H or lower alkyl;
Z is a single bond;

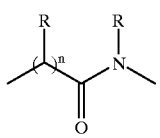

wherein n is 0, 1, 2, or 3 and each R is independently H, lower alkyl, or phenylalkyl;

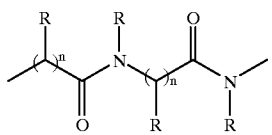

wherein n is 0, 1, 2, or 3 and each R is independently H, lower alkyl, or phenylalkyl;

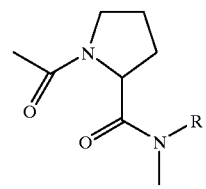

wherein R is H, lower alkyl, or phenylalkyl;

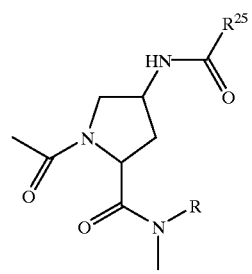

wherein R is H, lower alkyl, or phenylalkyl, and $R^{25}$ is phenylalkyl, wherein the alkyl chain may be substituted by OH or F;

one of

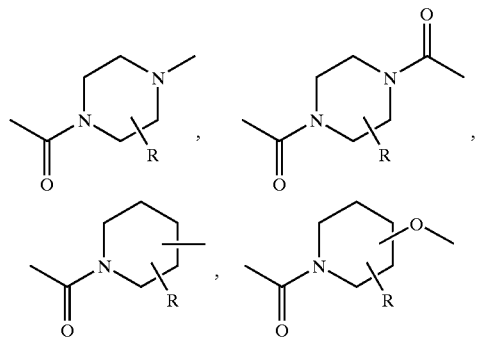

wherein each R is independently H, lower alkyl, or phenylalkyl;

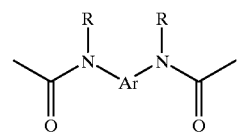

wherein each R is independently H or lower alkyl, and Ar is phenyl;

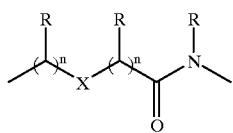

wherein n is 0, 1, or 2; X is O or S; and each R is independently H or lower alkyl;

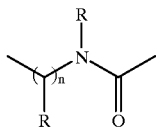

wherein n is 0, 1, 2, or 3; and each R is independently H or lower alkyl; or

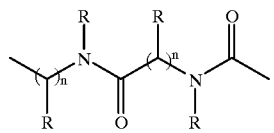

wherein n is 0, 1, 2, or 3; as independently H or lower alkyl;

A is a single bond or

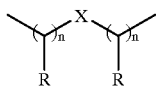

wherein n is 0, 1, 2, or 3; and X is O, S, single bond, double bond, triple bond, cycloalkane and each R is independently H or lower alkyl; and $R^3$ is H; optionally substituted phenyl, tetrahydronaphthyl, indanyl, thienyl, quinolyl, isoquinolyl, or optionally substituted cycloalkyl wherein the ring size is 3, 4, 5, or 6 atoms; wherein the substituents are independently one or more lower alkyl or alkenyl groups, halogeno, fluoroalkyl, hydroxy, alkyloxy, alkylthio, mercapto, amino, monosubstituted amino, disubstituted amino.

2. The method of claim 1, further comprising administering to said animal an antimicrobial agent, wherein said efflux pump inhibitor increases the susceptibility of said microbe to said antimicrobial agent.

3. The method of claim 1, wherein said efflux pump inhibitor has Structure 2 below:

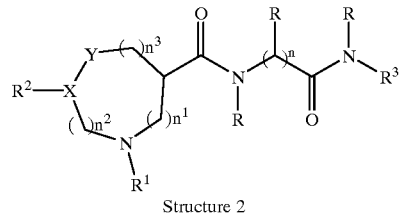

Structure 2 wherein n is 1 or 2;

each R is independently H, lower alkyl, or phenylalkyl;

$R^3$ is optionally substituted phenyl, tetrahydronaphthyl, indanyl, thienyl, quinolyl, isoquinolyl, or optionally substituted cycloalkyl wherein the ring size is 3, 4, 5, or 6 atoms; wherein the substituents are independently one or more lower alkyl or alkenyl groups, halogeno, fluoroalkyl, hydroxy, alkyloxy, alkylthio, mercapto, amino, monosubstituted amino, or disubstituted amino.

4. The method of claim 3, further comprising administering to said animal an antimicrobial agent, wherein said efflux pump inhibitor increases the susceptibility of said microbe to said antimicrobial agent.

5. The method of claim 1, wherein said efflux pump inhibitor has Structure 3 below:

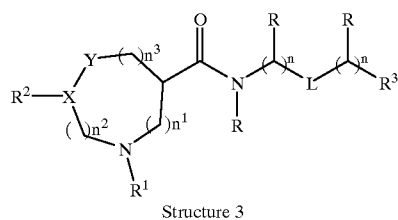

Structure 3 wherein n is 1, or 2;

L is O, S, NR, single bond, or double bond;

each R is independently H, lower alkyl, phenylalkyl; and $R^3$ is optionally substituted phenyl, tetrahydronaphthyl, indanyl, thienyl, quinolyl, isoquinolyl, or optionally substituted cycloalkyl wherein the ring size is 3, 4, 5, or 6 atoms; wherein the substituents are independently one or more lower alkyl or alkenyl groups, halogeno, fluoroalkyl, hydroxy, alkyloxy, alkylthio, mercapto, amino, monosubstituted amino, or disubstituted amino.

6. The method of claim 5, further comprising administering to said anirnal an antimicrobial agent, wherein said efflux pump inhibitor increases the susceptibility of said microbe to said antimicrobial agent.

7. The method of claim 1, wherein said efflux pump inhibitor has Structure 4 below:

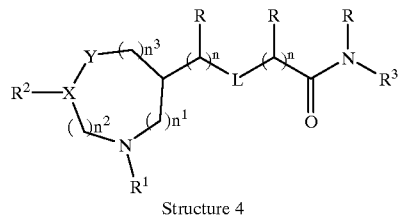

Structure 4 wherein n is 1 or 2; and $R^3$ is substituted phenyl, tetrahydronaphthyl, indanyl, thienyl, quinolyl, isoquinolyl, or substituted cycloalkyl wherein the ring size is 3, 4, 5, or 6 atoms; wherein the substituents are independently one or more lower alkyl or alkenyl groups, halogeno, fluoroalkyl, hydroxy, alkyloxy, alkylthio, mercapto, amino, monosubstituted amino, or disubstituted amino.

8. The method of claim 7, further comprising administering to said animal an antimicrobial agent, wherein said efflux pump inhibitor increases the susceptibility of said microbe to said antimicrobial agent.

9. The method of claim 1, wherein said efflux pump inhibitor has Structure 5 below:

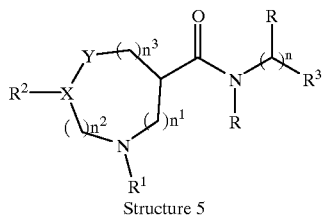

Structure 5 wherein
n is 1 or 2;
each R is independently H, lower alkyl, or phenylalkyl; and
$R^3$ is optionally substituted phenyl, tetrahydronaphthyl, indanyl, thienyl, quinolyl, isoquinolyl, or substituted cycloalkyl wherein the ring size is 3, 4, 5, or 6 atoms; wherein the substituents are independently one or more lower alkyl or alkenyl groups, halogeno, fluoroalkyl, hydroxy, alkyloxy, alkylthio, mercapto, amino, monosubstituted amino, or disubstituted amino.

10. The method of claim 9, further comprising administering to said animal an antimicrobial agent, wherein said efflux pump inhibitor increases the susceptibility of said microbe to said antimicrobial agent.

11. The method of claim 1, wherein said efflux pump inhibitor has Structure 6 below:

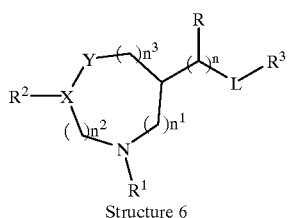

Structure 6 wherein
n is 1 or 2;
L is O, S, NR, single bond, double bond;
each R is independently H, lower alkyl, or phenylalkyl; and
$R^3$ is optionally substituted phenyl, tetrahydronaphthyl, indanyl, thienyl, quinolyl, isoquinolyl, or optionally substituted cycloalkyl wherein the ring size is 3, 4, 5, or 6 atoms; wherein the substituents are independently one or more lower alkyl or alkenyl groups, halogeno, fluoroalkyl, hydroxy, alkyloxy, alkylthio, mercapto, amino, monosubstituted amino, or disubstituted amino.

12. The method of claim 11, further comprising administering to said animal an antimicrobial agent, wherein said efflux pump inhibitor increases the susceptibility of said microbe to said antimicrobial agent.

13. A method for prophylactic treatment of an animal, comprising administering to an animal at risk of a microbial infection an efflux pump inhibitor, wherein said efflux pump inhibitor decreases the pathogenicity of a microbe in said animal, and wherein said efflux pump inhibitor has the chemical structure of Structure 1 below:

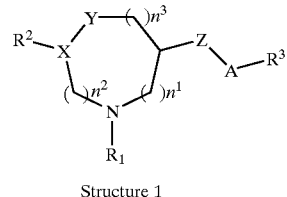

Structure 1 wherein:
$n^1$ is 0;
$n^2$ is 1;
$n^3$ is 1 or 2;
X is $CR^{2a}$; wherein $R^{2a}$ is H or lower alkyl;
Y is a single bond;
$R^1$ is H;
$R^2$ is

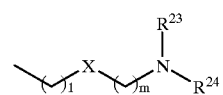

wherein l is 0, X is a single bond, m is 0, 1, 2 or 3, $R^{23}$ is H, lower alkyl, α-aminoacyl or β-aminoacyl and $R^{24}$ is H or lower alkyl;

Z is a single bond;

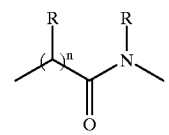

wherein n is 0, 1, 2, or 3 and each R is independently H, lower alkyl, or phenylalkyl;

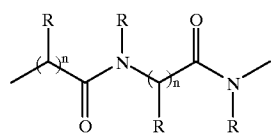

wherein n is 0, 1, 2, or 3 and each R is independently H, lower alkyl, or phenylalkyl;

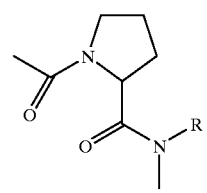

wherein R is H, lower alkyl, or phenylalkyl;

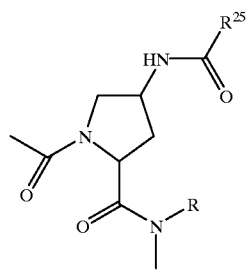

wherein R is H, lower alkyl, or phenylalkyl, and $R^{25}$ is phenylalkyl, wherein the alkyl chain may be substituted by OH or F;

one of

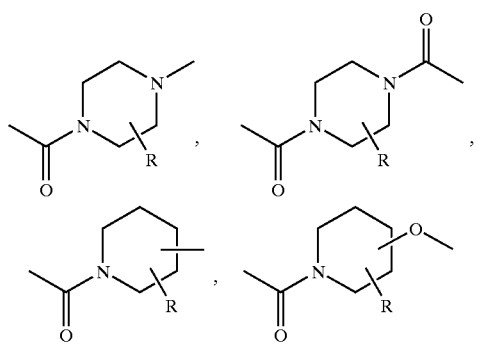

wherein each R is independently H, lower alkyl, or phenylalkyl;

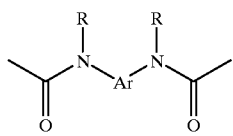

wherein each R is independently H or lower alkyl, and Ar is phenyl;

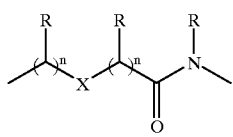

wherein n is 0, 1, or 2; X is O or S; and each R is independently H or lower alkyl;

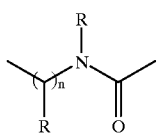

wherein n is 0, 1, 2, or 3; and each R is independently H or lower alkyl; or

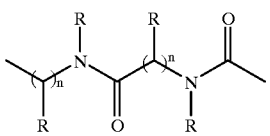

wherein n is 0, 1, 2, or 3; and each R is independently H or lower alkyl;

A is a single bond or

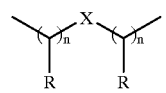

wherein n is 0, 1, 2, or 3; and X is O, S, single bond, double bond, triple bond, cycloalkane and each R is independently H or lower alkyl; and $R^3$ is H; optionally substituted phenyl, tetrahydronaphthyl, indanyl, thienyl, quinolyl, isoquinolyl, or optionally substituted cycloalkyl wherein the ring size is 3, 4, 5, or 6 atoms; wherein the substituents are independently one or more lower alkyl or alkenyl groups, halogeno, fluoroalkyl, hydroxy, alkyloxy, alkylthio, mercapto, amino, monosubstituted amino, disubstituted amino.

14. The method of claim 13, further comprising administering to said animal an antimicrobial agent, wherein said efflux pump inhibitor increases the susceptibility of said microbe to said antimicrobial agent.

15. The method of claim 13, wherein said efflux pump inhibitor has Structure 2 below:

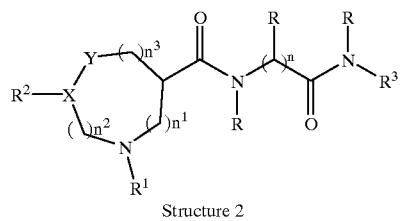

Structure 2 wherein n is 1 or 2;

each R is independently H, lower alkyl, or phenylalkyl;

$R^3$ is optionally substituted phenyl, tetrahydronaphthyl, indanyl, thienyl, quinolyl, isoquinolyl, or substituted cycloalkyl wherein the ring size is 3, 4, 5, or 6 atoms; wherein the substituents are independently one or more lower alkyl or alkenyl groups, halogeno, fluoroalkyl, hydroxy, alkyloxy, alylthio, mercapto, amino, monosubstituted amino, or disubstituted amino.

16. The method of claim 15, further comprising administering to said animal an antimicrobial agent, wherein said efflux pump inhibitor increases the susceptibility of said microbe to said antimicrobial agent.

17. The method of claim 13, wherein said efflux pump inhibitor has Structure 3 below:

Structure 3 wherein
n is 1, or 2;
L is O, S, NR, single bond, or double bond;
each R is independently H, lower alkyl, phenylalkyl; and
R³ is optionally substituted phenyl, tetrahydronaphthyl, indanyl, thienyl, quinolyl, isoquinolyl, or optionally substituted cycloalkyl wherein the ring size is 3, 4, 5, or 6 atoms; wherein the substituents are independently one or more lower alkyl or alkenyl groups, halogeno, fluoroalkyl, hydroxy, alkyloxy, alkylthio, mercapto, amino, monosubstituted amino, or disubstituted amino.

18. The method of claim 17, further comprising administering to said animal an antimicrobial agent, wherein said efflux pump inhibitor increases the susceptibility of said microbe to said antimicrobial agent.

19. The method of claim 13, wherein said efflux pump inhibitor has Structure 4 below:

Structure 4 wherein
n is 1 or 2; and
R³ is optionally substituted phenyl, tetrahydronaphthyl, indanyl, thienyl, quinolyl, isoquinolyl, or optionally substituted cycloalkyl wherein the ring size is 3, 4, 5, or 6 atoms; wherein the substituents are independently one or more lower alkyl or alkenyl groups, halogeno, fluoroalkyl, hydroxy, alkyloxy, alkylthio, mercapto, amino, monosubstituted amino, or disubstituted amino.

20. The method of claim 19, further comprising administering to said animal an antimicrobial agent, wherein said efflux pump inhibitor increases the susceptibility of said microbe to said antimicrobial agent.

21. The method of claim 13, wherein said efflux pump inhibitor has Structure 5 below:

Structure 5 wherein
n is 1 or 2;
each R is independently H, lower alkyl, or phenylalkyl; and
R³ is optionally substituted phenyl, tetrahydronaphthyl, indanyl, thienyl, quinolyl, isoquinolyl, or optionally substituted cycloalkyl wherein the ring size is 3, 4, 5, or 6 atoms; wherein the substituents are independently one or more lower alkyl or alkenyl groups, halogeno, fluoroalkyl, hydroxy, alkyloxy, alkylthio, mercapto, amino, monosubstituted amino, or disubstituted amino.

22. The method of claim 21, further comprising administering to said animal an antimicrobial agent, wherein said efflux pump inhibitor increases the susceptibility of said microbe to said antimicrobial agent.

23. The method of claim 13, wherein said efflux pump inhibitor has Structure 6 below:

Structure 6 wherein
n is 1 or 2;
L is O, S, NR, single bond, double bond;
each R is independently H, lower alkyl, or phenylalkyl; and
R³ is optionally substituted phenyl, tetrahydronaphthyl, indanyl, thienyl, quinolyl, isoquinolyl, or optionally substituted cycloalkyl wherein the ring size is 3, 4, 5, or 6 atoms; wherein the substituents are independently one or more lower alkyl or alkenyl groups, halogeno, fluoroalkyl, hydroxy, alkyloxy, alkylthio, mercapto, amino, monosubstituted amino, or disubstituted amino.

24. The method of claim 23, further comprising administering to said animal an antimicrobial agent, wherein said efflux pump inhibitor increases the susceptibility of said microbe to said antimicrobial agent.

25. The method of any of claims 1 or 13, wherein said animal is a mammal.

26. A method of enhancing the antimicrobial activity of an antimicrobial agent against a microbe, comprising contacting said microbe with said antimicrobial agent and an efflux pump inhibitor in an amount effective to inhibit an efflux pump in said microbe, wherein said efflux pump inhibitor has the chemical structure of Structure 1 below:

Structure 1 wherein
$n^1$ is 0;
$n^2$ is 1;
$n^3$ is 1 or 2;
X is $CR^{2a}$; wherein $R^{2a}$ is H or lower alkyl;
Y is a single bond;

$R^1$ is H;

$R^2$ is

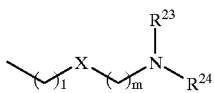

wherein l is 0, X is a single bond, m is 0, 1, 2 or 3, $R^{23}$ is H, lower alkyl, α-aminoacyl or β-aminoacyl and $R^{24}$ is H or lower alkyl;

Z is a single bond;

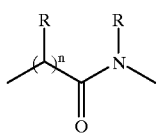

wherein n is 0, 1, 2, or 3 and each R is independently H, lower alkyl, or phenylalkyl;

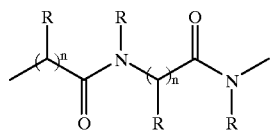

wherein n is 0, 1, 2, or 3 and each R is independently H, lower alkyl, or phenylalkyl;

one of

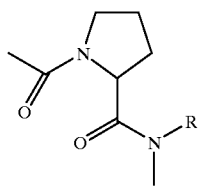

wherein R is H, lower alkyl, or phenylalkyl;

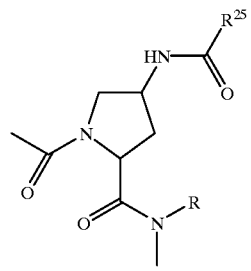

wherein R is H, lower alkyl, or phenylalkyl, and $R^{25}$ is phenylalkyl, wherein the alkyl chain may be substituted by OH or F;

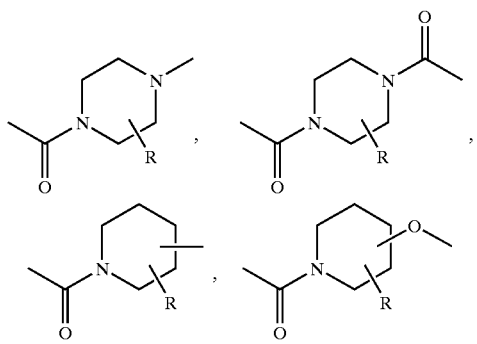

wherein each R is independently H, lower alkyl, or phenylalkyl;

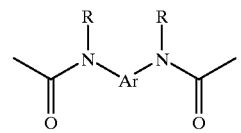

wherein each R is independently H or lower alkyl, and Ar is phenyl;

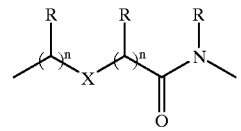

wherein n is 0, 1, or 2; X is O or S; and each R is independently H or lower alkyl;

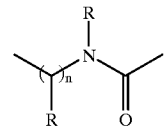

wherein n is 0, 1, 2, or 3; and each R is independently H or lower alkyl; or

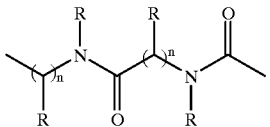

wherein n is 0, 1, 2, or 3; and each R is independently H or lower alkyl;

A is a single bond or

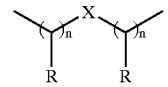

wherein n is 0, 1, 2, or 3; and X is O, S, single bond, double bond, triple bond, cycloalkane and each R is independently H or lower alkyl; and $R^3$ is H; optionally substituted phenyl, tetrahydronaphthyl, indanyl, thienyl, quinolyl, isoquinolyl, or optionally substituted cycloalkyl wherein the ring size is 3, 4, 5, or 6 atoms; wherein the substituents are independently one or more lower alkyl or alkenyl groups, halogeno, fluoroalkyl, hydroxy, alkyloxy, alkylthio, mercapto, amino, monosubstituted amino, disubstituted amino.

27. The method of claim 26, wherein said efflux pump inhibitor has Structure 2 below:

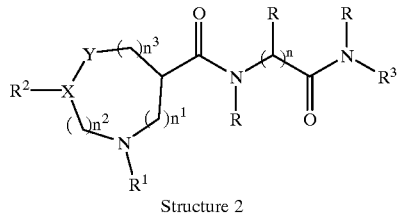

Structure 2 wherein n is 1 or 2;

each R is independently H, lower alkyl, or phenylalkyl;

$R^3$ is optionally substituted phenyl, tetrahydronaphthyl, indanyl, thienyl, quinolyl, isoquinolyl, or optionally substituted cycloalkyl wherein the ring size is 3, 4, 5, or 6 atoms; wherein the substituents are independently one or more lower alkyl or alkenyl groups, halogeno, fluoroalkyl, hydroxy, alkyloxy, alkylthio, mercapto, amino, monosubstituted amino, or disubstituted amino.

28. The method of claim 26, wherein said efflux pump inhibitor has Structure 3 below:

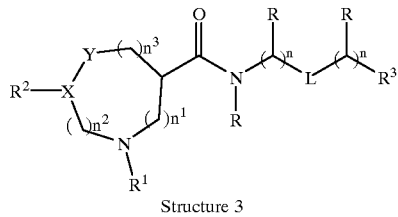

Structure 3 wherein n is 1, or 2;

L is O, S, NR, single bond, or double bond;

each R is independently H, lower alkyl, phenylalkyl; and $R^3$ is optionally substituted phenyl, tetrahydronaphthyl, indanyl, thienyl, quinolyl, isoquinolyl, or optionally substituted cycloalkyl wherein the ring size is 3, 4, 5, or 6 atoms; wherein the substituents are independently one or more lower alkyl or alkenyl groups, halogeno, fluoroalkyl, hydroxy, alkyloxy, alkylthio, mercapto, amino, monosubstituted amino, or disubstituted amino.

29. The method of claim 26, wherein said efflux pump inhibitor has Structure 4 below:

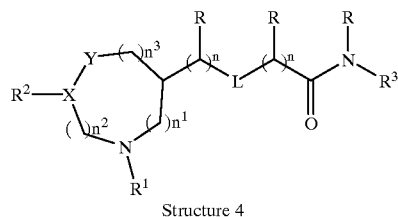

Structure 4 wherein n is 1 or 2; and $R^3$ is optionally substituted phenyl, tetrahydronaphthyl, indanyl, thienyl, quinolyl, isoquinolyl, or optionally substituted cycloalkyl wherein the ring size is 3, 4, 5, or 6 atoms; wherein the substituents are independently one or more lower alkyl or alkenyl groups, halogeno, fluoroalkyl, hydroxy, alkyloxy, alkylthio, mercapto, amino, monosubstituted amino, or disubstituted amino.

30. The method of claim 26, wherein said efflux pump inhibitor has Structure 5 below:

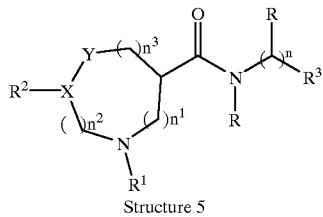

Structure 5 wherein n is 1 or 2;

each R is independently H, lower alkyl, or phenalalkyl; and $R^3$ is optionally substituted phenyl, tetrahydronaphthyl, indanyl, thienyl, quinolyl, isoquinolyl, or optionally substituted cycloalkyl wherein the ring size is 3, 4, 5, or 6 atoms; wherein the substituents are independently one or more lower alkyl or alkenyl groups, halogeno, fluoroalkyl, hydroxy, alkyloxy, alkylthio, mercapto, amino, monosubstituted amino, or disubstituted amino.

31. The method of claim 26, wherein said efflux pump inhibitor has Structure 6 below:

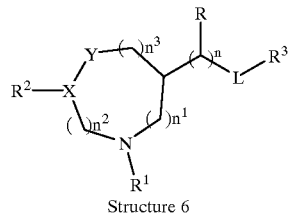

Structure 6 wherein n is 1 or 2;

L is O, S, NR, single bond, double bond;

each R is independently H, lower alkyl, or phenylalkyl; and $R^3$ is optionally substituted phenyl, tetrahydronaphthyl, indanyl, thienyl, quinolyl, isoquinolyl, or optionally substituted cycloalkyl wherein the ring size is 3, 4, 5, or 6 atoms; wherein the substituents are independently one or more lower alkyl or alkenyl groups, halogeno, fluoroalkyl, hydroxy, alkyloxy, alkylthio, mercapto, amino, monosubstituted amino, or disubstituted amino.

32. The method of any of claims 1, 13 or 26, wherein said microbe is a bacterium.

33. The method of claim 32, wherein said bacterial infection involves a bacterium selected from the group consisting of *Pseudomonas aeruginosa, Pseudomonas fluorescens, Pseudomonas acidovorans, Pseudomonas alcaligenes, Pseudomonas putida, Stenotrophomonas maltophilia, Burkholderia cepacia, Aeromonas hydrophilia, Escherichia coli, Citrobacter freundii, Salmonella typhimurium, Salmonella typhi, Salmonella paratyphi, Salmonella enteritidis, Shigella dysenteriae, Shigella flexneri, Shigella sonnei, Enterobacter cloacae, Enterobacter aerogenes, Klebsiella pneumoniae, Klebsiella oxytoca, Serratia marcescens, Francisella tularensis, Morganella morganii, Proteus mirabilis, Proteus vulgaris, Providencia alcalifaciens, Providencia rettgeri, Providencia stuartii, Acinetobacter calcoaceticus, Acinetobacter haemolyticus, Yersinia enterocolitica, Yersinia pestis, Yersinia pseudotuberculosis, Yersinia intermedia, Bordetella pertussis, Bordetella parapertussis, Bordetella bronchiseptica, Haemophilus influenzae, Haemophilus parainfluenzae, Haemophilus haemolyticus, Haemophilus parahaemolyticus, Haemophilus ducreyi, Pasteurella multocida, Pasteurella haemolytica, Branhamella catarrhalis, Helicobacter pylori, Campylobacter fetus, Campylobacter jejuni, Campylobacter coli, Borrelia burgdorferi, Vibrio cholerae, vibrio parahaemolyticus, Legionella pneumophila, Listeria monocytogenes, Neisseria gonorrhoeae, Neisseria meningitidis, Gardnerella vaginalis, Bacteroides fragilis, Bacteroides distasonis,* Bacteroides 3452A homology group, *Bacteroides vulgatus, Bacteroides ovalus, Bacteroides thetaiotaomicron, Bacteroides uniformis, Bacteroides eggerthii, Bacteroides splanchnicus, Clostridium difficile, Mycobacterium tuberculosis, Mycobacterium avium, Mycobacterium intracellulare, Mycobacterium leprae, Corynebacterium diphtheriae, Corynebacterium ulcerans, Streptococcus pneumoniae, Streptococcus agalactiae, Streptococcus pyogenes, Enterococcus faecalis, Enterococcus faecium, Staphylococcus aureus, Staphylococcus epidermidis, Staphylococcus saprophyticus, Staphylococcus intermedius, Staphylococcus hyicus* subsp. *hyicus, Staphylococcus haemolyticus, Staphylococcus hominis, Staphylococcus saccharolyticus.*

34. The method of any of claims 2, 14 or 26, wherein said microbial infection is a bacterial infection and said antimicrobial agent is an antibacterial agent.

35. The method of claim 34, wherein said antibacterial agent is selected from the group consisting of a quinolone, a tetracycline, a β-lactam, a coumermycin, chloramphenicol, a glycopeptide, an aminoglycoside, a macrolide, a rifamycin, and an oxazolidonone.

36. The method of any of claims 2, 14 or 26, wherein said antimicrobial agent is effluxed by a microbe.

37. A pharmaceutical composition effective for treatment of an infection of an animal by a microbe, comprising an efflux pump inhibitor and a pharmaceutically acceptable carrier, wherein said efflux pump inhibitor has the chemical structure of Structure 1 below:

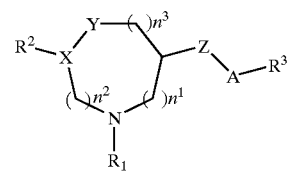

Structure 1 wherein $n^1$ is 0;

$n^2$ is 1;

$n^3$ is 1 or 2;

X is $CR^{2a}$; wherein $R^{2a}$ is H or lower alkyl;

Y is a single bond;

$R^1$ is H;

$R^2$ is

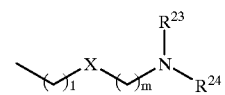

wherein l is 0, X is a single bond, m is 0, 1, 2 or 3, $R^{23}$ is H, lower alkyl, α-aminoacyl or β-aminoacyl and $R^{24}$ is H or lower alkyl;

Z is a single bond;

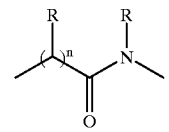

wherein n is 0, 1, 2, or 3 and each R is independently H, lower alkyl, or phenylalkyl;

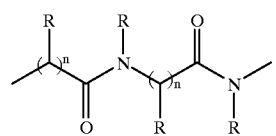

wherein n is 0, 1, 2, or 3 and each R is independently H, lower alkyl, or phenylalkyl;

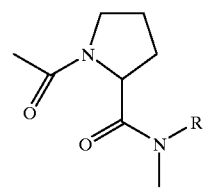

wherein R is H, lower alkyl or phenylalkyl;

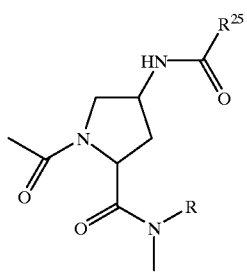

wherein R is H, lower alkyl, or phenylalkyl, and $R^{25}$ is phenylalkyl, wherein the alkyl chain may be substituted by OH or F;

one of

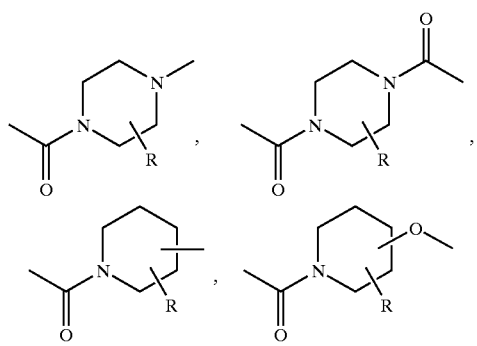

wherein each R is independently H, lower alkyl, or phenylalkyl;

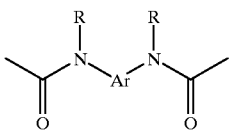

wherein each R is independently H or lower alkyl, and Ar is phenyl;

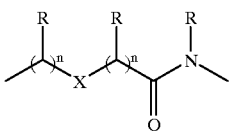

wherein n is 0, 1, or 2; X is O or S; and each R is independently H or lower alkyl;

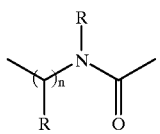

wherein n is 0, 1, 2, or 3; and each R is independently H or lower alkyl; or

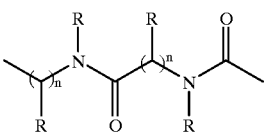

wherein n is 0, 1, 2, or 3; and each R is independently H or lower alkyl;

A is single bond or

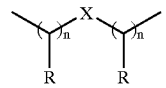

wherein n is 0, 1, 2, or 3; and X is O, S, single bond, double bond, triple bond, cycloalkane and each R is independently H or lower alkyl; and $R^3$ is H; optionally substituted phenyl, tetrahydronaphthyl, indanyl, thienyl, quinolyl, isoquinolyl, or optionally substituted cycloalkyl wherein the ring size is 3, 4, 5, or 6 atoms; wherein the substituents are independently one or more lower alkyl or alkenyl groups, halogeno, fluroalkyl, hydroxy, alkyloxy, alkylthio, mercapto, amino, monosubstituted amino, disubstituted amino.

38. The pharmaceutical composition of claim 37, wherein said efflux pump inhibitor has Structure 2 below:

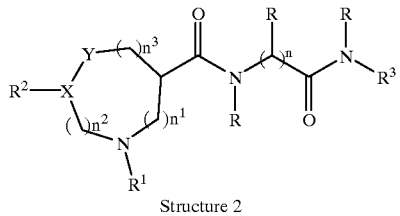

Structure 2 wherein n is 1 or 2;

each R is independently H, lower alkyl, or phenylalkyl;

$R^3$ is optionally substituted phenyl, tetrahydronaphthyl, indanyl, thienyl, quinolyl, isoquinolyl, or optionally substituted cycloalkyl wherein the ring size is 3, 4, 5, or 6 atoms; wherein the substituents are independently one or more lower alkyl or alkenyl groups, halogeno, fluoroalkyl, hydroxy, alkyloxy, alkylthio, mercapto, amino, monosubstituted amino, or disubstituted amino.

39. The pharmaceutical composition of claim 37, wherein said efflux pump inhibitor has Structure 3 below:

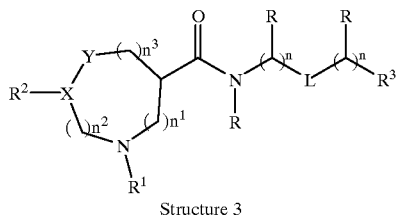

Structure 3 wherein n is 1, or 2;

L is O, S, NR, single bond, or double bond;

each R is independently H, lower alkyl, phenylalkyl; and

R³ is optionally substituted phenyl, tetrahydronaphthyl, indanyl, thienyl, quinolyl, isoquinolyl, or optionally substituted cycloalkyl wherein the ring size is 3, 4, 5, or 6 atoms; wherein the substituents are independently one or more lower alkyl or alkenyl groups, halogeno, fluoroalkyl, hydroxy, alkyloxy, alkylthio, mercapto, amino, monosubstituted amino, or disubstituted amino.

40. The pharmaceutical composition of claim 37, wherein said efflux pump inhibitor has Structure 4 below:

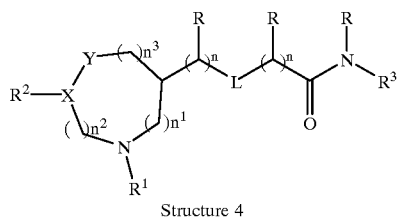

Structure 4 wherein n is 1 or 2; and

R³ is optionally substituted phenyl, tetrahydronaphthyl, indanyl, thienyl, quinolyl, isoquinolyl, or optionally substituted cycloalkyl wherein the ring size is 3, 4, 5, or 6 atoms; wherein the substituents are independently one or more lower alkyl or alkenyl groups, halogeno, fluoroalkyl, hydroxy, alkyloxy, alkylthio, mercapto, amino, monosubstituted amino, or disubstituted amino.

41. The pharmaceutical composition of claim 37, wherein said efflux pump inhibitor has Structure 5 below:

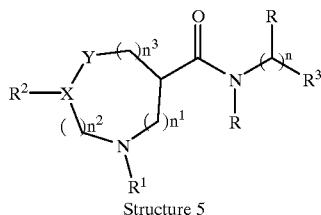

Structure 5 wherein n is 1 or 2;

each R is independently H, lower alkyl, or phenylalkyl; and

R³ is optionally substituted phenyl, tetrahydronaphthyl, indanyl, thienyl, quinolyl, isoquinolyl, or optionally substituted cycloalkyl wherein the ring size is 3, 4, 5, or 6 atoms; wherein the substituents are independently one or more lower alkyl or alkenyl groups, halogeno, fluoroalkyl, hydroxy, alkyloxy, alkylthio, mercapto, amino, monosubstituted amino, or disubstituted amino.

42. The pharmaceutical composition of claim 37, wherein said efflux pump inhibitor has Structure 6 below:

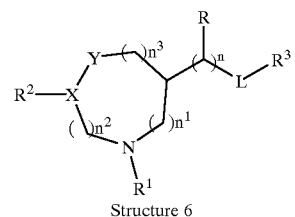

Structure 6 wherein n is 1 or 2;

L is O, S, NR, single bond, double bond;

each R is independently H, lower alkyl, or phenylalkyl; and

R³ is optionally substituted phenyl, tetrahydronaphthyl, indanyl, thienyl, quinolyl, isoquinolyl, or optionally substituted cycloalkyl wherein the ring size is 3, 4, 5, or 6 atoms; wherein the substituents are independently one or more lower alkyl or alkenyl groups, halogeno, fluoroalkyl, hydroxy, alkyloxy, alkylthio, mercapto, amino, monosubstituted amino, or disubstituted amino.

43. The pharmaceutical composition of claim 37, wherein said microbe is a bacterium.

44. The pharmaceutical composition of claim 37, further comprising an antimicrobial agent.

45. The pharmaceutical composition of claim 44, wherein said microbe is a bacterium.

46. The pharmaceutical composition of claim 45, wherein said antimicrobial agent is an antibacterial agent.

47. A method of suppressing growth of a bacterium expressing an efflux pump, comprising contacting said bacterium with an efflux pump inhibitor in the presence of a concentration of antibacterial agent below the MIC of said bacterium, wherein said efflux pump inhibitor has the chemical structure of Structure 1 below:

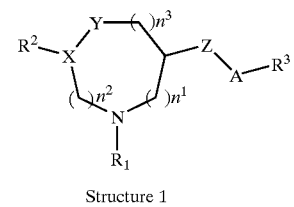

Structure 1 wherein $n^1$ is 0;

$n^2$ is 1;

$n^3$ is 1 or 2;

X is $CR^{2a}$; wherein $R^{2a}$ is H or lower alkyl;

Y is a single bond;

$R^1$ is H;

$R^2$ is

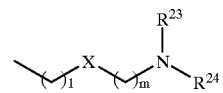

wherein l is 0, X is a single bond, m is 0, 1, 2 or 3, $R^{23}$ is H, lower alkyl, α-aminoacyl or β-aminoacyl and $R^{24}$ is H or lower alkyl;

Z is a single bond;

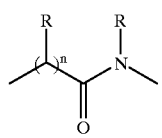

wherein n is 0, 1, 2, or 3 and each R is independently H, lower alkyl, or phenylalkyl;

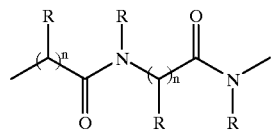

wherein n is 0, 1, 2, or 3 and each R is independently H, lower alkyl, or phenylalkyl;

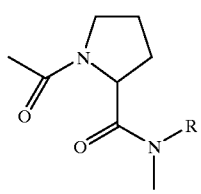

wherein R is H, lower alkyl, or phenyalkyl;

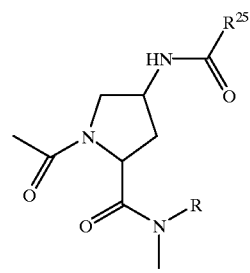

wherein R is H, lower alkyl, or phenylalkyl, and $R^{25}$ is phenylalkyl, wherein the alkyl chain may be substituted by OH or F;

one of

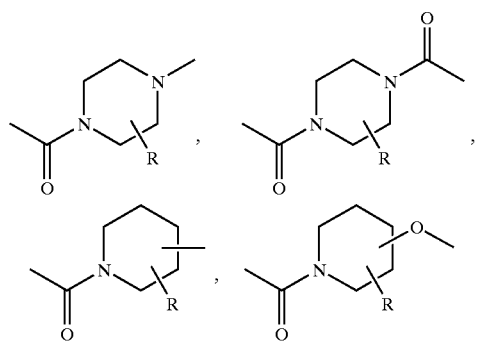

wherein each R is independently H, lower alkyl, or phenylalkyl;

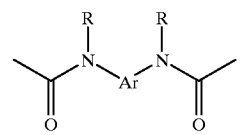

wherein each R is independently H or lower alkyl, and Ar is phenyl;

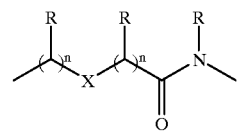

wherein n is 0, 1, or 2; X is O or S; and each R is independently H or lower alkyl;

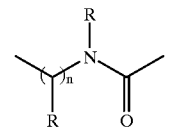

wherein n is 0, 1, 2, or 3; and each R is independently H or lower alkyl; or

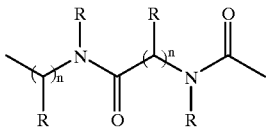

wherein n is 0, 1, 2, or 3; and each R is independently H or lower alkyl;

A is a single bond or

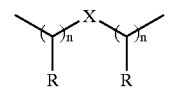

wherein n is 0, 1, 2, or 3; and X is O, S, single bond, double bond, triple bond, cycloalkane and each R is independently H or lower alkyl; and $R^3$ is H; optionally substituted phenyl, tetrahydronaphthyl, indanyl, thienyl, quinolyl, isoquinolyl, or optionally substituted cycloalkyl wherein the ring size is 3, 4, 5, or 6 atoms; wherein the substituents are independently one or more lower alkyl or alkenyl groups, halogeno, fluoroalkyl, hydroxy, alkyloxy, alkylthio, mercapto, amino, monosubstituted amino, disubstituted amino.

48. The method of claim 47, wherein said efflux pump inhibitor has Structure 2 below:

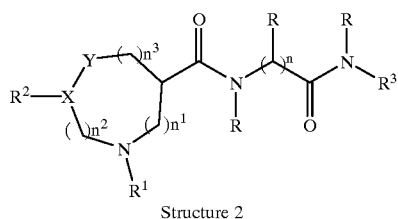

Structure 2 wherein
  n is 1 or 2;
  each R is independently H, lower alkyl, or phenylalkyl
  $R^3$ is optionally substituted phenyl, tetrahydronaphthyl, indanyl, thienyl, quinolyl, isoquinolyl, or optionally substituted cycloalkyl wherein the ring size is 3, 4, 5, or 6 atoms; wherein the substituents are independently one or more lower alkyl or alkenyl groups, halogeno, fluoroalkyl, hydroxy, alkyloxy, alkylthio, mercapto, amino, monosubstituted amino, or disubstituted amino.

49. The method of claim 47, wherein said efflux pump inhibitor has Structure 3 below:

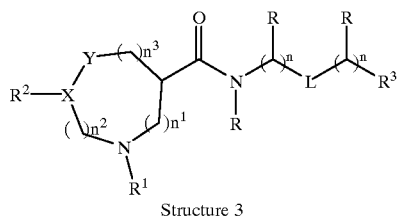

Structure 3 wherein
  n is 1, or 2;
  L is O, S, NR, single bond, or double bond;
  each R is independently H, lower alkyl, phenylalkyl; and
  $R^3$ is optionally substituted phenyl, tetrahydronaphthyl, indanyl, thienyl, quinolyl, isoquinolyl, or optionally substituted cycloalkyl wherein the ring size is 3, 4, 5, or 6 atoms; wherein the substituents are independently one or more lower alkyl or alkenyl groups, halogeno, fluoroalkyl, hydroxy, alkyloxy, alkylthio, mercapto, amino, monosubstituted amino, or disubstituted amino.

50. The method of claim 47, wherein said efflux pump inhibitor has Structure 4 below:

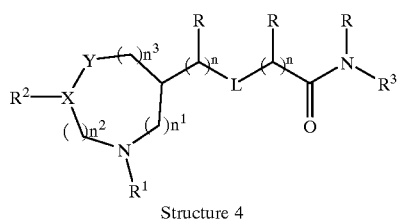

Structure 4 wherein
  n is 1 or 2; and
  $R^3$ is optionally substituted phenyl, tetrahydronaphthyl, indanyl, thienyl, quinolyl, isoquinolyl, or optionally substituted cycloalkyl wherein the ring size is 3, 4, 5, or 6 atoms; wherein the substituents are independently one or more lower alkyl or alkenyl groups, halogeno, fluoroalkyl, hydroxy, alkyloxy, alkylthio, mercapto, amino, monosubstituted amino, or disubstituted amino.

51. The method of claim 47, wherein said efflux pump inhibitor has Structure 5 below:

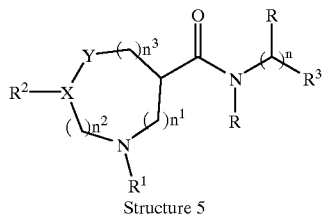

Structure 5 wherein
  n is 1 or 2;
  each R is independently H, lower alkyl, or phenylalkyl; and
  $R^3$ is optionally substituted phenyl, tetrahydronaphthyl, indanyl, thienyl, quinolyl, isoquinolyl, or optionally substituted cycloalkyl wherein the ring size is 3, 4, 5, or 6 atoms; wherein the substituents are independently one or more lower alkyl or alkenyl groups, halogeno, fluoroalkyl, hydroxy, alkyloxy, alkylthio, mercapto, amino, monosubstituted amino, or disubstituted amino.

52. The method of claim 47, wherein said efflux pump inhibitor has Structure 6 below:

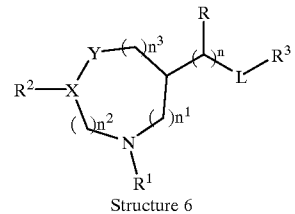

Structure 6 wherein
  n is 1 or 2;
  L is O, S, NR, single bond, double bond;
  each R is independently H, lower alkyl, or phenylalkyl; and
  $R^3$ is optionally substituted phenyl, tetrahydronaphthyl, indanyl, thienyl, quinolyl, isoquinolyl, or optionally substituted cycloalkyl wherein the ring size is 3, 4, 5, or 6 atoms; wherein the substituents are independently one or more lower alkyl or alkenyl groups, halogeno, fluoroalkyl, hydroxy, alkyloxy, alkylthio, mercapto, amino, monosubstituted amino, or disubstituted amino.

53. An efflux pump inhibitor compound, wherein said compound has the chemical structure of Structure 1 below:

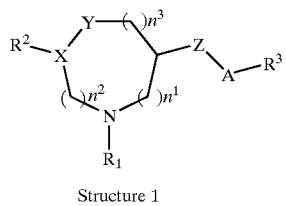

Structure 1 wherein
  $n^1$ is 0;
  $n^2$ is 1;

$n^3$ is 1 or 2;

X is $CR^{2a}$; wherein $R^{2a}$ is H or lower alkyl;

Y is a single bond;

$R^1$ is H;

$R^2$ is

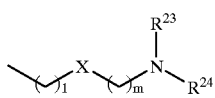

wherein l is 0, X is a single bond, m is 0, 1, 2 or 3, $R^{23}$ is H, lower alkyl, α-aminoacyl or β-aminoacyl and $R^{24}$ is H or lower alkyl;

Z is a single bond;

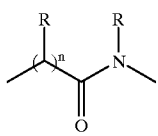

wherein n is 0, 1, 2, or 3 and each R is independently H, lower alkyl, or phenylalkyl;

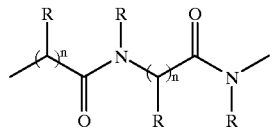

wherein n is 0, 1, 2, or 3 and each R is independently H, lower alkyl, or phenylalkyl;

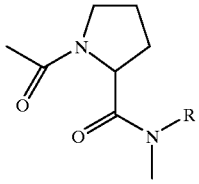

wherein R is H, lower alkyl, or phenylalkyl;

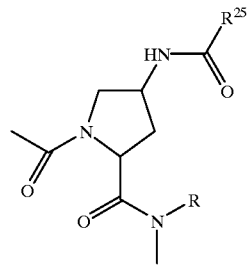

wherein R is H, lower alkyl, or phenylalkyl, and $R^{25}$ is phenylalkyl, wherein the alkyl chain may be substituted by OH or F;

one of

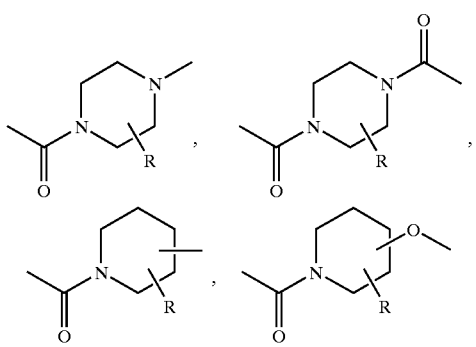

wherein each R is independently H, lower alkyl, or phenylalkyl;

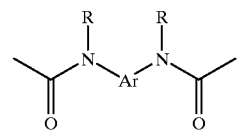

wherein each R is independently H or lower alkyl, and Ar is phenyl;

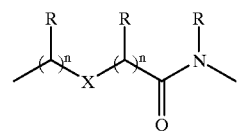

wherein n is 0, 1, or 2; X is O or S; and each R is independently H or lower alkyl;

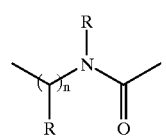

wherein n is 0, 1, 2, or 3; and each R is independently H or lower alkyl; or

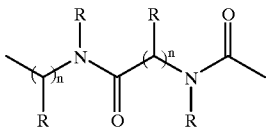

wherein n is 0, 1, 2, or 3; and each R is independently H or lower alkyl;

A is a single bond or

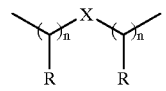

wherein n is 0, 1, 2, or 3; and X is O, S, single bond, double bond, triple bond, cycloalkane and each R is independently H or lower alkyl; and $R^3$ is H; optionally substituted phenyl, tetrahydronaphthyl, indanyl, thienyl, quinolyl, isoquinolyl, or optionally substituted cycloalkyl wherein the ring size is 3, 4, 5, or 6 atoms; wherein the substituents are independently one or more lower alkyl or alkenyl groups, halogeno, fluoroalkyl, hydroxy, alkyloxy, alkylthio, mercapto, amino, monosubstituted amino, disubstituted amino.

54. The efflux pump inhibitor compound of claim 53, wherein said compound has the chemical structure of Structure 2 below:

Structure 2 wherein n is 1 or 2;

each R is independently H, lower alkyl, or phenylalkyl;

$R^3$ is optionally substituted phenyl, tetrahydronaphthyl, indanyl, thienyl, quinolyl, isoquinolyl, or optionally substituted cycloalkyl wherein the ring size is 3, 4, 5, or 6 atoms; wherein the substituents are independently one or more lower alkyl or alkenyl groups, halogeno, fluoroalkyl, hydroxy, alkyloxy, alkylthio, mercapto, amino, monosubstituted amino, or disubstituted amino.

55. The efflux pump inhibitor compound of claim 53, wherein said compound has the chemical structure of Structure 3 below:

Structure 3 wherein n is 1, or 2;

L is O, S, NR, single bond, or double bond;

each R is independently H, lower alkyl, phenylalkyl; and $R^3$ is optionally substituted phenyl, tetrahydronaphthyl, indanyl, thienyl, quinolyl, isoquinolyl, or optionally substituted cycloalkyl wherein the ring size is 3, 4, 5, or 6 atoms; wherein the substituents are independently one or more lower alkyl or alkenyl groups, halogeno, fluoroalkyl, hydroxy, alkyloxy, alkylthio, mercapto, amino, monosubstituted amino, or disubstituted amino.

56. The efflux pump inhibitor compound of claim 53, wherein said compound has the chemical structure of Structure 4 below:

Structure 4 wherein n is 1 or 2; and $R^3$ is optionally substituted phenyl, tetrahydronaphthyl, indanyl, thienyl, quinolyl, isoquinolyl, or optionally substituted cycloalkyl wherein the ring size is 3, 4, 5 or 6 atoms; wherein the substituents are independently one or more lower alkyl or alkenyl groups, halogeno, fluoroalkyl, hydroxy, alkyloxy, alkylthio, mercapto, amino, monosubstituted amino, or disubstituted amino.

57. The efflux pump inhibitor compound of claim 53, wherein said efflux pump inhibitor has Structure 5 below:

Structure 5 wherein n is 1 or 2;

each R is independently H, lower alkyl, or phenylalkyl; and $R^3$ is optionally substituted phenyl, tetrahydronaphthyl, indanyl, thienyl, quinolyl, isoquinolyl, or optionally substituted cycloalkyl wherein the ring size is 3, 4, 5, or 6 atoms; wherein the substituents are independently one or more lower alkyl or alkenyl groups, halogeno, fluoroalkyl, hydroxy, alkyloxy, alkylthio, mercapto, amino, monosubstituted amino, or disubstituted amino.

58. The efflux pump inhibitor compound of claim 53, wherein said compound has the chemical structure of Structure 6 below:

Structure 6 wherein n is 1 or 2;

L is O, S, NR, single bond, double bond;

each R is independently H, lower alkyl, or phenylalkyl; and $R^3$ is optionally substituted phenyl, tetrahydronaphthyl, indanyl, thienyl, quinolyl, isoquinolyl, or optionally substituted cycloalkyl wherein the ring size is 3, 4, 5, or 6 atoms; wherein the substituents are independently one or more lower alkyl or alkenyl groups, halogeno, fluoroalkyl, hydroxy, alkyloxy, alkylthio, mercapto, amino, monosubstituted amino, or disubstituted amino.

59. A method of making a pharmaceutical composition comprising the steps of: identifying an efflux pump inhibitor having the chemical structure of Structure 1 below:

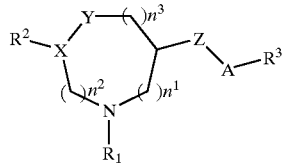

Structure 1 wherein
$n^1$ is 0;
$n^2$ is 1;
$n^3$ is 1 or 2;
X is $CR^{2a}$; wherein $R^{2a}$ is H or lower alkyl;
Y is a single bond;
$R^1$ is H;
$R^2$ is

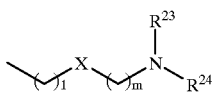

wherein l is 0, X is a single bond, m is 0, 1, 2 or 3, $R^{23}$ is H, lower alkyl, α-aminoacyl or β-aminoacyl and $R^{24}$ is H or lower alkyl;
Z is a single bond;

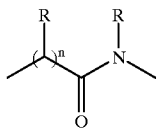

wherein n is 0, 1, 2, or 3 and each R is independently H, lower alkyl, or phenylalkyl;

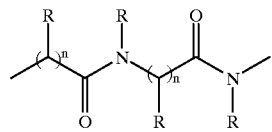

wherein n is 0, 1, 2, or 3 and each R is independently H, lower alkyl, or phenylalkyl;

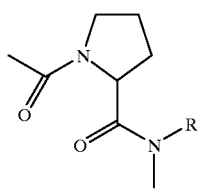

wherein R is H, lower alkyl, or phenylalkyl;

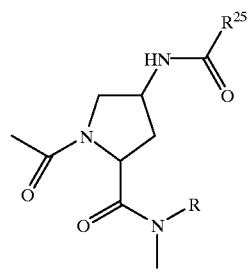

wherein R is H, lower alkyl, or phenylalkyl, and $R^{25}$ is phenylalkyl, wherein the alkyl chain may be substituted by OH or F;

one of

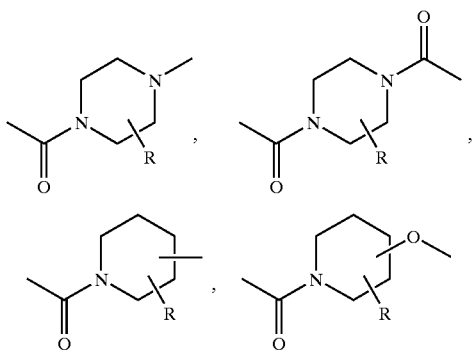

wherein each R is independently H, lower alkyl, or phenylalkyl;

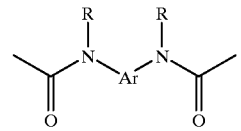

wherein each R is independently H or lower alkyl, and Ar is phenyl;

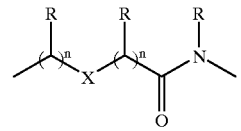

wherein n is 0, 1, or 2; X is O or S; and each R is independently H or lower alkyl;

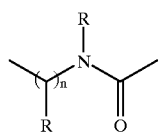

wherein n is 0, 1, 2, or 3; and each R is independently H or lower alkyl; or

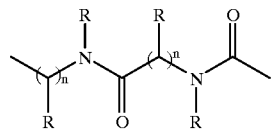

wherein n is 0, 1, 2, or 3; and each R is independently H or lower alkyl;

A is a single bond or

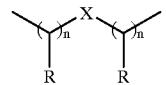

wherein n is 0, 1, 2, or 3; and X is O, S, single bond, double bond, triple bond, cycloalkane and each R is independently H or lower alkyl; and $R^3$ is H; optionally substituted phenyl, tetrahydronaphthyl, indanyl, thienyl, quinolyl, isoquinolyl, or optionally substituted cycloalkyl wherein the ring size is 3, 4, 5, or 6 atoms; wherein the substituents are independently one or more lower alkyl or alkenyl groups, halogeno, fluoroalkyl, hydroxy, alkyloxy, alkylthio, mercapto, amino, monosubstituted amino, disubstituted amino.

* * * * *